(12) United States Patent
Pinto et al.

(10) Patent No.: US 6,548,512 B1
(45) Date of Patent: Apr. 15, 2003

(54) NITROGEN CONTAINING HETEROAROMATICS AS FACTOR XA INHIBITORS

(75) Inventors: Donald Joseph Phillip Pinto, Newark, DE (US); James Russell Pruitt, Landenberg, PA (US); Joseph Cacciola, Newark, DE (US); John Matthew Fevig, Lincoln University, PA (US); Qi Han, Wilmington, DE (US); Michael James Orwat, Hockessin, DE (US); Mimi Lifen Quan, Newark, DE (US); Karen Anita Rossi, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/492,708

(22) Filed: Jan. 27, 2000

Related U.S. Application Data

(62) Division of application No. 08/995,834, filed on Dec. 22, 1997, now Pat. No. 6,020,357.
(60) Provisional application No. 60/050,304, filed on Jun. 20, 1997, and provisional application No. 60/033,437, filed on Dec. 23, 1996.

(51) Int. Cl.[7] ............... A61K 31/505; A61K 31/535; A61K 31/495; A61K 31/50; A61P 7/02; C07D 487/02; C07D 413/14; C07D 409/14; C07D 405/14
(52) U.S. Cl. .................. 514/275; 514/235.8; 514/236.5; 514/248; 514/252.02; 514/252.11; 514/252.18; 514/252.19; 514/255.05; 514/256; 514/269; 514/272; 514/273; 514/274; 544/120; 544/122; 544/123; 544/124; 544/235; 544/236; 544/238; 544/295; 544/296; 544/300; 544/310; 544/316; 544/317; 544/319; 544/320; 544/324; 544/327; 544/328; 544/331; 544/333
(58) Field of Search ........................ 514/275; 544/331

(56) References Cited

U.S. PATENT DOCUMENTS

| | | | |
|---|---|---|---|
| 5,082,949 A | 1/1992 | Sohn et al. .................. 548/378 |
| 5,262,412 A | 11/1993 | Ashton et al. ............ 514/236.5 |
| 5,317,103 A | 5/1994 | Baker et al. ................. 544/367 |
| 5,463,071 A | 10/1995 | Himmelsbach et al. ..... 548/251 |
| 5,550,147 A | 8/1996 | Matsuo et al. .............. 514/406 |
| 5,612,359 A | 3/1997 | Murugesan ................. 514/365 |
| 5,658,909 A | 8/1997 | Debernardis et al. ........ 514/252 |
| 5,691,329 A | 11/1997 | Degrado et al. ............. 514/210 |
| 5,998,424 A | 12/1999 | Galemmo, Jr. et al. ..... 514/269 |
| 6,020,357 A | * 2/2000 | Pinto et al. ................. 514/406 |
| 6,060,491 A | 5/2000 | Pruitt et al. ................. 514/355 |

FOREIGN PATENT DOCUMENTS

| | | |
|---|---|---|
| JP | 4247081 | 3/1992 |
| SA | 940435 | 1/1994 |
| WO | 9402477 | 2/1994 |
| WO | 9640143 | 12/1996 |
| WO | 9732583 | 9/1997 |
| WO | 9747299 | 12/1997 |

OTHER PUBLICATIONS

Tidewell et al., Journal of Medicinal Chemistry 1978, 21 (7), 613–623, "Diarylamidine Derivatives with One or Both of the Aryl Moieties Consisting of an Indole or Indole–like RIng. Inhibitors of Arginine–Specific Esteroproteases."

* cited by examiner

*Primary Examiner*—Brenda Coleman
(74) *Attorney, Agent, or Firm*—David H. Vance; Jing S. Belfield

(57) ABSTRACT

The present application describes nitrogen containing heteroaromatics and derivatives thereof of formula I:

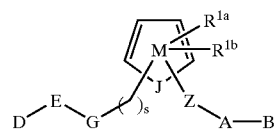

or pharmaceutically acceptable salt or prodrug forms thereof, wherein J is N or NH and D may be $C(=NH)NH_2$, which are useful as inhibitors of factor Xa.

52 Claims, No Drawings

NITROGEN CONTAINING HETEROAROMATICS AS FACTOR XA INHIBITORS

This is a divisional of application Ser. No. 08/995,834 filed Dec. 22, 1997, now U.S. Pat. No. 6,020,357, which claims priority to Provisional Application Nos. 60/033,437, filed Dec. 23, 1996 and 60/050,304, filed Jun. 20, 1997.

FIELD OF THE INVENTION

This invention relates generally to nitrogen containing heteroaromatics which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO 95/18111 addresses fibrinogen receptor antagonists, containing basic and acidic termini, of the formula:

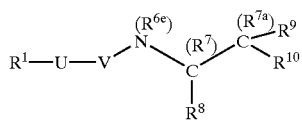

wherein $R^1$ represents the basic termini, U is an alkylene or heteroatom linker, V may be a heterocycle, and the right hand portion of the molecule represents the acidic termini. The presently claimed compounds do not contain the acidic termini of WO 95/18111.

In U.S. Pat. No. 5,463,071, Himmelsbach et al depict cell aggregation inhibitors which are 5-membered heterocycles of the formula:

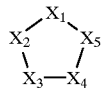

wherein the heterocycle may be aromatic and groups A—B—C— and F—E—D— are attached to the ring system. A—B—C— can be a wide variety of substituents including a basic group attached to an aromatic ring. The F—E—D— group, however, would appear to be an acidic functionality which differs from the present invention. Furthermore, use of these compounds as inhibitors of factor Xa is not discussed.

Baker et al, in U.S. Pat. No. 5,317,103, discuss 5-HT$_1$ agonists which are indole substituted five-membered heteroaromatic compounds of the formula:

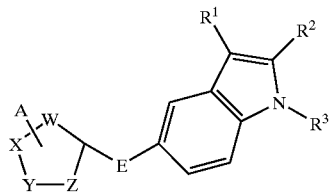

wherein $R^1$ may be pyrrolidine or piperidine and A may be a basic group including amino and amidino. Baker et al, however, do not indicate that A can be a substituted ring system like that contained in the presently claimed heteroaromatics.

Baker et al, in WO 94/02477, discuss 5-HT$_1$ agonists which are imidazoles, triazoles, or tetrazoles of the formula:

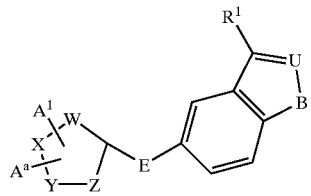

wherein $R^1$ represents a nitrogen containing ring system or a nitrogen substituted cyclobutane, and A may be a basic group including amino and amidino. Baker et al, however, do not indicate that A can be a substituted ring system like that contained in the presently claimed heteroaromatics.

Tidwell et al, in *J. Med. Chem.* 1978, 21(7), 613–623, describe a series of diarylamidine derivatives including 3,5-bis(4-amidinophenyl)pyrrole. This series of compounds was tested against thrombin, trypsin, and pancreatic kallikrein. The presently claimed invention does not include these types of compounds.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel nitrogen containing aromatic heterocycles which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

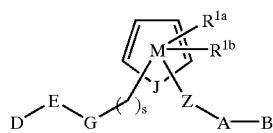

or pharmaceutically acceptable salt or prodrug forms thereof, wherein A, B, D, E, G, J, M, $R^{1a}$, $R^{1b}$, s and m/z are defined below, are effective factor Xa inhibitors.

DETAILED DESCRIPTION OF PREFERRED EMBODIMENTS

[1] Thus, in a first embodiment, the present invention provides novel compounds of formula I:

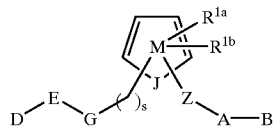

or a stereoisomer or pharmaceutically acceptable salt thereof, wherein;

ring M contains, in addition to J, 0–3 N atoms, provided that if M contains 2 N atoms then $R^{1b}$ is not present and if M contains 3 N atoms then $R^{1a}$ and $R^{1b}$ are not present;

J is N or NH;

D is selected from CN, $C(=NR^8)NR^7R^9$, $NHC(=NR^8)NR^7R^9$, $NR^8CH(=NR^7)$, $C(O)NR^7R^8$, and $(CR^8R^9)_tNR^7R^8$, provided that D is substituted meta or para to G on E;

E is selected from phenyl, pyridyl, pyrimidyl, pyrazinyl, pyridazinyl, and piperidinyl substituted with 1 R;

alternatively, D—E—G together represent pyridyl substituted with 1 R;

R is selected from H, halogen, $(CH_2)_tOR^3$, $C_{1-4}$ alkyl, $OCF_3$, and $CF_3$;

G is absent or is selected from $NHCH_2$, $OCH_2$, and $SCH_2$, provided that when s is 0, then G is attached to a carbon atom on ring M;

Z is selected from a $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_rNR^3C(O)(CH_2)_r$, $(CH_2)_rOC(O)O\ (CH_2)_r$, $(CH_2)_rOC(O)NR^3(CH_2)_r$, $(CH_2)_rNR^3C(O)O(CH_2)_r$, $(CH_2)_rNR^3C(O)NR^3(CH_2)_r$, $(CH_2)_rS(O)_p(CH_2)_r$, $(CH_2)_rSO_2NR^3(CH_2)_r$, $(CH_2)_rNR^3SO_2(CH_2)_r$, and $(CH_2)_rNR^3SO_2NR^3(CH_2)_r$, provided that Z does not form a N—N, N—O, N—S, $NCH_2N$, $NCH_2O$, or $NCH_2S$ bond with ring M or group A;

$R^{1a}$ and $R^{1b}$ are independently absent or selected from $-(CH_2)_r-R^{1"}$, $NCH_2R^{1"}$, $OCH_2R^{1"}$, $SCH_2R^{1"}$, $N(CH_2)_2(CH_2)_rR^{1"}$, $O(CH_2)_2(CH_2)_rR^{1"}$, and $S(CH_2)_2(CH_2)_rR^{1"}$, or combined to form a 5–8 membered saturated, partially saturated or unsaturated ring substituted with 0–2 $R^4$ and which contains from 0–2 heteroatoms selected from the group consisting of N, O, and S;

$R^{1'}$ is selected from H, $C_{1-3}$ alkyl, halo, $(CF_2)_rCF_3$, $OR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $NR^2C(O)R^{2b}$, $NR^2C(O)NHR^{2b}$, $NR^2C(O)_2R^{2a}$, $OC(O)NR^{2b}$, $C(O)NR^2R^{2a}$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1"}$ is selected from H, $C(O)R^{2b}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R_{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R_{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R_{4b}$, and 5–6 membered heterocyclic system containing from 1–4 heteroatoms selected from the group consisting of N, O, and S substituted with 0–2 $R^{4b}$;

alternatively, $R^2$ and $R^{2a}$ combine to form a 5 or 6 membered saturated, partially saturated or unsaturated ring substituted with 0–2 $R^{4b}$ which contains from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

A is selected from:
  $C_{3-10}$ carbocyclic residue substituted with 0–2 $R^4$, and
  5–10 membered heterocyclic system containing from 1–4 heteroatoms selected from the group consisting of N, O, and S substituted with 0–2 $R^4$;

B is selected from:
  X—Y, $NR^2R^{2a}$, $C(=NR^2)$ $NR^2R^{2a}$, $NR^2C(=NR^2)NR^2R^{2a}$,
  $C_{3-10}$ carbocyclic residue substituted with 0–2 $R^{4a}$, and
  5–10 membered heterocyclic system containing from 1–4 heteroatoms selected from the group consisting of N, O, and S substituted with 0–2 $R^{4a}$;

X is selected from $C_{1-4}$ alkylene, $-CR^2(CR^2R^{2b})(CH_2)_t-$, $-C(O)-$, $-C(=NR)-$, $-CR^2(NR^{1"}R^2)-$, $-CR^2(OR^2)-$, $-CR^2(SR^2)-$, $-C(O)CR^2R^{2a}-$, $-CR^2R^{2a}C(O)$, $-S(O)_p-$, $-S(O)_pCR^2R^{2a}-$, $-CR^2R^{2a}S(O)_p-$, $S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from:
  $(CH_2)_rNR^2R^{2a}$, provided that X—Y do not form a N—N, O—N, or S—N bond, $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

$R^4$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_tR^{1'}$, $O(CH_2)_2(CH_2)_tR^{1'}$, and $S(CH_2)_2(CH_2)_tR^{1'}$, alternatively, one $R^4$ is a 5–6 membered aromatic heterocycle containing from 1–4 heteroatoms selected from the group consisting of N, O, and S;

$R^{4a}$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R_{4b}$, at each occurrence, is selected from =O, $(CH_2)_rOR^3$, halo, $C_{1-4}$ alkyl, —CN, $NO_2$, $(CH_2)_rNR^3R^{3a}$, $(CH_2)_rC(O)R^3$, $NR^3C(O)R^{3a}$, $C(O)NR^3R^{3a}$, $NR^3C(O)NR^3R^{3a}$, $CH(=NR^3)NR^3R^{3a}$, $NH^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$ at each occurrence, is selected from H, $C_{1-6}$ alkyl and $(CH_2)_n$-phenyl;

n, at each occurrence, is selected from 0, 1, 2, and 3;

m, at each occurrence, is selected from 0, 1, and 2;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0 and 1;

provided that D—E—G—$(CH_2)_s$— and —Z—A—B are not both benzamidines.

[2] In a preferred embodiment, the present invention provides novel compounds of formulae Ia–Ih:

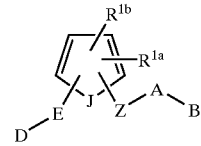
Ia

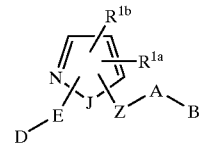
Ib

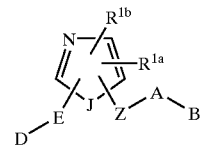
Ic

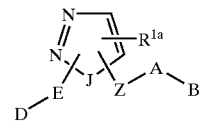
Id

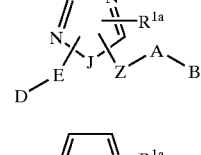
Ie

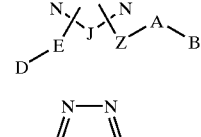
If

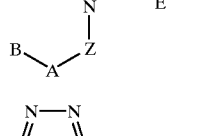
Ig

Ih wherein, groups D—E— and —Z—A—B are attached to adjacent atoms on the ring;

Z is selected from a $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$, $SO_2NH$, and $NHSO_2$, provided that Z does not form a N—N, N—O, $NCH_2N$, or $NCH_2O$ bond with ring M or group A;

A is selected from one of the following carbocyclic and heterocyclic systems which are substituted with 0–2 $R^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazolyl, thiadiazolyl, triazolyl, 1,2,3-oxadiazolyl, 1,2,4- oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

B is selected from: Y, X—Y, $NR^2R^{2a}$, $C(=NR^2)NR^2R^{2a}$, and $NR^2C(=NR^2)NR^2R^{2a}$;

X is selected from $C_{1-4}$ alkylene, —C(O)—, —C(=NR)—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$, O, —$CR^2R^{2a}O$—, and —$OCR^2R^{2a}$—;

Y is $NR^2R^{2a}$, provided that X—Y do not form a N—N or O—N bond;

alternatively, Y is selected from one of the following carbocyclic and heterocyclic systems which are substituted with 0–2 $R^{4a}$;

cylcopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

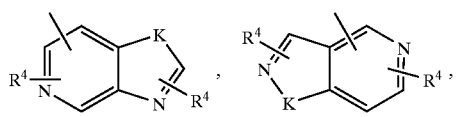

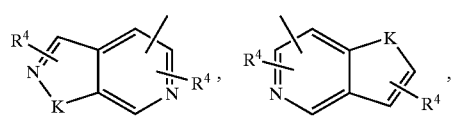

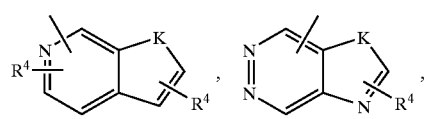

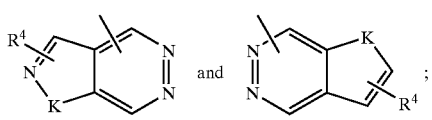

K is selected from O, S, NH, and N.

[3] In a more preferred embodiment, the present invention provides novel compounds of formulae IIa–IIf:

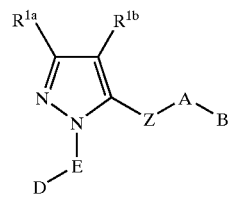

IIa

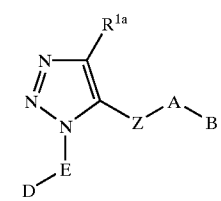

IIb

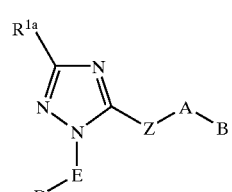

IIc

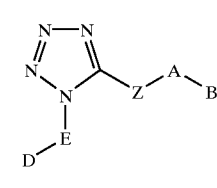

IId

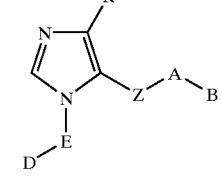

IIe

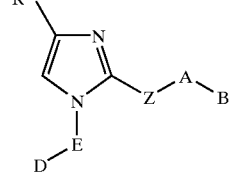

IIf wherein;

Z is selected from a C(O), $CH_2C(O)$, $C(O)CH_2$, NHC(O), C(O)NH, $C(O)N(CH_3)$, $CH_2S(O)_2$, $S(O)_2(CH_2)$, $SO_2NH$, and $NHSO_2$, provided that Z does not form a N—N or $NCH_2N$ bond with ring M or group A.

[4] In an even more preferred embodiment, the present invention provides novel compounds of formulae IIa–IIf, wherein;

E is phenyl substituted with R or 2-pyridyl substituted with R;

D is selected from $NH_2$, $C(O)NH_2$, $C(=NH)NH_2$, $CH_2NH_2$, $CH_2NHCH_3$, $CH(CH_3)NH_2$, and $C(CH_3)_2NH_2$, provided that D is substituted meta or para to ring M on E; and, R is selected from H, $OCH_3$, Cl, and F.

[5] In a further preferred embodiment, the present invention provides novel compounds of formulae IIa–IIf, wherein;

D—E is selected from 3-aminophenyl, 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl)phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, and 6-(2-amino-2-propyl)pyrid-2-yl.

[6] In another even more preferred embodiment, the present invention provides novel compounds of formulae IIa–IIf, wherein;

Z is C(O)CH$_2$ and CONH, provided that Z does not form a N—N bond with group A;

A is selected from phenyl, pyridyl, and pyrimidyl, and is substituted with 0–2 R$^4$; and, B is selected from X—Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$ at each occurrence, is selected from CF$_3$, C$_{1-6}$ alkyl, phenyl, and benzyl;

X is CH$_2$ or C(O); and,

Y is selected from pyrrolidino and morpholino.

[7] In another further preferred embodiment, the present invention provides novel compounds of formulae IIa–IIf, wherein;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-CF$_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-CF$_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[8] In another even more preferred embodiment, the present invention provides novel compounds of formulae IIa–IIf, wherein;

E is phenyl substituted with R or 2-pyridyl substituted with R;

D is selected from NH$_2$, C(O)NH$_2$, C(=NH)NH$_2$, CH$_2$NH$_2$, CH$_2$NHCH$_3$, CH(CH$_3$)NH$_2$, and C(CH$_3$)$_2$NH$_2$, provided that D is substituted meta or para to ring M on E; and, R is selected from H, OCH$_3$, Cl, and F;

Z is C(O)CH$_2$ and CONH, provided that Z does not form a N—N bond with group A;

A is selected from phenyl, pyridyl, and pyrimidyl, and is substituted with 0–2 R$^4$; and, B is selected from X—Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

[9] In another further preferred embodiment, the present invention provides novel compounds of formulae IIa–IIf, wherein;

D—E is selected from 3-aminophenyl, 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl)phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, 6-(2-amino-2-propyl)pyrid-2-yl;

A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl; and, B is selected from the group: 2-CF$_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-CF$_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

[10] In a still further preferred embodiment, the present invention provides a novel compound of formula IIa.

[11] In another still further preferred embodiment, the present invention provides a novel compound of formula IIb.

[12] In another still further preferred embodiment, the present invention provides a novel compound of formula IIc.

[13] In another still further preferred embodiment, the present invention provides a novel compound of formula IId.

[14] In another still further preferred embodiment, the present invention provides a novel compound of formula IIe.

[15] In another still further preferred embodiment, the present invention provides a novel compound of formula IIf.

[16] In another even more preferred embodiment, the present invention provides novel compounds of formulae IIa–IIf, wherein;

D is selected from C(=NR$^8$)NR$^7$R$^9$, C(O)NR$^7$R$^8$, NR$^7$R$^8$, and CH$_2$NR$^7$R$^8$, provided that D is substituted meta or para to ring M on E;

E is phenyl substituted with R or pyridyl substituted with R;

R is selected from H, Cl, F, OR$^3$, CH$_3$, CH$_2$CH$_3$, OCF$_3$, and CF$_3$;

Z is selected from C(O), CH$_2$C(O), C(O)CH$_2$, NHC(O), and C(O)NH, provided that Z does not form a N—N bond with ring M or group A;

R$^{1a}$ and R$^{1b}$ are independently absent or selected from —(CH$_2$)$_r$—R$^{1'}$, NCH$_2$R$^{1''}$, OCH$_2$R$^{1''}$, SCH$_2$R$^{1''}$, N(CH$_2$)$_2$(CH$_2$)$_r$R$^{1'}$, O(CH$_2$)$_2$(CH$_2$)$_r$R$^{1'}$, and S(CH$_2$)$_2$(CH$_2$)$_r$R$^{1'}$, or combined to form a 5–8 membered saturated, partially saturated or unsaturated ring substituted with 0–2 R$^4$ and which contains from 0–2 heteroatoms selected from the group consisting of N, O, and S;

R$^{1'}$, at each occurrence, is selected from H, C$_{1-3}$ alkyl, halo, (CF$_2$)$_r$CF$_3$, OR$^2$, NR$^2$R$^{2a}$, C(O)R$^{2c}$, (CF$_2$)$_r$CO$_2$R$^{2c}$, S(O)$_p$R$^{2b}$, NR$^2$(CH$_2$)$_r$OR$^2$, NR$^2$C(O)R$^{2b}$, NR$^2$C(O)$_2$R$^{2b}$, C(O)NR$^2$R$^{2a}$, SO$_2$NR$^2$R$^{2a}$, and NR$^2$SO$_2$R$^{2b}$;

A is selected from one of the following carbocyclic and heterocyclic systems which are substituted with 0–2 R$^4$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, and imidazolyl;

B is selected from: Y, X—Y, NR$^2$R$^{2a}$, C(=NR$^2$)NR$^2$R$^{2a}$, and NR$^2$C(=NR$^2$)NR$^2$R$^{2a}$;

X is selected from CH$_2$, —CR$^2$(CR$^2$R$^{2b}$)(CH$_2$)$_t$—, —C(O)—, —C(=NR)—, —CH(NR$^2$R$^{2a}$)—, —C(O)NR$^2$—, —NR$^2$C(O)—, —NR$^2$C(O)NR$^2$—, —NR$^2$—, and O;

Y is NR$^2$R$^{2a}$, provided that X—Y do not form a N—N or O—N bond;

alternatively, Y is selected from one of the following carbocyclic and heterocyclic systems which are substituted with 0–2 R$^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

R$^4$, at each occurrence, is selected from =O, OH, Cl, F, C$_{1-4}$ alkyl, (CH$_2$)$_r$NR$^2$R$^{2a}$, (CH$_2$)$_r$C(O)R$^{2b}$, NR$^2$C(O)R$^{2b}$, C(O)NR$^2$R$^{2a}$, CH(=NH)NH$_2$, NHC(=NH)NH$_2$, SO$_2$NR$^2$R$^{2a}$, NR$^2$SO$_2$—C$_{1-4}$ alkyl, NR$^2$SO$_2$R$^5$, S(O)$_p$R$^5$, and (CF$_2$)$_r$CF$_3$;

R$^{4a}$, at each occurrence, is selected from =O, OH, Cl, F, C$_{1-4}$ alkyl, (CH$_2$)$_r$NR$^2$R$^{2a}$, (CH$_2$)$_r$C(O)R$^{2b}$, NR$^2$C(O)R$^{2b}$, C(O)NR$^2$R$^{2a}$, CH(=NH)NH$_2$, NHC(=NH)NH$_2$, SO$_2$NR$^2$R$^{2a}$, NR$^2$SO$_2$—C$_{1-4}$ alkyl, NR$^2$SO$_2$R$^5$, S(O)$_p$R$^5$, (CF$_2$)$_r$CF$_3$, and 1-CF$_3$-tetrazol-2-yl;

R$^5$, at each occurrence, is selected from CF$_3$, C$_{1-6}$ alkyl, phenyl substituted with 0–2 R$^6$, and benzyl substituted with 0–2 R$^6$;

R$^6$, at each occurrence, is selected from H, =O, OH, OR$^2$, Cl, F, CH$_3$, CN, NO$_2$, (CH$_2$)$_r$NR$^2$R$^{2a}$, (CH$_2$)$_r$C(O)R$^{2b}$, NR$^2$C(O)R$^{2b}$, CH(=NH)NH$_2$, NHC(=NH)NH$_2$, and SO$_2$NR$^2$R$^{2a}$;

R$^7$, at each occurrence, is selected from H, OH, C$_{1-6}$ alkyl, C$_{1-6}$ alkylcarbonyl, C$_{1-6}$ alkoxy, C$_{1-4}$ alkoxycarbonyl, benzyl, C$_{6-10}$ aryloxy, C$_{6-10}$ aryloxycarbonyl, C$_{6-10}$ arylmethylcarbonyl, C$_{1-4}$ alkylcarbonyloxy C$_{1-4}$ alkoxycarbonyl, C$_{6-10}$ arylcarbonyloxy C$_{1-4}$ alkoxycarbonyl, C$_{1-6}$ alkylaminocarbonyl, phenylaminocarbonyl, and phenyl C$_{1-4}$ alkoxycarbonyl;

R$^8$, at each occurrence, is selected from H, C$_{1-6}$ alkyl and benzyl; and alternatively, R$^7$ and R$^8$ combine to form a morpholino group; and, R$^9$, at each occurrence, is selected from H, C$_{1-6}$ alkyl and benzyl.

[17] In a another further preferred embodiment, the present invention provides novel compounds of formulae IIa–IIf, wherein;

E is phenyl substituted with R or 2-pyridyl substituted with R;

R is selected from H, Cl, F, OCH$_3$, CH$_3$, OCF$_3$, and CF$_3$;

Z is selected from a C(O)CH$_2$ and C(O)NH, provided that Z does not form a N—N bond with group A;

R$^{1a}$ is selected from H, CH$_3$, CH$_2$CH$_3$, Cl, F, CF$_3$, OCH$_3$, NR$^2$R$^{2a}$, S(O)$_p$R$^{2b}$, CH$_2$S(O)$_p$R$^{2b}$, CH$_2$NR$^2$S(O)$_p$R$^{2b}$, C(O)R$^{2c}$, CH$_2$C(O)R$^{2c}$, C(O)NR$^2$R$^{2a}$, and SO$_2$NR$^2$R$^{2a}$;

R$^{1b}$ is selected from H, CH$_3$, CH$_2$CH$_3$, Cl, F, CF$_3$, OCH$_3$, NR$^2$R$^{2a}$, S(O)$_p$R$^{2b}$, CH$_2$S(O)$_p$R$^{2b}$, CH$_2$NR$^2$S(O)$_p$R$^{2b}$, C(O)R$^{2c}$, CH$_2$C(O)R$^{2c}$, C(O)NR$^2$R$^{2a}$, and SO$_2$NR$^2$R$^{2a}$;

A is selected from one of the following carbocyclic and heterocyclic systems which are substituted with 0–2 R$^4$;

phenyl, pyridyl, pyrimidyl, furanyl, thiophenyl, pyrrolyl, oxazolyl, isoxazolyl, thiazolyl, isothiazolyl, pyrazolyl, and imidazolyl;

B is selected from: Y and X—Y;

X is selected from CH$_2$, —CR$^2$(CR$^2$R$^{2b}$)—, —C(O)—, —C(=NR)—, —CH(NR$^2$R$^{2a}$)—, —C(O)NR$^2$—, —NR$^2$C(O)—, —NR$^2$C(O)NR$^2$—, —NR$^2$—, and O;

Y is NR$^2$R$^{2a}$, provided that X—Y do not form a N—N or O—N bond;

alternatively, Y is selected from one of the following carbocyclic and heterocyclic systems which are substituted with 0–2 R$^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

R$^2$, at each occurrence, is selected from H, CF$_3$, CH$_3$, benzyl, and phenyl;

R$^{2a}$, at each occurrence, is selected from H, CF$_3$, CH$_3$, benzyl, and phenyl;

R$^{2b}$, at each occurrence, is selected from CF$_3$, OCH$_3$, CH$_3$, benzyl, and phenyl;

R$^{2c}$, at each occurrence, is selected from CF$_3$, OH, OCH$_3$, CH$_3$, benzyl, and phenyl;

alternatively, R$^2$ and R$^{2a}$ combine to form a 5 or 6 membered saturated, partially unsaturated, or unsaturated ring which contains from 0–1 additional heteroatoms selected from the group consisting of N, O, and S;

R$^3$, at each occurrence, is selected from H, CH$_3$, CH$_2$CH$_3$, and phenyl;

R$^{3a}$, at each occurrence, is selected from H, CH$_3$, CH$_2$CH$_3$, and phenyl;

R$^4$, at each occurrence, is selected from OH, Cl, F, CH$_3$, CH$_2$CH$_3$, NR$^2$R$^{2a}$, CH$_2$NR$^2$R$^{2a}$, C(O)R$^{2b}$, NR$^2$C(O)R$^{2b}$, C(O)NR$^2$R$^{2a}$, and CF$_3$;

$R^{4a}$, at each occurrence, is selected from OH, Cl, F, $CH_3$, $CH_2CH_3$, $NR^2R^{2a}$, $CH_2NR^2R^{2a}$, $C(O)R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H, OH, $C_{1-3}$ alkyl, $C_{1-3}$ alkylcarbonyl, $C_{1-3}$ alkoxy, $C_{1-4}$ alkoxycarbonyl, benzyl, phenoxy, phenoxycarbonyl, benzylcarbonyl, $C_{1-4}$ alkylcarbonyloxy $C_{1-4}$ alkoxycarbonyl, phenylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $CH_3$, and benzyl; and, alternatively, $R^7$ and $R^8$ combine to form a morpholino group;

$R^9$, at each occurrence, is selected from H, $CH_3$, and benzyl.

[18] In a another still further preferred embodiment, the present invention provides novel compounds of formulae IIa–IIf, wherein;

$R^{1a}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2c}$, $CH_2C(O)R^{2c}$, and $SO_2NR^2R^{2a}$;

$R^{1b}$ is absent or is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $CH_2NR^2S(O)_pR^{2b}$, $C(O)R^{2b}$, $CH_2C(O)R^{2b}$, and $SO_2NR^2R^{2a}$;

A is selected from one of the following carbocyclic and heterocyclic systems which are substituted with 0–2 $R^4$;
phenyl, pyridyl, and pyrimidyl;

B is selected from: Y and X—Y;

X is selected from —C(O)— and O;

Y is $NR^2R^{2a}$, provided that X—Y do not form a O—N bond;

alternatively, Y is selected from one of the following carbocyclic and heterocyclic systems which are substituted with 0–2 $R^{4a}$;
phenyl, piperazinyl, pyridyl, pyrimidyl, morpholinyl, pyrrolidinyl, imidazolyl, and 1,2,3-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $SO_2NR^2R^{2a}$, $S(O)_pR^5$, and $CF_3$; and, $R^5$, at each occurrence, is selected from $CF_3$ and $CH_3$.

[19] Specifically preferred compounds of the present invention are selected from the group:
1-(3-amidinophenyl)-2-[[(2'-aminosulfonyl-[1,1']-biphen-4-yl)-aminocarbonyl]pyrrole;
1-(3-amidinophenyl)-2-[[(2'-tert-butylaminosulfonyl-[1,1']-biphen-4-yl)-aminocarbonyl]pyrrole;
1-(3-amidinophenyl)-2-[[(2'-aminosulfonyl-[1,1']-biphen-4-yl)-aminocarbonyl]-4-bromopyrrole;
1-(3-amidinophenyl)-2-[[5-(2'-aminosulfonylphen-1-yl)pyridin-2-yl]-aminocarbonyl]pyrrole;
1-benzyl-3-[(2'-aminosulfonyl-[1,1']-biphen-4-yl)aminocarbonyl]-4-(3-amidinophenyl)pyrrole;
1-benzyl-3-[(2'-tert-butylaminosulfonyl-[1,1']-biphen-4-yl)aminocarbonyl]-4-(3-amidinophenyl)pyrrole;
1-(3-amidinophenyl)-4-[(2'-aminosulfonyl-[1,1']-biphen-4-yl)aminocarbonyl]-imidazole;
1-(3-amidinophenyl)-4-[(2'-tert-butylaminosulfonyl-[1,1']-biphen-4-yl)aminocarbonyl]-imidazole;
1-(3-amidinophenyl)-2-[(2'-aminosulfonyl-[1,1']-biphen-4-yl)aminocarbonyl]-imidazole;
1-(3-amidinophenyl)-3-methyl-5-[(2'-aminosulfonyl-[1,1']-biphen-4-yl)aminocarbonyl]pyrazole;
1-(3-amidinophenyl)-3-methyl-5-[(2'-aminosulfonyl-[1,1']-biphen-4-yl)carbonylamino]pyrazole;
1-(3-amidinophenyl)-3-methyl-5-(2'-(5"$CF_3$-tetrazolyl)-[1,1']-biphen-4-yl)aminocarbonyl)pyrazole;
1-(3-amidinophenyl)-5-[(2'-aminosulfonyl-[1,1']-biphen-4-yl)aminocarbonyl]-4-chloro-3-methyl-pyrazole;
1-(3-amidinophenyl)-5-((2'-t-butylaminosulfonyl-[1,1']-biphen-4-yl)aminocarbonyl)-3-trifluoromethyl-pyrazole;
1-(3-amidinophenyl)-4-methoxy-5-((2'-aminosulfonyl-[1,1']-biphen-4-yl)aminocarbonyl)-3-trifluoromethyl-pyrazole;
1-(3-amidinophenyl)-3-methyl-5-(4'-(imidazol-1-yl-phenyl)aminocarbonyl)pyrazole;
1-(3-amidinophenyl)-3-methyl-5-[(4'-(2"-sulfonylmethyl)phenoxyphenyl)aminocarbonyl]pyrazole;
1-(3-amidinophenyl)-3-methyl-5-[(2'-aminosulfonyl-[1,1']-biphen-4-yl)methylcarbonylpyrazole;
1-(3-amidinophenyl)-5-[(2'-aminosulfonyl-[1,1']-biphen-4-yl)aminocarbonyl]-1,2,3-triazole;
1-(3-amidinophenyl)-5-((2'-trifluoromethyl-[1,1']-biphen-4-yl)aminocarbonyl)tetrazole;
1-(3-amidinophenyl)-5-((2'-aminosulfonyl-3-chloro-[1,1']-biphen-4-yl)methylthio)tetrazole;
1-(3-amidinophenyl)-5-[(2'-aminosulfonyl-3-chloro-[1,1']-biphen-4-yl)methylsulfoxide]tetrazole;
1-(3-amidinophenyl)-5-[(2'-aminosulfonyl-3-chloro-[1,1']-biphen-4-yl)methylsulfonyl]tetrazole;
1-(3-amidinophenyl)-5-[(2'-aminosulfonyl-[1,1']-biphen-4-yl)aminocarbonyl]tetrazole;
1-(3-amidinophenyl)-3-methyl-2-[[5-(2'-aminosulfonylphenyl-1-yl)pyridin-2-yl]-aminocarbonyl]pyrazole;
1-(3-amidinophenyl)-3-methyl-2-[[5-(2'-aminosulfonylphenyl-1-yl)pyrimidin-2-yl]-aminocarbonyl]pyrazole;
1-(3-amidinophenyl)-3-methyl-5-[(2'-aminosulfonyl-2-chloro-[1,1']-biphen-4-yl)aminocarbonyl]pyrazole;
1-(3-amidinophenyl)-3-methyl-5-[(2'-aminosulfonyl-2-fluoro-[1,1']-biphen-4-yl)aminocarbonyl]pyrazole;
1-(3-amidinophenyl)-3-methyl-5-[(2'-aminosulfonyl-4'-fluoro-[1,1']-biphen-4-yl)aminocarbonyl]pyrazole;
1-(3-amidinophenyl)-3-methyl-5-[(2'-trifluoromethyl-[1,1']-biphen-4-yl)aminocarbonyl]pyrazole;
1-(3-amidinophenyl)-3-methyl-5-[(3-chloro-2'-trifluoromethyl-[1,1']-biphen-4-yl)aminocarbonyl]pyrazole;

1-(3-amidinophenyl)-3-methyl-5-[(3-fluoro-2'-trifluoromethyl-[1,1']-biphen-4-yl)aminocarbonyl]pyrazole;

1-(3-amidinophenyl)-3-methyl-2-[[5-(2'-trifluoromethylphenyl-1-yl)pyridin-2-yl]-aminocarbonyl]pyrazole;

1-(3-amidinophenyl)-3-methyl-5-[(2'-fluoro-[1,1']-biphen-4-yl)aminocarbonyl]pyrazole;

1-(3-amidinophenyl)-3-methyl-5-[(3-chloro-2'-fluoro-[1,1']-biphen-4-yl)aminocarbonyl]pyrazole;

1-(3-amidinophenyl)-3-methyl-5-[(2'-methylsulfonyl-[1,1']-biphen-4-yl)aminocarbonyl]pyrazole;

1-(3-amidinophenyl)-3-methyl-5-((2'-aminosulfonyl-[1,1']-biphen-4-yl)(N'-methyl)aminocarbonyl]pyrazole;

1-(3-amidinophenyl)-3-n-butyl-5-[(2'-aminosulfonyl-[1,1']-biphen-4-yl)aminocarbonyl]pyrazole;

1-(3-amidinophenyl)-3-n-butyl-5-[((2'-aminosulfonylphenyl-1-yl)pyridin-2-yl)-aminocarbonyl]pyrazole;

1-(3-amidinophenyl)-3-n-butyl-5-[((2'-trifluoromethylphenyl-1-yl)pyridin-2-yl)-aminocarbonyl]pyrazole;

1-(3-amidinophenyl)-5-[(2'-methylsulfonyl-[1,1']-biphen-4-yl)aminocarbonyl]-3-trifluoromethyl-pyrazole;

1-(3-amidinophenyl)-5-[(2'-trifluoromethyl-[1,1']-biphen-4-yl)aminocarbonyl]-3-trifluoromethyl-pyrazole;

1-(3-amidinophenyl)-4-methoxy-5-((2'-trifluoromethyl-[1,1']-biphen-4-yl)aminocarbonyl)-3-trifluoromethyl-pyrazole;

1-(3-amidinophenyl)-3-methyl-5-[(4-trifluoromethylphenyl)aminocarbonylpyrazole;

1-(3-amidinophenyl)-4-methyl-5-[(2'-aminosulfonyl-[1,1']-biphen-4-yl)aminocarbonyl]-imidazole;

1-(3-amidinophenyl)-5-[((2'-aminosulfonylphenyl-1-yl)pyridin-2-yl)-aminocarbonyl]-1,2,3-triazole;

1-(3-amidinophenyl)-5-[(2'-trifluoromethyl-[1,1']-biphen-4-yl)aminocarbonyl]-1,2,3-triazole;

1-(3-amidinophenyl)-5-[(2'-aminosulfonyl-[1,1']-biphen-4-yl)aminocarbonyl]-3-trifluoromethyl-1,2,4-triazole;

3-methyl-1-(3-amidinophenyl)-5-(4'-(4"-chlorophenyl)thiazol-2'-yl)aminocarbonyl]pyrazole;

1-(3-amidino)phenyl-3-methyl-5-[(2'-trifluoromethylsulfide-[1,1']-biphen-4-yl)aminocarbonyl]pyrazole;

1-(3-amidino)phenyl-3-methyl-5-[(2'-trifluoromethylsulfoxide-[1,1']-biphen-4-yl)aminocarbonyl]pyrazole;

1-(3-amidino)phenyl-3-methyl-5-[(2'-trifluoromethylsulfonyl-[1,1']-biphen-4-yl)aminocarbonyl]pyrazole;

1-(3-amidino)phenyl-3-methyl-5-[4'-(carboxymethyl)phenylaminocarbonyl]pyrazole;

1-(3-amidino)phenyl-3-methyl-5-[4'-(N,N-dimethylaminocarbonyl)phenylaminocarbonyl]pyrazole;

1-(3-amidino)phenyl-3-methyl-5-[4'-(N,N-dimethylaminosulfonyl)phenylaminocarbonyl]pyrazole;

1-(3-amidino)phenyl-3-methyl-5-[(4'-tert-butylaminosulfonylphenyl)aminocarbonyl]pyrazole;

1-(3-amidino)phenyl-3-methyl-5-[(4'-aminosulfonylphenyl)aminocarbonyl]pyrazole;

1-(3-amidino)phenyl-3-methyl-5-[(4'-trifluoromethylphenyl)-aminocarbonyl]pyrazole;

1-(3-amidino)phenyl-3-methyl-5-[(4'-benzylsulfonylpiperidyl)-aminocarbonyl]pyrazole;

1-(3-amidinophenyl)-5-[(2'-aminosulfonyl-[1,1']-biphen-4-yl)-N-methylaminocarbonyl]-3-methyl-pyrazole;

1-(3-amidinophenyl)-5-[(4'-fluoro-[1,1']-biphen-4-yl)-aminocarbonyl]-3-methyl-pyrazole;

1-(3-amidinophenyl)-5-[[5(2'-aminosulfonylphenyl)pyridin-2-yl]aminocarbonyl]-3-methyl-pyrazole;

1-(3-cyanophenyl)-5-[[5-(2'-aminosulfonylphenyl)pyridin-2-yl]aminocarbonyl]-3-methyl-pyrazole;

1-(3-amidinophenyl)-5-[(2'-trifluoromethyl-[1,1']-biphen-4-yl)aminocarbonyl]-3-methyl-pyrazole;

1-(3-aminocarbonylphenyl)-5-[(2'-aminosulfonyl-[1,1']-biphen-4-yl)aminocarbonyl]-3-methyl-pyrazole;

1-(3-amidinophenyl)-5-[(2'-aminosulfonyl-3-chloro-[1,1']-biphen-4-yl)aminocarbonyl]-3-methyl-pyrazole;

1-(3-amidinophenyl)-5-[(2'-trifluoromethyl)-3-chloro-[1,1']-biphen-4-yl)aminocarbonyl]-3-methylpyrazole;

1-(3-amidinophenyl)-5-[(2'-aminosulfonyl-[1,1']-biphen-4-yl)aminocarbonyl]-3-n-butylpyrazole;

1-(3-amidinophenyl)-5-[(2'-trifluoromethyl-[1,1']-biphen-4-yl)aminocarbonyl]-3-n-butylpyrazole;

1-(3-amidinophenyl)-5-[[5-(2'-aminosulfonylphenyl)pyridin-2-yl]aminocarbonyl]-3-n-butylpyrazole;

1-(3-amidinophenyl)-5-[(2'-trifluoromethyl-[1,1']-biphen-4-yl)aminocarbonyl]-3-trifluoromethyl-4-methoxypyrazole;

1-(3-amidinophenyl)-5-[(2'-trifluoromethyl-[1,1']-biphen-4-yl)aminocarbonyl]-3-trifluoromethyl-pyrazole;

1-(3-amidinophenyl)-5-[(2'-sulfonylmethyl-[1,1']-biphen-4-yl)aminocarbonyl]-3-trifluoromethyl-pyrazole;

1-(3-amidinophenyl)-5-[(2'-aminosulfonyl-3-bromo-[1,1']-biphen-4-yl)aminocarbonyl]-3-methyl-pyrazole;

1-(3-aminocarbonylphenyl)-5-[-(2'-aminosulfonyl-3-bromo-[1,1']-biphen-4-yl)aminocarbonyl]-3-methyl-pyrazole;

1-(3-amidinophenyl)-3-methyl-5-[(2'-aminosulfonyl)-[1,1']-biphen-4-yl)methylcarbonyl]pyrazole;

1-(3-aminocarbonylphenyl)-5-[5-[(2'-aminosulfonylphen-1-yl)pyridin-2-yl]aminocarbonyl]-3-methyl-pyrazole;

1-(3-amidinophenyl)-5-[[5-(2'-t-butylaminosulfonylphenyl)pyrimidin-2-yl]aminocarbonyl]-3-trifluoromethyl-pyrazole;

1-(3-amidinophenyl)-5-[[5-(2'-aminosulfonylphenyl)pyrimidin-2-yl]aminocarbonyl]-3-trifluoromethyl-pyrazole;

1-(3-aminocarbonylphenyl)-5-[[5-(2'-aminosulfonylphenyl)pyrimidin-2-yl]aminocarbonyl]-3-trifluoromethyl-pyrazole;

1-(3-cyanophenyl)-5-[((4'-(imidazol-1-yl)phenyl)aminocarbonyl]-3-trifluoromethyl-pyrazole;

1-(3-amidinophenyl)-5-[(4'-(morpholin-1-yl)phenyl)-aminocarbonyl]-3-trifluoromethyl-pyrazole;

1-(3-aminocarbonylphenyl)-5-[(4'-(morpholin-1-yl)phenyl)-aminocarbonyl]-3-trifluoromethyl-pyrazole;

1-(3-amidinophenyl)-5-[[5-(2'-aminosulfonylphenyl)pyridin-2-yl]aminocarbonyl]-3-trifluoromethyl-pyrazole;

1-(3-aminocarbonylphenyl)-5-[[5-(2'-aminosulfonylphenyl)pyridin-2-yl]aminocarbonyl]-3-trifluoromethyl-pyrazole;

1-(3-amidinophenyl)-5-[(4'-(3-methyltetrazol-1-yl)phenyl)aminocarbonyl]-3-trifluoromethyl-pyrazole;

1-(3-amidinophenyl)-5-(2'-napthylaminosulfonyl)-3-methyl-pyrazole;

1-(3-amidinophenyl)-5-[(4-bromophenyl)aminosulfonyl]-3-methyl-pyrazole;

1-(3-aminomethylphenyl)-5-[(2'-aminosulfonyl-[1,1']-biphen-4-yl)aminocarbonyl]-3-methyl-pyrazole;

1-(3-aminbmethylphenyl)-5-[(2'-aminosulfonyl-[1,1']-biphen-4-yl)aminocarbonyl]-3-trifluoromethyl-pyrazole;

1-(3-amidinophenyl)-3-methyl-5-[((2'-trifluoromethylphenyl)pyrid-2-yl)aminocarbonyl]pyrazole;

1-(3-amidinophenyl)-3-methyl-5-[((2'-aminosulfonyl-1-yl)pyrimid-5-yl)aminocarbonyl]pyrazole;

1-(3-amidinophenyl)-3-methyl-5-[(2'-fluoro-[1,1']-biphen-4-yl)aminocarbonyl]pyrazole;

1-(3-amidinophenyl)-3-methyl-5-[3-chloro-(2'-fluoro-[1,1']-biphen-4-yl)aminocarbonyl]pyrazole;

1-(3-amidinophenyl)-3-methyl-5-[(3-fluoro-2'-fluoro-[1,1']-biphen-4-yl)aminocarbonyl]pyrazole;

1-(3-amidinophenyl)-3-methyl-5-[(3-fluoro-2'-aminosulfonyl-[1,1']-biphen-4-yl)aminocarbonyl]pyrazole;

1-(3-amidinophenyl)-3-methyl-5-[5-(2'-fluorophen-1-yl)pyrid-2-yl]aminocarbonyl]pyrazole;

1-(3-amidinophenyl)-3-methyl-5-[[5-(2'-tertbutylaminosulfonylphenyl)pyrimid-2-yl]aminocarbonyl]pyrazole;

1-(3-amidinophenyl)-3-methyl-5-[[5-(2'-aminosulfonylphenyl)-[1,6]-dihydropyrimid-2-yl]aminocarbonyl]pyrazole;

1-(3-amidinophenyl)-3-methyl-5-[(4-(pyrid-3'-yl)phen-1-yl)aminocarbonyl]pyrazole;

1-(3-amidinophenyl)-3-methyl-5-[[2-(2'-pyridyl)ethyl]aminocarbonyl]pyrazole;

1-(3-amidinophenyl)-3-methyl-5-[(3-phenylpropyl)aminocarbonyl]pyrazole;

1-(3-amidinophenyl)-3-methyl-5-[4-(pyrid-2'-yl)phen-1-ylaminocarbonyl]pyrazole;

1-(3-amidinophenyl)-3-methyl-5-[(4-(isopropyloxy)phenyl)aminocarbonyl]pyrazole;

1-(3-amidinophenyl)-3-methyl-5-[[5-(2'-trifluoromethylphenyl)-pyrimidin-2-yl)aminocarbonyl]pyrazole;

1-(3-amidinophenyl)-3-methyl-5-[(4-(piperidinosulfonyl)phenyl)aminocarbonyl]pyrazole;

1-(3-amidinophenyl)-3-methyl-5-[(4-(piperidinocarbonyl)phenyl)aminocarbonyl]pyrazole;

1-(3-amidino-4-fluorophenyl)-3-methyl-5-[(2'-aminosulfonyl-[1,1']-biphen-4-yl)aminocarbonyl]pyrazole;

1-(3-aminocarbonyl-4-fluorophenyl)-3-methyl-5-[(2'-aminosulfonyl-[1,1']-biphen-4-yl)aminocarbonyl]pyrazole;

1-methyl-3-(3-amidino)phenyl-4-[(2'-aminosulfonyl-[1,1']-biphen-4-yl)aminocarbonyl]pyrazole;

1-(3-amidinophenyl)-3-methyl-5-[[4-(pyrazol-4'-yl)phen-1-yl]aminocarbonyl]pyrazole;

1-(3-amidinophenyl)-3-methyl-5-([5-(2'-methylsulfonylphenyl)pyrid-2-yl]aminocarbonyl)pyrazole;

1-(3-amidinophenyl)-3-methyl-5-([5-(2'-methylsulfonylphenyl)pyrimid-2-yl]aminocarbonyl)pyrazole;

1-(3-cyanophenyl)-3-methyl-5-([5-(2'-methylsulfonylphenyl)pyrimid-2-yl]aminocarbonyl)pyrazole,;

1-(3-aminocarbonylphenyl)-3-methyl-5-([5-(2'-methylsulfonylphenyl)pyrimid-2-yl]aminocarbonyl)pyrazole;

1-(3-(N-aminoamidino)phenyl)-3-methyl-5-[(2'-tert-butylaminosulfonyl-[1,1']-biphen-4-yl)aminocarbonyl]pyrazole;

1-(3-(N-aminoamidino)phenyl)-3-methyl-5-[(2'-aminosulfonyl-[1,1']-biphen-4-yl)aminocarbonyl]pyrazole;

1-(3-(N-methyl-N-hydroxyamidino)phenyl)-3-methyl-5-[(4'-t-butylaminosulfonyl-[1,1']-biphen-4-yl)aminocarbonyl]pyrazole;

1-(3-(N-methylamidino)phenyl)-3-methyl-5-[(2'-tert-butylaminosulfonyl-[1,1']-biphen-4-yl)aminocarbonyl]pyrazole;

1-(3-(N-methylamidino)phenyl)-3-methyl-5-[(2'-aminosulfonyl-[1,1']-biphen-4-yl)aminocarbonyl]pyrazole;

1-(3-amidinophenyl)-5-[(2'-aminosulfonylphenyl)pyridin-2-yl]aminocarbonyl]tetrazole;

1-(3-aminocarbonylphenyl)-5-{[5-(2'-aminosulfonylphenyl)pyridin-2-yl]aminocarbonyl}tetrazole;

1-(3-amidinophenyl)-5-{[5-(2'-trifluoromethylphen-1-yl)pyridin-2-yl]aminocarbonyl}tetrazole;

1-(3-amidinophenyl)-5-[(4'-bromophen-1-yl)aminocarbonyl]tetrazole;

1-(3-aminocarbonylphenyl)-5-{[5-(2'-trifluoromethylphen-1-yl)pyridin-2-yl]aminocarbonyl}tetrazole;

5-(3-amidinophenyl)-1-[(2'-trifluoromethyl-[1,1']-biphen-4-yl)methyl]tetrazole;

1-[(3-amidinophenyl)methyl]-3-methyl-5-[(2'-aminosulfonyl-[1,1']-biphen-4-yl)aminocarbonyl]pyrazole;

1-[(4-amidinophenyl)methyl]-3-methyl-5-[(2'-aminosulfonyl-[1,1']-biphen-4-yl)aminocarbonyl]pyrazole 1-(3-amidinophenyl)-2-[(2'-aminosulfonyl-[1,1']-biphen-4-yl)aminocarbonyl]imidazole;

1-(3-amidinophenyl)-4-methyl-2-[(2'-aminosulfonyl-[1,1']-biphen-4-yl)aminocarbonyl]imidazole;

1-(3-amidinophenyl)-5-chloro-4-methyl-2-[(2'-aminosulfonyl-[1,1']-biphen-4-yl)aminocarbonyl]imidazole;

5-(3-amidinophenyl)-2-methyl-4-[(2'-aminosulfonyl-[1,1']-biphen-4-yl)aminocarbonyl]imidazole;

1-(3-amidinophenyl)-3-methyl-5-[(4'-(benzimidazol-1-yl)phen-1-yl)aminocarbonyl]pyrazole;

1-(3-aminocarbonylphenyl)-3-methyl-5-[(4'-(benzimidazol-1-yl)phen-1-yl)aminocarbonyl]pyrazole;

1-(3-amidinophenyl)-3-methyl-5-[(4'-(2-methylimidazol-1-yl)phenyl)aminocarbonyl]pyrazole;

1-(3-aminocarbonylphenyl)-3-methyl-5-[(4'-(2-methylimidazol-1-yl)phenyl)aminocarbonyl)pyrazole;

1-(3-amidinophenyl)-3-methyl-5-[[4'-(1,2,4-triazol-2-yl)-phenyl]aminocarbonyl]pyrazole;

1-(3-amidinophenyl)-3-methyl-5-((4'-cyclohexylphenyl)aminocarbonyl)pyrazole;

1-(3-amidinophenyl)-3-methyl-5-[[1,1']-biphen-4-ylaminocarbonyl]pyrazole;

1-(3-amidinophenyl)-3-methyl-5-((4'-morpholinophenyl)aminocarbonyl)pyrazole;

1-(3-amidinophenyl)-3-methyl-5-[(4'-((2-trifluoromethyl)tetrazol-1-yl)phenyl)aminocarbonyl]pyrazole;

1-(3-aminomethylphenyl)-3-methyl-5-[(4'-((2-trifluoromethyl)tetrazol-1-yl)phenyl)aminocarbonyl]pyrazole;

1-(3-amidinophenyl)-3-methyl-5-[((4'-(N,N-dimethylamino)carbonylamino)phen-1'-yl)aminocarbonyl]pyrazole;

1-(3-amidinophenyl)-3-methyl-5-[(4'-(N,N-diethylamino)phenyl)aminocarbonyl]pyrazole;

1-(3-aminocarbonylphenyl)-3-methyl-5-[((4'-N,N-diethylamino)phenyl)aminocarbonyl]pyrazole;

1-(3-amidinophenyl)-3-methyl-5-[(4'-(1-tetrazolyl)phenyl)aminocarbonyl)pyrazole;

1-(3-aminocarbonylphenyl)-3-methyl-5-((4'-(1-tetrazolyl)phenyl)aminocarbonyl)pyrazole;

1-(3-amidinophenyl)-3-methyl-5-[(4'-(N-acetylpiperizin-1-yl)phenyl)aminocarbonyl]pyrazole;

1-(3-amidinophenyl)-3-methyl-5-[(4'-(N-tert-butyloxycarbonylpiperizin-1-yl)phenyl)aminocarbonyl]pyrazole,;

1-(3-amidinophenyl)-3-methyl-5-((4'-piperizin-1-yl-phenyl) aminocarbonyl)pyrazole;
1-(3-amidinophenyl)-3-trifluoromethyl-5-((4'-cyclohexylphenyl)aminocarbonyl)pyrazole;
1-(3-amidinophenyl)-3-methyl-5-[(4'-(N-morpholino)-3'-chlorophenyl)aminocarbonyl]pyrazole;
1-(3-amidinophenyl)-5-[(2'-aminosulfonyl-[1,1']-biphen-4-yl)aminocarbonyl]-3-(methylthio)pyrazole;
1-(3-amidinophenyl)-5-[(2'-aminosulfonyl-[1,1']-biphen-4-yl)aminocarbonyl]-3-(methylsulfinyl)pyrazole;
1-(3-amidinophenyl)-5-[(2'-aminosulfonyl-[1,1']-biphen-4-yl)aminocarbonyl]-3-(methylsulfonyl)pyrazole;
1-(3-aminocarbonylphenyl)-5-[(2'-trifluoromethyl-[1,1']-biphen-4-yl)methyl]tetrazole;
1-(3-aminocarbonylphenyl)-5-{[(2'-aminosulfonyl-[1,1']-biphen-4-yl)methyl}tetrazole;
1-(3-amidinophenyl)-5-[(4'-cyclopentyloxyphenyl) aminocarbonyl]-3-methyl-pyrazole;
1-(3-amidinophenyl)-5-[(3-((pyrid-2-yl)methylamino) phenyl)aminocarbonyl]-3-methyl-pyrazole;
1-(3-amidinophenyl)-3-methyl-5-[(4'-(N-imidazolyl) phenyl)aminocarbonyl]pyrazole;
1-(3-amidinophenyl)-3-trifluoromethyl-5-[(4'-(N-morpholino)-3-chlorophenyl)aminocarbonyl]pyrazole;
1-(3-amidinophenyl)-3-methyl-5-[(4'-(N-pyrrolidinocarbonyl)-3'-chlorophenyl)aminocarbonyl]pyrazole;
1-(3-amidinophenyl)-3-methyl-5-[(4'-(N-morpholinocarbonyl)-3-chlorophenyl)aminocarbonyl]pyrazole;
1-(3-cyanophenyl)-5-[(4'-(N-imidazolyl)phenyl) aminocarbonyl]-3-trifluoromethyl-pyrazole;
1-(3-amidinophenyl)-5-[(4'-(N-imidazolyl)phenyl) aminocarbonyl]-3-trifluoromethyl-pyrazole;
1-(3-amidinophenyl)-5-[(4'-(N-methyltetrazolon-1-yl) phenyl)aminocarbonyl]-3-trifluoromethyl-pyrazole;
1-(3'-aminocarbonylphenyl)-5-[(2'-aminosulfonylphenyl-[1,1']-biphen-4-yl)methylcarbonyl]-3-methyl-pyrazole;
1-(3-amidinophenyl)-5-[4'-(pyrrolidinomethyl)phenyl) aminocarbonyl]-3-methyl-pyrazole;
1-(3-aminophenyl)-3-methyl-5-[(2'-aminosulfonyl-[1,1']-biphen-4-yl)aminocarbonyl]pyrazole;
1-(2'-aminophenyl)-3-methyl-5-[(2'-aminosulfonyl-[1,1']-biphen-4-yl)aminocarbonyl]pyrazole;
1-(3-amino-4'-chlorophenyl)-3-methyl-5-[(2'-aminosulfonyl-[1,1']-biphen-4-yl)aminocarbonyl] pyrazole;
1-(3-amino-4'-fluorophenyl)-3-methyl-5-[(2'-aminosulfonyl-[1,1']-biphen-4-yl)aminocarbonyl] pyrazole;
1-(3-amino-4'-methoxyphenyl)-3-methyl-5-[(2'-aminosulfonyl-[1,1']-biphen-4-yl)aminocarbonyl] pyrazole;
1-(3-amino-4'-chlorophenyl)-5-[(2'-aminosulfonyl-[1,1']-biphen-4-yl)aminocarbonyl]tetrazole;
1-(3-amino-4'-chlorophenyl)-5-{[(2'-aminosulfonylphenyl) pyridin-2-yl]aminocarbonyl}tetrazole;
1-(3-amino-4'-methoxyphenyl)-5-[(2'-aminosulfonyl-[1,1']-biphen-4-yl)aminocarbonyl]tetrazole;
1-(3-aminomethylphenyl)-5-[(2'-aminosulfonylphenyl) pyrid-2-yl)aminocarbonyl]-3-methyl-pyrazole;
1-(3-aminomethyl-4'-methylphenyl)-5-[(2'-aminosulfonyl-[1,1']-biphen-4-yl)aminocarbonyl]-3-methyl-pyrazole;
1-(3-aminomethyl-4'-fluorophenyl)-5-[(2'-aminosulfonyl-[1,1']-biphen-4-yl)aminocarbonyl]-3-methyl-pyrazole;
1-(3-aminomethylphenyl)-5-[(4'-(N-pyrrolidinocarbonyl) phenyl)aminocarbonyl]-3-trifluoromethyl-pyrazole;
1-(3-Ethylcarboxyamidinophenyl)-5-[(2'-aminosulfonyl-[1,1']-biphen-4-yl)-aminocarbonyl]-3-methyl-pyrazole;
1-(3-(1'-imino-1'-(N-morpholino))methyl)phenyl)-5-[(2'-tert-butylaminosulfonyl-[1,1']-biphen-4-yl) aminocarbonyl]-3-methyl-pyrazole;
1-(3-(1'-imino-1'-(N-morpholino))methyl)phenyl)-5-[(2'-aminosulfonyl-[1,1']-biphen-4-yl)aminocarbonyl]-3-methyl-pyrazole;
1-[3-[N-((5-methyl-2-oxo-1,3-dioxol-4-yl) methoxycarbonyl)amidino]phenyl]-5-((2'-aminosulfonyl-[1,1']-biphen-4-yl)aminocarbonyl)-3-methyl-pyrazole;
1-(pyrid-2-yl)-3-methyl-5-[(3-fluoro-2'-aminosulfonyl-[1,1']-biphen-4-yl)aminocarbonyl]pyrazole;
1-(6-bromopyridin-2-yl)-3-methyl-5-[(3-fluoro-2'-aminosulfonyl-[1,1']-biphen-4-yl)aminocarbonyl] pyrazole;
1-(3-amino-4-chlorophenyl)-5-[(2'-aminosulfonyl-3-chloro-[1,1']-biphen-4-yl)aminocarbonyl]tetrazole;
1-(3-amino-4-chlorophenyl)-5-[(4'-(1-pyrrolidinocarbonyl) phenyl)aminocarbonyl]tetrazole;
1-(3-aminomethylphenyl)-5-[(2'-aminosulfonyl-[1,1']-biphen-4-yl)aminocarbonyl]tetrazole;
1-(3-aminomethylphenyl)-5-[(2'-aminosulfonyl-3-fluoro-[1,1']-biphen-4-yl)aminocarbonyl]tetrazole;
1-(3-aminomethylphenyl)-5-[(2'-aminosulfonyl-[1,1']-biphen-4-yl)aminocarbonyl]imidazole;
1-(3-aminomethylphenyl)-5-[(2'-methylsulfonylmethyl-[1,1']-biphen-4-yl)aminocarbonyl]imidazole;
1-(3-amidinophenyl)-5-[(2'-aminosulfonyl-[1,1']-biphen-4-yl)aminocarbonyl]imidazole;
1-[3-(methylaminomethyl)phenyl]-5-[(2'-aminosulfonyl-3-fluoro-[1,1']-biphen-4-yl)aminocarbonyl]-3-methyl-pyrazole;
1-[3-(methylaminomethyl)phenyl]-5-[(2'-methylsulfonyl-3-fluoro-[1,1']-biphen-4-yl)aminocarbonyl]-3-methyl-pyrazole;
1-(3-aminomethylphenyl)-5-[(2'-methylsulfonyl-[1,1']-biphen-4-yl)aminocarbonyl]-4-methoxy-3-trifluoromethyl-pyrazole;
1-(3-aminomethylphenyl)-5-[(2-fluoro-4-(N-pyrrolidinocarbonyl)phenyl)aminocarbonyl]-3-trifluoromethyl-pyrazole;
1-(3-aminomethylphenyl)-5-[(3-fluoro-4-(N-pyrrolidinocarbonyl)phenyl)aminocarbonyl]-3-trifluoromethyl-pyrazole;
1-(3-aminomethylphenyl)-5-[(2'-sulfonylmethyl-[1,1']-biphen-4-yl)aminocarbonyl]-3-trifluoromethyl-pyrazole;
1-(3-aminomethylphenyl)-5-[(2'-aminosulfonyl-3-fluoro-[1,1']biphen-4-yl)aminocarbonyl]-3-trifluoromethyl-pyrazole;
1-(3-aminomethylphenyl)-5-[(5-(2'-aminosulfonylphenyl)-[1,6-dihydro]pyrimid-2-yl)aminocarbonyl]-3-trifluoromethyl-pyrazole;
1-(3-aminomethylphenyl)-5-[(5-(2'-aminosulfonylphenyl) pyrimid-2-yl)aminocarbonyl]-3-trifluoromethyl-pyrazole;
1-[3-(2'-ethylaminophenyl)-5-[(2'-aminosulfonyl-[1,1']-biphen-4-yl)aminocarbonyl]-3-trifluoromethyl-pyrazole;
1-[3-(1-(N-morpholino)imino)phenyl]-5-[(2'-aminosulfonyl-3-fluoro-[1,1']-biphen-4-yl) aminocarbonyl]-3-trifluoromethyl-pyrazole;
1-(3-aminomethylphenyl)-5-[2-(2'-aminosulfonyl-[1,1']-biphen-4-yl)-1-hydroxyethyl]-3-trifluoromethyl-pyrazole;
1-(3-aminomethylphenyl)-5-[(3-fluoro-2'-methylsulfonyl-[1,1']-biphen-4-yl)aminocarbonyl]-3-trifluoromethyl-pyrazole;

1-(3-aminomethylphenyl)-5-[(5-(2'-methylsulfonylphenyl)pyrimid-2-yl)aminocarbonyl]-3-trifluoromethyl-pyrazole;

1-[3-amidinophenyl]-5-[(3-fluoro-2'-methylsulfonyl-[1,1']-biphen-4-yl)aminocarbonyl]-3-trifluoromethyl-pyrazole;

1-[3-amidinophenyl]-5-[(3-fluoro-2'-aminosulfonyl-[1,1']-biphen-4-yl)aminocarbonyl]-3-trifluoromethyl-pyrazole;

1-(3-aminomethyl)phenyl-5-[(2'-aminosulfonyl-[1,1']-biphen-4-yl)carbonylmethyl]-3-trifluoromethyl-pyrazole;

1-(3-aminomethyl)phenyl-5-[(2'-aminosulfonyl-[1,1']-biphen-4-yl)aminocarbonyl]-3-(methylsulfonylmethyl)pyrazole;

1-(3-amidino)phenyl-5-[(2'-aminosulfonyl-[1,1']-biphen-4-yl)aminocarbonyl]-3-(methylaminosulfonylmethyl)pyrazole;

1-(3-aminomethylphenyl)-5-[(2'-aminosulfonyl-3-fluoro-[1,1']-biphen-4-yl)aminocarbonyl]-3-(methylaminosulfonylmethyl)pyrazole;

1-(3-(N-carboxymethyl)amidinophenyl)-5-[(5-(2'-aminosulfonylphenyl)pyrimid-2-yl)aminocarbonyl]-3-methyl-pyrazole;

1-(3-aminomethylphenyl)-5-[(2'-methylsulfonyl-[1,1']-biphen-4-yl)aminocarbonyl]-3-methyl-pyrazole;

1-(3-aminomethylphenyl)-5-[(2'-aminosulfonyl-3-methyl-[1,1']-biphen-4-yl)aminocarbonyl]-3-trifluoromethyl-pyrazole;

1-(3-aminomethylphenyl)-5-[(3-fluoro-2'-methylsulfonyl-[1,1']-biphen-4-yl)aminocarbonyl]-1,2,3-triazole;

1-(3-aminomethyl-4-methyl)phenyl-5-[(2'-aminosulfonyl-[1,1']-biphen-4-yl)aminocarbonyl]-3-methyl-pyrazole;

1-(3-aminomethyl-4-fluoro)phenyl-5-[(2'-aminosulfonyl-[1,1']-biphen-4-yl)aminocarbonyl]-3-methyl-pyrazole;

1-(3-aminomethyl-4-chloro)phenyl-5-[(2'-aminosulfonyl-[1,1']-biphen-4-yl)aminocarbonyl]-3-methyl-pyrazole;

1-(3-aminomethyl-4-fluoro)phenyl-5-[(2'-aminosulfonyl-3-fluoro-[1,1']-biphen-4-yl)aminocarbonyl]-3-trifluoromethyl-pyrazole;

1-(3-aminomethyl)phenyl-5-[(2'-aminosulfonyl-3-fluoro-[1,1']-biphen-4-yl)aminocarbonyl]-3-methyl-pyrazole;

1-(3-aminomethyl)phenyl-5-[(3-fluoro-2'-methylsulfonyl-[1,1']-biphen-4-yl)aminbcarbonyl]-3-trifluoromethyl-pyrazole;

1-(3-amidinophenyl)-3-methyl-5-[(3-fluoro-4-(N-morpholino)phenyl)aminocarbonyl]pyrazole;

1-(3-aminomethylphenyl)-3-methyl-5-[(3-fluoro-4-(N-morpholino)phenyl)aminocarbonyl]pyrazole;

1-(3-aminomethylphenyl)-3-trifluoromethyl-5-((3-fluoro-4-(2-methylimidazol-1-yl)phenyl)aminocarbonyl)pyrazole;

1-(3-cyanophenyl)-3-trifluoromethyl-5-(([1,1']-biphen-4-yl)oxymethyl)pyrazole;

1-(3-amidinophenyl)-3-trifluoromethyl-5-[([1,1']-biphen-4-yl)oxymethyl]pyrazole;

1-(3-carboxamidophenyl)-3-trifluoromethyl-5-(([1,1']-biphen-4-yl)oxymethyl)pyrazole;

1-(3-amidinophenyl)-3-trifluoromethyl-5-((2-fluoro-4-(N-morpholino)phenyl)aminocarbonyl)pyrazole;

1-(3-carboxamidophenyl)-3-trifluoromethyl-5-((2-fluoro-4-(N-morpholino)phenyl)aminocarbonyl)pyrazole;

1-(3-aminomethylphenyl)-3-trifluoromethyl-5-((3-trifluoromethyl-4-(N-morpholino)phenyl)aminocarbonyl)pyrazole;

1-(3-aminomethylphenyl)-3-ethyl-5-[(3-fluoro-2'-tert-butylaminosulfonyl-[1,1']-biphen-4-yl)aminocarbonyl]pyrazole;

1-(3-aminomethylphenyl)-3-ethyl-5-((3-fluoro-2'-methylsulfonyl-[1,1']-biphen-4-yl))aminocarbonyl)pyrazole;

1-(3-aminomethylphenyl)-3-ethyl-5-[(2-fluoro-4-(2-methylsulfonylimidazol-1-yl)phenyl]aminocarbonyl)pyrazole;

1-[(6-(aminomethyl)pyrid-2-yl)]-3-methyl-5-[(2'-aminosulfonyl-[1,1']-biphen-4-yl)aminocarbonyl]pyrazole;

1-[(6-(N-hydroxyamidino)pyrid-2-yl)]-3-methyl-5-[(2'-tert-butylaminosulfonyl-[1,1']-biphen-4-yl)aminocarbonyl]pyrazole;

1-[(6-amidinopyrid-2-yl)]-3-methyl-5-[(2'-aminosulfonyl-[1,1']-biphen-4-yl)aminocarbonyl]pyrazole;

1-[6-amidinopyrid-2-yl]-3-methyl-5-[3-fluoro-(2'-methylsulfonyl-[1,1']-biphen-4-yl)aminocarbonyl]pyrazole;

1-(3-aminomethylphenyl)-3-methyl-5-((2-methoxy-4-(N-morpholino)phenyl)aminocarbonyl)pyrazole;

1-(3-aminomethylphenyl)-3-methyl-5-[4'-(3"-methyl-5"-oxo-3"'-pyrazolin-2"-yl)-phenyl)aminocarbonyl]pyrazole;

1-[3-(aminomethyl)phenyl]-5-[(2'-methylsulfonyl-[1,1']-biphen-4-yl)aminocarbonyl]-3-(methylthio)pyrazole;

1-(3-aminomethyl-4-fluorophenyl)-3-trifluoromethyl-5-[(3-fluoro-2'-methylsulfonyl-[1,1']-biphen-4-yl)aminocarbonyl]pyrazole;

ethyl 1-[3-(aminomethyl)-phenyl]-5-[3-fluoro-2'-methylsulfonyl-[1,1']-biphen-4-yl)aminocarbonyl]pyrazole-3-carboxylate;

1-[3-(aminomethyl)phenyl]-5-[(3-fluoro-2'-methylsulfonyl-[1,1']-biphen-4-yl)aminocarbonyl]pyrazole-3-carboxylic acid;

1-[3-(aminomethyl)phenyl]-3-[aminocarbonyl]-5-[3-fluoro-(2'-methylsulfonyl-[1,1']-biphen-4-yl)aminocarbonyl]pyrazole;

ethyl 1-[3-(aminomethyl)-phenyl]-3-trifluoromethyl-5-[(3-fluoro-2'-methylsulfonyl-[1,1']-biphen-4-yl)aminocarbonyl]pyrazole-4-carboxylate;

1-[3-(aminomethyl)phenyl]-5-[(3-fluoro-2'-methylsulfonyl-[1,1']-biphen-4-yl)aminocarbonyl]-3-(methylthio)pyrazole;

1-[3-(aminomethyl)phenyl]-5-[(3-fluoro-2'-methylsulfonyl-[1,1']-biphen-4-yl)aminocarbonyl]-3-(methylsulfonyl)pyrazole;

1-[3-(aminomethyl)phenyl]-5-[(4-(5-(methoxyaminocarbonyl)imidazol-1-yl)phen-1-yl)aminocarbonyl]-3-trifluoromethyl-pyrazole; and, 1-(3-aminomethylphenyl)-5-[(4-(5-methyl-1,2,3-triazol-1-yl)phen-1-yl)aminocarbonyl]-3-trifluoromethyl-pyrazole;

and pharmaceutically acceptable salts thereof.

In a second embodiment, the present invention provides novel pharmaceutical compositions, comprising: a pharmaceutically acceptable carrier and a therapeutically effective amount of a compound of formula (I) or a pharmaceutically acceptable salt form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue", is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is C($=$NR$^7$)NH$_2$ or its tautomer C($=$NH)NHR$^7$ and R$^7$ is selected from OH, C$_{1-4}$ alkoxy, C$_{6-10}$ aryloxy, C$_{1-4}$ alkoxycarbonyl, C$_{6-10}$ aryloxycarbonyl, C$_{6-10}$ arylmethylcarbonyl, C$_{1-4}$ alkylcarbonyloxy C$_{1-4}$ alkoxycarbonyl, and C$_{6-10}$ arylcarbonyloxy C$_{1-4}$ alkoxycarbonyl. More preferred prodrugs are where R$^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The compounds of Formula I in which ring M is pyrrole can be prepared by the procedures described in Schemes 1–9. In Scheme 1 is shown how to prepare pyrroles in which the group Q—E is attached to the pyrrole nitrogen, wherein Q is a functionality that can be converted into D of Formula I, R$^e$ is functionality that can be converted into Z—A—B of Formula I and R$^f$ is or can be converted into R$^{1a}$ of Formula I. Oxidation of a furan with bromine in acetic acid can afford a 2,5-diacetoxydihydrofuran which can react with amine Q—E—NH$_2$ to afford a pyrrole. Vilsmeier-Haack formylation with phosphorous oxychloride and DMF preferentially can acylate the pyrrole ring at C-2. Oxidation of the resulting aldehyde can give a carboxylic acid. The carboxylic acid can then be converted into amine derivatives using either the Hofmann degradation of the derived primary amide (Huisgen et. al. *Chem. Ber.* 1960, 93, 65) or the Curtius rearrangement of the derived acyl azide (*J. Prakt. Chem.* 1909, 42, 477). Derivatives which contain a sulfur atom attached to the pyrrole ring can be obtained by direct sulfonation with pyridine sulfur trioxide complex to give the sulfonic acids or treatment with copper (II) thiocyanate (*J. Het. Chem.* 1988, 25, 431) followed by the reduction of the intermediate thiocyanate with sodium borohydride to give a mercaptan.

Scheme 1

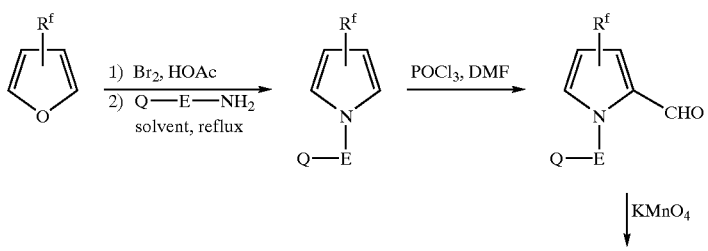

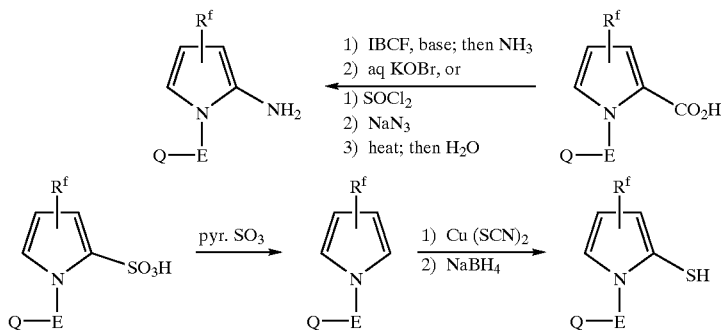

In Scheme 2 is shown how to prepare pyrroles in which Q—E is attached to the 2-position, wherein $R^f$ and $R^g$ collectively are hydrogen or a group that can be converted into $R^{1a}$ and $R^{1b}$ of Formula I. The Hantzsch pyrrole synthesis is a versatile reaction involving the cyclization of an appropriate β-ketoester with an α-halo ketone or aldehyde in the presence of a primary amine (*Ber. Dtsch. Chem. Ges.* 1890, 23, 1474). The β-ketoesters can be prepared from acid chlorides (X=Cl) by the addition of the magnesium anion of potassium alkylmalonate followed by decarboxylation (*Synthesis* 1993, 290). Alternatively, β-ketoesters can be prepared from an appropriate aldehyde,(R=H) by Reformatsky reaction with an α-bromoacetate followed by oxidation. Cyclization with an α-halo ketone or aldehyde in the presence of a primary amine can afford pyrroles. Acidic hydrolysis of the 3-carboalkoxy pyrrole can afford the carboxylic acids. Pyrroles which contain a 3-amino substituent can be prepared from the acids by treatment with phosphoryl azide and triethylamine to effect a curtius rearrangement to afford the isocyanates (*J. Med. Chem.* 1981, 24, 33) which upon hydrolysis can yield 3-aminopyrroles. Pyrroles which contain a sulfur atom at C-3 can be prepared from the acids by employing the Hunsdiecker procedure to give the 3-bromo derivatives. Halogen-metal exchange at low temperature with an alkyllithium reagent can afford the 3-lithio derivative which can be quenched with a variety of electrophiles, such as $S_8$ to afford thiols directly or $Cu(SCN)_2$ to afford a thiocyanate which can be reduced with sodium borohydride. The thiols can further be oxidized to the sulfonic acid derivatives by an oxidant such as $KMnO_4$.

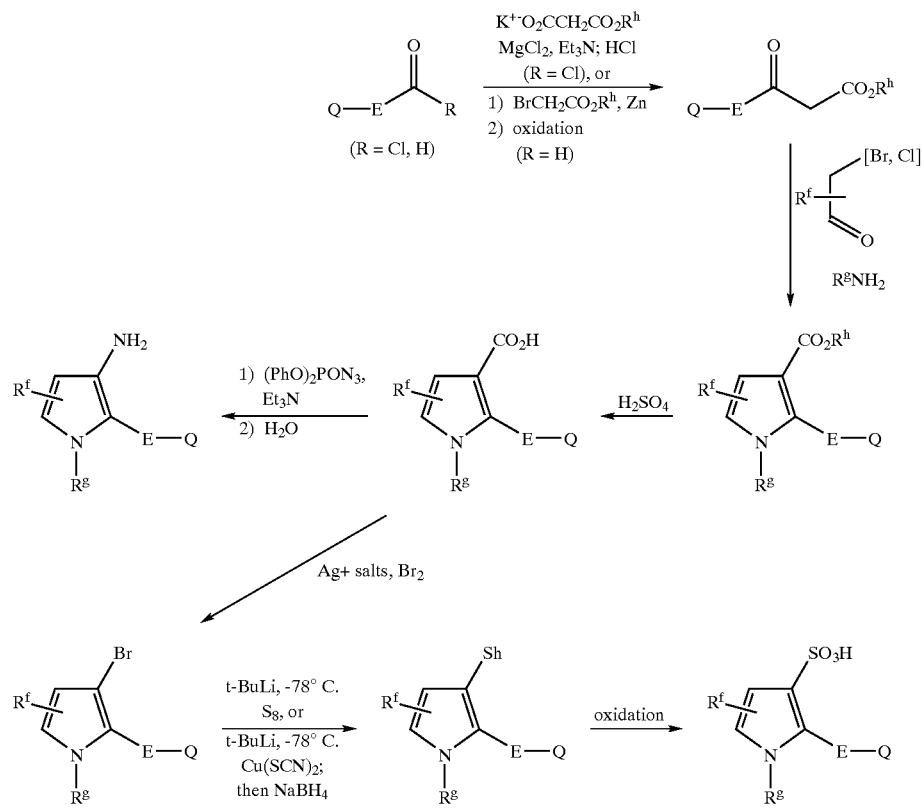

Scheme 2

In Scheme 3 is shown how to prepare pyrroles in which Q—E is attached to the 3-position. This scheme relies upon the extremely versatile Knorr pyrrole synthesis, which involves condensation of α-aminoketones with β-ketoesters. The α-aminoketones can be prepared from β-ketoesters (Scheme 2) by nitrosation followed by reduction with zinc/acetic acid. Condensation of α-aminoketones with appropriate β-ketoesters can afford good yields of pyrroles. These intermediates are very versatile and can be converted into pyrroles with a wide variety of substituents with varying substitution patterns. For cases wherein $R^e$ (Z—A—B precursor) is at the 2-position, acidic hydrolysis can selectively hydrolyze the C-3 ester. Heating should then effect decarboxylation. Hydrolysis of the 2-carboxylic acid can be achieved under basic conditions. Curtius rearrangement of the acid as described previously can afford the amino derivatives. To prepare compounds with a sulfur atom attached to C-2, basic hydrolysis and decarboxylation can afford the C-2 unsubstituted pyrroles. These pyrroles can undergo electrophilic substitution to afford thiols (Cu(SCN)$_2$, then NaBH$_4$) and sulfonic acids (pyridine SO$_3$ complex or chlorosulfonic acid). The $R^{1a}$ group contained in Formula I can be derived either from the remaining ester or from $R^f$. Alternatively, the thiol and sulfonic acid derivatives can also be derived form the C-2 acids by manipulation of the carboxylic acid group as described previously.

In Scheme 4 is shown how to prepare pyrroles in which Q—E is attached to the 3-position. Cyclization of α-aminoketones as described previously with β-ketoesters can afford pyrroles. Hydrolysis under basic conditions can selectively hydrolyze the C-2 ester which upon heating should undergo decarboxylation to afford 2-unsubstituted pyrroles. The C-3 ester can then be hydrolyzed under acidic conditions to afford the 3-carboxypyrroles. Curtius rearrangement under conditions described previously can afford the 3-aminopyrroles. The carboxylic acids can be used to prepare the 3-mercapto and 3-sulfonic acid derivatives. The Hunsdiecker procedure can be used to prepare the 3-bromopyrroles. Halogen metal exchange with t-BuLi at low temperature followed by quenching with copper isocyanate should introduce an isocyanate group at C-3. This intermediate can be reduced with sodium borohydride to afford the 3-mercaptopyrroles. Alternatively, the carboxylic acids can be decarboxylated to afford pyrroles which can be N-protected with a bulky protecting group such as triisopropylsilyl (TIPS). This bulky group directs electrophilic substitution to C-3 of the pyrrole ring. Thus, reaction with copper isocyanate followed by sodium borohydride reduction and then fluoride induced TIPS deprotection can afford 3-mercaptopyrroles. Sulfonation of N-protected pyrrole with pyridine sulfur trioxide complex can again be directed to C-3 of the pyrrole to afford, after TIPS deprotection, the 3-sulfonic acids.

Scheme 3

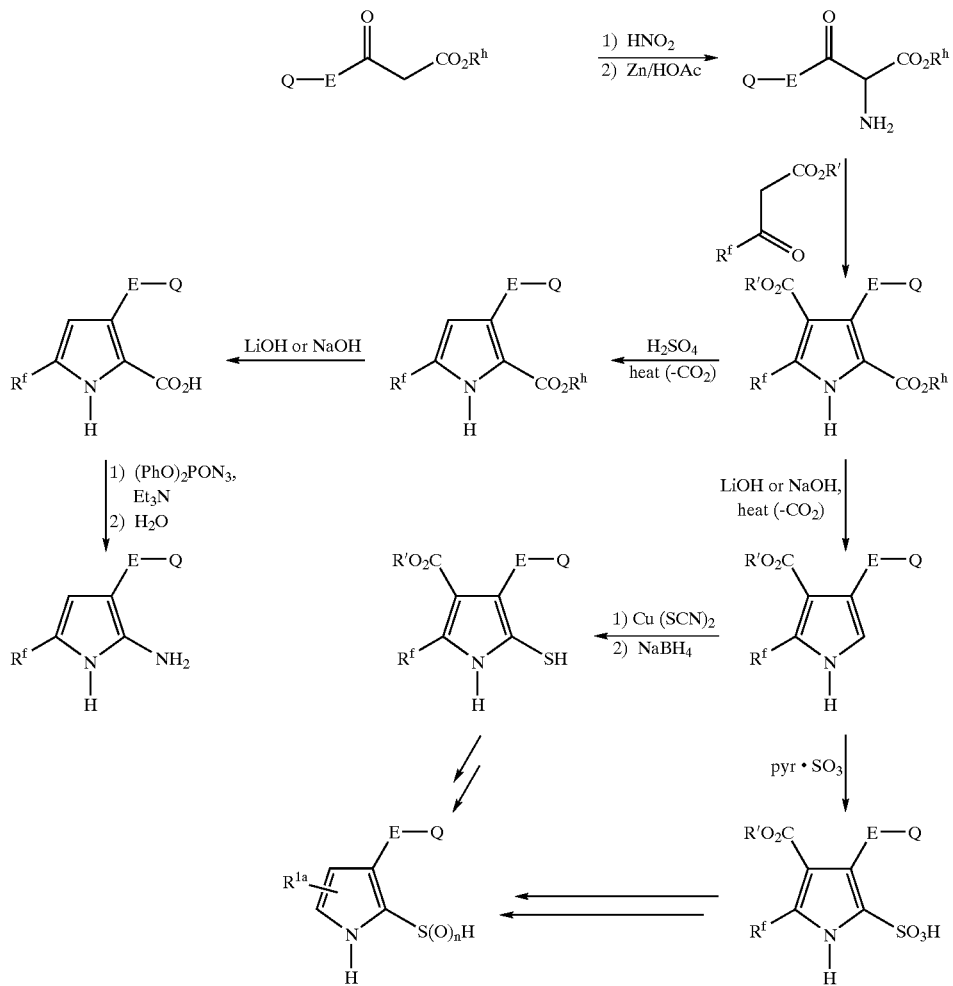

Scheme 4

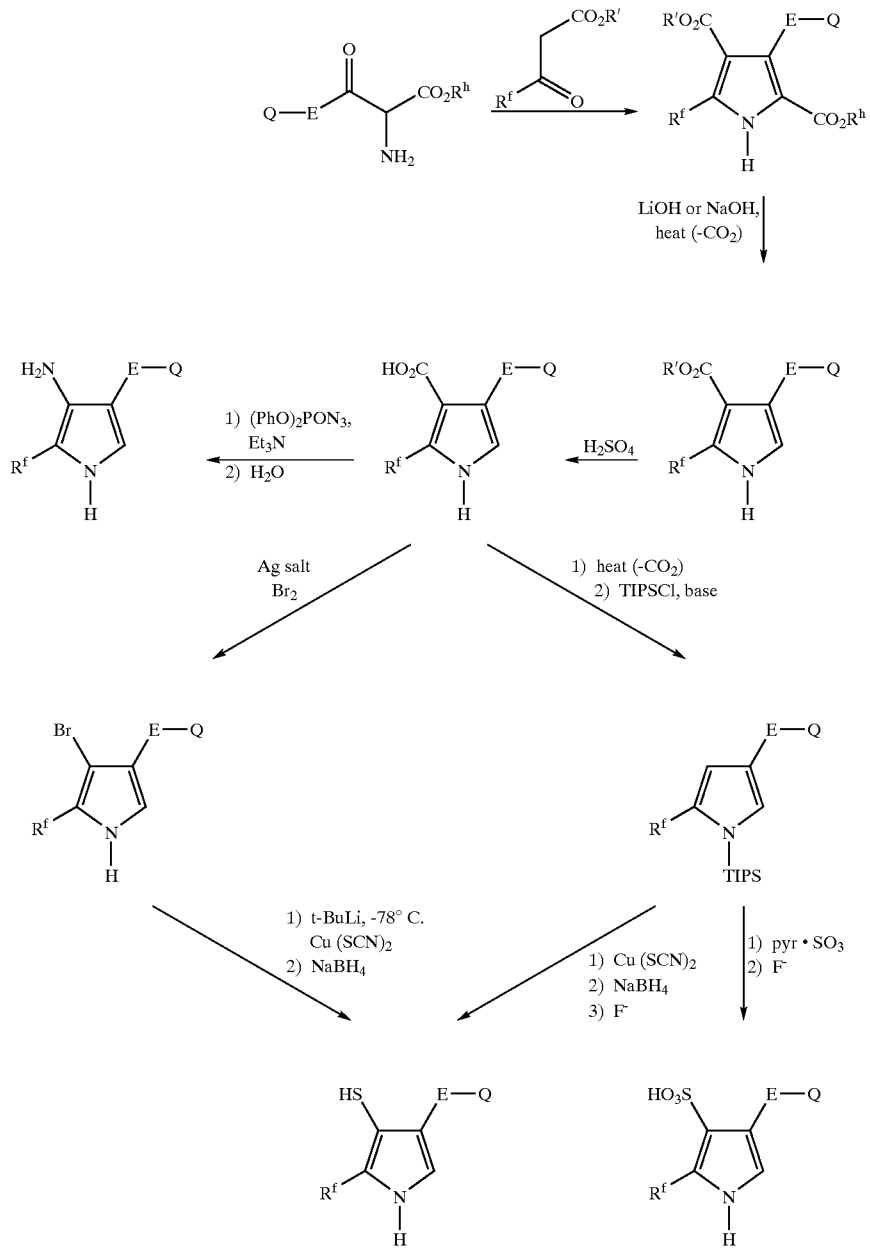

Another general method of pyrrole synthesis that can be used to prepare compounds of the present invention is shown in Scheme 5. This approach (Cushman et. al. *J. Org. Chem.* 1996, 61, 4999) uses N-protected α-aminoketones and N-protected α-aminoaldehydes which are readily available from α-amino acids by initial preparation of the N-methoxy-N-methylamides followed by addition of an alkyl Grignard reagent (to produce ketones) or by reduction with a hydride reducing agent such as lithium aluminum hydride or diisobutylaluminum hydride. These aldehydes and ketones can be allowed to react with the enolates of additional ketones to afford intermediate aldol addition products which under acidic conditions cyclize to form pyrroles. The reacting partners in this approach can be of wide scope and can be chosen so that one skilled in the art will be able to prepare varied pyrroles.

Scheme 5

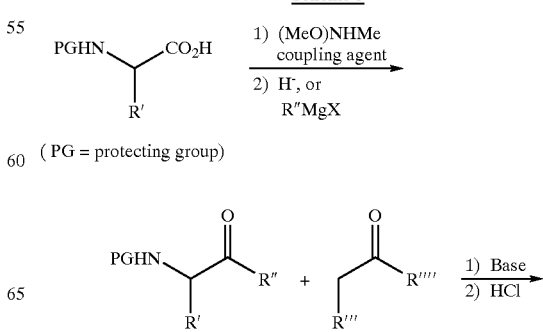

( PG = protecting group)

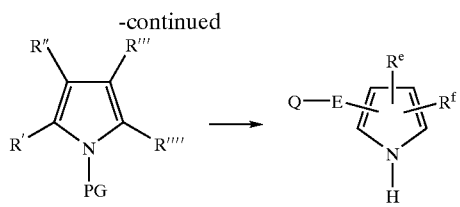

Another very general method of pyrrole synthesis useful for preparing compounds of the present invention is the Paal-Knorr reaction shown in Scheme 6. This reaction involves the reacting 1,4-diketones or 1,4-ketoaldehydes with primary amines to afford pyrroles. The starting 1,4-diketones and 1,4-ketoaldehydes can be prepared using standard enolate chemistry or by other procedures which are familiar to those skilled in the art of organic synthesis. The reaction is of wide scope and the starting materials can be chosen so that a variety of pyrroles can be prepared.

Scheme 6

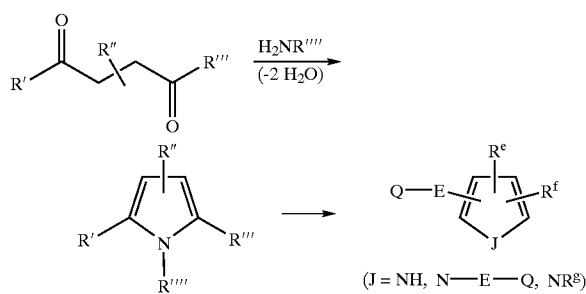

In Scheme 7 is shown how the compounds of Schemes 1–6 wherein $R^e$ is a carboxylic ester group can be converted into compounds containing the Z—A—B residue. For the amide linker (Formula I, Z=—CONH—), when $R^e$=carboalkoxy, it can be hydrolyzed to the acid under either basic or acidic conditions depending on the substitution pattern, as described previously. Formation of the acid chloride with thionyl chloride followed by the addition of an appropriate amine $H_2N$—A—B can afford the amide-linked compounds. Alternatively, the acid can be combined with amine $H_2N$—A—B in the presence of a suitable peptide coupling agent, such as BOP—Cl, HBTU or DCC. In another method the ester can be directly coupled with an aluminum reagent, prepared by the addition of trimethylaluminum to the amine $H_2N$—A—B.

To form ether- or thioether-linked compounds of Formula I (Z=—$CH_2O$—, —$CH_2S$—) the acid can be reduced to the alcohol. Preferred procedures for this transformation are reduction with borane THF complex, or a procedure involving the reduction of the mixed anhydride with sodium borohydride (IBCF=isobutyl chloroformate and NMM=N-methylmorpholine). Completion of the ether and thioether linked compounds of Formula I can readily be accomplished by the Mitsonobu protocol with an appropriate phenol, thiophenol or hydroxy- or mercaptoheterocycle HX—A–B (X=O,S) (Formula I, A=aryl or heteroaryl). Other ethers or thioethers (X=O,S) can be prepared following initial conversion of the alcohol to a suitable leaving group, such as tosylate. Where X=S, thioethers can be further oxidized to prepare the sulfones (Formula I, Z=—$CH_2SO_2$–).

To prepare the amine-linked compounds of Formula I (Z=—$CH_2NH$—) the alcohol can be oxidized to the aldehyde by a number of procedures, two preferred methods of which are the Swern oxidation and oxidation with pyridinium chlorochromate (PCC). Alternatively, the aldehyde may be directly prepared by direct formylation of the pyrrole ring by the Vilsmeier-Haack procedure in certain cases, as described in previous schemes. Reductive amination of the aldehyde with an appropriate amine $H_2N$—A—B and sodium cyanoborohydride can then afford the amine linked compounds.

The aldehyde also can be used to prepare the ketone-linked compounds of Formula I (Z=—$COCH_2$—). Treatment with an organometallic species can afford the alcohol. The organometallic species (wherein M=magnesium or zinc) can preferably be prepared from the corresponding halide by treatment with metallic magnesium or zinc. These reagents should readily react with aldehydes to afford alcohols. Oxidation of the alcohol by any of a number of procedures, such as the Swern oxidation or PCC oxidation, can afford the ketones-linked compounds.

Scheme 7

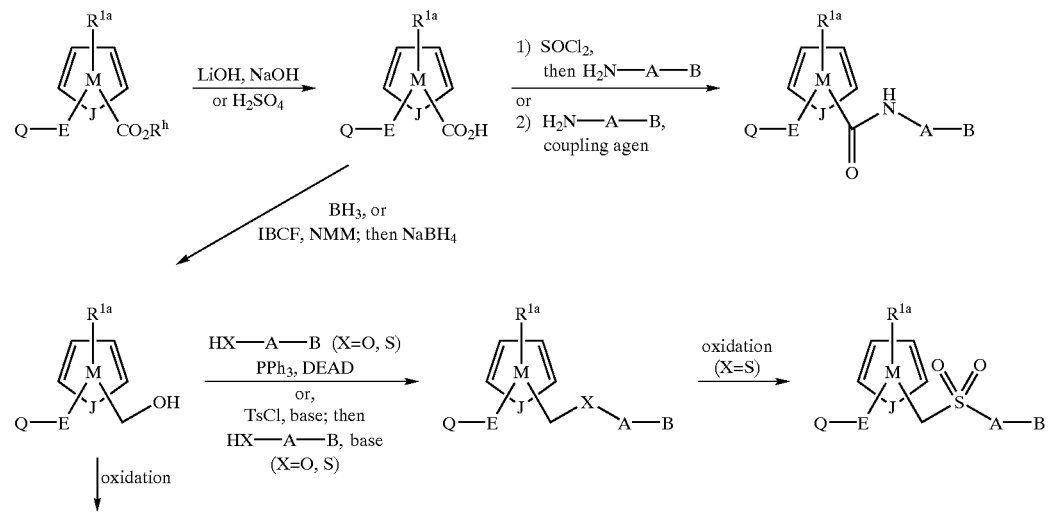

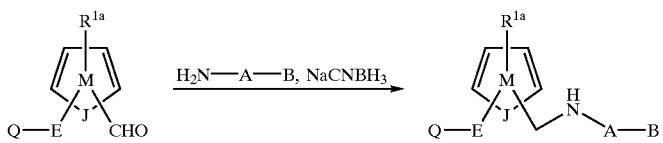

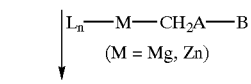

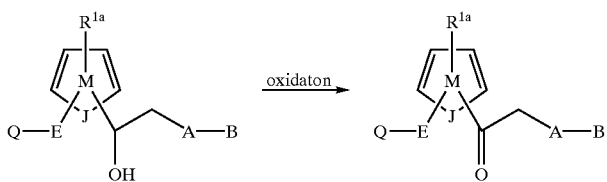

Additional compounds of Formula I in which the linking group m/z contains a nitrogen atom attached to ring M can be prepared by the procedures described in Scheme 8. The amines can be converted to sulfonamides (Formula I, m/z-NHSO$_2$—) by treatment with an appropriate sulfonyl chloride B—A—SO$_2$Cl in the presence of a base such as triethylamine. The amines can be converted into amides (Formula I, Z=—NHCO—) by treatment with an appropriate acid chloride Cl—CO—A—B in the presence of a base or by treatment with an appropriate carboxylic acid HO—CO—A—B in the presence of a suitable peptide coupling agent, such as DCC, HBTU or BOP. The amines can also be converted into amine-linked compounds (Formula I, Z=—NHCH$_2$—) by reductive amination with an appropriate aldehyde OHC—A—B.

Scheme 8

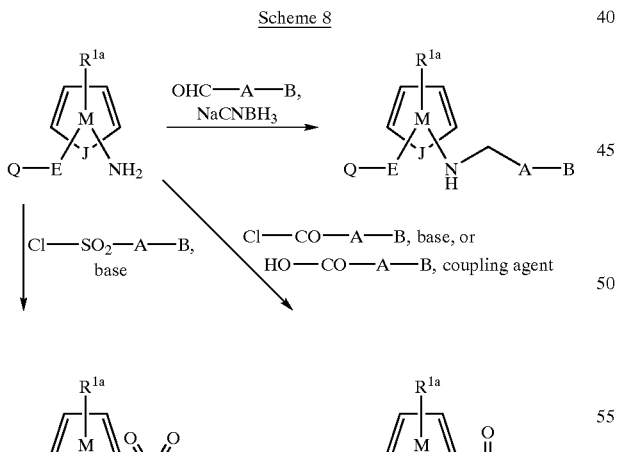

Additional compounds of Formula I in which the linking group Z contains a sulfur atom attached to ring M can be prepared by the procedures described in Scheme 9. Treatment of sulfonic acids with phosphorous pentachloride followed by treatment with an appropriate amine H$_2$N—A—B can afford sulfonamide-linked compounds (Formula I, Z=—SO$_2$NH—). The thiols can be alkylated with a suitable alkylating reagent in the presence of a base to afford thioethers (Formula I, Z=—SCH$_2$—). These compounds can be further oxidized by a variety of reagents to afford the sulfone-linked compounds (Formula I, Z=—SO$_2$CH$_2$—).

Scheme 9

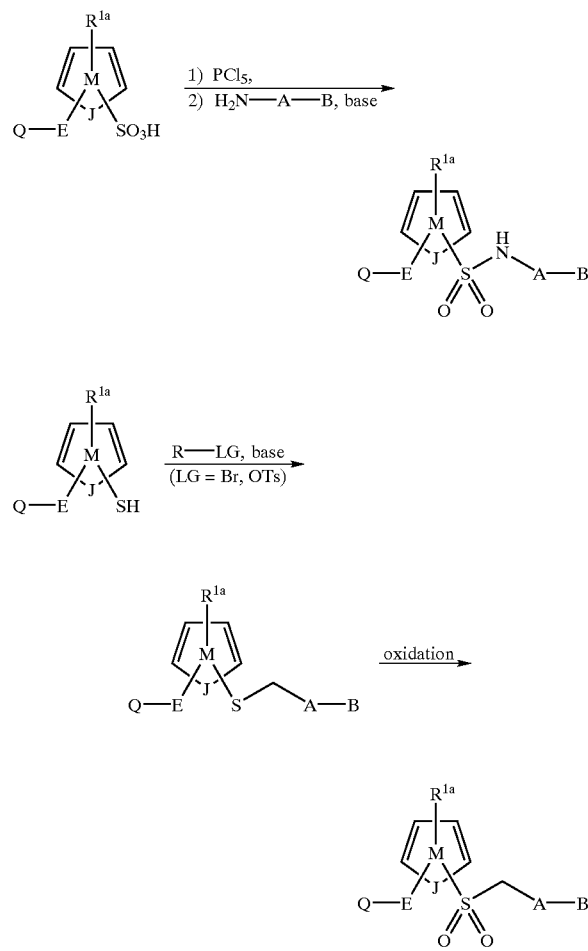

Compounds of Formula I wherein ring M is an imidazole can be formed using procedures described in Schemes 10–16. N-Substituted imidazole derivatives can be made by the general procedure shown in Scheme 10, wherein V' is either V or a precursor of $(CH_2)_nV$, V is nitro, amino, thio, hydroxy, sulfonic acid, sulfonic ester, sulfonyl chloride, ester, acid, or halide, n is 0 and 1, and PG is either a hydrogen or a protecting group. Substitution can be achieved by coupling an imidazole with a halogen containing fragment Q—E—G—Hal in the presence of a catalyst, such as base, Cu/CuBr/base, or Pd/base, followed by conversion of V' to $(CH_2)_nV$. Then, Q can be converted to D, and finally V can be converted to —Z—A—B following the procedures outlined in Schemes 7–9. Alternatively, V can be converted to Z—A—B followed by deprotection of N. This product can then be coupled as before to obtain the desired imidazole.

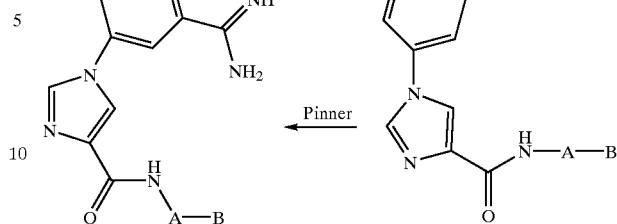

1,2-Disubstituted and 1,5-disubstituted imidazole derivatives can be made by the general procedures described in

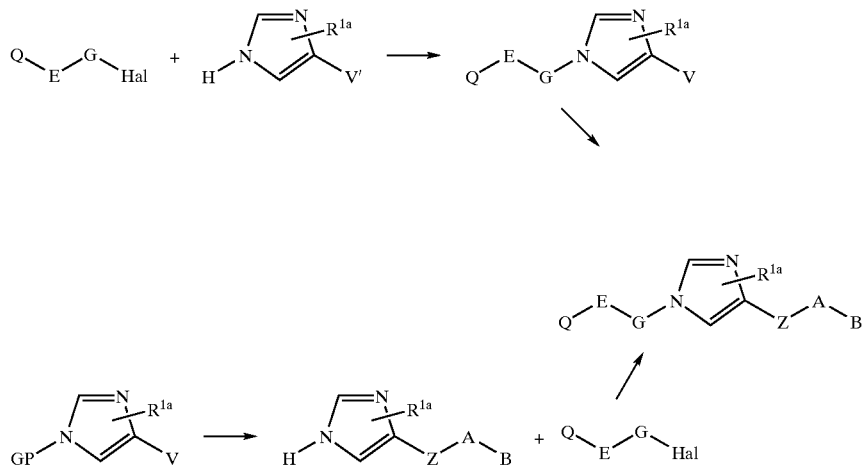

One way to make amidino-phenyl-imidazole derivatives is shown in Scheme 11. 4-Imidazole carboxylic acid can be treated with thionyl chloride and then coupled with $H_2N$—A—B in the presence of a base and then be heated with 3-fluorobenzonitrile in the presence of a base. The Pinner reaction using standard procedures known to those of skill in the art can be used to form the amidino group.

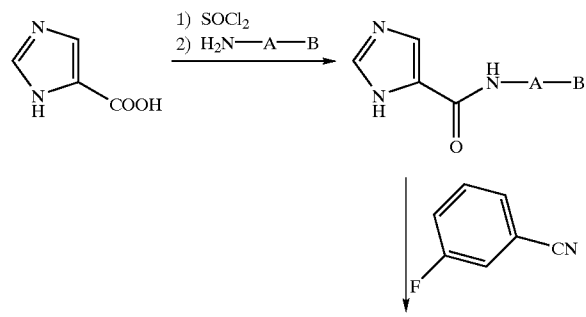

Scheme 12, wherein $R^{1b}$ is either a hydrogen or an alkyl group and U is aldehyde, ester, acid, amide, amino, thiol, hydroxy, sulfonic acid, sulfonic ester, sulfonyl chloride, or methylene halide. Step a involves coupling in the presence of a catalyst, such as base, Cu/CuBr/base, or Pd/base. When $R^{1b}$ is a hydrogen, it can be deprotonated with a lithium base and trapped by formate, formamide, carbon dioxide, sulfonyl chloride (sulfur dioxide and then chlorine), or isocyanate to give 1,2-disubstituted imidazoles (Route b1). Also, in Route b1 when $R^{1b}$ is $CH_3$, it can be oxidized with $SeO_2$, $MnO_2$, $NaIO_4$/cat. $RhCl_3$, or NBS to form U. When $R^{1b}$ is hydrogen, sequential deprotonation and quenching with a lithium base and trimethysilyl chloride, followed by a second deprotonation with a lithium base and quenching with formate, formamide, carbon dioxide, sulfonyl chloride (sulfur dioxide and then chlorine), or isocyanate can afford 1,5-disubstituted imidazoles (Route b2). When $R^{1b}$ is not hydrogen, the procedure of Route b2 can again be used to form 1,5-disubstituted imidazoles (Route b3).

Scheme 12

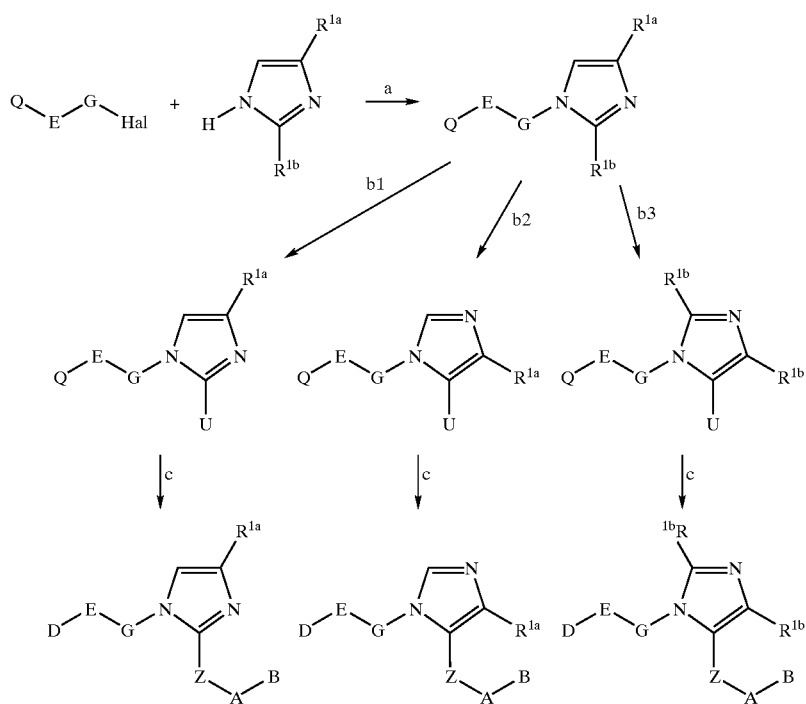

A preferred way of making 1,2-disubstituted and 1,5-disubstituted imidazole derivatives is shown in Scheme 13. Imidazole can be heated with 3-fluorobenzonitrile in the presence of a base. The coupled product can then be treated with an alkyl lithium base and quenched with ClCO$_2$Me to give the 1,2-disubstituted compound. Further treatment with a solution prepared of H$_2$N—A—B in trimethylaluminum can give the amide, which can be further modified via the Pinner reaction to form the desired compound. The 1,5-disubstituted compounds can be made using the same procedure, except that the initial anion is protected and a second anion is formed which is then quenched as noted above. Further modifications can follow the same procedures as the 1,2-disubstituted compounds.

Scheme 13

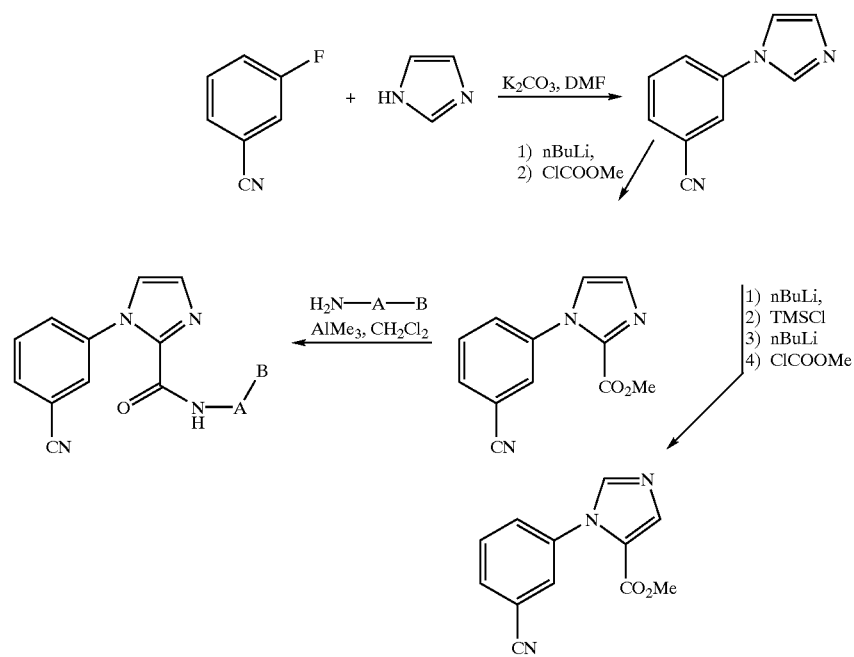

Another way of making 1,2-disubstituted imidazole derivatives is described in Scheme 14. By reacting an N-substituted imidazole with a cyanate, the amide can be obtained. This amide can then be coupled with group B as will be described later.

Scheme 14

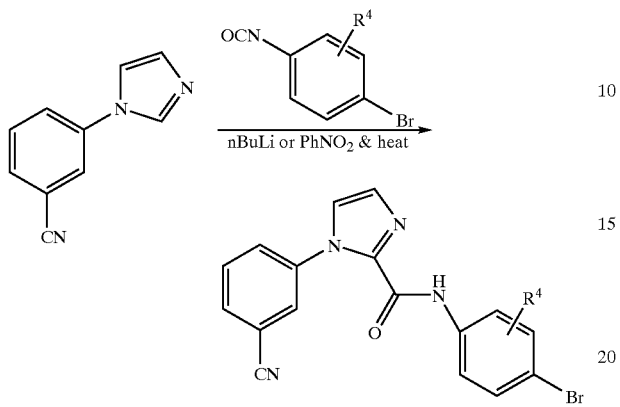

Another means of making 1,5-disubstituted imidazole derivatives is described in Scheme 15. Alkylation with 2-bromoethylacetate and subsequent reaction with Gold's reagent in the presence of a base, such as NaOMe, or LDA, can form ester substituted imidazoles which can be further modified as previously discribed.

Scheme 15

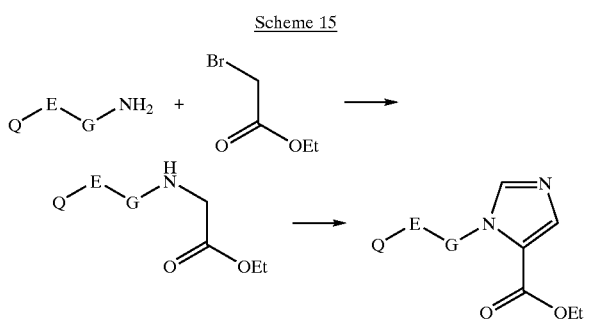

A general procedure to make 2,4,5-trisubstituted or 4,5-disubstituted imidazole derivatives is shown in Scheme 16. After metal halogen exchange of the Q—E—G fragment, it can be reacted with the amide shown, brominated with NBS and cyclized with excess $NH_3$ and $R^{1a}CO_2H$ to afford an imidazole. This can then be modified as before.

A general procedure to make 4,5-disubstituted triazole derivatives is described in Scheme 17. Ethyl propiolate can be substituted in the presence of CuI/Pd and then reacted with $NaN_3$ to form a triazole. The triazole can be converted as described previously.

Scheme 17

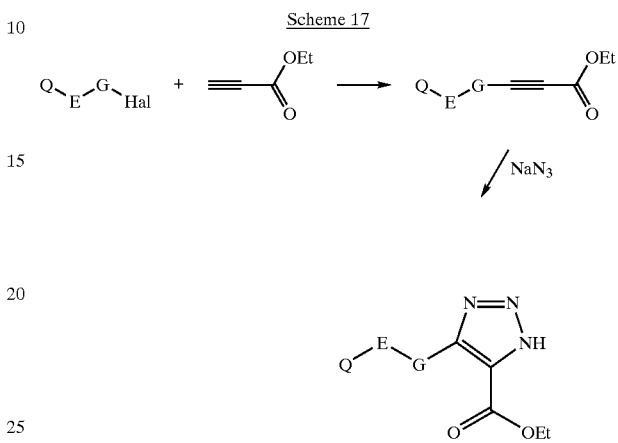

The tetrazole compounds of the present invention where Z is —CONH— can be prepared as exemplified in Scheme 18. An appropiately substituted amine can be acylated with ethyl oxalyl chloride. The resulting amide can be converted to the tetrazole either by the methods described by Duncia (*J. Org. Chem.* 1991, 2395–2400) or Thomas (*Synthesis* 1993, 767–768). The amide can be converted to the iminoyl chloride first and the reacted with $NaN_3$ to form the 5-carboethoxytetrazole (*J. Org. Chem.* 1993, 58, 32–35 and *Bioorg. & Med. Chem. Lett.* 1996, 6, 1015–1020). The 5-carboethoxytetrazole can then be further modified as described in Scheme 7.

The tetrazole compounds of the present invention where Z is —CO— can also be prepared via iminoyl chloride (*Chem. Ber.* 1961, 94, 1116 and *J. Org. Chem.* 1976, 41, 1073) using an appropriately substituted acyl chloride as starting material. The ketone-linker can be reduced to compounds wherein Z is alkyl.

Scheme 16

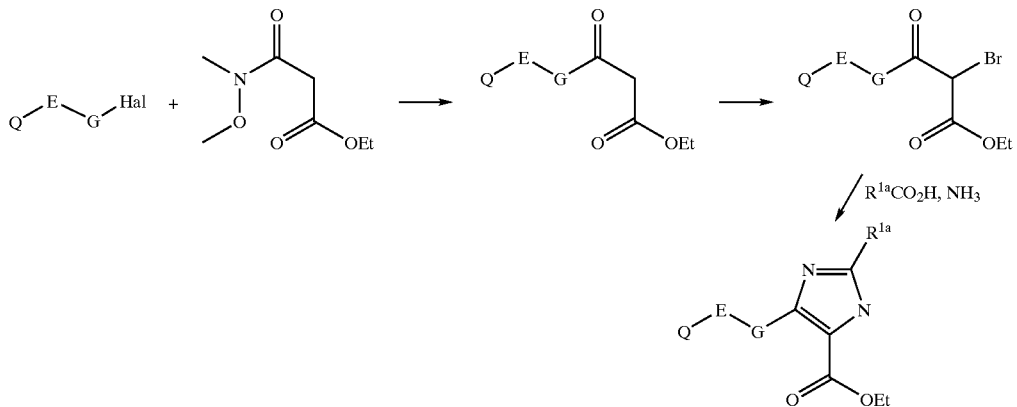

Scheme 18

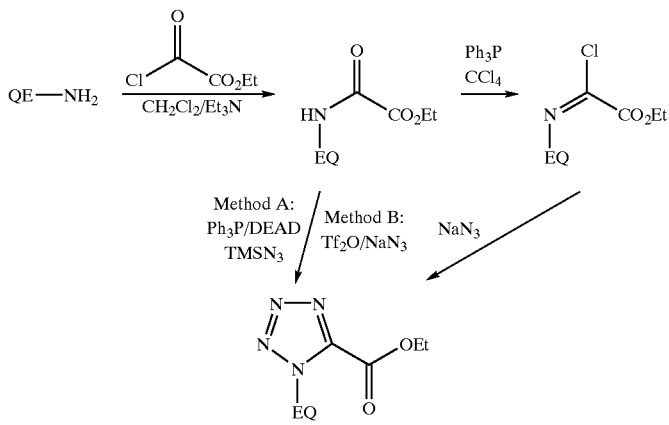

The methods described in Scheme 18 can also be used to synthesize compounds where the E—Q is linked to the carbon atom of the tetrazole as shown in Scheme 19. The 5-substituted tetrazole can then be alkylated or acylated to give the desired products.

Scheme 19

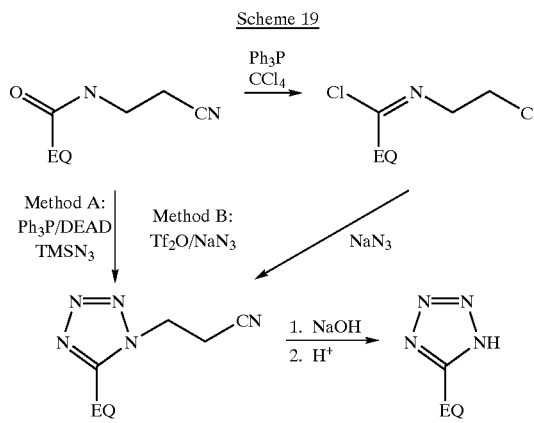

The tetrazole compounds of the present invention wherein Z is —SO$_2$NH—, —S—, —S(O)—, SO$_2$— can be prepared from the thiol prepared as shown in Scheme 20. Appropiately substituted thioisocyanate can be reacted with sodium azide to give the 5-thiotetrazole (*J. Org. Chem.* 1967, 32, 3580–3592). The thio-compound can be modified as described in Scheme 9.

The tetrazole compounds of the present invention wherein Z is —O— can be prepared via the same method described in Scheme 20 by using appropiately substituted isocyanate as the starting material. The hydroxy compound can be modified similarity to the thiols described in Scheme 9.

Scheme 20

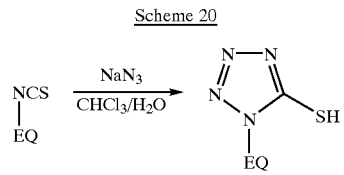

The tetrazole compounds of the present invention wherein Z is —NH—, —NHCO—, —NHSO$_2$— can be prepared from 5-aminotetrazole, which can be prepared by Smiles Rearrangement as shown in Scheme 21. The thio-compound prepared as described in Scheme 20 can be alkylated with 2-chloroacetamide. The resulting compound can then be refluxed in ethanolic sodium hydroxide to give the corresponding 5-amino-tetrazole (*Chem. Pharm. Bull.* 1991, 39, 3331–3334). The resulting 5-amino-tetrazole can then be alkylated or acylated to form the desired products.

Scheme 21

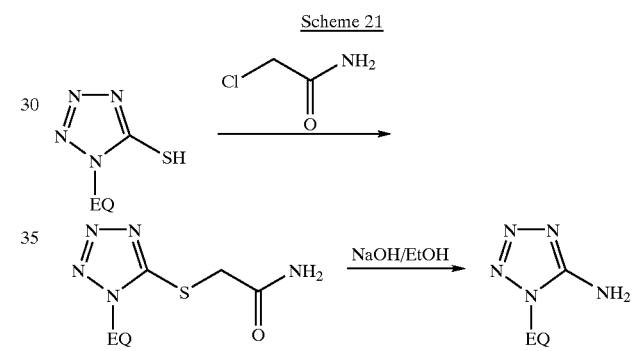

Pyrazoles of Formula I (such as those described in Scheme 22) can be prepared by the condensation of an appropriately substituted hydrazine with a variety of diketo esters. Condensations of this type typically afford a mixture of pyrazole regioisomers which can be effectively separated via silica gel column chromatography. The esters can be converted to Z—A—B as previously described.

Alternatively, if in Scheme 22, the starting diketone contains CH$_3$ in place of CO$_2$Et, then the resulting methyl pyrazole can be separated and oxidized as in Route b1 in Scheme 12 to form the pyrazole carboxylic acid.

Scheme 22

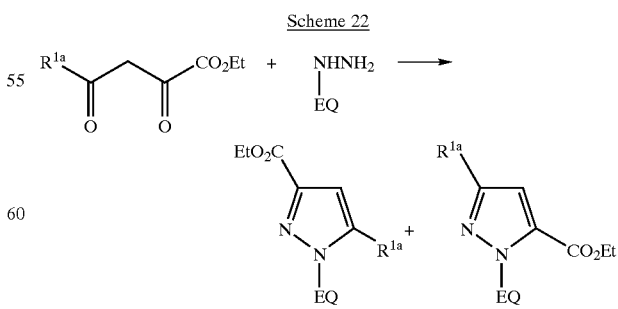

When ketoimidates are used for condensations with hydrazines the corresponding pyrazole amino esters are obtained (Scheme 23). Conversion of these intermediates to the final compounds of formula I can then be accomplished by the protection of the amino functionality with a suitable protecting group or by derivatization (e.g. sulfonamide) and then modifying the ester as previously noted.

NBS in either dichloromethane or acetic acid) of the initial pyrazole. Conversion of 4-bromo-pyrazole to 4-carboxylic acid pyrazole can be accomplished by a number of methods commonly known to those in the art of organic synthesis.

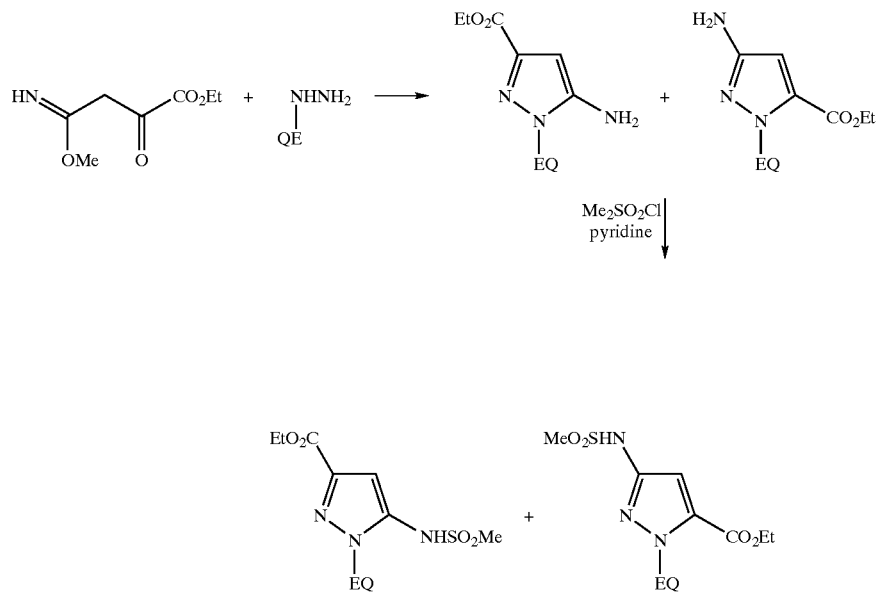

As shown in Scheme 24, pyrazoles wherein the 4-position is substituted can be prepared by bromination (bromine or Further manipulations as previously described can afford pyrazoles of the present invention.

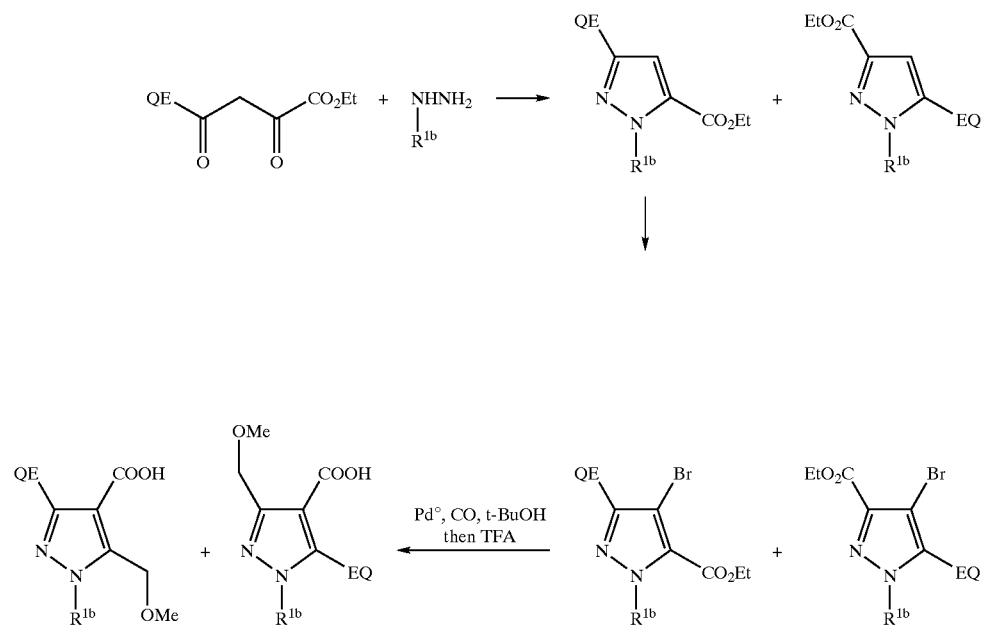

Pyrazoles can also be prepared according to method described in Scheme 25. The bromo-pyrazoles are formed as in Scheme 24. QE can then be coupled using palladium catalysed Suzuki cross-coupling methodology. Further modification is achieved as previously described.

dichloromethane) or bromide (POBr$_3$) followed by palladium Suzuki cross-coupling with an apppropriately substituted phenylboronic acid should then afford 5-substituted pyrazoles. Conversion of this intermediate to the 4-bromo derivative followed by its carbonylation as described in Scheme 24 should then afford the appropriate ester which can be further afford the compounds of formula I.

Scheme 25

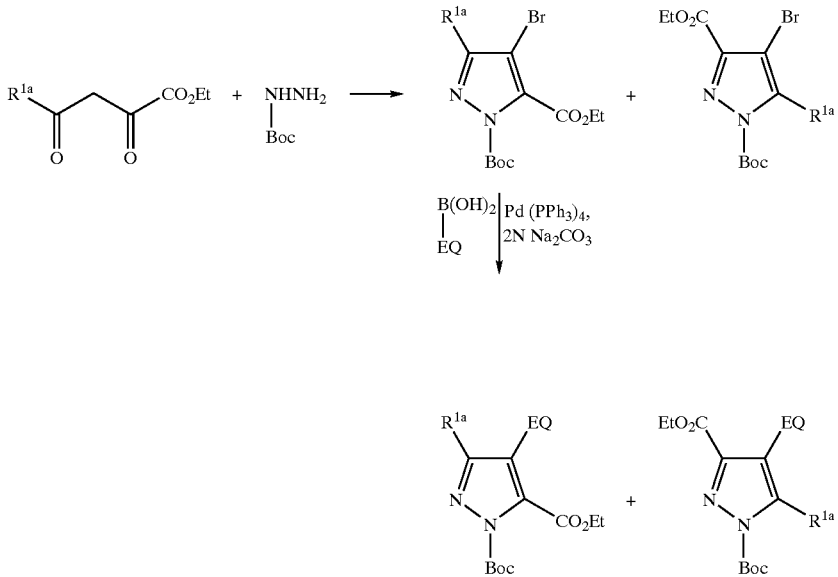

5-substituted phenylpyrazoles can be prepared by the method shown in Scheme 26. Conversion of the 5-hydroxy pyrazole to its triflate (triflic anhydride, lutidine in Scheme 26

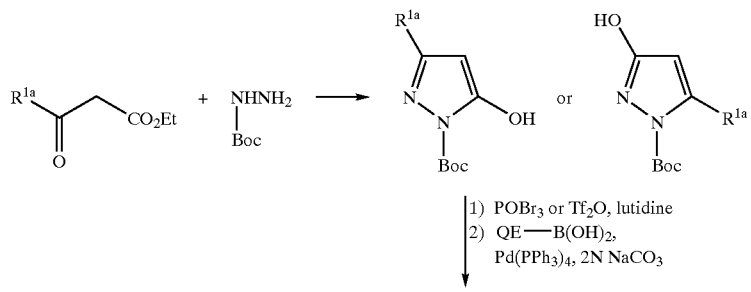

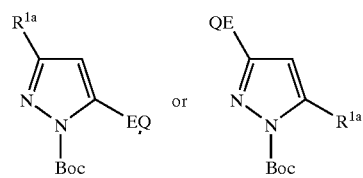

1-Substituted-1,2,3-triazoles of the present invention can be prepared by the treatment of an appropriately substituted azide with a variety of dipolarophiles (*Tetrahedron* 1971, 27, 845 and *J. Amer. Chem. Soc.* 1951, 73, 1207) as shown in Scheme 27. Typically a mixture of regioisomers are obtained which can be easily separated and elaborated to the triazole carboxylic acids. Further transformations as previously described can then afford the compounds of the present invention.

-continued

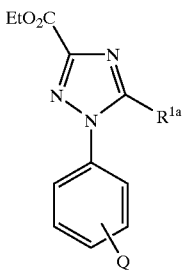

Scheme 27

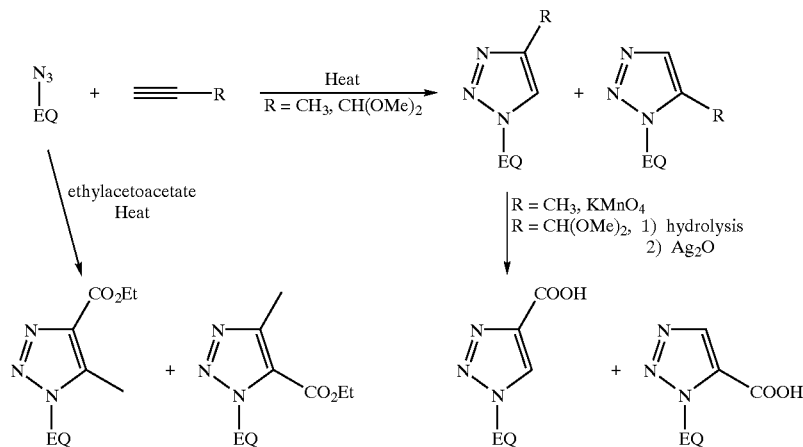

1,2,4-Triazoles of the present invention can be obtained by the methodology of Huisgen et al (*Liebigs Ann. Chem.* 1962, 653, 105) by the cycloaddition of nitriliminium species (derived from the treatment of triethylamine and chloro hydrazone) and an appropriate nitrile dipolarophile (Scheme 28). This methodology provides a wide variety of 1,2,4 triazoles with a varied substitution pattern at the 1, 3, and 5 positions.

Scheme 28

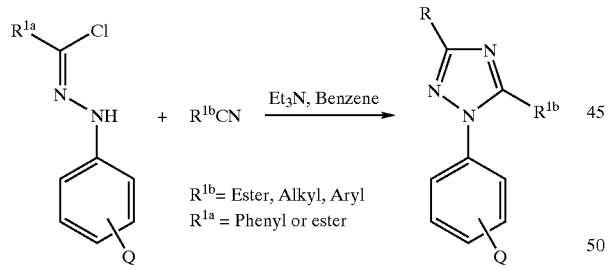

1,2,4 Triazoles can also be prepared by the methodology of Zecchi et al (*Synthesis* 1986, 9, 772) by an aza Wittig condensation (Scheme 29).

Scheme 29

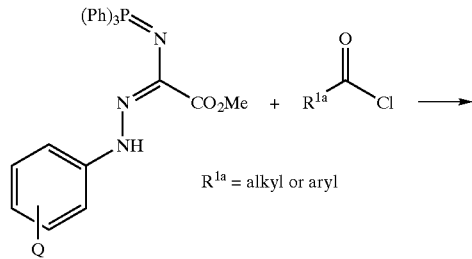

1,2,4-Triazoles wherein the —E—D(Q) substituent is at the 5-position of the triazole can be obtained as shown in Scheme 30.

Scheme 30

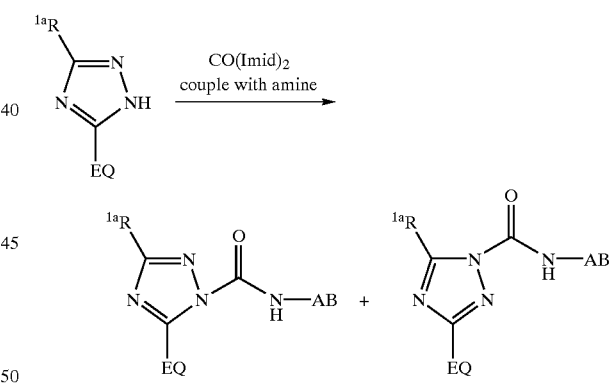

1,3,4-Triazoles of the present invention can be obtained via the methodology of Moderhack et al (*J. Prakt. Chem.* 1996, 338, 169). As shown in Scheme 31, this reaction involves the condensation of a carbazide with an appropriately substituted commercially available thioisocyanate to form the cyclic thiourea derivative. Alkylation or nucleophilic displacement reactions on the thiono-urea intermediate can then afford a thio-alkyl or aryl intermediate which can be hydrolysed, oxidized and decarboxylated to the 5-H 2-thio-triazole intermediate which can be converted to the compounds of the present invention. Alternatively the thiono-urea intermediate can be oxidized directly to the 2-H triazole which can then be converted to the ester and modified as previously described. The thiono-urea intermediate can also be oxidized to the sulfonyl chloride by methods shown previously.

Scheme 31

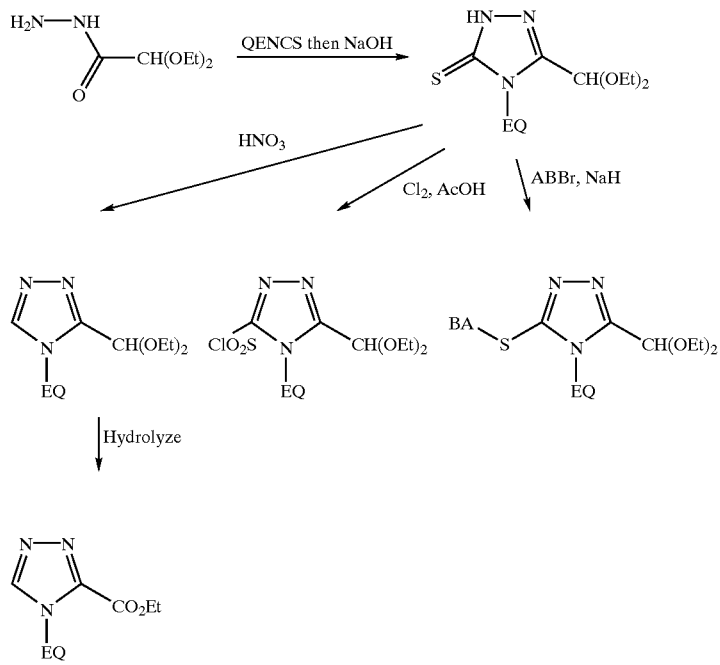

The imidazole core shown in Scheme 32 can be prepared by the condensation of 3-cyanoaniline with n-butylglyoxylate to afford the imine which can then be treated with TosylMIC in basic methanol to afford the desired imidazole compound. Coupling of the ester under standard conitions then affords a variety of analogs which then can be further manipulated to afford e.g. the benzylamine or the benzamidines.

Scheme 32

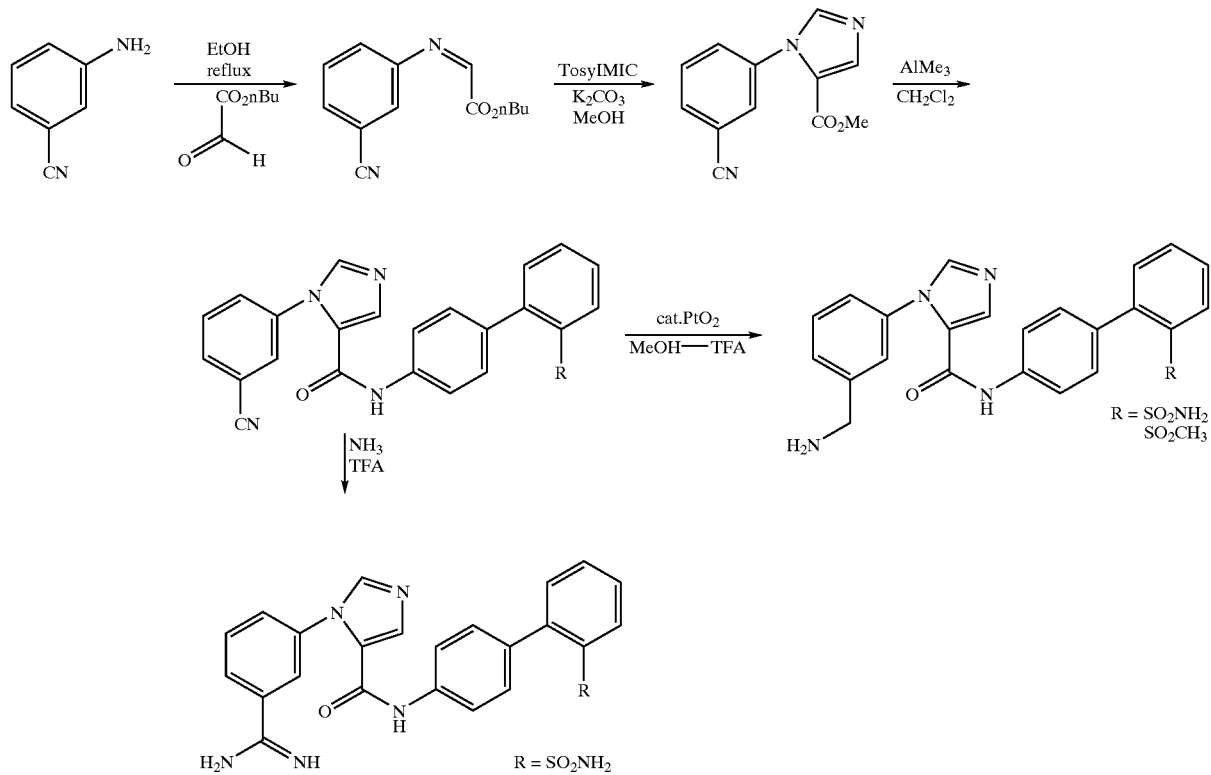

Compounds of the present invention wherein AB is a biphenylamine or similar amine may be prepared as shown in Scheme 33. 4-Bromoaniline can be protected as Boc-derivative and coupled to a phenylboronic acid under Suzuki conditions (*Bioorg. Med. Chem. Lett.* 1994, 189). Deprotection with TFA provides the aminobiphenyl compound. Other similar amines wherein A and/or B are heterocycles can be prepared by the same method using appropiately substituted boronic acids and arylbromide. The bromoaniline can also be linked to the core ring structures first as described above, and then undergo a Suzuki reaction to give the desired product.

Scheme 33

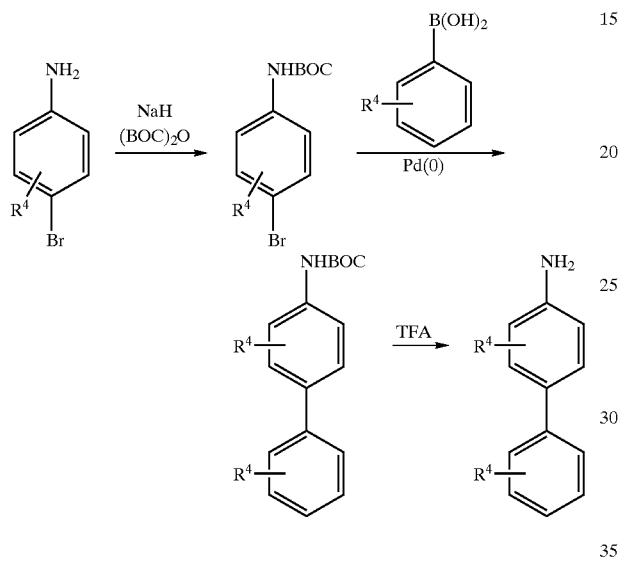

Compounds of the present invention wherein A—B is A—X—Y can be prepared like the piperazine derivative shown in Scheme 34.

Scheme 34

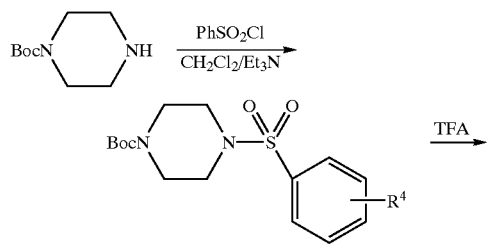

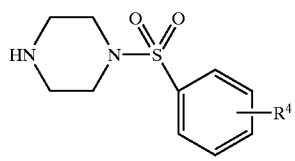

Scheme 35 shows how one can couple cyclic groups wherein X=NH, O, or S.

Scheme 35

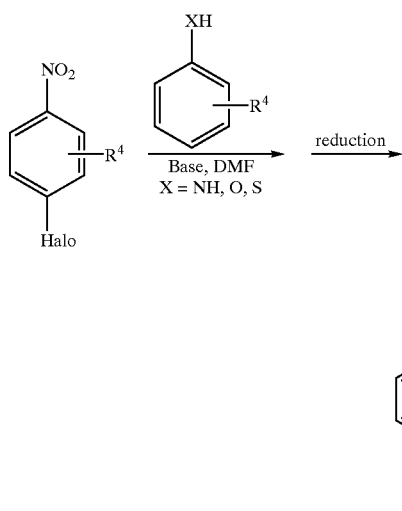

When B is defined as X—Y, the following description applies. Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sufonamide and Sulfamide linkages between A and B.

| Rxn. No. | if A contains: | then the reactive substituent of y is: | to give the following product A-X-Y: |
|---|---|---|---|
| 1 | A-NHR$^2$ as a substituent | ClC(O)—Y | A-NR$^2$—C(O)—Y |
| 2 | a secondary NH as part of a ring or chain | ClC(O)—Y | A-C(O)—Y |

TABLE A-continued

Preparation of Amide, Ester, Urea, Sufonamide and Sulfamide linkages between A and B.

| Rxn. No. | if A contains: | then the reactive substituent of y is: | to give the following product A-X-Y: |
|---|---|---|---|
| 3 | A-OH as a substituent | ClC(O)—Y | A-O—C(O)—Y |
| 4 | A-NHR$^2$ as a substituent | ClC(O)—CR$^2$R$^{2a}$—Y | A-NR$^2$—C(O)—CR$^2$R$^{2a}$—Y |
| 5 | a secondary NH as part of a ring or chain | ClC(O)—CR$^2$R$^{2a}$—Y | A-C(O)—CR$^2$R$^{2a}$—Y |
| 6 | A-OH as a substituent | ClC(O)—CR$^2$R$^{2a}$—Y | A-O—C(O)—CR$^2$R$^{2a}$—Y |
| 7 | A-NHR$^3$ as a substituent | ClC(O)NR$^2$—Y | A-NR$^2$—C(O)NR$^2$—Y |
| 8 | a secondary NH as part of a ring or chain | ClC(O)NR$^2$—Y | A-C(O)NR$^2$—Y |
| 9 | A-OH as a substituent | ClC(O)NR$^2$—Y | A-O—C(O)NR$^2$—Y |
| 10 | A-NHR$^2$ as a substituent | ClSO$_2$—Y | A-NR$^2$—SO$_2$—Y |
| 11 | a secondary NH as part of a ring or chain | ClSO$_2$—Y | A-SO$_2$—Y |
| 12 | A-NHR$^2$ as a substituent | ClSO$_2$—CR$^2$R$^{2a}$—Y | A-NR$^2$—SO$_2$—CR$^2$R$^{2a}$—Y |
| 13 | a secondary NH as part of a ring or chain | ClSO$_2$—CR$^2$R$^{2a}$—Y | A-SO$_2$—CR$^2$R$^{2a}$—Y |
| 14 | A-NHR$^2$ as a substituent | ClSO$_2$—NR$^2$—Y | A-NR$^2$—SO$_2$—NR$^2$—Y |
| 15 | a secondary NH as part of a ring or chain | ClSO$_2$—NR$^2$—Y | A-SO$_2$—NR$^2$—Y |
| 16 | A-C(O)Cl | HO—Y as a substituent | A-C(O)—O—Y |
| 17 | A-C(O)Cl | NHR$^2$—Y as a substituent | A-C(O)—NR$^2$—Y |
| 18 | A-C(O)Cl | a secondary NH as part of a ring or chain | A-C(O)—Y |
| 19 | A-CR$^2$R$^{2a}$C(O)Cl | HO—Y as a substituent | A-CR$^2$R$^{2a}$C(O)—O—Y |
| 20 | A-CR$^2$R$^{2a}$C(O)Cl | NHR$^2$—Y as a substituent | A-CR$^2$R$^{2a}$C(O)—NR$^2$—Y |
| 21 | A-CR$^2$R$^{2a}$C(O)Cl | a secondary NH as part of a ring or chain | A-CR$^2$R$^{2a}$C(O)—Y |
| 22 | A-SO$_2$Cl | NHR$^2$—Y as a substituent | A-SO$_2$—NR$^2$—Y |
| 23 | A-SO$_2$Cl | a secondary NH as part of a ring or chain | A-SO$_2$—Y |
| 24 | A-CR$^2$R$^{2a}$SO$_2$Cl | NHR$^2$—Y as a substituent | A-CR$^2$R$^{2a}$SO$_2$—NR$^2$—Y |
| 25 | A-CR$^2$R$^{2a}$SO$_2$Cl | a secondary NH as part of a ring or chain | A-CR$^2$R$^{2a}$SO$_2$—Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of ketone linkages between A and B.

| Rxn. No. | if A contains: | then the reactive substituent of Y is: | to give the following product A-X-Y: |
|---|---|---|---|
| 1 | A-C(O)Cl | BrMg—Y | A-C(O)—Y |
| 2 | A-CR$^2$R$^{2a}$C(O)Cl | BrMg—Y | A-CR$^2$R$^{2a}$2C(O)—Y |
| 3 | A-C(O)Cl | BrMgCR$^2$R$^{2a}$—Y | A-C(O)CR$^2$R$^{2a}$—Y |
| 4 | A-CR$^2$R$^{2a}$C(O)Cl | BrMgCR$^2$R$^{2a}$—Y | A-CR$^2$R$^{2a}$C(O)CR$^2$R$^{2a}$—Y |

The coupling chemistry of Table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temeprature (−20° C. or lower) and with a large excess of acid chloride or with catalytic or stoichiometric copper bromide.dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al. (Tetrahedron Lett., (1984) 4805), or a coupling mediated by manganese (II) catalysis (Cahiez and Laboue, Tetrahedron Lett., 33(31), (1992) 4437).

TABLE C

Preparation of ether and thioether linkages between A and B

| Rxn. No. | if A contains: | then the reactive substituent of Y is: | to give the following product A-X-Y: |
|---|---|---|---|
| 1 | A-OH | Br—Y | A-O—Y |
| 2 | A-CR$^2$R$^{2a}$—OH | Br—Y | A-CR$^2$R$^{2a}$O—Y |

TABLE C-continued

Preparation of ether and thioether linkages between A and B

| Rxn. No. | if A contains: | then the reactive substituent of Y is: | to give the following product A-X-Y: |
|---|---|---|---|
| 3 | A-OH | Br—CR$^2$R$^{2a}$—Y | A-OCR$^2$R$^{2a}$—Y |
| 4 | A-SH | Br—Y | A-S—Y |
| 5 | A-CR$^2$R$^{2a}$—SH | Br—Y | A-CR$^2$R$^{2a}$S—Y |
| 6 | A-SH | Br—CR$^2$R$^{2a}$—Y | A-SCR$^2$R$^{2a}$—Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of —SO— and —SO2— linkages from thioethers of Table 3.

| Rxn. No. | if the starting material is: | and it is oxidized with Alumina (wet)/ Oxone (Greenhalgh, Synlett, (1992) 235) the product is: | and it is oxidized with m-chloroperbenzoic acid (Satoh et al., Chem. Lett. (1992) 381), the product is: |
|---|---|---|---|
| 1 | A-S—Y | A-S(O)—Y | A-SO$_2$—Y |
| 2 | A-CR$^2$R$^{2a}$S—Y | A-CR$^2$R$^{2a}$S(O)—Y | A-CR$^2$R$^{2a}$SO$_2$—Y |
| 3 | A-SCR$^2$R$^{2a}$—Y | A-S(O)CR$^2$R$^{2a}$—Y | A-SO$_2$CR$^2$R$^{2a}$—Y |

The thioethers of Table C serve as a convenient starting material for the preparation of the sulfoxide and sulfone analogs of Table D. A combination of wet alumina and oxone can provide a reliable reagent for the oxidation of the thioether to the sulfoxide while m-chloroperbenzoic acid oxidation will give the sulfone.

TABLE E

Methods of Preparing Group E

| Rxn | Q | D is to be | then a transformation that may be used is: |
|---|---|---|---|
| 1 | —CN | —C(=NH)NH2 | E—C≡N $\xrightarrow{\text{i) HCl MeOH}}_{\text{ii) NH}_3\text{OAc, MeOH}}$ E—C(NH$_2$)=NH |
| 2 | —CN | —CH2NH2 | E—C≡N $\xrightarrow{\text{LiAlH}_4}_{\text{Et}_2\text{O}}$ E—CH$_2$NH$_2$ |
| 3 | —CO2H | —CH2NH2 | E—C(=O)OH $\xrightarrow[\text{ii) MsCl, Et}_3\text{N, CH}_2\text{Cl}_2]{\substack{\text{i) iBuOC(O)Cl} \\ \text{NMM, THF} \\ \text{then NaBH}_4\text{, H}_2\text{O/THF}}}$ E—CH$_2$NH$_2$ <br> iii) NaN$_3$, DMF <br> iv) SnCl$_2$, MeOH |

TABLE E-continued

Methods of Preparing Group E

| Rxn | Q | D is to be | then a transformation that may be used is: | |
|---|---|---|---|---|
| 4 | —CO2H | —NH$_2$ | i) iBuOC(O)Cl, NMM, THF then NaN$_3$ and heat<br>ii) tBuOH, reflux<br>iii) HCl, Et$_2$O | E—C(=O)OH → E—NH$_2$ |

In Table E several methods of transforming a functional group Q into group D of Formula 1 are shown. While not all possible functional groups for Q and D are listed and the synthetic methods suggested are not comprehensive, Table E is meant to illustrate strategies and transformations available to a practitioner skilled in the art of organic synthesis for preparing compounds of Formula 1. In reaction 1 of Table E the transformation of a nitrile into an amidine by the Pinner methodology is shown; in reaction 2 the direct reduction of a nitrile by a hydride reducing agent to a methylene amine is illustrated. In reaction 3, the utility of a carboxylic acid, which may be readily derived from its ester or a nitrile if necessary, in the preparation of a methylene amine is shown. This synthetic route is exceptionally flexible because of the several stable intermediates prepared en route to the final product. As outlined, formation of an activated analog, such as the mixed anhydride, allows for the mild reduction of the acid to the methylene alcohol, this may in turn be transformed into a leaving group by sulfonylation or halogenation or protected with a suitable protecting group to be transformed later in the synthesis as the chemistry demands. Once the methylene alcohol is so activated, displacement by an efficient nitrogen nucleophile, such as azide anion, can again provide another suitably stable analog, —the methylene azide—which may be used as a protected form of the methylene amine or transformed directly into the methylene amine group by reduction. Reaction 4 addresses the problem of appending the amine functionality directly through a bond to group E of Formula 1. Once again, the carboxylic acid provides a convenient entre into this selection for group D. The well-know Curtius rearrangement is illustrated here; an activated acid analog can be used to form an acyl azide which upon thermal decomposition is rearranged to the corresponding isocyanate. The isocyanate intermediate may then be captured as a stable carbamate by the addition of a suitable alcohol and further heating. This carbamate can be used as a stable protecting group for the amine or cleaved directly to the desired D. Alternatively, it may be convenient to quench the isocyanate intermediate with water to give the amine directly.

Other features of the invention will become apparent in the course of the following descriptions of exemplary embodiments which are given for illustration of the invention and are not intended to be limiting thereof.

EXAMPLES

Fluoro-methylsulfone Intermediate

4-Amino-3-fluoro-2'-methylsulfonyl-[1,1']-biphenyl, Hydrochloride

Part A: Preparation of 4-Bromo-N-t-butoxycarbonyl-2-fluoroaniline.

Sodium hydride (1.16 g, 60%, 29 mmol) was added to a 0° C. solution of 4-bromo-2-fluoro aniline (5.01 g, 26 mmol) in dry DMF (75 mL). The ice bath was removed and the reaction was stirred at room temperature for 1 h. Di-t-butyl dicarbonate (6.33 g, 29 mmol) was added, and the reaction was heated at 65° C. for 17 h. The reaction was quenched dropwise with H$_2$O, then extracted 4 times with H$_2$O. The first two aqueous extracts were combined and extracted twice with EtOAc. The organic extracts were combined, dried over Na$_2$SO$_4$, filtered and evaporated. The crude product was taken up in a mixture of CH$_2$Cl$_2$, CHCl$_3$, and EtOAc and filtered to remove a purple impurity, then concentrated and chromatographed on silica gel (30% CH$_2$Cl$_2$/hexanes) to yield an orange solid (4.76 g, 62%). $^1$HNMR (DMSO) δ: 9.07 (bs, 1H), 7.57 (td, 1H, J=8.7, J'=2.2), 7.49, (dd, 1H, J=10.2, J'=2.2), 7.30 (dt, 1H, J=8.8, J'=1.1), 1.42 (s, 9H) ppm.

Part B: Preparation of 4-(t-Butoxycarbonylamino)-3-fluoro-2'-methylthio-[1,1']-biphenyl.

A flask containing a mixture of 4-bromo-N-t-butoxycarbonyl-2-fluoroaniline (6.44 g, 22 mmol), 2-(methylthio)phenylboronic acid (6.00 g, 36 mmol), aq. sodium carbonate (2.0 M, 36 mL, 72 mmol), tetrabutylammonium bromide (360 mg, 1.1 mmol), and bis(triphenylphosphine)palladium(II) chloride in benzene (180 mL) was evacuated twice under brief high vacuum, filled with argon, and heated at reflux for 5 h. After cooling to room temperature, the layers were separated, and the aqueous layer was extracted with EtOAc. The organic extracts were combined, dried over Na$_2$SO$_4$, filtered, and evaporated. The crude product was chromatographed on silica gel (0–30% EtOAc/hexanes) to yield the desired product (6.50 g, 88%). $^1$HNMR (CHCl$_3$) δ: 8.14 (bt, 1H, J=8.1), 7.30 (m, 2H), 7.17 (m, 4H), 6.75 (bs, 1H), 2.37 (s, 3H), 1.54 (s, 9H) ppm.

Part C: Preparation of 4-(t-Butoxycarbonylamino)-3-fluoro-2'-methylsulfonyl-[1,1']-biphenyl.

4-(t-Butoxycarbonylamino)-3-fluoro-2'-methylthio-[1,1']-biphenyl (6.50 g, 19.5 mmol) was dissolved in CH$_2$Cl$_2$ (150 mL) and cooled to 0° C. m-CPBA (14.8 g, 57–86%) was added and the reaction stirred at room temperature for 3 h. The reaction was extracted with sat. sodium sulfite, and the aqueous layer was extracted with CH$_2$Cl$_2$. The organic extracts were combined, dried over Na$_2$SO$_4$, filtered, and evaporated. The crude product was chromatographed on silica gel (20–30% EtOAc/hexanes) to yield the desired product (6.92 g, 97%). $^1$HNMR (CHCl$_3$) δ: 8.22 (dd, 2H, J=7.7, J'=1.5), 7.64 (td, 1H, J=7.3, J'=1.5), 7.56 (td, 1H, J=7.7 J'=1.5), 7.35 (dd, 1H, J=7.3, J'=1.5), 7.30 (dd, J=11.7, J'=2.2), 7.17 (d, 1H, J=8.8), 6.82 (bs, 1H), 2.69 (s, 3H), 1.55 (s, 9H) ppm.

Part D: Preparation of 4-Amino-3-fluoro-2'-methylsulfonyl-[1,1']-biphenyl, Hydrochloride.

4-(t-Butoxycarbonylamino)-3-fluoro-2'-methylsulfonyl-[1,1']-biphenyl (1.04 g, 2.8 mmol) was dissolved in HCl/ dioxane (4.0 M, 10 mL) and stirred 19 h. A solid was triturated with $Et_2O$ and filtered to yield a white solid (813 mg, 95%). $^1$HNMR (DMSO) δ: 8.03 (dd, 1H, J=8.0, J'=1.4), 7.69 (td, 1H, J=7.7, J'=1.1), 7.59 (t, 1H, J=7.4), 7.36 (d, 1H, J=7.3), 7.12 (d, 1H, J=12.4), 6.94 (m, 2H), 2.78 (s, 3H) ppm.

Examples 1 and 2

1-(3-Amidinophenyl)-2-[[(2'-aminosulfonyl-[1,1']-biphen-4-yl)-aminocarbonyl]pyrrole, Trifluoroacetic Acid Salt (Example 1) and 1-(3-Amidinophenyl)-2-[[(2'-tert-butylaminosulfonyl-[1,1']-biphen-4-yl)-aminocarbonyl]pyrrole, Trifluoroacetic Acid Salt (Example 2)

Part A. Preparation of 1-(3-Cyanophenyl)pyrrole.

3-aminobenzonitrile (47.45 g, 0.401 mol) and 58.4 g (0.441 mol, 59.5 ml) of 2,5-dimethoxytetrahydrofuran were dissolved in 200 ml of acetic acid and heated to reflux over night. The solution, was allowed to cool to room temperature and diluted with 250 ml of ethylacetate and was washed 3 times with brine (200 ml) and then by a solution of saturated aq sodium carbonate (200 ml). The organics were dried over magnesium sulfate and filtered through a plug of silica gel. The volatiles were removed in vacuo and the residue was recrystallized from methanol to yield the title compound as a beige solid (62.82 g, 93%) MS ($H_2O$—CI) 169 $(M+H)^+$.

Part B. Preparation of 1-(3-Cyanophenyl)pyrrole-2-carboxaldehyde.

Phosphorous oxychloride, over the course of 15 minutes, was added to dimethylformamide (14.02 g, 191.84 mmol, 14.1 ml) at 0° C. The mixture was warmed to room temperature and stirred for 15 minutes; the solution was again cooled to 0° C. followed by the addition of 100 ml of 1,2 dichloroethane. A solution of 1-(3-cyanophenyl) pyrrole (29.33 g, 191.84 mmol) in 250 ml of 1,2 dichloroethane was added slowly via an addition funnel and the mixture heated to reflux for 15 minutes. The solution was cooled to room temperature and 86.55 g (1.05 mol) of sodium acetate was added and the solution heated to reflux for 15 minutes. The solution was diluted with 250 ml of ethyl acetate and the organics washed with brine then saturated aq sodium carbonate (250 ml). The organics were dried over magnesium sulfate, filtered through a plug of silica gel and the volatiles removed in vacuo. The product was recrystallized from ethyl acetate to yield 28.4 g (83%) of the title compound. MS ($NH_3$—CI) 214 $(M+NH_4)^+$.

Part C. Preparation of 1-(3-Cyanophenyl)pyrrole-2-carboxylic Acid.

To a cooled (0° C.) solution of 1-(3-cyanophenyl) pyrrole-2-carboxaldehyde (5.14 g, 26.20 mmol) in 300 ml of 1:1 acetone/water was added potassium permanganate (12.42 g, 78.60 mmol) over a period of 15 minutes and the reaction was allowed to warm to room temperature. After consumption of the starting material, 10.90 g (104.8 mmol) of sodium bisulfite was added and the solution made acidic with 10% HCl. The solution was filtered through a plug of celite, diluted with ethyl acetate and washed with 200 ml of brine. The organics were dried over magnesium sulfate, filtered and dried in vacuo. The organics were recrystallized from methanol to yield the title compound (4.11 g, 74%) as a pale white solid. MS (ESI) 211.2 $(M–H)^-$.

Part D. Preparation of 1-(3-Cyanophenyl)-2-[[(2'-tert-butylaminosulfonyl-[1,1']-biphen-4-yl)-aminocarbonyl] pyrrole.

To a solution of 1-(3-cyanophenyl)pyrrole-2-carboxylic acid (2.77 g, 13.05 mmol) in 50 ml of anhydrous DMF was added triethylamine (1.98 ml, 19.58 mmol), benzotriazole-1-yloxy-tris(dimethylamino)phosphonium hexafluorophosphate (8.66 g, 19.58 mmol) and (2'-N-tert-butylaminosulfonyl-[1,1']-biphen-4-yl)-amine (6.03 g, 19.84 mmol) and heated to 50° C. overnight. The solution was diluted with ethyl acetate and washed repeatedly with brine. The organic layer was dried over magnesium sulfate and the volatiles removed in vacuo. The residue was subjected to flash chromatography purification with 3:2 hexane/ethyl acetate and the volatiles removed in vacuo to yield 1.9 g (29%) of the title compound. MS ($NH_3$—CI) 516 $(M+NH_4)^+$.

Part E. Preparation of 1-(3-Amidinophenyl)-2-[[(2'-aminosulfonyl-[1,1']-biphen-4-yl)-aminocarbonyl]pyrrole, Trifluoroacetic Acid Salt (Example 1) and 1-(3-Amidinophenyl)-2-[[(2'-tert-butylaminosulfonyl-[1,1']-biphen-4-yl)-aminocarbonyl]pyrrole, Trifluoroacetic Acid Salt (Example 2).

1-(3-Cyanophenyl)-2-[[(2'-tert-butylaminosulfonyl-[1,1']-biphen-4-yl)-aminocarbonyl] (0.37 g, 0.74 mmol) of pyrrole was added to a solution of 60 ml of anhydrous methyl acetate and anhydrous methanol (0.30 ml, 7.4 mmol) and cooled in an ice water bath. Gaseous HCl was bubbled in for 15 minutes, the solution stoppered and allowed to stir overnight at room temperature. The volatiles were removed in vacuo. The residue was dried under high vacuum for 1 hr. The residue was then dissolved in 100 ml of anhydrous methanol and combined with 0.43 g (4.45 mmol) of ammonium carbonate and stirred overnight at room temperature. The volatiles were removed in vacuo and the residue was purified by preparative HPLC (C18 reverse phase column, elution with a $H_2O/CH_3CN$ gradient with 0.5% TFA) to yield 1-(3-amidinophenyl)-2-[[(2'-aminosulfonyl-[1,1']-biphen-4-yl)-aminocarbonyl] pyrrole, trifluoroacetic acid salt (Example 1) as a white solid following lyophilization. MS (ESI) 460.3 $(M+H)^+$; also isolated was 1-(3-amidinophenyl)-2-[[(2'-tert-butylaminosulfonyl-[1,1']-biphen-4-yl)-aminocarbonyl] pyrrole, trifluoroacetic acid salt (Example 2). MS (ESI) 516.4 (M+H)+.

Example 3

1-(3-Amidinophenyl)-2-[[(2'-aminosulfonyl-[1,1']-biphen-4-yl)-aminocarbonyl]-4-bromopyrrole, Trifluoroacetic Acid Salt Part A. Preparation of 1-(3-Cyanophenyl)-2-formyl-4-bromo-pyrrole.

1-(3-Cyanophenyl) pyrrole-2-carboxaldehyde from Example 1, Part B (6.06 g, 30.89 mmol) was combined with 6.60 g (37.06 mmol) of N-bromosuccinimide in 150 ml of anhydrous THF and stirred at room temperature overnight. The residue was heated in $CCl_4$ and filtered. The residue was then dissolved in $CHCl_3$/EtOAc, filtered through a silica gel plug and the volatiles removed. The residue was recrystallized from ethyl acetate to yield the title compound as a light brown solid (4.49 g, 53%). MS ($NH_3$—CI) 292 $(M+NH_4)^+$.

Part B. Preparation of 1-(3-Amidinophenyl)-2-[[(2'-aminosulfonyl-[1,1']-biphen-4-yl)-aminocarbonyl]-4-bromopyrrole, Trifluoroacetic Acid Salt.

Following the procedures described in Example 1, Parts C–E, 1-(3-cyanophenyl)-2-formyl-4-bromo-pyrrole was converted into the title compound as a white powder following HPLC purification. MS (ESI) 538.2 $(M+H)^+$.

Example 4

1-(3-Amidinophenyl)-2-[[5-(2'-aminosulfonylphenyl)-1-yl)pyridin-2-yl]-aminocarbonyl]pyrrole, Trifluoroacetic Acid Salt Part A. Preparation of 1-(3-Cyanophenyl)-2-[[5-(2'-tert-butylaminosulfonylphenyl)-1-yl)pyridin-2-yl]aminocarbonyl]pyrrole.

1-(3-Cyanophenyl) pyrrole-2-carboxylic acid from Example 1, Part C (1.00 g, 4.7 mmol), oxalyl chloride (0.61 ml, 7.06 mmol) and 3 drops of DMF were combined at room temperature in 50 ml of anhydrous $CH_2Cl_2$ and stirred for 4 hours. The volatiles were removed in vacuo and the residue was dried under high vacuum for 1 hour. The residue was then dissolved in 50 ml of $CH_2Cl_2$ followed by the addition of 4-dimethylaminopyridine (1.15 g, 9.4 mmol), the solution stirred at room temperature for 5 minutes followed by the addition of [5-(2'-aminosulfonylphenyl)-1-yl) pyridin-2-yl]-amine (1.44 g, 4.7 mmol) and stirred at room temperature overnight. The solution was filtered through a silica gel plug and the volatiles removed. The residue was purified by flash chromatography (1:2 hexane/EtOAc) to yield 0.84 g (36%) of the title compound as a tan solid. MS (ESI) 500.3 $(M+H)^+$.

Part B. Preparation of 1-(3-Amidinophenyl)-2-[[5-(2'-aminosulfonylphenyl)-1-yl)pyridin-2-yl]-aminocarbonyl]pyrrole, Trifluoroacetic Acid Salt.

Following the procedures described in Example 1, Part E, 1-(3-cyanophenyl)-2-[[5-(2'-tert-butylaminosulfonylphenyl)-1-yl)pyridin-2-yl]aminocarbonyl]pyrrole was converted into the title compound as a white powder following HPLC purification. MS (ESI) 461.3 $(M+H)^+$.

Examples 5 and 6

1-Benzyl-3-[(2'-aminosulfonyl-[1,1']-biphen-4-yl)aminocarbonyl]-4-(3-amidinophenyl)pyrrole, Trifluoroacetic Acid Salt (Example 5) and 1-Benzyl-3-[(2'-tert-butylaminosulfonyl-[1,1']-biphen-4-yl)aminocarbonyl]-4-(3-amidinophenyl)pyrrole, Trifluoroacetic Acid Salt (Example 6)

Part A: Preparation of Ethyl 3-(3-Cyanophenyl)propiolate.

To a solution of ethyl propiolate (25.0 g, 0.25 mol) in 750 mL of tetrahydrofuran at −78° C. was added n-butyllithium (102 mL of a 2.5 M solution in hexane, 0.25 mol) dropwise. After stirring at the same temperature for 1 h, zinc chloride (104.2 g, 0.76 mol) was added in 900 mL of tetrahydrofuran. The mixture was allowed to gradually warm to room temperature over 1 h. To this solution was added 3-iodobenzonitrile (29.2 g, 0.13 mol) and bis triphenylphosphine palladium (II) chloride (4.56 g, 6.5 mmol) and the resulting mixture was stirred at 50° C. overnight. To the mixture was added 150 mL of water and 150 mL of ether and the mixture was filtered through a celite pad. The filtrate was extracted 3 times with ether and the combined extracts were washed with brine, dried ($MgSO_4$) and filtered through a thick pad of silica gel. The solvents were removed in vacuo and the residue was recrystallized from hexane ethyl acetate to afford 8.8 g (35%) of the title compound as a tan solid. $^1$HNMR ($CDCl_3$) δ: 7.85 (s, 1H), 7.8 (d, 1H), 7.72 (d, 1H), 7.52 (t, 1H), 4.30 (q, 2H), 1.37 (t, 3H).

Part B: Preparation of 1-Benzyl-3-carboethoxy-4-(3-cyanophenyl)-$\Delta^3$-pyrroline.

To a solution of N-benzyl-N-(trimethylsilylmethyl)-aminomethyl methyl ether (12.25 g, 51.2 mmol) in 400 mL of methylene chloride at 0° C. was added ethyl 3-(3-cyanophenyl)propiolate (6.79 g, 34.1 mmol) followed by trifluoroacetic acid (0.20 mL, 2.6 mmol). The mixture was allowed to warm to room temperature and was stirred for 16 h. The reaction mixture was washed with saturated aqueous $NaHCO_3$ and brine, dried over $K_2CO_3$, filtered through a large pad of silica gel and concentrated in vacuo. The residue was purified by flash chromatography (elution with 5:1 hexanes/ethyl acetate) to afford 3.2 g (28%) of the title compound. MS (ESI) 333.4 (M+H)+.

Part C: Preparation of 1-Benzyl-3-[(2'-tert-butylaminosulfonyl-[1,1']-biphen-4-yl)aminocarbonyl]-4-(3-cyanophenyl)-$\Delta^3$-pyrroline.

To a solution of (2'-tert-butylaminosulfonyl-[1,1']-biphen-4-yl)-amine (1.10 g, 3.6 mmol) in 50 mL of methylene chloride at room temperature was added trimethylaluminum (6.6 mL of a 2.0 M solutiion in toluene, 13.2 mmol) dropwise. The solution was stirred (30 min) until gas evolution had ceased followed by the addition of 1-benzyl-3-carboethoxy-4-(3-cyanophenyl)-$\Delta^3$-pyrroline (1.0 g, 3.0 mmol) in 5 mL of methylene chloride. The resulting solution was stirred at 40° C. for 2 h, cooled to room temperature and quenched with saturated aq $NH_4Cl$. The mixture was diluted with ethyl acetate, washed with water and brine, dried (MgSO4) and concentrated in vacuo. The residue was purified by flash chromatography (elution with 4:1 hexane/ethyl acetate) to afford 0.58 g (34%) of the title compound. MS (ESI) 591.5 (M+H)+.

Part D: Preparation of 1-Benzyl-3-[(2'-tert-butylaminosulfonyl-[1,1']-biphen-4-yl)aminocarbonyl]-4-(3-cyanophenyl)pyrrole.

To a solution of 1-benzyl-3-[(2'-tert-butylaminosulfonyl-[1,1']-biphen-4-yl)aminocarbonyl]-4-(3-cyanophenyl)-$\Delta^3$-pyrroline (0.47 g, 0.8 mmol) in 20 mL of benzene was added 2,3-dichloro-5,6-dicyano-1,4-benzoquinone (DDQ) (0.27 g, 1.2 mmol) and the resulting mixture was stirred at 70° C. for 16 h. The mixture was cooled and filtered and concentrated in vacuo. The residue was purified by flash chromatography (elution with 5:1 hexane/ethyl acetate) to afford 0.25 g (53%) of the title compound. MS (ESI) 589.6 (M+H)+.

Part E: Preparation of 1-Benzyl-3-[(2'-aminosulfonyl-[1,1']-biphen-4-yl)aminocarbonyl]-4-(3-amidinophenyl)pyrrole, Trifluoroacetic Acid Salt (Example 5) and 1-Benzyl-3-[(2'-tert-butylaminosulfonyl-[1,1']-biphen-4-yl)aminocarbonyl]-4-(3-amidinophenyl)pyrrole, Trifluoroacetic Acid salt (Example 6).

A solution of 1-benzyl-3-[(2'-tert-butylaminosulfonyl-[1,1']-biphen-4-yl)aminocarbonyl]-4-(3-cyanophenyl)pyrrole (0.25 g, 0.42 mmol) in 50 mL of anhydrous methanol was cooled to 0° C. Anhydrous HCl gas was bubbled through the solution for about 30 min (until solution saturated). The flask was sealed and allowed to stand for 16 h at 0° C. The reaction mixture was concentrated in vacuo. The resulting solid was dissolved in 20 mL of anhydrous methanol, ammonium carbonate (0.20 g, 2.1 mmol) was added, and the mixture was allowed to stir at room temperature for 24 h. The reaction mixture was concentrated in vacuo and purified by prep HPLC (C18 reverse phase column, elution with a $H_2O/CH_3CN$ gradient with 0.5% TFA) to afford 120 mg (40%) of 1-benzyl-3-[(2'-aminosulfonyl-[1,1']-biphen-4-yl)aminocarbonyl]-4-(3-amidinophenyl)pyrrole, trifluoroacetic acid salt (Example 5) as a white powder following lyophilization. MS (ESI) 550.3 (M+H)+. The preparation also afforded 40 mg (13%) of 1-benzyl-3-[(2'-tert-butylaminosulfonyl-[1,1'-biphen-4-yl)aminocarbonyl]-4-(3-amidinophenyl)pyrrole, trifluoroacetic acid salt (Example 6) as a white powder following lyophilization. MS (ESI) 606.5 (M+H)+.

Examples 7 and 8

1-(3-Amidinophenyl)-4-[(2'-aminosulfonyl-[1,1']-biphen-4-yl)aminocarbonyl]-imidazole (Example 7) and 1-(3-Amidinophenyl)-4-[(2'-tert-butylaminosulfonyl-[1,1']-biphen-4-yl) aminocarbonyl]-imidazole (Example 8)

Part A: Preparation of 4-[(2'-tert-Butylaminosulfonyl-[1,1']-biphen-4-yl)aminocarbonyl]-imidazole To a suspension of 4-imidazolecarboxylic acid (168 mg, 1.5 mmol) in $CH_3CN$ (30 mL) was added thionyl chloride (714 mg, 6 mmol), and the resulting mixture was heated at 80° C. for 2 hours. After removal of volatiles, a yellow residue reacted with 4-[(o-$SO_2$-t-Bu)-phenyl]aniline (304 mg, 1 mmol) in pyridine (10 mL) at room temperature for 24 hours. Evaporation of the pyridine gave a residue which was dissolved in EtOAc and washed with water, brine, and dried over $MgSO_4$. Concentration and purification by column chromatography of the crude material provided the title compound (378 mg, 95% yield). $^1$HNMR ($CD_3OD$) δ: 8.10 (dd, J=7.7 Hz, 1.1 Hz, 1H), 7.79 (d, J=3.7 Hz, 2H), 7.76 (d, J=8.4 Hz, 2H), 7.58 (td, J=7.7 Hz, J=1.5 Hz, 1H), 7.49 (dd, J=8.1 Hz, J=1.5 Hz, 1H), 7.45 (d, J=8.4 Hz, 2H), 7.34 (dd, J=7.7 Hz, J=1.5 Hz, 1H), 1.06 (s, 9H); LRMS: 399.3 (M+H)$^+$.

Part B: Preparation of 1-(3-Cyanophenyl)-4-[(2'-tert-butylaminosulfonyl-[1,1']-biphen-4-yl)aminocarbonyl]-imidazole 4-[(2'-tert-Butylaminosulfonyl-[1,1']-biphen-4-yl) aminocarbonyl]-imidazole was heated with 3-fluorobenzonitrile (121 mg, 1mmol) in the presence of $K_2CO_3$ in DMF at 100° C. for 8 hours to give the title compound in almost quantitative yield. $^1$HNMR (acetone-$d_6$) δ: 9.47 (s, 1H), 8.39 (d, J=1.5 Hz, 1H), 8.34 (d, J=1.5 Hz, 1H), 8.25 (d, J=1.5 Hz, 1H), 8.15–8.10 (m, 1H), 8.02 (d, J=8.4 Hz, 2H), 7.88–7.79 (m, 2H), 7.65 (td, J=7.3 Hz, J=1.5 Hz, 1H), 7.56 (dd, J=7.7 Hz, J=1.5 Hz, 1H), 7.50 (d, J=8.4 Hz, 2H), 7.38 (dd, J=8.4 Hz, J=1.5 Hz, 1H), 2.80 (s, 1H), 1.03 (s, 9H); LRMS: 500.1 (M+H)$^+$.

Part C: Preparation of 1-(3-Amidinophenyl)-4-[(2'-aminosulfonyl-[1,1']-biphen-4-yl)aminocarbonyl]-imidazole (Example 7) and 1-(3-Amidinophenyl)-4-[(2'-tert-butylaminosulfonyl-[1,1']-biphen-4-yl)aminocarbonyl]-imidazole (Example 8)

1-(3-Cyanophenyl)-4-[(2'-tert-butylaminosulfonyl-[1,1']-biphen-4-yl)aminocarbonyl]-imidazole was further subjected to a Pinner reaction by standard procedures to give Examples 7 (309 mg, 62% yield) and 8 (67 mg, 12% yield).

For Example 7: $^1$HNMR ($CD_3OD$) δ: 8.32 (d, J=1.4 Hz, 2H), 8.12 (s, 1H), 8.10 (d, J=8.1 Hz, 1H), 8.08 (dd, J=7.7 Hz, J=1.4 Hz, 1H), 7.88–7.81 (m, 2H), 7.78 (d, J=8.4 Hz, 2H), 7.61 (td, J=7.7 Hz, J=1.5 Hz, 1H), 7.52 (td, J=7.7 Hz, J=1.5 Hz, 1H), 7.44 (d, J=8.4 Hz, 2H), 7.35 (dd, J=7.3 Hz, J=1.1 Hz, 1H); $^{13}$C NMR ($CD_3OD$) δ: 167.59, 162.59, 143.08, 141.63, 139.32, 138.97, 138.68, 137.58, 137.33, 133.72, 132.94, 132.44, 131.62, 131.28, 128.72, 128.66, 128.49, 127.66, 122.94, 122.12, 121.00; ESMS: 461.3 (M+H)$^+$; HRMS: 461.1387 (obs.), 461.1396 (calcd.).

For Example 8: $^1$HNMR ($CD_3OD$) δ: 8.33 (s, 2H), 8.12 (s, 1H), 8.10 (dd, J=8.4 Hz, J=1.5 Hz, 1H), 8.05 (dd, J=8.1 Hz, J=2.2 Hz, 1H), 7.88–7.80 (m, 3H), 7.79 (d, J=8.4 Hz, 2H), 7.61 (td, J=7.7 Hz, J=1.5 Hz, 1H), 7.53 (td, J=7.7 Hz, J=1.2 Hz, 1H), 7.47 (d, J=8.4 Hz, 2H), 7.35 (dd, J=7.3 Hz, J=1.5 Hz, 1H), 1.02 (s, 9H); $^{13}$C NMR ($CD_3OD$) δ: 167.58, 162.57, 143.51, 141.65, 139.02, 138.68, 138.68, 137.30, 133.89, 133.05, 132.44, 131.64, 131.52, 128.72, 129.53, 128.77, 128.50, 127.65, 122.96, 122.12, 120.99, 55.06, 30.11; ESMS: 517.4 (M+H)$^+$; HRMS: 517.2025 (obs.), 517.2022 (calcd.); Anal.: ($C_{27}H_{28}N_6O_3S_1$+1.35TFA+0.17HCl+0.6$H_2O$) C, H, N, S, F, Cl.

Example 9

1-(3-Amidinophenyl)-2-[(2'-aminosulfonyl-[1,1']-biphen-4-yl)aminocarbonyl]-imidazole Part A: Preparation of 1-(3-Cyanophenyl)imidazole 3-Fluorobenzonitrile (4.84 g, 40 mmol) was heated with imidazole (2.72 g, 40 mmol) in the presence of $K_2CO_3$ in DMF at 100° C. for 8 hours to give the title compound as a white solid in quantitative yield. $^1$HNMR ($CDCl_3$) δ: 7.89 (s, 1H), 7.70 (d, J=0.8 Hz, 1H), 7.68–7.58 (m, 3H), 7.30 (d, J=1.0 Hz, 1H), 7.26 (s, 1H); LRMS: 170 (M+H)$^+$.

Part B: Preparation of Methyl 1-(3-Cyanophenyl)imidazol-2-yl Carboxylate 1-(3-Cyanophenyl)imidazole (1.52 g, 9 mmol) was slowly treated with n-BuLi (1.6 M, 6.3 mL) in THF (60 mL) at −78° C. for 40 minutes and was then slowly quenched with chloromethylformate (942 mg, 10 mmol) at this temperature. The resulting mixture was stirred at −78° C. and warmed to room temperature over 2 hours and then poured into water and ethyl acetate. The organic layer was separated and washed with water, brine, and dried over $MgSO_4$. After removal of the ethyl acetate the residue was purified by column chromatography with ethyl acetate and methylene chloride (1:1) to afford the title compound (1.33 g, 65%) as a white solid. $^1$HNMR ($CDCl_3$) δ: 7.80–7.77 (m, 1H), 7.65–7.61 (m, 3H), 7.33 (s, 1H), 7.20 (s, 1H); LRMS: 228 (M+H)$^+$.

Part C: Preparation of 1-(3-Cyanophenyl)-2-[(2'-tert-butylaminosulfonyl-[1,1']-biphen-4-yl)aminocarbonyl]-imidazole To a-stirred solution of 4-[(o-$SO_2$tBu)-phenyl]aniline (304 mg, 1 mmol) in $CH_2Cl_2$ (20 mL) was slowly added trimethylaluminum (2M in hexane, 1 mL) at 0° C. and the resulting mixture was warmed to room temperature over 15 minutes. After addition a solution of methyl 1-(3-cyanophenyl)imidazol-2-yl carboxylate in $CH_2Cl_2$ (5 mL) and the resulting mixture was refluxed for 2 hours. The mixture was quenched with water, diluted with ethyl acetate and filtered through Celite. The organic layer was separated, washed with water, and brine and dried over $MgSO_4$. After removal of the ethyl acetate, a residue was purified by column chromatography with ethyl acetate and methylene chloride (1:1) to afford the title compound (260 mg, 52%) as a white solid. $^1$HNMR ($CDCl_3$) δ: 9.41 (s, 1H), 8.15 (dd, J=7.7 Hz, J=1.5 Hz, 1H), 7.78 (dd, J=7.3 Hz, J=1.1 Hz, 1H), 7.74–7.57 (m, 6H), 7.55 (td, J=7.7 Hz, J=1.1 Hz, 1H), 7.49 (dd, J=8.8 Hz, J=1.8 Hz, 2H), 7.29 (dd, J=8.1 Hz, J=1.5 Hz, 1H), 7.28 (d, J=0.8 Hz, 1H), 7.22 (d, J=0.8 Hz, 1H), 3.64 (s, 1H), 0.99 (s, 9H); LRMS: 500.1 (M+H)$^+$.

Part D: Preparation of 1-(3-Amidinophenyl)-2-[(2'-aminosulfonyl-[1,1']-biphen-4-yl)aminocarbonyl]-imidazole 1-(3-Cyanophenyl)-2-[(2'-tert-butylaminosulfonyl-[1,1']-biphen-4-yl)aminocarbonyl]-imidazole was subjected to the Pinner reaction to form the title compound (120 mg, 50%): $^1$HNMR ($CD_3OD$) δ: 8.08 (dd, J=7.7 Hz, J=1.1 Hz, 1H), 7.91–7.88 (m, 2H), 7.83 (dd, J=8.4 Hz, J=1.5 Hz, 1H), 7.74 (t, J=8.0 Hz, 1H), 7.65 (d, J=8.4 Hz, 2H), 7.58 (dd, J=7.3 Hz, J=1.1 Hz, 1H), 7.50 (s, 2H), 7.39 (d, J=8.4 Hz, 2H), 7.32 (s, 1H), 7.30 (dd, J=7.3 Hz, J=1.1 Hz, 1H); ESMS: 461 (M+H)$^+$.

Example 10

1-(3-Amidinophenyl)-3-methyl-5-[(2'-aminosulfonyl-[1,1']-biphen-4-yl)aminocarbonyl]-pyrazole, Trifluoroacetic Acid

Part A: Preparation of Ethyl 1-(3-Bromophenyl)-3-methyl-pyrazol-5-yl Carboxylate and Ethyl 1-(3-Bromophenyl)-5-methyl-pyrazol-3-yl Carboxylate 2-Bromophenylhydrazine hydrochloride (6.5 g, 0.029 mol) was added in portions to a ethanolic solution of 3-methoxy-trichloroacetylcrotonate (Fischer et. al. *Synthesis* 1991, 83). The reaction mixture was refluxed for 48 h cooled and concentrated. The residue was dissolved in ethyl acetate (100 mL) and washed with HCl (1N, 50 mL), brine (50 mL) and dried (magnesium sulfate). Evaporation afforded an oil which was subjected to silica gel column chromatography (hexane:ethylacetate, 6:1) to afford ethyl 1-(3-bromophenyl)-5-methyl-pyrazol-3-yl carboxylate (3.73 g) and ethyl ethyl 1-(3-bromophenyl)-3-methyl-pyrazol-5-yl carboxylate (3.65 g) as pure compounds. The pyrazole carboxylate obtained this way were used directly in part B.

Part B: Preparation of Ethyl 1-(3-Cyanophenyl)-3-methyl-pyrazol-5-yl Carboxylate Ethyl 1-(3'bromophenyl)-3-methyl-pyrazol-5-yl carboxylate (2.3 g) was dissolved in N-methyl-pyrrolidinone (4 mL) and to this solution was added CuCN (1 g). The reaction mixture was refluxed for 2 h then stirred at room temperature overnight. The mixture was quenched with water (100 mL) and the organics were extracted with ethylacetate (2×100 mL) and dried (magnesium sulfate). Silica gel column chromatography (hexane:ethylacetate, 3:1) then afforded the title compound (0.59 g). $^1$HNMR (CDCl$_3$) δ: 7.76 (t, 1H), 7.70 (dd, 1H), 7.58 (t, 1H), 6.86 (s, 1H), 4.3 (q, 2H), 2.36 (s, 3H), 1.31 (t, 3H) ppm; IR (neat), 2230, 1728, 1586, 1540, 1494, 1438, 1298, 1242, 1106, 1046, 760, 682 cm$^{-1}$. Chemical Ionization mass spectrum m/z (rel. intensity) 256 (M+H, 100).

Part C: Preparation of 1-(3-Cyanophenyl)-3-methyl-pyrazol-5-yl Carboxylic Acid

Ethyl 1-(3-cyanophenyl)-3-methyl-pyrazol-5-yl carboxylate (0.55 g) was dissolved in THF (20 mL) and to this was added LiOH (0.5M, 5, 6 mL). The reaction mixture was stirred at room temperature for 18 h then quenched with water (50 mL). The unreacted organics were extracted with ethylacetate (2×50 mL). The aqueous layer was acidified and extracted with ethylacetate (2×50 mL) dried (magnesium sulfate) and evaporated to afford pure acid. $^1$HNMR (DMSO d$_6$) δ: 8.02 (t, 1H), 7.91 (d, 1H), 7.82 (dd, 1H), 7.09 (t, 1H), 6.89 (s, 1H), 2.27 (s, 3H) ppm; IR (PEC) 2930, 2232, 1724, 1710, 1540, 1496, 1458, 1276, 1230, 1186, 1146, 1112, 900, 768, 754, 690 cm$^{-1}$; Chemical ionization mass spectrum m/z (rel. intensity) 228 (M+H, 100).

Part D: Preparation of 1-(3-Cyanophenyl)-3-methyl-5-[(2'-tert-butylaminosulfonyl-[1,1']-biphen-4-yl)aminocarbonyl]-pyrazole To a dichloromethane solution (20 mL) of 1-(3-cyanophenyl)-3-methyl-pyrazol-5-yl carboxylic acid (0.2 g) was added oxalyl chloride (0.11 mL). The reaction mixture was stirred at room temperature for 2 h then to this solution was added 2-tert-butylsulfonamide-1-biphenyl aniline (0.27 g) and triethylamine (0.5 mL). The reaction mixture was stirred at room temperature for 24 h then quenched with water (50 mL) and the organics were extracted with ethylacetate (2×50 mL), washed with brine (50 mL) and dried (magnesium sulfate). Evaporation afforded an oil which was chromatographed on silica gel column (dichloromethane:MeOH, 9:1) to afford the title compound (0.45g). $^1$HNMR (CDCl$_3$) δ: 8.16 (d, 1H), 8.05 (s, 1H), 7.8 (d, 1H), 7.76 (d, 1H), 7.68 (d, 3H), 7.58 (m, 2H), 7.50 (md, 3H), 7.30 (d, 1H), 6.76 (s, 1H), 3.64 (s, 1H), 2.42 (s, 3H), 1.03 (s, 9H) ppm; IR(PEC), 3320, 2976, 2232, 1682, 1592, 1540, 1522, 1488, 1464, 1438, 1368, 1320, 1242, 1152, 1128, 758, 682, 608 cm$^{-1}$; Chemical ionization mass spectum m/z (rel intensity) 458 (M=H, 100).

Part E: Preparation of 1-(3-Amidinophenyl)-3-methyl-5-[(2'-aminosulfonyl-[1,1']-biphen-4-yl)aminocarbonyl]-pyrazole, Trifluoroacetic Acid 1-(3-Cyanophenyl)-3-methyl-5-[(2'-tert-butylaminosulfonyl-[1,1']-biphen-4-yl)aminocarbonyl]-pyrazole (0.39 g) was dissolved in a saturated HCl solution of anhydrous MeOH (20 mL). The reaction mixture was stirred at room temperature for 24 h then MeOH was evaporated. The residue was redissolved in MeOH (20 mL) and excess ammonium carbonate added. The reaction mixture was stirred at room temperature for 18 h. MeOH was evaporated and the residue was purified via HPLC to afford the desired compound as its TFA salt (0.15 g). $^1$HNMR (DMSO d$_6$) δ: 10.66 (s, 1H), 9.44 (s, 1.5H), 9.09 (s, 1.5H), 8.03 (d, 1H), 7.97 (s, 1H), 7.83 (t, 1H), 7.75 (d, 1H), 7.70 (d, 2H), 7.62 (m, 2H), 7.37 (d, 2H), 7.32 (d, 1H), 7.27 (s, 2H), 7.03 (s, 1H), 2.50 (s, 3H) ppm; IR (PEC) 3288, 1704, 1660, 1592, 1526, 1484, 1438, 1322, 1206, 1160, 762, 724 cm$^{-1}$; High resolution mass spectrum calcd. for $C_{24}H_{22}N_6O_3S$ 475.155236, found 475.153767.

Example 11

1-(3-Amidinophenyl)-3-methyl-5-[(2'-aminosulfonyl-[1,1']-biphen-4-yl)carbonylamino]-pyrazole, Trifluoroacetic Acid

Part A. Preparation of 5-Amino-1-(3'cyanophenyl)-3-methylpyrazole.

3-aminocrotonitrile (1 g, 12.2 mmol) and 3-cyanophenyl hydrazine hydrochloride (2 g, 11.8 mmol) were combined and heated to reflux in 1:1 ethanol/acetic acid (20 mL) for 4 h. The reaction was concentrated and the residue basified with diluted NaOH and extracted with ethyl acetate. The crude product was purified by flash chromatography on silica gel using hexanes/ethyl acetate (4:1) as eluent to afford 1.2 g of a still impure amine. This amine was dissolved in dilute HCl and extracted with ethyl acetate. The aqueous layer was basified with NaOH and extracted with ethyl acetate and dried (MgSO$_4$) to afford 0.66 g (28%) of amine; $^1$HNMR (CDCl$_3$) δ: 7.97 (s, 1H), 7.92 (m, 1H), 7.57 (s+d, 2H), 5.51 (s, 1H), 3.75 (s, 2H), 2.23 (s, 3H); MS (H2O/GC) m/z 199 (M+H$^+$).

Part B. Preparation of 1-(3'Cyanophenyl)-3-methyl-5-((4'-bromophenyl)carbonylamino)pyrazole.

To the product of part A (0.66 g, 3.3 mmol) in methylene chloride (20 mL) at 0° C. was added 2M trimethylaluminum (8.3 mL, 16.7 mmol) in heptane. The mixture was stirred for 15 minutes and methyl-4-bromobenzoate (0.72 g, 3.3 mmol) was added. The reaction was stirred overnight. The reaction was quenched with 1N HCl and extracted with methylene chloride and dried (Na$_2$SO$_4$). Recrystallization from methylene chloride/hexanes yielded 0.48 g (45%) of the title compound; $^1$HNMR (CDCl$_3$) δ: 7.86 (s, 1H), 7.78 (d, J=7.69 Hz, 1H), 7.67 (d, J=7.69 Hz, 1H), 7.63 (m, 4H), 7.60 (m, 1H), 6.52 (s, 1H), 2.36 (s, 3H); MS (ESI) m/z 381.1–383.1 (M+H$^+$).

Part C. Preparation of 1-(3-Cyanophenyl)-3-methyl-5-[(2'-aminosulfonyl-[1,1']-biphen-4-yl)carbonylamino]-pyrazole, Trifluoroacetic Acid.

A mixture of the above part B amide (0.4 g, 1 mmol), 2-(t-butylsulfonamide)-phenylboronic acid (0.38 g, 1.5 mmol), 2M Na$_2$CO$_3$ (1.3 mL), toluene (10 mL) and ethanol (10 mL) was degassed with nitrogen and then tetrakistriphenylphosphine palladium (10 mg) was added. The reaction was heated to reflux overnight then cooled, filtered and concentrated. The residue was diluted with water and then extracted with ethyl acetate and dried ($MgSO_4$). The crude product was purified by flash chromatography on silica gel using hexanes/ethyl acetate (2:1) as eluent to afford 0.46 g (86%) of a foam; $^1$HNMR ($CDCl_3$) δ: 7.94 (m, 5H), 7.63 (m, 7H), 7.32 (d, J=7.7 Hz, 1H), 6.55 (s, 1H), 4.13 (s, 1H), 2.39 (s, 3H), 0.99 (s, 9H); MS m/z 514.3 (M+H$^+$).

Part D. Preparation of 1-(3-Amidinophenyl)-3-methyl-5-[(2'-aminosulfonyl-[1,1']-biphen-4-yl)carbonylamino]-pyrazole, Trifluoroacetic Acid.

The product from part D was then subjected to the standard Pinner amidine sequence to obtain the desired benzamidine after preparative HPLC (acetonitrile/water, containing 0.05% TFA) as colorless crystals (44% yield). $^1$HNMR (DMSO-$d_6$) δ: 10.57 (s, 1H), 9.43 (s, 1.5H), 9.14 (s, 1.5H), 8.07 (s, 1H), 8.05 (m, 1H), 7.94 (d, J=6.96 Hz, 1H), 7.89 (d, J=8.42 Hz, 2H), 7.76 (m, 2H), 7.65 (m, 2H), 7.53 (d, J=8.42 Hz, 2H), 7.39 (s, 2H), 7.35 (m, 1H), 2.29 (s, 3H); MS (ESI) m/z 475.2 (M+H$^+$); Analysis calculated for $C_{24}H_{22}N_6O_3S_1$ (TFA) 1.4 (H2O) 1: C, 49.36; H, 3.93; N, 12.89; found C, 49.69; H, 3.71; N, 12.77.

Example 12

1-(3-Amidinophenyl)-3-methyl-5-(2'-(5"-$CF_3$-tetrazolyl)-[1,1']-biphen-4-yl)aminocarbonyl) pyrazole Part A. Preparation of 2-(5'-$CF_3$-Tetrazolyl)biphenylaniline.

To a cold (0° C.) $CCl_4$ (3 mL) solution of 2'-trifluoroacetanilide-1-nitro-biphenyl (0.15 g, 0.48 mmoL) was added triphenylphosphine (0.24 g, 0.97 mmol) and the reaction stirred cold for 0.15 min, allowed to warm to room temperature and then gently refluxed overnight. Evaporation of the solvent afforded a residue which was treated with hexane (20 mL) filtered and evaporated to afford crude chloroimine which was dissolved in acetonitrile (10 mL). To this solution was added sodium azide (0.038 g, 0.58 mmoL) and the reaction mixture was stirred at room temperature over night. Evaporation of the solvent followed by purification via silica gel flash chromatography (hexane/ethylacetate 4:1) afforded the desired nitro-biphenyltetrazole precursor (0.12 g) as a pale yellow solid. $^1$HNMR ($CDCl_3$) δ: 8.2 (d, 2H), 7.80 (t, 1H), 7.70 (t, 1H), 7.61 (d, 1H), 7.50 (d, 1H), 7.3 (d, 2H) ppm; Ammonia CI mass spectrum analysis m/z (rel. intensity) 353.0 (M+$NH_4^+$100).

The above nitro biphenyl compound was then hydrogenated in ethanol (20 mL) over 10% Pd/C for 6 h to afford after filtration the title compound (0.11 g). $^1$HNMR ($CDCl_3$) δ: 7.70 (t, 1H), 7.59 (d, 1H), 7.50 (t, 1H), 7.40 (d, 1H), 6.8 (d, 2H0, 6.55 (d, 2H), 3.75 (bd, 2H) ppm; Ammonia CI mass spectrum analysis m/z (rel. intensity) 323 (M+$NH_4^+$100).

Part B. Preparation of 1-(3-Cyanophenyl)-3-methyl-5-(2'-(5"-$CF_3$-tetrazolyl)-[1,1']-biphen-4-yl)aminocarbonyl) pyrazole.

The 2-(5'-$CF_3$-tetrazolyl)-[1,1']-biphenylaniline was then coupled to the 1-(3-cyanophenyl)-3-methyl-pyrazole-5-carboxylic acid (0.09 g, 0.39 mmoL) via the acid chloride methodology described previously to afford the title compound (0.12 g) as a colorless solid after silica gel column chromatography (dichloromethane methanol, 9.6:0.4); $^1$HNMR ($CDCl_3$) δ: 7.82 (s, 1H), 7.70 (m, 4H), 7.61 (m, 2H), 7.45 (m, 3H), 7.05 (d, 2H), 6.65 (s, 1H), 3.50 (d, 1H), 2.40 (s, 3H) ppm; Ammonia CI mass spectrum analysis m/z (rel. intensity) 532.0 (M+$NH_4^+$, 100).

Part C. Preparation of 1-(3-Amidinophenyl)-3-methyl-5-(2'-(5"-$CF_3$-tetrazolyl)-[1,1']-biphen-4-yl)aminocarbonyl) pyrazole.

The product from part B was then subjected to the Pinner amidine reaction sequence as described previously to afford the title; compound as colorless crystal s after prep. HPLC (acetonitrile:water containing 0.05% TFA); $^1$HNMR (DMSOd$_6$) δ: 10.61 (s, 1H), 9.42 (s, 2H), 9.12 (m, 2H), 7.94 (s, 1H), 7.89 (d, 1H), 7.82 (t, 2H), 7.75 (m, 4H), 7.62 (d, 2H), 7.02 (s, 2H), 6.98 (s, 1H), 2.32 (s, 3H) ppm; ESI mass spectrum analysis m/z (rel. intensity) 532.4 (M+H, 100); High resolution mass spectrum calcd. for CHNFO 532.182116, found 532.18271.

Example 13

1-(3-Amidinophenyl)-5-[(2'-aminosulfonyl-[1,1']-biphen-4-yl)aminocarbonyl]-4-chloro-3-methyl-pyrazole, Trifluoroacetic Acid Part A. Preparation of 4-Chloro-1-(3'cyanophenyl)-3-methyl-5-((2'-t-butylaminosulfonyl-[1,1']-biphen-4-yl) aminocarbonyl)pyrazole.

Chlorination of methyl-1-(3'cyanophenyl)-3-methyl-pyrazole-5-carboxylate (255 mg, 1 mmol) with NCS (139 mg, 1.05 mmol) in refluxing acetonitrile (10 mL) for 3 hours gave the desired 4-chloropyrazole carboxylate in quantitative yield. $^1$HNMR ($CDCl_3$) δ: 7.72–7.70 (m, 2H), 7.65–7.54 (m, 2H), 4.31 (q, J=7.0 Hz, 2H), 2.35 (s, 3H), 1.28 (t, J=7.0, 3H); LRMS: 290 (M+H). The ester in dichloromethane (5 mL) was added to a pretreated dichloromethane (20 mL) solution of 2'-t-butyl-sulfonamide-biphenylaniline and trimethylaluminum (2M in hexane, 1 mL) at 0° C. and the resulting mixture was warmed to room temperature over 15 minutes then refluxed for 3 hours. The mixture was quenched with water, extracted with $CH_2Cl_2$ (200 mL), filtered through Celite. The organic layer was separated, washed with water, and brine and dried over $MgSO_4$. After removal of the $CH_2Cl_2$, a residue was purified by column chromatography with ethylacetate and methylene chloride (1:1) to afford the title compound (330 mg, 60.3%) as a white solid. $^1$HNMR ($CDCl_3$) δ: 8.38 (s, 1H), 8.17 (dd, J=8.7, J=1.5 Hz, 1H), 7.78 (d, J=1.5 Hz, 1H), 7.73–7.69 (m, 2H), 7.67 (d, J=8.4 Hz, 2H), 7.60 (d, J=7.7 Hz, 1H), 7.55 (dd, J=7.7 Hz, J=1.5 Hz, 1H), 7.52 (d, J=8.7 Hz, 2H), 7.51–7.48 (m, 1H), 7.29 (dd, J=7.3 Hz, J=1.5 Hz, 1H), 3.62 (s, 1H), 2.40 (s, 3H), 1.03 (s, 9H); LRMS: 548 (M+H).

Part B. Preparation of 1-(3-Amidinophenyl)-5-[(2'-aminosulfonyl-[1,1']-biphen-4-yl)aminocarbonyl]-4-chloro-3-methyl-pyrazole, Trifluoroacetic Acid The product of part A was then subjected to the standard Pinner amidine sequence to afford after preparation HPLC and purification with $CH_3CN$—$H_2O$-TFA the title compound (350 mg). $^1$HNMR ($CD_3OD$) δ: 8.09 (dd, J=8.1 Hz, J=1.4 Hz, 1H), 8.00 (t, J=1.8 Hz, 1H), 7.81 (td, J=7.7 Hz, J=1.9 Hz, 2H), 7.71 (d J=8.1 Hz, 1H), 7.64 (d, J=8.4 Hz, 2H), 7.59 (dd, J=7.3 Hz, J=1.4 Hz, 1H), 7.52 (td, J=7.7 Hz, J=1.4 Hz, 1H), 7.42 (d, J=8.4 Hz, 2H), 7.32 (dd, J=8.4 Hz, J=1.4 Hz, 1H), 2.36 (s, 3H); ESMS: 509.1 (M+H)$^+$.

Example 14

1-(3-Amidinophenyl)-5-((2'-t-butylaminosulfonyl-[1,1']-biphen-4-yl)aminocarbonyl)-3-trifluoromethylpyrazole Part A. Preparation of 1-(3-Cyanophenyl)-5-methyl-3-trifluoromethylpyrazole.

1,1,1-Trifluoro-2,4-pentanedione (1.35 mL, 11.2 mmol) was combined with 3-bromophenylhydrazine hydrochloride (3 g, 13.4 mmol) in glacial acetic acid (20 mL), 2-methoxyethanol (10 mL) and heated to reflux 2 h. The solvents were removed in vacuo and the residue was dissolved in ethyl acetate. The ethyl acetate solution was washed successively with dilute HCl, sat'd NaHCO$_3$, brine, and dried (MgSO$_4$). The crude material was purified by flash chromatography on silica gel using hexanes/ethyl acetate (8:1) as eluent. The product was an 88/12 mixture of the two isomers with the desired 5-methylpyrazole isomer predominating. This mixture was combined with 1-methyl pyrrolidine (7 mL) and copper cyanide (1.3 g, 14.5 mmol) and heated to reflux overnight. The reaction was cooled, diluted with ethyl acetate and filtered. The filtrate was washed with water and brine and dried (MgSO$_4$). Purification by flash chromatography on silica gel afforded the desired 5-methylpyrazole isomer (0.66 g, 24%); $^1$HNMR (CDCl$_3$) δ: 7.81 (d, J=1.8 Hz, 1H), 7.77 (m, 2H), 7.67 (t, J=8.06 Hz, 1H), 6.52 (s, 1H), 2.42 (s, 3H); MS (NH$_3$) m/z 252.1 (M+H$^+$), 269.2 (M+NH$_4^+$).

Part B. Preparation of 1-(3-Cyanophenyl)-5-hydroxymethyl-3-trifluoromethylpyrazole.

To the compound obtained in part A (0.65 g, 2.59 mmol), n-bromosuccinimide (0.48 g, 2.7 mmol), and benzoyl peroxide (20 mgs) were added and the reaction mixture was heated to reflux in carbon tetrachloride (20 mL) for 6 h. The reaction was cooled, filtered, and concentrated to yield the crude bromide. The bromide was combined with 1:1 dioxane/water (20 mL) and calcium cabonate (0.46 g, 4.6 mmol) and heated on a steam bath for 6 h. The reaction was cooled, filtered and the filtrate concentrated. The aqueous residue was extracted with ethyl acetate and dried (MgSO$_4$). The crude product was purified by flash chromatography on silica gel using hexanes/ethyl acetate (1:1) as eluent to afford a yellow solid (0.31 g, 44%); $^1$HNMR (CDCl$_3$) δ: 8.07 (s, 1H), 8.01 (dd, J=2.2, 8.05 Hz, 7.77 (d, J=7.7 Hz, 1H), 7.68 (t, J=8.05 Hz, 1H), 6.76 (s, 1H), 4.72 (d, J=5.85 Hz, 2H), 2.02 (t, J=5.86 Hz, 1H); MS (NH$_3$) m/z 268.1 (M+H$^+$), 285 (M+NH$_4^+$).

Part C. Preparation of 1-(3-Cyanophenyl)-3-trifluoromethylpyrazole-5-carboxylic Acid.

To the above alcohol (0.18 g, 0.67 mmol) was added acetonitrile (5 mL), sodium periodate (0.3 g, 1.4 mmol) in water (5 mL), and one crystal of ruthenium(III)chloride hydrate. The reaction was stirred for 18 h at room temperature. The reaction was filtered and concentrated. The aqueous residue was extracted with ethyl acetate and dried (MgSO$_4$) to give 0.17 g (89.9%) of acid. $^1$HNMR (CDCl$_3$+DMSO-d$_6$) δ: 7.82 (d, J=1.47 Hz), 7.78 (dd, J=8.0, 1.47 Hz, 1H), 7.63 (t, J=7.3, 8.42, 1H), 7.29 (s, 1H); MS (ESI-) m/z 280.2 (M-H).

Part D. Preparation of 1-(3-Cyanophenyl)-5-((2'-t-butylaminosulfonyl-[1,1']-biphen-4-yl)aminocarbonyl)-3-trifluoromethylpyrazole.

To the acid (0.35 g, 1.2 mmol) in methylene chloride was added oxalyl chloride (0.15 mL, 1.7 mmol) and 2 drops of DMF. The reaction was stirred for 2 h at room temperature then concentrated in vacuo. The acid chloride was combined with 2'-t-butylsulfonamide-biphenylaniline (0.38 g, 1.25 mmol), methylene chloride (10 mL), and N,N-dimethylaminopyridine (0.38 g, 3.1 mmol). The reaction was stirred overnight at room temperature. The reaction was washed with dilute HCl, sat'd NaHCO$_3$, brine and dried (MgSO$_4$). The crude product was purified by flash chromatography on silica gel using hexanes/ethyl acetate (1:1) as eluent to afford 0.41 g (58%) of a yellow foam. $^1$HNMR (CDCl$_3$+DMSO-d$_6$) δ: 9.88 (s, 1H), 8.18 (dd, J=7.69, 1.47 Hz, 1H), 7.87 (d, J=1.83 Hz, 1H), 7.79 (m, 4H), 7.64 (m, 3H), 7.50 (m, 3H), 7.30 (d, J=7.3 Hz, 1H), 3.67 (s, 1H), 1.02 (s, 9H); MS (ESI) m/z 590.14 (M+Na).

Part E. Preparation of 1-(3-Amidinophenyl)-5-((2'-t-butylaminosulfonyl-[1,1']-biphen-4-yl)aminocarbonyl)-3-trifluoromethylpyrazole.

The product from part D was then subjected to the standard Pinner amidine sequence to obtain the title compound after preparative HPLC (acetonitrile/water, containing 0.05% TFA) as colorless crystals (46% yield). $^1$HNMR (DMSO-d$_6$) δ: 10.85 (s, 1H), 9.47 (s, 1.5H), 9.20 (s, 1.5H), 8.05 (s, 1H), 8.04 (dd, J=7.69, 1.84 Hz, 1H), 7.96 (m, 2H), 7.82 (d, J=7.69 Hz, 1H), 7.75 (s, 1H), 7.68 (d, J=8.79 Hz, 2H), 7.62 (m, 2H), 7.39 (d, J=8.43 Hz, 2H), 7.32 (s+m, 3H); MS (ESI) m/z 529.03 (M+H$^+$); Analysis calculated for $C_{24}H_{19}F_3N_6O_3S_1$ (TFA) 1.2 (H$_2$O) 1: C, 46.40; H, 3.27; N, 12.30; found C, 46.11; H, 3.06; N, 12.05.

Example 15

1-(3-Amidinophenyl)-4-methoxy-5-((2'-aminosulfonyl-[1,1']-biphen-4-yl)aminocarbonyl)-3-trifluoromethylpyrazole Part A. Preparation of 1-(3-Bromophenyl)-4-methoxy-5-methyl-3-trifluoromethylpyrazole.

3-Bromophenylhydrazine (9.4 g, 50.5 mmol) and trifluoroacetaldehyde hydrate (8.7 g, 75 mmol) were heated to 100° C. for 1 h. The reaction was cooled, diluted with methylene chloride, washed with brine and dried (MgSO$_4$). To the crude hydrazone was added 40% aqueous pyruvic aldehyde (22.6 g, 126 mmol), MgSO$_4$ (13 g), butyl acetate (150 mL) and several drops of acetic acid and the reaction was heated to reflux overnight. The reaction was filtered and concentrated. The residue was dissolved in 1N NaOH and extracted with diethyl ether. The aqueous layer was acidified with HCl and extracted with ethyl acetate and dried (MgSO$_4$). A crude orange solid (11.3 g, 70%) was collected. To the solid was added acetone (50 mL), K$_2$CO$_3$ (7.3 g, 53 mmol), and iodomethane (8.8 mL, 140 mmol) and the mixture was heated to reflux for 2 h. The reaction was filtered, concentrated and the crude product was purified by flash chromatography on silica gel using hexanes/ethyl acetate (4:1) as eluent to afford 6.9 g (60%) of yellow oil. $^1$HNMR (CDCl$_3$) δ: 7.65 (d, J=1.83 Hz, 1H), 7.58 (dd, J=2.2, 6.96 Hz, 1H), 7.39 (s+m, 2H), 3.85 (s, 3H), 2.31 (s, 3H); MS (H20/GC) m/z 335–337 (M+H$^+$).

Part B. Preparation of 1-(3-Cyanophenyl)-4-methoxy-5-methyl-3-trifluoromethylpyrazole.

1-(3-Bromophenyl)-4-methoxy-5-methyl-3-trifluoromethyl pyrazole (6.9 g, 20.6 mmol) and CuCN (2.8 g, 30.9 mmol) were combined in N-methylpyrrolidinone (12 mL) and heated to reflux for 18 h. The reaction was diluted with water and extracted with ethyl acetate. The organic layers were washed with water, brine and dried (MgSO$_4$). The product was purified by flash chromatography on silica gel using hexanes/ethyl acetate (4:1) as eluent to afford 4.2 g (72%) of yellow solid. $^1$HNMR (CDCl$_3$) δ: 7.79 (s, 1H), 7.74 (m, 2H), 7.66 (d, J=7.3 Hz, 1H), 3.86 (s, 3H), 2.35 (s, 3H); MS (H$_2$O/GC) m/z 282 (M+H$^+$); IR (KBr) 2232, 1588, 1320, 1170, 1120, 804 cm$^{-1}$; Analysis calculated for $C_{13}H_{10}F_3N_{3O1}$: C, 55.52; H, 3.58; N, 14.94; found C, 55.44; H, 3.76; N, 14.95.

Part C. Preparation of 5-Bromomethyl-1-(3-Cyanophenyl)-4-methoxy-3-trifluoromethylpyrazole.

To the product of part B (2.65 g, 9.40 mmol) was added n-bromosuccinimide (1.76 g, 9.90 mmol), CC14 (15 mL) and benzoyl peroxide (10 mg). The reaction was heated to reflux for 4 h, then cooled and filtered. The crude bromide was dissolved in 1:1 dioxane/water (20 mL) and CaCO$_3$ (1.7 g, 16.9 mmol) was added. The reaction was stirred at room temperature overnight. The product was purified by flash chromatography on silica gel using hexanes/ethyl acetate (2:1) as eluent to afford 2.2 g (79%) solid. A sample was recrystallized from methylene chloride/hexanes. $^1$HNMR (CDCl$_3$) δ: 8.10 (m, 1H), 8.05 (dd, J=8, 1.46 Hz, 1H), 7.74 (d, J=7.7 Hz, 1H), 7.66 (t, J=7.69 Hz, 1H), 4.67 (d, J=5.13 Hz, 2H), 3.95 (s, 3H), 2.17 (t, J=5.13 Hz, 1H); MS (ESI) m/z 288.2 (M+H$^+$); Analysis calculated for C$_{13}$H$_{10}$F$_3$N$_{3O2}$: C, 52.53; H, 3.39; N, 14.14; found C, 52.35; H, 3.21; N, 14.13.

Part D. Preparation of 1-(3-Cyanophenyl)-4-methoxy-3-trifluoromethylpyrazole-5-carboxylic Acid.

To the product of part C (0.64 g, 2.2 mmol) in CH$_3$CN (5 mL) at 0° C. was added sodium periodate (0.98 g, 4.5 mmol) in water (5 mL) followed by one crystal of ruthenium(III) chloride. The reaction was stirred cold for 30 minutes, then at room temperature for 30 minutes. The reaction was concentrated and partioned between ethyl acetate and dilute NaOH. The ethyl acetate layer was dried (MgSO$_4$), filterd and concentrated to afford the aldehyde (0.42 g, 66%). The basic layer was acidified, extracted with ethyl acetate and dried (MgSO$_4$) to afford the carboxylic acid (0.16 g , 23%). To the aldehyde (0.42 g , 1.40 mmol) was added ethanol (50 mL), silver nitrate (0.48 g, 2.8 mmol), and 0.5N NaOH (12 mL). The reaction was stirred 3 h, then filtered through celite and concentrated. The aqueous layer was extracted with ethyl cetate and dried (MgSO$_4$) to yield the title compound (0.4 g, 91%). $^1$HNMR (CDCl$_3$+DMSO-d$_6$) δ: 7.80 (m, 3H), 7.61 (m, 1H), 4.01 (s, 3H).

Part E. Preparation of 1-(3-Cyanophenyl)-4-methoxy-5-((2'-t-butylaminosulfonyl-[1,1']-biphen-4-yl)aminocarbonyl)-3-trifluoromethylpyrazole-5-carboxylic Acid.

To the acid of part D (0.44 g, 1.4 mmol) was added methylene chloride (15 mL), oxalyl chloride (0.17 mL, 1.9 mmol) and 2 drops of DMF. The reaction was stirred for 3 h then, concentrated. To the crude acid chloride was added 2'-t-butylsulfonamide-biphenylaniline (0.43 g, 1.4 mmol), methylene chloride (15 mL), and triethylamine (0.8 mL, 5.6 mmol). The reaction was stirred 18 h then, diluted with methylene chloride and washed with dilute HCl, sat'd NaHCO$_3$, brine and dried (MgSO$_4$) to yield 0.6 g (52%) foam. $^1$HNMR (CDCl$_3$) δ: 9.03 (s, 1H), 8.18 (m, 1H), 7.80 (s, 1H), 7.78 (m, 2H), 7.66 (d, J=8.79 Hz, 2H), 7.65 (m, 1H), 7.56 (m, 2H), 7.52 (d, J=8.79 Hz, 2H), 7.27 (m, 1H), 4.19 (s, 3H), 1.03 (s, 9H); MS (ESI) m/z 598.4 (M+H$^+$).

Part F. Preparation of 1-(3-Amidinophenyl)-4-methoxy-5-((2'-aminosulfonyl-[1,1']-biphen-4-yl)aminocarbonyl)-3-trifluoromethylpyrazole.

The product from part D was subjected to the standard Pinner amidine sequence to obtain the desired benzamidine after preparative HPLC (acetonitrile/water, containing 0.05% TFA) as colorless crystals (46% yield). $^1$HNMR (DMSO-d$_6$) δ: 11.05 (s, 1H), 9.49 (s, 1.5H), 9.22 (s, 1.5H), 8.03 (m, 2H), 7.89 (m, 3H), 7.65 (m+d, J=8.05 Hz, 4H), 7.39 (m+d, J=8.40 Hz, 5H), 3.96 (s, 3H); MS (ESI) m/z 559.4 (M+H$^+$); Anaiysis calculated for C$_{25}$H$_{21}$F$_3$N$_6$O$_4$S (TFA): C, 48.22; H, 3.31; N, 12.50; found C, 47.86; H, 3.34; N, 12.24.

Example 16

1-(3-Aminophenyl)-3-methyl-5-(4'-(imidazol-1-yl-phenyl)aminocarbonyl)pyrazole

Part A. Preparation of 1-(4-Aminophenyl)imidazole.

1-(4-Nitrophenyl)imidazole (5.0 g) and 200 mL of methanol were combined to form a solution at ambient temperature. The addition of a catalytic amount of 10% palladium on carbon turned the solution into a suspension. Placement of the reaction mixture under a hydrogen atmosphere initiated the reduction. The reaction proceeded overnight (15 h) at ambient temperature. Filtration through a celite pad separated out the catalyst. Concentration of the filtrate under reduced pressure gave the title product as a pale yellow solid (3.99 g). $^1$HNMR (DMSO d$_6$) δ: 7.95 (s, 1H), 7.45 (s, 1H), 7.18 (d, 2H), 6.99 (s, 1H), 6.60 (d, 2H), 5.25 (s, 2H) ppm. LRMS(GC/MS) m/z 160 (M+H, 100).

Part B. Preparation of N-(3-Cyanophenyl)-3-methyl-5-[((4'-imidazol-1-yl)-phenyl)aminocarbonyl]pyrazole.

To 0.203 g of N-(3-cyanophenyl)-3-methyl-pyrazole 5-carboxylic acid and 10 mL dichloromethane was added oxalyl chloride and 2 drops of DMF. The reaction proceeded overnight. Concentration of the reaction mixture and placement under high vacuum gave the crude acid chloride which was then coupled to the product of part A under standard conditions to afford after standard purification techniques the title compound (0.118 g). $^1$HNMR (DMSO-d$_6$) δ: 10.73 (s, 1H) 9.35 (s, 1H) 8.13 (s, 1H) 7.95 (s, 1H) 7.90–7.60 (complex, 8H) 7.00 (s, 1H) 2.30 (s, 3H) ppm. LRMS(ESI) m/z 369.2 (M+H, 100). HRMS(NH$_3$—CI) calc. 369.146384, found 369.145884.

Part C. Preparation of N-(3-Amidinophenyl)-3-methyl-5-[((4'-imidazol-1-yl)-phenyl)aminocarbonyl]pyrazole.

Standard transformation of the benzonitrile obtained in part B to the benzamidine via the ethyl imidate converted 0.113 g of benzonitrile to 0.070 g of the benzamidine bis-TFA salt after HPLC purification. $^1$HNMR (DMSO-d$_6$): 10.65 (s, 1H) 9.40 (s, 2H) 9.00 (s, 2H) 8.19 (s, 1H) 7.90 (s 1H) 7.80–7.55 (complex, 8H), 7.06 (s 1H) 7.00 (s 1H) 2.30 (s, 3H) ppm. LRMS(ESI) m/z 386.1 (M+H, 2) 193.7 (100). HRMS(FAB) calc. 386.172933, found 386.173388.

Example 17

1-(3-Amidinophenyl)-3-methyl-5-[(4'-(2"-sulfonylmethyl)phenoxyphenyl)aminocarbonyl] pyrazole Part A. Preparation of 1-(3-Cyanophenyl)-3-methyl-5-[(4'-(2"-sulfonylmethyl)phenoxyphenyl)aminocarbonyl [pyrazole.

Coupling of 4-(2'-sulfonylmethyl)phenoxy-1-aminophenyl with 1-(3-cyano)phenyl-3-methyl-5-pyrazole carboxylic acid via standard acid chloride protocols described previously afforded the title compound; $^1$HNMR (CDCl$_3$) δ: 8.05 (d, 1H), 7.82 (s, 1H), 7.78 (d, 1H), 7.65 (d, 2H), 7.55 (m, 4H), 7.10 (d, 2H), 6.95 (d, 2H), 6.65 (s, 1H), 3.32 (s, 3H), 2.40 (s, 3H) ppm; Ammonia mass spectrum analysis m/z (rel. intensity) 490 (M+NH$_4^+$, 100).

Part B. Preparation of 1-(3-Amidinophenyl)-3-methyl-5-[(4'-(2"-sulfonylmethyl)phenoxyphenyl)aminocarbonyl] pyrazole Subjecting the product obtained in part A to the Pinner amidine reaction sequence afforded after preparative HPLC (acetonitrile:water containing 0.05% TFA) the title compound as colorless crystals. $^1$HNMR (DMSO d$_6$) δ: 10.64 (s, 1H), 9.43 (s, 2H), 9.08 (s, 2H), 7.95 (m, 2H), 7.83 (d, 1H), 7.75 (d, 2H), 7.67 (m, 2H), 7.34 (t, 2H), 7.17 (d, 2H), 7.03 (s, 1H), 6.98 (d, 1H), 3.35 (s, 3H), 2.34 (s, 3H) ppm; ESI mass spectrum analysis m/z (rel. intensity) 490 (M+H, 100); high resolution mass spectrum calcd for CHNSO 490.153564, found 490.153759.

Example 18

1-(3-Amidinophenyl)-3-methyl-5-[(2'-aminosulfonyl-1']-biphen-4-yl)methylcarbonyl]-pyrazole

Part A. Preparation of 1-(3-Cyanophenyl)-5-[(4'-bromophenyl)methylcarbonyl]-methylpyrazole.

To zinc dust (0.19 g, 2.9 mmol) in THF (3 mL) was added several drops of dibromoethane and the mixture was heated to reflux for 5 minutes, then cooled to 0° C. To the activated zinc was added 4-bromobenzyl bromide (0.59 g, 2.3 mmol) in THF (6 mL) dropwise over 5 minutes. The reaction was stirred at 0° C. for 2 h and then it was cannulated into a THF (5 mL) solution of LiCl (0.2 g, 4.7 mmol) and CuCN (0.21 g, 2.3 mmol) at −78° C. The mixture was warmed to −10° C. for 5 minutes, then cooled to −78° C. and the acid chloride of 1-(3-cyanophenyl)-5-carboxy-3-methylpyrazole (0.45 g, 1.98 mmol) in THF (5 mL) was added. The reaction was allowed to warm to room temperature overnight. The reaction was diluted with ethyl acetate and washed with sat'd $NaHCO_3$, brine and dried ($Na_2SO_4$). The product was purified by flash chromatography on silica gel using hexanes/ethyl acetate (2:1) as eluent to afford 0.15 g (17%) solid: $^1$HNMR ($CDCl_3$) δ: 7.67 (dd, J=1.83, 6.96 Hz, 1H), 7.62 (s, 1H), 7.54 (m, 2H), 7.49 (d, J=8.42 Hz, 2H), 7.13 (d, J=8.42 Hz, 2H), 6.90 (s, 1H), 4.10 (s, 2H), 2.39 (s, 3H), MS (NH3) m/z 380–382 (M+H)$^+$, 397–399 (M+NH$_4$)$^+$.

Part B. Preparation of 1-(3-Cyanophenyl)-5-[2'-t-butylaminosulfonyl-[1,1']-biphen-4-yl)methylcarbonyl]-3-methylpyrazole.

A mixture of the bromide above (0.14 g, 0.37 mmol), 2M $Na_2CO_3$ (1 mL), 2-t-butylsulfonimide boronic acid (0.13 g, 0.50 mmol) and 1:1 ethanol/toluene (15 mL) was degassed with nitrogen for 15 minutes. Tetrakids(triphenylphoshine) palladium (2 mg) was added and the reaction was heated to reflux for 18 h. The reaction was concentrated and the residue was taken up in ethyl acetate, washed with water and dried ($MgSO_4$). The product was purified by flash chromatography on silica gel using hexanes/ethyl acetate (2:1) as eluent to afford 0.19 g (100%) of a clear viscous oil: $^1$HNMR ($CDCl_3$) δ: 8.18 (dd, J=1.46, 7.69 Hz, 1H), 7.68 (m,-2H), 7.58 (m, 2H), 7.52 (d, J=8.40 Hz, 2H), 7.51 (m, 2H), 7.34 (d, J=8.05 Hz, 2H), 7.33 (m, 1H), 6.95 (s, 1H), 4.21 (s, 2H), 3.48 (s, 1H), 2.40 (s, 3H), 0.97 (s, 9H); MS (ESI) m/z 535.19 (M+Na)$^+$.

Part C. Preparation of 1-(3-Amidinophenyl)-3-methyl-5-((2'-aminosulfonyl-[1,1']-biphen-4-yl)methylcarbonyl]-pyrazole.

The title compound was obtained in 37% yield following the standard Pinner-amidine sequence outlined previously. $^1$HNMR (DMSO-d$_6$) δ: 9.39 (s, 1.5H), 9.03 (s, 1.5H), 8.03 (dd, J=7.32, 1.83 Hz, 1H), 7.85 (m, 2H), 7.68 (m, 2H), 7.59 (m, 2H), 7.44 (s, 1H), 7.36 (m, 7H), 4.34 (s, 2H), 2.34 (s, 3H); MS (ESI) m/z 474.18 (M+H)$^+$.

Example 19

1-(3-Amidinophenyl)-5-[(2'-aminosulfonyl-[1,1']-biphen-4-yl)aminocarbonyl]-1,2,3-triazole

The title compound was obtained as colorless crystals from N-1 (meta-cyanophenyl)-1,2,3-triazole-2-carboxylic acid (Sheehan et. al. *J. Amer. Chem. Soc.* 1951, 73, 1207) following the general method described previously. $^1$HNMR (DMSO d$_6$) δ: 10.9 (s, 1H), 9.49 (bs, 1.5H), 9.20 (bs, 1.5H), 9.60 (s, 1H), 8.11 (s, 1H), 8.06–7.95 (m, 3H), 7.88–7.80 (t, 1H), 7.69–7.56 (m, 2H), 7.38 (d, 2H), 7.29 (bs, 3H) ppm; ESI mass spectral analysis m/z rel. intensity) 463 (M+H, 100); High resolution mass spectrum analysis calcd. for $C_{21}H_{19}N_8SO_3$ 463.130084, found 463.129575.

Example 20

1-(3-Amidinophenyl)-5-((2'-trifluoromethyl-[1,1']-biphen-4-yl)aminocarbonyl)tetrazole, Trifluoroacetic Acid Salt

Part A. Preparation of 1-(3-Cyanophenyl)-5-[(4'-bromophenyl)aminocarbonyl]tetrazole.

4-Bromoaniline was dissolved in $CH_2Cl_2$ (25 mL). Trimethylaluminum (2 M in heptane 7.0 mL, 14 mmol) was added slowly. The mixture was stirred at room temperature under $N_2$ for 15 min. Then, a solution of 1-(3-cyanophenyl)-5-carboethoxy-tetrazole (0.77 g, 3.16 mmol) in $CH_2Cl_2$ (25 mL) was added (prepared in part A of Example 24). The mixture was stirred at room temperature over the weekend. The reaction mixture was quenched carefully with 1N HCl. It was diluted with $CH_2Cl_2$ and washed with water and brine, it was dried over $MgSO_4$, concentrated, and chromatographed on silica gel (eluted with $CH_2Cl_2$) to give 0.30 g of the desired product. $^1$HNMR (DMSO-d6) δ: 6.05 (q, 4H); 7.85 (t, 1H); 8.10 (t, 2H; 8.35 (s, 1H); 11.5 (s, 1H). MS (NH$_3$—CI) 386 (M+NH$_4$)$^+$.

Part B. Preparation of 1-(3-Cyanophenyl)-5-((2'-trifluoromethyl-[1,1']-biphen-4-yl)aminocarbonyl)tetrazole The material from Part A (0.30 g, 0.813 mmol) and 2-trifluoromethyl phenylboronic acid (0.2 g, 1.06 mmol) were dissolved in EtOH/toluene (4.2 mL/10 mL). The mixture was stirred at room temperature and bubbled $N_2$ for 30 min. Then $K_2CO_3$ (0.82 mL of 2 M, 1.63 mmol), tetrabutylammonium bromide (13 mg, 0.04 mmol) and tetrakis (triphenylphosphine)-palladium(0) (46 mg, 0.04 mmol) were added. The mixture was refluxed under $N_2$ for 4 hours. The reaction mixture was cooled and filter through celite. The solvent was removed. The residue was dissolved in EtOAc, washed with water and brine, it was dried over $MgSO_4$, concentrated and chromatographed on silica gel (eluted with $CH_2Cl_2$) to give 0.35 g of the title compound. $^1$HNMR ($CDCl_3$) δ: 7.15 to 7.95 (m, 12H); 9.15 (s, 1H). MS (NH$_3$—CI) 452 (M+NH$_4$)$^+$.

Part C. Preparation of 1-(3-Amidinophenyl)-5-((2'-trifluoromethyl-[1,1']-biphen-4-yl)aminocarbonyl)tetrazole, Trifluoroacetic Acid Salt.

The material from part B was dissovled in 10 mL anhydrous $CHCl_3$ and 10 mL anhydrous $CH_3OH$. The mixture was cooled in an ice-bath and HCl gas was bubbled-in until the solution was saturated. The reaction mixture was sealed and kept at refrigerator for 12 h. The solvent was removed and the solid was dried under vacuum. The solid was redissolved in 20 mL of anhydrous $CH_3OH$ and ammonium acetate (0.63 g, 10 eq) was added. The mixture was sealed and stirred at room temperature for 12 h. The solvent was removed. The solid was dissolved in $CH_3CN/H_2O/TFA$ and purified by reversed phase HPLC to give 150.0 mg of the desired product. $^1$HNMR (DMSO-d6) δ: 7.30 to 8.25 (m, 12H); 9.20 (s, 1H); 9.50 (s, 1H); 11.55 (s, 1H). MS (ESI) 452.2 (M+H)$^+$.

Example 21

1-(3-Amidinophenyl)-5-((2'-aminosulfonyl-3-chloro-[1,1']-biphen-4-yl)methylthio)tetrazole, Trifluoroacetic Acid Salt

Part A. Preparation of 1-(3-Cyanophenyl)-5-thio-tetrazole
m-Cyanophenylthioisocyanate (3.20 g, 20 mmol) was dissolved in 40 mL of $CHCl_3$. The mixture was heated to dissolve the starting material and a solution of $NaN_3$ (2.64 g, 80 mmol) in 30 mL of $H_2O$ was added. The mixture was refluxed under $N_2$ for 1.5 h. The mixture was cooled and the two layers were separated. The aqueous layer was acidified with conc. HCl. The white precipitate was filtered and dried to give 3.33 g of the desired product. $^1$HNMR (acetone-$d_6$) δ: 7.86 (t, 1H); 7.97 (d, 1H); 8.38 (d, 1H), 8.53 (s, 1H).

Part B. Preparation of 2'-t-Butylaminosulfonyl-4-bromomethyl-3-chloro-[1,1']-biphenyl.

2'-t-Butylaminosulfonyl-3-chloro-4-methyl-[1,1']-biphenyl was converted to the bromo-compound by reluxing in NBS/$CCl_4$.

Part C. Preparation of 1-(3-Cyanophenyl)-5-((2'-t-butylaminosulfonyl-3-chloro-[1,1']-biphen-4-yl)methylthio)tetrazole.

1-(3-Cyanophenyl)-5-thio-tetrazole (0.22 g, 1.08 mmol) and 2'-t-Butylaminosulfonyl-4-bromomethyl-3-chloro-[1,1']-biphenyl (0.45 g, 1.08 mmol) were added together with 20 mL of THF. Triethylamine (0.15 mL, 1.08 mmol) aws added and the mixture was refluxed under $N_2$ for 30 min. The solvent was removed, the residue was dissolved in $CH_2Cl_2$ and chromatographed on silica gel with 30% EtOAc in hexane to give 0.40 g white foam. $^1$HNMR ($CDCl_3$) δ: 1.03 (s, 9H); 3.58 (s, 1H); 4.82 (s, 2H); 7.26 (d, 1H); 7.37 (d, 1H); 7.53 (m, 3H); 7.75 (d, 2H); 7.82–7.92 (m, 3H), 8.16 (d, 1H). MS(ESI) 5.39.3 $(M+H)^+$.

Part D. Preparation of 1-(3-Amidinophenyl)-5-((2'-aminosulfonyl-3-chloro-[1,1']-biphen-4-yl)methylthio) tetrazole, Trifluoroacetic Acid Salt 1-(3-cyanophenyl)-5-[(2'-t-butylaminosulfonyl-3-chloro-[1,1']-biphen-4-yl)methylthio]tetrazole (0.24 g, 0.45 mmol) was dissolved in 20 mL of $CHCl_3$ and 2 mL of anhydrous $CH_3OH$. The mixture was cooled in an ice-bath and HCl gas was bubbled-in until the solution was saturated. The reaction mixture was sealed and stirred at room temperature for 12 h. The solvent was removed and the solid was dried under vacuum. The solid was redissolved in 10 mL of anhydrous $CH_3OH$ and ammonium acetate (0.21 g, 6 eq) was added. The mixture was sealed and stirred at room temperature for 12 h. The solvent was removed. The solid was dissolved in $CH_3CN/H_2O/TFA$ and purified by reversed phase HPLC to give 0.11 g of the title compound. $^1$HNMR (DMSO-$d_6$) δ: 4.79 (s, 2H); 7.30–7.69 (m, 8H); 7.90 (t, 1H); 8.02 (m, 3H); 8.11 (s, 1H); 9.20 (s, 2); 9.48 (s, 2H). MS(ESI) 500.2 $(M+H)^+$.

Examples 22 and 23

1-(3-Amidinophenyl)-5-[(2'-aminosulfonyl-3-chloro-[1,1']-biphen-4-yl)methylsulfoxide]tetrazole, Trifluoroacetic Acid Salt (Example 22) and 1-(3-Amidinophenyl)-5-[(2'-aminosulfonyl-3-chloro- [1,1']-biphen-4-yl)methylsulfonyl]tetrazole, Trifluoroacetic Acid Salt (Example 23)

1-(3-amidinophenyl)-5-[(2'-aminosulfonyl-3-chloro-[1,1']-biphen-4-yl)methylthio]tetrazole, trifluoroacetic acid salt (80.0 mg, 0.13 mmol) was dissovled in 10 mL of methanol. Oxone (0.32 g, 0.52. mmol) was added. The mixture was stirred at room temperature under $N_2$ for 72 h. The mixture was filtered and the solid was washed with methanol. The filtrate was concentrated and then dissolved in $CH_3CN/H_2O/$TFA and purified by reversed phase HPLC to give 48 mg of the the sulfoxide and 23 mg of the sulfone. $^1$HNMR (sulfoxide, $CH_3OH$-$d_4$) δ: 5.08 (q, 2H); 7.25–7.32 (m, 4H); 7.50–7.63 (m, 4H); 7.85 (m, 2H); 8.00–8.10 (m, 3H). MS(ESI) 500.2 $(M+H)^+$. $^1$HNMR (sulfonyl,DMSO-$d_6$) δ: 5.37 (s, 2H); 7.30–7.69 (m, 7H); 7.82–8.10 (m, 5H); 8.20 (s, 1H); 9.18 (s, 2H); 9.52 (s, 2H). MS(ESI) 532.2 $(M+H)^+$.

Example 24

1-(3-Amidinophenyl)-5-[(2'-aminosulfonyl-[1,1']-biphen-4-yl)aminocarbonyl]tetrazole, Trifluoroacetic Acid Salt Part A. Preparation of 1-(3-Cyanophenyl)-5-carboethoxy-tetrazole.

3-aminobenzonitrile (5.0 g, 42.3 mmol) was dissolved in $CH_2Cl_2$ (100 mL). Triethylamine (6.5 mL, 46.5 mmol) was added followed by ethyl oxalyl chloride (4.73 mL, 42.3 mmol). The mixture was stirred at room temperature under $N_2$ for 15 min. It was diluted with $CH_2Cl_2$ and washed with water and brine. the $CH_2Cl_2$ solution was dried over $MgSO_4$ and concentrated to a tan solid (6.33 g). The amide (3.00 g, 13.72 mmol) was then refluxed 20 h with a solution of triphenylphosphine (5.4 g, 20.58 mmol) in 50 mL of CCl4. The solution was stirred at 0° C. for 15 min before the amide was added. The reaction mixture was cooled and hexane was added. The precipitate was filtered off. The filtrate was concentrated to a solid. It was then dissolved in 100 mL of $CH_3CN$ and $NaN_3$ (0.89 g, leq) was added. The mixture was stirred at room temperature under $N_2$ for 12 h. The solvent was removed. The solid was dissolved in EtOAc and washed with water and brine. It was dried over $MgSO_4$ and concentrated, and chromatographed on silica gel (eluted with $CH_2Cl_2$) to give 2.50 g of the desired product. $^1$HNMR (acetone-$d_6$) δ: 1.24 (t, 3H); 4.38 (q, 2H); 7.90 (t, 1H); 8.11 (m, 2H); 8.24 (s, 1H). MS(DCI—$NH_3$) 261 $(M+NH_4)^+$.

Part B. Preparation of 1-(3-Cyanophenyl)-5-[(2'-t-butylaminosulfonyl-[1,1']-biphen-4-yl)aminocarbonyl] tetrazole.

2'-t-Butylaminosulfonyl-4-amino-[1,1']-biphenyl (0.25 g, 0.82 mmol) was dissolved in 10 mL of anhydrous $CH_2Cl_2$, and trimethylaluminium (1.64 mL of 2.0 M solution in heptane) was added slowly. The mixture was stirred at room temperature under $N_2$ for 15 min, and 1-(3-cyanophenyl)-5-carboethoxy-tetrazole (0.20 g, 0.82 mmol) was added. The reaction mixture was stirred at room temperature under $N_2$ for 18 h. The reaction was quenched carefully with 0.1N aqueous HCl. It was diluted with $CH_2Cl_2$ and washed with water and brine. The organic solution was then dried over $MgSO_4$, concentrated, and chromtographed on silica gel (5% EtOAc/$CH_2Cl_2$) to give 0.22 g of the desired product. MS(ESI) 502.3 $(M+H)^+$.

Part C. Preparation of 1-(3-Amidinophenyl)-5-[(2'-aminosulfonyl-[1,1']-biphen-4-yl)aminocarbonyl] tetrazole, Trifluoroacetic Acid Salt The material from Part B was dissolved in 20 mL of anhydrous $CHCl_3$ and 5 mL of anhydrous $CH_3OH$. The mixture was cooled in an ice-bath and HCl gas was bubbled-in until the solution was saturated. The reaction mixture was sealed and stirred at room temperature for 12 h. The solvent was removed and the solid was dried under vacuum. The solid was redissolved in 10 mL of anhydrous $CH_3OH$ and ammonium acetate (0.34 g, 10 eq) was added. The mixture was sealed and stirred at room temperature for 12 h. The solvent was removed. The solid was dissolved in $CH_3CN/H_2O/$TFA and purified by reversed phase HPLC to give 80.0 mg of the desired product. $^1$HNMR (DMSO-$d_6$) δ: 7.28 (m, 3H); 7.37 (d, 2H); 7.60 (m, 2H); 7.78 (d, 2H); 7.89 (t, 1H); 8.02 (t, 2H); 8.15 (d, 1H); 8.20 (s, 1H), 9.14 (s, 2H); 9.50 (s, 2H);11.52 (s, 1H). MS(ESI) 463.3 $(M+H)^+$.

Examples 25–48, shown in Table 1a below, were prepared using the above described procedures.

Example 49

3-Methyl-1-(3-amidinophenyl)-5-(4'-(4"-chlorophenyl)thiazol-2'-yl)aminocarbonyl)pyrazole Part A. Preparation of 3-Methyl-1-(3-cyanophenyl)-5-(4'-(4"-chlorophenyl)thiazol-2'-ylaminocarbonyl)pyrazole.

1-(3-cyanophenyl)-3-methylpyrazole-5-carboxylic acid (70 mg, 0.31 mmol) was reacted with 2-amino-4-(4'-chlorophenyl)thiazole (168 mg, 0.8 mmol) in the presence of DMAP (191 mg, 1.5 mmol) and BOP reagent (benzotriazol-1-yloxytris(dimethylamino)phosphonium hexafluorophosphate, 442 mg, 1 mmol) in DMF (5 mL) at 60° C. for 16 h to give the title compound (100 mg, 77%).
Part B. Preparation of 3-Methyl-1-(3-amidinophenyl)-5-(4'-(4"-chlorophenyl)thiazol-2'-ylaminocarbonyl)pyrazole.

A Pinner reaction under standard procedures was used to form the title compound (39 mg, 17%): $^1$HNMR (CD$_3$OD) δ: 7.93 (d, J=1.8 Hz, 1H), 7.90 (d, J=8.8 Hz, 2H), 7.86 (dd, J=7.3 Hz, J=1.8 Hz, 1H), 7.79–7.77 (m, 1H), 7.70 (t, J=7.7 Hz, 1H), 7.44 (s, 1H), 7.38 (d, J=8.4 Hz, 2H), 7.07 (s, 1H), 2.38 (s, 3H); HRMS: 437.0951 (M+H)$^+$.

Example 50

1-(3-Amidino)phenyl-3-methyl-5-[(2'-trifluoromethylsulfide-[1,1']-biphen-4-yl) aminocarbonyl]pyrazole Part A. Preparation of 2'-Trifluoromethylthio-1-aminobiphenyl.

Palladium catalysed Suzuki cross-coupling methodology of 4-aminotrifluoromethylacetyl-phenylboronic acid with 2-bromo-1-trifluoromethylthio-benzene afforded 2'-trifluoromethylthio-1-aminotrifluoromethylacetyl-biphenyl in 72% yield; $^1$HNMR (CDCl$_3$) δ: 8.53 (bs, 1H), 7.78 (d, J=8 Hz, 1H), 7.62 (d, J=8 Hz, 2H), 7.48–7.60 (m, 1H), 7.29–7.46 (m, 5H), ppm; $^{19}$F NMR (CDCl$_3$) δ: 42.5 (s, 3F) and −76.2 (s, 3F); Ammonia CI mass spectrum m/z (rel int.) 383 (M+NH$_4$, 100) 366 (M+H, 100). Saponification (1N NaOH in methanol) then afforded the title compound in 80% yield; $^1$HNMR (CDCl$_3$) δ: 7.77 (d, J=8 Hz, 1H), 7.30–7.55 (m, 4H), 7.09 (d, J=4 Hz, 2H), 6.70 (d, J=8 Hz, 2H), 3.69–3.80 (bs, 2H) ppm; Ammonia CI mass spectrum m/z (rel. int.) 256 (M+H, 100); $^{19}$F NMR (CDCl$_3$) δ: −42.5 ppm.

Part B. Preparation of 1-(3-Cyanophenyl)-3-methyl-5-[(2'-trifluoromethylsulfide-[1,1']-biphen-4-yl)aminocarbonyl]-pyrazole.

Coupling of the product obtained in part A with the pyrazole acid chloride as illustrated in Example 10 then afforded the desired coupled phenylnitrile analog in 75% yield; $^1$HNMR (CDCl$_3$) δ: 8.13 (bs, 1H), 7.70 (dd, J=1.8 & 7.4 Hz, 1H), 7.51 (m, 2H), 7.48 (t, j=7.7 Hz, 2H), 7.38 (t, J=7.6 Hz, 2H), 7.28 (m, 2H), 6.67 (s, 1H), 2.36 (s, 3H) ppm; ESI mass spectrum m/z (rel. int.) 501 (M+Na, 92), 479 (M+H, 100); $^{19}$F NMR (CDCl$_3$) δ: −42.4 ppm.

Part C. Following the Pinner amidation reaction protocol as illustrated for Example 10 afforded the desired benzamidine compound in 50% yield after preparative HPLC (reverse phase, CH$_3$CN:water) as colorless crystals; $^1$HNMR (DMSO-d$_6$) δ: 10.7 (s, 1H), 9.43 (bs, 1.5H), 9.07 (bs, 1.5H), 7.98 (s, 1H), 7.89–7.65 (m, 8H), 7.58–7.49 (m, 2H), 7.35 (d, J=8 Hz, 2H), 7.04 (s, 1H), 2.37 (s, 1H) ppm; ESI mass spectrum m/z (rel. int.) 496 (M+H, 100); HRMS calcd for C$_{25}$H$_{21}$N$_5$F$_3$SO 496.141892, Found 496.142995.

Examples 51 and 52

1-(3-Amidino)phenyl-3-methyl-5-[(2'-trifluoromethylsulfoxide-[1,1']-biphen-4-yl) aminocarbonyl]pyrazole (Example 51) and 1-(3-Amidino)phenyl-3-methyl-5-[(2'-trifluoromethylsulfonyl-[1,1']-biphen-4-yl) aminocarbonyl]pyrazole (Example 52)

The product obtained in part C of Example 50 was subjected to oxidation with OXONE®(10 eq.) in methanol/water 9:1 to afford a mixture of the sulfoxide and sulfonyl products. Preparative HPLC (reverse phase, CH$_3$CN:water) afforded pure sulfoxide in 45% yield (colorless crystals after lyophilization); $^1$HNMR (DMSO-d$_6$) δ: 9.40 (bs, 1.5H), 9.04 (bs, 2H), 8.08 (d, J=8 Hz, 1H), 7.96 (s, 1H), 7.84–7.68 (m, 8H), 7.50 (m, 3H), 7.04 (s, 1H), 2.35 (s, 3H) ppm; ESI mass spectrum m/z 512. The sulfonyl product waas also obtained as colorless crystals in 15% yield (colorless crystals after lyophilization); $^1$HNMR (DMSO-d$_6$) δ: 9.43 (bs, 1.5H), 9.07 (bs, 2H), 8.23 (d, 1H), 7.99 (m, 1H), 7.98 (s, 1H), 7.89–7.69 (m, 7H), 7.55 (d, j=8 Hz, 1H), 7.26 (d, J=8 Hz, 1H), 7.0 (s, 1H), 2.37 (s, 2H) ppm; ESI mass spectrum m/z 528.1.

Example 53

1-(3-Amidino)phenyl-3-methyl-5-[4'-(carboxymethyl)phenylaminocarbonyl]pyrazole Methyl-4-amino-benzoate was coupled to the pyrazole acid chloride via the method illustrated for Example 10 to obtain the benzonitrile coupled product in quantitative yield. $^1$HNMR (CDCl$_3$) δ: 8.01 (d, J=8 Hz, 2H), 7.97 (s, 1H), 7.80 (s, 1H), 7.78–7.53 (m, 4H), 6.70 (s, 1H), 3.90 (s, 2H), 2.39 (s, 3H) ppm; ESI mass spectrum m/z (rel. int.) 361 (M+H, 100); The nitrile was then subjected to the Pinner amidine reaction sequence as illustrated for Example 10 to obtain after preparative HPLC separation the desired product in 50% yield (colorless crystals); $^1$HNMR (DMSO-d$_6$) δ: 9.40 (bs, 1.5H), 9.18 (bs, 1.5H), 7.91 (m, 3H), 7.86–7.64 (m, 6H), 7.08 (s, 1H), 3.81 (s, 3H), 2.37 (s, 2H) ppm; ESI mass spectrum m/z (rel. int) 378 (M+H, 100); HRMS calcd for C$_{20}$H$_{20}$N$_5$O$_3$ 378.156615, Found 378.158283.

Example 54

1-(3-Amidino)phenyl-3-methyl-5-[4'-(N,N-dimethylaminocarbonyl) phenylaminocarbonyl] pyrazole The coupled benzonitrile pyrazole methyl ester obtained above was subjected to saponification (LiOH, THF/water) followed by acidification (1N HCl) to obtain the corresponding carboxylic acid product which was then coverted to the dimethyl amide derivative via its acid chloride. Following the Pinner amidine reaction protocols adopted for Example 10 then afforded the desired product as colorless crystals in 50% yield; $^1$HNMR (DMSO-d$_6$) δ: 10.7 (s, 1H), 9.40 (bs, 2HO, 9.04 (bs, 2H), 7.96 (m, 1H), 7.84–7.68 (m, 6H), 7.38 (d, J=8.0 Hz, 2H), 7.03 (s, H), 2.95 (bs,.6H), 2.36 (s, 3H) ppm; ESI mass spectrum m/z (rel. int.) 391 (M+H, 100).

Example 55

1-(3-Amidino)phenyl-3-methyl-5-[4'-(N,N-dimethylaminosulfonyl)phenylaminocarbonyl] pyrazole Coupling of 4-amino-N,N-dimethylbenzene-sulfonamide with the pyrazole acid chloride obtained for Example 10 afforded the desired benzonitrile-pyrazole coupled product in 90% yield. $^1$HNMR (CDCl$_3$) δ: 8.09 (s, 1HO, 7.80–7.65 (m, 7H), 7.54 (m, 1H), 6.77 (s, 1H), 2.71 (s, 6H), 2.40 (s, 3H) ppm; Ammonia CI mass spectrum (rel. int) 410 (M+H, 100). Subjecting the nitrile obtained above to the Pinner amidine reaction protocol as illustrated for Example 10 afforded the desired product in 70% yield as colorless crystals following preparative HPLC (reverse phase, acetonitrile:water) purification. $^1$HNMR (DMSO-d$_6$) δ: 10.8 (s, 1H), 9.39 (bs, 1.5H), 9.17 (bs, 1.5H), 7.89 (m, 3H), 7.79 (m, 1H), 7.77–7.63 (m, 4H), 7.06 (s, 1H), 2.30 (s, 3H), 2.45 (s, 3H) ppm; ESI mass spectrum m/z (rel. int) 426 (M+H, 100).

Examples 56 and 57

1-(3-Amidino)phenyl-3-methyl-5-[(4'-tert-butylaminosulfonylphenyl)aminocarbonyl]pyrazole (Example 56) and 1-(3-Amidino)phenyl-3-methyl-5-[(4'-aminosulfonylphenyl)aminocarbonyl]pyrazole (Example 57)

Coupling of 4-amino-N-tert-butylbenzene-sulfonamide with the pyrazole acid chloride obtained for Example 10 afforded the desired coupled benzonitrile precursor in 80% yield. $^1$HNMR (CDCl$_3$) δ: 8.35 (bs, 1H), 7.77 (m, 4H), 7.71 (m, 1H), 7.69–7.64 (m, 3H), 7.53 (t, 1H), 6.89 (s, 1H), 2.39 (s, 3H), 1.20 (s, 9H) ppm; ESI mass spectrum m/z (rel. int.) 460 (M+Na, 100), 438 (M+H, 20). Subjecting the nitrile obtained above to the Pinner amidine reaction protocol as illustrated for Example 10 afforded the desired product in 5% yield as colorless crystals following preparative HPLC (reverse phase, acetonitrile:water) purification. $^1$HNMR (DMSO-d$_6$) δ: 10.8 (s, 1H), 9.41 (bs, 1.5H), 9.20 (bs, 1.5H), 7.97 (s, 1H), 7.84–7.77 (m, 9H), 7.47 (s, 1H), 7.08 (s, 1H), 3.73 (s, 1H), 2.35 ((s, 3H) ppm; ESI mass spectrum m/z (rel. int.) 455 (M+H, 100). The de-tertbutylated sulfonamide was obtained in 30% yield (colorless crystals); $^1$HNMR (DMSO-d$_6$) δ: 10.85 (s, 1H), 9.40 (bs, 4), 7.95 (s, 1H), 7.89–7.66 (m, 7H), 7.07 (s, 1HH), 2.34 (s, 3H) ppm; ESI mass spectrum 381.3.

Example 58

1-(3-Amidino)phenyl-3-methyl-5-[(4'-trifluoromethylphenyl)-aminocarbonyl]pyrazole Coupling of 4-amino-1-trifluoromethylbenzene with the acid chloride obtained in Example 10 afforded the desired benzonitrile precursor in 80% yield. $^1$HNMR (CDCl$_3$) δ: 8.17 (s, 1H), 7.79 (s, 1H), 7.75–7.50 (m, 7H), 6.73 (s, 1H), 2.39 (s, 3H) ppm; Ammonia CI mass spectrum 388 (M+NH$_4$, 34), 371 (M+H, 100). Subjecting the nitrile obtained above to the Pinner amidine reaction protocol as illustrated for Example 10 afforded the desired product in 60% yield as colorless crystals following preparative HPLC (reverse phase, acetonitrile:water) purification. $^1$HNMR (DMSO-d$_6$) δ: 9.40 (bs, 1.5H), 9.20 (bs, 1.5H), 8.09 (s, 1H), 7.90 (s, 1H), 7.83–7.75 (dd, J=7.6 & 8.4 Hz), 7.68–7.53 (m, 4H), 6.97 (s, 1H), 2.29 (s, 2H) ppm; ESI mass spectrum m/z (rel. int.) 388.1 (M+H, 100); HRMS calcd for C$_{19}$H$_{17}$N$_5$F$_3$O 388.138520, Found 388.139013.

Example 59

1- (3-Amidino)phenyl-3-methyl-5-[(4'-benzylsulfonylpiperidyl)-aminocarbonyl]pyrazole Coupling of 4-amino-1-benzylsulfonylpiperidine with the acid chloride obtained in Example 10 afforded the desired coupled product which when subjected to the Pinner amidine reaction protocol as illustrated for Example 10 afforded the desired product in 15% yield as colorless crystals following preparative HPLC (reverse phase, acetonitrile:water) purification. $^1$HNMR (DMSO-d$_6$) δ: 9.40 (bs, 1.5H), 9.00 (bs, 1.5H), 8.59 (d, J=8 Hz, 1H), 7.86 (s, 1H), 7.77 (m, 1H), 7.75 (m, 3H), 7.38 (m, 5H), 6.79 (s, 1H), 4.40 (s, 2H), 3.50 (bd, 2H), 2.73 (m, 2H), 1.74 (m, 2H), 1.50 (m, 2H), 2.28 (s, 3H) ppm; ESI mass spectrum m/z (rel. int.) 481 (M+H, 100); HRMS calcd. for C$_{24}$H$_{29}$N$_6$ 481.202186. Found 481.201227.

Example 60

1-(3-Amidinophenyl)-5-[(2'-aminosulfonyl-[1,1']-biphen-4-yl)-N-methylaminocarbonyl]-3-methylpyrazole, Trifluoroacetic Acid Salt Part A. Synthesis of 1-(3-Cyanophenyl)-5-[(2'-aminosulfonyl-[1,1']-biphen-4-yl)-N-methylaminocarbonyl]-3-methylpyrazole.

Standard coupling of 1-(3-cyanophenyl)-3-methyl-pyrazol-5-yl carboxylic acid and 2-tert-butylsulfonamide-1-biphenyl-N-methyl aniline afforded a yellow foam (67%), $^1$HNMR (CDCl$_3$) δ: 8.16 (d, j=7.69 Hz, 1H), 7.63 (m, 6H), 7.33 (m, 3H), 6.83 (bdr m, 2H), 6.23 (s, 1H), 3.43 (s and m, 4H), 2.27 (s, 3H), 1.02 (s, 9H); MS (ESI) m/z 528.4 (M+H)$^+$, 550.4 (M+Na)$^+$.

Part B: The Pinner amidine reaction protocol as illustrated for Example 10 afforded the desired product. $^1$HNMR (DMSO-d$_6$) δ: 9.45 (s, 1.5H), 9.12 (s, 1.5H), 8.16 (d, j=7.69 Hz, 1H), 7.81 (m, 7H), 7.30 (m, 5H), 7.15 (m, 2H), 3.10 (s, 3H), 2.12 (s, 3H) ppm; HRMS 489.170886 (calcd); 489.170289 (obs.); Analysis calcd for C$_{25}$H$_{24}$N$_6$O$_3$S (TFA) 1.1 (H$_2$O) 0.3 C: 52.74, H: 4.18, N: 13.57; found C: 52.67, H: 4.28, N: 13.57.

Example 61

1-(3-Amidinophenyl)-5-[(4'-fluoro-[1,1']-biphen-4-yl)-aminocarbonyl]-3-methylpyrazole, Trifluoroacetic Acid Salt Part A. Preparation of 2-tert-Butylsulfonamide-4-fluoro-1-biphenyl Trifluoroacetamide.

Standard Suzuki coupling between 1-bromo-2-tert-butylsulfonamide-4-fluorobenzene (J. Indian Chem. Soc. Vol. 38, No. 2, 1961, 117) and 4-trifluoracetamide-1-phenyl boronic acid afforded a solid (57%). $^1$HNMR (CDCl$_3$) δ: 8.11 (dd, j=2.19, 6.59 Hz, 1H), 8.03 (s, 1H), 7.76 (m, 1H), 7.70 (d, j=8.79 Hz, 2H), 7.61 (d, j=8.79 Hz, 2H), 7.30 (m, 1H), 4.78 (s, 1H), 1.27 (s, 9H) ppm; MS (DCI) m/z 436 (M+NH$_4$)+; Analysis calcd for C$_{18}$H$_{18}$F$_4$N$_2$O$_3$S$_1$ C: 51.67, H: 4.34, N: 6.70, found C: 51.66, H: 4.26, N: 6.65.

Part B. Preparation of 2-tert-Butylsulfonamide-4-fluoro-1-biphenyl Aniline.

To the compound from part A (0.93 g, 2.2 mmol) in methanol was added 0.5 M LiOH (8 mL, 4 mmol)and heated to reflux 2 h. The reaction was cooled and concentrated. The aqueous residue was extracted with CH$_2$Cl$_2$. The combined organic layers were washed with water, brine and dried (MgSO$_4$) to afford 0.7 g (98%) solid; mp=158–160 OC, $^1$HNMR (CDCl$_3$) δ: 8.07 (dd, j=2.2, 6.96 Hz, 1H), 7.66 (m, 1H), 7.40 (d, j=8.43 Hz, 2H), 4.75 (s,: 1H), 3.80 (s, 2H), 1.25 (s, 9H) ppm, MS (DCI) m/z 340 (M+NH$_4$)$^+$.

Part C: Standard coupling of 1-(3-Cyanophenyl)-3-methyl-pyrazol-5-yl carboxylic acid and 2-tert-butylsulfonamide-4-fluoro-1-biphenyl aniline afforded a 85% yield of impure nitrile that was carried on to the next step. MS (DCI) m/z 531 (M+H)$^+$, 549 (M+NH$_4$)$^+$.

Part D: The nitrile from part C was subjected to the standard Pinner conditions to give the title amidine, $^1$HNMR (DMSO-d$_6$) δ: 10.7 (s, 1H), 9.43 (s, 1.5H), 9.01 (s, 1.5H), 7.99 (m, 3H), 7.81 (d, j=7.69 Hz, 2H), 7.81 (m, 5H), 7.68 (d, j=8.79 Hz, 2H), 7.55 (t, j=8.79 Hz, 1H), 7.06 (s, 1H), 2.27 (s, 3H); HRMS 493.145814 (calcd); 493.145228 (obs.).

Example 62

1-(3-Amidinophenyl)-5-[[5-(2'-aminosulfonylphenyl)pyridin-2-yl]aminocarbonyl]-3-methylpyrazole, Trifluoroacetic Acid Salt Part A. Synthesis of 1-(3-Cyanophenyl)-5-[[5-(2'-t-butylaminosulfonylphenyl)pyridin-2-yl]aminocarbonyl]-3-methylpyrazole.

Standard coupling of 1-(3-cyanophenyl)-3-methyl-pyrazol-5-yl carboxylic acid and 2-t-butylsulfonamide-1-pyridyl phenyl aniline afforded the title compound (44%), $^1$HNMR (CDCl$_3$) δ: 8.59 (s, 1H), 8.37 (m, 1H), 8.23 (t, j=8.42, 2H), 7.94 (m, 7H), 6.77 (s, 1H), 3.94 (s, 1H), 2.41 (s, 3H), 1.10 (s, 9H), ppm, MS (ESI) 515.4 (M+H)$^+$.

Part B: The above compound was subjected to standard Pinner 35 reaction and HPLC purification (35%) $^1$HNMR (DMSO-d$_6$) δ: 11.21 (s, 1H), 9.44 (s, 1.5H), 9.23 (s, 1.5H), 8.37 (t, j=1.47 Hz, 1H), 8.07 (dd, j=7.30, 1.47 Hz, 1H), 7.99 (d, j=7.69 Hz, 2H), 7.85 (m, 1H), 7.79 (dd, j=9.52, 2.20 Hz, 2H), 7.73 (d, j=7.69 Hz, 1H), 7.69 (m, 2H), 7.44 (s, 2H), 7.40 (dd, j=2.20, 7.60 Hz, 1H), 7.18 (s, 1H), 2.33 (s, 3H) ppm; HRMS 476.150485 (calcd), 476.149493 (observed); Analysis calcd for C$_{23}$H$_{21}$N$_7$O$_3$S (TFA) 1.9 C: 46.51, H: 3.33, N: 14.17, found C; 46.60, H: 3.51, N: 14.17.

Example 63

1-(3-Cyanophenyl)-5-[[5-(2'-aminosulfonylphenyl)pyridin-2-yl]aminocarbonyl]-3-methylpyrazole, Trifluoroacetic Acid Salt 1-(3-cyanophenyl)-5-[[5-(2'-t-butylaminosulfonylphenyl)pyridin-2-yl]aminocarbonyl]-3-methylpyrazole (0.18 g, 0.28 mmol) was heated to reflux in trifluoracetic acid (6 mL) for 15 minutes. The reaction was concentrated and the residue purified by HPLC to afford 69 mg (43%) of the title compound. $^1$HNMR (DMSO-d$_6$) δ: 11.15 (s, 1H), 8.37 (d, j=2.20 Hz, 1H), 8.07 (m, 3H), 7.89 (d, j=7.69 Hz, 1H), 7.82 (m, 2H), 7.70 (d, j=8.05 Hz, 1H), 7.67 (m, 2H), 7.42 (s, 1H), 7.40 (dd, j=1.83, 6.96 Hz, 2H), 7.18 (s, 1H), 2.32 (s, 3H) ppm; HRMS 459.123936 (calcd), 459.122035 (obs.); Analysis calcd for C$_{23}$H$_{18}$N$_6$O$_3$S$_1$ (TFA) 0.6: C: 55.16, H: 3.56, N: 15.950, found C: 54.89, H: 3.69, N: 15.67.

Example 64

1-(3-Amidinophenyl)-5-[(2'-trifluoromethyl-[1,1']-biphen-4-yl)aminocarbonyl]-3-methylpyrazole, Trifluoroacetic Acid Salt Part A: 2-Trifluoromethylbromobenzene and 4-trifluoroacetamide phenylboronic acid were combined in standard Suzuki reaction to afford a 28% yield of 2-trifluoromethyl-1-biphenyl trifluoroacetamide, after purification by flash chromatography on silica gel using hexanes/ethyl acetate (6:1) as eluent. $^1$HNMR (CDCl$_3$) δ: 7.90 (s, 1H), 7.77 (d, j=7.69 Hz, 1H), 7.64 (d, j=8.43 Hz, 2H), 7.58 (d, j=6.59 Hz, 1H). 7.51 (m, 1H), 7.39 (d, j=8.42 Hz, 2H), 7.33 (m, 1H) ppm MS (ESI) m/z 334 (M+H)$^+$. 2-trifluoromethyl-1-biphenyl trifluoroacetamide was hydrolyzed with base as described above to give the free aniline (90%) which was used in next step without purification.MS (DCI) m/z 238.1 (M+H)$^+$, 255.1 (M+NH$_4$)$^+$.

Part B. Preparation of 1-(3-Cyanophenyl)-5-[(2'-trifluoromethyl-[1,1']-biphen-4-yl)-aminocarbonyl]-3-methyl Pyrazole.

Standard coupling of 1-(3-cyanophenyl)-3-methyl-pyrazol-5-yl carboxylic acid and 2-trifluoromethyl-1-biphenyl aniline afforded a yellow foam (50%) which was used in the next step without purification. MS (ESI) m/z 447.3 (M+H)$^+$.

Part C: The nitrile from part B was subjected to standard Pinner conditions, purified via HPLC and freeze-dried to yield the title compound (32%). $^1$HNMR (DMSO-d$_6$) δ: 10.68 (s, 1H), 9.44 (s, 1.5H), 9.10 (s, 1.5H), 7.97 (s, 1H), 7.84 (d, j=7.7 Hz, 2H), 7.76 (m, 5H), 7.67 (m, 1H), 7.40 (d, j=7.33 Hz, 1H), 7.31 (d, j=8.40 Hz, d), 7.04 (s, 1H), 2.35 (s, 3H) ppm, HRMS: 464.169820 (calcd), 464.171171 (obs.); Analysis calcd for C$_{25}$H$_{20}$F$_3$N$_5$O (TFA) C: 56.16, H: 3.67, N: 12.13, found C: 55.77, H: 3.79, N: 11.85.

Example 65

1-(3-aminocarbonylphenyl)-5-[(2'-aminosulfonyl-[1,1']-biphen-4-yl)aminocarbonyl]-3-methylpyrazole To 1-(3-cyanophenyl)-5-[(2'-t-butylaminosulfonyl-[1,1']-biphen-4-yl-aminocarbonyl]-3-methylpyrazole (0.18 g, 0.36 mmol) was added concentrated sulfuric acid (5 mL) and reaction stirred for 48 h. Ice and water were added a solid precipitated. The mixture was extracted with ethyl acetate, washed with sat'd sodium bicarbonate and dried (MgSO$_4$). Purification by flash chromatography on silica gel using 1–10% methanol in methylene chloride as eluent afforded 88 mg (52%) of the title compound, $^1$HNMR (DMSO-d$_6$) δ: 10.63 (s, 1H), 8.12 (s, 1H), 8.04 (m, 2H), 7.90 (m, 1H), 7.69 (d, j=8.42 Hz, 2H), 7.62 (m, 5H), 7.36 (d, j=8.42 Hz, 2H), 7.32 (m, 1H), 7.24 (s, 2H), 6.93 (s, 1H), 2.50 (s, 3H) ppm, HRMS 476.139251 (calcd), 476.139200 (observed).

Example 66

1-(3-Amidinophenyl)-5-[(2'-aminosulfonyl)-3-chloro-[1,1']-biphen-4-yl)aminocarbonyl]-3-methylpyrazole Part A: 1-(3-Cyanophenyl)-3-methyl-pyrazol-5-yl carboxylic acid and 4-bromo-2-chloroaniline were coupled via standard conditions (67%). $^1$HNMR (CDCl$_3$) δ: 8.27 (d, j=8.79 Hz, 1H), 8.17 (s, 1H), 7.82 (t, j=1.80 Hz, 1H), 7.75 (m, 2H), 7.59 (m, 2H), 7.42 (dd, j=8.78, 2.2 Hz, 1H), 6.72 (s, 1H), 2.41 (s, 3H) ppm.

Part B: The bromo compound from part A (0.4 g, 0.96 mmol), 2-t-butylsulfonamide phenylboronic acid (0.32 g, 1.2 mmol), 2M sodium carbonate (1 mL), and 1:1 toluene/ethanol were combined and degassed with nitrogen. Tetrakistriphenyphosphine palladium(0) (1 mg) was added and the reaction refluxed for 18 h. The reaction was filtered, concentrated and extacted with ethyl acetate and dried (MgSO$_4$). Purification by flash chromatography on silica gel using 1:1 hexanes/ethyl acetate as eluent afforded 0.43 g (81%). $^1$HNMR (CDCl$_3$) δ: 8.45 (d, j=8.42 Hz, 1H), 8.32 (s, 1H), 8.18 (dd, j=1.47, 7.69 Hz, 1H), 7.85 (d, j=1.83 Hz, 1H), 7.79 (d.j=8.05 Hz, 1H), 7.72 (d, j=7.69 Hz, 1H), 7.61 (m, 4H), 7.39 (dd, j=2.20, 8.79 Hz, 1H), 7.28 (m, 1H), 6.76 (s, 1H), 3.67 (s, 1H), 2.43 (s, 3H), 1.07 (s, 9H) ppm., MS (ESI) m/z 548.3 (M+H)$^+$, 570.3 (M+Na)$^+$.

Part C: The nitrile from part B was subjected to the standard Pinner conditions to afford the amidine (43%). $^1$HNMR (DMSO-d$_6$) δ: 10.36 (s, 1H), 9.43 (s, 1.5H), 9.09 (s, 1.5H), 8.05 (dd, j=6.96, 2.20 Hz, 1H), 7.96 (s, 1H), 7.82 (d, j=7.32 Hz, 2H), 7.71 (m, 1H), 7.65 (m, 2H), 7.57 (d, j=6.59 Hz, 1H), 7.54 (s, 1H), 7.46 (s, 2H), 7.39 (m, 2H), 7.06 (s, 1H), 2.35 (s, 3H) ppm, HRMS 509.116263 (calcd), 509.117360 (observed); Analysis calcd for $C_{24}H_{21}ClN_6O_3S_1$ (TFA) ($H_2O$) C: 48.72, H: 3.77, N: 13.11, found C: 48.56, H: 3.53, N: 12.75.

Example 67

1-(3-Amidinophenyl)-5-[(2'-trifluoromethyl)-3-chloro-[1,1']-biphen-4-yl)aminocarbonyl]-3-methylpyrazol, Trifluoroacetic Acid Salt Part A: N-(2-chloro-4-bromophenyl)-1-(3-cyanophenyl)-3-methylpyrazole carboxamide (0.4 g, 0.96 mmol), 2-trifluoromethylphenylboronic acid (0.24 g, 1.2 mmol), 1M sodium carbonate (1 mL) in 1:1 toluene/ethanol (10 mL) were degassed with nitrogen. Tetrakistriphenyphosphine palladium(0) (1 mg) was added and the reaction refluxed for 18 h. The reaction was filtered, concentrated and extacted with ethyl acetate and dried ($MgSO_4$). Purification by flash chromatography on silica gel using 1:1 hexanes/ethyl acetate as eluent afforded 0.41 g (90%). $^1$HNMR ($CDCl_3$) δ: 8.40 (d, j=8.42 Hz, 1H), 8.29 (7.85 (d, j=1.83 Hz, 1H), 7.77 (d, j=8.05 Hz, 2H), 7.71 (d, j=7.60 Hz, 1H), 7.60 (t, j=8.05 Hz, 2H), 7.52 (t, j=7.69 Hz, 1H), 7.42 (d, j=1.84 Hz, 1H), 7.29 (m, 1H), 6.75 (s, 1H), 4.11 (s, 1H), 2.42 (s, 3H) ppm, MS (ESI) m/z 481.2 (M+H)$^+$, 503 (M+Na)$^+$.

Part B: The nitrile from part A was subjected to the standard Pinner conditions to afford the amidine (36%). $^1$HNMR (DMSO-$d_6$) δ: 10.4 (s, 1H), 9.43 (s, 1.5H), 9.13 (s, 1.5H), 7.96 (d, j=1.83, 1H), 7.87 (m, 3H), 7.76 (m, 3H), 7.62 (d, j=8.06 Hz, 1H), 7.52 (d, j=1.83 Hz, 1H), 7.47 (d, j=7.69 Hz, 1H), 7.34 (dd, j=8.42, 1.83 Hz, 1H), 7.07 (s, 1H), 2.35 (s, 3H) ppm, HRMS 498.130848 (calcd), 498.128257 (observed); Analysis for $C_{25}H_{19}ClF_3N_5O$ (TFA) calcd C: 53.00, H: 3.29, N: 11.44, found C: 53.33, H: 3.36, N: 11.55.

Example 68

1-(3-Amidinophenyl)-5-[(2'-aminosulfonyl-[1,1']-biphen-4-yl)aminocarbonyl]-3-n-butylpyrazole, Trifluoroacetic Acid Salt Part A. Synthesis of ethyl 1-(3-Cyanophenyl)-3-n-butyl-pyrazol-5-yl Carboxylate.

Ethyl 2-methoxyimino-4-oxooctanoate (W. T. Aston, et al, J.Het.Chem., 30 (1993) 2, 307) (0.69 g, 3.0 mmol) and 3-cyanophenyl hydrazine hydrochloride (0.66 g, 3.9 mmol) were combined in acetic acid (15 mL) and heated to reflux for 18 h. The reaction was concentrated and the residue was partioned between ethyl acetate and 1N HCl. The organic layer was washed with water and dried ($MgSO_4$). A mixture of regioisomers (ca.9:1) was obtained and separated by flash chromatography on silica gel using 4:1 hexanes/ethyl acetate as eluent affording 0.56 g (63%) of the desired isomer as a yellow oil. $^1$HNMR ($CDCl_3$) δ: 7.77 (d, j=1.83 Hz, 1H), 7.70 (d, j=7.69, 1.83 Hz, 2H), 7.58 (t, j=7.69 Hz, 1H), 6.88 (s, 1H), 4.30 (q, j=6.96 Hz, 2H), 2.72 (t, j=7.69 Hz, 2H), 1.71 (m, 2H), 1.45 (m, 2H), 1.32 (t, j=6.96 Hz, 3H), 0.98 (t, j=7.33 Hz, 3H) ppm;MS (DCI) m/z 298 (M+H)$^+$.

Part B. Preparation of 1-(3-Cyanophenyl)-3-n-butyl-pyrazol-5-yl Carboxylic Acid.

The ester from part A. (0.96 g, 3.2 mmol) was hydrolized with 1N NaOH (5 mL) in THF/water (5 mL) for 18 h. Acid-base workup afforded 0.8 g (92%) acid. $^1$HNMR ($CDCl_3$) δ: 7.79 (d, j=1.83 Hz, 1H), 7.75 (dd, j=1.1, 8.05 Hz, 1H), 7.66 (d, j=7.69 Hz, 1H), 7.56 (t, j=7.69 Hz, 1H), 6.88 (s, 1H), 2,71 (t, j=7.32 Hz, 2H), 1.70 (m, 2H), 1.45 (m, 2H), 0.97 (t, j=7.32 Hz, 3H) ppm; MS (DCI) m/z 270 (M+H)$^+$.

Part C: Preparation of 1-(3-Cyanophenyl)-5-[(2'-t-butylaminosulfonyl-[1,1']-biphen-4-yl)aminocarbonyl]-3-N-butylpyrazole.

Standard coupling of ethyl 1-(3-cyanophenyl)-3-n-butyl-pyrazol-5-yl carboxylate 2-t-butylsulfonamide-1-biphenyl aniline afforded a yellow solid (73%), $^1$HNMR ($CDCl_3$) δ: 8.17 (dd, j=1.1, 7.69 Hz, 1H), 8.03 (s, 1H), 7.82 (s, 1H), 7.77 (d, j=8.06, 1H), 7.68 (s+d, j=7.69 Hz, 3H), 7.55 (m, 5H, 7.77 (d, j=1.4, 7.7 Hz, 1H), 6.76 (s, 1H), 3.64 (s.1H), 2.77 (t, j=7.69 Hz, 2H), 1.75 (m, 2H), 1.44 (m, 2H), 1.03 (s, 9H), 1.00 (t, j=7.69 Hz, 3H) ppm.

Part D: The nitrile from part A. was subjected to standard Pinner conditions to afford the title amidine (57%). $^1$HNMR (DMSO-$d_6$) δ: 10.65 (s, 1H), 9.44 (s, 1.5H), 9.08 (s, 1.5H), 7.83 (m, 3H), 7.70 (d, j=9.15 Hz, 2H) 7.64 (m, 2H), 7.37 (d, j=8.42 Hz, 2H), 7.32 (d, j=7.32 Hz, 1H), 7.28 (s, 2H), 7.06 (s, 1H), 2.72 (t, j=7.69 Hz, 2H), 1.71 (m, 2H), 1.43 (m, 2), 0.97 (t, j=7.33 Hz, 3H) ppm, HRMS 517.202186 (calcd), 517.201333 (obs.); Analysis calcd for $C_{27}H_{28}N_6O_3S$ (TFA) ($H_2O$) 0.8, C: 54.00, H: 4.78, N: 3.03; found C: 54.23, H: 4.46, N: 12.80.

Example 69

1-(3-Amidinophenyl)-5-[(2'-trifluoromethyl-[1,1']-biphen-4-yl)aminocarbonyl]-3-N-butylpyrazole, Trifluoroacetic Acid Salt Part A: Preparation of 1-(3-Cyanophenyl)-5-[(2'-trifluoromethyl-[1,1']-biphen-4-yl)aminocarbonyl]-3-N-butylpyrazole.

Standard coupling of ethyl 1-(3-cyanophenyl)-3-n-butylpyrazol-5-yl carboxylate and 2-trifluoromethyl-1-biphenyl aniline afforded the nitrile. $^1$HNMR ($CDCl_3$) δ: 7.86 (s, 1H), 7.74 (m, 3H), 7.66 (m, 2H), 7.56 (m, 4H), 7.33 (m, 3H), 6.69 (s, 1H), 2.76 (t, j=7.96 Hz, 2H), 1.75 (m, 2H), 1.44 (m, 2H), 0.98 (t, j=7.32 Hz, 3H) ppm; MS (ESI) m/z 489 (M+H)$^+$.

Part B: 1-(3-Amidinophenyl)-5-[(2'-trifluoromethyl-[1,1']-biphen-4-yl)aminocarbonyl]-3-N-butyl pyrazole was prepared from the nitrile from part A by standard Pinner conditions. $^1$HNMR (DMSO-$d_6$) δ: 10.00 (s, 1H), 9.43 (s, 1.5H), 9.02 (s, 1.5 H), 7.96 (s, 1H), 7.84–7.70 (m, 7H), 7.63 (t, j=7.69 Hz, 1H), 7.40 (d, j=7.33 Hz, 1H), 7.31 (d, j=8.42 Hz, 2H), 7.08 (s, 1H), 2.72 (t, j=7.33 Hz, 2H), 1.73 (m, 2H), 1.45 (m, 2H), 0.97 (T, j=7.33 Hz, 3H) ppm; HRMS 506.216771 (calcd.), 506.214378 (obs.); Analysis for $C_{28}H_{26}F_3N_5O$ (TFA) ($H_2O$) 0.8: C: 56.84, H: 4.55, N: 11.05, found C: 56.99, H: 4.41, N: 10.99.

Example 70

1-(3-Amidinophenyl)-5-[[5-(2'-aminosulfonylphenyl)pyridin-2-yl]aminocarbonyl]-3-n-butylpyrazole, Trifluoroacetic Acid Salt Part A: Preparation of 1-(3-Cyanophenyl)-5-[[5-(2'-tert-butylsulfonaminocarbonylphenyl)pyridin-2-yl]-aminocarbonyl]-3-n-butylpyrazole.

Standard coupling of 1-(3-cyanophenyl)-3-n-butylpyrazol-5-yl carboxylic acid and 5-(2'-tert-butylsulfonaminocarbonylphenyl)pyridin-2-yl amine afforded the nitrile (25%). $^1$HNMR ($CDCl_3$) δ: 8.59 (1H, s), 8.37 (d, j=2.20 Hz, 1H), 8.24 (m, 2H), 7.85 (m, 2H), 7.78 (m, 1H), 7.76 (m, 1H), 7.70 (m, 3H), 7.30 (dd, j=1.47, 9.15 Hz, 1H), 6.79 (s, 1H), 3.95 (s, 1H), 2.76 (t, j=7.33 Hz, 2H), 1.73 (m, 2H), 1.47 (m.2H), 1.10 (s, 9H), 0.98 (t, j=7.33 Hz, 3H) ppm; MS (ESI) m/z 557.29 (M+H)$^+$, 579.27 (M+NH$_4$)$^+$.

Part B: 1-(3-Amidinophenyl)-5-[[5-(2'-aminosulfonyl-phenyl)pyridin-2-yl]aminocarbonyl]-3-n-butylpyrazole, trifluoroacetic acid salt was prepared (51%) from the nitrile in part A by standard Pinner conditions. $^1$HNMR (DMSO-$d_6$) δ: 11.21 (s, 1H), 9.43 (s, 1.5H), 9.04 (s, 1.5H), 8.37 (d, j=2.20Hz, 1H), 8.07 (dd, j=1.83, 7.32 Hz, 8.02 (d, j=8.79 Hz, 1H), 7.96 (s, 1H), 7.84 (m, 3H), 7.73 (d, j=7.69 Hz, 1H), 7.86 (m, 2H), 7.44 (s, 2H), 7.40 (dd, j=1.83, 6.96 Hz, 1H), 7.24 (s, 1H), 2.70 (t, j=7.32 Hz, 2H), 1.69 (m, 2H), 1.45 (m, 2H), 0.97 (t, j=7.32 Hz, 3H) ppm; HRMS 518.197453 (calcd), 518.195873 (obs.); Analysis calc'd for $C_{26}H_{27}N_7O_3S$ (TFA) 1.5: C: 50.58, H: 4.17, N: 14.24, found C: 50.76, H: 4.12, N: 14.26.

Example 71

1-(3-Amidinophenyl)-5-[(2'-trifluoromethyl-[1,1']-biphen-4-yl)aminocarbonyl]-3-trifluoromethyl-4-methoxypyrazole, Trifluoroacetic Acid Salt Part A: 1-(3-Cyanophenyl)-3-trifluoromethyl-4-methoxy-5-[(2'-trifluoromethyl-[1,1']-biphen-4-yl)aminocarbonyl] pyrazole, $^1$HNMR (CDCl$_3$) δ: 8.97 (s, 1H), 7.80 (t, j=1.83 Hz, 1H), 7.76 (s+m, 3H), 7.61 (d+m, j=8.70Hz, 4H), 7.50 (t, j=7.32 Hz, 7.34 (d+m, j=8.0 Hz, 3H), 4.17 (s, 3H) ppm; MS (DCI) m/z 531.2 (M+H)$^+$.

Part B: 1-(3-Amidinophenyl)-5-[(2'-trifluoromethyl-[1,1']-biphen-4-yl)aminocarbonyl]-3-trifluoromethyl-4-methoxy-pyrazole, trifluoroacetic acid salt was prepared from the nitrile of part A by standard Pinner conditions. $^1$HNMR (DMSO-$d_6$) δ: 11.06 (s, 1H), 9.47 (s, 1.5H), 9.15 (s, 1.5H), 8.03 (s, 1H), 7.92 (m, 4H), 7.75 (m, 1H), 7.70 (m, 3H), 7.40 (d, j=7.33 Hz, 1H), 7.33 (d, j=8.42 Hz, 2H), 3.96 (s, 3H), ppm; HRMS 548.152120 (calcd), 548.150458 (obs.); Analysis calcd for $C_{26}H_{19}F_6N_5O_2$ (TFA) 1.3 (H$_2$O) 0.5: C: 48.75, H: 3.05, N: 9.94, found C: 49.04, H: 2.70, N: 9.85.

Example 72

1-(3-Amidinophenyl)-5-[(2'-trifluoromethyl-[1,1']-biphen-4-yl)aninocarbonyl]-3-trifluoromethylpyrazole, Trifluoroacetic Acid Salt Part A: Preparation of 1-(3-Cyanophenyl)-3-trifluoromethyl-5-(4-bromobenzene)aminocarbonyl] pyrazole.

Standard coupling of 1-(3-cyanophenyl)-3-trifluoromethylpyrazole-5-yl carboxylic acid and 4-bromoaniline afforded the title compound in 77% yield ms (DCI) m/z 452–454 (M+H)$^+$.

Part B: Prepartion of 1-(3-Cyanophenyl)-3-trifluoromethyl-5-[(2'-trifluoromethyl-[1,1']-biphen-4-yl)aminocarbonyl] pyrazole.

Standard Suzuki coupling of the bromo compound from Part A and 2-trifluoromethyl phenyl boronic acid afforded the title compound (80.7%). $^1$HNMR (CDC$_3$) δ: 7.88 (m, 5H), 7.65 (d, j=8.06 Hz, 1H), 7.59 (m, 4H), 7.35 (d, j=8.79 Hz, 2H), 7.29 (s, 1H), 7.15 (s, 1H) ppm; MS (ESI) m/z 501.2 (M+H)$^+$.

Part C: 1-(3-Amidinophenyl)-5-[(2'-trifluoromethyl-[1,1']-biphen-4-yl)aminocarbonyl]-3-trifluoromethyl-pyrazole, trifluoroacetic acid salt was prepared from the nitrile in part B by standard Pinner conditions. $^1$HNMR (DMSO-$d_6$) δ: 10.86 (s, 1H), 9.46 (s, 1.5H), 9.11 (s, 1.5H), 8.05 (s, 1H), 7.95 (d, j=8.06 Hz, 2H), 7.84 (d, j=9.16 Hz, 1H), 7.78 (m, 3H), 7.73 (d, j=8.43 Hz, 2H), 7.63 (m, 1H), 7.40 (d, j=7.69 Hz, 1H), 7.32 (d, j=8.43 Hz, 2H) ppm; HRMS 518.141555 (calcd), 518.141456 (obs.); Analysis calcd for $C_{25}H_{17}F_6N_5O$ (TFA) 1.1: C: 50.82, H: 2.84, N: 10.89, found C: 50.57, H: 2.96, N: 10.75.

Example 73

1-(3-Amidinophenyl)-5-[(2'-sulfonylmethyl-[1,1']-biphen-4-yl)aminocarbonyl]-3-trifluormethyl-pyrazole, Trifluoroacetic Acid Salt Part A: 1-(3-Cyanophenyl)-5-[(2'-sulfonylmethyl-[1,1']-biphen-4-yl)aminocarbonyl]-3-trifluoromethyl-pyrazole.

Standard coupling of 1-(3-cyanophenyl)-3-trifluoromethylphenyl and 2-sulfonylmethyl-1-biphenyl aniline afforded the nitrile in 65% yield. $^1$HNMR (CDCl$_3$) δ: 9.81 (s, 1H), 8.24 (d, j=8.06 Hz, 1H), 7.86 (d, j=1.83 Hz, 1H), 7.82 (m, 4H), 7.66 (m, 3H), 7.46 (s, 1H), 7.44 (d, j=6.23 Hz, 2H), 7.37 (dd, j=7.30, 1.46 Hz, 1H), 2.68 (s, 3H) ppm; MS (ESI) 533.11 (M+Na)$^+$.

Part B: The title compound was prepared from the nitrile in part A by standard Pinner conditions, $^1$HNMR (DMSO-$d_6$) δ: 10.92 (s, 1H), 9.47 (s, 1.5H), 9.27 (s, 1.5H), 8.11 (dd, j=7.69, 1.1 Hz, 1H), 8.06 (s, 1H), 7.97 (m, 2H), 7.79 (m, 6H), 7.41 (s+m, 2H), 2.85 (s, 3H) ppm; HRMS 528.131721 (calcd), 528.1331 (obs.); Analysis calcd for $C_{25}H_{20}F_3N_5O_3S$ (TFA)(H2O) 0.6: C: 49.71, H: 3.43, N: 10.74, found C: 49.48, H: 3.35, N: 10.97.

Example 74

1-(3-Amidinophenyl)-5-[(2'-aminosulfonyl-3-bromo-[1,1']-biphen-4-yl)aminocarbonyl]-3-methyl-pyrazole, Trifluoroacetic Acid Salt Part A: Synthesis of 1-(3-Cyano)phenyl-3-methyl-5-[(2'-t-butylaminosulfonyl-3-bromo-[1,1']-biphen-4-yl)aminocarbonyl]-pyrazole.

The title compound was obtained by standard acid chloride coupling, of 1-(3-cyanophenyl)-3-methyl-pyrazole acid-and 4-amino-2'-t-butylaminosulfonyl-3-bromo-[1,1']-biphen-4-yl (71%). $^1$HNMR (CDCl$_3$) δ: 8.44 (d, j=8.79 Hz, 1H), 8.34 (s, 1H), 8.18 (dd, j=1.47, 7.69 Hz, 1H), 7.84 (m, 1H), 7.75 (d, j=1.83 Hz, 1H), 7.69 (m, 1H), 7.61 (m, 3H), 7.43 (dd, j=1.83, 8.43 Hz, 1H), 7.28 (m, 1H), 6.77 (s, 1H), 3.66 (s, 1H), 2.43 (s, 3H), 1.08 (s, 9H) ppm; MS (ESI) 614–616 (M+Na)$^+$.

Part B: The title compound was prepared from the nitrile in part A by standard Pinner conditions. $^1$HNMR (DMSO-$d_6$) δ: $^1$HNMR (DMSO-$d_6$) δ: 10.35 (s, 1H), 9.43 (s, 1.5H), 9.08 (s, 1.5H), 8.05 (m, 1H), 7.97 (s, 1H), 7.81 (m, 2H), 7.74 (d, j=7.69, 1H), 7.70 (d, j=1.83 Hz, 1H), 7.65 (m, 2H), 7.53 (d, j=8.05 Hz, 1H), 7.46 (m, 3H), 7.37 (m, 1H), 7.05 (s, 1H), 2.35 (s, 3H), HRMS 553.065747 (calcd), 553.066135 (obs.); Analysis calcd for $C_{24}H_{21}BrN_6O_3S$ (TFA)(H2O) 0.5: C: 46.16, H: 3.43, N: 12.42. found C: 46.06, H: 3.15, N: 12.14.

Example 75

1-(3-Aminocarbonylphenyl)-5-[(2'-aminosulfonyl-3-bromo-[1,1']-biphen-4-yl)aminocarbonyl]-3-methylpyrazole, Trifluoroacetic Acid Salt To 1-(3-cyano)phenyl-3-trifluoromethyl-5-[(2'-t-butylaminosulfonyl-3-bromo-[1,1']-biphen-4-yl) aminocarbonyl]-pyrazole (Part A Example 74) (82 mg, 0.14 mmol), cooled to 0° C. was added conc. sulfuric acid (5 mL). The reaction was allowed to warm to room temperature and was stirred 18 h. Water was added and the reaction was extracted with methylene chloride. Purification by HPLC afforded 35 mg (46%) of the title amide, $^1$HNMR (DMSO-$d_6$) δ: 10.27 (s, 1H), 8.11 (s, 1H), 8.05 (m, 2H), 7.90 (d, j=7.32 Hz, 1H), 7.68 (d, j=1.84 Hz, 1H), 7.64 (m, 3H), 7.56 (dd, j=8.4, 2.2 Hz, 2H), 7.51 (s, 1H), 7.44 (m, 3H), 7.36 (m, 1H), 6.96 (s, 1H), 2.34 (s, 3H) ppm; HRMS 554.049762 (calcd), 554.051045 (obs.).

Example 76

1-(3-Amidinophenyl)-3-methyl-5-[(2'-aminosulfonyl)-[1,1']-biphen-4-yl)methylcarbonyl]pyrazole, Trifluoroacetic Acid Salt Part A: Preparation of 1-[(3-Cyanophenyl)-5-(4-bromophenyl)acetyl]-3-methylpyrazole.

To zinc dust (0.56 g, 8.6 mmol) in THF (10 mL) was added 5 drops of 1, 2-dibromoethane. The mixture was heated to reflux for 5 minutes, then cooled to 0° C. and 4-bromobenzylbromide (1.85 g, 7.4 mmol) in THF (15 mL) was added dropwise. The reaction was stirred at 0° C. for 2 h, then it was cannulated into a suspension of LiCl (0.6 g, 1.4 mmol), CuCN (0.62 g, 7.0 mmol) and THF (20 mL). After warming to −20° C. for 5 minutes, the reaction was re-cooled to −78° C. and freshly prepared 1-(3-cyanophenyl)-3-methylpyrazol-5-yl carboxylic acid chloride (1.4 g, 5.7 mmol) in THF (15 mL) was added. The reaction was allowed to warm to room temperature and stirred 18 h. The reaction was diluted with ethyl acetate and washed with brine and dried ($Na_2SO_4$). Purification by chromatography on silica gel using 2:1 hexanes/ethyl acetate-as eluent afforded 0.62 g (28%) of the title compound. $^1$HNMR ($CDCl_3$) δ: 7.67 (dd, j=1.83, 6.96 Hz, 1H), 7.62 (s, 1H), 7.54 (m, 2H), 7.49 (s, j=8.42 Hz, 2H), 7.13 (d, j=8.42 Hz, 2H), 6.90 (s, 1H), 4.10 (s, 2H), 2.39 (s, 3H) ppm; MS (NH3—CI) 380–382 $(M+H)^+$, 397–399 $(M+NH_4)^+$.

Part B: To the product from part A (0.6 g, 1.6 mmol) was added 2-t-butylaminosulfonyl phenylboronic acid (0.57 g, 2.2 mmol), 2M sodium carbonate (3 mL) in 1:1 ethanol/toluene. The reaction mixture was degassed with a stream of nitrogen for 15 minutes. Tetrakistriphenylphosphine palladium (0.3 g) was added and the reaction was heated to reflux for 24 h. The reaction was cooled, filtered and concentrated. The aqueous residue was extracted with ethyl acetate, washed with brine and dried ($MgSO_4$). Purification by chromatography on silica gel using 3:1 hexanes/ethyl acetate as eluent afforded 0.62 g (77%) of the title compound. $^1$HNMR ($CDCl_3$) δ: 8.18 (dd, j=1.46, 7.69 Hz, 1H), 7.68 (m, 2H), 7.58 (m, 2H), 7.52 (d+m, j=8.40 Hz, 4H), 7.34 (d+m, j=8.05 Hz, 3H), 6.95 (s, 1H), 4.21 (s, 2H), 3.48 (s, 1H), 2.40 (s, 3H), 0.97 (s, 9H) ppm; MS (ESI) 513.2 $(M+H)^+$, 535.2 $(M+Na)^+$.

Part C: Standard Pinner amidine reaction sequence then afforded the title compound as colorless crystals. $^1$HNMR (DMSO-$d_6$) δ: 9.39 (s, 1.5H), 9.03 (s, 1.5H), 8.03 (dd, j=7.32, 1.83 Hz, 1H), 7.85 (m, 2H), 7.68 (m, 2H), 7.59 (m, 2H), 7.44 (s, 1H), 7.36 (m, 7H), 4.34 (s, 2H), 2.34 (s, 3H) ppm; HRMS 474.159987 (calcd), 474.161536 (obs.); Analysis calcd for $C_{25}H_{23}N_5O_3S$ (TFA)(H2O) 0.5: C: 54.36, H: 4.22, N: 11.74, found C: 54.39, H: 3.87, N: 11.65.

Example 77

1-(3-Aminocarbonylphenyl)-5-[5-[(2'-aminosulfonylphen-1-yl)pyridin-2-yl]aminocarbonyl]-3-methylpyrazole, Trifluoroacetic Acid Salt 1-(3-cyanophenyl)-5-[[5-[(2'-t-butylaminosulfonylphen-1-yl)pyridin-2-yl]aminocarbonyl]-3-methylpyrazole was converted to the title amide by the procedure described previously (Example 75); $^1$HNMR (DMSO-$d_6$) δ: 11.15 (s, 1H), 8.35 (d, j=2.19 Hz, 1H), 8.12 (m, 4H), 7.90 (m, 1H), 7.81 (dd, j=2.2, 8.79 Hz, 1H), 7.66 (m, 2H), 7.55 (m, 2H), 7.48 (s, 1H), 7.41 (m, 3H), 7.08 (s, 1H), 2.32 (s, 3H) ppm; HRMS 477.134500 (calcd), 477.135223 (obs.).

Example 78

1-(3-Amidinophenyl)-5-[[5-(2'-t-butylaminosulfonylphenyl)pyrimidin-2-yl]aminocarbonyl]-3-trifluoromethyl-pyrazole, Trifluoroacetic Acid Salt Part A: 1-(3-Cyanophenyl)-5-[[5-(2'-t-butylaminosulfonylphenyl)pyrimidin-2-yl]aminocarbonyl]-3-trifluoromethyl pyrazole was obtained via standard coupling protocols. $^1$HNMR ($CDCl_3$) δ: 9.13 (s, 1H), 8.64 (s, 2H), 8.22 (dd, j=1.47, 7.69 Hz, 1H), 7.89 (m, 1H), 7.85 (m, 1H), 7.75 (dd, j=1.46, 6.59 Hz, 1H), 7.65 (m, 3H), 7.30 (m, 2H), 4.60 (s, 1H), 1.13 (s, 9H) ppm; MS (ESI) 570.1 $(M+H)^+$, 592.1 $(M+Na)^+$.

Part B: Standard Pinner amidine reaction sequence then afforded the title compound as colorless crystals. $^1$HNMR (DMSO-$d_6$) δ: 11.64 (s, 1H), 9.46 (s, 1.5H), 9.11 (s, 1.5H), 8.63 (s, 2H), 8.09 (dd, j=7.69, 1.83 Hz, 1H), 8.04 (s, 1H), 7.96 (m, 2H), 7.81 (m, 2H), 7.76 (m, 2H), 7.42 (dd, j=1.46, 8.79 Hz, 1H), 7.32 (s, 1H), 1.03 (s, 9H) ppm;HRMS 587.180069 (calcd), 587.177999 (obs.); Analysis calcd for $C_{26}H_{25}F_3N_8O_3S$ (TFA) 1.1: C: 47.57, H: 3.69, N: 15.74, found C: 47.51, H: 3.54, N: 15.41.

Example 79

1-(3-Amidinophenyl)-5-[[5-(2'-aminosulfonylphenyl)pyrimidin-2-yl]aminocarbonyl]-3-trifluoromethyl-pyrazole, Trifluoroacetic Acid Salt 1-(3-cyanophenyl)-5-[[5-(2-t-butylaminosulfonylphenyl)pyrimidin-2-yl]-aminocarbonyl]-3-trifluoromethyl-pyrazole, (0.275 g, 0.39 mmol) was heated to reflux in TFA for 1 h. Removal of TFA and purification by HPLC afforded 0.2 g (80%) title compound. $^1$HNMR (DMSO-$d_6$) δ: 11.63 (s, 1H), 9.46 (s, 1.5H), 9.42 (s, 1.5H), 8.66 (s, 2H), 8.08 (m, 2H), 7.96 (m, 2H), 7.83 (s, 1H), 7.81 (m, 1H), 7.72 (m, 2H), 7.54 (s, 2H), 7.45 (m, 1H) ppm; HRMS 531.117468 (calcd), 531.117523 (obs.); Analysis calcd for $C_{22}H_{17}F_3N_8O_3S$ (TFA) 1.1 ($H_2O$) 0.5: C: 43.71, H: 2.90, N: 16.85, found C: 43.99, H: 2.62, N: 16.54.

Example 80

1-(3-Aminocarbonylphenyl)-5-[[5-(2'-aminosulfonylphenyl)pyrimidin-2-yl]aminocarbonyl]-3-trifluoromethylpyrazole 1-(3-cyanophenyl)-5-[[5-(2'-t-butylaminosulfonylphenyl)pyrimidin-2-yl]aminocarbonyl]-3-trifluoromethyl pyrazole (0.5 g, 0.8 mmol) was cooled to 0° C. and con. $H_2SO_4$ (5 mL) was added. The reaction was kept cold 24 h. Ice water was added and the precipitated solid was collected, dissolved in ethyl acetate and dried ($MgSO_4$). Purification, first, by chromatography on silica gel using 1–10% methanol/methylene chloride as eluent, then by HPLC afforded 72 mg (14%) of the title amide. $^1$HNMR (DMSO-$d_6$) δ: 11.59 (s, 1H), 8.64 (s, 2H), 8.16 (s, 1H), 8.03 (s, 3H), 7.72 (m, 4H), 7.64 (d, j=7.33 Hz, 1H), 7.58 (m, 1H), 7.51 (s, 2H), 7.43 (d, j=7.33 Hz, 1H) ppm; HRMS 532.096112 (calcd), 532.098037 (obs.); Analysis calcd for $C_{22}H_{16}F_3N_7O_4S$ (TFA) 0.5: C: 46.99, H: 2.83, N: 16.66, found C: 46.86, H: 2.74, N: 16.35.

Example 81

1-(3-Cyanophenyl)-5-[((4'-(imidazol-1-yl)phenyl)aminocarbonyl]-3-trifluoromethylpyrazole, Trifluoroacetic Acid Salt Part A: 1-(3-Cyanophenyl)-3-trifluoromethyl-pyrazol-5-yl carboxylic acid (0.5 g, 1.8 mmol) was coupled with 4-imidazoyl aniline (0.3 g, 1.8 mmol) by standard conditions and purified by HPLC to afford 0.67 g (71%) product. $^1$HNMR (DMSO-d$_6$) δ: 9.55 (s, 1H), 8.22 (d, j=5.49 Hz, 2H), 8.04 (d, j=7.69 Hz, 1H), 7.96 (d, j=8.06 Hz, 1H), 7.89 (s+d, j=8.79 Hz, 3H), 7.80 (m, 4H) ppm; HRMS 423.118119 (calcd), found 423116015 (obs.); Analysis calcd for C$_{21}$H$_{13}$F$_3$N$_6$O (TFA) C: 51.50, H: 2.63, N: 15.67, found C: 51.52, H: 2.71, N: 15.49.

Part B: 1-(3-Cyanophenyl)-5-((4'-(imidazol-1-yl)phenyl) aminocarbonyl]-3-trifluoromethylpyrazole was subjected to standard Pinner and purification conditions to afford title amidine (79%) as colorless crystals. $^1$HNMR (DMSO-d$_6$) δ: 11.02 s, 1H), 9.46 (s, 1.5H), 9.42 (s.1H), 9.22 (s, 1.5H), 8.17 (s, 1H), 8.06 (s, 1H), 7.97 (t, j=7.69 Hz, 2H), 7.88 (d, j=8.79 Hz, 2H), 7.80 (m, 3H), 7.79 (d, j=9.0 Hz, 2H) ppm; HRMS 440.144668 (calcd), 440.144557 (obs.).

Examples 82 and 83

1-(3-Amidinophenyl)-5-[(4'-(morpholin-1-yl) phenyl)-aminocarbonyl]-3-trifluoromethylpyrazole, Trifluoroacetic Acid Salt (Example 82) and 1-(3-Aminocarbonylphenyl)-5-[(4'-(morpholin-1-yl) phenyl)aminocarbonyl]-3-trifluoromethylpyrazole, Trifluoroacetic Acid Salt (Example 83)

Part A: 1-(3-Cyanophenyl)-3-trifluoromethyl-pyrazol-5-yl carboxylic (0.34 g, 1.2 mmol) was coupled with 4-(4-morpholin) aniline (0.22 g, 1.2 mmol) by standard conditions to afford 0.53 g (69%) product. $^1$HNMR (CDCl$_3$) δ: 9.63 (s, 1H), 7.85 (d, j=1.46 Hz, 1H), 7.79 (m, 1H), 7.74 (d, j=7.69 Hz, 1H), 7.60 (t, j=8.06 Hz, 1H), 7.53 (d, j=8.79 Hz, 2H), 7.37 (s, 1H), 6.89 (d, j=9.15 Hz, 2H), 3.87 (m, 4H), 3.87 (m, 4H) ppm; MS (ESI) 442.1 (M+H)$^+$.

Part B: Synthesis of 1-(3-Amidinophenyl)-5-[(4'-(morpholin-1-yl)phenyl)aminocarbonyl]-3-trifluoromethylpyrazole, Trifluoroacetic Acid Salt.

The nitrile from part A was subjected to standard Pinner conditions to afford 65% yield of the amidine as colorless crystals. $^1$HNMR (DMSO-d$_6$) δ: 10.56 (s, 1H), 9.45 (s, 1.5H), 9.13 (s, 1.5H), 8.02 (s, 1H), 7.94 (m, 2H), 7.79 (t, j=7.69 Hz, 1H), 7.69 (s, 1H), 7.51 (d, j=9.16 Hz, 2H), 6.94 (d, j=8.80 Hz, 2H), 3.74 (m, 4H), 3.08 (m, 4H) ppm; HRMS 459.175634 (calcd), 459.173592 (obs.); Analysis calcd for C$_{22}$H$_{21}$F$_3$N$_6$O$_2$ (TFA) 2.7 (H$_2$O) 0.1: C: 42.85, H: 3.14, N: 10.94, found C: 42.87, H: 2.78, N: 10.80.

Part C: The amide was also isolated from the Pinner reaction in the part B. $^1$HNMR (DMSO-d$_6$) δ: 10.54 (s, 1H), 8.15 (m, 2H), 7.68 (m, 1H), 7.60 (s, 1H), 7.55 (m, 1H), 7.50 (d, j=8.78 Hz, 2H), 6.94 (d, j=8.78 Hz, 2H), 3.73 (m, 4H), 3.07 (m, 4H), ppm; MS (ESI) 460.1 (M+H)$^+$, 482 (M+Na)$^+$.

Examples 84 and 85

1-(3-Amidinophenyl)-5-[[5-(2'-aminosulfonylphenyl)pyridin-2-yl]aminocarbonyl]-3-trifluoromethyl Pyrazole, Trifluoroacetic Acid Salt (Example 84) and 1-(3-Aminocarbonylphenyl)-5-[[5-(2'-aminosulfonylphenyl)pyridin-2-yl] aminocarbonyl]-3-trifluoromethylpyrazole, Trifluoroacetic Acid Salt (Example 85)

Part A: 1-(3-Cyanophenyl)-5-[[5-[(2'-t-butylaminosulfonyl)-1-yl)pyridin-2-yl]-aminocarbonyl]-3-trifluoromethylpyrazole. $^1$HNMR (CDCl$_3$) δ: 8.75 (s, 1H), 8.35 (d, j=1.83 Hz, 1H), 8.21 (m, 2H), 7.87 (m, 4H), 7.66 (t, j=7.69 Hz, 1H), 7.59 (m, 2H), 7.29 (m, 2H), 4.30 (s, 1H), 1.11 (s, 9H) ppm; MS (ESI) 569.1 (M+H)$^+$, 591.1 (M+Na)$^+$.

Part B: Standard Pinner amidine reaction sequence then afforded the title compound as colorless crystals; $^1$HNMR (DMSO-d$_6$) δ: 11.4:6 (s, 1H), 9.47 (s, 1.5H), 9.21 (s, 1.5H), 8.39 (d, j=1.84 Hz, 1H), 8.06 (m, 2H), 7.97 (m, 4H), 7.82 (m, 2H), 7.56 (m, 2H), 7.45 (s, 2H), 7.40 (dd, j=2.20 Hz, 7.69 Hz, 1H) ppm; MS (ESI) 530.1 (M+H)+. Analysis calcd for C$_{23}$H$_{18}$F$_3$N$_7$O$_3$S (TFA)$_2$: C: 42.81, H: 2.66, N: 12.44, found C: 42.99, H: 2.44, N: 12.77.

Part C: The amide was also isolated from the Pinner reaction in the part B; $^1$HNMR (DMSO-d$_6$) δ: 11.42 (s, 1H), 8.37 (d, 1H), 8.06 (s, 1H), 8.03 (m, 4H), 7.82 (m, 2H), 7.70 (m, 4H), 7.56 (s, 1H), 7.42 (s, 2H), 7.39 (dd, j=7.69, 2.2 Hz, 1H) ppm; HRMS 531.106235 (calcd), 531.108937 (obs.).

Example 86

1-(3-Amidinophenyl)-5-[(4'-(3-methyltetrazol-1-yl) phenyl)aminocarbonyl]-3-trifluoromethylpyrazole, Trifluoroacetic Acid Salt Part A: Synthesis of 4-Tetrazoyl Nitrobenzene.

4-Nitrobenzonitrile (2 g, 13.5 mmol), sodium azide (0.92 g, 14 mmol), and tributyltin chloride (3.8 mL, 14 mmol) were combined in toluene (30 mL) and heated to reflux 18 h. The reaction mixture was extracted with excess 1N NaOH. The aqueous layer was cooled, acidified with con. HCl, and the precipitated solid was filtered off and dried in vacuo. The aqueous layer was extracted with ethyl acetate, combined with the solid and dried (MgSO4) to afford 1.4 g (56%). $^1$HNMR (DMSO-d6) δ: 8 8.48 (d, j=8.79 Hz, 2H), 8.34 (d, j=8.79 Hz, 2H) ppm; MS (ES−) 190.0 (M−H). Part B: To 4-tetrazoyl nitrobenzene (1.16 g, 6.1 mmol) and iodomethane (0.53 mL, 8.5 mmol) in DMF (10 mL) at 0° C. was added 60% sodium hydride (0.29 g, 7.3 mmol). The reaction was allowed to warm to room temperature and stirred 24 h. The reaction was quenched with water and extracted with ethyl acetate and dried (MgSO$_4$). Purification by chromatography on silica gel using 4:1 hexanes/ethyl acetate as eluent afforded 0.9 g (72%) of the major isomer, 4-(3-methyltetrazole) nitrobenzene. $^1$HNMR (CDCl$_3$) δ: 8.38 (d, j=9.16 Hz, 2H), 8.35 (d, j=9.52 Hz, 2H), 4.45 (s, 3H) ppm; MS (NH$_3$—CI) 206 (M+H)$^+$, 176 (M+H−NO).

Part C: 4-(3-Methyltetrazole) nitrobenzene (0.67 g, 3.3 mmol) was placed in ethanol (15 mL) and trifluoroacetic acid (1 mL). A catalytic amount of 10% Palladium on carbon was added and the mixture was placed under a hydrogen balloon. The reaction was stirred 4 h, then filtered and concentrated. The 4-(3-methyltetrazole) aniline trifluoroacetic acid salt obtained (MS 176 (M+H)$^+$) was used directly in the next step. 4-(3-Methyltetrazole) aniline trifluoroacetic acid salt and 1-(3-cyanophenyl)-3-trifluoromethylpyrazol-5-yl carboxylic acid were coupled by standard conditions to give 1-(3-cyanophenyl)-5-[(4'-(3-methyltetrazol-1-yl) phenyl) aminocarbonyl]-3-trifluoromethylpyrazole. $^1$HNMR (CDCl$_3$) δ: 10.45 (s, 1H), 8.11 (d, j=8.79 Hz, 2H), 7.86 (s, 1H), 7.82 (d, j=8.79 Hz, 2H), 7.77 (dd, j=7.69, 1.46 Hz, 2H), 7.63 (t, j=7.69 Hz, 1H), 7.50 (s, 1H), 4.40 (s, 3H) ppm; MS (ESI) 439 (M+H)$^+$, 460.9 (M+Na)$^+$.

Part D: The nitrile from part C was subjected to ths standard Pinner conditions to give 1-(3-amidinophenyl)-5-[(4'-(3-methyltetrazol-1-yl)phenyl)aminocarbonyl]-3-trifluoromethylpyrazole, Trifluoroacetic Acid Salt. $^1$HNMR (DMSO-d$_6$) δ: 10.97 (s, 1H), 9.47 (s, 1.5H), 9.24 (s, 1.5H), 8.07 (d, j=8.79 Hz, 2H), 8.06 (m, 1H), 7.97 (m, 2H), 7.86 (d, j=8.78 Hz, 2H), 7.80 (m, 2H), 4.41 (s, 3H) ppm; HRMS 456.150816 (calcd), 456.152474 (obs.); Analysis calcd for C$_{20}$H$_{16}$F$_3$N$_9$O (TFA) 1.2: C: 45.43, H: 2.93, N: 21.29, found C: 45.37, H: 3.18, N: 21.39.

Example 87

1-(3-Amidinophenyl)-5-(2'-napthylaminosulfonyl)-3-methylpyrazole, Trifluoroacetic Acid Salt Part A: To 5-amino-1-(3-cyanophenyl)-3-methylpyrazole (0.5 g, 2.5 mmol) in methylene chloride (15 mL) was added 2-napthylsulfonyl chloride (0.63 g, 2.8 mmol) and triethylamine (0.46 mL, 3.3 mmol). The reaction was stirred 18 h at room temperature, but did not appear complete by TLC. A few crystals of N,N-dimethylaminopyridine were added and the reaction was heated to reflux for 5 h. The reaction was cooled, diluted and washed with 1N HCl, sat'd NaHCO$_3$, brine and dried (MgSO$_4$). Crude NMR and Mass Spectrum indicated that the major product was the bis-sulfonamide, MS (ESI) 579 (M+H)$^+$, 601. (M+Na)$^+$.

Part B: The crude bis-sulfonamide from part A was subjected to the standard Pinner conditions and purified by HPLC to afford 0.3 g (50%) of the desired mono-sulfonamide title compound, $^1$HNMR (DMSO-d$_6$) δ: 9.36 (s, 1.5H), 9.07 (s, 1.5H), 8.29 (s, 1H), 8.14 (d, j=7.69 Hz, 1H), 8.09 (t, j=8.79 Hz, 2H), 7.86 (s, 1H), 7.79 (m, 6H), 7.60 (d, j=7.69 Hz, 1H), 5.79 (s, 1H), 2.12 (s, 3H) ppm; HRMS 406.133772 (calcd), 406.133617 (obs.).

Example 88

1-(3-Amidinophenyl)-5-[(4-bromophenyl) aminosulfonyl]-3-methylpyrazole, Trifluoroacetic Acid Salt Part A: To 5-amino-1-(3-cyanophenyl)-3-methylpyrazole (0.5 g, 2.5 mmol) in methylene chloride (15 mL) was added 4-bromobenzenesulfonyl chloride (0.7 g, 2.8 mmol) and triethylamine (0.46 mL, 3.3 mmol). The reaction was stirred 18 h at room temperature, but did not appear complete by tlc. A few crystals of N,N-dimethylaminopyridine were added and the reaction was heated to reflux for 5 h. The reaction was cooled, diluted and washed with 1N HCl, sat'd NaHCO$_3$, brine and dried (MgSO$_4$). Crude NMR and Mass Spectrum indicated that the major product was the bis-sulfonamide, MS (ESI) 634–636.6 (M+H)$^+$, 655–657.2 (M+Na)$^+$.

Part B: The crude bis-sulfonamide from part A was subjected to the standard Pinner conditions and purified by HPLC to afford 0.22 g (44%) of the desired mono-sulfonamide title compound, $^1$HNMR (DMSO-d$_6$) δ: 9.40 (s, 1.5H), 9.18 (s, 1.5H), 7.88 (s, 1H), 7.79 (m, 1H), 7.74 (d, j=8.40 Hz, 2H), 7.69 (m, 2H), 7.53 (d, j=8.42 Hz, 2H), 5.89 (s, 1H), 2.17 (s, 3H) ppm; HRMS 434.028633 (calcd), 434.029892 (obs.).

Example 89

1-(3-Aminomethylphenyl)-5-[(2'-aminosulfonyl-[1,1']-biphen-4-yl)aminocarbonyl]-3-methylpyrazole, Trifluoroacetic Acid Salt To 1-(3-cyanophenyl)-5-[(2'-aminosulfonyl-[1,1']-biphen-4-yl) aminocarbonyl]-3-methylpyrazole (0.19 g, 0.41 mmol) was added ethanol (20 mL), TFA (0.5 mL), and 10% Palladium on carbon (10 mg). The mixture was stirred under H2 (1 atmos.) for 18 h. The reaction was filtered, concentrated and purified by HPLC to afford 17 mg (9%) of the title compound. $^1$HNMR (DMSO-d$_6$) δ: 10.66 (s, 1H), 8.22 (brd, 2H), 8.03 (dd, j=1.47, 6.22 Hz, 1H), 7.70 (d, j=8.79 Hz, 2H), 7.67 (m, 2H), 7.64 (m, 5H), 7.37 (d, j=8.43 Hz, 2H), 7.32 (m, 2H), 6.93 (s, 1H), 4.13 (d, j=4.03 Hz, 2H), 2.33 (s, 3H) ppm; HRMS 462.159987 (calcd), 462.158938 (found).

Example 90

1-(3-Aminomethylphenyl)-5-[(2'-aminosulfonyl-[1,1']-biphen-4-yl)aminocarbonyl]-3-trifluoromethylpyrazole, Trifluoroacetic Acid Salt 1-(3-cyanophenyl)-5-[(2'-aminosulfonyl-(1,1'-biphen-4-yl)aminocarbonyl]-3-trifluoromethylpyrazole was reduced by hydrogenation to the title compound, $^1$HNMR (DMSO-d$_6$) δ: 10.89 (s, 1H), 8.25 (brd s, 1H), 8.04 (d, j=7.33 Hz, 1H), 7.75 (s, 1H), 7.69 (d+s, j=6.96 Hz, 3H), 7.60 (m, 4H), 7.39 (d, j=8.43 Hz, 2H), 7.32 (s+d, j=6.94 Hz, 3H), 4.17 (d, j=5.49 Hz, 2H) ppm; HRMS 516.131721 (calcd), 516.130109 (obs.); Analysis calcd for C$_{24}$H$_{20}$F$_3$N$_5$O$_3$S (TFA) 1.2: C: 48.61, H: 3.28, N: 10.74, found C: 48.35, H: 3.18, N: 10.69.

Example 91

1-(3-Amidinophenyl)-3-methyl-5-[((2"-trifluoromethylphenyl)pyrid-2-yl)aminocarbonyl] pyrazole, Trifluoroacetic Acid Salt The title compound was prepared as colorless crystals following the standard Pinner amidine reaction sequence and purification protocols outlined previously. $^1$HNMR (DMSO) δ: 11.21 (s, 1H); 9.39 (s, 2H); 9.11 (s, 2H); 8.31 (s, 1H); 8.00 (d, 1H); 7.93 (s, 1H); 7.86–7.63 (m, 7H); 7.45 (d, 1H); 7.16 (s, 1H); 2.29 (s, 3H) ppm; LRMS (ESI) 465.3 (M+H)+HRMS for C24H20N6F3O1 465.165069 (calcd), 465.165566 (obs).

Example 92

1-(3-Amidinophenyl)-3-methyl-5-[((2'-aminosulfonyl-1-yl)pyrimid-5-yl)aminocarbonyl] pyrazole, Trifluoroacetic Acid Salt The title compound was prepared as colorless crystals following the standard Pinner amidine reaction sequence and purification protocols outlined previously; $^1$HNMR (DMSO) δ: 11.39 (s, 1H); 9.43 (s, 2H); 9.08 (s, 2H); 8.65 (s, 2H); 8.08–8.05 (m, 1H); 7.96 (s, 1H); 7.83 (m, 1H); 7.78–7.68 (m, 4H); 7.54 (s, 2H); 7.46–7.43 (m, 1H); 7.09 (s, 1H); 2.33 (s, 3H), ppm; LRMS (ESI) 477.2 (M+H)+;HRMS for C22H21N8O3S1 477.148419 (calcd), 477.146755 (obs).

Example 93

1-(3-Amidinophenyl)-3-methyl-5-[(2'-fluoro-[1,1']-biphen-4-yl)aminocarbonyl]pyrazole, Trifluoroacetic Acid Salt The title compound was prepared as colorless crystals following the standard Pinner amidine reaction sequence and purification protocols outlined previously; $^1$HNMR (DMSO) δ: 10.68 (s, 1H); 9.43 (s, 2H); 9.13 (s, 2H); 7.96 (s, 1H); 7.83–7.67 (m, 6H); 7.55 (d, 2H); 7.41 (m, 1H); 7.33–7.27 (m, 2H); 7.05 (s, 1H); 2.35 (s, 3H) ppm; LRMS (ESI) 414.3 (M+H)+; HRMS for C$_{24}$H$_{21}$N$_5$O$_1$F$_1$ 414.173014 (calcd); 414.172475 (obs).

Example 94

1-(3-Amidinophenyl)-3-methyl-5-[3-chloro-(2'-fluoro-[1.1']-biphen-4-yl)aminocarbonyl]pyrazole, Trifluoroacetic Acid Salt The title compound was prepared as colorless crystals following the standard Pinner amidine reaction sequence and purification protocols outlined previously; $^1$HNMR (DMSO) δ: 10.43 (s, 1H): 9.43 (S, 2H); 9.10 (s, 2H); 7.95 (s, 1H); 7.82 (m, 2H); 7.73 (m, 2H); 7.68–7.54 (m, 3H); 7.46 (m, 1H); 7.38–7.30 (m, 2H); 7.07 (s, 1H); 2.35 (s, 3H) ppm; LRMS (ESI) 448.2 (M+H)+;HRMS for C$_{24}$H$_{20}$N$_5$OFCl 448.134041 (calcd), 448.133737 (obs).

Example 95

1- (3-Amidinophenyl)-3-methyl-5-[3-fluoro-(2'-fluoro-[1,1']-biphen-4-yl)aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 10.47 (s, 1H): 9.43 (s, 2H); 9.09 (s, 2H): 7.96 (s, 1H); 7.87–7.60 (m, 6H); 7.52 (m, 1H); 7.46 (d, 1H); 7.30 (d, 1H); 7.18 (d, 1H); 7.07 (s, 1H); 2.34 (s, 3H) ppm; LRMS (ESI) 482.2 (M+H)+; HRMS for $C_{25}H_2N_5OF_4$ 482.160398 (calcd); 482.157655 (obs).

Example 96

1-(3-Amidinophenyl)-3-methyl-5-[3-fluoro-(2'-aminosulfonyl-[1,1']-biphen-4-yl)aminocarbonyl] pyrazole, Trifluoroacetic Acid Salt The title compound was prepared as colorless crystals following the standard Pinner amidine reaction sequence and purification protocols outlined previously; ¹HNMR (DMSO) δ: 10.45 (s, 1H); 9.43 (s, 2H); 9.09 (s, 2H); 8.04 (m, 1); 7.96 (s, 1H); 7.80 (m, 2H); 7.73 (d, 1H); 7.65 (m, 3H); 7.43 (s, 2H); 7.36–7.29 (m, 2H); 7.22 (m, 1H); 7.06 (s, 1H); 2.34 (s, 3H) ppm; LRMS (ESI) 493.2 (M+H)+; HRMS for $C_{24}H_{22}N_6O_3SF$ 493.145814 (calcd), 493.146092 (obs).

Example 97

1-(3-Amidinophenyl)-3-methyl-5-[5-(2'-fluorophen-1-yl)pyrid-2-yl]aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 11.25 (s, 1H); 9.43 (s, 2H); 9.09 (s, 2H); 8.59 (s, 1H); 8.10–8.07 (d, j=8.79, 1H); 8.02–7.96 (m, 2H); 7.85–7.79 (m, 2H); 7.73–7.70 (d, j=8.06, 1H); 7.64–7.59 (m, 1H); 7.49–7.44 (m, 1H); 7.39–7.31 (m, 2H); 7.21 (s, 1H): 2.33 (s, 3H) ppm; LRMS (ESI) 415.2 (M+H)+; HRMS for $C_{23}H_2ON_6F$ 415.168263 (calcd); 425.168444 (obs).

Example 98

1-(3-Amidinophenyl)-3-methyl-5-[[5-(2'-tertbutylaminosulfonylphenyl)pyrimid-2-yl] aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 11.40 (s, 1H); 9.43 (s, 2H); 9.08 (s, 2H); 8.62 (s, 2H); 8.09–8.06 (m, 1H); 7.95 (s, 1H); 7.83–7.65 (m, 6H); 7.43–7.40 (m, 1H); 7.08 (s, 1H); 2.32 (s, 3H); 1.04 (s, 9H) ppm; LRMS (ESI) 533.3 (M+H)+; HRMS for $C_{26}H_{29}N_8O_3S$ 533.208334 (calcd), 533.207170 (obs).

Example 99

1- (3-Amidinophenyl)-3-methyl-5-[[5-(2'-aminosulfonylphenyl)-[1,6]-dihydropyrimid-2-yl] aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 9.95 (s, 1H); 9.38 (s, 2H); 9.29 (s, 1H); 9.25 (s, 2H); 7.95–7.92 (m, 2H); 7.84 (d, j=7.81, 1H); 7.79 (d, j=8.79 Hz, 1H); 7.70–7.66 (t, j=8.06, j=7.81, 1H); 7.58–7.56 (t, j=7.57, 1H); 7.54–7.49 (t, j=7.57, 1H); 7.48 (s, 2H); 7.40 (d, j=7.57, 1H); 6.86 (s, 1H); 6.13 (s, 1H); 4.24 (s, 2H); 2.28 (s, 3H) ppm; LRMS (ESI) 579.2 (M+H)+; HRMS for $C_{22}H_{23}N_8O_3S$ 579.161384 (calcd), 579.161293 (obs).

Example 100

1-(3-Amidinophenyl)-3-methyl-S-[(4-(pyrid-3'-yl) phen-1-yl)aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 10.71 (s, 1H); 9.43 (s, 2H); 9.11 (s, 2H); 8.98 (s, 1H); 8.64 (m, 1H); 8.28–8.25 (d, J=8.43, 1H); 7.97 (s, 1H); 7.84–7.06 (m, 8H); 7.06s, 1H); 2.35 (s, 3H), ppm LRMS (ESI) 379.2 (M+H)+; HRMS for $C_{23}H_{21}N_6O$ 379.177685 (calcd), 379.176514 (obs)

Example 101

1-(3-amidinophenyl)-3-methyl-5-[[2-(2'-pyridyl) ethyl]aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 9.40 (s, 2H); 9.16 (s, 2H); 8.81 (m, 1H); 8.68 (m, 1H); 8.09 (m, 1H); 7.85 (s, 1H); 7.80–7.77 (d, j=8.06, 1H); 7.64–7.54 (m, 4H); 6.72 (s, 1H); 3.61–3.55 (q, 2H); 3.09–3.05 (t, 2H); 2.26 (s, 3H), ppm; LRMS (ESI) 349.1 (M+H)+; HRMS for $C_{19}H_{21}N_6O$ 349.177685 (calcd); 349.175374 (obs).

Example 102

1-(3-Amidinophenyl)-3-methyl-5-[(3-phenylpropyl) aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 9.41 (s, 2H); 9.11 (s, 2H); 8.72 (m, 1H); 7.88 (s, 1H); 7.81–7.77 (m, 1H); 7.68 (m, 2H); 7.31–7.18 (m, 5H); 6.77 (s, 1H); 3.21–3.14 (q, j=6.60, 2H); 2.62–2.57 (t, j=7.69, 2H); 2,28 (s, 3H); 1.82–1.73 (qu, j=7.32, 2H) ppm; LRMS (ESI) 362.1 (M+H)+; HRMS for $C_{21}H_{24}N_5O$ 362.198086 (calcd); 362.197157 (obs).

Example 103

1-(3-Amidinophenyl)-3-methyl-S-[4-(pyrid-2'-yl) phen-1-ylaminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 10.70 (s, 1H); 9.43 (s, 2H); 9.08 (s, 2H); 8.66 (m, 1H); 8.10 (m, 2H); 7.96–7.88 (m, 3H); 7.84–7.76 (m, 4H); 7.73 (m, 1H); 7.38 (m, 1H); 7.06 (s, 1H); 2.35 (s, 3H) ppm; LRMS (ESI) 397.1 (M+H)+; HRMS for $C_{23}H_{21}N_6O$ 397.177685 (calcd); 397.179670 (obs).

Example 104

1-(3-Amidinophenyl)-3-methyl-5-[(4-(isopropyloxy) phenyl)aminocarbonyl]pyrazole, Trifluoroacetic Acid Salt The title compound was prepared as colorless crystals following the standard Pinner amidine reaction sequence and purification protocols outlined previously; ¹HNMR (DMSO) δ: 10.40 (s, 1H); 9.42 (s, 2H); 9.06 (s, 2H); 7.94 (s, 1H); 7.82 (d, j=7.32, 1H); 7.75–7.65 (m, 2H); 7.54 (d, j=9.16, 2H); 6.96 (s, 1H); 6.89 (d, j=8.79, 2H); 4.57–4.53 (m, 1H); 2.32 (s, 3H); 1.25 (s, 3H); 1.23 (s, 3H), ppm LRMS (ESI) 378.1 (M+H)+; HRMS for $C_{21}H_{24}N_5O_2$ 378.193000 (calcd); 378.194610 (obs).

Example 105

1-(3-Amidinophenyl)-3-methyl-5-[(5-(2'-trifluoromethylphenyl)-pyrimidin-2-yl) aminocarbonyl]pyrazole, Trifluoroacetic Acid Salt The title compound was prepared as colorless crystals following the standard Pinner amidine reaction sequence and purification protocols outlined previously; $^1$HNMR (DMSO) δ: 11.45 (s, 1H): 9.43 (s, 2H); 9.09 (s, 2H); 8.69 (s, 2H); 7.96 (s, 1H): 7.93 (d, j=8.06, 1H); 7.84–7.67 (m, 5H); 7.57 (d, j=7.69, 1H); 7.10 (s, 1H); 2.32 (s, 3H) ppm; LRMS (ESI) 466.1 (M+H)+; HRMS for $C_{23}H_{19}N_7F_3O$ 466.163004 (calcd), 466.161823 (obs).

Example 106

1-(3-Amidinophenyl)-3-methyl-5-[(4-(piperidinosulfonyl)phenyl)aminocarbonyl]pyrazole, Trifluoroacetic Acid Salt The title compound was prepared as colorless crystals following the standard Pinner amidine reaction sequence and purification protocols outlined previously; $^1$HNMR (DMSO) δ: 10.90 (s, 1H); 9.42 (s, 2H); 9.19 (s, 2H): 7.95 (m, 3H); 7.80 (m, 2H); 7.70 (m, 3H); 7.08 (s, 1H); 2.85 (m, 4H); 2.35) s, 3H); 1.54 (m, 4H); 1.35 (brd, 2H); ppm LRMS (ESI) (M+H)+467.1; HRMS for $C_{23}H_{27}N_6O_3S$ 467.186536 (calcd); 467.185030 (obs).

Example 107

1-(3-Amidinophenyl)-3-methyl-5-[(4-(piperidinocarbonyl)phenyl)aminocarbonyl] pyrazole, Trifluoroacetic Acid Salt The title compound was prepared as colorless crystals following the standard Pinner amidine reaction sequence and purification protocols outlined previously; $^1$HNMR (DMSO) δ: 10.69 (s, 1H); 9.43 (s, 2H); 9.12 (s, 2H); 7.95 (s, 1H); 7.83 (m, 1H): 7.77–7.96 (m, 4H); 7.37 (d, j=8.79, 2H); 7.04 (s, 1H); 3.31 (brd, 2H); 3.54 (brd, 2H); 2.34 (s, 3H); 1.60 (brd, 2H); 1.50 (brd, 4H) ppm; LRMS (ESI) 431.1 (M+H)+.

Examples 108 and 109

1-(3-Amidino-4-fluorophenyl)-3-methyl-5-[(2'-aminosulfonyl-[1,1']-biphen-4-yl)aminocarbonyl]-pyrazole, Trifluoroacetic Acid Salt (Example 108) and 1-(3-Aminocarbonyl-4-fluorophenyl)-3-methyl-5-[(2'-aminosulfonyl-[1,1']-biphen-4-yl) aminocarbonyl]-pyrazole (Example 109)

Part A: Preparation of 2-Fluoro-5-aminobenzonitrile.

To a solution of 2-fluoro-5-nitrobenzonitrile (2.0 g, 12 mmol) in ethyl acetate (50 mL) was added stannous chloride (27.0 g, 120 mmol). The reaction mixture was stirred at reflux 1.5 h, then cooled to room temperature. Partitioned between ethyl acetate (150 mL) and saturated sodium bicarbonate (150 mL). Organic phase was separated and washed with water (5×75 mL), brine (75 mL); dried over sodium sulfate (anhy.); filtered and concentrated to give 2-fluoro-5-aminobenzonitrile (1.4 g) as pure compound.

Part B: Preparation of 3-Cyano-4-fluorophenylhydrazine Tin Chloride.

To a solution of 2-fluoro-5-aminobenzonitrile (1.4 g, 10.3 mmol) in HCl (conc., 15 mL) at 0° C. was added a solution of sodium nitrite (0.71 g, 10.3 mmol) in cold water (3 mL) dropwisely. After addition, the mixture was stirred at 0° C. 0.5 h, a solution of stannous chloride (6.95 g, 30.9 mmol) in cold water (5 mL) was added dropwisely. The slurry was cooled in refrigerate overnight, the solid was filtered and washed with brine (20 mL), petroleum ether:ether (2:1, 30 mL) and air dried to leave 3-cyano-4-fluorophenylhydrazine tin chloride (2.5 g).

Part C: Preparation of Ethyl 1-(3-Cyano-4-fluorophenyl)-3-methyl-pyrazol-5-yl Carboxylate.

To a mixture of 3-cyano-4-fluorophenylhydrazine tin chloride (0.9 g, 2.65 mmol) in acetic acid (15 mL) was added oxime. The reaction mixture was brought to reflux overnight. Acetic acid was removed on rotary evaporator under reduced pressure. Residue was partitioned between ethylacetate (30 mL) and sodium bicarbonate (25 mL). Organic phase was separated and washed with water (3×20 mL), dried over sodium sulfate; filtered and concentrated; flash chromatography (ethylacetate:hexane, 1:5) to give ethyl 1-(3-cyano-4'-fluorophenyl)-3-methyl-pyrazol-5-yl carboxylate (0.7 g).

Part D: Preparation of 1-(3-Cyano-4-fluorophenyl)-3-methyl-5-[(2'-tert-butylaminosulfonyl-[1,1']-biphen-4-yl)aminocarbonyl]-pyrazole.

To a solution of biphenyl amine (167 mg, 0.55 mmol) in methylene chloride (5 mL) was added trimethyl aluminum (2.0M in hexane, 0.55 mL, 1.1 mmol) via syringe at 0° C. The mixture was slowly warmed to room temperature and stirred for 20 minutes followed by portionwise addition of a solution of ethyl 1-(3-cyano-4'-fluorophenyl)-3-methyl-pyrazol-5-yl carboxylate (100 mg, 0.37 mmol) in methylene chloride (5 mL). The reaction mixture was stirred at 45° C. under nitrogen overnight. Methylene chloride was removed, the residue quenched with HCl (10%, 5 mL), and partitioned between ethylacetate (20 mL) and HCl (10%, 15 mL). The organic phase was separated and washed with HCl (10%, 3×10 mL) and water (2×10 mL); dried over sodium sulfate; filtered and concentrated to leave 1-(3-cyano-4-fluorophenyl)-3-metyl-5-((2'-tert-butylaminosulfonyl-[1,1']-biphen-4-yl)aminocarbonyl]-pyrazole (150 mg) as a pure compound. $^1$HNMR (CDCl$_3$) δ: 8.21 (s, 1H), 8.17–8.14 (m, 1H), 7.75 (d, 1H), 7.72 (t, 1H), 7.66 (d, 2H), 7.60–7.46 (m, 5H), 7.31–7.28 (m, 2H), 6.78 (s, 1H), 3.67 (s, 1H), 2.41 (s, 3H), 1.03 (s, 9H) ppm; ESI m/z (rel. intensity) 554 (M+Na, 100).

Part E: Preparation of 1-(3-Amidino-4-fluorophenyl)-3-methyl-5-((2'-aminosulfonyl-[1,1']-biphen-4-yl) aminocarbonyl]-pyrazole, Trifluoroacetic Acid Salt and 1-(3-Carboxamido-4-fluorophenyl)-3-methyl-S-[(2'-aminosulfonyl-[1,1']-biphen-4-yl)aminocarbonyl]-pyrazole 1-(3-cyano-4-fluorophenyl)-3-metyl-5-[(2'-tert-butylaminosulfonyl-[1,1']-biphen-4-yl)aminocarbonyl]-pyrazole (150 mg) was dissolved in a saturated HCl solution of anhydrous methanol (10 mL). The reaction mixture was stirred at room temperature for 24 h. Then methanol was evaporated. The residue was redissolved in methanol (10 mL) and excess ammonium carbonate added. The reaction mixture was stirred at room temperature overnight. Methanol was evaporated and the residue was purified via HPLC to afford 1-(3-amidino-4-fluorophenyl)-3-methyl-5-[(2'-aminosulfonyl-[1,1']-biphen-4-yl)aminocarbonyl]-pyrazole as its TFA salt (20 mg). $^1$HNMR (CD$_3$OD) δ: 8.07–8.04 (m, 3H), 7.63 (d, 2H), 7.58 (s, 1H), 7.42–7.55 (m, 2H), 7.38 (d, 2H), 7.35 (d, 2H), 6.80 (s, 1H), 2.34 (s, 3H) ppm; ESI m/z (rel. intensity) 493 (M+H, 100) and 1-(3-aminocarbonyl-4-fluorophenyl)-3-methyl-5-[(2'-aminosulfonyl-[1,1']-biphen-4-yl)aminocarbonyl]-pyrazole (10 mg). $^1$HNMR (DMSO d$_6$) δ: 10.59 (s, 1H), 7.99 (dd, 1H), 7.81 (br, 1H), 7.72–7.67 (m, 2H), 7.63 (d, 2H), 7.60–7.49 (m, 4H), 7.38–7.26 (m, 4H), 7.21 (s, 2H), 6.90 (s, 1H), 2.29 (s, 3H). High resolution mass spectrum calcd. for $C_{24}H_{20}FN_5O_4S$ (M+H): 494.129829, found: 494.131923.

Example 110

1-Methyl-3-(3-amidino)phenyl-4-[(2'-aminosulfonyl-[1,1']-biphen-4-yl)aminocarbonyl] pyrazole Part A: A mixture of ethyl-3-cyanobenzoylacetate (2.01 g) and N,N-dimethyldiethylacetal (50 mL) were heated to gentle reflux overnight. Evaporation of the solvent in vacuo afforded a thick viscous reddish oil which was redissolved in anhydrous methanol (50 mL). To this solution was then added N-methylhydrazine (0.43 g) dropwise. The reaction mixture was stirred at room temperature overnight. Then concentrated to a viscous oil containing a regioisomeric mixture of pyrazoles. Without any further purification the mixture of pyrazoles obtained above (0.45 g, 1.79 mmol) was added to a dichloromethane (50 mL) solution of 2'-tert-butylsulfonamide-1-aminobiphenyl (0.54 g, 1.79 mmol) and trimethylaluminum (5.37 mL, 10.7 mmol). The reaction mixture was stirred at room temperature overnight followed by quenching with dil. HCl (1N). The organics were extracted with ethylacetate (2×50 mL), dried ($MgSO_4$) and evaporated to a colorless residue. Silica gel column chromatography (dichoromethane:MeOH, 9:1) afforded regioisomeric mixtures of coupled pyrazoles. Preparatory HPLC reverse phase (acetonitrile:water gradient flow) allowed for the separation of pure 1-methyl-3-(3-cyano)phenyl-4-[(2'-tert-butylaminosulfonyl-[1,1']-biphen-4-yl)aminocarbonyl] pyrazole as a colorless oil (0.35 g); $^1$HNMR ($CDCl_3$) δ: 8.14 (d, 1H), 8.01 (s, 1H), 7.83–7.65 (m, 4H), 7.60–7.41 (m, 6H), 7.27 (m, 2H), 3.78 (s, 3H), 3.63 (s, 1H), 1.00 (s, 9H) ppm; ESI mass spectrum 536 (M+Na, 45), 514 (M+H, 100).

Part B: The product from part A was then subjected to the Pinner amidine reaction sequence as outlined in Example 10 to obtain after preparative HPLC separation and lyophilization colorless crystals of the title compound (0.15 g); $^1$HNMR (DMSO-$d_6$) δ: 9.90 (s, 1H), 9.37 (bs, 1.5H), 9.29 (bs, 1.5H), 8.24 (s, 1H), 8.00 (d, 1H), 7.90 (bs, 2H), 7.84 (d, 1H), 7.73 (m, 1H), 7.69–7.50 (m, 4H), 7.37–7.27 (m, 3H), 7.17 (bs, 1H), 3.98 (s, 3H) ppm; ESI mass spectrum m/z (rel. int.) 475.3 (M+H, 100).

Example 111

1-(3-Amidinophenyl)-5-[[4-(pyrazol-4'-yl)phen-1-yl]aminocarbonyl]pyrazole, Trifluoroacetic Acid Salt Part A: 4-Iodopyrazole (20 mmol) was treated with Et3N (30 mmol) and (Boc) 20 (22 mmol) in THF (60 mL) at r.t. for 2 hours to form N-Boc-4-iodopyrazole (5.88 g, 100%). N-Boc-4-iodopyrazolyle in THF (100 mL) was reacted with hexamethylditin (20 mmol) in the presence of Pd($Ph_3$P) 4 (1.1 g, 1 mmol) under nitrogen at 78° C. overnight. To it was added aqueous 10% KF and the resulting mixture was stirred for 30 minutes, and then filtered through a pad of Celite. The filtrate was extracted with EtOAc. The EtOAc layer was washed with water, and dried over $MgSO_4$. Filtration and concentration followed by purification of the mixture by column chromatography afforded the 3-trimethyltinpyrazole derivative (5 g, 75%) as a white solid.

Part B: The product from part A (10 mmol) was treated with with 4-nitrobromobenzene (10 mmol) in the presence of Pd($Ph_3$P)$_4$ (0.36 g, 0.3 mmol) under nitrogen at 78° C. overnight, followed by workup as described above afforded the 4-pyrazolo-nitrobenzene derivative (0.95 g, 33%). Hydrogenation (0.85 g, 2.94 mmol) in MeOH (150 mL) in the presence of Pd (5% on C, 0.09 g) at r.t. for 16 hours afforded the aniline derivative (0.76 g, 100%).

Part C: Standard coupling of the product from part B with the pyrazole acid chloride under reflux for 1.5 with Et3N (1 mL) followed by usual workup and purification afforded the coupled amide pyrazole-benzonitrile derivative (255 mg, 55%) which was subjected to the Pinner amidine sequence to afford after purification the title compound as colorless (148 mg, 70%). $^1$HNMR ($CD_3OD$) δ: 7.93 (bs, 2H), 7.90–7.87 (m, 1H), 7.80 (td, J=7.4 Hz, J=1.2 Hz, 2H), 7.70 (t, J=7.8 Hz, 1H), 7.57 (d, J=7.4 Hz, 2H), 7.60–7.54 (m, 2H), 6.93 (d, J=1.9 Hz, 1H), 2.38 (s, 3H); $^{13}$C NMR ($CD_3OD$) δ: 167.92, 159.84, 151.36, 142.27, 139.28, 137.30, 131.43, 131.07, 130.51, 128.33, 126.99, 125.48, 122.48, 110.77, 13.29; ESMS: m/z 386.3 (M+H, 100); HRMS calcd for $C_{21}H_{20}N_7O_1$ 386.1729, found 386.1738.

Example 112

1-(3-Amidinophenyl)-3-methyl-5-([5-(2'-methylsulfonylphenyl)pyrid-2-yl]aminocarbonyl) pyrazole Trifluoroacetate Part A: Preparation of 2-(Tertbutoxycarbonyl)amino-5-bromopyridine and 2-[bis(Tertbutoxycarbonyl)amino]-5-bromopyridine.

Sodium hydride (1.27 g, 60%, 32 mmol) was added to 2-amino-5-bromopyridine (5.0 g, 29 mmol) in THF (75 mL) at 0° C. The ice bath was removed and the reaction stirred 25 min at room temp. Di-t-butyl dicarbonate (6.94 g, 32 mmol) was added and the reaction was refluxed 15 h. After cooling, the reaction was carefully quenched with water and extracted into EtOAc. The combined organics were washed with sat. $NH_4Cl$ and sat. $NaHCO_3$, dried over $Na_2SO_4$, filtered, and evaporated. The crude mixture was chromatographed on silica gel (5–7.5% EtOAc/hexanes, followed with 100% $CHCl_3$) to yield both the mono-protected (2.85 g, 36%) and bis-protected (1.87 g, 17%) products. $^1$HNMR (mono, $CDCl_3$) δ: 8.32 (d, 1H, J=2.2), 8.13 (bs, 1H), 7.91 (d, 1H, J=8.8), 7.75 (dd, 1H, J=8.8, J'=2.2), 1.54 (s, 9H); $^1$HNMR (bis, $CDCl_3$) δ: 8.53 (d, 1H, J=2.5), 7.84 (dd, 1H, J=8.5, J'=2.5), 7.18 (d, 1H, J=8.4), 1.45 (s, 18H).

Part B: Preparation of 2-[bis(Tertbutoxycarbonyl)amino]-5-(2'-methylthiophenyl)pyridine.

2-[Bis(tertbutoxycarbonyl)amino-5-bromopyridine (1.87 g, 5.0 mmol) was dissolved in benzene (120 mL). 2-Methylthiophenylboronic acid (1.95 g, 11.5 mmol), aq. sodium carbonate (12 mL, 2.0 M, 24 mmol), tetrabutyl ammonium bromide (80 mg, 0.25 mmol), and bis(triphenylphosphine)palladium(II)chloride (175 mg, 0.25 mmol) were added, and the resulting mixture was purged with vacuum and argon and then refluxed 16 h. The cooled mixture was diluted with EtOAc and water. The layers were separated, and the organic phase was washed with brine, dried over $Na_2SO_4$, filtered, and evaporated. The crude product was chromatographed on silica gel (10–20% EtOAc/hexanes) to yield a thick oil (1.82 g, 87.1%). $^1$HNMR ($CDCl_3$) δ: 8.51 (d, 1H, J=2.2), 7.83 (dd, 1H, J=8.1, J'=2.2), 7.30 (m, 5H), 2.35 (s, 3H), 1.47 (s, 18H).

Part C: Preparation of 2-[bis(Tertbutoxycarbonyl)amino-5-(2'-methylsulfonylphenyl)pyridine 2-[Bis(tertbutoxycarbonyl)amino]-5-(2'-methylthiophenyl)pyridine (1.69 g, 4.1 mmol) was dissolved in MeOH (20 mL). In a separate beaker, a solution of Oxone (10 g) was generated by dilution to 49 mL with water. A portion of this solution (14.5 mL, 4.8 mmol) was removed and adjusted to pH 4 with sat. $Na_3PO_4$ solution (4.0 mL). This mixture was added to the reaction and stirred 22 h at room temp. The resulting mixture was diluted with water, extracted with $CHCl_3$, dried over $Na_2SO_4$, filtered, and evaporated. The crude product was chromatographed on silica gel (40–75% EtOAc/hexanes) to yield the sulfone (1.19 g, 65%). $^1$HNMR ($CDCl_3$) δ: 8.48 (d, 1H, J=1.8), 8.26 (dd, 1H, J=8.1, J'=1.5), 7.95 (dd, 1H, J=8.1, J'=2.2), 7.71 (td, 1H, J=7.4, J'=1.5), 7.64 (td, 1H, J=7.7, J'=1.4), 7.40 (dd, 1H, J=7.3, J'=1.4), 7.36 (d, 1H, J=8.8), 2.68 (s, 3H), 1.48 (s, 18H).

Part D: Preparation of 2-Amino-5-(2'-methylsulfonylphenyl)pyridine Hydrochloride.

2-[Bis(tertbutoxycarbonyl)amino-5-(2'-methylsulfonylphenyl)pyridine (1.18 g, 2.6 mmol) and 2-(tertbutoxycarbonyl)amino-5-(2'-methylsulfonylphenyl)pyridine (1.62 g, 4.6 mmol) were suspended in HCl/dioxane (30 mL, 4.0 M) and stirred 23 h at room temp. The resulting mixture was diluted with $Et_2O$ and filtered to yield a tan solid (2.27 g, 100%). $^1$HNMR (DMSO) δ: 8.09 (m, 3H), 7.98 (d, 1H, J=1.8), 7.90 (dd, 1H, J=9.1, J'=2.2), 7.75 (m, 2H), 7.45 (dd, 1H, J=7.3, J'=1.1), 6.98 (d, 1H, J=9.1), 3.04 (s, 3H).

Part E: Preparation of 1-(3-Cyanophenyl)-3-methyl-5-([5-(2'-methylsulfonylphenyl)pyrid-2-yl]aminocarbonyl) pyrazole.

Oxalyl chloride (175 μl, 2.0 mmol) and DMF (2 drops) were added to 1-(3-cyanophenyl)-3-methylpyrazole-5-carboxylic acid (300 mg, 1.3 mmol) in $CH_2Cl_2$ (5 mL) and stirred under argon 160 min. The resulting solution was evaporated and redissolved in $CH_2Cl2$ (5 mL). 4-Dimethylaminopyridine (484 mg, 4.0 mmol) and 2-amino-5-(2'-methylsulfonylphenyl)pyridine hydrochloride (376 mg, 1.3 mmol) were added and stirred at room temperature under argon for days. The reaction was evaporated and chromatographed on silica gel (50–100% EtOAc/hexanes, followed by 1% MeOH/EtOAc) to yield the desired product (303 mg, 50%). $^1$HNMR (CDCl$_3$) δ: 8.54 (s, 1H), 8.39 (d, 1H, J=2.2), 8.25 (d, 2H, J=8.4), 7.82 (m, 2H), 7.66 (m, 5H), 7.37 (dd, 1H, J=7.7, J'=1.5), 6.76 (s, 1H), 2.7 (s, 3H), 2.41 (s, 3H).

Part F: Preparation of 1-(3-Amidinophenyl)-3-methyl-5-([5-(2'-methylsulfonylphenyl)pyrid-2-yl]aminocarbonyl) pyrazole Trifluoroacetate.

1-(3-cyanophenyl)-3-methyl-5-([5-(2'-methylsulfonylphenyl)pyrid-2-yl]aminocarbonyl)pyrazole (300 mg, 0.66 mmol) was dissolved in dry CHCl$_3$ (15 mL) and dry MeOH (5 mL) and cooled to 0° C. HCl (g) was generated by the addition of $H_2SO_4$ (45 mL) to NaCl (200 g) over 90 min, and bubbled into the reaction. The generator was removed, and the reaction was sealed and placed in the refrigerator (4° C.) overnight. The reaction was evaporated and redissolved in dry MeOH (10 mL). Ammonium carbonate (316 mg, 3.3 mmol) was added and the reaction was stirred 20 h at room temp, and evaporated. The crude product was purified by prep HPLC on a C-18 reverse phase column (10–70% MeCN/H$_2$O/0.05% TFA) to yield a white powder (161 mg, 42%). $^1$HNMR (DMSO) δ: 11.21 (s, 1H), 9.38 (s, 2H), 8.96 (s, 2H), 8.36 (s, 1H), 8.07 (d, 1H, J=7.3), 7.99 (d, 1H, J=8.5), 7.92 (s, 1H), 7.73 (m, 6H), 7.42 (d, 1H, J=7.7), 7.16 (s, 1H), 2.92 (s, 3H), 2.29 (s, 3H). HRMS calc. for $C_{24}H_{23}N_6O_3S$: 475.1552; found, 475.1554.

Examples 113, 114, and 115

1-(3-Amidinophenyl)-3-methyl-5-([5-(2'-methylsulfonylphenyl)pyrimid-2-yl]aminocarbonyl) pyrazole Trifluoroacetate, (Example 113) 1-(3-Cyanophenyl)-3-methyl-5-([5-(2'-methylsulfonylphenyl)pyrimid-2-yl]aminocarbonyl) pyrazole, (Example 114) and 1-(3-Aminocarbonylphenyl)-3-methyl-5-([5-(2'-methylsulfonylphenyl)pyrimid-2-yl]aminocarbonyl) pyrazole (Example 115)

Part A: Preparation of 2-Methylthiophenylboronic Acid.

2-Bromothioanisole (29.0 g, 143 mmol) was dissolved in dry THF (400 mL) and cooled to −75° C. N-BuLi (62.0 mL, 2.5 M in hexane, 155 mmol) was added over 50 min. After stirring 25 min, triisopropyl borate (46 mL, 199 mmol) was added over 35 min. The cold bath was removed and the reaction was stirred at room temperature for 16 h. The resulting solution was cooled in an ice bath, and 6 M HCl (100 mL) was added. This mixture was stirred at room temp 5 h and concentrated to about half of the original volume.

The concentrated solution was partitioned between $Et_2O$ and water. The organic layer was extracted with 2 M NaOH, which was subsequently reacidified with 6 M HCl and extracted several times back into $Et_2O$. These $Et_2O$ washes were dried over $Na_2SO_4$, filtered, and evaporated to yield a beige solid (20.4 g, 85%). $^1$HNMR (CDCl$_3$) δ: 8.01 (dd, 1H, J=7.3, J'=1.4), 7.53 (dd, 1H, J=7.7, J'=1.1), 7.43 (td, 1H, J=7.3, J'=1.8), 7.34 (td, 1H, J=7.3, J'=1.5), 6.22 (s, 2H), 2.50 (s, 3H).

Part B: Preparation of 2-[bis(tert-Butoxycarbonyl)amino]-5-bromopyrimidine.

Sodium hydride (5.06 g, 60%, 127 mmol) was added in 2 portions to 2-amino-5-bromopyrimidine (10.0 g, 57 mmol) in dry THF (500 mL) at 0° C. After stirring 30 min, di-t-butyl dicarbonate (27.6 g, 126 mmol) was added. The resulting mixture was refluxed 17 h, quenched carefully with water, and concentrated. The concentrated mixture was diluted with EtOAc and extracted with water. The combined aqueous layers were extracted with EtOAc. All of the organic layers were combined, dried over $Na_2SO_4$, filtered, and evaporated. The crude product was chromatographed on silica gel (10–15% EtOAc/hexanes) to yield the desired product (15.48 g, 72%). $^1$HNMR (CDCl$_3$) δ: 8.78 (s, 2H), 1.47 (s, 18H).

Part C: Preparation of 2-[bis(tert-Butoxycarbonyl)amino]-5-(2'-methylthiophenyl)pyrimidine.

2-(Bis (tert-butoxycarbonyl)amino]-5-bromopyrimidine (2.00 g, 5.3 mmol) was dissolved in benzene (130 mL). 2-methylthiophenylboronic acid (2.24 g, 13.3 mmol), aq. sodium carbonate (13 mL, 2.0 M, 26 mmol), tetrabutyl ammonium bromide (86 mg, 0.26 mmol), and bis(triphenylphosphine)palladium(II)chloride (190 mg, 0.27 mmol) were added, and the resulting mixture was purged with vacuum and argon and then refluxed 17 h. The cooled mixture was diluted with EtOAc and water. The layers were separated, and the organics were dried over $Na_2SO_4$, filtered, and evaporated. The crude product was chromatographed on silica gel (50% EtOAc/hexanes), evaporated, and chromatographed a second time on silica gel (30–50% EtOAc/hexanes) to yield the desired product (2.13 g, 96%). $^1$HNMR (CDCl$_3$) δ: 8.81 (s, 2H), 7.41 (m, 2H), 7.25 (m, 2H), 2.39 (s, 3H), 1.49 (s, 18H).

Part D: Preparation of 2-[bis(tert-Butoxycarbonyl)amino]-5-(2'-methylsulfonylphenyl)pyrimidine.

2-[Bis(tertbutoxycarbonyl)amino]-5-(2'-methylthiophenyl)pyrimidine (2.13 g, 5.1 mmol) was dissolved in MeOH (20 mL) and cooled to 0° C. In a separate beaker, a solution of Oxone (5.49 g) was generated by dilution to 27 mL with water. A portion of this solution (17 mL, 5.6 mmol) was removed and adjusted to pH 4.2 with sat. $Na_3PO_4$ solution (4.7 mL). This mixture was added to the reaction and stirred 23 h at room temp. The resulting mixture was diluted with water and extracted with CHCl$_3$. The organics were combined, washed with water and brine, dried over $Na_2SO_4$, filtered, and evaporated. The crude product was chromatographed on silica gel (50–100% EtOAc/hexanes) to yield the sulfone (1.28 g, 56%). $^1$HNMR (CDCl$_3$) δ: 8.81 (s, 2H), 8.28 (dd, 1H, J=7.6, J'=1.4), 7.72 (m, 2H), 7.39 (dd, 1H, J=7.3, J'=1.4), 2.76 (s, 3H), 1.50 (s, 18H).

Part E: Preparation of 2-Amino-5-(2'-methylsulfonylphenyl) pyrimidine Hydrochloride.

2-[Bis(tertbutoxycarbonyl)amino]-5-(2'-methylsulfonylphenyl)pyrimidine (1.28 g, 2.8 mmol) was suspended in HCl/dioxane (10 mL, 4.0 M) and stirred 20 h at room temp. The resulting mixture was triturated with Et₂O and filtered to yield a white solid (772 mg, 95%). ¹HNMR (CDCl₃+few drops MeOD) δ: 8.53 (s, 2H), 8.22 (dd, 1H, J=7.7, J'=1.8), 7.77 (m, 2H), 7.40 (dd, 1H, J=7.4, J'=1.5), 2.94 (s, 3H).

Part F: Preparation of 1-(3-Cyanophenyl)-3-methyl-5-([5-(2'-methylsulfonylphenyl)pyrimid-2-yl]aminocarbonyl) pyrazole.

Oxalyl chloride (175 μl, 2.0 mmol) and DMF (2 drops) were added to 1-(3-cyanophenyl)-3-methylpyrazole-5-carboxylic acid (300 mg, 1.3 mmol) in CH$_2$Cl$_2$ (5 mL) and stirred under argon for 120 min. The resulting solution was evaporated and redissolved in CH$_2$Cl$_2$ (5 mL). 4-Dimethylaminopyridine (480 mg, 3.9 mmol) and 2-amino-5-(2'-methylsulfonylphenyl)pyrimidine hydrochloride (377 mg, 1.3 mmol) were added and stirred at room temp under argon 5 days. The crude reaction was chromatographed on silica gel (2–5% MeOH/CHCl$_3$) to yield crude product, which was redissolved in CHCl$_3$ and extracted with 1 M HCl. The organics were dried over Na$_2$SO$_4$, filtered, and evaporated to yield clean product (486 mg, 80%). ¹HNMR (CDCl$_3$) δ: 8.69 (s, 2H), 8.64 (s, 1H), 8.25 (dd, 1H, J=7.7, J'=1.5), 7.84 (m, 1H), 7.73 (m, 4H), 7.55 (t, 1H, J=7.6), 7.35 (dd, 1H, J=7.3, J'=1.4), 6.79 (s, 1H), 2.80 (s, 3H), 2.42 (s, 3H).

Part G: Preparation of 1-(3-Amidinophenyl)-3-methyl-5-([5-(2'-methylsulfonylphenyl)pyrimid-2-yl]aminocarbonyl) pyrazole trifluoroacetate, and 1-(3-Aminocarbonylphenyl)-3-methyl-5-([5-(2'-methylsulfonylphenyl)pyrimid-2-yl]aminocarbonyl)pyrazole.

1-(3-cyanophenyl)-3-methyl-5-([5-(2'-methylsulfonylphenyl)pyrimid-2-yl]aminocarbonyl) pyrazole (471 mg, 1.0 mmol) was dissolved in dry CHCl$_3$ (15 mL) and dry MeOH (5 mL) and cooled to 0° C. HCl (g) was generated by the addition of H$_2$SO$_4$ (45 mL) to NaCl (480 g) over 30 min, and bubbled into the reaction. The generator was removed, and the reaction was sealed and placed in the refrigerator (4° C.) for 18 h. The reaction was evaporated and redissolved in dry MeOH (15 mL). Ammonium carbonate (487 mg, 5.1 mmol) was added and the reaction was stirred for 20 h at room temp, and evaporated. The crude product was dissolved/suspended in a mixture of MeCN, water, TFA, DMSO, and MeOH. The soluble portion was purified by prep HPLC on a C-18 reverse phase column (10–70% MeCN/H$_2$O/0.05% TFA) to yield the desired amidine as its TFA salt (0.31 g, 51%). ¹HNMR (DMSO) δ: 11.38 (s, 1H), 9.39 (s, 2H), 9.00 (s, 2H), 8.67 (s, 2H), 8.10 (dd, 1H, J=8.1, J'=1.5), 7.92 (m, 1H), 7.74 (m, 5H), 7.49 (dd, 1H, J=7.3, J'=1.1), 7.06 (s, 1H), 3.03 (s, 3H), 2.29 (s, 3H). HRMS calc. for C$_{23}$H$_{22}$N$_7$O$_3$S: 476.1505; found, 476.1529. A second product was isolated from the prep HPLC and combined with the insoluble solid from above for purification on silica gel (10% MeOH/CHCl$_3$). The crude amide was suspended in toluene and filtered. The white solid thus obtained was the desired amide (52 mg, 11%). ¹HNMR (DMSO) δ: 11.33 (s, 1H), 8.64 (s, 2H), 8.08 (m, 2H), 7.92 (s, 1H), 7.77 (m, 3H), 7.48 (m, 4H), 6.95 (s, 1H), 3.01 (s, 3H), 2.27 (s, 3H). HRMS calc. for C$_{23}$H$_{21}$N$_6$O$_4$S: 477.1345; found, 477.1350.

Example 116

1-(3-(N-Aminoamidino)phenyl)-3-methyl-5-[(2'-tert-butylaminosulfonyl-[1,1']-biphen-4-yl) aminocarbonyl]pyrazole, Trifluoroacetic Acid Salt 1-(3-Cyanophenyl)-3-methyl-5-[(2'-tert-butylaminosulfonyl-[1,1']-biphen-4-yl)aminocarbonyl] pyrazole (150 mg) was dissolved in anhydrous CH$_3$OH and cooled to 0° C. Anhydrous HCl was bubbled through the rxn for 15 minutes. The resulting solution was allowed to warm to rt over 18 hrs. The mixture was concentrated in vacuo. LRMS (M+H)+=489 C$_{25}$H$_{23}$N$_5$O$_4$S$_1$. 50 mg was dissolved in 10 mL of anhydrous CH$_3$OH. Hydrazine (0.10 mL) was added and the resulting mixture was stirred at rt for 4 hours. The mixture was concentrated under vacuo. Purification was done by HPLC yielding 2.5 mg (98% purity by HPLC). HRMS for C$_{28}$H$_{31}$N$_7$O$_3$S$_1$ (M+H)⁺ calc. 490.162947, found 490.164868. ¹HNMR (CD$_3$OD) δ: 1.02 (s, 9H), 2.38 (s, 3H), 6.94 (s, 1H), 7.305 (d, 1H, J=7.69 Hz), 7.53 (t, 1H, 7.69 Hz), 6.64–7.85 (m 7H), 8.085 (d, 1H, J=8.06 Hz).

Example 117

1-(3-(N-Aminoamidino)phenyl)-3-methyl-5-[(2'-aminosulfonyl-[1,1']-biphen-4-yl)aminocarbonyl] pyrazole, Trifluoroacetic Acid Salt 3-[4-(2-(N-butylaminosulfonyl)phenyl)aminophenyl-3-methyl-5-carboxypyrazole]cyanophenyl (1.0 g) was dissolved in anhydrous CH$_3$OH and cooled to 0° C. Anhydrous HCl was bubbled through the rxn for 15 minutes. The resulting solution was allowed to warm to rt over 18 hrs. The mixture was concentrated in vacuo. LRMS (M+H)+=489 C$_{25}$H$_{23}$N$_5$O$_4$S$_1$. 300 mg was dissolved in 10 mL of anhydrous CH$_3$OH. Hydrazine (0.023 mL) was added and the resulting mixture was stirred at rt for 4 hours. The mixture was concentrated under vacuum. Purification was done by HPLC yielding 23 mg (98% purity by HPLC). HRMS for C$_{24}$H$_{23}$N$_7$O$_3$S$_1$ (M+H)+ calc. 546.228735, found 546.228088. ¹HNMR (CD$_3$OD) δ: 2.38 (s, 3H), 6.94, (s, 1H), 7.31 (d, 1H, J=7.33 Hz), 7.495 (d, 2H, J=7.33 Hz), 7.59–7.86 (m, 7H), 8.08 (d, 1H, J=7.69 Hz).

Example 118

1-(3-(N-Methyl-N-hydroxyamidino)phenyl)-3-methyl-5-[(2'-t-butylaminosulfonyl-[1,1']-biphen-4-yl)aminocarbonyl]pyrazole, Trifluoroacetic Acid Salt 3-[4-(2-(t-butylaminosufonyl)phenyl)amino phenyl-3-methyl-5-carboxypyrazole]cyanophenyl (300 mg) was dissolved/suspended in 25 mL of CH$_3$OH. Triethylamine (0.098 mL) added along with N,N-methylhydroxylamine hydrochloride (0.048 g). The reaction was stirred at 50° C. for 15 hours. The mixture was concentrated under vacuo. Purification was done on silica gel using 10% CH$_3$OH/ CH2Cl2 as the eluent yielding 360 mg. HRMS for C$_{29}$H$_{32}$N$_6$O$_4$S$_1$ (M+H)+ calc. 561.228401, found 561.22987. ¹HNMR (CD3OD) δ: 1.02 (s, 9H), 2.38 (s, 3H), 3.40 (s, 3H), 3.62 (s, 1H), 6.96 (s, 1H), 7.305 (d, 1H, J=7.69 Hz), 7.42 (d, 2H, J=8.79 Hz), 3.53 (t, 1H, J=8.06 Hz), 7.60 (t, 1H, J=7.32 Hz), 7.65 (d, 2H, J=8.06 Hz), 7.70–7.78 (m, 4H), 8.085 (d, 1H, J=7.69 Hz).

Example 119

1-(3-(N-Methylamidino)phenyl)-3-methyl-5-[(2'-tert-butylaminosulfonyl-[1,1']-biphen-4-yl) aminocarbonyl]pyrazole, Trifluoroacetic Acid Salt 1-(3-(N-Methyl-N-hydroxy-amidino)phenyl)-3-methyl-5-[(2'-n-butylaminosulfonyl-[1,1']-biphen-4-yl) aminocarbonyl]pyrazole (300 mg) was dissolved in acetic acid (25 mL). Trifluoroacetic anhydride (0.106 mL) was added and the reaction was stirred at rt for 35 minutes. 10% Pd/C (300 mg) was added and the reaction vessel was placed on the Parr Shaker (50 psi H$_2$) for 17 hours. The reaction was filtered through C-lite and the mixture was concentrated under vacuum. Purification was done by HPLC yielding 33 mg (97% purity by HPLC). HRMS for $C_{29}H_{32}N_6O_3S_1$ (M+H)+ calc. 545.233486, found 545.233079; $^1$HNMR (CD$_3$OD) δ: 1.02 (s, 9H), 2.38 (s, 3H), 3.09 (s, 3H), 6.94 (s, 1H), 7.30 (d, 1H, J=7.33 Hz), 7.425 (d, 2H, J=8.42 Hz) 7.50 (t, 1H, J=7.69 Hz), 7.57–7.64 (m, 3H, 7.685 (d, 1H, J=7.32 Hz), 7.73–7.77 (m, 2H), 7.87 (s, 1H), 8.085 (d, 1H, J=7.70 Hz).

Example 120

1-(3-(N-Methylamidino)phenyl)-3-methyl-5-[(2'-aminosulfonyl-[1,1']-biphen-4-yl)aminocarbonyl] pyrazole, Trifluoroacetic Acid Salt 1-(3'-(N-Methyl-N-hydroxy-amidino)phenyl)-3-methyl-5-[(2'-n-butylaminosulfonyl-[1,1']-biphen-4-yl) aminocarbonyl]pyrazole (347 mg) was dissolved in trifluoroacetic acid (10 mL) and stirred at 50° C. for 1 hour. The mixture was concentrated in vacuo (346 mg). LRMS for $C_{25}H_{24}N_6O_4S_1$ (M+H)$^+$=505. This material (346 mg) was dissolved in acetic acid (100 mL). Trifluoroacetic anhydride (0.116 mL) was added and the reaction was stirred at rt for 35 minutes. 10% Pd/C (300 mg) was added and the rxn was placed on the Parr shaker (50 psi H2) for 18 hours. The reaction was filtered through Celite and the mixture was concentrated in vacuo . Purification was done by HPLC yielding 80 mg (98% purity by HPLC). HRMS for $C_{25}H_{24}N_6O_3S_1$ (M+H)+ calc. 489.172971, found 489.172971; $^1$HNMR (CD$_3$OD) δ: 2.38 (s, 3H), 3.08 (s, 3H), 6.94 (s, 1H), 7.31 (d, 1H, J=7.33 Hz), 7.395 (d, 2H, J=8.79 Hz) 7.51 (t, 1H, J=7.32 Hz), 7.57–7.68 (m, 6H), 8.085 (d, 1H, J=7.47 Hz).

Example 121

1-(3-Amidinophenyl)-5-[(2'-aminosulfonylphenyl) pyridin-2-yl]aminocarbonyl]tetrazole, Trifluoroacetic Acid Salt The title compound was prepared as colorless crystals following the standard Pinner amidine reaction sequence and purification protocols outlined previously (Example 24); $^1$HNMR (DMSO) δ: 8.40–6.95 (m, 11H); 9.25 (s, 1H); 9.50 (s, 1H); 11.55 (s, 1H). MS (ESI) 464.17 (M+H)$^+$.

Example 122

1-(3-Aminocarbonylphenyl)-5-([5-(2'-aminosulfonylphenyl)pyridin-2-yl]aminocarbonyl) tetrazole The title compound was prepared as colorless crystals following the standard Pinner followed by hydrolysis and purification protocols outlined previously; $^1$HNMR (DMSO) δ: 8.40–7.39 (m, 11H); 11.55 (s, 1H). MS (ESI) 465.11 (M+H)$^+$.

Example 123

1-(3-Amidinophenyl)-5-{[5-(2'-trifluoromethylphen-1-yl)pyridin-2-yl]aminocarbonyl}tetrazole, Trifluoroacetic Acid Salt The title compound was prepared as colorless crystals following the standard Pinner amidine reaction sequence and purification protocols outlined previously; $^1$HNMR (DMSO) δ: 8.40–7.49 (m, 11H); 9.25 (s, 1H); 9.5 (s, 1H); 11.60 (s, 1H); MS (ESI) 453.20 (M+H)$^+$.

Example 124

1-(3-Amidinophenyl)-5-[(4'-bromophen-1-yl) aminocarbonyl]tetrazole, Trifluoroacetic Acid Salt The title compound was prepared as colorless crystals following the standard Pinner amidine reaction sequence and purification protocols outlined previously; $^1$HNMR (DMSO) δ: 8.20–7.55 (m, 8H); 9.20 (s, 1H); 9.5 (s, 1H); 11.55 (s, 1H); MS (ESI) 386.03 (M+H)$^+$.

Example 125

1-(3-Aminocarbonylphenyl)-5-{[5-(2'-trifluoromethylphen-1-yl)pyridin-2-yl] aminocarbonyl}tetrazole The title compound was prepared as colorless crystals following the standard Pinner followed by hydrolysis reaction sequence and purification protocols outlined previously; $^1$HNMR (DMSO) δ: 8.40–7.50 (m, 11H); 11.60 (s, 1H). MS (ESI) 454.12 (M+H)$^+$.

Example 126

5-(3-Amidinophenyl)-1-[(2'-trifluoromethyl-[1']-biphen-4-yl)methyl]tetrazole, Trifluoroacetic Acid Salt Part A. Preparation of N-(4-Bromophenylmethyl)-3-cyanobenzamide.

4-Bromobenzylamine HCl (3.36 g, 15.1 mmol) was dissolved in CH$_2$Cl$_2$ (100 mL). Triethylamine (8.4 mL, 60 mmol) was added followed by 3-cyanobenzyl chloride (2.50 g, 15.1 mmol). The mixture was stirred at room temperature under N$_2$ for 15 min. It was diluted with CH$_2$Cl$_2$ and washed with water and brine. The CH$_2$Cl$_2$ solution was dried over MgSO$_4$ and concentrated to 3.5 g of the desired product. $^1$HNMR (CDCl$_3$) δ: 4.60 (d, 2H); 7.0 (s, 1H); 7.20 to 8.20 (m, 8H). MS (DCI–NH$_3$) 315 (M+H)$^+$.

Part B. Preparation of 1-(4-Bromophenylmethyl)-5-(3-cyanophenyl)tetrazole.

The material from Part A (3.2 g, 10 mmol) was dissolved in CH$_3$CN (100 mL) and NaN$_3$ (0.7 g, 10 mmol) was added. The mixture was cooled in an ice bath and triflic anhydride (1.7 mL, 10 mmol) was added. Then, the ice bath was removed and stirred at room temperature under N$_2$ overnight. The reaction mixture was diluted with EtOAc and washed with water and brine. It was dried over MgSO$_4$, concentrated, and chromatographed on silica gel (CH$_2$Cl$_2$) to give 2.0 g of the desired product. $^1$HNMR (CDCl$_3$) δ: 5.60 (s, 2H); 7.05 to 7.90 (m, 8H). MS (NH$_3$—CI) 340, 342 (M+H)$^+$.

Part C. Preparation of 5-(3-Cyanophenyl)-1-[(2'-trifluoromethyl-[1,1']-biphen-4-yl)methyl]tetrazole.

The material from Part B (0.36 g, 1.06 mmol), and 2-trifluoromethyl phenylboronic acid (0.24 g, 1.26 mmol) were dissolved in benzene (30 mL). The mixture was stirred at room temperature and bubble N$_2$ for 30 min. Then K$_2$CO$_3$ (2 mL of 2 M, 4 mmol), tetrabutylammonium bromide (50 mg, 0.15 mmol) and tetrakis(triphenylphosphine)-palladium (0) (200 mg, 0.17 mmol) were added. The mixture was refluxed under N$_2$ for 4 hours. The solvent was removed. The residue was dissolved in CH$_2$Cl$_2$ and washed with water and brine. It was dried over MgSO$_4$, concentrated, and chromatographed on silica gel (eluted with CH$_2$Cl$_2$) to give 0.41 g of the desired product. $^1$HNMR (CDCl$_3$) δ: 5.70 (s, 2H); 7.10 to 7.85 (m, 12H), MS (NH$_3$—CI) 406.1 (M+H)$^+$.

Part D. Preparation of 5-(3-Amidinophenyl)-1-[(2'-trifluoromethyl-[1,1']-biphen-4-yl)methyl]tetrazole, Trifluoroacetic Acid Salt.

The material from part C was dissovled in 10 mL anhydrous $CHCl_3$ and 10 mL anhydrous $CH_3OH$. The mixture was cooled in an ice bath and HCl gas was bubbled in until the solution was saturated. The reaction mixture was sealed and kept at 0° C. for 12 h. The solvent was removed and the solid was dried under vacuum. The resulting solid was redissolved in 20 mL of anhydrous $CH_3OH$ and ammonium acetate (0.77 g, 10 eq) was added. The mixture was sealed and stirred at room temperature for 12 h. The solvent was removed. The solid was dissolved in $CH_3CN/H_2O/TFA$ and purified by reverse phase HPLC to give 150.0 mg of the desired product. $^1HNMR$ (DMSO-d6) δ: 5.95 (s, 1H); 7.19 to 8.20 (m, 12H); 9.35 (s, 1H); 9.50 (s, 1H). (ESI) 423.17 $(M+H)^+$.

Example 127

1-[(3-Amidinophenyl)methyl]-3-methyl-5-[(2'-aminosulfonyl-[1,1']-biphen-4-yl)aminocarbonyl] pyrazole, Trifluoroacetic Acid Salt Part A. Preparation of Ethyl 1-[(3-Cyanophenyl)methyl]-3-methylpyrazole-5-carboxylate.

To a solution of ethyl 3-methylpyrazole-5-carboxylate (2.0 g, 13.0 mmol) in 50 mL of dimethylformamide was added 3-cyanobenzyl bromide (2.54 g, 13.0 mmol) and potassium iodide (6.46 g, 38.9 mmol). The resulting mixture was allowed to stir at 65° C. for 16 h. The reaction mixture was cooled to room temperature, diluted with ethyl acetate, washed with saturated aq. sodium thiosulfate (2 times) and brine (2 times), dried ($MgSO_4$) and concentrated in vacuo. The residue was purified by flash chromatography (elution with 1:1 hexanes/ethyl acetate) to give 2.5 g (71%) of the title compound. MS (ESI) 270 (M+H)+.

Part B. Preparation of 1-[(3-Cyanophenyl)methyl]-3-methylpyrazole-5-carboxylate.

To a solution of ethyl 1-[(3-cyanophenyl)methyl]-3-ethylpyrazole-5-carboxylate (2.37 g, 8.80 mmol) in 20 mL of ethanol and 20 mL of water was added sodium hydroxide (0.70 g, 17.6 mmol) and the resulting solution was stirred at room temperature for 16 h. The mixture was acidified with 10% aq HCl, diluted with ethyl acetate, washed with brine (2 times), dried ($MgSO_4$) and concentrated in vacuo to afford the title compound (1.9 g, 90%) which was used without purification. MS (ESI) 242 (M+H)+.

Part C. Preparation of 1-[(3-Cyanophenyl)methyl]-3-methyl-5-[(2'-tert-butylaminosulfonyl-[1,1']-biphen-4-yl) aminocarbonyl]pyrazole.

To a solution of 1-[(3-cyanophenyl)methyl]-3-methylpyrazole-5-carboxylate (1.80 g, 7.46 mmol) in 20 mL of dimethylformamide was added (2'-tert-butylaminosulfonyl-[1,1']-biphen-4-yl)amine (2.50 g, 8.21 mol), benzotriazol-1-yloxytris(dimethylamino) phosphonium hexafluorophosphate (BOP reagent, 4.95 g, 11.19 mmol) and triethylamine (1.13 g, 11.19 mmol). The resulting mixture was stirred at 60° C. for 16 h. The reaction was allowed to cool to room temperature and then was diluted with ethyl acetate, washed with brine (4 times), dried (MgSO4) and concentrated in vacuo. The residue was purified by flash chromatography (elution with 1:1 hexanes/ethyl acetate) to afford 1.9 g (49%) of the title compound. MS (ESI) 528 (M+H)+.

Part D. Preparation of 1-[(3-Amidinophenyl)methyl]-3-methyl-5-[(2'-aminosulfonyl-[1,1']-biphen-4-yl) aminocarbonyl]pyrazole, Trifluoroacetic Acid Salt.

To a solution of 1-[(3-cyanophenyl)methyl]-3-methyl-5-[(2'-tert-butylaminosulfonyl-[1,1']-biphen-4-yl) aminocarbonyl]pyrazole (1.77 g, 3.35 mmol) in 40 mL of methyl acetate was added anhydrous methanol (1.36 mL, 33.5 mmol). The solution was cooled to 0° C. Then anhydrous HCl was bubbled through the solution for 15 minutes. The solution was stoppered and allowed to stir overnight at room temperature. The volatiles were removed in vacuo. The residue was dried under high vacuum for 1 hr. The residue was then dissolved in 100 mL of anhydrous methanol. Ammonium carbonate (1.93 g, 20.21 mmol) was added and the reaction was stirred overnight at room temperature. The volatiles were removed in vacuo and the residue was purified by preparative HPLC (C18 reverse phase-column, elution with a $H_2O/CH_3CN$ gradient with 0.5% TFA) to yield the title compound as a white powder. MS (ESI) 489 $(M+H)^+$.

Example 128

1-[(4-Amidinophenyl)methyl]-3-methyl-5-[(2'-aminosulfonyl-[1,1']-biphen-4-yl)aminocarbonyl] pyrazole, Trifluoroacetic Acid Salt Part A. Preparation of Ethyl 1-[(4-Cyanophenyl)methyl]-3-methylpyrazole-5-carboxylate.

Ethyl-3-methylpyrazole-5-carboxylate (2.50 g, 16.21 mmol) was allowed to react with 4-cyanobenzyl bromide (3.18 g, 16.21 mmol) and potassium iodide (8.07 g, 48.65 mmol) to afford 3.1 g (70%) of the title compound. MS (ESI) 270 (M+H)+.

Part B. Preparation of 5-Carboxy-1-[(4-cyanophenyl) methyl]-3-methylpyrazole.

Ethyl-1-[(4-cyanophenyl)methyl]-3-methylpyrazole-5-carboxylate (2.96 g, 10.99 mmol) was converted into 2.4 g (91%) of the title compound following the procedure outlined previously; MS (ESI) 242 (M+H)+.

Part C. Preparation of 1-[(4-Cyanophenyl)methyl]-3-methyl-5-[(2'-tert-butylaminosulfonyl-[1,1']-biphen-4-yl) aminocarbonyl]pyrazole.

5-carboxy-1-[(4-cyanophenyl)methyl]-3-methylpyrazole-5-carboxylate (2.29 g, 9.49 mmol) was converted into 2.0 g (40%) of the title compound following the procedure outlined previously; MS (ESI) 528 (M+H)+.

Part D. Preparation of 1-[(4-Amidinophenyl)methyl]-3-methyl-5-[(2'-aminosulfonyl-[1,1']-biphen-4-yl) aminocarbonyl]pyrazole, Trifluoroacetic Acid Salt.

1-[(4-cyanophenyl)methyl]-3-methyl-5-[(2'-tert-butylaminosulfonyl-[1,1']-biphen-4-yl)aminocarbonyl] pyrazole (0.78 g, 1.47 mmol) was converted into the title compound following methods described previously; MS (ESI) 489 $(M+H)^+$.

Example 129

1-(3-Amidinophenyl)-2-[(2'-aminosulfonyl-[1,1']-biphen-4-yl)aminocarbonyl]imidazole, Trifluoroacetic Acid Salt Part A: 3-Fluorobenzonitrile (4.84 g, 40 mmol) was heated with imidazole (2.72 g, 40 mmol) in the presence of $K_2CO_3$ in DMF at 100° C. for 8 hours to afford the coupled product as a white solid in quantitative yield. $^1HNMR$ ($CDCl_3$) δ: 7.89 (s, 1H), 7.70 (d, J=0.8 Hz, 1H), 7.68–7.58 (m, 3H), 7.30 (d, J=1.0 Hz, 1H), 7.26 (s, 1H); LRMS: 170 $(M+H)^+$.

Part B: Product from part A (1.52 g, 9 mmol) was slowly treated with n-BuLi (1.6 M, 6.3 mL) in THF (60 mL) at −78° C. for 40 minutes and was then slowly quenched with chloromethylformate (942 mg, 10 mmol) at this temperature. The resulting mixture was stirred at −78° C. and warmed to room temperature over 2 hours. Then poured into water and ethyl acetate. The organic layer was separated and washed with water, brine, and dried over MgSO$_4$. After removal of the ethyl acetate, a residue was purified by column chromatography with ethyl acetate and methylene chloride (1:1) to afford the 2-imidazolylphenylethylester derivative (1.33 g, 65%) as a white solid. $^1$HNMR (CDCl$_3$) δ: 7.80–7.77 (m, 1H), 7.65–7.61 (m, 3H), 7.33 (s, 1H), 7.20 (s, 1H); LRMS: 228 (M+H)$^+$.

Part C: To a stirred solution of 4-[(o-SO$_2$tBu)-phenyl]aniline (304 mg, 1 mmol) in CH$_2$Cl$_2$ (20 mL) was slowly added trimethylaluminum (2M in hexane, 1 mL) at 0° C. and the resulting mixture was warmed to room temperature over 15 minutes. The product from part B in CH$_2$Cl$_2$ (5 mL) was added dropwise and the resulting mixture was refluxed for 2 hours. The mixture was quenched with water, diluted with ethyl acetate and filtered through Celite. The organic layer was separated, washed with water, brine and dried over MgSO$_4$. After removal of the ethyl acetate, a residue was purified by column chromatography with ethyl acetate and methylene chloride (1:1) as eluent to afford the coupled product (260 mg, 52%) as a white solid. $^1$HNMR (CDCl$_3$) δ: 9.41 (s, 1H), 8.15 (dd, J=7.7 Hz, J=1.5 Hz, 1H), 7.78 (dd, J=7.3 Hz, J=1.1 Hz, 1H), 7.74–7.57 (m, 6H), 7.55 (td, J=7.7 Hz, J=1.1 Hz, 1H), 7.49 (dd, J=8.8 Hz, J=1.8 Hz, 2H), 7.29 (dd, J=8.1 Hz, J=1.5 Hz, 1H), 7.28 (d, J=0.8 Hz, 1H), 7.22 (d, J=0.8 Hz, 1H), 3.64 (s, 1H), 0.99 (s, 9H); LRMS: 500.1 (M+H)$^+$.

Part D: Standard Pinner Amidine and Purification Methods then Afforded the Titled Product (120 mg, 50%): $^1$HNMR (CD$_3$OD) δ: 8.08 (dd, J=7.7 Hz, J=1.1 Hz, 1H), 7.91–7.88 (m, 2H), 7.83 (dd, J=8.4 Hz, J=1.5 Hz, 1H), 7.74 (t, J=8.0 Hz, 1H), 7.65 (d, J=8.4 Hz, 2H), 7.58 (dd, J=7.3 Hz, J=1.1 Hz, 1H), 7.50 (s, 2H), 7.39 (d, J=8.4 Hz, 2H), 7.32 (s, 1H), 7.30 (dd, J=7.3 Hz, J=1.1 Hz, 1H); ESMS: 461 (M+H)$^+$.

Example 130

1-(3-Amidinophenyl)-4-methyl-2-[(2'-aminosulfonyl-[1,1']-biphen-4-yl)aminocarbonyl] imidazole Ethyl-1-(3-cyanophenyl)-4-methyl-imidazolyl-2-carboxylate was prepared following the standard coupling procedure outlined previously. This was coupled following the standard Weinreb conditions (trimethylaluminum) and subjected to the Pinner amidine reaction protocols followed by usual methods of purification to afford the title compound as colorless crystals. $^1$HNMR (CD$_3$OD) δ: 8.09 (dd, J=8.1 Hz, J=1.1 Hz, 1H), 7.89 (t, J=1.5 Hz, 1H), 7.87 (d, J=1.8 Hz, 1H), 7.81–7.78 (m, 1H), 7.72 (t, J=8.1 Hz, 1H), 7.64 (d, J=8.4 Hz, 2H), 7.57 (dd, J=7.7 Hz, J=1.5 Hz, 1H), 7.50 (td, J=7.7 Hz, J=1.5 Hz, 1H), 7.38 (d, J=8.4 Hz, 2H), 7.30 (dd, J=7.7 Hz, J=1.5 Hz, 1H), 7.26 (s, 1H), 2.33 (s, 3H); $^{13}$C NMR (CD$_3$OD) δ: 167.73, 158.04, 143.04, 141.49, 140.47, 139.62, 138.64, 137.53, 133.65, 133.45 132.93, 132.76, 132.35, 131.25, 130.55, 129.09, 128.74, 128.63, 126.69, 120.87, 13.27; ESMS: m/z 475.19 (M+H, 100); HRMS: calcd. for C$_{24}$H$_{23}$N$_6$O$_3$S$_1$ 475.1552 found 475.1548.

Example 131

1-(3-Amidinophenyl)-5-chloro-4-methyl-2-[(2'-aminosulfonyl-[1,1']-biphen-4-yl)aminocarbonyl] imdazole Chlorination of ethyl-1-(3-cyanophenyl)-4-methyl-imidazole-2-carboxylate with NCS in refluxing carbontetrachloride afforded the 5-chloroimidazole derivative which was then subjected to the Pinner amidine reaction protocols followed by usual methods of purification to afford the title compound as colorless crystals (145 mg, 34.8%). $^1$HNMR (CD$_3$OD) δ: 8.07 (d, J=7.7 Hz, 1H), 7.96 (d, J=7.3 Hz, 1H), 7.82 (s, 1H), 7.78 (d, J=7.7 Hz, 1H), 7.73 (d, J=8.1 Hz, 1H), 7.61 (d, J=8.5 Hz, 2H), 7.57 (d, J=8.8 Hz, 1H), 7.49 (t, J=7.7 Hz, 1H), 7.37 (d, J=8.4 Hz, 2H), 7.29 (d, J=7.7 Hz, 1H), 2.32 (s, 3H); $^{13}$C NMR (CD$_3$OD) δ: 167.63, 157.41, 143.05, 141.47, 139.26, 138.46, 138.32, 137.59, 135.51, 134.27, 133.63, 132.91, 131.48, 131.22, 130.84, 129.98, 128.74, 128.61, 128.43, 120.98, 12.22; ESMS: m/z 509.1 (M+H, 100); HRMS: calcd. for C$_{24}$H$_{22}$Cl$_1$N$_6$O$_3$S$_1$ 509.1163 found 509.1172.

Example 132

5-(3-Amidinophenyl)-2-methyl-4-[(2'-aminosulfonyl-[1,1']-biphen-4-yl)aminocarbonyl] imidazole Part A: Ethyl-2-methyl-4-(3'cyano)phenyl-5-carboxylate was prepared via the reaction of ethyl-2-bromo-(3-cyano) benzoylacetate and ammonium acetate in acetic acid in 20% yield. $^1$HNMR (CDCl$_3$) δ: 10.03 (BS, 1H), 8.25 (bs, 1H), 8.17 (bd, 1H), 7.40 (d, 1H), 7.44 (t, 1H), 4.30 (q, 2H), 2.50 (s, 3H), 1.30 (t, 3H) ppm; Ammonia CI mass spectrum 272 (M+H, 100).

Part B: Weinreb coupling of the product from part A with the -2'tert-butylaminosulfonyl-1-aminobiphenyl and trimethyl aluminum afforded the desired coupled product which when subjected to the standard Pinner amidine reaction and the usual purification protocols to afford the title compound as colorless crystals; $^1$HNMR (CD$_3$OD) δ: 8.29 (s, 1H), 8.10 (dd, J=7.9 Hz, J=1.2 Hz, 1H), 8.06 (d, J=7.8 Hz, 1H), 7.83 (d, J=7.6 Hz, 1H), 7.73 (d, J=7.8 Hz, 1H), 7.70 (bs, 2H), 7.61 (td, J=7.6 Hz, J=1.5 Hz, 1H), 7.52 (td, J=7.6 Hz, J=1.5 Hz, 1H), 7.42 (d, J=6.8 Hz, 2H), 7.33 (dd, J=7.6 Hz, J=1.2 Hz, 1H), 2.53 (bs, 3H); ESMS: m/z 475.1 (M+H, 100) for C$_{24}$H$_{22}$N$_6$O$_3$S$_1$.

Examples 133 and 134

1-(3-Amidinophenyl)-3-methyl-5-[(4'-(benzimidazol-1-yl)phen-1-yl)aminocarbonyl] pyrazole and 1-(3-Aminocarbonylphenyl)-3-methyl-5-[(4'-(benzimidazol-1-yl)phen-1-yl)aminocarbonyl] pyrazole Part A. Preparation of N-(4-Nitrophenyl)benzimidazole.

Made a suspension of 1.26 g of 4-bromonitrobenzene and 0.74 g of benzimidazole in 50 mL of anhydrous dimethylformamide. Added 0.94 g of potassium carbonate to reaction mixture. Warmed reaction mixture to 80° C. for 72H. Diluted reaction mixture with 100 mL water and extracted 3 times with 50 mL ethyl acetate portions. Combined extracts and dried. Filtered and concentrated resulting organics in vacuo to give the crude product. LRMS (NH3—CI): 240, (M+H, 100), $^1$HNMR (CDCl$_3$) δ: 8.50 (d, 2H), 8.20 (s, 1H), 7.93 (complex, 1H), 7.75 (d, 2H), 7.63 (complex, 1H), 7.42 (complex, 2H).

Part B. Preparation of N-(4-Aminophenyl)benzimidazole.

Made a suspension of 0.6 g crude N-(4-nitrophenyl) benzimidazole and a catalytic amount of 10% palladium on carbon in 20 mL methanol. Placed reaction mixture under 1 atmosphere of hydrogen and let stir for 15H. Passed reaction mixture through a 1" celite pad and concentrated filtrate in vacuo to give the crude product. LRMS (NH3—CI): 210 (M+H, 100), $^1$HNMR (DMSO-d6) δ: 9.25 (s, 1H), 7.83 (complex, 1H), 7.60 (complex, 1H), 7.47 (complex, 2H), 7.35 (d, 2H), 6.80 (d, 2H).

Part C. Preparation of N-(3-Cyanophenyl)-3-methyl-5-[(4'-(benzimidazol-1-yl)phen-1-yl)aminocarbonyl]pyrazole.

To 0.16 g of N-(3-cyanophenyl)-3-methyl-pyrazole 5-carboxylic acid and 25 mL dichloromthane was added 0.07 mL oxalyl chloride and 2 drops DMF. The reaction proceeded overnight. Concentration of the reaction mixture and placement under high vacuum gave the crude acid chloride which was then coupled to the product of part B under standard conditions to afford crude N-(3-cyanophenyl-)3-methyl-5-((4'-N-benzimidazol-1-yl-phenyl) aminocarbonyl)pyrazole. LRMS (ESI): 419 (M+H, 20), 210 (M+2H)$^{++}$.

Part D. Preparation of N-(3-Amidinophenyl)-3-methyl-5-[(4'-benzimidazol-1-yl)phen-1-yl)aminocarbonyl]pyrazole.

Standard transformation of the benzonitrile obtained in part C to the benzamidine via the ethyl imidate converted 0.24 g of the crude benzonitrile to 0.02 g of the benzamidine bis-TFA salt after standard HPLC purification. LRMS (ES+): 436.21 (M+H), HRMS (FAB): Calc: 436.188584 Mass: 436.191317 and 0.003 g of the benzamide LRMS (ES+): 437 (M+H), 459 (M+Na), HRMS (NH3—CI): Calc: 437.172599 Mass: 437.173670. $^1$HNMR (DMSO-d6, 300 MHz) δ: 10.76 (s, 1H), 9.40 (s, 2H), 9.02 (s, 2H), 8.59 (s, 1H), 7.94 (s, 1H), 7.88 (d, 2H), 7.76 (complex, 3H), 7.64 (complex, 4H), 7.32 (complex, 2H), 7.05 (s, 1H), 2.30 (s, 3H).

Examples 135 and 136

1-(3-Amidinophenyl)-3-methyl-5-[(4'-(2-methylimidazolyl)phenyl)aminocarbonyl]pyrazole and 1-(3-Aminocarbonylphenyl)-3-methyl-5-[(4'-(2-methylimidazolyl)phenyl)aminocarbonyl)pyrazole Part A. Preparation of N-(4-Nitrophenyl)-2-methylimidazole.

2-Methylimidazole (1.04 g) was treated with 0.56 g 60% sodium hydride in an oil dispersion in 60 mL DMF with cooling. After 0.33H added 4-bromonitrobenzene in three portions over 0.5 H. Let reaction mixture warm to ambient temperature overnight. Diluted mixture with 100 mL of 1.0 M HCl solution and extracted three times with 30 mL portions of ethyl acetate. Combined extracts and dried over magnesium sulfate. Concentrated resulting organics in vacuo. Purified crude material by standard chromatographic techniques to give the purified product as a crystalline solid. LRMS (NH3—CI): 204 (M+H, 100); $^1$HNMR (CDCl$_3$) δ: 8.40 (d, 2H), 7.50 (d, 2H), 7.05 (d, 2H), 2.43 (s, 3H).

Part B. Preparation of 1-(4-Aminophenyl)-2-methylimidazole.

N-(4-nitrophenyl)-2-methylimidazole (0.47 g) was treated with a catalytic amount of 10% palladium on carbon in 15 mL methanol. The mixture was placed under an atmosphere of hydrogen. The reaction mixture was stirred for 3H and then passed through a 1" celite pad. The resulting filtrate was concentrated under reduced pressure to give the title compound. LRMS (NH$_3$—CI): 174 (M+H, 100), $^1$HNMR (CDCl$_3$) δ: 7.05 (d, 1H), 6.97 (d, 2h), 6.77 (d, 1H), 6.60 (d, 2H), 5.34 (s, 2H), 2.13 (s, 3H).

Part C. Preparation of N-(3-Cyanophenyl)3-methyl-5-((4'-2-methylimidazolylphenyl)aminocarbonyl)pyrazole.

To 0.24 g of N-(3-cyanophenyl)-3-methyl-pyrazole 5-carboxylic acid and 20 mL dichloronthane was added 0.14 mL oxalyl chloride and 2 drops DMF. The reaction proceeded overnight. Concentration of the reaction mixture and placement under high vacuum gave the crude acid chloride which was then coupled to the product of part B under standard conditions to afford the title compound isolated as the hydrochloride salt. LRMS (ESI): 383 (M+H, 100), $^1$HNMR (DMSO-d$_6$) δ: 10.90 (s, 1H), 7.95 (s, 1H), 7.90 (d, 2H), 7.83 (m, 2H), 7.75 (m, 2H), 7.63 (m, 1H), 7.57 (d, 2H), 7.10 (s, 1H), 2.49 (s, 3H), 2.30 (s, 3H).

Part D. Preparation of 1-(3-Amidinophenyl)-3-methyl-5-[(4'-2-methylimidazolyl)phenyl)aminocarbonyl]pyrazole and 1-(3-Aminocarbonylphenyl)-3-methyl-5-[(4'-2-methylimidazolyl)phenyl)aminocarbonyl]pyrazole.

The N-(3-cyanophenyl)-3-methyl-5-((4'-2-methylimidazolylphenyl)aminocarbonyl)pyrazole was converted to the corresponding benzamidine via Pinner synthesis and amidination by subsequent treatment of the imidate with ammonium carbonate. The crude mixture was then purified by standard HPLC technique to give the benzamidine as a white solid after lyophilization LRMS (ES+): 400 (M+H, 100); HRMS: Calc: 400.188584, Mass: 400.188113 $^1$HNMR (DMSO-d$_6$, 300 MHz) δ: 10.87 (s, 1H), 9.40 (s, 2H), 9.30 (s, 2H), 7.95 (s, 1H), 7.89 (d, 2H), 7.80 (m, 2H), 7.75 (m, 2H), 7.65 (m, 1H), 7.55 (d, 2H), 7.05 (s, 1H) 2.47 (s, 3H), 2.30 (S, 3H). The corresponding benzamide was isolated as a by-product during purification. LRMS (ES+): 401 (M+H) HRMS (NH$_3$—CI): Calc. 401.172599 Mass: 410.170225; $^1$HNMR (DMSO-d$_6$, 300MHz) δ: 10.77 (s, 1H), 8.78 (s, 1H), 8.09 (s, 1H), 7.94 (s, 1H), 7.87 (m, 3H), 7.77 (m, 1H), 7.65 (d, 2H), 7.63 (m, 1H), 7.50 (complex, 3H), 7.36 (m, 2H), 6.95 (s, 1H), 2.30 (s, 3H).

Example 137

1-(3-Amidinophenyl)-3-methyl-5-[[4'-(1,2,4-triazol-2-yl)-phenyl]aminocarbonyl]pyrazole Part A. 1-(3-Cyanophenyl)-3-methyl-5-((4'-(1,2,4-triazolyl)phenyl)aminocarbonyl)pyrazole.

The pyrazole acid chloride was generate by standard method and coupled to 0.18 g of commercially available 4-(1-N-1,2,4-triazolo)aniline using the standard DMAP coupling to give the 1-(3-cyanophenyl)-3-methyl-5-((4'-(1,2,4-triazol-1-yl)phenyl)aminocarbonyl)pyrazole. The crude product was recrystallized from 2:1 methylene chloride to methanol to give the product as a white solid. LRMS (NH$_3$—CI): 370 (M+H), $^1$HNMR (DMSO-d$_6$, 300 MHz) δ: 10.57 (s, 1H), 9.20 (s, 1H), 8.19 (s, 1H), 7.97 (s, 1H), 7.80 (complex, 6H), 7.65 (t, 1H), 7.00 (s, 1H), 2.29 (s, 3H).

Part B. Preparation of 1-(3-Amidinophenyl)-3-methyl-5-((4'-(1,2,4-triazolyl)phenyl)aminocarbonyl)pyrazole.

Standard transformation of the benzonitrile obtained in part A to the benzamidine via the ethyl imidate converted 0.13 g of the benzonitrile to the benzamidine bis-TFA salt after standard HPLC purification. LRMS (ES+): 387 (M+H) HRMS (NH3—CI): Calc: 387.168182 Mass: 387.166790; $^1$HNMR (DMSO-d$_6$, 300 Mhz) δ: 10.70 (s, 1H), 9.39 (s, 2H), 9.20 (2, 1H), 9.02 (s, 2H), 8.19 (s, 1H), 7.91 (s, 1H), 7.79 (m, 5H), 7.70 (m, 2H), 7.02 (s, 1H), 2.31 (s, 3H).

Example 138

1-(3-Amidinophenyl)-3-methyl-5-((4'-cyclohexylphenyl)aminocarbonyl)pyrazole

Part A. Preparation of 1-(3-Cyanophenyl)-3-methyl-5-((4'-cyclohexylphenyl)aminocarbonyl)pyrazole.

The pyrazole acid chloride was generate in the standard method and coupled to 0.19 g of commercially available 4-cyclohexylaniline using the standard DMAP coupling to give the 1-(3-cyanophenyl)-3-methyl-5-((4'-cyclohexylphenyl)aminocarbonyl)pyrazole. LRMS (NH$_3$—CI): 385 (M+H), 402 (M+NH4), $^1$HNMR (DMSO, 300 MHZ) δ: 10.40 (s, 1H), 7.92 (s, 1H), 7.82 (d, 1H), 7.72 (d, 1H), 7.61 (t, 1H), 7.50 (d, 2H), 7.13 (d, 2H), 6.92 (s, 1H), 3.31 (s, 1H), 2.25 (s, 3H), 1.71 (complex, 5H), 1.13 (complex, 5H).

Part B. Preparation of 1-(3-Amidinophenyl)-3-methyl-5-((4'-cyclohexylphenyl)aminocarbonyl)pyrazole.

Standard transformation of the benzonitrile obtained in part A to the benzamidine via the ethyl imidate converted the crude benzonitrile to the benzamidine TFA salt. The crude product was purified by standard HPLC purification. LRMS (ES+): 402 (M+H) HRMS (NH3—CI): Calc: 402.229386 Mass: 402.227504 $^1$HNMR (DMSO-d$_6$, 300 MHz) δ: 10.30 (s, 1H), 9.38 (s, 2H), 9.07 (s, 2H), 7.90 (s, 1H), 7.77 (m, 1H), 7.69 (m, 2H), 7.50 (d, 2H), 7.12 (d, 2H), 6.93 (s, 1H), 3.31 (m, 1H), 2.28 (s, 3H), 1.71 (complex, 5H), 1.32 (complex, 5H).

Example 139

1-(3-Amidinophenyl)-3-methyl-5-[[1,1']-biphen-4-ylaminocarbonyl]pyrazole

Part A. Preparation of 1-(3-Cyanophenyl)-3-methyl-5-[[1,1']-biphen-4-ylaminocarbonyl]pyrazole.

The pyrazole acid chloride was generate by standard method and coupled to 0.19 g of commercially available 4-aminobiphenyl using standard DMAP coupling to give the 1-(3-cyanophenyl)-3-methyl-5-[[1,1']-biphen-4-ylaminocarbonyl]pyrazole. LRMS (NH$_3$—CI): 379 (M+H), 396 (M+NH4) HRMS (NH$_3$—CI): Calc: 396.182436 Mass: 396181736. $^1$HNMR (DMSO-d$_6$, 300 MHz) δ: 10.57 (s, 1H), 9.20 (s, 1H), 8.19 (s, 1H), 7.97 (s, 1H), 7.80 (complex, 6H), 7.65 (t, 1H), 7.00 (s, 1H), 2.29 (s, 3H).

Part B. Preparation of 1-(3-Amidinophenyl)-3-methyl-5-[[1,1']-biphen-4-ylaminocarbonyl]pyrazole.

Standard transformation of the benzonitrile obtained in part B to the benzamidine via the ethyl imidate converted of the crude benzonitrile to the benzamidine TFA salt. The crude product was purified by standard HPLC purification technique. LRMS (ES+): 396 (M+H) HRMS (NH3—CI): Calc: 396.181736 Mass: 396.182436; $^1$HNMR (DMSO, 300 MHz) δ: 10.60 (s, 1H), 9.40 (s, 2H), 8.99 (s, 2H), 7.91 (m, 1H), 7.80 (complex, 5H), 7.61 (m, 4H), 7.41 (m, 2H), 7.30 (m, 1H), 7.00 (s, 1H), 2.29 (s, 3H).

Example 140

1-(3-Amidinophenyl)-3-methyl-5-((4'-morpholinophenyl)aminocarbonyl)pyrazole Part A. 1-(3-Cyanophenyl)-3-methyl-5-((4'-morpholinophenyl)aminocarbonyl)pyrazole.

The pyrazole acid chloride was generate from the pyrazole acid by standard method and coupled to 0.26 g of commercially available 4-morpholinoaniline using the standard DMAP coupling to give the 1-(3-cyanophenyl)-3-methyl-5-((4'-morpholinophenyl)aminocarbonyl)pyrazole. LRMS (NH3—CI): 388 (M+H), $^1$HNMR (DMSO, 300 MHz) δ: 10.30 (s, 1H), 7.90 (m, 1H), 7.82 (d, 1H), 7.71 (m, 1H), 7.62 (t, 6H), 7.49 (d, 2H), 6.89 (s, 1H), 6.87 (d, 2H), 3.69 (t, 4H), 3.02 (t, 4H), 2.25 (s, 3H).

Part B. Standard transformation of the benzonitrile obtained in part A to the benzamidine via the ethyl imidate converted the crude benzonitrile to the benzamidine bis-TFA salt. The crude product was purified by standard HPLC purification. LRMS (ES+): 405 (M+H) HRMS (NH3—CI): Calc: 405.203899 Mass: 405.201545 $^1$HNMR (DMSO-d$_6$, 300 MHz) δ: 10.38 (s, 1H), 9.40 (s, 2H), 9.12 (s, 2H), 7.90 (s, 1H), 7.78 (d, 1H), 7.68 (m, 2H), 7.49 (d, 2H), 6.92 (s, 1H), 6.90 (d, 2H), 3.80 (t, 4H), 3.01 (t, 4H), 2.29 (s, 3H).

Example 141

1-(3-Amidinophenyl)-3-methyl-5-[(4'-((2-trifluoromethyl)tetrazol-1-yl)phenyl)aminocarbonyl]pyrazole Part A. Preparation 4-(2-Trifluoromethyltetrazolyl)nitrobenzene.

3.0 g of commercially available 4-nitroaniline was trifluoromethylacetylated in the presence of trifluoroacetic anhydride to give the crude N-trifluoroacetyl-4-nitroaniline. LRMS (NH$_3$—CI): 252 (M+NH4); $^1$HNMR (DMSO-d6, 300 Mhz) δ: 11.75 (s, 1H), 8.28 (d, 2H), 7.92 (d, 2H) The crude material was then treated with triphenylphosphine in carbon tetrachloride to give the chloroimine. $^1$HNMR (CDCl$_3$, 300 MHz) δ: 8.35 (d, 2H), 7.15 (d, 2H) The crude chloroimine was cyclized to the 4-(2-trifluoromethyltetrazole)nitrobenzene with sodium azide in acetonitrile. $^1$HNMR (CDCl$_{3, 300}$ MHz) δ: 8.54 (d, 2H), 7.80 (d, 2H). The crude 2-trifluoromethyltetrazoloaniline was triturated to give the semi-crude product which was catalytically reduced to the aniline with 10% palladium on carbon. LRMS (NH$_4$—CI): 230 (M+H), 247 (M+NH4), $^1$HNMR (DMSO-d$_6$, 300 MHz) δ: 7.256 (d, 2H), 6.65 (d, 2H).

Part B. Preparation of 1-(3-Cyanophenyl)-3-methyl-5-[(4'-((2-trifluoromethyl)tetrazolyl)phenyl)aminocarbonyl] pyrazole.

The pyrazole acid chloride was generate by standard method and coupled to 0.49 g of 4-(2-trifluoromethyltetrazolo)aniline using the standard DMAP coupling to give the 1-(3-cyanophenyl)-3-methyl-5-((4'-(2-trifluoromethyltetrazol)-1-yl-phenyl)aminocarbonyl) pyrazole. LRMS (NH$_3$—CI): 439 (M+H), 461 (M+Na+), 877 (2 M+H), 899 (2M+Na); $^1$HNMR (DMSO-d$_6$, 300 MHz) δ: 10.87 (s, 1H), 8.00 (s, 1H), 7.91 (d, 2H), 7.84 (m, 1H), 7.77 (m, 1H), 7.69 (d, 2H), 7.63 (t, 1H), 7.02 (s, 1H), 2.29 (s, 3H).

Part C. Preparation of 1-(3-Amidinophenyl)-3-methyl-5-[(4'-((2-trifluoromethyl)tetrazolyl)phenyl)aminocarbonyl] pyrazole.

Standard transformation of the benzonitrile obtained in part B to the benzamidine via the ethyl imidate converted the crude benzonitrile to the benzamidine TFA salt after HPLC purification. LRMS (ES+): 456 (M+H) HRMS (NH$_3$—CI): Calc: 456.150816 Mass: 456.150428; $^1$HNMR (DMSO-d$_6$, 300 MHz) δ: 10.92 (s, 1H), 9.40 (s, 2H), 9.18 (s, 2H), 7.90 (complex, 3H), 7.78 (m, 2H), 7.67 (complex, 3H), 7.08 (s, 1H), 2.32 (s, 3H).

Example 142

1-(3-Aminomethylphenyl)-3-methyl-5-[(4'-((2-trifluoromethyl)tetrazol-1-yl)phenyl)aminocarbonyl]pyrazole 0.06 g of 1-(3-cyanophenyl)-3-methyl-5-((4'-(2-trifluoromethyltetrazolyl)phenyl)aminocarbonyl)pyrazole was reacted with 10% palladium on carbon in TFA/methanol under a hydrogen.atmosphere. After a few hours the reaction mixture was filtered through a 1 inch celite pad. The filtrate was concentrated under reduced pressure and the residue was purified by standard HPLC method to give the desired compound. LRMS (NH$_4$—CI): 443 (M+H) HRMS (NH$_4$—CI): calc: 443.155567 mass: 443.155567; $^1$HNMR (DMSO-d$_6$, 300 MHz) δ: 10.90 (s, 1H), 8.20 (brd. s, 2H), 7.90 (d, 2H), 7.69 (d, 2H), 7.62 (s, 1H), 7.42 (complex 3H), 6.97 (s, 1H), 4.09 (m, 2H), 2.29 (s, 3H).

Example 143

1-(3-Amidinophenyl)-3-methyl-5-[((4'-(N,N-dimethylamino)carbonylamino)phen-1'-yl)aminocarbonyl]pyrazole Part A. Preparation of 4-((N,N-Dimethylamino)carbonylamino)-1-nitrobenzene.

1.56 g of 4-nitroaniline was treated with 0.50 g sodium hydride in 60% oil dispersion in DMF at 0° C. After 20 minutes added 1.04 mL of N,N-dimethylcarbamyl chloride dropwise. Let mixture warm to ambient temperature overnight. Pourred reaction mixture into 150 mL ice water. Let stand for 1 h. Isolated precipitate via vacuum filtration. LRMS (NH3—CI): 210 (M+H), 227 (M+NH$_4$), $^1$HNMR (DMSO-d$_6$, 300 MHz) δ: 8.97 (s, 1H), 8.12 (d, 2H), 7.70 (d, 2H) 2.91 (s, 6H).

Part B. Preparation of 1-Amino-4-((N,N-dimethylamino)carbonylamino)benzene.

Treated 1.66 g of 4-N,N-dimethylurea nitrobenzene with a catalytic amount of 10% palladium on carbon in methanol and placed under 35 psi hydrogen for 1 H. Passed through a 1 inch celite pad and concentrated filtrate to give a solid after high vacuum. LRMS (NH3—CI): 180 (M+H).

Part C. Preparation of 1-(3-Cyanophenyl)-3-methyl-5-[(4'-((N,N-dimethylamino)carbonylamino)phen-1'-yl)aminocarbonyl]pyrazole.

0.37 g of 4-N,N-dimethylurea aniline was coupled to 0.46 g of N-(3-cyanophenyl)-3-methyl-pyrazole-5-carboxylic acid chloride via standard DMAP coupling in dichloromethane. A few drops of DMF was added to catalyze the reaction. The N-(3-cyanophenyl)-3-methyl-pyrazole-5-carboxylic acid chloride was prepared by the previously disclosed procedure. The desired product was purified by standard purification techniques. LRMS (ES+): 389 (M+H), 411 (M+Na+), 777 (2M+H), 799 (2M+Na), $^1$HNMR (DMSO-d$_6$, 300 MHz) δ: 10.35 (s, 1H), 8.22 (s, 1H), 7.91 (s, 1H), 7.82 (d, 1H), 7.71 (d, 1H), 7.63 (t, 1H), 7.46 (d, 2H), 7.37 (d, 2H), 6.91 (s, 1H), 2.88 (s, 6H), 2.29 (s, 3H).

Part D. Preparation of 1-(3-Amidinophenyl)-3-methyl-5-[(4'-((N,N-dimethylamino)carbonylamino)phen-1'-yl)aminocarbonyl]pyrazole.

Standard transformation of the benzonitrile obtained in part C to the benzamidine via the ethyl imidate converted the crude benzonitrile to the benzamidine TFA salt after HPLC purification. LRMS (ES+): 406 (M+H), 811 (H+−dimer) HRMS (NH$_3$—CI): Calc: 406.199148 Mass: 406.198887; $^1$HNMR (DMSO-d$_6$, 300 MHz) δ: 10.37 (s, 1H), 9.40 (s, 2H), 9.02 (s, 2H), 8.23 (s, 1H), 7.91 (s, 1H), 7.78 (d, 1H), 7.68 (m, 2H), 7.43 (d, 2H), 7.38 (d, 2H), 6.95 (s, 1H), 2.87 (s, 6H), 2.29 (s, 3H).

Examples 144 and 145

1-(3-Amidinophenyl)-3-methyl-5-[(4'-(N,N-diethylamino)phenyl)aminocarbonyl]pyrazole (Example 144) and 1-(3-Aminocarbonylphenyl)-3-methyl-5-((4'-N,N-diethylamino)phenyl)aminocarbonyl)pyrazole (Example 145)

Part A. Preparation of 1-(3-Cyanophenyl)-3-methyl-5-[(4'-(N,N-diethylamino)phenyl)aminocarbonyl]pyrazole.

The pyrazole acid chloride was generated by the standard method and coupled to 0.24 g of commercially available N,N-diethyl-1,4-phenylenediamine using the standard DMAP coupling to give the 1-(3-cyanophenyl)-3-methyl-5-((4'-N,N-diethylaminoaniline)aminocarbonyl)pyrazole. LRMS (NH$_3$—CI): 374 (M+H), 747 (2M+H); $^1$HNMR (DMSO-d$_6$, 300 MHz) δ: 10.16 (s, 1H), 7.90 (s, 1H), 7.81 (m, 1H), 7.71 (m, 1H), 7.60 (t, 1H), 7.37 (d, 2H), 6.88 (s, 1H), 6.59 (d, 2H), 3.26 (m, 4H), 2.25 (s, 3H), 1.02 (t, 6H).

Part B. Preparation of 1-(3-Amidinophenyl)-3-methyl-5-[(4'-(N,N-diethylamino)phenyl)aminocarbonyl]pyrazole.

Standard transformation of the benzonitrile obtained in part B to the benzamidine via the ethyl imidate converted 0.24 g of the crude benzonitrile to 0.256 g of the benzamidine bis-TFA salt after HPLC purification. LRMS (ES+): 391 (M+H) HRMS (NH$_3$—CI): Calc: 391.224635 Mass: 391.224109. 0.017 g of the benzamide was also isolated during HPLC purification. LRMS (ESI+): 392 (M+H) HRMS (NH$_3$—CI) calc: 392.208650 mass: 392.207700.

Examples 146 and 147

1-(3-Amidinophenyl)-3-methyl-5-[(4'-(1-tetrazolyl)phenyl)aminocarbonyl)pyrazole (Example 146) and 1-(3-Aminocarbonylphenyl)-3-methyl-5-((4'-(1-tetrazolyl)phenyl)aminocarbonyl)pyrazole (Example 147)

Part A. Preparation of 4-N-Formylaminonitrobenzene.

Treated 0.69 g of 4-aminonitrobenzene with acetic formic anhydride in THF at 0° C. Then warmed reaction mixture to 55° C. for 2 H. Concentrated mixture under reduced pressure and placed residue on high vacuum to give the crude product. LRMS (NH$_3$—CI): 184 (M+NH4).

Part B. Preparation of 4-(1-Tetrazolyl)nitrobenzene.

Made a solution of above compound, 2.63 g triphenylphosphine, 1.15 g TMS azide and 1.75 g DEAD reagent in THF. Let stir for 24 H. Diluted reaction mixture with water and extracted with methylene chloride. Dried and concentrated organic extracts to give the crude product which was purified by standard chromatographic technique. LRMS (NH3—CI): 209 (M+NH4), $^1$HNMR (DMSO-d$_6$, 300 MHz) δ: 10.35 (s, 1H), 8.48 (d, 2H), 8.20 (d, 2H).

Part C. Preparation of 4-(1-Tetrazolyl)aniline.

Treated 4-(1-tetrazolyl)nitrobenzene with 10% palladium on carbon in methanol and placed under 40 psi of hydrogen for 2 H. Passed reaction mixture through a 1 inch celite pad and concentrated filtrate to give the crude product. LRMS (NH3–CI): 162 (M+H), 179 (M+NH4), $^1$HNMR (DMSO-d$_6$, 300 MHz) δ: 9.79 (s, 1H), 7.42 (d, 2H), 6.67 (d, 2H).

Part D. Preparation of 1-(3-Cyanophenyl)-3-methyl-5-[(4'-(1-tetrazolyl)phenyl)aminocarbonyl]pyrazole.

The pyrazole acid chloride was generate in the standard method and coupled to 0.26 g 4-(1-tetrazolyl)aniline using the standard DMAP coupling to give the 1-(3-cyanophenyl)-3-methyl-5-((4'-(1-tetrazolyl)phenyl)aminocarbonyl)pyrazole. This crude material was used directly.

Part E. Preparation of 1-(3-Amidinophenyl)-3-methyl-5-((4'-(1-tetrazolyl)phenyl)aminocarbonyl)pyrazole.

Standard transformation of the benzonitrile obtained in part D to the benzamidine via the ethyl imidate converted the crude benzonitrile to 0.014 g of the benzamidine TFA salt after HPLC purification. LRMS (ES+): 388 (M+H) HRMS (NH3—CI): Calc: 388.163431 Mass: 388.165343 $^1$HNMR (DMSO-d$_6$, 300 MHz) δ: 10.79 (s, 1H), 10.01 (s, 1H), 9.40 (bs, 2H), 8.99 (bs, 2H), 7.93 (s, 1H), 7.85 (m, 4H), 7.77 (m, 2H), 7.67 (m, 1H), 7.04 (s, 1H), 2.31 (s, 3H). 0.007 g of the benzamide was also isolated during HPLC purification. LRMS (ESI+): 799 (2M+Na) 777 (2M+H) HRMS (NH$_3$—CI): calc: 389.147447 mass: 389.149952; $^1$HNMR (DMSO-d$_6$, 300 MHz) δ: 10.77 (s, 1H), 10.00 (s, 1H), 7.94 (m, 1H), 7.87 (m, 6H), 7.51 (m, 1H), 6.96 (s, 1H), 2.30 (s, 3H).

Examples 148, 149, and 150

1-(3-Amidinophenyl)-3-methyl-5-[(4'-(N-acetylpiperizin-1-yl)phenyl)aminocarbonyl]pyrazole, 1-(3-Amidinophenyl)-3-methyl-5-[(4'-(N-tert-butyloxycarbonylpiperizin-1-yl)phenyl)aminocarbonyl]pyrazole, and 1-(3-Amidinophenyl)-3-methyl-5-((4'-piperizin-1-yl-phenyl)aminocarbonyl)pyrazole Part A. Preparation of 1-(3-Cyanophenyl)-3-methyl-5-[(4'-(N-tert-butyloxycarbonylpiperizin-1-yl)phenyl)aminocarbonyl]pyrazole.

The pyrazole acid chloride was generate by the standard method and coupled to 0.23 g of 4-(N-boc-piperizine)aniline (which is readily available from commercially available 1-(4-nitrophenyl)piperazine) using the standard DMAP coupling to give the crude 1-(3-cyanophenyl)-3-methyl-5-((4'-N-tert-butyloxycarbonylpiperizine-1-phenyl)aminocarbonyl)pyrazole. The crude product was purified by standard chromatographic technique. LRMS ($NH_3$—CI): 487 (M+H) $^1$HNMR (DMSO-$d_6$, 300 MHz) δ: 10.60 (s, 1H), 7.90 (s, 1H), 7.81 (m, 1H), 7.73 (m, 1H), 7.61 (t, 1H), 7.47 (d, 2H), 6.90 (s, 1H), 6.88 (d, 2H), 3.41 (complex, 4H), 3.01 (complex, 4H), 2.28 (s, 3H), 1.37 (s, 9H).

Part B. Preparation of 1-(3-Amidoximephenyl)-3-methyl-5-[(4'-(N-tert-butyloxycarbonylpiperizin-1-yl)phenyl]aminocarbonyl]pyrazole.

Treated 0.29 g of 1-(3-cyanophenyl)-3-methyl-5-((4'-N-tert-butyloxycarbonylpiperizin-1-ylphenyl)aminocarbonyl)pyrazole with 0.15 g hydroxylamine hydrochloride and 0.11 g of sodium carbonate in ethanol/water. Warmed reaction mixture to reflux temperature for 5 H. Worked up reaction mixture with aqueous washings, dried resulting organic, and concentrated in vacuo to give the crude amidoxime.

Part C. Preparation of 1-(3-Amidinophenyl)-3-methyl-5-[(4'-(N-tert-butyloxycarbonylpiperizin-1-yl)phenyl)aminocarbonyl]pyrazole and 1-(3-Amidinophenyl)-3-methyl-5-[(4'-(N-acetylpiperazin-1-yl)phenyl)aminocarbonyl]pyrazole.

Treated crude amidoxime with acetic acid and acetic anhydride for 0.5 H. Added a catalytic amount of 10% palladium on carbon to reaction mixture and placed on Parr hydrogenator at 50 psi for 4 H. Passed through a 1 inch celite pad and concentrated filtrate to give the crude benzamidine. Purified via standard HPLC technique. The N-acetyl compound LRMS (ES+): 446 (M+H, 100) HRMS (FAB+): calc. –446.230448 mass-446.231327 $^1$HNMR (DMSO-$d_6$, 300 MHz) δ: 10.33 (s, 1H), 9.39 (bs, 2H), 9.04 (bs, 2H), 7.90 (s, 1H), 6.77 (d, 1H), 7.69 (m, 2H), 7.48 (d, 2H), 6.94 (s, 1H), 6.90 (d, 2H), 3.52 (m, 4H), 3.02 (M, 4H), 2.28 (s, 3H), 2.00 (s, 3H). 1-(3-amidinophenyl)-3-methyl-5-[(4'-(N-acetylpiperazin-1-yl)phenyl)aminocarbonyl]pyrazole-was isolated as a by-product in addition to the N-boc compound LRMS (ES+): 504 (M+H) HRMS ($NH_3$—CI): calc-504.272313 mass-504.272536 $^1$HNMR (DMSO-$d_6$, 300 MHz) δ: 10.34 (s, 1H), 9.38 (bs, 2H), 9.05 (bs, 2H), 7.90 (m, 1H), 7.77 (m, 1H), 7.67 (m, 2H), 7.47 (d, 2H), 6.94 (s, 1H), 6.90 (d, 2H), 3.42 (m, 4H), 3.00 (m, 4H), 2.29 (s, 3H), 1.37 (s, 9H).

Part D. Preparation of 1-(3-Amidinophenyl)-3-methyl-5-[(4'-(N-piperizin-1-yl)phenyl)aminocarbonyl]pyrazole.

0.043 g of 1-(3-amidinophenyl)-3-methyl-5-((4'-N-tert-butyloxycarbonylpiperizin-1-phenyl)aminocarbonyl)pyrazole was treated with TFA at ambient temperature for 3 H. Concentrated reaction mixture under reduced pressure to give the crude product. Purified crude material by standard HPLC technique. LRMS (ES+): 404 (M+H) HRMS ($NH_3$—CI): calc-404.219884 mass-404.221193 $^1$HNMR (DMSO-$d_6$, 300 MHz) δ: 10.36 (s, 1H), 9.39 (bs, 2H), 9.18 (bs, 2H), 7.90 (s, 1H), 7.77 (d, 1H), 7.67 (m, 2H), 7.01 (d, 2H), 6.92 (m, 3H), 3.22 (m, 8H), 2.29 (s, 3H).

Example 151

1-(3-Amidinophenyl)-3-trifluoromethyl-5-((4'-cyclohexylphenyl)aminocarbonyl)pyrazole Part A. Preparation of 1-(3-Cyanophenyl)-3-trifluoromethyl-5-((41-cyclohexylphenyl)aminocarbonyl)pyrazole.

0.25 g of N-(3-cyanophenyl)-3-methyl-pyrazole-5-carboxylic acid was converted to its corresponding acid chloride by standard procedure and reacted with 0.15 g of 4-cyclohexylaniline in the presence of DMAP in methylene chloride to afford the title compound after workup and purification by standard chromatographic technique. LRMS (ES+): 461 (M+Na+), 899 (Na+–dimer), $^1$HNMR (DMSO-$d_6$, 300 MHz) δ: 10.57 (s, 1H), 8.13 (s, 1H), 7.95 (d, 1H), 7.86 (d, 1H), 7.69 (t, 1H), 7.65 (s, 1H), 7.50 ( d, 2H), 7.15 (d, 2H), 2.41 (complex, 1H), 1.70 (complex, 5H), 1.25 (complex, 5H).

Part B. Preparation of 1-(3-Amidinophenyl)-3-trifluoromethyl-5-((4'-cyclohexylphenyl)aminocarbonyl)pyrazole.

The cyano derivative was converted to the amidino derivative via the amidoxime as previously described. The amidoxime was reduced to the benzamidine by conversion to the corresponding acetate by acetic acid/acetic anhydride and catalytic reduction with 10% palladium on carbon under a hydrogen atmosphere, also previously described. The crude product was purified by standard HPLC technique to give the TFA salt. LRMS (ES+): 456 (M+H) HRMS ($NH_3$—CI): calc-456.199783 mass-456.201120 $^1$HNMR (DMSO-$d_6$, 300 MHz) δ: 10.62 (s, 1H), 9.40 (s, 2H), 9.16 (s, 2H), 7.99 (s, 1H), 7.88 (m, 2H), 7.72 (t, 1H), 7.69 (s, 1H), 7.50 (d, 2H), 7.14 (d, 2H), 2.41 (complex, 1H), 1.69 (complex, 5H), 1.25 (complex, 5H).

Example 152

1-(3-Amidinophenyl)-3-methyl-5-[(4'-(N-morpholino)-3'-chlorophenyl)aminocarbonyl]pyrazole Part A. Preparation of 1-(3-Cyanophenyl)-3-methyl-5-[(4'-(N-morpholino)-3'-chlorophenyl))aminocarbonyl]pyrazole.

N-(3-cyanophenyl)-3-methyl-pyrazole-5-carboxylic acid was converted to its corresponding acid chloride by standard procedure. 0.30 g of the acid chloride was reacted with 0.26 g of commercially available 2-chloro-4-morpholinoaniline in the presence of DMAP in methylene chloride to afford the product after workup and purification by standard chromatographic technique. LRMS (ES+): 422 (M+H), $^1$HNMR (DMSO-$d_6$, 300 MHz) δ: 10.57 (s, 1H), 8.13 (s, 1H), 7.95 (d, 1), 7.86 (d, 1H), 7.69 (t, 1H), 7.65 (s, 1H), 7.50 (d, 2H), 7.15 (d, 2H), 2.41 (complex, 1H), 1.70 (complex, 5H), 1.25 (complex, 5H).

Part B. Preparation of 1-(3-Amidinophenyl)-3-methyl-5-[(4'-(N-morpholino)-3'-chlorophenyl))aminocarbonyl]pyrazole.

The cyano derivative was converted amidino derivative via the amidoxime as previously described. The amidoxime was reduced to the benzamidine by conversion to the corresponding acetate by acetic acid/acetic anhydride and catalytic reduction of the acetate with 10% palladium on carbon under a hydrogen atmosphere, also previously described. The crude product was purified by standard HPLC technique to give the bis TFA salt. LRMS (ES+): 439

(M+H) HRMS (NH$_3$—CI): calc 439.164927 found 439.163814 $^1$HNMR (DMSO-d$_6$, 300 MHz) δ: 10.54 (s, 1H), 9.38 (s, 2H), 9.06 (s, 2H), 7.89 (s, 1H), 7.78 (m, 2H), 7.67 (m, 2H), 7.51 (dd, 1H), 7.12 (d, 1H), 6.96 (s, 1H), 3.69 (t, 4H), 2.88 (t, 4H), 2.46 (m, 3H).

Example 153

1-(3-Amidinophenyl)-5-[(2'-aminosulfonyl-[1,1']-biphen-4-yl)aminocarbonyl]-3-(methylthio)pyrazole, Trifluoroacetic Acid Salt Part A. Preparation of Ethyl N-(3-Cyanophenyl)glycine.

To a solution of 15.11 g (128 mmol) of 3-aminobenzonitrile in 200 mL of DMF under N$_2$ was added 23.50 g (141 mmol) of ethyl bromoacetate and 14.95 g (141 mmol) anhydrous sodium carbonate. The mixture was heated to 70° C. for 5 hours and then cooled to room temperature. Water (500 mL) was added and the mixture stirred vigorously until a precipitate formed. The solid was collected, washed with 100 mL water and then dried in vacuo to give 19.97 g (76%) of the desired compound as a yellow-orange solid. $^1$HNMR (CDCl$_3$) δ: 7.26 (t, 1H); 7.03 (d, 1H); 6.81 (d, 1H); 6.79 (s, 1H); 4.53 (br s, 1H); 4.03 (q, 2H); 3.92 (d, 2H); 1.21 (t, 3H).

Part B. Preparation of N-(3-Cyanophenyl)glycine.

To a solution of 17.00 g (83.2 mmol) of ethyl N-(3-cyanophenyl)glycine in 100 mL of THF under N$_2$ was added 3.67 g (87.4 mmol) of lithium hydroxide monohydrate in 20 mL water. After 15 hours, the mixture was acidified with concentrated hydrochloric acid to pH 3 and a precipitate formed. The solid was collected, washed with 100 mL water and then dried in vacuo to give 14.15 g (97%) of the desired compound as a light yellow solid. $^1$HNMR (CDCl$_3$) δ: 7.28 (dt, 1H); 7.05 (dd, 1H); 6.83 (dd, 1H); 6.82 (d, 1H); 4.00 (s, 2H).

Part C. Preparation of N-(3-Cyanophenyl)-N-nitrosoglycine.

Sodium nitrite (5.54 g, 80.3 mmol) in 15 mL of water was added to a suspension of N-(3-cyanophenyl)glycine (14.15 g, 80.3 mmol) in 65 mL of water under N$_2$. This was allowed to stir at room temperature for 14 hours. The solution was acidified with concentrated hydrochloric acid to pH 3 and a precipitate formed. The solid was collected, washed with 50 mL water and then dried in vacuo to give 16.06 g (98%) of the desired compound as a grey solid. $^1$HNMR (CDCl$_3$) δ: 13.22 (br s, 1H); 8.10 (dd, 1H); 7.99 (ddd, 1H); 7.87 (dd, 1H), 7.72 (t, 1H), 4.78 (s, 2H).

Part D. Preparation of 1-(3-Cyanophenyl)-4-oxy-1,2,3-oxadiazole.

N-(3-cyanophenyl)-N-nitrosoglycine (6.97 g, 34 mmol) was dissolved in 32 mL of acetic anhydride and heated to 70° C. for 5 hours. The reaction mixture was cooled and then poured into 200 mL of ice-water. After stirring for 30 minutes to decompose the excess acetic anhydride, the reaction mixture was filter to provide 5.99 g (94%) of a white solid. $^1$HNMR (CDCl$_3$) δ: 8.08 (s, 1H), 8.02 (d, J=8.4, 1H), 7.99 (d, J=7.7, 1H), 7.82 (dd, J=8.4, 7.7, 1H), 6.81 (s, 1H).

Part E. Preparation of 1-(3-Cyanophenyl)-4-oxy-5-methylthio-1,2,3-oxadiazole.

1-(3-cyanophenyl)-4-oxy-1,2,3-oxadiazole (1.48 g, 7.9 mmol) was dissolved in 30 mL of dry DMSO and cooled to 0° C. Acetyl chloride (1.25 g, 15.9 mmol) was added very slowly via syringe below the surface of the liquid under N$_2$. The reaction mixture was allowed to stir at room temperature for 14 hours. The reaction mixture was diluted with 100 mL Et$_2$O and washed twice with 25 mL saturated aqueous NaHCO$_3$. Then washed three times with 25 mL water to remove the DMSO. The organic extract was dried with MgSO$_4$ and concentrated in vacuo to give 1.5 g of a red solid which was used without further purification. MS (NH$_3$—CI) m/z 234.0 (M+H).

Part F. Preparation of Methyl 1-(3-Cyanophenyl)-3-methylthio-pyrazole-5-carboxylate.

The crude 1-(3-cyanophenyl)-4-oxy-5-methylthio-1,2,3-oxadiazole (0.95 g, 3.90 mmol) and methyl propriolate (3.28 g, 39.1 mmol) were dissolved in 40 mL of CH$_2$Cl$_2$ and the quartz reaction vessel was purged with N$_2$. The reaction mixture was irradiated in a Rayonet RPR-100 photochemical reactor for 14 hours. The crude product was concentrated in vacuo and then chromatographed with 20% EtOAc/hexanes on silica to provide 0.34 g (32%) of a yellow solid. $^1$HNMR (CDCl$_3$) δ: 7.77 (t, J=1.8, 1H); 7.70 (m, 2H); 7.57 (t, J=8.1, 1H); 6.94 (s, 1H 3.83 (s, 3H); 2.57 (s, 3H).

Part G. Preparation of 1-(3-Cyanophenyl)-5-[(2'-t-butylaminosulfonyl-[1,1']-biphen-4-yl)aminocarbonyl]-3-(thiomethyl)pyrazole.

4-Amino-2'-methylsulfonyl-[1,1']-biphenyl (65.7 mg, 0.216 mmol) was suspended in 2 mL of CH$_2$Cl$_2$ and 0.51 mL of a 2M solution of trimethylaluminum in heptane was added slowly via syringe. The reaction was stirred for 30 minutes at room temperature and methyl 1-(3-cyanophenyl)-3-methylthio-pyrazole-5-carboxylate (56.2 mg, 0.206 mmol) was added. The reaction mixture was stirred at room temperature for an additional 14 hours. The aluminum reagent was quenched by careful addition of 1N HCl to pH 2. Then the reaction mixture extracted with 10 mL of CH$_2$Cl$_2$ three times. The combined organic extracts were washed with water and brine, dried over MgSO$_4$ and the solvent evaporated. The desired product was obtained (83 mg, 74%) after silica gel chromatography with 30% EtOAc/hexane. $^1$HNMR (CDCl$_3$) δ: 8.16 (dd, J=7.7, 1.5, 1H); 7.84 (br s, 1H); 7.84 (t, J=1.8, 1H); 7.76 (m, 1H); 7.70–7.46 (m, 8H); 7.50 (d, J=8.8, 2H); 7.25 (d, J=7.5, 1H); 6.81 (s, 1H); 2.62 (s, 3H).

Part H. Preparation of 1-(3-Amidinophenyl)-5-[(2'-aminosulfonyl-[1,1']-biphen-4-yl)aminocarbonyl]-3-(methylthio)pyrazole, Trifluoroacetic Acid Salt.

1-(3-Cyanophenyl)-5-[(2'-t-butylaminosulfonyl-[1,1']-biphen-4-yl)aminocarbonyl]-3-(thiomethyl)pyrazole (83 mg, 0.15 mmol) was dissolved in 5 mL of methanol and 10 mL of chloroform. The reaction mixture was cooled in an ice bath and HCl gas was bubbled in for 30 minutes to saturate the solution. The mixture was sealed and allowed to stir at room temperature for 14 hours. The solvents were removed in vacuo. and the resulting solid was used in the next step.

The imidate formed above was added to 0.15 g (1.6 mmol) of ammonium carbonate and 10 mL of methanol. The mixture was allowed to stir under N$_2$ for 14 hours. The solvent was removed at reduced pressure. The crude benzamidine was purified by HPLC (C18 reversed phase) eluting with 0.5% TFA in H$_2$O/CH$_3$CN to give 64 mg (84%) of the desired salt. $^1$HNMR (DMSO-d$_6$) δ: 10.66 (s, 1H); 9.41 (br s, 2H); 8.97 (br s, 2H); 7.96 (m, 2H); 7.79–7.66 (m, 7H); 7.63 (d, J=9.0, 2H); 7.56 (t, J=6.6, 1H); 7.33 (d, J=9.0, 2H); 7.27 (m, 1H); 7.19 (s, 1H); 2.55 (s, 3H). HRMS 507.1268 (M+H).

Examples 154 and 155

1-(3-Amidinophenyl)-5-[(2'-aminosulfonyl-[1,1']-biphen-4-yl)aminocarbonyl]-3-(methylsulfinyl) pyrazole, Trifluoroacetic Acid Salt (Example 154) and 1-(3-Amidinophenyl)-5-[(2'-aminosulfonyl-[1,1']-biphen-4-yl)aminocarbonyl]-3-(methylsulfonyl) pyrazole, Trifluoroacetic Acid Salt (Example 155)

To a solution of 1-(3-amidinophenyl)-5-[(2'-aminosulfonyl-[1,1']-biphen-4-yl)aminocarbonyl]-3-(methylthio)pyrazole, trifluoroacetic acid salt (54 mg, 0.11 mmol) in 10 mL methanol was added Oxone® (66 mg, 0.11 mol) and the reaction stirred for 14 hours. The solvent was removed at reduced pressure. The crude sulfoxide was purified by HPLC (C18 reversed phase) eluting with 0.5% TFA in $H_2O/CH_3CN$ to give 22 mg (38%) of the desired salt. $^1$HNMR (DMSO-$d_6$) δ: 10.84 (s, 1H); 9.43 (br s, 2H); 9.00 (br s, 2H); 8.00 (s, 1H); 7.99 (m, 1H); 7.87 (m, 2H); 7.75 (m, 2H), 7.65 (d, J=9.6, 2H); 7.56 (m, 2H); 7.34 (d, J=8.4, 2H); 7.27 (m, 3H); 2.99 (s, 3H). HRMS 523.1220 (M+H). Another product, the sulfone, (28 mg, 47%), was isolated from the column. $^1$HNMR (DMSO-$d_6$) δ: 10.89 (s, 1H); 9.52 (br s, 2H); 9.09 (br s, 2H); 8.09 (s, 1H); 8.06 (d, J=7.3, 1H1); 7.98 (m, 2H); 7.86 (s, 1H), 7.84 (t, J=9.0, 1H), 7.72 (d, J=8.8, 2H); 7.64 (m, 2H); 7.41 (d, J=8.4, 2H); 7.33 (m, 3H); 3.45 (s, 3H). HRMS 539.1175 (M+H).

Example 156

1-(3-Aminocarbonylphenyl)-5-[(2'-trifluoromethyl-[1,1']-biphen-4-yl)methyl]tetrazole The title compound was prepared via the method described previously. $^1$HNMR (DMSO-d6) δ: 5.85 (s, 2H); 7.10 to 8.25 (m, 12H). MS (ESI) 424.14 (M+H)$^+$.

Example 157

1-(3-Aminocarbonylphenyl)-5-{[(2'-aminosulfonyl-[1,1']-biphen-4-yl)methyl}tetrazole The title-compound was prepared via the method described previously. $^1$HNMR (DMSO-d6) δ: 5.85 (s, 2H); 7.15 to 8.25 (m, 12H). MS (ESI) 435.12 (M+H)$^+$.

Example 158

1-(3-Amidinophenyl)-5-[(4'-cyclopentyloxyphenyl) aminocarbonyl]-3-methyl-pyrazole, Trifluoroacetic Acid Salt Part A: Standard coupling protocol of 4-Cyclopenyloxy-aniline (obtained by the displacement of 4-fluoronitrobenzene with the anion of cyclopentanol, followed by catalytic (10% Pd/C) reduction in methanol) with the acid chloride derived for N1-(3-cyanophenyl)-3-methyl-pyrazole-5-carboxylic acid afforded the amide precursor as a pale yellow oil; $^1$HNMR (CDCl$_3$) δ: 7.79 (bs, 1H), 7.75–7.50 (m, 7H), 6.95 (d, 1H), 6.85 (m, 1H), 4.75 (m, 1H), 1.95–1.70 (m, 6H), 1.60 (bm, 2H), 2.30 (m, 3H) ppm; ESI mass spectrum m/z (rel intensity) 387 (M+H, 100).
Part B: The title compound was obtained as colorless crystals after purification (via standard techniques) following the standard Pinner/amidine reaction sequence. $^1$HNMR (DMSO, $d_6$) δ: 10.39 (s, 1H), 9.42 (bs, 2H), 9.05 (bs, 2H), 7.94 (s, 1H), 7.82–7.68 (cp, 3H), 7.71 (d, 2H), 6.97 (s, 1H), 6.88 (d, 2H), 4.77 (m, 1H), 2.33 (s, 3H), 1.84–1.59 (cp, 8H) ppm; ESI mass spectrum m/z (rel intensity) 404.2 (M+H, 100).

Example 159

1-(3-Amidinophenyl)-5-[(3-((pyrid-2-yl)methylamino)phenyl) aminocarbonyl]-3-methyl-pyrazole, Trifluoroacetic Acid Salt Part A: Standard coupling of 3-((pyrid-2-yl)methylamino) aniline [obtained in a two step sequence (condensation and reduction) from 3-nitroaniline and 2-pyridylcarboxaldehyde afforded the desired bis aniline derivative; $^1$HNMR (CDCl$_3$) δ: 8.58 (d, J=5.13, 1H); 7.67 (t, J=7.69, 1H); 7.35 (d, J =7.69, 1H); 7.19 (m, 1H); 6.99 (t, J=7.69, 8.06, 1H); 6.14 (m, 2H); 6.01 (m, 1H); 4.66 (brd, 1H); 4.44 (s, 2H); 3.56 (brd, 2H) ppm; Mass spectrum analysis (NH3—CI) 200 (M+H, 100)].

With the acid chloride derived from 1-(3-cyanophenyl)-3-methyl-pyrazole-5-carboxylic acid afforded the coupled benzonitrile precursor which was then subjected to the standard Pinner amidine reaction sequence to afford the desired benzamidine compound as colorless crystals; $^1$HNMR (DMSO) δ: 10.28 (s, 1H); 9.42 (s,2H); 9.08 (s, 2H): 8.58 (d, J=4.39, 1H): 7.83 (m, 3H); 7.72 (m, 2H); 7.46 (d, J=8.06, 1H); 7.40 (t, J=5.49, 6.59, 1H); 7.01 (m, 3H); 6.88 (d, J=8.05, 1H); 6.34 (d, J=8.06, 1H ); 4.39 (S, 2H): 2.31 (s, 3H) ppm; ESI mass spectrum analysis m/z (rel intensity) 426.1 (M+H, 100); HRMS for $C_{24}H_{24}N_7O$ 426.204234 (calcd.), 426.201998 (obs).

Example 160

1-(3-Amidinophenyl)-3-methyl-5-[(4'-(N-imidazolyl)phenyl)aminocarbonyl]pyrazole

Part A. Preparation of N-(4-Nitrophenyl)imidazole.

4-Imidazolo-nitrobenzene (5 g) was hydrogenated (10% Pd/C) in 200 mL methanol for 20 h. the reaction mixture was filtered through a celite pad and evaporated the solvent to afford 3.99 g of the crude product which was used directly in the next step. Mass spectrum analysis ($H_2O$–GC/MS): 160 (M+H, 100).

Part B. Preparation of 1-(3-Cyanophenyl)-3-methyl-5-[(4'-(N-imidazolyl)phenyl)aminocarbonyl]pyrazole.

The product from part A was then coupled to 1-(3-cyanophenyl)-3-methylpyrazole-5-carboxylic acid via the acid chloride methodology described previously to afford the desired amide which was then purified via standard reverse phase HPLC techniques to afford the desired material. $^1$HNMR (DMSO-d6, 300 MHz) δ: 10.73 (s, 1H) 9.35 (bs, 1H) 8.13 (s, 1H) 7.95 (s, 1H) 7.90–7.60 (complex, 8H) 7.0 (s, 1H) 2.30 (s, 3H) ppm; ESI mass spectrum analysis m/z (rel. intensity) 369 (m+H, 100); HRMS calc. mass 369.146384; found 369.145884.

Part C. Preparation of 1-(3-Amidinophenyl)-3-methyl-5-[(4'-(N-imidazolyl)phenyl)aminocarbonyl]pyrazole.

The product from part B was then subjected to the standard Pinner amidine reaction sequence to afford the desired benzamidine after HPLC purification. $^1$HNMR (DMSO-d6, 300 Mhz) δ: 10.65 (s, 1H) 9.40 (bs, 2H) 9.00 (bs, 2H) 8.19 (s, 1H) 7.90 (s, 1H) 7.80–7.55 (complex, 8H) 7.06 (s, 1H) 7.00 (s, 1H) 2.30 (s, 3H) ppm; ESI mass spectrum analysis m/z (rel. intensity) 386 (M+H, 100). HRMS (FAB), calc. mass 386.172933; found 386.173388.

Example 161

1-(3-Amidinophenyl)-3-trifluoromethyl-5-[(4'-(N-morpholino)-3-chlorophenyl)aminocarbonyl]pyrazole Part A. Preparation of 1-(3-Cyanophenyl)-3-trifluoromethyl-5-[(4'-(N-morpholino)-3-chlorophenylaminocarbonyl]pyrazole.

Standard coupling of commercially available 2-chloro-4-morpholinoaniline with N-(3-cyanophenyl)-3-trifluoromethyl-pyrazole-5-carboxylic acid via its acid chloride under usual conditions afforded the desired coupled product. $^1$HNMR (DMSO-d6, 300 MHz) δ: 10.66 (s, 1H), 8.12 (s, 1H), 7.97 (d, 1H), 7.87 (d, 1H), 7.70 (complex, 3H), 7.50 (dd, 1H), 7.14 (d, 2H), 3.70 (m, 4H), 2.90 (m, 4H) ppm; ESI mass spectrum analysis m/z (rel. intensity) 476 (M+H, 100).

Part B: Preparation of 1-(3-Amidinophenyl)-3-trifluoromethyl-5-((4'-N-morpholino)-3-chlorophenyl)aminocarbonyl)pyrazole.

The cyano compound from part A was converted to the amidino derivative via the amidoxime as previously described. The amidoxime was reduced to the title compound (acetic acid/acetic anhydride and catalytic reduction of the acetate with 10% palladium on carbon under a hydrogen atmosphere) as previously described. The crude product was purified by standard HPLC technique to afford the desired compound as its bis TFA salt. $^1$HNMR (DMSO-d6, 300 MHz) δ: 10.73 (s, 1H) 9.41 (bs, 2H) 9.09 (bs, 2H) 7.98 (s, 1H) 7.89 (m, 2H) 7.73 (complex, 3H) 7.50 (d, 1H) 7.14 (d, 1H) 3.69 (complex, 4H) 2.89 (complex, 4H) ppm; ESI mass spectrum analysis m/z (rel. intensity) 493 (M+H, 100); HRMS(FAB+): calc-493.136662, obs. 493.136951.

Example 162

1-(3-Amidinophenyl)-3-methyl-5-[(4'-(N-pyrrolidinocarbonyl)-3'-chlorophenyl)aminocarbonyl]pyrazole Part A: Preparation of 4'-Pyrrolidinocarbonyl-3-chloronitrobenzene.

To a dichloromethane solution of 4-nitro-3-chlorobenzoic acid (1.61 g) was added N-methylmorpholine (1.93 mL) and isobutylchloroformate (1.04 mL) followed by the addition of pyrrolidine (0.67 mL) and the reaction mixture was warmed to ambient temperature. Concentration of the reaction mixture followed by aqueous workup and extraction with ethylacetate afforded crude product which was used directly into the next reaction. LRMS(NH3—CI): 255 (m+H).

Part B. Preparation of 4'-(Pyrrolidinocarbonyl)-3-chloroaniline.

The crude 4'-(pyrrolidinocarbonyl)-3-chloronitrobenzene was treated with a catalytic amount 10% palladium on carbon in 20 mL methanol and placed under 10 psi hydrogen for 15 h. Passed through a 1" Celite pad and concentrated filtrate. The residue was washed with ethyl acetate and 3×20 mL portions 1.0M HCl, dried (magnesium sulfate) and concentrated in vacuo. Recrystallized from methylene chloride/methanol to afford 1.80 g of crystalline 4'-carboxamidopyrrolindino-3-chloroaniline. $^1$HNMR (DMSO-d6, 300MHz) δ: 6.94 (d, 1H, J=8.42), 6.55 (d, 1d, J=1.83), 6.47 (dd, 1d, J=8.43, J=7.69), 3.36 (t, 2H, J=6.23, J=6.95), 3.09 (t, 2H, J=6.22, J=6.23, 1.78 (m, 4H) ppm; Mass spectrum analysis (NH3—CI): 225 (m+H, 100).

Part C. Preparation of 1-(3-Cyanophenyl)-3-methyl-5-[(4'-(pyrrolidinocarbonyl)-3-chlorophenyl)]aminocarbonyl)pyrazole.

Standard coupling of the product from part B with the acid chloride derived from 1-(3-cyanophenyl)-3-methyl-pyrazole 5-carboxylic acid chloride afforded the desired coupled product. HNMR (DMSO-d6, 300MHz) δ: 10.71 (s, 1H), 7.97 (d, 1H), 7.84 (m, 2H), 7.76 (m, 1H), 7.63 (m, 2H), 7.32 (d, 1H), 7.00 (s, 1H), 3.42 (t, 2H), 3.06 (t, 2H), 2.29 (s, 3H), 1.80 (m, 4H) ppm; ESI mass spectrum analysis m/z (rel. intensity) 434. (M+Na, 100).

Part D. Preparation of 1-(3-Amidinophenyl)-3-methyl-5-[(4'-pyrrolidinocarbonyl)-3-chlorophenyl)aminocarbonyl]pyrazole.

The benzonitrile product from part C was then converted to the desired benzamidine via standard conditions described previously. Purification via reverse phase HPLC afforded the title compound as its trifluoro-acetate salt. $^1$HNMR (DMSO-d6, 300 MHz) δ: 10.73 (s, 1H), 9.38 (s, 2H), 9.04 (s, 2H), 7.91 (s, 1H), 7.85 (s, 1H), 7.79 (d, 1H), 7.74 (d, 1H), 7.67 (d, 1H), 7.62 (m, 1d), 7.02 (s, 1H), 3.41 (t, 2H), 3.06 (t, 2H), 2.30 (s, 3H), 1.82 (m, 4H) ppm; ESI mass spectrum analysis m/z (rel. intensity) 451 (M+H, 100). HRMS(CI): obs. 451.164788 calc. 451.164927.

Example 163

1-(3-Aminophenyl)-3-methyl-5-[(4'-(N-morpholinocarbonyl)-3-chlorophenyl)aminocarbonyl]pyrazole Part A. Preparation of 4-(N-Morpholinocarbonyl)-3-chloronitrobenzene.

To a dichloromethane solution of 4-nitrobenzoyl chloride (2.41 g) was added morpholine (3.40 mL) in 75 mL methylene chloride at 0° C. The reaction mixture was warmed to ambient temperature over 20 h, then diluted with water (100 mL). The organic layer was separated, washed with water (50 mL), 1.0M HCl (50 mL), dried (magnesium sulfate) and concentrated in vacuo. The crude material was used directly into the next step without further purification. Mass spectrum analysis (NH3—CI): 237 (m+H, 100). The product obtained above was then subjected to catalytic reduction (10% palladium on carbon in 60 mL methanol and placed under 60 psi hydrogen for 3 h), filtered through a celite pad and evaporated to afford the desired aniline derivative. $^1$HNMR (DMSO-d6; 300 MHz) δ: 7.09 (d, 2H), 6.50 (d, 2H), 3.54 (t, 4H), 3.44 (t, 4H), 3.29 (S, 2) ppm; Mass. spectrum analysis (NH3—CI): 207 (m+H, 100).

Part B. Preparation of 1-(3-Cyanophenyl)-3-methyl-5-[4'-(N-morpholinocarbonyl)-3-chlorophenyl)aminocarbonyl]pyrazole.

Standard coupling of the product from part A with the acid chloride derived from N-(3-cyanophenyl)-3-methylpyrazole-5-carboxylic acid followed by usual workup afforded the desired product after silica gel column chromatography (oil); $^1$HNMR (DMSO-d6, 300 MHz) δ: 10.63 (s, 1H), 7.94 (s, 1H), 7.83 (d, 1d, J=7.69), 7.75 (dd, 1d, J=8.06, J=8.06), 7.70 (d, 2H, J=8.42), 7.63 (t, 1H, J=7.69, J=8.05), 7.37 (d, 2H, J=8.06), 6.98 (s, 1H), 3.28 (d, 8H, J=6.96), 2.28 (s, 3H); ESI mass spectrum analysis m/z (rel. intensity) 438 (M+Na), 416 (M+H, 100).

Part C. Preparation of 1-(3-Amidinophenyl)-3-methyl-5-[(4'-(N-morpholinocarbonyl)phenyl)aminocarbonyl]pyrazole.

Standard conversion of the product from part B to the benzamidine afforded after purification via reverse phase HPLC the desired product. $^1$HNMR (DMSO-d6, 300 MHz) δ: 10.66 (s, 1H), 9.38 (bs, 2H), 9.04 (bs, 2H), 7.90 (d, 1d, J=9.52), 7.78 (d, 1d, J=7.33), 7.73–7.62 (complex, 4H), 7.37 (d, 2H, J=8.42,) 7.00 (s, 1H), 3.55–3.46 (complex, 8H), 2.30 (s, 3H). ESI mass spectrum analysis m/z (rel. intensity) 433 (M+H, 100); HRMS obs. 433.199045; calc. 433.198814.

Example 164

1-(3-Cyanophenyl)-5-[(4"-(N-Imidazolyl)phenyl)aminocarbonyl]-3-trifluoromethylpyrazole, Trifluoroacetic Acid 1-(3-Cyanophenyl)-3-trifluoromethyl-pyrazol-5-yl carboxylic acid (0.5 g, 1.8 mmol) was coupled with 4-imidazoyl aniline (0.3 g,1.8 mmol) by standard conditions and purified by HPLC to afford 0.67 g (71%) product. $^1$HNMR (DMSO-d$_6$) δ: 10.99 (s, 1H), 9.55 (s, 1H), 8.22 (d, j=5.49 Hz, 2H), 8.04 (d, j=7.69 Hz, 1H), 7.96 (d, j=8.06 Hz, 1H), 7.89 (s+d, j=8.79 Hz, 3H), 7.80 (m, 4H) ppm; HRMS 423.118119 (calc'd), 423.116015 (obs.); Analysis calc'd for C$_{21}$H$_{13}$F$_3$N$_6$O (TFA): C: 51.50, H: 2.63, N: 15.67, found C: 51.52, H: 2.71, N: 15.49.

Example 165

1-(3-Amidinophenyl)-5-[(4'-(N-imidazolyl)phenyl) aminocarbonyl]-3-trifluoromethylpyrazole, Trifluoroacetic Acid 1-(3-Cyanophenyl)-5-[(4'-imidazol-1-ylphenyl) aminocarbonyl]-3-trifluoromethylpyrazole was subjected to standard Pinner amidine reaction sequence and purified under standard conditions to afford title amidine (79%). $^1$HNMR (DMSO-d$_6$) δ: 11.02 (s, 1H), 9.46 (s, 1.5H), 9.42 (s. 1H), 9.22 (s, 1.5H), 8.17 (s, 1H), 8.06 (s, 1H), 7.97 (t, j=7.69 Hz, 2H), 7.88 (d, j=8.79 Hz, 2H), 7.80 (m, 3H), 7.79 (d,j=9.0 Hz, 2H) ppm; HRMS 440.144668 (calc'd), 440.144557 (obs.); Analysis calc'd for C$_{21}$H$_{16}$F$_3$N$_7$O (TFA)2 (H$_2$O)1: C: 43.81, H: 2.94, N: 14.30, found C: 43.76, H: 2.70, N: 13.95.

Example 166

1-(3-Amidinophenl)-5-[(4'-(N-methyltetrazolon-1-yl)phenyl)aminocarbonyl]-3-trifluoromethylpyrazole, Trifluoroacetic Acid Part A. 4-Nitrobenzoic acid was converted to the 4-nitrophenyltetrazolone according to the procedure of Toselli, M. and Zaneratio, P., *J.C.S. Perk. Trans.* 1992, 1, 1101. $^1$HNMR (DMSO-d$_6$) δ: 8.46 (d, j=9.15 Hz, 2H), 8.22 (d, j=9.16 Hz, 2H).

Part B. To 4-nitrophenyltetrazolone (0.8 g, 3.9 mmol) in DMF (10 mL) at 0° C. was added iodomethane (0.38 mL) and 60% sodium hydride (0.23 g). The reaction was allowed to warm to ambient temperature and stirred 24 h. The reaction was quenched with water and extracted with ethyl acetate and dried (MgSO$_4$). The crude product was purified by chromatogaphy on silica gel and recyrstallized from methylene chloride/hexanes to afford 0.35 g (41%) product, MS (DCI) m/z 192 (M+H–NO)$^+$, 209 (M+NH$_4$–NO)$^+$.

Part C. The nitro compound (0.215 g, 0.97 mmol) from part B was hydrogenated under 1 atmosphere of hydrogen in the presence of a catallytic amount of 10% palladium on carbon to the aniline, Mass spectrum analysis (DCI) m/z 192 (M+H)$^+$, 209 (M+NH4)$^+$.

Part D. 1-(3-Cyanophenyl)-3-trifluoromethyl-pyrazol-5-yl carboxylic acid (0.38 g, 1.4 mmol) was coupled with the aniline from part C by standard procedure to afford the nitrile in 43% yield. $^1$HNMR (CDCl$_3$) δ: 8.04 (s, 1H), 7.95 (d, j=9.16 Hz, 2H), 7.85 (s, 1H), 7.79 (m, 2H), 7.67 (m, 3H), 7.21 (s, 1H), 3.71 (s, 3H) ppm; MS (ESI) m/z=454.9 (M+H)$^+$, 477 (M+Na)$^+$.

Part E. The nitrile from part D was subjected to the standard Pinner conditions to afford the title amidine in 53% yield. $^1$HNMR (DMSO-d$_6$) δ: 10.93 (s, 1H), 9.46 (s, 1.5H), 9.12 (s, 1.5H), 8.04 (s, 1H), 7.95 (d, j=7.69 Hz, 2H), 7.84 (s, 4H), 7.81 (m, 2H), 3.61 (s, 3H) ppm; HRMS 472.145731 (calc'd), 472.145205 (obs.); Analysis calcd for C$_{20}$H$_{16}$F$_3$N$_9$O$_2$ (TFA) 1.2: C: 44.23, H: 2.85, N: 20.73, found C: 44.40, H: 2.85, N: 20.15.

Example 167

1-(3'-Aminocarbonylphenyl)-5-[(2'-aminosulfonylphenyl-[1,1']-biphen-4-yl) methylcarbonyl]-3-methyl-pyrazole The title amide was isolated from the Pinner reaction via HPLC separation protocols. $^1$HNMR (DMSO-d$_6$) δ: 10.63 (s, 1H), 8.06 (s, 1H), 8.03 (dd, j=2.19, 7.32 Hz, 1H), 7.87 (s, 1H), 7.61 (m, 2H), 7.53 (m+d, j=7.33 Hz, 3H), 7.44–7.26 (m, 6H), 7.21 (s, 2H), 4.33 (s, 2H), 2.33 (s, 3H) ppm; ESI mass spectrum analysis m/z (rel. intensity) 497 (M+Na, 100) 433 (M+H).

Example 168

1-(3-Amidinophenyl)-5-[4'-(pyrrolidinomethyl) phenyl)aminocarbonyl]-3-methyl-pyrazole, Trifluoroacetic Acid Salt Standard coupling of 4-(pyrrolidinomethyl)aniline with the acid chloride derived from 1-(3-cyanophenyl)-3-methyl-pyrazole-5-carboxylic acid afforded the coupled benzonitrile precursor which was then subjected to the standard Pinner amidine reaction sequence to afford after purification the title compound as colorless crystals; $^1$HNMR (DMSO) δ: 10.69 (s, 1H); 9.42 (s, 2H); 9.20 (s, 2H); 7.96 (s, 1H); 7.84 (m, 1H); 7.75–7.68 (m, 4H); 7.48 (d, 2H, J=8.79); 7.04 (s, 1H); 4.31 (m, 2H); 3.35 (brd, 2H); 3.05 (brd, 2H); 2.34 (S, 3H); 2.05 (brd, 2H); 1.85 (brd, 2H) ppm; ESI mass spectrum m/z (rel. intensity) 403 (M+H, 100); HRMS found for C$_{23}$H$_{27}$N$_6$O 403.224635 (calcd), 403.222719 (obs).

Example 169

1-(3-Aminophenyl)-3-methyl-5-[(2'-aminosulfonyl-[1,1]-biphen-4-yl)aminocarbonyl]pyrazole Part A: To commercially available 3-nitrophenylhydrazine hydrochloride (1.00 g, 5.27 mmol) in 15 mL of absolute ethanol was added 1,1,1-trichloro-4-methoxy-3-penten-2-one (1.15 g, 5.27 mmol) and the reaction brought to reflux for 12 h. The solvent was evaporated and the residue subjected to silica gel flash chromatography eluting with 20% ethyl acetate in hexanes. The first fraction to elute was the desired ethyl (3-nitrophenyl)-3-methyl-5-pyrazole carboxylate. MS (ES+) 276.1 (M+H)$^+$ (100%). The ester (110 mg, 0.400 mmol) was coupled with (2'-tert-butylaminosulfonyl-[1,1']-biphen-4-yl)amine (122 mg, 0.400 mmol) using Weinreb's trimethylaluminium procedure. After preparative TLC (eluent 50% ethyl acetate/hexanes) 178.2 mg (83% yield) of 1-(3-nitrophenyl)-3-methyl-5-[(2'-tert-butylaminosulfonyl-[1,1']-biphen-4-yl) aminocarbonyl]pyrazole was isolated as a colorless solid. MS (ES+) 551.24 (M+NH$_4$)$^+$ (30%); 556.18 (M+Na)$^+$ (100%).

Part B: The product from part 170.5 mg (0.320 mmol) was refluxed in 5 mL of trifluoroacetic acid for 12 h. Preparative TLC (eluent 10% methanol/chloroform) afforded 1-(3-nitrophenyl)-3-methyl-5-[(2'-butylaminosulfonyl-[1,1']-biphen-4-yl)aminocarbonyl]pyrazole as a colorless solid. MS (ES+) 478.23 (M+H)$^+$ (30%); 500.21 (M+Na)$^+$ (100%). HRMS (FAB+)(M+H)$^+$: calc. 478.118516; found 478.117673.

Part C: The product from part B 64.3 mg (0.135 mmol) was subjected to catalytic hydrogenation (5% Pd/C in ethanol under 1 atm of hydrogen) to afford the title compound as a colorless solid. $^1$HNMR (CD$_3$OD) δ: 8.08 (d, J=7.7 Hz, 1H), 7.61–7.30 (m, 8H), 7.13 (t, J=7.7 Hz, 1H), 6.72 (m, 3H), 2.33 (s, 3H). MS (ESI+): 448.11 (M+H)$^+$ (35%); 470.16 (M+Na)$^+$ (100%). HRMS (FAB+)(M+H)$^+$: calc. 448.144337; found 448.144965.

Example 170

1-(2'-Aminophenyl)-3-methyl-5-[(2'-aminosulfonyl-[1,1']-biphen-4-yl)aminocarbonyl]pyrazole The title compound was made in a similar manner to Example 169. $^1$HNMR (CD$_3$OD) δ: 8.14–8.03 (m, 2H), 7.58–6.74 (m, 11H), 2.47 (s, 3H). MS (ES+) 448.12 (M+H)+ (60%); 470.16 (M+Na)+ (100%).

Example 171

1-(3-Amino-4'-chlorophenyl)-3-methyl-5-[(2'-aminosulfonyl-[1,1']-biphen-4-yl)aminocarbonyl]pyrazole The title compound was made in a similar manner to Example 169. $^1$HNMR (CD$_3$OD) δ: 8.08 (d, J=6.9 Hz, 1H), 8.07–7.23 (m, 8H), 6.91 (d, J=2.2 Hz, 1H), 6.75 (s, 1H), 6.66 (dd, J=8.43, 2.56 Hz, 1H), 2.33 (s, 3H). MS (ES+) 482.0 (M+H)+ (80%); 484.0 (30%); 504.0 (M+Na)+ (100%); 506.0 (40%).

Example 172

1-(3-Amino-4'-fluorophenyl)-3-methyl-5-[(2'-aminosulfonyl-[1,1']-biphen-4-yl)aminocarbonyl]pyrazole The title compound was made in a similar manner to Example 169. $^1$HNMR (CD$_3$OD) δ: 8.14–8.03 (m, 2H), 7.58–6.74 (m, 11H), 2.47 (s, 3H). MS (ES+) 466.0 (M+H)+ (5%); 488.0 (M+Na)+ (100%).

Example 173

1-(3-Amino-4'-methoxyphenyl)-3-methyl-5-[(2'-aminosulfonyl-[1,1']-biphen-4-yl)aminocarbonyl]pyrazole The title compound was made in a similar manner to Example 169. $^1$HNMR (CD$_3$OD) δ: 8.10 (d, J=6.6 Hz, 1H), 7.63–7.31 (m, 7H), 6.89–6.72 (m, 4H), 3.88 (s, 3H), 2.34 (s, 3H). MS (ES+) 478.1 (M+H)+ (25%); 500.0 (M+Na)+ (100%).

Example 174

1-(3-Amino-4'-chlorophenyl)-5-[(2'-aminosulfonyl-[1,1']-biphen-4-yl)aminocarbonyl]tetrazole, Trifluoroacetic Acid Salt Part A. Preparation of 1-(3-Nitro-4-chlorophenyl)-5-carboethoxytetrazole.

4-Chloro-3-nitroaniline (10.36 g, 60 mmol) was dissolved in CH$_2$Cl$_2$ (100 mL). Triethylamine (10 mL, 70 mmol) was added followed by ethyl oxalyl chloride (6.8 mL, 60 mmol). The mixture was stirred at room temperature under N$_2$ for 15 min. It was diluted with CH$_2$Cl$_2$ and washed with water and brine. The CH$_2$Cl$_2$ solution was dried over MgSO$_4$ and concentrated to a light yellow solid (15.53 g).

The above amide (5.5 g, 20.2 mmol) was refluxed 4 h with a solution of triphenylphosphine (7.87 g, 30 mmol) in 100 mL of CCl$_4$ (The solution was stirred at 0° C. for 15 min before the amide was added). The reaction mixture was cooled and the precipitate was filtered off. The filtrate was concentrated to a solid. It was then dissolved in 100 mL of CH$_3$CN and NaN$_3$ (1.31 g, 1 eq) was added. The mixture was stirred at room temperature under N$_2$ for 12 h. The solvent was removed. The solid was dissolved in EtOAc and washed with water and brine. It was dried over MgSO$_4$, concentrated, and chromatographed on silica gel (CH$_2$Cl$_2$) to afford 3.19 g of the desired product. $^1$HNMR (CDCl$_3$) δ: 1.35 (t, 3H); 4.42 (q, 2H); 7.50–7.70 (m, 2H); 8.10 (s, 1H). MS (DCI-NH$_3$) 315 (M+NH$_4$)+.

Part B. Preparation of 1-(3-Nitro-4-chlorophenyl)-5-[(2'-t-butylaminosulfonyl-[1,1']-biphen-4-yl)aminocarbonyl]tetrazole.

2'-t-Butylaminosulfonyl-4-amino-[1,1']-biphenyl (1.33 g, 4.37 mmol) was dissolved in 40 mL of anhydrous CH$_2$Cl$_2$, and trimethylaluminum (11 mL of 2M solution in heptane) was added slowly. The mixture was stirred at room temperature under N$_2$ for 15 min. Then, a solution of material from part A (1.30 g, 4.37 mmol) in anhydrous CH$_2$Cl$_2$ (40 mL) was added. The mixture was stirred at room temperature under N$_2$ for 18 h. The reaction mixture was quenched carefully with 1N HCl. It was diluted with CH$_2$Cl$_2$ and washed with water and brine. The organic solution was then dried over MgSO$_4$, concentrated, and chromatographed on silica gel (CH$_2$Cl$_2$) to give 1.5 g of the desired product. MS (ESI) 554.1 (M–H)+.

Part C. Preparation of 1-(3-Nitro-4-chlorophenyl)-5-[(2'-aminosulfonyl-[1,1']-biphen-4-yl)aminocarbonyl]tetrazole.

The material from Part B (1.5 g, 2.7 mmol), and trifluoroacetic acid (20 mL) was stirred at room temperature under N$_2$ overnight. The trifluoroacetic acid was removed and chromatographed on silica gel (10% EtOAc/CH$_2$Cl$_2$) to afford 0.72 g of desired product. $^1$HNMR (DMSO-d6) δ: 7.25 to 8.20 (m, 11H); 8.69 (s, 1H); 11.55 (s, 1H). MS (ESI) 497.9:499.9 (3:1) (M–H)+.

Part D. Preparation of 1-(3-Amino-4-chlorophenyl)-5-[(2'-aminosulfonyl-[1,1']-biphen-4-yl)aminocarbonyl]tetrazole, Trifluoroacetic Acid Salt.

The material from part C (0.72 g, 1.44 mmol) was dissolved in EtOAc (30 mL). SnCl$_2$2H$_2$O (2.59 g, 11.52 mmol) was added. The reaction mixture was brought to reflux for 1 h and then cooled it to the room temperature. Saturated NaHCO$_3$ was added to the mixture until the pH 8.0. The mixture was partitioned between EtOAc and NaHCO$_3$ layer. The EtOAc layer was washed with water and brine. It was dried over MgSO$_4$ and concentrated. The solid was dissolved in CH$_3$CN/TFA and purified by reversed phase HPLC to give 300 mg of the desired product. $^1$HNMR (DMSO-d6) δ: 6.80 to 8.00 (m, 11H); 11.40 (s, 1H). MS (DCI-NH$_3$) 470.0 (M+H)+.

Example 175

1-(3-Amino-4'-chlorophenyl)-5-{[(2'-aminosulfonylphenyl)pyridin-2-yl]aminocarbonyl}tetrazole, Trifluoroacetic Acid Salt The title compound was prepared via the method of Example 171. $^1$HNMR (DMSO-d6) δ: 6.80 to 8.40 (m, 10H); 11.70 (s, 1H). MS (ESI) 471.20 (M+H)+.

Example 176

1-(3-Amino-4'-methoxyphenyl)-5-[(2'-aminosulfonyl-[1,1']-biphen-4-yl)aminocarbonyl]tetrazole, Trifluoroacetic Acid Salt The title compound was prepared via the method of Example 174. $^1$HNMR (DMSO-d6) δ: 6.80 to 8.05 (m, 11H); 11.15 (s, 1H). MS (ESI) 466.0 (M+H)+.

Example 177

1-(3-Aminomethylphenyl)-5-[(2'-aminosulfonylphenyl)pyrid-2-yl)aminocarbonyl]-3-methylpyrazole, Trifluoroacetic Acid Part A: Ethyl-1-(3-cyanophenyl)-3-methyl-5-pyrazolecarboxylate (2.7 g, 10.58 mmol) was dissolved in methanol (50 mL). To this solution was added glacial acetic acid (2 mL) and 10% palladium on carbon (cat.). The reaction mixture was hydrogenated (50 psi) for 12 h, filtered over celite and evaporated to the crude benzylamine salt. Without further purification the crude amine was converted to the carbo-benzyloxy derivative by treatment with CBzCl in saturated sodium bicarbonate solution. The organics were extracted with ethyl acetate (2×100 mL) dried over magnesium sulfate and evaporated to the crude product (2.15 g obtained). The oil was then hydrolysed with LiOH (0.22 g, 5.5 mmoL) in aqueous THF for 16 h. The reaction mixture was quenched with water (500 mL) and unreacted products were extracted with ethyl acetate (2×100 mL). The aqueous layer was carefully acidified (1NHCl) followed by extraction with ethyl acetate (2×100 mL) dried (magnesium sulfate) and evaporated to pure acid (1.23 g); ESI (–ve) 362 (M–H, 100).

Part B: Standard coupling (TBTU, triethylamine in anhydrous THF) of the product from part A with 2-amino-5-(2'-tert-butylaminosulfonylphenyl)pyridine afforded the desired amide derivative which was dehydrogenated (10% Pd/C, methanol, balloon) overnight. The reaction mixture was filtered over celite and evaporated to a pale yellow oil. The desired product was obtained as colorless crystals after purification via standard reverse phase techniques; $^1$HNMR (DMSO-d$_6$) δ: 8.35 (d, 1H), 8.19 (bs, 1H), 8.00 (t, 1H), 7.78 (dd, 1H), 7.63 (t, 2H), 7.77–7.37 (m, 6H), 7.06 (s, 1H), 4.13 (m, 2H) 2.30 (s, 3H) ppm; ESI mass spectrum analysis m/z (rel intensity) 463.3 (M+H, 100).

Example 178

1-(3-Aminomethyl-4'-methylphenyl)-5-[(2'-aminosulfonyl-[1,1']-biphen-4yl)aminocarbonyl]-3-methyl-pyrazole, Trifluoroacetic Acid Salt Part A: Ethyl 1-(3-cyano-4-methylphenyl)-3-methyl-5-pyrazole-carboxylate was prepared as colorless crystals following the standard condensation (3-cyano-4-methylphenyl-hydrazine and ethyl 2-(N-(methoxy)imino)-4-oxopentanoate in acetic acid) reaction protocol discussed previously. $^1$HNMR (CDCl$_3$) δ: 7.68 (s, 1H), 7.57 (dd, 1H), 7.58 (d, 1H), 6.82 (s, 1H), 4.24 (q, 2H), 2.40 (s, 3H0, 2.37 (s, 3H), 1.27 (t, 3H) ppm; ESI mass spectrum analysis (270 (M+H, 100).

Part B: Standard Weinreb coupling protocol of the product from part A with 1-amino-2'-tert-butylaminosulfonyl-biphenyl afforded the desired coupled product. $^1$HNMR (CDCl$_3$) δ: 8.30 (bs, 1H), 8.13 (bd, 1H), 7.78–7.23 (m, 10H), 6.78 (s, 1H), 3.68 (s, 1H), 2.60 (s, 3H), 2.40 (s, 3H0, 1.01 (s, 9H) ppm; ESI mass spectrum analysis ESI mass spectrum m/z (rel intensity) 550 (M+Na, 100).

Part C: The product from part B was then hydrogenated at 50 psi in acidic methanol as previously described, then treatment with TFA (neat) and purified via standard reverse phase chromatography to afford the title compound as colorless crystals. $^1$HNMR (DMSO, d$_6$) δ: 10.6 (s, 1H), 8.14 (bs, 2H), 8.01 (d, 1H), 7.68 (d, 2H), 7.54 (m, 2H), 7.26 (m, 5H), 6.91 (s, 1H), 4.07 (bd, 2H), 2.38 (s, 3H), 2.33 (s, 3H) ppm; ESI mass spectrum m/z (rel intensity) 476 (M+H, 100).

Example 179

1-(3-Aminomethyl-4'-fluorophenyl)-5-[(2'-aminosulfonyl-[1,1']-biphen-4yl)aminocarbonyl]-3-methyl-pyrazole, Trifluoroacetic Acid Salt The title benzylamine was obtained from 3-cyano-4-fluorophenyl hydrazine via methods described previously. $^1$HNMR (DMSO, d$_6$) δ: 8.25 (bs, 3H), 8.00 (d, 1H), 7.78–7.23 (cp, 12H), 6.95 (s, 1H), 4.14 (m, 2H), 2.30 (s, 3H) ppm; ESI mass spectrum m/z (rel intensity) 480 (M+H, 100).

Example 180

1-(3-Aminomethylphenyl)-5-[(4'-(N-pyrrolidino-carbonyl)phenyl)aminocarbonyl]-3-trifluoromethylpyrazole, Trifluoroacetic Acid Part A. Preparation of 1-(3-cyanophenyl)-5-[(4'-(N-pyrrolidinocarbonyl)phenyl)aminocarbonyl]-3-trifluoromethylpyrazole.

1-(3-Cyanophenyl)-3-trifluoromethyl-pyrazol-5-yl carboxylic acid (0.5 g, 1.8 mmol) was coupled with 4-(N-pyrrolidinocarbonyl)aniline (0.3 g, 1.8 mmol) by standard conditions to afford 0.4 g (56%) of a white solid. $^1$HNMR (CDCl$_3$) δ: 9.72 (s, 1H), 7.78–7.72 (m, 4H), 7.61 (t, j=7.69 Hz, 1H), 7.23 (s, 4H), 3.67 (t, j=6.59 Hz, 2H), 3.43 (t, j=6.59 Hz, 2H), 1.98 (q, j=6.23 Hz, 2H), 1.89 (q, j=6.23 Hz, 2H) ppm; ESI mass spectrum analysis m/z (rel. intensity) 476 (M+Na, 100), 454.1 (M+H).

Part B. The nitrile from part A (0.4 g, 0.88 mmol), 10% palladium on carbon (50 mg) and ethanol (20 mL) was placed in a Parr apparatus and hydrogenated 18 h at 40 psi. The reaction was filtered and concentrated. The crude product was purified by reverse phase HPLC and freeze-dried to afford 0.38 g (76%) of the title amine. $^1$HNMR (DMSO-d$_6$) δ: 10.91 (s, 1H), 8.23 (brd s, 2H), 7.73 (m, 3H), 7.71 (d, j=8.79 Hz, 2H), 7.59 (m, 2H), 7.54 (d, j=8.42 Hz, 2H), 4.16 (d, j=5.50 Hz, 2H), 3.45 (q, j=7.32 Hz, 4H), 1.83 (brd m, 4H) ppm; Analysis calc'd for $C_{23}H_{22}F_3N_5O_2$ (TFA) 1 (H$_2$O) 0.5: C:51.73, H:4.17, N:12.06, found C:51.45, H:3.95, N:11.73.

Example 181

1-(3-Ethylcarboxyamidinophenyl)-5-[(2'-aminosulfonyl-[1,1'-biphen-4-yl)-aminocarbonyl]-3-methyl Pyrazole To 1-(3-cyanophenyl)-5-[(2'-t-butylaminosulfonyl-[1,1']-biphen-4-yl)aminocarbonyl]-3-methylpyrazole (88 mg, 0.15 mmol) in DMF (5 mL) was added ethyl chloroformate (0.017 mL, 0.17 mmol) and triethylamine (0.052 mL, 0.037 mmol) and the reaction was stirred 72 h. The mixture was diluted with ethyl acetate and washed successively with water and brine and dried (MgSO$_4$). Purification by chromatography on silica gel using 3–10% methanol/methylene chloride as eluent afforded 27 mg (33%) of the title compound. $^1$HNMR (DMSO-d$_6$) δ: 10.62 (s, 1H), 9.18 (s, 1H), 8.16 (s, 1H), 8.05 (m, 2H), 7.70 (d, 2H), 7.60 (5H, m), 7.37 (d, 2H), 7.30 (d, 1H), 7.24 (s, 2H), 6.95 (s, 1H), 4.10 (q, 2H), 2.35 (s, 3H), 1.20 (t, 3H) ppm; HRMS 547.176365 (calcd), 547.178880 (obs.).

Examples 182 and 183

1-(3-(1'-Imino-1'-(N-morpholino))methyl)phenyl)-5-[(2'-tert-butylaminosulfonyl-[1,1']-biphen-4-yl)aminocarbonyl]-3-methyl-pyrazole, Trifluoroacetic Acid Salt and 1-(3-(1'-Imino-1'-(N-morpholino))methyl)phenyl)-5-[(2'-aminosulfonyl-[1,1']-biphen-4-yl)aminocarbonyl]-3-methyl-pyrazole, Trifluoroacetic Acid Salt Part A: The morpholino amidine compound was prepared from the precursor nitrile via the standard Pinner reaction protocol, with anhydrous morpholine as the nucleophile. Standard HPLC purification then afforded the desired morpholino amidine compound as colorless crystals; $^1$HNMR (DMSO) δ: 11.39 (s, 1H); 9.67 (s, 1H); 9.27 (s, 1H); 8.62 (s, 2H); 8.09 (d, J=7.69, 1H); 7.79 (s, 1H); 7.73–7.61 (m, 5H); 7.42 (d, J=7.32, 1H); 7.30 (s, 1H); 7.08 (s, 1H); 3.81 (brd, 2H); 3.74 (brd, 2H); 3.63 (brd, 2H); 3.37 (brd, 2H); 2.31 (s, 3H); 1.04 (s, 9H) ppm; ESI mass spectrum analysis m/z (rel intensity) 603.2 (M+H, 100).

Part B: Removal of the tert-butyl group was then effected by heating the product from part A in TFA, followed by standard HPLC purification techniques afforded the desired morpholino amidine compound as colorless crystals; $^1$HNMR (DMSO) δ: 11.38 (s, 1H): 9.67 (s, 1H): 9.27 (s, 1H); 8.65 (s, 2H); 8.08 (m, 1H): 7.78 (s, 1H): 7.73–7.67 (m, 5H); 7.62 (m, 1H); 7.55 (s, 1H); 7.45 (m, 1H); 7.09 (s, 1H); 3.81 (brd, 2H); 3.74 (brd, 2H); 3.62 (brd, 2H); 3.37 (brd, 2H); 2.31 (s, 3H) ppm; ESI mass spectrum analysis m/z (rel intensity) 547.0 (M+H, 100). HRMS for $C_{26}H_{27}N_8O_4S$ 547.187599 (calcd), 547.186294 (obs).

Example 184

1-[3-[N-((5-Methyl-2-oxo-1,3-dioxol-4-yl) methoxycarbonyl)amidino]phenyl]-5-((2'-aminosulfonyl-[1,1']-biphen-4-yl) aminocarbonyl)-3-methylpyrazole Part A. To 4-hydroxymethyl-5-methyl-1,3-dioxol-2-one (0.227 g, 1.75 mmol) (Alpegiani, M. et al, *Syn. Com.* 1992, 22 (9), 1277) in chloroform (5 mL) at 0° C. was added pyridine (0.15 mL) and 4-nitrophenyl chloroformate (0.387 g, 1.9 mmol). The reaction was allowed to warm to ambient temperature and was stirred 18 h. The reaction mixture was washed with water, brine and dried ($Na_2SO_4$). The crude dioxolone was used in the next step.

Part B. To 1-(3-amidinophenyl)-5-[(2'-aminosulfonyl-[1,1']-biphen-4-yl)aminocarbonyl]-3-methylpyrazole (80 mg, 0.14 mmol) in DMF (1mL) was added the dioxolone from part A and triethylamine (0.038 mL). The reaction was stirred 18 h. The reaction was diluted with ethyl acetate and washed with water and dried ($MgSO_4$). Purification by chromatography on silica gel using 3–5% methanol in methylene chloride afforded 47 mg (55%) of the title dioxolone. $^1$HNMR (DMSO-$d_6$) δ: 10.63 (s, 1H), 8.25 (s, 1H), 8.05 (t, 2H), 7.62 (d, 2H), 7.50 (m, 5H), 7.37 (m, 4H), 7.25 (s, 2H), 6.93 (s, 1H), 4.92 (s, 2H), 2.37 (s, 3H), 2.15 (s, 3H) ppm; HRMS 631.161109 (calcd), 631.160927 (obs.).

Example 185

1-(Pyrid-2-yl)-3-methyl-5-[(3-fluoro-2'-aminosulfonyl-[1,1']-biphen-4-yl)aminocarbonyl] pyrazole The title compound was prepared by previously described methodology using 2-pyridine hydrazine.HCl. LRMS (M+H)$^+$ m/z: 452.

Example 186

1-(6-Bromopyridin-2-yl)-3-methyl-5-[(3-fluoro-2'-aminosulfonyl-[1,1']-biphen-4-yl)aminocarbonyl] pyrazole By using previously described methodology, ethyl 3-methyl-1-(pyridin-2-yl)-1H-pyrazolecarboxylate was obtained. This compound was then treated with N-bromosuccinamide according to the following procedure.

A mixture of 3-methyl-1-(pyridin-2-yl)-1H-pyrazolecarboxylic acid (7.0483 mmol, 1.63 g) and N-bromosuccinimide (2.51 g, 2.0 eq.) in carbon tetrachloride (40 mL) was stirred at ambient temperature for 18 h. The reaction mixture was filtered through celite to remove solid impurity and washed with carbon tetrachloride (30 mL). The filtrate was evaporated and purified by flash chromatography on a silica gel column (200 g) eluted with 3:1 hexane:ethyl acetate to give 0.258 g of pure 3-methyl-1-(6-bromopyridin-2-yl)-1H-pyrazolecarboxylic acid (12%).

Thereafter, following previously described procedures the acid chloride of 3-methyl-1-(6-bromopyridin-2-yl)-1H-pyrazolecarboxylic acid was coupled with 3-fluoro-4-((2-N-t-butylsulfonamido)phenyl)aniline, and t-butyl protecting group removed with refluxing trifluoroacetic acid to obtain the title compound; LRMS (M+H)$^+$ m/z: 530.

Example 187

1-(3-Amino-4-chlorophenyl)-5-[(2'-aminosulfonyl-3-chloro-[1,1']-biphen-4-yl)aminocarbonyl]tetrazole, Trifluoroacetic Acid Salt The title compound was prepared by the same method described in Example 174. $^1$HNMR (DMSO-$d_6$) δ: 10.90 (s, 1H); 8.02 (d, 1H); 7.78 (d, 1H); 7.62 (m, 2H); 7.55 (s, 1H); 7.26–7.34 (m, 5H); 7.03 (s, 1H); 6.81 (d, 1H), 5.89 (bs, 2H). High resolution mass spectrum analysis: cald 504.0412, found 504.0411.

Example 188

1-(3-Amino-4-chlorophenyl)-5-[(4'-(1-pyrrolidinocarbonyl)phenyl)aminocarbonyl] tetrazole, Trifluoroacetic Acid Salt The title compound was prepared by the same method. described in Example 174. $^1$HNMR (DMSO-$d_6$) δ: 11.26 (bs, 1H); 7.80 (t, 1H); 7.49 (d, J=11.0 Hz, 1H); 7.42 (d, J=8.4 Hz, 1H); 7.40 (d, J=8.1 Hz, 1H); 7.04 (d, J=2.6 Hz, 1H); 6.79 (dd, J=8.4 and 2.6 Hz, 1H); 3.45 (t, J=6.2 Hz, 2H), 3.40 (t, J=5.8 Hz, 2H), 1.85 (m, 4H). ESI mass spectrum analysis m/z (relative intensity): 430.0 (M+H)$^+$; 452.0, (M+Na)$^+$.

Example 189

1-(3-Aminomethylphenyl)-5-[(2'-aminosulfonyl-[1,1']-biphen-4-yl)aminocarbonyl]tetrazole, Trifluoroacetic Acid Salt 1-(3-cyanophenyl)-5-[2'-(t-butylaminosulfonyl-[1,1']-biphen-4-yl)aminocarbonyl]tetrazole prepared as shown in Part B of Example 24 (0.20 g, 0.40 mmol) was dissolved in 10 mL of EtOAC and 10 mL of EtOH. TFA (1 mL) and Palladium on carbon (10%) were added. The mixture was hydrogenated at 30 psi for 18 h. The reaction mixture was filtered through celite and washed with EtOAc. The filtrate was concentrated to a brown oil. It was dissolved in 5 mL of TFA and refluxed under $N_2$ for 30 mimutes. The solvent was removed in vacuo and the resulting material was purified by reversed phase HPLC to give 59.8 mg of the title compound with 98% purity. $^1$HNMR (DMSO-$d_6$) δ: 11.54 (s, 1H); 8.25 (bs, 3H); 8.02 (d, J=6.3 Hz, 1H); 7.84 (bs, 1H); 7.77 (t, J=5.8 Hz, 2H); 7.72 (t, J=6.9 Hz, 2H); 7.60 (m, 2H); 7.39 (d, J=8.8 Hz, 2H), 7.32 (m, 1H), 7.31 (s, 2H), 4.18 (bs, 2H). ESI mass spectrum analysis m/z (relative intensity): 450.2 (M+H, 100)$^+$.

Example 190

1-(3-Aminomethylphenyl)-5-[(2'-aminosulfonyl-3-fluoro-[1,1']-biphen-4-yl)aminocarbonyl]tetrazole, Trifluoroacetic Acid Salt The title compound was prepared by the same method described in Example 189. $^1$HNMR (DMSO-$d_6$) δ: 11.28 (s, 1H); 8.23 (bs, 3H); 7.99 (d, J=6.6 Hz, 1H); 7.80 (bs, 1H);

7.70 (m, 2H); 7.60 (m, 2H); 7.41 (s, 2H); 7.31 (d, J=9.5 Hz, 2H), 7.20 (d, J=8.1 Hz, 1H), 4.14, (m, 2H). ESI mass spectrum analysis m/z (relative intensity): 467.9, (M+H, 100)+.

Example 191

1-(3-Aminomethylphenyl)-5-[(2'-aminosulfonyl-[1,1']-biphen-4-yl)aminocarbonyl]imidazole, Trifluoroacetic Acid Salt Part A: A solution of 3-amino-benzonitrile (6.3 g, 53.4 mmol) in ethyl alcohol (50 mL) was treated with n-butyl glyoxylate (7.0 g, 53.8 mmol). After stirring for 18 h at rt, the reaction mixture was concentrated at reduced pressure. The residue was purified by flash-chromatography (hexane/ethyl acetate, 1:1) affording an imine (4.0 g, 33%) as a colorless oil. ESI mass spectrum analysis m/z (relative intensity): 232 (M+H, 100).

Part B: To the solution of the imine from part A (1.6 g, 6.9 mmol) in methyl alcohol (10 mL) was added potassium carbonate (1.9 g, 13.9 mmol) and tosylmethyl isocyanate (2.3 g, 11.8 mmol). The solution was stirred for 1 h at rt, then solvent was removed under reduced pressure. The residue was treated with the saturated sodium chloride solution and the mixture was extracted with methylene chloride. The organic extract was concentarted and triturated with methyl alcohol. The precipitate was collected and dried to afford the desired methyl 1-(3-cyanophenyl)-imidazole-5-carboxylate (1.5 g, 94%). ESI mass spectrum analysis m/z (relative intensity): 227 (M+H, 100)

Part C: A solution of (2'-tert-butylaminosulfonyl-[1,1']-biphen-4-yl)amine (3.5 mmol) in methylene chloride (3 mL) was treated dropwise with AlMe3 (2M in hexanes, 1.8 mL, 3.5 mmol). The resultant reaction mixture was stirred for 0.5 h at rt, then treated with the product from part B (0.16 g, 0.7 mmoL) and allowed to stir for 18 h. The mixture was carefully quenched with 10% HCl, extracted with methylene chloride, dried over magnesium sulfate and concentrated. Purification by flash chromatography (methanol/methylene chloride, 1:9) afforded the coupled amide compound (0.22 g, 28%). ESI mass spectrum analysis m/z (relative intensity): 500 (M+, 100). Reduction of the benzonitrile to the benzylamine followed by standard HPLC purification protocols via methods previously described afforded pure titled compound as colorless crystals. $^1$HNMR (CD$_3$OD) δ: 8.61 (bs, 1H), 8.14 (bs, 1H), 8.09 (dd, J=7.7 Hz, 1H), 7.65–7.50 (m, 12H), 7.40 (dd, J=8.8 Hz, 2H); 7.32 (dd, j=7.3 Hz, 1H), 4.91 (s, 3H) ppm. ESI mass spectrum analysis m/z (relative intensity): 448.2 (M+H, 100).

Example 192

1-(3-Aminomethylphenyl)-5-[(2'-methylsulfonylmethyl-[1,1']-biphen-4-yl)aminocarbonyl]imidazole, Trifluoroacetic Acid Salt The title compound was prepared in a similar manner to Example 197. $^1$HNMR (CD$_3$OD) δ: 8.57 (s, 1H), 8.15 (m, 2H), 7.72–7.58 (m, 12H), 7.40 (m, 3H), 4.22 (s, 2H0, 2.72 (s, 3H) ppm. ESI mass spectrum analysis m/z (relative intensity): 447 (M+H, 100).

Example 193

1-(3-Amidinophenyl)-5-[(2-aminosulfonyl[1,1']-biphen-4-yl)aminocarbonyl]imidazole, Trifluoroacetic Acid Salt The benzonitrile obtained in part C in Example 197 was subjected to the Pinner-amidine reaction protocol and further purified via methods described previously to obtain the title compound as colorless crystals. ESI mass spectrum analysis m/z (relative intensity): $^1$HNMR (CD$_3$OD) δ: 8.76 (s, 1H), 8.21 (s, 1H), 8.07 (d, J=7.7 Hz, 1H), 7.98 (d, J=8.4 Hz, 1H), 7.89 (d, J=8.4 Hz, 1H0, 7.79 (t, J=7.7 Hz, 1H), 7.59 (m, 3H), 7.50 (t, J=7.7 Hz, 1H), 7.38 (d, J=8.5 Hz, 2H), 7.30 (d, J=8.7 Hz, 1H) ppm. ESI mass spectrum analysis m/z (relative intensity) 461.2 (M+H, 100).

Example 194

1-[3-(Methylaminomethyl)phenyl]-5-[(2'-aminosulfonyl-3-fluoro-[1,1']-biphen-4-yl)aminocarbonyl]-3-methylpyrazole, Trifluoroacetic Acid Salt Part A. Preparation of Ethyl 1-[3-(N-t-butoxycarbonyl-aminomethyl)phenyl]-3-methylpyrazolecarboxylate.

To a solution of 1.52 g (5.14 mmol) of ethyl 1-[3-(aminomethyl)phenyl]-3-methylpyrazolecarboxylate hydrochloride in 10 mL of THF under N$_2$ was added 1.49 g (14.7 mmol) of triethylamine and 1.35 g (6.17 mmol) di-t-butyl dicarbonate. The mixture was allowed to stir at room temperature for 16 hours. Water (25 mL) was added and the mixture was extracted with 25 mL ether three times. The combined organic extracts were dried over MgSO$_4$ and the solvent evaporated to give the desired product (1.85 g, 74%) as a white solid. $^1$HNMR (CDCl$_3$) δ: 7.34 (m, 4H); 6.81 (s, 1H); 4.87 (b s, 1H); 4.37 (d, J=7, 2H); 4.22 (q, J=7, 2H); 2.35 (s, 3H); 1.45 (t, 9H); 1.24 (t, J=7, 3H).

Part B. Preparation of Ethyl 1-[3-(N-t-butoxycarbonyl-N-methylaminomethyl)phenyl]-3-methylpyrazolecarboxylate.

To a solution of 1.85 g (5.15 mmol) of ethyl 1-(3-(N-t-butoxycarbonylaminomethyl)phenyl]-3-methylpyrazolecarboxylate in 10 mL of THF under N$_2$ was added 0.15 g (5.88 mmol) of 95% sodium hydride. After 1 hour, the gas evolution ceased and 0.83 g (5.88 mmol) of methyl iodide was added. The mixture was allowed to stir at room temperature for 16 hours. Water (25 mL) was added and the mixture was extracted with 25 mL ether three times. The combined organic extracts were dried over MgSO$_4$ and the solvent evaporated and then chromatographed with 20% EtOAc/hexanes on silica to give the desired product (0.52 g, 27%) as a white solid. An additional 0.83 g of non-methylated starting material was also isolated. $^1$HNMR (CDCl$_3$) δ: 7.40 (m, 1H); 7.30 (m, 3H); 6.81 (s, 1H); 4.47 (b s, 2H); 4.22 (q, J=7, 2H); 2.83 (b m, 3H); 2.34 (s, 3H); 1.47 (b s, 9H); 1.23 (t, J=7, 3H).

Part C. Preparation of 1-[3-(N-t-Butoxycarbonyl-N-methylaminomethyl)phenyl]-3-methylpyrazolecarboxylic Acid.

To a solution of 0.52 g (1.39 mmol) of ethyl 1-[3-(N-t-butoxycarbonyl-N-methylaminomethyl)phenyl]-3-methylpyrazole-carboxylate in 5 mL of THF was added 1.4 mL (1.4 mmol) of 1M aqueous lithium hydroxide. The mixture was allowed to stir at room temperature for 6 hours. Water (10 mL) was added and the mixture was extracted with 25 mL ether twice. The aqueous layer was acidified with 1N HCl to pH 4 and extracted with 25 mL ether three times. The combined organic layers from the second set of extractions were dried over MgSO$_4$ and the solvent evaporated to give the desired product (0.35 g, 74%) as a white solid. $^1$HNMR (CDCl$_3$) δ: 7.38 (m, 4H); 6.87 (s, 1H); 4.46 (b s, 2H); 2.83 (b m, 3H), 2.37 (s, 3H), 1.46 (b s, 9H).

Part D. Preparation of 1-[3-(Methylaminomethyl)phenyl]-5-[(2'-aminosulfonyl-3-fluoro-[1,1']-biphen-4-yl)aminocarbonyl]-3-(methyl)pyrazolecarboxamide, Trifluoroacetic Acid Salt.

To a solution of 1-[3-(N-t-butoxycarbonyl-N-methylaminomethyl)phenyl]-3-methylpyrazolecarboxylic acid (0.176 g, 0.509 mmol) in 10 mL of CH$_2$Cl$_2$ was added 10 μL of DMF and oxalyl chloride (97 mg, 0.763 mmol). The solution was allowed to stir for 1.5 hours under Ar and then solvent was evaporated under high vacuum. The resulting solid was redissolved in 10 mL and triethylamine (0.15 g, 1.53 mmol) and 2'-(t-butylaminosulfonyl)-3-fluoro-[1,1']-biphenyl (0.172 g, 0.534 mmol) were added. After stirring for 16 hours under Ar, the reaction mixture was added to water and extracted with ethyl acetate. The solvent was evaporated and the mixture was dissolved in 5 mL of TFA. This solution was heated to 50° C. for 4 hours, cooled to room temperature and the solvent evaporated. The crude benzylamine was purified by HPLC (C18 reversed phase) eluting with 0.5% TFA in H$_2$O/CH$_3$CN to give 60 mg (19%) of the desired salt. $^1$HNMR (DMSO-d$_6$) δ: 8.75 (br s, 2H); 8.00 (m, 1H); 7.63–7.15 (m, 10H); 6.94 g (s, 1H); 4.15 (b t, J=6, 2H); 2.54 (t, J=5, 2H); 2.45 (s, 3H). ESI mass spectrum analysis m/z (relative intensity): 494.1 (M+H, 100).

Example 195

1-[3-(Methylaminomethyl)phenyl]-5-[(2'-methylsulfonyl-3-fluoro-[1,1']-biphen-4-yl)aminocarbonyl]-3-methylpyrazole, Trifluoroacetic Acid Salt To a solution of 1-[3-(N-t-butoxycarbonyl-N-methylaminomethyl)phenyl]-3-methylpyrazolecarboxylic acid (0.176 g, 0.509 mmol) in 10 mL of CH$_2$Cl$_2$ was added 10 μL of DMF and oxalyl chloride (97 mg, 0.763 mmol). The solution was allowed to stir for 1.5 hours under Ar and then solvent was evaporated under high vacuum. The resulting solid was redissolved in 10 mL and triethylamine (0.15 g, 1.53 mmol) and 2'-(methylsulfonyl)-3-fluoro-[1,1']-biphenyl (0.172 g, 0.534 mmol) were added. After stirring for 16 hours under Ar, the reaction mixture was added to water and extracted with ethyl acetate. The solvent was evaporated and the mixture was dissolved in 5 mL of TFA. This solution was heated to 50° C. for 4 hours, cooled to room temperature and the solvent evaporated. The crude benzylamine was purified by HPLC (C18 reversed phase) eluting with 0.5% TFA in H$_2$O/CH$_3$CN to give 140 mg (45%) of the desired salt. $^1$HNMR (DMSO-d$_6$) δ: 8.76 (br s, 2H); 8.06 (dd, J=8, 1, 1H); 7.77–7.61 (m, 4H); 7.52–7.31 (m, 5H); 7.19 (dd, J=8, 1.5, 1H); 6.95 (s, 1H); 4.17 (b t, J=6, 2H); 2.90 (s, 3H); 2.54 (t, J=5, 2H); 2.29 (s, 3H). ESI mass spectrum analysis m/z (relative intensity): 492.2 (M+H).

Example 196

1-(3-Aminomethylphenyl)-5-[(2'-methylsulfonyl-[1,1']-biphen-4-yl)aminocarbonyl]-4-methoxy-3-trifluoromethyl Pyrazole, Trifluoroacetic Acid Salt Part A. To 1-(3-Cyanophenyl)-4-methoxy-3-trifluoromethylpyrazole carboxylic acid (0.69 g, 2.2 mmol) was added CH$_2$Cl$_2$ (15 mL), oxalyl chloride (0.27 mL, 3.1 mmol), and three drops of DMF. The reaction was stirred for 2 h. The solvents were removed and fresh CH$_2$Cl$_2$ (15 mL), 4-bromo-aniline (0.38 g, 2.2 mmol) and DMAP (0.68 g, 5.5 mmol) were added and the reaction was stirred 18 h. Dilution with CH$_2$Cl$_2$, followed by washing successively with 1N HCl, saturated NaHCO$_3$, brine, drying (MgSO$_4$) and recrystallization with CH$_2$Cl$_2$/hexanes afforded 0.5 g (48%) pure product and 0.43 g from filtrate. $^1$HNMR (CDCl$_3$) δ: 8.90 (s, 1H), 7.79 (m, 2H), 7.72 (dd, J=1.83, 6.96 Hz, 1H), 7.63 (t, J=8.06 Hz, 1H), 7.46 (s, 4H), 4.15 (s, 3H) ppm; ESI mass spectrum analysis m/z (relative intensity): 482–484 (M+H, 100).

Part B To the bromo compound (0.4 g, 0.86 mmol) from Part A was added 2-thiomethyl phenylboronic acid (0.18 g, 1.1 mmol), 2M Na$_2$CO$_3$ (1 mL), toluene (15 mL), and ethanol (15 mL). The mixture was degassed and tetrakistriphenylphosphine palladium (0) (40 mg) was added and the reaction was heated to reflux 18 h. The reaction was cooled, filtered, concentrated, and extracted with ethyl acetate and dried (MgSO$_4$). The compound was purified by chromatography on silica gel eluting with (4:1) hexanes/ethyl acetate to afford 0.195 g (46%) yellow solid. $^1$HNMR (CDCl$_3$) δ: 8.95 (s, 1H), 7.80 (m, 3H), 7.63 (d, J=8.42 Hz, 2H), 7.61 (m, 1H), 7.44 (d, J=8.43 Hz, 2H), 7.34 (m, 2H), 7.20 (m, 2H), 4.15 (s, 3H), 2.37 (s, 3H) ppm.

Part C To the product (0.19 g, 0.37 mmol) of Part B in CH$_2$Cl$_2$ (15 mL), cooled to 0° C., m-chloroperbenzoic acid (0.33 g, 1.1 mmol) was added. The reaction warmed to ambient temperature overnight. The reaction was washed with water, sodium bisulfite solution, NaHCO$_3$ and dried (MgSO$_4$). The compound was purified by chromatography on silica gel eluting with (1:1) hexanes/ethyl acetate to afford 0.192 g (95%) yellow solid. $^1$HNMR (CDCl$_3$) δ: 9.02 (s, 1H), 8.24 (dd, J=1.46, 7.69 Hz, 1H), 7.80 (m, 3H), 7.66 (d, J=8.06 Hz, 2H), 7.65 (m, 3H); 7.49 (d, J=8.79 Hz, 2H), 7.37 (dd, J=1.46, 7.69 Hz, 1H); 4.18 (s, 3H), 2.68 (s, 3H); ESI mass spectrum analysis m/z (relative intensity): 563 (M+Na, 100).

Part D The product of Part C was hydrogenated in EtOH/TFA with 10% palladium on carbon catalyst at 50 psi for 24 h. Purification by reverse phase HPLC and freeze-drying afforded the title compound 0.16 g (69.6%), $^1$HNMR (DMSO-d$_6$) δ: 11.11 (s, 1H), 8.25 (brd s, 2H), 8.10 (d, J=8.06 Hz , 1H), 7.77 (s+d, J=8.79 Hz, 2H), 7.69 (s+d, J=7.32 Hz, 3H), 7.60 (s+m, 3H); 7.41 (m, 3H), 4.15 (brd s, 2H), 3.95 (s, 3H) 2.88 (s, 3H) ppm; HRMS 545.147037 (calc'd), 545.146284 (obs.); Elemental analysis calc'd for C$_{26}$H$_{23}$F$_3$N$_4$O$_4$S (TFA) (H$_2$O) 1.3: C: 49.31, H: 3.93, N: 8.22, found C: 49.46, H: 3.62, N: 8.09.

Example 197

1-(3-Aminomethylphenyl)-5-[(2-fluoro-4-(N-pyrrolidinocarbonyl)phenyl)aminocarbonyl]-3-trifluoromethylpyrazole, Trifluoroacetic Acid Salt Part A. To 1-(3-cyanophenyl)-3-trifluoromethylpyrazole carboxylic acid (0.29 g, 1.0 mmol) in CH$_2$Cl$_2$ (40 mL) was added oxalyl chloride (0.135 mL, 1.6 mmol) and several drops DMF. The reaction was stirred for 2 h, then concentrated. To the acid chloride was added fresh CH$_2$Cl$_2$ (40 mL), 2-fluoro-4-(N-pyrrolidinocarbonyl)aniline (0.22 g, 1 mmol), and DMAP (0.32 g, 2.6 mmol) and the reaction was stirred 18 h. The reaction was washed successively with 1N HCl, NaHCO$_3$, and dried (MgSO$_4$). The compound was purified by chromatography on silica gel eluting with (1:1.5) hexanes/ethyl acetate to afford 0.345 g (71%). $^1$HNMR (CDCl$_3$) δ: 9.03 (s, 1H), 7.86 (m, 4H), 7.63 (t, J=8.05 Hz, 1H), 7.55 (s, 1H), 7.21 (m, 2H), 3.67 (t, J=8.05 Hz, 2H), 3.43 (t, J=6.59 Hz, 2H), 2.02 (q, J=6.22 Hz, 2H), 1.92 (q, J=6.22 Hz, 2H) ppm; ESI mass spectrum analysis m/z (relative intensity): 472.1 (M+H)$^+$, 494 (M+Na)$^+$.

Part B. The product of Part A was hydrogenated in EtOH/TFA with 10% palladium on carbon catalyst at 50 psi for 24 h. Purification by reverse phase HPLC and freeze-drying afforded 0.34 g (80%) product. $^1$HNMR (DMSO-d$_6$) δ: 10.8 (s, 1H), 8.23 (s, 2H), 7.72 (m+d, J=8.06 Hz, 3H), 7.59 (m, 3H), 7.49 (dd, J=1.84, 11.36 Hz, 1H), 7.39 (dd, J=8.06, 1.83 Hz, 1H), 4.15 (q, J=5.86 Hz, 2H), 3.47 (t, J=6.6 Hz, 2H), 3.42 (t, J=6.2 Hz, 2H), 1.89 (m, 4H) ppm; ESI mass spectrum analysis m/z: 476.2 (M+H)$^+$; Elemental analysis calc'd for $C_{23}H_{21}F_4N_5O_2$ (TFA) ($H_2O$) 0.5: C: 50.17, H: 3.87, N: 11.70, found C: 50.05, H: 3.87, N: 11.43

Example 198

1-(3-Aminomethylphenyl)-5-[(3-fluoro-4-(N-pyrrolidinocarbonyl)phenyl)aminocarbonyl]-3-trifluoromethylpyrazole, Trifluoroacetic Acid Salt Part A. 1-(3-Cyanophenyl)-3-trifluoromethylpyrazole carboxylic acid and 3-fluoro-4-(N-carbonylpyrrolidino)aniline were coupled via the acid chloride as in the previous Example in 81% yield. $^1$HNMR (CDCl$_3$) δ: 10.01 (s, 1H), 7.79 (m, 4H), 7.61 (t, J=7.69 Hz, 1H), 7.16 (dd, J=1.84, 10.99 Hz, 1H), 7.06 (t, J=8.06 Hz, 1H), 6.93 (dd, J=1.83, 8.05 Hz, 1H), 3.68 (t, J=6.59 Hz, 2H), 3.34 (t, J=6.59 Hz, 2H), 2.00 (q, J=6.59 Hz, 2H), 1.94 (q, J=6.59 Hz, 2H) ppm; ESI mass spectrum analysis m/z (relative intensity): 472.1 (M+H)$^+$, 494 (M+Na)$^+$.

Part B. The product of Part A was hydrogenated in EtOH/TFA with 10% palladium on carbon catalyst at 50 psi for 24 h. Purification by reverse phase HPLC and freeze-drying afforded 0.38 g (84%) product. $^1$HNMR (DMSO-d$_6$) δ: 11.07 (s, 1H), 8.24 (s, 2H), 7.73 (m, 3H), 7.63 (m, 3H), 7.50 (m, 2H), 4.16 (d, j=5.49 Hz, 2H), 3.47 (t, J=6.23 Hz, 2H), 3.23 (t, J=6.23 Hz, 2H), 1.89 (m, 4H) ppm; HRMS 476.170963 (calc'd), 476.171044 (obs.); Elemental Analysis calc'd for $C_{23}H_{21}F_4N_5O_2$ (TFA) ($H_2O$) 0.5: C: 50.17, H: 3.87, N: 11.70, found C: 50.17, H: 3.85, N: 11.48.

Example 199

1-(3-Aminomethylphenyl)-5-[(2'-sulfonylmethyl-[1,1']-biphen-4-yl)aminocarbonyl]-3-trifluoromethyl-pyrazole, Trifluoroacetic Acid Salt 1-(3-Cyanophenyl)-5-[(2'-sulfonylmethyl-[1,1']-biphen-4-yl)aminocarbonyl]-3-trifluoromethyl-pyrazole (synthesis previously described) was hydrogenated in EtOH/TFA with 10% palladium on carbon catalyst at 50 psi for 24 h. Purification by reverse phase HPLC and freeze-drying afforded the title compound. $^1$HNMR (DMSO-d$_6$) δ: 10.92 (s, 1H), 8.24 (bd s, 2H), 8.10 (d, J=7.69 Hz, 1H), 7.79 (m, 6H), 7.60 (m, 3H), 7.41 (s+d, J=8.79 Hz, 3H), 4.17 (q, J=5.12 Hz, 2H), 2.85 (s, 3H) ppm, HRMS 515.136472 (calc'd), 515.137193 (obs).

Example 200

1-(3-Aminomethylphenyl)-5-[(2'-aminosulfonyl-3-fluoro-[1,1']biphen-4-yl)aminocarbonyl]-3-trifluoromethyl-pyrazole, Trifluoroacetic Acid Salt Part A. 1-(3-Cyanophenyl)-3-trifluoromethylpyrazole carboxylic acid and 1-(2'-tertbutylaminosulfonyl-[1,1']-3-fluorobiphenylaniline were coupled via the acid chloride as in previous Examples in 76% yield. $^1$HNMR (CDCl$_3$) δ: 8.31 (t, J=8.43 Hz, 1H), 8.18 (dd, J=1.47, 7.69 Hz, 1H), 8.04 (s, 1H), 7.88 (d, J=1.46 Hz, 1H), 7.83 (m, 2H), 7.68 (d, J=8.06 Hz, 1H), 7.62 (m, 2H), 7.42 (dd, J=1.83, 11.72 Hz, 1H), 7.29 (d, J=1.47 Hz, 1H), 7.22 (m, 2H), 3.69 (s, 1H), 1.07 (s, 9H) ppm; ESI mass spectrum analysis m/z (relative intensity): 607.9 (M+Na, 100).

Part B. The product of Part A was refluxed in TFA for 30 minutes then hydrogenated in EtOH/TFA with 10% palladium on carbon catalyst at 50 psi for 24 h and then with platinum (II) oxide catalyst at 50 psi for 24 h. Purification by reverse phase HPLC and freeze-drying afforded 0.16 g (44%)product. $^1$HNMR (DMSO-d$_6$) δ: 10.71 (s, 1H), 8.24 (bd s, 2H), 8.05 (dd, J=1.47, 6.96 Hz, 1H), 7.74 (s, 1H), 7.69 (s, 1H), 7.66 (m, 6H), 7.43 (s, 2H), 7.35 (m, 2H), 7.23 (d, J=8.42 Hz, 1H), 4.16 (q, J=5.49 Hz, 2H) ppm; ESMS 534.1 (M+H); Elemental Analysis calc'd for $C_{24}H_{19}F_4N_5O_3S$ (TFA)1.1 ($H_2O$) 0.6: C: 46.99, H: 3.21, N: 10.46, found C: 47.06, H: 2.86, N: 10.37.

Examples 201 and 202

1-(3-Aminomethylphenyl)-5-[(5-(2'-aminosulfonylphenyl)-[1,6-dihydro]pyrimid-2-yl)aminocarbonyl]-3-trifluoromethyl-pyrazole, Trifluoroacetic Acid Salt and 1-(3-Aminomethylphenyl)-5-[(5-(2'-aminosulfonylphenyl)pyrimid-2-yl)aminocarbonyl]-3-trifluoromethyl-pyrazole, Trifluoroacetic Acid Salt 1-(3-Cyanophenyl)-5-[(5-(2'-tertbutylaminosulfonylphenyl-4-yl)pyrimid-2-yl)aminocarbonyl]-3-trifluoro-methyl pyrazole (0.3 g, 0.5 mmol) (synthesis previously described) was hydrogenated in ethanol/acetic acid for 24 h at 40 psi, first with 10% palladium on carbon and then with added platinum (II) oxide. The reaction was filtered, concentrated, and refluxed in TFA for 30 minutes. Purification by reverse phase HPLC and freeze-drying afforded small amounts of two products. The dihydro-compound was the first product obtained (64.5 mg). $^1$HNMR (DMSO-d$_6$) δ: 9.76 (s, 1H), 9.10 (s, 1H), 8.22 (brd, 2H), 7.95 (dd, J=1.10, 7.69 Hz, 1H), 7.65 (s, 1H), 7.61 (m, 5H), 7.49 (s, 2H), 7.41 (dd, J=1.46, 7.32 Hz, 1H), 7.19 (s, 1H), 6.10 (d, J=4.40 Hz, 1H), 4.22 (s, 2H), 4.15 (q, J=5.86 Hz, 2H) ppm; HRMS 520.137869 (calc'd); 520.138256 (obs); Elemental Analysis calc'd for $C_{22}H_{20}F_3N_7O_3S$ (TFA) 2: C: 41.77, H: 2.97, N: 13.12, found C: 41.98, H: 3.02, N: 12.97. The second product was the pyrimidyl analog. $^1$HNMR (DMSO-d$_6$) δ: 11.61 (s, 1H), 8.66 (s, 2H), 8.24 (brd, 2H), 8.08 (dd, J=2.20, 6.95 Hz, 1H), 7.73 (m, 4H), 7.60 (m, 5H), 7.48 (m, 1H), 4.16 (m, 2H); HRMS 518.122219 (calc'd); 518.122803 (obs); Elemental Analysis calc'd for $C_{22}H_{18}F_3N_7O_3S$ (TFA) 1.3 ($H_2O$) C: 43.79, H: 3.03, N: 14.53, found C: 43.92, H: 2.99, N: 14.37.

Example 203

1-[3-(2'-Ethylaminophenyl)-5-[(2'-aminosulfonyl-[1,1']-biphen-4-yl)aminocarbonyl]-3-trifluoromethyl Pyrazole, Trifluoroacetic Acid Salt Part A. To 1-(3-cyanophenyl)-5-hydroxymethyl-3-trifluoromethyl pyrazole (1.8 g, 6.7 mmol) in DMF (12 mL) was added tert-butyldimethylsilylchloride (1 g, 7.1 mmol) and imidazole (0.94 g, 13.8 mmol). The reaction was stirred for 3 h, then partitioned between ethyl acetate and water. Extraction with ethyl acetate, drying (MgSO$_4$) and purification by chromatography on silica gel eluting with (4:1) hexanes/ethyl acetate to afford 1.88 g (73%).

Part B. To the product of Part A (0.4 g, 1.0 mmol) in THF (15 mL) at 0° C. was added methyl magnesium chloride (0.9 mL, 2.6 mmol) and the reaction was stirred at ambient temperature for 2 h. After cooling to 0° C., methanol (25 mL) and then sodium borohydride (0.2 g, 5 mmol) were added and the reaction was stirred for 1 h. The reaction was quenched with water, filtered and concentrated. The residue was extracted into ethyl acetate and dried (MgSO$_4$). The crude oil was dissolved in CH$_2$Cl$_2$, cooled to 0° C. and ditert-butylcarbamate (0.23 g, 1.1 mmol) and triethylamine (0.15 mL) were added. The reaction was stirred 18 h, then washed with saturated ammonium chloride, brine and dried (MgSO$_4$). The crude material was dissolved in THF and tetrabutylammonium fluoride in THF (1.46 mL) was added.

The reaction stirred for 3 h, then concentrated. The residue was dissolved in $CH_2Cl_2$, and washed with water, brine and dried ($MgSO_4$). Purification by chromatography on silica gel eluting with (2:1) hexanes/ethyl acetate afforded 0.187 g (47%). $^1$HNMR ($CDCl_3$) δ: 7.58 (s, 1H), 7.47 (m, 2H), 7.38 (m, 1H), 6.70 (s, 1H), 4.92 (bd, 1H), 4.78 (m, 1H), 4.65 (m, 2H), 2.91 (bd, 1H), 1.49 (d, J=6.96 Hz, 3H), 1.40 (s, 9H) ppm; MS ESI mass spectrum analysis m/z (relative intensity): 407.8 (M+Na, 100).

Part C. To the product of Part B (0.17 g, 0.44 mmol) in acetonitrile (5 mL) at 0° C. was added a few crystals of ruthenium (III) chloride and aqueous solution of sodium periodinate (0.2 g, 0.9 mmol). The reaction was stirred 18 h, then filtered and concentrated. The aqueous residue was extracted with ethyl acetate and dried ($MgSO_4$). ESI (–ve) mass spectrum analysis m/z (relative intensity): 398 (M–H, 100).

Part D. To the product of Part C (0.17 g, 0.4 mmol) and 4-bromoaniline (0.073 g, 0.4 mmol) in $CH_2Cl_2$ (5 mL) was added 1-ethyl-3-(3-dimethylaminopropyl)carbodiimide hydrochloride (0.11 g, 0.57 mmol). The reaction was stirred 18 h, then washed with water, brine and dried ($MgSO_4$). Filtration through a plug of silica gel eluting with (1:1) hexanes/ethyl acetate afforded 0.148 g of a white foam. ESI mass spectrum analysis m/z (relative intensity): 575–577 (M+Na)$^+$.

Part E. The product of Part D (0.14 g, 0.26 mmol) was coupled to 2-tert-butylsulfonamide phenyl boronic acid by standard Suzuki procedure. The crude product of this reaction was heated to reflux in TFA for 20 minutes. Purification by reverse phase HPLC and freeze-drying afforded 77 mg product (46%). $^1$HNMR (DMSO-$d_6$) δ: 10.86 (s, 1H), 8.32 (brd, 2H), 8.04 (dd, j=7.69, 1.42 Hz, 1H), 7.76 (s, 1H), 7.68 (d, j=8.42 Hz, 2H), 7.67 (m, 6H), 7.39 (d, J=8.79 Hz, 2H), 7.32 (dd, J=9, 1.32 Hz, 1H), 7.29 (s, 2H), 4.56 (m, 1H), 1.52 (d, J=6.96 Hz, 3H) ppm; HRMS 530.147371 (cal'd), 530.148939 (obs); Elemental Analysis calc'd for $C_{25}H_{22}F_3N_5O_3S$ (TFA) 1.1: C: 49.88, H: 3.55, N: 10.69, found C: 49.49, H: 3.49, N: 10.60.

Example 204

1-[3-(1-(N-Morpholino)imino)phenyl]-5-[(2'-aminosulfonyl-3-fluoro-[1,1']-biphen-4-yl)aminocarbonyl-3-trifluoromethylpyrazole, Trifluoroacetic Acid Salt To 1-(3-cyanophenyl)-5-[(2'-tert-butylaminosulfonyl-3-fluoro-[1,1']-biphen-4-yl)aminocarbonyl]-3-trifluoromethyl pyrazole (0.23 g, 0.39 mmol) in (2:1) $CHCl_3$/MeOH (30 mL) at 0° C. was bubbled HCl gas for 15 minutes. The flask was sealed and placed in the refrigerator for 18 h. The solvent was removed and morpholine (0.2 mL) and fresh methanol were added. The reaction was stoppered and stirred for 48 h. The solvent was removed and the residue was heated to reflux in TFA for 15 minutes. Purification by reverse phase HPLC and freeze-drying afforded 0.146 g product (51%). $^1$HNMR (DMSO-$d_6$) δ: 10.70 (s, 1H), 9.69 (s, 1H), 9.32 (s, 1H), 8.05 (dd, j=6.96, 2.20 Hz, 1H), 7.94 (s, 1H), 7.89 (d, J=8.05 Hz, 1H), 7.80 (m, 2H), 7.65 (m, 3H), 7.42 (s, 2H), 7.35 (d, J=8.50 Hz, 2H), 7.23 (d, J=9.52 Hz, 1H), 3.81 (bs, 2H), 3.74 (bd s, 2H), 3.56 (bd s, 2H), 3.32 (bd s, 2H) ppm; ESMS 616.9 (M+H). Elemental Analysis calc'd for $C_{28}H_{24}F_4N_6O_4S$ (TFA) 1.1 ($H_2O$) 1.2: C: 47.50, H: 3.63, N: 11.01, found C: 47.39, H: 3.28, N: 10.69.

Example 205

1-(3-Aminomethylphenyl)-5-[2-(2'-aminosulfonyl-[1,1']-biphen-4-yl)-1-hydroxyethyl]-3-trifluoromethyl-pyrazole, Trifluoroacetic Acid Salt Part A. To 1-(3-cyanophenyl)-3-trifluoromethylpyrazole-5-carboxylic acid (1 g, 3.6 mmol) in $CH_2Cl_2$ (40 mL) was added oxalyl chloride (0.4 mL, 4.9 mmol) and several drops of DMF. The reaction was stirred for 3 h, then the solvent was removed in vacuo. In a separate flask, dibromoethane (0.1 mL), was added to activated Zn (0.35 g, 5.3 mmol) in THF (5 mL). The mixture was heated to reflux for 5 minutes, then cooled to 0° C. and 4-bromo-benzylbromide (1.1 g, 4.3 mmol) in THF (5 mL) was added slowly over 0.5 h. The reaction was kept at 0° C. for 3 h, then cannulated into a mixture of CuCN (0.38 g , 4.3 mmol), LiCl (0.36 g, 8.5 mmol) and THF (10 mL) at –78° C. The reaction was warmed to –20° C. for 5 minutes, then recooled to –78° C. The solid acid chloride was suspended in THF (20 mL) and added to the above cold mixture. The reaction was allowed to slowly warm to room temperature, then, filtered and concentrated. Purification by chromatography on silica gel eluting with (2:1) hexanes/ethyl acetate afforded 0.55 g (37%) white foam. MS (ESI) m/z=433.9–432 (M–H)$^+$.

Part B. The product of Part A (0.53 g, 1.2 mmol) was coupled by standard Suzuki procedures to 2-tert-butylaminosulfonyl-phenyl boronic acid (0.39 g, 1.7 mmol). Purification by chromatography on silica gel eluting with (4:1) hexanes/ethyl acetate afforded 0.32 g (46%) the ketonitrile coupled product. MS (ESI) m/z=565 (M–H)$^+$.

Part C. To the product from Part B (0.05 g, 0.08 mmol) was added $CH_2Cl_2$ (10 mL) and tetra-N-butylammonium borohydride (0.08 g, 0.31 mmol) and the mixture was heated to reflux 18 h. The solvent was removed and replaced with 10% HCl and heated to reflux for 1 h. The reaction was cooled, extracted with diethyl ether, basefied with 50% NaOH, extracted with ethyl acetate and dried ($MgSO_4$). The diethyl ether layer contained tert-butyl protected intermediate. The ether was concentrated and the residue heated in TFA for 15 minutes. All product was combined and purification by reverse phase HPLC and freeze-drying afforded 0.01 g of product (18%). $^1$HNMR (DMSO-$d_6$) δ: 8.23 (brd, 2H), 8.03 (d, j=6.96 Hz, 1H), 7.63 (m, 6H), 7.28 (s+d, j=7.69 Hz, 3H), 7.18 (s, 2H), 7.11 (s+d, j=6.59 Hz, 3H), 5.83 (m, 1H), 4.81 (m, 1H), 4.15 (m, 2H), 3.09 (d, j=6.60 Hz, 2H) ppm; HRMS 517.152122(calc'd), 517.152222(obs.).

Example 206

1-(3-Aminomethylphenyl)-5-[(3-fluoro-2'-methylsulfonyl-[1,1']-biphen-4-yl)aminocarbonyl]-3-trifluoromethyl Pyrazole, Trifluoroacetic Acid Salt Part A. To 1-(3-cyanophenyl)-3-trifluoromethylpyrazole-5-carboxylic acid (1 g, 3.6 mmol) in $CH_2Cl_2$ (40 mL) was added oxalyl chloride (0.43 mL, 4.9 mmol) and several drops of DMF. The reaction was stirred 18 h, then the solvent was removed in vacuo. Fresh $CH_2Cl_2$ (40 mL) was added followed by 4-bromo-2-fluoroaniline (0.68 g, 3.6 mmol) and 4-dimethylaminopyridine (1.09 g, 8.9 mmol). After stirring 18 h, the reaction was washed with 1N HCl, sat'd $NaHCO_3$, dried ($Na_2SO_4$), filtered and concentrated to afford 1.55 g crude bromide. ESI (–ve) mass pectrum analysis m/z (relative intensity) 450.8–452.8 (M–H, 100).

Part B. The bromide from Part A (0.5 g, 1.1 mmol), 2-thiomethyl phenylboronic acid (0.26 g, 1.5 mmol), and 2M $Na_2CO_3$ (2 mL), were combined in (1:1) ethanol/toluene (20 mL) and degassed by bubbling nitrogen through for 30minutes. Tetrakis-triphenylphosphine palladium (0) (50 mg) was added and the reaction heated to reflux 18 h. The reaction was cooled, concentrated, extracted with ethyl acetate and dried ($MgSO_4$). The coupled product was purified through a plug of silica gel using (1:1) hexane/ethyl acetate as eluent and carried onto the next step. The thiomethyl compound was dissolved in $CH_2Cl_2$ (50 mL), cooled to 0° C., and MCPBA (0.67 g, 2.2 mmol) was added. The reaction was stirred 748 h, then washed successively with aqueous sodium bisulfite, brine, and dried (MgSO$_4$). The sulfone was purified through a plug of silica gel using (1:1) hexane/ethyl acetate as eluent to afford 0.34 g. $^1$HNMR (CDCl$_3$) δ: 8.25 (t, 1H), 7.90–7.15 (m, 12H), 2.39 (s, 3H) ppm. ESI mass spectrum analysis m/z 550.7(M+Na)$^+$, 526.7 (M–H)$^+$.

Part C. The product of Part B (0.34 g, 0.6 mmol) was hydrogenated in (1:2)methanol/ethanol (70 mL) and TFA (1 mL) with 10% palladium on carbon catalyst at 50 psi for 24 h. Purification by reverse phase HPLC and freeze-drying afforded 0.21 g (50%) product. $^1$HNMR (DMSO-d$_6$) δ: 10.75 (s, 1H), 8.23 (m, 3H), 8.11 (dd, j=7.69, 1.46 Hz, 1H), 7.96 (dd, j=6.96, 1.47 Hz, 1H), 7.81 (m, 8H), 7.26 (dd, j=1.47, 8.06 Hz, 1H), 4.16 (q, j=5.49 Hz, 2H), 2.94 (s, 3H) ppm; ESI mass pectrum analysis m/z 532.9 (M+H, 100); Elemental Analysis calc'd for C$_{25}$H$_{20}$F$_4$N$_4$O$_3$S (TFA) 1.1: C: 49.65, H: 3.23, N: 8.52, found C: 49.73, H: 2.98, N: 8.40.

Example 207

1-(3-Aminomethylphenyl)-5-[(5-(2'-methylsulfonyl-phenyl)pyrimid-2-yl)aminocarbonyl]-3-trifluoromethyl Pyrazole, Trifluoroacetic Acid Salt Part A. 1-(3-Cyanophenyl)-3-trifluoromethylpyrazole carboxylic-5-acid (2.2, 7.8 mmol) was heated to reflux in methanol containing con. sulfuric acid (1 mL) for 48 h. The solvent was removed and the residue was dissolved in ethyl acetate, washed with NaHCO$_3$ (sat.), brine and dried (MgSO$_4$). The ester was hydrogenated in MeOH/TFA with 10% palladium on carbon catalyst at 40 psi for 24 h. The reaction was filtered and concentrated. The residue was suspended in CH$_2$Cl$_2$, cooled to 0° C. and 1N NaOH (35 mL) and benzyl chloroformate (1.2 mL, 8.6 mmol) were added. The reaction was stirred 2 h then separated and the organics dried (MgSO$_4$) and concentrated. The residue was dissolved in MeOH, cooled to 0° C. and a solution of LiOH (0.5 g, 11.8 mmol) in water was added. The reaction was stirred 18 h. The reaction was concentrated and the residue was acidified and extracted with ethyl acetate and dried (MgSO$_4$) to afford 1.83 g (57%) white solid. ESI mass spectrum analysis m/z (relative intensity): 417.9 (M–H, 100).

Part B. The acid from Part A (0.46 g, 1.1 mmol) was coupled with 2-amino-5-(2'-methylsulfonylphenyl)pyrimidine (0.31 g, 1.1 mmol) by the standard acid chloride procedure to afford 0.3 g (42%) of the carbobenzyloxy protected intermediate. The intermediate was heated to reflux in TFA for 45 minutes and purification by reverse phase HPLC and freeze-drying afforded 0.16 g (23% overall)product. $^1$HNMR (DMSO-d$_6$) δ: 11.65 (s, 1H), 8.72 (s, 2H), 8.24 (bd, 2H), 8.15 (d, J=7.69 Hz, 1H), 7.87 (m, 4H), 7.58 (s+m, 3H), 7.54 (d, J=7.32 Hz, 1H), 4.16 (q, J=5.49 Hz, 2H), 3.07 (s, 3H) ppm; HRMS 517.126970 (calc'd), 517.125600 (obs); Elemental Analysis calc'd for C$_{23}$H$_{19}$F$_3$N$_6$O$_3$S (TFA) 1.2: C: 46.70, H: 3.12, N: 12.86, found C: 46.78, H: 3.04, N: 12.56.

Example 208

1-[3-Amidinophenyl]-5-[(3-fluoro-2'-methylsulfonyl-[1,1']-biphen-4-yl)aminocarbonyl]-3-trifluoromethyl Pyrazole, Trifluoroacetic Acid Salt The nitrile prepared as in Example 206 was subjected to standard Pinner reaction conditions and purification by reverse phase HPLC and freeze-drying afforded 0.067 g (27%) of the desired titled product. $^1$HNMR (DMSO-d$_6$) δ: 10.74 (s, 1H), 9.45 (s, 1.5H), 9.13 (s, 1.5H), 8.11 (d, J=7.69 Hz, 1H), 8.04 (s, 1H), 7.95 (d, J=8.42 Hz, 2H), 7.81 (m, 5H), 7.44 (m, 2H), 7.26 (d, J=8.42 Hz, 1H), 2.94 (s, 3H) ppm. ESI mass spectrum analysis m/z (relative intensity): 546 (M+H, 100).

Example 209

1-[3-Amidinophenyl]-5-[(3-fluoro-2'-aminosulfonyl-[1,1']-biphen-4-yl)aminocarbonyl]-3-trifluoromethyl Pyrazole, Trifluoroacetic Acid Salt The nitrile prepared in Example 207 was subjected to standard Pinner reaction conditions and purification by reverse phase HPLC and freeze-drying afforded 0.042 g (25%) product. HRMS 547.117549 (calc'd), 547.117400 (obs).

Example 210

1-(3-Aminomethyl)phenyl-5-[(2'-aminosulfonyl-[1,1']-biphen-4-yl)carbonylmethyl]-3-trifluoromethyl Pyrazole, Trifluoroacetic Acid Salt Part A. To the N-carbobenzyloxy protected carboxylic acid (5 g, 11.9 mmol) (described in Example 207) in CH$_2$Cl$_2$ (100 mL) was added oxalyl chloride (1.5 mL, 16.7 mmol) and DMF (0.5 mL). The reaction was stirred 18 h, then the solvents were removed and the resultant yellow solid set aside. In a separate flask, dibromoethane (0.3 mL), was added to activated Zn (1.87 g, 28 mmol) in THF (30 mL). The mixture was heated to reflux for 5 minutes, then cooled to 0° C. and 4-bromo-benzylbromide (5.96 g, 24.9 mmol) in THF (45 mL) was added slowly over 0.5 h. The reaction was kept at 0° C. for 3 h, then cannulated into a mixture of CuCN (2.24 g, 25 mmol), LiCl (1.52 g, 36 mmol) and THF (15 mL) at −78° C. The reaction was warmed to −20° C. for 5 minutes, then recooled to −78° C. The solid acid chloride was suspended in THF (50 mL) and added to the above cold mixture. The reaction was kept at −78° C. for 1 h, 0° C. for 1 h, then at 20° C. for 1 h. The reaction was quenched with saturated. NH$_4$Cl, filtered, and extracted with ethyl acetate. The aqueous layer was carefully acidified, extracted with ethyl acetate and the combined organic layers dried (Na$_2$SO$_4$). Purification by chromatography on silica gel eluting with (1:1) hexanes/ethyl acetate and recrystalization (CH$_2$Cl$_2$/hexanes) afforded 2.8 g pure product and 2.5 g slightly impure product from the filtrate. $^1$HNMR (CDCl$_3$) δ: 7.47 (d, j=8.4 Hz, 2H), 7.42 (m, 8H), 7.08 (d, J=8.4 Hz, 2H), 7.00 (d, J=8.4 Hz, 1H), 5.13 (s, 2H), 4.43 (d, J=5.9 Hz, 2H), 4.09 (s, 2H), 3.11 (AB, J=13.5, 46.9 Hz, 2H) ppm; ESI (−ve) mass spectrum analysis m/z (relative intensity): 569.7–571.6 (M–H)$^+$.

Part B. The product of Part A (0.5 g, 0.88 mmol) was coupled by standard Suzuki procedures with 2-tert-butylaminosulfonylphenyl boronic acid (0.3 g, 1.1 mmol). Purification by chromatography on silica gel eluting with (2:1) hexanes/ethyl acetate afforded 0.36 g coupled product. Deprotection in boiling TFA (20 minutes), and purification by reverse phase HPLC and freeze drying afforded 0.2 g (64%) product. $^1$HNMR (DMSO-d$_6$) δ: 8.16 (m, 3H), 8.13 (dd, J=6.9, 2.2 Hz, 1H), 7.61 (m, 5H), 7.45 (m, 1H), 7.33 (m, 7H), 4.45 (s, 2H), 4.14 (d, J=5.9 Hz, 2H) ppm; ESI mass spectrum analysis m/z (relative intensity): 514.8 (M+H, 100); Elemental Analysis calc'd for C$_{25}$H$_{21}$F$_3$N$_4$O$_3$S (TFA) 1.3: C: 50.02, H: 3.39, N: 8.45, found C: 50.10, H: 3.35, N: 8.39.

Example 211

1-(3-Aminomethyl)phenyl-5-[(2'-aminosulfonyl-[1,1']-biphen-4-yl)aminocarbonyl]-3-(methylsulfonylmethyl)pyrazole, Trifluoroacetic Acid Salt Part A. The pyrazole (1 g, 3.92 mmol) obtained in part B of Example 10 was dissoved in CCl$_4$, then NBS (1.1 g, 6.27 mmol) and benzoylperoxide (0.038 g, 0.5 mmol) were added. The mixture was heated to reflux for 18 hr. After removal of the solvent, 50 mL water was added, then extracted with EtOAc, washed the organic layer with brine and dried over $MgSO_4$. Filtration and concentration of the filtrate in vacuo was followed by purification using flash chromatography (2:3/Hexane:Methlene chloride) to afford 0.55 g of the desired bromomethyl product as a light yellow solid. $^1$HNMR ($CDCl_3$) δ: 7.77–7.69 (m, 3H); 7.61 (t, J=7.69, 1H); 7.13 (s, 1H); 4.51 (s, 2H); 4.32 (q, J=6.95, 2H); 1.33 (t, J=6.96 3H) ppm; Ammonia CI mass spectrum analysis m/z (relative intensity): 334.0 (97) and 336.0 (100).

Part B. To the product of part A (0.55 g, 1.65 mmol) in DMF was added KSMe (0.16 g, 1.81 mmol). The mixture was headed to reflux over night. The solution was quenched with water (100 mL) and extracted with EtOAc. The organic layer was washed with brine and dried over $MgSO_4$. Filtration, bubbling air through the filtrate for 2 h. and concentration of the filtrate in vacuo was followed by purification using flash chromatography (3:2/Hex:EtOAc) to afford 0.14 g methylsulfonylmethyl compound as a colorless oil. Ammonia CI mass spectrum analysis m/z (relative intensity): 334.1 (M+H, 100). $^1$HNMR ($CDCl_3$) δ: 7.77–7.69 (m, 4H); 7.61 (t, J=8.05, 1H); 4.38 (s, 2H); 4.30 (q, J=6.96, 2H); 2.94 (s, 3H); 1.32 (t, J=6.96, 3H) ppm.

Part C. Standard Weinreb coupling procedures of the product from part B with 2'-tert-butylaminosulfonyl-[1,1']-biphenyl aniline followed by the usual acid quench and silica gel flash chromatography afforded 0.13 g of the desired coupled product. ESI mass spectrum analysis m/z (relative intensity): 613.8 (75). $^1$HNMR ($CDCl_3$) δ: 8.35 (s, 1H); 8.16 (m, 1H); 7.82 (s, 1H), 7.75–7.55 (m, 8H); 7.50–7.45 (m, 2H); 7.30 (m, 1H), 7.16 (S, 1H); 4.42 (S, 2H); 3.00 (s, 3H); 1.02 (s, 9H) ppm.

Part D. To the product from part C (0.13 g, 0.22 mmol) dissolved in ethanol (50 mL) was added 10% Pd/C (20 mg) and 2 mL AcOH. Hydrogenation of this solution on the Parr at 50 psi for 18 h followed by filtration through a pad of Celite and concentration afforded a crude reduced product which was treated TFA (6 mL) and heated to reflux for 50 min. After removal of the solvent and purification via standard HPLC reverse phase techniques and lyophilization afforded the title compound as a colorless solid. ESI mass spectrum analysis m/z (relative intensity): 540.1 (M+H, 100).

Example 212

1-(3-Amidino)phenyl-5-[(2'-aminosulfonyl-[1,1']-biphen-4-yl)aminocarbonyl]-3-(methylaminosulfonylmethyl)pyrazole, Trifluoroacetic Acid Salt Part A. To the product (1.1 g, 3.29 mmol) from part A (Example 211)) in DMF was added $NaN_3$ (0.24 g, 3.62 mmol). The mixture was stirred at R.T. for 18 h. The reaction mixture was quenched with water (200 mL) and extracted with EtOAc. Washed the organic layer with water and brine and dried over $MgSO_4$. The mixture was filtered and concentrated to afford 0.93 g of the crude azidomethyl compound. ESI mass spectrum analysis m/z (relative intensity): 297.1 (M+H, 100). $^1$HNMR ($CDCl_3$) δ: 7.77 (m, 3H); 7.59 (m, 1H); 7.08 (s, 1H); 4.44 (s, 2H); 4.30 (q, J=7, 2H); 1.31 (t, J=7, 3H) ppm.

Part B. To the product (0.54 g, 1.82 mmol) from part A in THF, was added $PPh_3$ (0.53 g, 2.01 mmol). The reaction mixture was stirred at rt for 4 h and the solvent was evaporated. HCl (1N, 50 mL) was added and the organics were extracted with EtOAc. The organic layer was washed with brine and dried over $MgSO_4$. Evaporation in vacuo afforded the desired aminomethyl compound (0.32 g) as a white solid. ESI mass spectrum analysis m/z (relative intensity): 271.1 (M+H, 100). $^1$HNMR ($CDCl_3$) δ: 7.77 (s, 1H); 7.72 (m, 2H); 7.59 (m, 1H): 7.01 (s, 1H); 4.30 (q, J=7, 2H); 3.96 (s, 2H); 1.31 (t, J=7, 3H) ppm.

Part C. To the product (0.43 g, 1.59 mmol) from part B in $CH_2Cl_2$ was added triethylamine (1.5 eq.). The reaction mixture was cooled to 0° C. and $CH_3SO_2Cl$ (1 eq.) was added. The reaction mixture was stirred at R.T. for 18 hr. diluted with $CH_2Cl_2$ and washed with 1N HCl, $NaHCO_3$ (sat.), brine, then dried over $MgSO_4$. Evaporation in vacuo was followed by purification via flash chromatography (4:1/Hex:EtOAc) to afford 0.42 g of the desired methylsulfonamide pyrazole precursor. Ammonia CI mass spectrum analysis m/z (relative intensity): 349.0 (M+H, 100). $^1$HNMR ($CDCl_3$) δ: 7.76 (m, 2H); 7.73 (m, 1H); 7.61 (m, 1H); 7.08 (s, 1H); 4.44 (d, J=6.3, 2H); 4.29 (q, J=7.3, 2H); 3.325 (s, 1H); 3.01 (s, 3H); 1.31 (t, J=7.3, 3H) ppm.

Part D. Standard Weinreb coupling procedures of the product from part B with 2'-tert-butylaminosulfonyl-[1,1']-biphenylamine followed by the usual acid quench and silica gel flash chromatography afforded the desired coupled product. ESI (–ve) mass spectrum analysis m/z (relative intensity): 605.1 (M–H, 100). $^1$HNMR ($CDCl_3$) d: 8.55 (s, 1H); 8.16 (m, 1H); 7.74 (m, 5H); 7.56 (m, 6H); 7.30 (m, 1H); 7.02 (s, 1H); 4.46 (d, 2H); 3.81 (s, 1H); 3.06 (s, 3H); 1.04 (s, 9H) ppm.

Part C. Standard Pinner-amidine reaction protocol followed by purification via reverse phase HPLC techniques and lyophilization afforded the desired compound as colorless crystals. $^1$HNMR ($CDCl_3$) δ: 10.69 (s, 1H); 9.43 (s, 2H); 9.15 (s, 2H); 8.05 (m, 1H); 7.95 (s, 1H); 7.85 (m, 1H); 7.80 (m, 1H); 7.70 (m, 4H); 7.60 (m, 2H); 7.35 (m, 2H); 7.30 (m, 1H); 7.20 (m, 3H); 4.28 (d, J=6.1, 2H); 2.97 (s, 3H) ppm. ESI mass spectrum analysis m/z (relative intensity): 568.0 (100) HRMS for $C_{25}H_{26}N_7O_5S_2$ 568.143686 (calcd); 568.145471 (obs).

Example 213

1-(3-Aminomethylphenyl)-5-[(2'-aminosulfonyl-3-fluoro-[1,1']-biphen-4-yl)aminocarbonyl]-3-(methylaminosulfonylmethyl)pyrazole, Trifluoroacetic Acid Salt Part A: Standard Weinreb coupling of the product from part C (Example 203) with 4-bromo-2-fluoroaniline afforded the desired amide. $^1$HNMR ($CDCl_3$) d: 8.13 (t, J=8.4, 1H); 7.90 (brd, 1H); 7.79 (m, 1H); 7.78 (m, 2H); 7.61 (m, 1H); 7.35 (m, 2H); 6.96 (s, 1H); 4.86 (m, 1H); 4.44 (d, J=6.2, 2H); 3.04 (s, 3H) ppm. ESI (–ve) mass spectrum analysis m/z (relative intensity): 489.8 (85) and 491.8 (100).

Part B: Standard Suzuki coupling of the product from part A with 2-thiomethylboronic acid afforded the desired 2'-thiomethyl-biphenyl intermediate. $^1$HNMR ($CDCl_3$) δ: 8.25 (brd, 1H); 8.00 (brd, 1H); 7.83 (s, 1H); 7.75 (m, 2H); 7.62 (m, 1H); 7.35 (m, 6H); 6.96 (s, 1H); 4.85 (m, 1H); 4.48 (d, J=5.9, 2H); 3.05 (s, 3H); 2.39 (s, 1H) ppm. ESI mass spectrum analysis m/z (relative intensity): 557.9 (M+Na, 100). ESI (–ve) mass spectrum analysis m/z (relative intensity): 533.8 (M–H, 100).

Part C: To the product from part B (0.54 g, 1.01 mmol) in $CH_2Cl_2$ was added MCPBA (0.5 g, 3.03 mmol) and the reaction mixture was stirred at R.T. for overnight. The mixture was then $CH_2Cl_2$ and washed with $NaHCO_3$ (sat.), sodium bisulfite, brine and dried over $MgSO_4$. Filtration and concentration of the filtrate in vacuo was followed by purification using flash chromatography (1:1/Hex:EtOAc) to afford 0.53 g of the sulfonylmethyl derivative as white solid. $^1$HNMR (CDCl$_3$) δ: 10.53 (s, 1H); 8.07 (m, 1H); 7.97 (s, 1H); 7.85 (m, 1H); 7.8 (m, 6H); 7.41 (m, 1H); 7.35 (m, 1H); 7.23 (m, 2H); 4.23 (s, 2H); 2.94 (s, 3H); 2.89 (s, 3H) ppm. ESI (–ve) mass spectrum analysis m/z (relative intensity): 565.8 (70).
Part D: The product from part C was hydrogenated as described previously to afford the desired benzylamine analog as colorless crystals following reverse phase HPLC and lyophilization techniques. $^1$HNMR (DMSO) δ: 10.53 (s, 1H); 8.16 (brd, 2H); 8.07 (m, 1H); 7.75 (m, 1H): 7.72 (m, 4H); 7.49 (m, 5H); 7.21 (m, 2H); 4.23 (d, J=6.2, 2H); 4.09 (m, 2H); 2.93 (s, 3H); 2.90 (s, 3H) ppm. ESI mass spectrum analysis m/z (relative intensity): 571.9 (M+H, 100). HRMS calc'd for C26H27N5O5FS2 572.143766 (calcd); 572.145154 (obs).

Example 214

1-(3-(N-Carboxymethyl)amidinophenyl)-5-[(5-(2'-aminosulfonylphenyl)pyrimid-2-yl)aminocarbonyl]-3-methyl Pyrazole, Trifluoroacetic Acid Salt To the Example 92 compound (100 mg, 0.19 mmol) in DMF was added methylchloroformate (36 mg, 0.38 mmol) and Et3N. The mixture was stirred at R.T. for 2.5 hr. Diluted with 100 mL water and extracted with EtOAc, the organic layer was washed with water, brine and dried over MgSO$_4$, filtered and concentrated in vacuo and purified using reverse phase HPLC techniques to afford the the desired carbamate [ESI mass spectrum analysis m/z (relative intensity): 590.9 (100)], which was then treated with TFA and heated to gentle reflux for 0.5 h. Evaporation of the TFA followed by purification via HPLC reverse phase and lyophilization afforded the title compound. $^1$HNMR (DMSO) δ: 11.34 (S, 1H); 8.61 (s, 2H); 8.01 (m, 1H); 7.95 (m, 1H): 7.80 (m, 1H); 7.69 (m, 1H); 7.64 (m, 3H); 7.49 (s, 2H); 7.40 (m, 1H); 7.03 (s, 1H): 3.79 (s, 3H); 2.28 (s, 3H) ppm. ESI mass spectrum analysis m/z (relative intensity): 535.0 (M+H, 100). HRMS calc'd for C$_{24}$H$_{22}$N$_8$O$_3$S 535.151213 (calcd); 535.151600 (obs).

Example 215

1-(3-Aminomethylphenyl)-5-[(2'-methylsulfonyl-[1']-biphen-4-yl)aminocarbonyl]-3-methylpyrazole, Trifluoroacetic Acid Salt
Part A: Standard Weinreb coupling of 2'sulfonylmethyl-biphenylamine to the pyrazole ester obtained in part B of Example 10 followed by standard workup afforded after silica gel purification the desired coupled amide precursor. $^1$HNMR (CDCl$_3$) δ: 8.24 (d, J=7.7, 1H); 7.87 (s, 1H); 7.81 (s, 1H); 7.76 (m, 1H); 7.69 (m, 6H); 7.45 (m, 2H); 7.35 (m, 1H); 6.71 (s, 1H); 2.68 (s, 3H); 2.42 (s, 3H) ppm. ESI mass spectrum analysis m/z (relative intensity): 478.9 (M+Na, 100). ESI (–ve) mass spectrum analysis m/z (relative intensity): 454.9 (M–H, 100).
Part B: To the product from from part A (0.48 g, 1.05 mmol) in EtOH was added 10% Pd/C (80 mg) and 1 mL TFA. The mixture was hydrogenated on a Parr apparatus at 50 psi for 18 hr. After filteration through a pad of Celite and concentration the filtrate in vacuo, purified using reversed phase prep HPLC to afford the title compound. $^1$HNMR (DMSO) δ: 10.65 (s, 1H); 8.17 (brd, 2H); 8.06 (d, J=7,7, 1H); 7.75 (m, 5H); 7.49 (m, 6H); 6.92 (s, 1H); 4.10 (m, 2H); 2.81 (s, 3H): 2.29 (s, 3H); ppm. ESI mass spectrum analysis m/z (relative intensity): 460.9 (M+H, 100). HRMS calc'd for C$_{25}$H$_{25}$N$_4$O$_3$S 461.164738 (calcd); 461.164405 (obs).

Example 216

1-(3-Aminomethylphenyl)-5-[(2'-aminosulfonyl-3-methyl-[1,1']-biphen-4-yl)aminocarbonyl]-3-trifluoromethyl Pyrazole, Trifluoroacetic Acid Salt
Part A: Standard Weinreb coupling of 2'-tert-butylaminosulfonyl-2-methyl-biphenylamine with the previously obtained pyrazole ester afforded the desired coupled amide precursor. $^1$HNMR (CDCl$_3$) δ: 8.17 (d, J=7.7, 1H); 7.83 (m, 4H): 7.64 (M, 2H): 7.56 (m, 2H): 7.4 (m, 3H); 7.15 (s, 1H); 3.61 (s, 1H): 2.36 (s, 3H); 1.04 (s, 9H) ppm. ESI mass spectrum analysis m/z (relative intensity): 604.1 (M+Na, 100). ESI (–ve) mass spectrum analysis m/z (relative intensity): 580.3 (M–H, 100).
Part B: Reduction of the benzonitrile to the benzylamine followed by removal of the tert-butyl group and standard reverse phase HPLC purification afforded the title compound. $^1$HNMR (DMSO) δ: 10.33 (s, 1H); 8.23 (bd, 2H); 8.02 (m, 1H); 7.76 (s, 1H); 7.66 (m, 6H); 7.40 (d, J=8.1, 1H); 7.31 (m, 5H): 4.15 (m, 2H); 2.25 (s, 3H) ppm. ESI mass spectrum analysis m/z (relative intensity): 530.2 (M+H, 100).

Example 217

1-(3-Aminomethylphenyl)-5-[(3-fluoro-2'-methylsulfonyl-[1,1']-biphen-4-yl)aminocarbonyl]-1,2,3-triazole, Trifluoroacetic Acid Salt Standard Weinreb coupling of 4-bromo-2-fluoro-aniline with the previously obtained 1,2,3-triazole-5-carboxylic acid as used in the preparation of Example 46 afforded after purification via flash silica-gel chromatography the coupled amide triazole derivative. $^1$HNMR (CDCl$_3$) d: 8.23 (s, 1H); 8.11 (m, 1H); 7.86 (m, 4H); 7.68 (m, 1H); 7.34 (m, 2H) ppm. ESI (–ve) mass spectrum analysis m/z (relative intensity): 383.8 (100) and 385.7 (80). Standard Suzuki coupling of this intermediate with 2-thiomethyl boronic acid followed by oxidation with MCPBA in dichloromethane afforded the desired biphenylsulfonyl derivative. $^1$HNMR (CDCl$_3$) δ: 8.34 (m, 3H); 8.05 (bd, 1H); 7.93 (m, 3H); 7.74 (m, 3H); 7.37 (m, 2H); 7.24 (m, 1H); 2.74 (s, 3H) ppm. ESI (–ve) mass spectrum analysis m/z (relative intensity): 459.9 (M–H, 100). This intermediate was then reduced to the benzylamine and purified via standard conditions described previously. $^1$HNMR (DMSO) δ: 10.76 (s, 1H); 8.53 (s, 1H); 8.21 (bd, 2H); 8.05 (m, 1H); 7.77 (m, 7H); 7.39 (m, 2H); 7.22 (m, 1H); 4.14 (m, 2H); 2.89 (s, 3H) ppm. ESI (–ve) mass spectrum analysis m/z (relative intensity): 465.9 (M+H, 100). HRMS calc'd for C$_{23}$H$_{21}$N$_5$O$_3$FS, 466.134915, found 466.136900.

Example 218

1-(3-Aminomethyl-4-methyl)phenyl-5-[(2'-aminosulfonyl-[1,1']-biphen-4-yl)aminocarbonyl]-3-methylpyrazole, Trifluoroacetic Acid Salt
Part A: To a cold (0° C.) acidic (Con HCl, 100 mL) solution of 2-methyl-4-amino-benzonitrile (10 g, 78.12 mmoL) was added sodium nitrite (8.08 g, 117.19 mmoL) previously dissolved in water (20 mL). The reaction temperature was kept cold throughout the addition of sodium nitrite. After stiring for an additional 0.5 h a solution of SnCl$_2$ in con HCl (50 mL) was added dropwise. A precipitate immediately ensued. The reaction mixture was allowed to stir at 0° C. for an additional 18 h then filtered, washed with cold water (1000 mL) followed by a solution of Petroleum ether/ether (2:1,500 mL). The residue was dried in vacuo overnight to afford a total weight of 8.15 g crude hydrazine tin salt.

Part B: The tin salt obtained in part A was stirred in glacial acetic acid (100 mL). To this solution was then added methoxy-oxime derived from ethyl 2,4-dioxovalerate (4.59 g, 24.55 mmoL). The reaction mixture was gently refluxed overnight. Acetic Acid was evaporated off and the residue was then quenched with water (200 mL). The organics were extracted with ethyl acetate (2×100 mL) washed with saturated sodium bicarbonate (2×50 mL), brine (50 mL) and dried (magnesium sulfate). Column chromatography (silica gel, ethyl acetate:hexane 2:8) then afforded the desired pyrazole carboxylate (4 g) as a pale yellow oil which crystallized on standing.

Part C: The product from part B was then subjected to the standard Weinreb trimethylaluminum coupling protocol with 2'-tert-butylaminosulfonyl-[1,1']-biphen-4-yl-amine as described previously. The crude was then subjected to silica gel column chromatography (methylene chloride:methanol, 9:1) to afford pure material in 90% yield. $^1$HNMR (CDCl$_3$) δ: 8.30 (bs, 1H), 8.13 (bd, 1H), 7.78–7.23 (m, 10H), 6.78 (s, 1H), 3.68 (s, 1H), 2.60 (s, 3H), 2.40 (s, 3H), 1.01 (s, 9H) ppm; ESI mass spectrum analysis m/z (relative intensity) 528 (M+H, 100).

Part D: The product from part D was then subjected reduction (Parr apparatus) at 50 psi hydrogen pressure in an acidic media (methanol, acetic acid) using 10% palladium on carbon overnight. The solvents were evaporated and the crude was then stirred in TFA (reflux) for 0.5 h. Evaporation of the solvents then afforded crupe benzylamine product which was then subjected to a preparative HPLC purification technique (acetonitrile:water, gradient containing 5% TFA) to afford the desired benzylamine as flaky colorless crystals. $^1$HNMR (DMSO-d$_6$) δ: 10.6 (s, 3H), 8.14 (bs, 2H), 8.01 (d, 1H), 7.68 (d, 2H), 7.64–7.54 (m, 2H), 7.38–7.26 (m, 5H), 6.91 (s, 1H), 4.07 (bd, 2H), 2.38 (s, 3H), 2.33 (s, 3H) ppm; ESI mass spectrum analysis m/z (relative intensity) 476.2 (M+H, 100).

Example 219

1-(3-Aminomethyl-4-fluoro)phenyl-5-[(2'-aminosulfonyl-[1,1']-biphen-4-yl)aminocarbonyl]-3-methylpyrazole, Trifluoroacetic Acid Salt The pyrazole compound was prepared from readily accessible 4-fluoro-3-cyano-phenylhydrazine.tin salt (obtained from the corresponding aniline) and the oxime derived from ethyl-2,4-dioxovalerate via procedures described previously. Standard Weinreb coupling of the pyrazole with 2'-tert-butylaminosulfonyl-[1,1']-biphen-4-yl-amine afforded the desired coupled amide presursor which was then subjected to the standard reductive protocol (50 psi hydrogen pressure, methanol:acetic acid) using 10% palladium on carbon. Evaporation of the solvents followed by treatment with TFA for 0.5 h and then preparative HPLC as described before afforded the title compound as colorless crystals. $^1$HNMR (DMSO-d$_6$) δ: 8.25 (bs, 3H), 8.00 (d, 1H), 7.78–7.23 (cp, 12H), 6.95 (s, 1H), 4.14 (m, 2H), 2.30 (s, 3H) ppm. ESI mass spectrum analysis m/z (relative intensity) 480.2 (M+H, 100).

Example 220

1-(3-Aminomethyl-4-chloro)phenyl-5-[(2'-aminosulfonyl-[1,1']-biphen-4-yl)aminocarbonyl]-3-methylpyrazole, Trifluoroacetic Acid Salt The pyrazole compound was prepared from readily accessible 4-chloro-3-cyano-phenylhydrazine tin salt (obtained from the corresponding aniline) and the oxime derived from ethyl-2,4-dioxovalerate via procedures described previously. $^1$HNMR (CDCl$_3$) δ: 7.78 (d, 1H), 7.86–7.55 (m, 2H), 6.86 (s, 1H), 4.24 (q, 2H), 2.35 (s, 3H), 1.28 (t, 3H) ppm; ESI mass spectrum analysis m/z (relative intensity) 290 (M+H, 100). Standard Weinreb coupling of the pyrazole obtained above with 2'-tert-butylaminosulfonyl-[1,1']-biphen-4-yl-amine afforded the desired coupled amide presursor which was then subjected to the treatment with tetrabutylammonium borohydride (1.5 equiv.) in dichloromethane for 24 h. The solvent was evaporated and the residue was then gently refluxed in TFA for 0.5 h. Evaporation of the solvent followed by preparative HPLC as described before afforded the title compound as colorless crystals: $^1$HNMR (DMSO-d$_6$) δ: 8.25 (bs, 3H), 8.00 (d, 1H), 7.78–7.23 (cp, 12H), 6.95 (s, 1H), 4.14 (m, 2H), 2.30 (s, 3H) ppm. ESI mass spectrum analysis m/z (relative intensity) 497.1 (M+H, 100).

Example 221

1-(3-Aminomethyl-4-fluoro)phenyl-5-[(2'-aminosulfonyl-3-fluoro-[1,1']-biphen-4-yl)aminocarbonyl]-3-trifluoromethylpyrazole, Trifluoroacetic Acid Salt The reduction of the benzonitrile precursor prepared as described before (10% palladium on carbon, methanol/acetic Acid at 50 psi hydrogen) afforded the title compound as colorless crystals after preparative HPLC purification and lyophilization techniques. $^1$HNMR (DMSO-d$_6$) δ: 10.68 (s, 1H), 8.27 (bs, 2H), 8.02 (dd, 1H), 7.81 (m, 1H), 7.73 (s, 1H), 7.68–7.60 (m, 4H), 7.61–7.43 (m, 3H), 7.38–7.30 (m, 2H), 7.20 (dd, 2H), 4.18 (bd, 2H) ppm; ESI mass spectrum analysis m/z (relative intensity) 551.9 (M+H, 100).

Example 222

1-(3-Aminomethyl)phenyl-5-[(2'-aminosulfonyl-3-fluoro-[1,1']-biphen-4-yl)aminocarbonyl]-3-methylpyrazole, Trifluoroacetic Acid Salt Part A: The coupling of ethyl 1-(3-cyanophenyl)-3-methyl-5-carboxylate with 2'-tert-butylaminosulfonyl-3-fluoro-[1,1']-biphen-4-yl-amine via the Weinreb protocol as described previously afforded the desired coupled amide compound. In this case 1.5 equivalents of the biphenyl analog was used to facilitate the coupling. Purification via silicagel (methylene chloride/methanol, 9/1) afforded pure amide (60%) as a pale yellow oil. $^1$HNMR (CDCl$_3$) δ: 8.35 (t, 1H), 8.15 (dd, 1H), 7.96 (m, 1H), 7.82 (s, 1H), 7.78–7.68 (m, 4H), 7.60–7.48 (m, 4H), 7.20 (m, 1H), 6.74 (s, 1H), 3.67 (s, 1H), 2.04 (s, 3H) 1.04 (s, 9H) ppm; ESI mass spectrum analysis m/z (relative intensity) 553.9 (M+Na, 100). ESI (–ve) mass spectrum analysis m/z (relative intensity) 529.9 (M–H, 100).

Part B: The product obtained from part A was then converted to the corresponding benzylamine via the reductive methodology (10% Pd/C, MeOH/AcOH at 50 psi hydrogen pressure) described previously. Evaporation of the solvent followed by standard removal of the tert-butyl group with TFA and purification via preparative HPLC techniques afforded pure title compound as colorless crystals (60%). $^1$HNMR (DMSO-d$_6$) δ: 10.42 (s, 1H), 8.20 (bs, 2H), 8.02 (dd, 1H), 7.70–7.59 (m, 4H), 7.55–7.29 (m, 6H), 7.19 (dd, 1H), 6.97 (s, 1H), 4.11 (bd, 2H), 2.50 (s, 2H) ppm; ESI mass spectrum analysis m/z (relative intensity) 480 (M+H, 100).

Example 223

1-(3-Aminomethyl)phenyl-5-[(3-fluoro-2'-methylsulfonyl-[1,1']-biphen-4-yl)aminocarbonyl]-3-trifluoromethylpyrazole, Trifluoroacetic Acid Salt Part A: The coupling of ethyl 1-(3-cyanophenyl)-3-methyl-5-carboxylate with 2'-methylsulfonyl-3-fluoro-[1,1']- biphen-4-yl-amine (previously prepared via the Suzuki coupling methodology of 2-thiomethylphenylboronic acid with 4-bromo-2-fluoro aniline)via the Weinreb protocol as described previously afforded the desired coupled amide compound. Purification via silica gel (methylene chloride/methanol, 9/1) afforded pure amide (80%) as a colorless solid. The amide was also obtaine by first coupling (Weinreb) of 2-fluoro-4-bromo-aniline with the above pyrazole carboxylate followed by Suzuki coupling with 2-thiomethyl-phenylboronic acid and oxidation to the sulfonyl derivative. $^1$HNMR (CDCl$_3$) δ: 8.39 (t, 1H), 8.20 (dd, 1H), 7.96 (bd, 1H), 7.83 (s, 1H), 7.78–7.59 (m, 5H), 7.41–7.96 7.17 (d, 1H), 6.74 (s, 1H), 2.73 (s, 3H), 2.40 (s, 3H) ppm; ESI mass spectrum analysis m/z (relative intensity) 593 (M+Na, 100). ESI (−ve) mass spectrum analysis m/z (relative intensity) 572 (M−H, 100).

Part B: Reduction of the product from part A via procedures described previously and HPLC purification afforded the desired compound as colorless crystals (70%). $^1$HNMR (DMSO-d$_6$) δ: 10.45 (s, 1H), 8.20 (bs, 3H), 8.08 (dd, 1H), 7.80–7.66 (m, 4H), 7.55–7.37 (m, 5H), 7.21 (dd, 1H), 6.98 (s, 1H), 4.12 (s, 2H), 2.94 (s, 3H), 2.50 (s, 3H) ppm; ESI mass spectrum analysis m/z (relative intensity) 479 (M+H, 100).

Example 224

1-(3-Amidinophenyl)-3-methyl-5-[(3-fluoro-4-(N-morpholino)phenyl)aminocarbonyl]pyrazole bis-Trifluoroacetate Part A. Preparation of N-(3-Fluoro-4-nitrophenyl) morpholine.

3,4-Difluoronitrobenzene (10.0 g, 62.86 mmol) was dripped into a cooled solution (0° C.) of morpholine (6.03 mL, 69.14 mmol), diisopropylamine (11.83 mL, 67.89 mmol) and 35 mL ethyl-acetate over 1.5 H. The reaction mixture was allowed to warm to ambient temperature over 48 H. Diluted reaction mixture with 25 mL methylene chloride, 100 mL ethyl acetate and 50 mL water. Separated and extracted aqueous 2×25 mL EtOAc. Combined oraganics, dried over magnesium sulfate and concentrated under reduced pressure to give a yellow solid. The crude material was recrystallized from acetone and water to give 12.55 g of a yellow crystalline solid. $^1$HNMR (DMSO-d6) δ: 7.99 (m, 2H) 7.14 (t, 1H, J=8.79 Hz) 3.71 (bt, 4H, J=4.56 Hz) 3.23 (bt, 4H, J=4.76 Hz). ESI mass spectrum analysis m/z (relative intensity) 227 (M+H).

Part B. Preparation of N-(3-Fluoro-4-aminophenyl) morpholine.

N-(3-fluoro-4-nitrophenyl)morpholine (6.01 g, 26.59 mmol) and a catalytic amount of palladium on carbon (10%) were suspended in 100 mL methanol in a Parr flask. The reaction mixture was placed on the Parr Hydrogenator at 60 psi for 2 H. The reaction mixture was passed through a Celite pad and the filtrate was concentrated under reduced pressure to give 4.50 g of N-(3-fluoro-4-aminophenyl) morpholine an off-colored solid. $^1$HNMR (DMSO-d6) δ: 6.73 (t, 1H, J=9.34), 6.28 (m, 2H), 3.64 (bt, 4H, J=4.58 Hz), 2.76 (bt, 4H, J=4.58 Hz). ESI mass spectrum analysis m/z (relative intensity) 197 (M+H, 100). $^{19}$FNMR (DMSO-d6) δ: −124.455.

Part C. Preparation of 1-(3-cyanophenyl)-3-methyl-5-((3-fluoro-4-(N-morpholino)phenyl)aminocarbonyl)pyrazole.

Dimethylaminopyridine (0.28 g, 2.25 mmol) was added to a solution of 1-(3-cyanophenyl)-3-methyl-pyrazole-5-carboxylic acid chloride (0.46 g, 1.88 mmol) and N-(3-fluoro-4-aminophenyl)morpholine (0.37 g, 1.88 mmol) in 20 mL methylene chloride. The reaction mixture was stirred at ambient temperature for 72 H and then concentrated under reduced pressure. The resulting residue was purified via flash chromatography to give 0.070 g of pure 1-(3-cyanophenyl)-3-methyl-5-((3-fluoro-4-(N-morpholino)phenyl)aminocarbonyl)pyrazole. $^1$HNMR (DMSO-d6) δ: 10.50 (s, 1H) 7.93 (s, 1H), 7.83 (d, 1H, J=7.33 Hz), 7.73 (d, 1H, J=8.79 Hz), 7.62 (t, 1H, J=7.87 Hz), 7.53 (m, 1H), 7.34 (d, 1H, J=9.15 Hz), 6.99 (t, 1H, J=9.34 Hz), 6.93 (s, 1H), 3.69 (bt, 4H, J=4.58 Hz), 2.92 (bt, 4H, J=4.58 Hz), 2.28 (s, 3H). ESI mass spectrum analysis m/z (relative intensity) 406 (M+H, 100), 833 (2M+Na). $^{19}$F NMR (dmso-d6, 300 MHz) δ: −122.081.

Part D. Preparation of 1-(3-Amidinophenyl)-3-methyl-5-((3-fluoro-4-(N-morpholino)phenyl)aminocarbonyl) pyrazole.

1-(3-Cyanophenyl)-3-methyl-5-((3-fluoro-4-(N-morpholino)phenyl)aminocarbonyl)pyrazole (0.070 g, 0.173 mmol) was dissovled in 2 mL chloroform and 2 mL ethanol at 0° C. Hydrogen chloride gas was bubbled into the reaction mixture for 1 H. The reaction mixture was allowed to warm to ambient temperature over 15 H and was concentrated under reduced pressure. The resulting solid was placed under high vacuum for 2 H. Then the crude imidate was dissolved in 2 mL ethanol and ammonium carbonate (025 g, 2.60 mmol) was added to the solution at ambient temperature. The reaction mixture was stirred for 72 H and concentrated under reduced pressure. The crude product was purified by standard HPLC methods to give 0.016 g of pure 1-(3-amidinophenyl)-3-methyl-5-((3-fluoro-4-(N-morpholino)phenyl)aminocarbonyl)pyrazole. $^1$HNMR (DMSO-d6) δ: 10.53 (s, 1H), 9.40 (s, 2H), 9.12 (s, 2H), 7.93 (d, 1H, J=1.71 Hz, 2H), 7.81 (m, 1H), 7.70 (m, 2H), 7.53 (dd, 1H, J=15 Hz), 7.35 (d, 1H, J=8.79 Hz), 7.01 (m, 2H), 3.72 (bt, 4H, J=4.52 Hz), 2.95 (bt, 4H, J=4.6 Hz), 2.29 (s, 3H). ESI mass spectrum analysis m/z (relative intensity) 423 (M+H, 100). $^{19}$FNMR (DMSO-d6) δ: −73.790 and −121.040. HRMS Calculated for C22H24N6O2F1: 423.194478, found 423.192755.

Example 225

1-(3-Aminomethylphenyl)-3-methyl-5-[(3-fluoro-4-(N-morpholino)phenyl)aminocarbonyl]pyrazole bis-Trifluoroacetate Part A. Preparation of 1-(3-Cyanophenyl)-3-methyl-5-((3'-fluoro-4'-(N-morpholino)phenyl)aminocarbonyl)pyrazole.

Dimethylaminopyridine (0.18 g, 1.47 mmol) was added to a solution of N-(cyanophenyl)-3-methyl-pyrazole-5-carboxylic acid chloride (0.30 g, 1.22 mmol) and previously described N-(3-fluoro-4-aminophenyl)morpholine (0.24 g, 1.22 mmol) in 20 mL methylene chloride. The reaction mixture was stirred at ambient temperature for 72 H and then concentrated under reduced pressure. The resulting residue was purified via flash chromatography to give 0.070 g of pure 1-(3-cyanophenyl)-3-methyl-5-((3'-fluoro-4'-(N-morpholino)phenyl)aminocarbonyl)pyrazole. $^1$HNMR (DMSO-d6) δ: 10.50 (s, 1H), 7.93 (s, 1H), 7.83 (d, 1H, J=7.33 Hz), 7.73 (d, 1H, J=8.79 Hz), 7.62 (t, 1H, J=7.87 Hz), 7.53 (m, 1H), 7.34 (d, 1H, J=9.15 Hz), 6.99 (t, 1H, J=9.34 Hz), 6.93 (s, 1H), 3.69 (bt, 4H, J=4.58 Hz), 2.92 (bt, 4H, J=4.58 Hz), 2.28 (s, 3H). ESI mass spectrum analysis m/z (relative intensity) 406 (M+H, 100) 833 (2M+Na). $^{19}$F NMR (DMSO-d6) δ: −122.078.

Part B. Preparation of 1-(3-Aminomethylphenyl)-3-methyl-5-((3'-fluoro-4'-(N-morpholino)phenyl)aminocarbonyl)-pyrazole.

1-(3-Cyanophenyl)-3-methyl-5-((3'-fluoro-4'-(N-morpholino)phenyl)aminocarbonyl)pyrazole (0.21 g, 0.519 mmol) was suspended with a catalytic amount of palladium on carbon (10%) in 15 mL methanol and 1 mL trifluoroacetic acid. The reaction mixture was placed on the Parr Hydrogenator at 60 psi for 20 H. The reaction mixture was passed through a Celite pad and the filtrate was concentrated under reduced pressure. The crude material was purified by standard HPLC methods to give pure 1-(3-aminomethylphenyl)-3-methyl-5-((3'-fluoro-4'-(N-morpholino)phenyl) aminocarbonyl)pyrazole. $^1$HNMR (DMSO-d6) δ: 10.53 (s, 1H), 8.18 (bs, 2H), 7.60 (s, 1H), 7.53 (dd, 1H, $J_1$=15.0 Hz, $J_2$=2.2 Hz), 7.44 (m, 2H), 7.33 (d, 2H, J=7.33 Hz), 6.98 (dd, 1H, $J_1$=9.3 Hz, $J_2$=9.2 Hz), 6.86 (s, 1H) 4.07 (bt, 2H, $J_1$=2.9 Hz, $J_2$=2.6 Hz), 3.69 (bt, 4H, $J_1$=4.4 Hz, $J_2$=4.8 Hz), 2.91 (bt, 4H, $J_1$=4.9 Hz, $J_2$=4.8 Hz), 2.47 (s, 3H). ESI mass spectrum analysis m/z (relative intensity) 410 (M+H, 100). $^{19}$F NMR (DMSO-d6) δ: −74.991 and −122.105. HRMS calculated for C22H25N5O2F: 410.199224, found 410.197598.

Example 226

1-(3-Aminomethylphenyl)-3-trifluoromethyl-5-((3-fluoro-4-(2-methylimidazol-1-yl)phenyl) aminocarbonyl)pyrazole bis-Trifluoroacetate Part A. Preparation of 3-Fluoro-4-(2-methylimidazol-1-yl) nitro-benzene.

2-Methylimidazole (1.0 g, 12.18 mmol) was added to a solution of 3,4-difluoronitrobenzene in 100 mL DMF. Added potassium carbonate (2.02 g, 14.61 mmol) to the reaction mixture and stirred vigorously for 24 H. Concentrated reaction mixture under reduced pressure and took up residue in 100 mL ethyl acetate. Washed organics 6×50 mL water and 3×50 mL brine solution. Dried resulting organics over magnesium sulfate and concentrated resulting organics under reduced pressure to give 1.66 g of crude 3-fluoro-4-N-(2-methylimidazol-1-yl)nitro-benzene. $^1$HNMR (dmso-d6, 300 MHz) δ: 8.42 (dd, 1H, $J_1$=2.4 Hz, $J_2$=10 Hz), 8.21 (m, 1H), 7.86 (t, 1H, J=8.4), 7.34 (s, 1H), 6.98 (s, 1H), 2.21 (s, 1H). ESI mass spectrum analysis m/z (relative intensity) 221.9 (M+H, 100). $^{19}$F NMR (DMSO-d6) δ: −118.512.

Part B. Preparation of 3-Fluoro-4-(2-methylimidazol-1-yl) aniline.

3-Fluoro-4-N-(2-methylimidazol-1-yl) nitro-benzene (1.66 g, 7.51 mmol) was added to a suspension of palladium on carbon (10%) in 30 mL menthanol. The reaction mixture was placed on the Parr Hydrogenator at 60 psi for 20 H. Filtered reaction mixture through a Celite pad and concentrated filtrate under reduced pressure to give 1.40 g of the crude 3-fluoro-4-N-(2-methylimidazol-1-yl)aniline. $^1$HNMR (dmso-d6, 300 MHz) δ: 7.02 (m, 2H), 6.83 (s, 1H), 6.43 (m, 2H), 5.70 (bs, 1H), 2.07 (s, 3H). ESI mass spectrum analysis m/z (relative intensity). $^{19}$F NMR (DMSO-d6) δ: −124.344.

Part C. Preparation of 1-(3-Cyanophenyl)-3-trifluoromethyl-5-((3'-fluoro-4'-(2-methylimidazol-1-yl) phenyl)-aminocarbonyl)pyrazole.

Dimethylaminopyridine (0.19 g, 1.56 mmol) was added to a solution of N-(3-cyanophenyl)-3-trifluoromethyl-pyrazole-5-carboxylic acid chloride (0.39 g, 1.30 mmol) and 3-fluoro-4-(2-methylimidazol-1-yl)aniline (0.25 g, 1.30 mmol) in 10 mL methylene chloride. The reaction mixture was stirred at ambient temperature for 5 H and then concentrated under reduced pressure. The resulting residue was purified via flash chromatography to give 0.16 g of pure 1-(3-cyanophenyl)-3-trifluoromethyl-5-((3'-fluoro-4'-(2-methylimidazol-1-yl) phenyl)-aminocarbonyl)pyrazole. ESI mass spectrum analysis m/z (relative intensity) 455.2 (M+H, 100).

Part D. Preparation of 1-(3-Aminomethylphenyl)-3-trifluoro-methyl-5-((3'-fluoro-4'-(2-methylimidazol-1-yl) phenyl)aminocarbonyl)pyrazole bis-Trifluoroacetate.

Standard transformation of the benzonitrile (0.16 g, 0.344 mmol) obtained in part C to the benzylamine via catalytic hydrogenation yeilded 0.050 g 1-(3-methylaminophenyl)-3-trifluoromethyl-5-((3'-fluoro-4'-(2-methylimidazol-1-yl) phenyl)aminocarbonyl)pyrazole bis-trifluoroacetate after HPLC purification. $^1$HNMR (DMSO-d6) δ: 11.25 (s, 1H), 7.91–7.52 (m, 10H), 4.12 (m, 2H), 2.43 (s, 3H). ESI mass spectrum analysis m/z (relative intensity) 459.1 (M+H, 100). HRMS (NH$_3$—CI): Calculated for C22H19N$_6$OF4: 459.155647, found 459.154688.

Example 227

1-(3-Cyanophenyl)-3-trifluoromethyl-5-((1,1']-3-biphen-4-yl)oxymethyl)pyrazole

Part A. Preparation of 1-(3-Cyanophenyl)-3-trifluoromethyl-5-(([1,1']-biphen-4-yl)oxymethyl)pyrazole.

Diethylazodicarboxylate (0.41 mL, 2.59 mmol) was dripped into a solution of previously described 1-(3-cyanophenyl)-3-trifluoromethyl-5-hydroxymethylpyrazole (0.46 g, 1.73 mmol), 4-hydroxy-[1,1']-biphenyl (0.44 g, 2.59 mmol), and triphenylphosphine (0.68 g, 2.59 mmol) in 15 mL THF over 1 H. Let reaction mixture stir for 48 h. Diluted reaction mixture with 30 mL water and extracted with ethyl acetate. Combined organics, dried over magnesium sulfate and purified crude material by flash chromatography to give 0.040 g of pure 1-(3-cyanophenyl)-3-trifluoromethyl-5-(([1,1']-biphen-4-yl)oxymethyl) pyrazole. $^1$HNMR (DMSO-d6) δ: 8.01 (m, 1H), 7.91 (m, 1H), 7.75 (m, 1H), 7.58 (m, 4H), 7.44 (m, 2H), 7.34 (m, 1H), 6.99 (m, 2H), 6.88 (s, 1H), 5.05 (s, 2H). ESI mass spectrum analysis m/z (relative intensity) 420 (M+H, 100), 437 (M+NH4, 63).

Examples 228 and 229

1-(3-Amidinophenyl)-3-trifluoromethyl-5-[([1,1']-biphen-4-yl)oxymethyl]pyrazole (Example 228) and 1-(3-Carboxamidophenyl)-3-trifluoromethyl-5-(([1, 1']-biphen-4-yl)oxymethyl)pyrazole (Example 229)

Part A. Preparation of 1-(3-Amidinophenyl)-3-trifluoromethyl-5-(([1,1']-biphen-4-yl)oxymethyl)pyrazole and 1-(3-Carboxamidophenyl)-3-trifluoromethyl-5-(([1,1']-biphen-4-yl)oxymethyl)pyrazole.

Standard Pinner-amidine transformation of the 1-(3-cyanophenyl)-3-trifluoromethyl-5-(([1,1']-biphen-4-yl) oxymethyl)pyrazole as previously described afforded 0.022 g of 1-(3-amidinophenyl)-3-trifluoromethyl-5-(([1,1']-biphen-4-yl)oxymethyl)pyrazole trifluoroacetate. $^1$HNMR (DMSO-d6) δ: 9.42 (bs, 2H), 9.16 (bs, 2H), 8.06 (s, 1H), 8.01 (d, 1H, J=8.1 Hz), 7.91 (d, 1H, J=8.1 Hz), 7.79 (t, 1H, J=8.1 Hz), 7.56 (m, 4H), 7.39 (m, 2H), 7.28 (m, 1H), 7.23 (m, 1H), 7.01 (d, 2H, J=8.79 Hz), 5.26 (s, 2H). ESI mass spectrum analysis m/z (relative intensity) 437 (M+H, 100). HRMS (NH3—CI): Calculated for C24H20N$_4$OF3: 437.158921, found 437.157809 and 0.002 g of 1-(3-carboxaminophenyl)-3-trifluoromethyl-5-(([1,1']-biphen-4-yl)oxymethyl)pyrazole after HPLC purification. $^1$HNMR (dmso-d6, 300 MHz) δ: 8.18 (s, 1H) 7.99 (d, 1H, J=7.7 Hz), 7.78 (d, 1H, J=9.2 Hz), 7.68–7.53 (m, 5H), 7.39 (t, 2H, J=7.7 Hz), 7.27 (dd, 2H, $J_1$=7.3 Hz, $J_2$=7.0 Hz), 7.18 (s, 1H), 7.01 (d, 2H, J=8.8 Hz), 5.21 (s, 2H). ESI mass spectrum analysis m/z (relative intensity) 479 (M+H+MeCN). HRMS (NH3—CI): Calculated for C24H20N4OF3: 437.15892, found 437.157809.

Examples 230 and 231

1-(3-Amidinophenyl)-3-trifluoromethyl-5-((2-fluoro-4-(N-morpholino)phenyl)aminocarbonyl)pyrazole bis-Trifluoro Acetate and 1-(3-Carboxamidophenyl)-3-trifluoromethyl-5-((2-fluoro-4-(N-morpholino)phenyl)aminocarbonyl) Pyrazole Part A. Preparation of 2-Fluoro-4-(-N-morpholino)aniline.

Morpholine (10.0 mL, 115 mmol) was added to a mixture of 4-bromo-2-fluoroaniline (1.03 g, 5.42 mmol), copper (I) bromide (0.039 g, 0.27 mmol) and potassium carbonate (1.50 g, 10.84 mmol). The reaction mixture was heated to 130° C. for 48 h, concentrated under reduced pressure and purified by flash chromotography to afford 0.11 g of pure 2-fluoro-4-(-N-morpholino)aniline. $^1$HNMR (DMSO-d6) δ: 6.73 (dd, 1H, $J_1$=8.8 Hz, $J_2$=9.9 Hz), 6.64 (dd, 1H, $J_1$=2.6 Hz, $J_2$=13.2 Hz), 6.57 (m, 1H), 3.85 (m, 4H), 3.02 (m, 4H). ESI mass spectrum analysis m/z (relative intensity) 197 (M+H, 100). $^{19}$FNMR (dmso-d6, 300 MHz) δ: −133.

Part B. Preparation of 1-(3-Cyanophenyl)-3-trifluoromethyl-5-((2'-fluoro-4'-(N-morpholino)phenyl)aminocarbonyl)pyrazole.

2-Fluoro-4-(N-morpholino)aniline (0.11 g, 0.56 mmol) in 5 mL methylene chloride was dripped into a stirring solution of N-(3-cyanophenyl)-3-trifluoromethyl-pyrazole-5-carboxylic acid chloride (0.17 g, 0.56 mmol) and dimethylaminopyridine (0.082 g, 0.67 mmol) in 10 mL methylene chloride. The reaction mixture was stirred at ambient temperature for 20 h. The reaction mixture was concentrated under reduced pressure and purified by flash chromatography to give 0.19 g of pure 1-(3-cyanophenyl)-3-trifluoromethyl-5-[(2'-fluoro-4'-(N-morpholino)phenyl)aminocarbonyl]pyrazole. $^1$HNMR (DMSO-d6) δ: 7.94 (m, 1H), 7.86 (s, 1H), 7.77 (m, 3H), 7.61 (dd, 2H, $J_1$=7.7 Hz, $J_2$=8.1 Hz), 7.12 (s, 1H), 3.85 (m, 4H), 3.14 (m, 4H).

Part C. Preparation of 1-(3-Amidinophenyl)-3-trifluoromethyl-5-((2'-fluoro-4'-(N-morpholino)phenyl)aminocarbonyl)pyrazole bis-Trifluoroacetate and 1-(3-Carboxamidophenyl)-3-trifluoromethyl-5-((2'-fluoro-4'-(N-morpholino)phenyl)aminocarbonyl)pyrazole.

Standard Pinner-amidine transformation of the 1-(3-cyanophenyl)-3-trifluoromethyl-5-((2'-fluoro-4'-(N-morpholino)phenyl)aminocarbonyl)pyrazole afforded 0.10 g of 1-(3-amidinophenyl)-3-trifluoromethyl-5-[(2'-fluoro-4'-(N-morpholino)phenyl)aminocarbonyl]pyrazole bis-trifluoroacetate. $^1$HNMR (dmso-d6, 300 MHz) δ: 10.35 (s, 1H), 9.40 (bs, 2H), 9.11 (bs, 2H), 7.96 (s, 1H), 7.87 (t, 2H), 7.72 (t, 1H), 7.67 (s, 1H), 7.27 (t, 1H), 6.84–6.71 (m, 2H), 3.70–3.66 (m, 4H), 3.09–3.06 (m, 4H). ESI mass spectrum analysis m/z (relative intensity) 476.5 (M+H, 100). HRMS (CI): Calculated for C22H21N6O2F4 477.166212, found 477.166415. $^{19}$F NMR (dmso-d6, 300 MHz) δ: −61.354, −74.772 and 0.002 g of 1-(3-carboxamidophenyl)-3-trifluoromethyl-5-((2'-fluoro-4'-(N-morpholino)phenyl)aminocarbonyl)pyrazole after HPLC purification. $^1$HNMR (DMSO-d6) δ: 10.31 (s, 1H), 8.10 (s, 1H), 7.98–7.94 (m, 2H), 7.64–7.50 (m, 2H), 7.33–7.27 (m, 1H), 6.83–6.70 (m, 2H), 3.70–3.66 (m, 4H), 3.09–3.06 (m, 4H). ESI mass spectrum analysis m/z (relative intensity) 477.5 (M+H, 100). $^{19}$F NMR (DMSO-d6) δ: −61.274, 74.363. HRMS (CI): Calculated for C22H20N5O3F4 478.150228, found 478.147507.

Example 232

1-(3-Aminomethylphenyl)-3-trifluoromethyl-5-((3-trifluoromethyl-4-(N-morpholino)phenyl)aminocarbonyl)pyrazole bis-Trifluoroacetate Part A. Preparation of 3-Trifluoromethyl-4-N-morpholinoaniline.

3-Trifluoromethyl-4-N-morpholinonitrobenzene (1.0 g, 3.62 mmol) was added to a suspension of palladium on carbon (10%) in 25 mL methanol. The reaction mixture was placed under 1 atmosphere $H_2$ at ambient temperature for 24 h. Passed reaction mixture through a Celite pad and concentrated filtrate under reduced pressure to give the desired aniline in quantitative yeild. $^1$HNMR (DMSO-d6) δ: 7.20 (d, 1H, J=7.2 Hz), 6.92 (d, 1H, J=2.6), 6.81 (dd, 1H, $J_1$=2.9 Hz, $J_2$=8.4 Hz), 3.80 (m, 4H), 3.74 (bs, 2H), 2.83 (bt, 4H, J=4.4 Hz), 3.70–3.66 (m, 4H), 3.09–3.06 (m, 4H). Ammonia CI mass spectrum analysis m/z (relative intensity) 247 (M+H, 100).

Part B. Preparation of 1-(3-Cyanophenyl)-3-trifluoromethyl-5-((3'-trifluoromethyl-4'-(N-morpholino)phenyl)aminocarbonyl)pyrazole.

Dimethylaminopyridine (0.25 g, 2.01 mmol) was added to a slight suspension of 3-trifluoromethyl-4-N-morpholinoaniline (0.41 g, 1.67 mmol) and N-(3-cyanophenyl)-3-trifluoromethyl-pyrazole-5-carboxylic acid chloride (0.50 g, 1.67 mmol) in 20 mL methylene chloride. The reaction mixture was stirred at ambient temperature for 24 h, concentrated under reduced pressure and purified by flash chromatography to give 0.38 g of pure 1-(3-cyanophenyl)-3-trifluoromethyl-5-((3'-trifluoromethyl-4'-(N-morpholino)phenyl)aminocarbonyl)pyrazole. $^1$HNMR (dmso-d6, 300 MHz) δ: 7.79 (m, 5H), 7.62 (dd, 1H, $J_1$=7.7 Hz, $J_2$=8.1 Hz), 7.38 (d, 1H, J=8.4 Hz), 7.15 (s, 1H), 3.83 (bt, 4H, J=4.4), 2.91 (bt, 4H, J=4.4 Hz). Ammonia CI mass spectrum analysis m/z (relative intensity) 510 (M+H, 100). $^{19}$F NMR (DMSO-d6) δ: −61.033 and −62.854.

Part C. Preparation of 1-(3-Amidinophenyl)-3-trifluoromethyl-5-((3'-trifluoromethyl-4'-(N-morpholino)phenyl)aminocarbonyl)pyrazole bis-Trifluoroacetate.

The 1-(3-cyanophenyl)-3-trifluoromethyl-5-((3'-trifluoromethyl-4'-(N-morpholino)phenyl)aminocarbonyl)pyrazole (0.38 g, 0.75 mmol) was transformed to the corresponding benzylamine by standard catalytic reduction as described previously to afford 0.19 g of 1-(3-amidinophenyl)-3-trifluoromethyl-5-((3'-trifluoromethyl-4'-(N-morpholino)phenyl)aminocarbonyl)-pyrazole bis-trifluoroacetate after HPLC purification. $^1$HNMR (DMSO-d6) δ: 10.92 (s, 1H), 7.99 (d, 1H, J=2.6 Hz), 7.88–7.85 (m, 1H), 7.68 (s, 1H), 7.63 (s, 1H), 7.55–7.49 (m, 4H), 4.11 (bs, 2H), 3.67–3.64 (m, 4H), 2.78 (bt, 4H, J=4.4 Hz). ESI mass spectrum analysis m/z (relative intensity) 514 (M+H, 100). $^{19}$F NMR (dmso-d6, 300 MHz) δ: −59.557, −1.305, and −74.290. HRMS (CI): Calculated for C23H22N5O2F6: 514.167770 found 514.166332.

Example 233

1-(3-Aminomethylphenyl)-3-ethyl-5-[(3-fluoro-2'-tert-butylaminosulfonyl-[1,1']-biphen-4-yl)aminocarbonyl]pyrazole Part A. Preparation of Ethyl-2,4-dioxohexanoate.

Sodium metal (16.50 g, 717.39 mmol) was dissolved in 200 mL ethanol. When the solution had cooled 2-butanone (64.26 mL, 717.39 mmol) was added to the solution. After 0.10 h diethyl oxalate (97.43 mL, 717.39 mmol) was added to the reaction mixture. Warmed reaction mixture to 65° C. for 4 h, concentrated under reduced pressure and treated with 200 mL 1.0M hydrochloric acid solution. Extracted with 200 mL EtOAc and washed organics 2×150 mL water and 2×150 mL brine solution. Dried resulting organics over magnesium sulfate, concentrated under reduced pressure and purified by flash chromatography to give 21.13 g of pure ethyl-2,4-dioxohexanoate. $^1$HNMR (CDCl$_3$) δ: 14.40 (bs, 1H), 6.38 (s, 1H), 4.40–4.32 (m, 2H), 2.54 (q, 2H, J=7.7 Hz), 1.41–1.36 (m, 3H), 1.18 (t, 3H, J=7.2 Hz).

Part B. Preparation of Ethyl (2-methylimino)-4-oxohexanoate.

Ethyl 2,4-dioxohexanoate (21.13 g, 0.12 mmol) and methoxylamine hydrochloride (10.26 g, 0.12 mmol) were added to a suspension of 3 § molecular sieves (30 g) in 500 mL anhydrous ethanol. The reaction mixture was stirred mechanically for 24 h. Then the suspension was filtered through a Celite pad and the resulting filtrate was concentrated to give the crude product. Flash chromatography of the crude material gave 6.07 g of pure ethyl (2-methylimino)-4-oxohexanoate. $^1$HNMR (DMSO-d6) δ: 4.33 (q, 2H, J=7.2 Hz), 4.06 (s, 3H), 3.71 (s, 3H), 2.51 (q, 2H, J=7.2 Hz), 1.35 (t, 3H, J=7.2 Hz), 1.08 (t, 3H, J=7.2 Hz). Ammonia CI mass spectrum analysis m/z (relative intensity) 201 (M+H, 60), 219 (M+NH4, 100).

Part C. Preparation of Ethyl (N-(3-cyanophenyl)-3-ethyl)pyrazole-5-carboxylate

To a solution of ethyl (2-methoxyimino)-4-oxohexanoate (1.0 g, 4.98 mmol) in 50 mL glacial acetic Acid was added 3-cyano-phenylhydrazine hydrochloride (0.84 g, 4.98 mmol). The reaction mixture was warmed to reflux temperature for 4 h, concentrated under reduced pressure and purified by flash chromatography to give 0.98 g of ethyl (N-(3-cyanophenyl)-3-ethyl)pyrazole-5-carboxylate. $^1$HNMR (DMSO-d6) δ: 7.77–7.76 (m, 1H), 7.72–7.68 (m, 2H), 7.56 (t, 1H, J=8.0 Hz), 6.89 (s, 1H), 4.30–4.23 (m, 2H), 2.73 (q, 2H, J=8.0 Hz), 1.33–1.27 (m, 6H). Ammonia CI mass spectrum analysis m/z (relative intensity) 270 (M+H, 100).

Part D. Preparation of 1-(3-Cyanophenyl)-3-ethyl-5-((4-bromo-2-fluorophenyl))aminocarbonyl)pyrazole.

To a solution of 4-bromo-2-fluoroaniline(2.06 g, 10.82 mmol) and ethyl (3-cyanophenyl)-3-ethyl)pyrazole-5-carboxylate (0.97 g, 3.61 mmol) in 20 mL methylene chloride was added trimethylaluminum (2.0M in hexanes, 5.41 mL, 10.82 mmol) in a dropwise fashion over 0.3 h. The reaction mixture was stirred at ambient temperature for 72 h, quenched carefully with 1.0M hydrochloric acid solution, washed 4×50 mL 1.0M hydrochloric acid solution, dried over magnesium sulfate and concentrated under reduced pressure. The resulting residue was purified by flash chromatography to afford 0.23 g of 1-(3-cyanophenyl)-3-ethyl-5-[(4-bromo-2-fluorophenyl)]aminocarbonyl)pyrazole. $^1$HNMR (DMSO-d6) δ: 8.17 (t, 1H, J=8.0 Hz), 7.82 (m, 2H), 7.71 (m, 2H), 7.56 (dd, 1H, J$_1$=8.0 Hz, J$_2$=7.7 Hz), 7.3 (m, 1H), 672 (s, 1H), 2.77 (m, 2H), 1.34 (t, 3H, J=7.7 Hz). Ammonia CI mass spectrum analysis m/z (relative intensity) 415 (M+H, 100).

Part E. Preparation of 1-(3-Cyanophenyl)-3-ethyl-5-[(3-fluoro-2-tertbutylaminosulfonyl-[1,1']-biphen-4-yl)aminocarbonyl]pyrazole.

To a nitrogen purged solution of 1-(3-cyanophenyl)-3-ethyl-5-((4-bromo-2-fluorophenyl))aminocarbonyl)pyrazole(0.23 g, 0.56 mmol), 2-tert-butylaminosulfonylphenylboronic acid(0.17 g, 0.67 mmol) and sodium carbonate(0.12 g, 1.12 mmol) in 10 mL ethanol and 20 mL toluene was added catalytic tetrakistriphenylphosphine palladium. The reaction mixture was heated to 80° C. for 15 h, concentrated under reduced pressure and purified by flash chromatography to afford 0.13 g of 1-(3-aminomethylphenyl)-3-ethyl-5-[(2'-fluoro-2-tertbutylaminosulfonyl-[1,1']-biphen-4-yl)aminocarbonyl]pyrazole. $^1$HNMR (DMSO-d6) δ: 8.36 (t, 1H, J=8.0 Hz), 8.16 (m, 1H), 7.97 (bd, 1H, J=3.0 Hz), 7.85 (s, 1H), 7.77 (d, 1H, J=8.1 Hz), 7.70 (d, 1H, J=7.8 Hz), 7.54 (m, 3H), 7.41 (dd, 1H, J$_1$=1.8 Hz, J$_2$=11.7 Hz), 7.25 (m, 2H) 6.76 (s, 1H), 3.67 (s, 1H), 2.79 (q, 2H, J=8.0 Hz), 1.36 (t, 3H, J=8.0 Hz), 1.06 (s, 9H). Ammonia CI mass spectrum analysis m/z (relative intensity) 546 (M+H, 100). $^{19}$F NMR (dmso-d6, 300 MHz) δ: −130.963.

Part F. Preparation of 1-(3-Aminomethylphenyl)-3-ethyl-5-[(3-fluoro-(2-tertbutylaminosulfonyl-[1,1']-biphen-4-yl))aminocarbonyl]pyrazole.

Standard transformation of the benzonitrile obtained in part C to the benzylamine via the catalytic reduction followed by treatment with refluxing trifluoroacetic acid converted the 1-(3-cyanophenyl)-3-ethyl-5-[(3-fluoro-2-tertbutylaminosulfonyl-[1,1']-biphen-4-yl)aminocarbonyl]pyrazole to 1-(3-aminomethylphenyl)-3-ethyl-5-[(3-fluoro-2-aminosulfonyl-[1,1']-biphen-4-yl)aminocarbonyl]pyrazole trifluoroacetate. The crude product was purified by standard HPLC purification technique. $^1$HNMR (DMSO-d6) δ: 8.01–7.98 (m, 1H), 7.63–7.56 (m, 4H), 7.45–7.25 (m, 5H), 7.16 (d, 1H, J=8.4 Hz), 6.96 (s, 1H), 3.95 (s, 2H), 266 (q, 2H, J=7.7 Hz), 1.24 (t, 3H, J=7.7 Hz). ESI mass spectrum analysis m/z (relative intensity) 493.9 (M+H, 100). HRMS (CI): Calculated for C25H24N5O3FS 493.158390, found 493.156279.

Example 234

1-(3-Aminomethylphenyl)-3-ethyl-5-((3-fluoro-2'-methylsulfonyl-[1,1']-biphen-4-yl))aminocarbonyl) pyrazole Trifluoroacetate Part A. Preparation of 1-(3-Cyanophenyl)-3-ethyl)pyrazole-5-carboxylic Acid Chloride.

To a chilled solution (0° C.) of ethyl 1-(3-cyanophenyl)-3-ethyl)pyrazole-5-carboxylate (7.13 g, 26.51 mmol) in 100 mL water and 150 mL tetrahydrofuran was added lithium hydroxide (1.33 g, 31.81 mmol). The reaction mixture was allowed to warm to ambient temperature overnight and was concentrated under reduced pressure. The resulting aqueous solution was washed 3×100 mL diethylether and acidified with concentrated hydrochloric acid solution to give a white precipitate that was isolated by vacuum filtration. The white solid was place under high vacuum for 24 h and a portion (0.31 g, 1.27 mmol) was treated with oxalyl chloride (0.17 mL, 1.90 mmol) and dimethylformamide (0.1 mL) in 10 mL methylene chloride. After 24 h at ambient temperature the reaction mixture was concentrated and the resulting solid was placed under high vacuum to give the crude 1-(3-cyanophenyl)-3-ethyl)pyrazole-5-carboxylic acid chloride. The crude acid chloride was used without further purification.

Part B. Preparation of 1-(3-Cyanophenyl)-3-ethyl-5-((3-fluoro-2'-methylsulfonyl-[1,1']-biphen-4-yl)aminocarbonyl) pyrazole.

To a solution of 2-fluoro-2'-methylsulfonylphenyl)aniline hydrochloride(0.38 g, 1.27 mmol) and crude 1-(3-cyanophenyl)-3-ethyl)pyrazole-5-carboxylic acid chloride (1.27 mmol) in 10 mL dichloromethane was added dimethylaminopyridine (0.34 g, 2.79mmol). The reaction mixture was stirred at ambient temperature for 24 h, concentrated under reduced pressure and purified by flash chromatography to afford 0.23 g of 1-(3-cyanophenyl)-3-ethyl-5-((2'-fluoro-2-methylsulfonyl-[1,1]-biphen-4-yl))aminocarbonyl) pyrazole. $^1$HNMR (DMSO-d6) δ: 10.42 (s, 1H), 8.06 (dd, 1H,J$_1$=2.0 Hz,J$_2$=8.0 Hz), 7.95–7.94 (m, 1H), 7.85–7.60 (m, 6H), 7.42–7.32 (m, 2H), 7.20 (dd, 1H, J$_1$=2.0 Hz, J$_2$=8.0 Hz), 7.08 (s, 1H), 2.89 (s, 3H), 2.67 (q, 2H, J=7.7 Hz), 1.24 (t, 3H, J=7.7 Hz). Ammonia CI mass spectrum analysis m/z (relative intensity) 489 (M+H, 100).

Part C. Preparation of 1-(3-Aminomethylphenyl)-3-ethyl-5-(3-fluoro-2'-methylsulfonyl-[1,1']-biphen-4-yl)aminocarbonyl) pyrazole.

To a suspension of 1-(3-cyanophenyl)-3-ethyl-5-((2'-fluoro-2'-methylsulfonyl-[1,1']-biphen-4-yl)aminocarbonyl) pyrazole (0.103 g, 0.211 mmol) and cobalt chloride (0.003 g, 0.021 mmol) in 10 mL methanol was added sodium borohydride (0.016 g, 0.422 mmol). After 1H additional sodium borohydride (0.016 g, 0.422 mmol) was added. Let reaction mixture stir for 2 h. Then concentrated reaction mixture under reduced pressure and took up resulting residue in 1.0M hydrochloric acid solution to give a white precipitate. Isolated precipitate by vacuum filtration and purified solid by HPLC to give 0.030 g of pure 1-(3-aminomethylphenyl)-3-ethyl-5-(3-fluoro-2'-methylsulfonyl-[1,1']-biphen-4-yl)aminocarbonyl)pyrazole trifluoroacetate. $^1$HNMR (DMSO-d6) δ: 10.45 (s, 1H) 8.06 (dd, 1H,$J_1$=2.0 Hz, $J_2$=8.0 Hz), 7.77–761 (m, 5H), 7.47–7.31 (m, 4H), 7.21–7.17 (m, 1H), 7.01 (s, 1H), 4.07–4.06 (m, 2H), 2.90 (s, 3H), 2.66 (q, 2H,J=7.7 Hz), 1.24 (t, 3H,J=7.7 Hz). ESI mass spectrum analysis m/z (relative intensity) 493 (M+H, 100). HRMS Calculated for C26H26N4O3FS: 493.170966, found 493.172100.

Example 235

1-(3-Aminomethylphenyl)-3-ethyl-5-[(2-fluoro-4-(2-methylsulfonylimidazol-1-yl)phenyl)]aminocarbonyl)pyrazole Trifluoroacetate Part A. Preparation of 4-(2'-Methylthioimidazol-1-yl) nitrobenzene.

To a stirred suspension of potassium carbonate(40.07 g, 22.60 mmol) in 175 mL acetone was added 1-(4-nitrophenyl) imidazoline-2-thione(5.0 g, 22.60 mmol). Dripped iodomethane (1.44 mL, 23.05 mmol) into reaction mixture and heated to reflux temperature for 20 h. Concentrated reaction mixture under reduced pressure and took up resulting solid in 200 mL water. Extracted aqueous three times with ethyl acetate. Combined extracts, dried over magnesium sulfate and concentrated in vacuo to give 5.29 g of crude 4-(2'-methylthioimidazol-1-yl)nitrobenzene. $^1$HNMR (DMSO-d6) δ: 10.45 (s, 1H) 8.06 (dd, 1H, $J_1$=2.0 Hz, $J_2$=8.0 Hz), 8.38–8.33 (m, 2H), 7.77–7,72 (m, 2H), 7.61 (d, 1H, J=1.5 Hz), 7.14 (d, 1H, J=1.5 Hz), 2.52 (s, 3H), ESI mass spectrum analysis m/z (relative intensity) 236 (M+H, 100).

Part B. Preparation of 4-(2'-Methylsulfonylimidazol-1-yl) nitrobenzene.

To a cooled solution (0° C.) of 4-(2'-methylthioimidazol-1-l)nitrobenzene (1.05 g, 4.47 mmol) in 40 mL dichloromethane was added meta-chloroperoxybenzoic acid(1.54 g, 8.94 mmol). The reaction mixture was allowed to warm to ambient temperature over 20H. Washed reaction mixture 3×75 mL 1.0M sodium hydroxide solution. Dried resulting organics over magnesium sulfate and concentrated under reduced pressure to give 0.98 g of crude 4-(2'-methylsulfonylimidazol-1-yl)nitrobenzene. $^1$HNMR (DMSO-d6) δ: 8.39 (d, 2H, J=8.7 Hz), 7.73 (d, 2H J=8.7 Hz), 7.28–7.23 (m, 2H), 3.43 (s, 3H). Ammonia CI mass spectrum analysis m/z (relative intensity) 268 (M+H, 100).

Part C. Preparation of 4-(2'-Methylsulfonylimidazol-1-yl) aniline.

Standard catalytic reduction of 4-(2'-methylsulfonylimidazol-1-yl)nitrobenzene (0.98 g, 3.67 mmol) with palladium on carbon(10%) in methanol gave 0.80 g of 4-(2'-methylsulfonylimidazol-1-yl)aniline. $^1$HNMR (CDCl3) δ: 7.24 (d, 2H,J=8.7 Hz), 7.15 (dd, 2H,$J_1$=18.3 Hz, $J_2$=18.6 Hz), 6.72 (d, 2H, J=8.7 Hz), 3.30 (s, 3H). Ammonia CI mass spectrum analysis m/z (relative intensity) 238 (M+H, 100).

Part C. Preparation of 1-(3-Cyanophenyl)-3-ethyl-5-((2'-fluoro-4'-(2-methylsulfonylimidazol-1-yl)phenyl)) aminocarbonyl)pyrazole.

Dimethylaminopyridine (0.42 g, 3.48 mmol) was added to a solution of 4-(2'-methylsulfonylimidazol-1-yl)aniline(0.37 g, 1.58 mmol) and 1-(3-cyanophenyl)-3-ethyl)pyrazole-5-carboxylic acid chloride (1.58 mmol) in 15 mL dichloromethane. The reaction mixture was stirred at ambient temperature for 15H, concentrated under reduced pressure and purified by flash chromatography to give 0.37 g of 1-(3-cyanolphenyl)-3-ethyl-5-[(2'-fluoro-4'-(2-methylsulfonylimidazol-1-yl)phenyl)]aminocarbonyl) pyrazole. ESI mass spectrum analysis m/z (relative intensity) 460.9 (M+H, 100), 482.9 (M+Na).

Part D. Preparation of 1-(3-Aminomethylphenyl)-3-ethyl-5-[(2'-fluoro-4'-(2-methylsulfonylimidazol-1-yl)phenyl)] aminocarbonyl)pyrazole.

Standard catalytic reduction of 1-(3-cyanophenyl)-3-ethyl-5-[(2'-fluoro-4'-(2-methylsulfonylimidazol-1-yl) phenyl)]aminocarbonyl)pyrazole with palladium on carbon (10%) in methanol gave 0.10 g of 1-(3-aminomethylphenyl)-3-ethyl-5-[(2'-fluoro-4'-(2-methylsulfonylimidazol-1-yl)phenyl)]aminocarbonyl) pyrazole trifluoroacetate after HPLC purification. $^1$HNMR (CDCl$_3$, 300 MHz) δ: 10.78 (s, 1H), 7.76 (d, 2H, J=8.8 Hz), 7.63 (d, 2H, J=1.1 Hz), 7.49–7.35 (m, 5H) 7.26 (d, 1H, J=1.1 Hz), 6.98 (s, 1H), 4.08 (s, 2H), 3.35 (s, 3H), 2.67 (q, 2H, J=7.7 Hz), 1.24 (t, 3H, J=7.7 Hz). ESI mass spectrum analysis m/z (relative intensity) 464.9 (M+H, 100). HRMS calculated for C23H25N6O3S: 465.170886, found 465.172332.

Example 236

1-[(6-(Aminomethyl)pyrid-2-yl)]-3-methyl-5-[(2'-aminosulfonyl-[1,1']-biphen-4-yl)aminocarbonyl] pyrazole, Trifluoroacetic Acid Salt.

Part A. Preparation of Ethyl 1-[Pyrid-2-yl]-3-methylpyrazole-5-carboxylate.

To a solution of 2-hydrazinopyridine (0.68 g, 6.24 mmol) in 15 mL of glacial acetic acid was added ethyl 2-methoxyimino-4-oxopentanoate (0.90 g, 4.80 mmol). The resulting mixture was allowed to stir at 100° C. for 2 h. The reaction mixture was cooled to room temperature and concentrated in vacuo. The residue was diluted with ethyl acetate, washed with saturated aq sodium carbonate and brine, dried (MgSO$_4$) and concentrated in vacuo. The residue was purified by flash chromatography (elution with 3:1 hexanes/ethyl acetate) to give 0.4 g (36%) of the title compound. $^1$HNMR (CDCl$_3$) δ: 8.45 (dd, 1H), 7.82 (td, 1H), 7.61 (d, 1H), 7.29 (dd, 1H), 6.70 (s, 1H), 4.25 (q, 2H), 2.38 (s, 3H), 1.23 (t, 3H). Ammonia CI mass spectrum analysis m/z (relative intensity) 232 (M+H, 100).

Part B. Preparation of Ethyl 1-[6-Cyanopyrid-2-yl]-3-methylpyrazole-5-carboxylate.

To a solution of of ethyl 1-[pyrid-2-yl]-3-methylpyrazole-5-carboxylate (1.4 g, 6.05 mmol) in 10 mL of glacial acetic acid was added 6 mL (large excess) of 30% H$_2$O$_2$. The reaction was stirred at 100° C. for 3 h and then was allowed to cool to room temperature and was poured into saturated aq sodium carbonate. The resulting mixture was extracted with ethyl acetate and the combined organic extracts were washed with brine, dried (MgSO$_4$) and concentrated in vacuo. The resulting crude N-oxide was dissolved in 20 mL of tetrahydrofuran and then there was added trimethylsilyl cyanide (2.4 mL, 18.2 mmol) followed by dimethylcarbamoyl chloride (1.7 mL, 18.2 mmol). The reaction was allowed to stir at 65° C. for 18 h. The reaction was allowed to cool and was diluted with ethyl acetate, washed with saturated aq sodium bicarbonate and brine, dried (MgSO$_4$) and concentrated in vacuo. The residue was purified by flash chromatography (elution with 3:1 hexanes/ethyl acetate) to give 0.66 g (43%) of the title compound as a white solid. $^1$HNMR (CDCl$_3$) δ: 7.98 (m, 2H), 7.61 (td, 1H), 6.67 (s, 1H), 4.38 (q, 2H), 2.38 (s, 3H), 1.32 (t, 3H). Ammonia CI mass spectrum analysis m/z (relative intensity) 257 (M+H, 100).

Part C. Preparation of 1-[(6-Cyanopyrid-2-yl)]-3-methyl-5-[(2'-tert-butylaminosulfonyl-[1,1']-biphen-4-yl)aminocarbonyl]pyrazole.

To a solution of (2'-tert-butylaminosulfonyl-[1,1']-biphen-4-yl)amine (0.24 g, 0.78 mmol) in 20 mL of methylene chloride at 25° C. was added trimethylaluminum (1.2 mL of a 2.0 M solution in toluene, 2.34 mmol) dropwise. The resulting solution was allowed to stir until no more gas evolution was observed (~15 min). To this solution was added ethyl 1-[6-cyanopyrid-2-yl]-3-methylpyrazole-5-carboxylate (0.20 g, 0.78 mmol) as a solution in methylene chloride. The resulting solution was stirred at 40° C. for 3 h and then was cooled to 25° C. and quenched by the addition of saturated aq NH$_4$Cl. After diluting with ethyl acetate, the layers were separated and the organic layer was washed with brine, dried (MgSO$_4$) and concentrated in vacuo. The residue was purified by flash chromatography (elution with 1:1 hexanes/ethyl acetate) to afford 0.15 g (38%) of the title compound as a solid. $^1$HNMR (CDCl$_3$) δ: 10.63 (s, 1H), 8.20 (t, 1H), 8.08 (d, 1H) 7.98 (m, 2H), 7.64 (d, 2H), 7.59 (td, 1H), 7.51 (td, 1H), 7.34 (d, 2H), 7.28 (d, 1H), 6.80 (s, 1H), 6.46 (s, 1H), 2.31 (s, 3H), 0.97 (s, 9H). ESI mass spectrum analysis m/z (relative intensity) 515.1 (M+H, 100).

Part D. Preparation of 1-[(6-(Aminomethyl)pyrid-2-yl)]-3-methyl-5-[(2'-aminosulfonyl-[1,1']-biphen-4-yl)aminocarbonyl]pyrazole, Trifluoroacetic acid Salt.

To a solution of 1-[(6-cyanopyrid-2-yl)]-3-methyl-5-[(2'-tert-butylaminosulfonyl-[1,1']-biphen-4-yl)aminocarbonyl]pyrazole (0.14 g, 0.27 mmol) in 15 mL of absolute ethanol was added 12 N HCl (0.023 mL, 0.27 mmol) and 10% Pd/C catalyst (30 mg). The resulting mixture was stirred under 1 atm of H$_2$ for 18 h. The mixture was then filtered through a pad of celite and was concentrated in vacuo. The residue was taken up in 3 mL of trifluoroacetic acid and stirred at 80° C. for 20 min. This solution was cooled and concentrated in vacuo. The residue was purified by prep HPLC (C18 reverse phase column, elution with a H$_2$O/CH$_3$CN gradient with 0.5% TFA) and lyophilized to afford 70 mg (45%) of the title compound as a white powder. $^1$HNMR (DMSO-d6) δ 10.56 (s, 1H), 8.18 (broad s, 3H), 8.02 (m, 2H), 7.64 (m, 4H), 7.58 (m, 2H), 7.45 (d, 1H), 7.33 (d, 2H), 7.27 (m, 2H), 6.84 (s, 1H), 4.02 (broad q, 2H), 2.30 (s, 3H). ESI mass spectrum analysis m/z (relative intensity) 462.9 (M+H, 100).

Example 237

1-[(6-(N-Hydroxyamidino)pyrid-2-yl)]-3-methyl-5-[(2'-tert-butylaminosulfonyl-[1,1']-biphen-4-yl)aminocarbonyl]pyrazole Preparation of 1-[(6-(N-Hydroxyamidino)pyrid-2-yl)]-3-methyl-5-[(2'-tert-butylaminosulfonyl-[1,1']-biphen-4-yl)aminocarbonyl]pyrazole.

To a solution of 1-[(6-cyanopyrid-2-yl)]-3-methyl-5-[(2'-tert-butylaminosulfonyl-[1,1']-biphen-4-yl)aminocarbonyl]pyrazole (0.11 g, 0.21 mmol) in 5 mL of absolute ethanol was added hydroxylamine hydrochloride (0.054 g, 0.77 mmol) and sodium carbonate (0.039 g, 0.36 mmol). This mixture was stirred at 80° C. for 1 h and then was allowed to cool. The mixture was diluted with ethyl acetate, washed with brine, dried (MgSO$_4$) and concentrated in vacuo. The solid residue was triturated with ether to afford 80 mg (68%) of the title compound as a white solid. $^1$HNMR (CDCl$_3$) δ: 10.79 (s, 1H), 9.95 (s, 1H), 8.0 (dd, 1H), 7.95 (t, 1H), 7.80 (d, 1H), 7.68 (m, 3H), 7.59 (td, 1H), 7.51 (td, 1H), 7.35 (m, 3H), 6.68 (s, 1H), 6.65 (s, 1H), 5.43 (broad s, 2H), 2.31 (s, 3H), 0.96 (s, 9H). ESI mass spectrum analysis m/z (relative intensity) 548.1 (M+H, 100).

Example 238

1-[(6-Amidinopyrid-2-yl)]-3-methyl-5-[(2'-aminosulfonyl-[1,1']-biphen-4-yl)aminocarbonyl]pyrazole, Trifluoroacetic Acid Salt Preparation of 1-[(6-Amidinopyrid-2-yl)]-3-methyl-5-[(2'-aminosulfonyl-[1,1']-biphen-4-yl)aminocarbonyl]pyrazole, Trifluoroacetic Acid Salt.

To a solution of 1-[(6-cyanopyrid-2-yl)]-3-methyl-5-[(2'-tert-butylaminosulfonyl-[1,1']-biphen-4-yl)aminocarbonyl]pyrazole (0.28 g, 0.54 mmol) in 20 mL of absolute ethanol was added triethylamine (0.38 mL, 2.7 mmol). Hydrogen sulfide gas was bubbled slowly through this solution (excess H$_2$S was scrubbed through Chlorox bleach) for 20 min. The flask was stoppered tightly and allowed to stand at room temperature overnight. The solution was concentrated in vacuo. The crude thioamide residue was dissolved in 10 mL of acetone and then there was added 2 mL (large excess) of methyl iodide. The resulting solution was stirred at 60° C. for 2 h and then was cooled and concentrated in vacuo. The residue was dissolved in methanol and then there was added ammonium acetate (1.8 mL of a 1.5 M solution in methanol, 2.7 mmol). The resulting mixture was stirred at 60° C. for 2 h and then was cooled and concentrated in vacuo. The residue was dissolved in trifluoroacetic acid and stirred at 80° C. for 20 min and then was allowed to cool and was concentrated in vacuo. The residue was purified by prep HPLC (C18 reverse phase column, elution with a H$_2$O/CH$_3$CN gradient with 0.5% TFA) and lyophilized to afford 78 mg (24%) of the title compound as a white powder. $^1$HNMR (d6-DMSO) δ: 10.70 (s, 1H), 9.36 (broad s, 2H), 9.04 (broad s, 2H), 8.31 (t, 1H), 8.13 (m, 2H), 8.00 (d, 1H), 7.63 (d, 2H), 7.58 (m, 2H), 7.34 (d, 2H), 7.28 (d, 1H), 7.23 (broad s, 2H), 6.87 (s, 1H), 2.33 (s, 3H). ESI mass spectrum analysis m/z (relative intensity) 476.2 (M+H, 100). HRMS: calculated for C$_{23}$H$_{22}$N$_7$O$_3$S: 476.150485; Observed: 476.152830.

Example 239

1-[6-Amidinopyrid-2-yl]-3-methyl-5-[3-fluoro-(2'-methylsulfonyl-[1,1']-biphen-4-yl)aminocarbonyl]pyrazole, Trifluoroacetic acid Salt Part A. Preparation of Ethyl 1-[(6-thiocarbonylamino)pyrid-2-yl]-3-methylpyrazole-5-carboxylate.

To a solution of ethyl 1-[6-cyanopyrid-2-yl]-3-methylpyrazole-5-carboxylate in 100 mL of absolute ethanol was added triethylamine (2.7 mL, 19.4 mmol). Hydrogen sulfide gas was slowly bubbled through this solution (excess H$_2$S was scrubbed through Chlorox bleach) for 20 min. The flask was stoppered tightly and allowed to stand at room temperature overnight. The solution was concentrated in vacuo. The residue was dissolved in ethyl acetate, washed with 10% aq HCl and brine; dried (MgSO$_4$) and concentrated in vacuo to afford 1.1 g (97%) of the title compound which was sufficiently pure to be used without purification. $^1$HNMR (CDCl$_3$) δ: 9.01 (broad s, 1H), 8.55 (dd, 1H), 7.92 (t, 1H), 7.82 (dd, 1H), 7.58 (broad s, 1H), 6.66 (s, 1H), 4.22

(q, 2H), 2.33 (s, 3H), 1.18 (t, 3H). ESI (–ve) mass spectrum analysis m/z (relative intensity) 288.9 (M–H, 100).
Part B. Preparation of 1-[(6-Thiocarbonylamino)pyrid-2-yl]-3-methyl-5-[(1-bromo-3-fluorophenyl-4-yl)aminocarbonyl]pyrazole.

To a solution of 4-bromo-2-fluoroaniline (2.17 g, 11.4 mmol) in 150 mL of methylene chloride was added trimethylaluminum (11.4 mL of a 2M solution in toluene, 22.8 mmol) dropwise. This solution was stirred until gas evolution ceased (15–20 min) and then there was added ethyl 1-[(6-thiocarbonylamino)pyrid-2-yl]-3-methylpyrazole-5-carboxylate (1.1 g, 3.8 mmol) in methylene chloride. The resulting solution was allowed to stir at reflux for 18 h and then it was cooled and quenched by dropwise addition of saturated aq ammonium chloride. The mixture was diluted with ethyl acetate, the layers were separated, the organic layer was washed with water and brine, dried (MgSO$_4$) and concentrated in vacuo. The solid residue was purified by trituration with ether and the remaining solid was dried in vacuo to afford 1.26 g (76%) of the title compound. $^1$HNMR (d6-DMSO) δ: 10.62 (broad s, 1H), 10.20 (broad s, 1H), 8.84 (broad s, 1H), 8.33 (dd, 1H), 8.12 (t, 1H), 7.98 (d, 1H), 7.72 (t, 1H), 7.58 (dd, 1H), 7.39 (d, 1H), 6.75 (s, 1H), 2.30 (s, 3H) ppm.
Part C. Preparation of 1-[(6-(N-tert-Butyloxycarbonyl)aminoiminomethyl)pyrid-2-yl]-3-methyl-5-[(1-bromo-3-fluorophenyl-4-yl)aminocarbonyl]pyrazole.

To a solution of 1-[(6-thiocarbonylamino)pyrid-2-yl]-3-methyl-5-[(1-bromo-3-fluorophenyl-4-yl)aminocarbonyl]pyrazole (1.09 g, 2.51 mmol) in 100 mL of acetone was added 12 mL (large excess) of methyl iodide. The resulting solution was stirred at 60° C. for 2 h and then was cooled and concentrated in vacuo. The residue was dissolved in methanol and then there was added ammonium acetate (8.3 mL of a 1.5 M solution in methanol, 12.5 mmol). The resulting mixture was stirred at 60° C. for 2 h and then was cooled and concentrated in vacuo to afford 1.0 g of the crude amidine. To 0.5 g (1.2 mmol) of this residue in 10 mL of pyridine was added di-tert-butyl dicarbonate (0.52 g, 2.4 mmol) and 49-dimethylaminopyridine (0.29 g, 2.4 mmol). This mixture was allowed to stir at room temperature for 18 h and then was concentrated in vacuo. The residue was dissolved in ethyl acetate, washed with water, 10% aq HCl and brine, dried (MgSO$_4$) and concentrated in vacuo. The residue was purified by flash chromatography (elution with 1:1 hexanes/ethyl acetate) to afford 0.15 g (24%) of the title compound. $^1$HNMR (CDCl$_3$) δ: 9.08 (broad s, 1H), 8.22 (m, 3H), 7.95 (d, 1H), 7.85 (t, 1H), 7.25 (m, 2H), 6.53 (s, 1H), 2.33 (s, 3H), 1.49 (s, 9H) ppm. ESI mass spectrum analysis m/z 516.9/518.9 (M+H)+.
Part D. Preparation of 1-[(6-(N-tert-Butyloxycarbonyl)aminoiminomethyl)pyrid-2-yl]-3-methyl-5-[3-fluoro-(2'-thiomethoxy-[1,1']-biphen-4-yl)aminocarbonyl]pyrazole.

To a solution of 1-[(6-(N-tert-butyloxycarbonyl)aminoiminomethyl)pyrid-2-yl]-3-methyl-5-[(1-bromo-3-fluorophenyl-4-yl)aminocarbonyl]pyrazole (0.15 g, 0.29 mmol) in 15 mL of benzene was added 2-thiomethoxyphenyl boronic acid (0.07 g, 0.42 mmol), tetrabutylammonium bromide (0.01 g, 0.03 mmol), sodium carbonate (0.09 g, 0.85 mmol) and 0.80 mL of water. This mixture was degassed with a stream of nitrogen and then tetrakis triphenylphosphine palladium (0.06 g, 0.05 mmol) was added The mixture was stirred at 80° C. for 24 h. The reaction was allowed to cool and then was diluted with ethyl acetate, washed with saturated aq sodium bicarbonate and brine, dried (MgSO$_4$), filtered through celite and concentrated in vacuo to afford 0.157 g (95%) of the title compound. This material was sufficiently pure to be used without purification. $^1$HNMR (CDCl$_3$) δ: 8.40 (t, 1H), 8.02 (broad s, 2H), 7.60–7.20 (m, 10H), 6.56 (s, 1H), 2.34 (s, 3H), 2.33 (s, 3H), 1.46 (s, 9H) ppm. ESI mass spectrum analysis m/z (relative intensity) 560.9 (M+H, 100).
Part E. Preparation of 1-[6-Amidinopyrid-2-yl]-3-methyl-5-[3-fluoro-(2'-methylsulfonyl-[1,1']-biphen-4-yl)aminocarbonyl]pyrazole, Trifluoroacetic Acid Salt.

To a solution of 1-[(6-(N-tert-butyloxycarbonyl)aminoiminomethyl)pyrid-2-yl]-3-methyl-5-[3-fluoro-(2'-thiomethoxy-[1,1']-biphen-4-yl)aminocarbonyl]pyrazole (0.157 g, 0.28 mmol) in 20 mL of methylene chloride was added 3-chloroperoxybenzoic acid (0.17g, 0.99 mmol). The resulting mixture was stirred at room temperature for 24 h and then was diluted with ethyl acetate, washed with saturated aq sodium metabisulfite, saturated aq sodium bicarbonate and brine, dried (MgSO$_4$) and concentrated in vacuo. The residue was dissolved in 5 mL of trifluoroacetic acid and stirred at 80° C. for 20 min. The reaction was cooled and concentrated in vacuo. The residue was purified by prep HPLC (C18 reverse phase column, elution with a H$_2$O/CH$_3$CN gradient with 0.5% TFA) and lyophilized to afford 80 mg (47%) of the title compound as a white powder. $^1$HNMR (d6-DMSO) δ: 10.52 (s, 1H), 9.42 (broad s, 2H), 9.08 (broad s, 2H), 8.31 (t, 1H), 8.12 (m, 3H), 7.78–7.73 (m, 3H), 7.42 (d, 1H), 7.32 (d, 1H), 7.20 (d, 1H), 6.89 (s, 1H), 2.89 (s, 3H), 2.33 (s, 3H) ppm. ESI mass spectrum analysis m/z (relative intensity) 493.9 (M+H, 100).

Example 240

1-(3-Aminomethylphenyl)-3-methyl-5-((2-methoxy-4-(N-morpholino)phenyl)aminocarbonyl)pyrazole Trifluoroacetate Part A: Preparation of 1-(3-N-(Benzyloxycarbonyl)aminophenyl)-3-methyl-5-((2-methoxy-4-(N-morpholino)phenyl)aminocarbonyl)pyrazole.

To a solution of 1-(3-N-(benzyloxycarbonyl)aminophenyl)-3-methyl-pyrazole-5-carboxylic acid (183 mg, 0.5 mmol) in DMF (10 mL) was added PyBrop (bromo-tris-pyrrolidino-phosphonium hexafluorophosphate, 280 mg, 0.6 mmol) and the resulting solution was stirred at room temperature for 10 min. N,N-diisopropylethylamine (1 mL) was added and stirred for additional 10 min. To this solution was then added 2-methoxy-4-N-morpholine-aniline (125 mg, 0.6 mmol) and the resulting mixture was stirred at 60° C. for 3 hours. After the mixture was cooled to room temperature, to it was added DOWEX (50W×8–100 ion-exchange resin, 0.5 g) and stirred for additional 0.5 h. The mixture was filtered and the residue was washed with EtOAc (50 mL). The filtrate was washed with brine (5×10 mL), dried over MgSO$_4$, and purified by column chromatography with EtOAc to give the product (261 mg, 95%). $^1$HNMR (CDCl$_3$) δ: 7.42–7.31 (m, 10H), 7.03 (s, 1H), 6.94 (d, J=8.8 Hz, 1H), 6.50 (d, J=2.6 Hz, 1H), 6.42 (dd, J=8.4 Hz, J=2.6 Hz, 1H), 4.70 (s, 1H), 4.41 (d, J=3.9 Hz, 2H), 3.84 (t, J=4.8 Hz, 4H), 3.78 (s, 3H), 3.09 (t, J=4.8 Hz, 4H), 2.35 (s, 3H) ppm. ESI mass spectrum analysis m/z (relative intensity) 556 (M+H, 100).
Part B: Preparation of 1-(3-Aminophenyl)-3-methyl-5-((2-methoxy-4-(N-morpholino)phenyl)aminocarbonyl)pyrazole Trifluoroacetate.

To 1-(3-N-(benzyloxycarbonyl)aminophenyl)-3-methyl-5-((2-methoxy-4-(N-morpholino)phenyl)aminocarbonyl)pyrazole (100 mg, 0.18 mmol) was added trifluoroacetic acid (5 mL) and the resulting solution was refluxed for 4 hours. The solution was concentrated and purified on TLC plate with ethyl acetate to a viscous liquid (60 mg, 80%).

¹HNMR (CD₃OD) δ: 7.58 (s, 1H), 7.53–7.48 (m, 3H), 7.06 (s, 1H), 6.91 (d, J=8.4 Hz, 1H), 6.63 (d, J=2.6 Hz, 1H), 6.47 (dd, J=8.8 Hz, J=2.6 Hz, 1H), 4.15 (s, 2H), 3.79 (t, J=4.8 Hz, 4H), 3.76 (s, 3H), 3.09 (t, J=4.8 Hz, 4H), 2.35 (s, 3H) ppm. ESI mass spectrum analysis m/z (relative intensity) 422 (M+H, 100).

Example 241

1-(3-Aminomethylphenyl)-3-methyl-5-[4'-(3"-methyl-5"-oxo-3'-pyrazolin-2"-yl)-phenyl) aninocarbonyl]pyrazole Trifluoroacetate Part A: Preparation of 1-(3-N-(Benzyloxycarbonyl) aminophenyl)-3-methyl-5-((4'-(3"-methyl-5"-oxo-3"-pyrazolin-2'-yl)-phenyl)aminocarbonyl)-pyrazole.

To a solution of 1-(3-N-(benzyloxycarbonyl) aminophenyl)-3-methyl-pyrazole-5-carboxylic acid (150 mg, 0.41 mmol) in DMF (5 mL) was added PyBrop (bromo-tris-pyrrolidino-phosphonium hexafluorophosphate, 233 mg, 0.5 mmol) and the resulting solution was stirred at room temperature for 10 min. To this solution was added N,N-dimethylpyridine (70 mg, 0.57 mmol) and stirred for an additional 10 min. 2-(4-aminophenyl)-3-methyl-3-pyrazolin-5-one (125 mg, 0.6 mmol) was added and the resulting mixture was stirred at 60° C. for 24 hours. The mixture was diluted with EtOAc (100 mL), washed with 1N HCl (10 mL) and brine (5×10 mL), dried over MgSO₄, and purified by column chromatography with EtOAc to afford the product (260 mg). ESI mass spectrum analysis m/z (relative intensity) 537.2 (M+1, 100).

Part B: Preparation of 1-(3-Aminophenyl)-3-methyl-5-((2'-methoxy-4'-(N-morpholino)phenyl)aminocarbonyl) pyrazole Trifluoroacetate.

To 1-(3-N-(benzyloxycarbonyl)aminophenyl)-3-methyl-5-((4'-(3"-methyl-5"-oxo-3"-pyrazolin-2"-yl)-phenyl) aminocarbonyl)-pyrazole (260 mg) was added trifluoroacetic acid (5 mL) and the resulting solution was refluxed for 2 hours. The solution was concentrated and purified on TLC plate with ethyl acetate to a viscous liquid (120 mg, 74.6% for two steps). ¹HNMR (CD₃OD) δ: 7.69 (d, J=8.8 Hz, 2H), 7.55 (7.55 (bs, 1H), 7.52–7.46 (m, 3H), 7.35 (d, J=8.8 Hz, 2H), 6.87 (s, 1H), 5.57 (s, 1H), 4.14 (s, 2H), 2.35 (s, 3H), 2.21 9 (s, 3H) ppm. ESI mass spectrum analysis m/z (relative intensity) 403.1 (M+H, 100).

Example 242

1-[3-(Aminomethyl)phenyl]-5-[(2'-methylsulfonyl-[1,1']-biphen-4-yl) aminocarbonyl]-3-(methylthio) pyrazole, Trifluoroacetic Acid Salt Part A: Preparation of 1,1-di(Methylthio)ethylene.

In a 2 L flask fitted with mechanical stirrer, condenser, under argon, methyl magnesium bromide (3.0 M in Et₂O, 84 mL, 252 mmol) was diluted to 1.0 M in THF (168 mL), keeping the pot temperature below 40° C. Carbon disulfide (22.6 mL, 376 mmol) in THF (23 mL) was added over 30 min., and the reaction was maintained at 40° C. for 135 min. Heat was removed and the reaction was cooled to -72° C. Lithium diisopropylamide (2.0 M in heptane, THF, and ethylbenzene, 126 mL, 252 mmol) was added over 35 min., keeping the internal temperature below -60° C. The resulting thick, dark orange-red paste was maintained near -60° C. for 160 min. Dimethyl sulfate (48 mL, 504 mmol) was added over 45 min., and the reaction-was allowed to warm to room temperature over 70 min. The mechanical stirrer was turned off, and the reaction stood at room temperature for 17 h. The resulting mixture was diluted with Et₂O (300 mL) and poured into aq. sodium bicarbonate (20%, 500 mL). An argon atmosphere was maintained for all manipulations. The layers were separated, and the organics were extracted with aq. sodium bicarbonate (25%, 200 mL), dried over MgSO₄, filtered, and concentrated to about 100 mL. The resulting oil was distilled under vacuum (70° C. head temperature, 10 Torr) to yield 25.37 g product contaminated with ethylbenzene, for an estimated yield of pure product (15.59 g, 52%). ¹HNMR (CDCl₃) δ: 5.24 (s, 2H), 2.36 (s, 6H) ppm.

Part B: Preparation of Methyl 4,4-di(Methylthio)-2-oxo-but-3-enoate.

A solution of 1,1'-di(methylthio)ethylene (19.73 g containing 9.95 g of compound, 83 mmol) in Et₂O (125 mL) was cooled to -60° C. under argon. Oxalyl chloride (5.6 mL, 64 mmol) was added over 3 min., allowing the internal temperature to reach -55° C. The reaction was warmed to -15° C. over 20 min., and dry methanol (20 mL, 494 mmol) was added over 2 min. The reaction continued to warm and stir at room temperature for 2 h. The resulting mixture was diluted with Et₂O and filtered under argon to yield a yellow solid (8.28 g, 63%). ¹HNMR (CDCl₃) δ: 6.84 (s, 1H), 3.87 (s, 3H), 2.57 (s, 3H), 2.55 (s, 3H) ppm.

Part C: Preparation of Methyl 1-(3-Cyanophenyl)-3-(methylthio)pyrazole-5-carboxylate.

A mixture of methyl 4,4-di(methylthio)-2-oxo-but-3-enoate (2.0 g, 9.7 mmol), triethylamine (1.5 mL, 10.7 mmol), and m-cyanophenylhydrazine hydrochloride (1.81 g, 10.7 mmol) were combined in dry methanol (20 mL) and heated at reflux for 47 h. The reaction was evaporated and chromatographed on silica gel (CH₂Cl₂ followed by 40% EtOAc/hexanes) to yield a partially purified intermediate (1.91 g), which was redissolved in acetonitrile (85 mL) and refluxed 23 h. The crude reaction mixture was chromatographed on silica gel in CH₂Cl₂ to yield desired pyrazole (780 mg, 29%). ¹HNMR (CDCl₃) δ: 7.78 (s, 1H), 7.70 (m, 2H), 7.57 (m, 1H), 6.95 (s, 1H), 3.83 (s, 3H), 2.57 (s, 3H) ppm.

Part D: Preparation of Methyl 1-[3-(Aminomethyl)phenyl]-3-(methylthio)pyrazole-5-carboxylate.

To a solution of methyl 1-(3-cyanophenyl)-3-(methylthio) pyrazole-5-carboxylate (777 mg, 2.8 mmol) in dry DMF (50 mL), CoCl₂ (39 mg, 0.30 mmol) and NaBH₄ (158 mg, 4.2 mmol) were added. The initial solution was emerald green, then turned dark black. After stirring for 2 h., additional NaBH₄ (145 mg, 3.8 mmol) was added. After another 3 h., additional CoCl₂ (330 mg, 2.5 mmol) was added. The reaction continued stirring at room temperature for 17 h. Methanol (10 mL) was added and stirred 40 min. to quench the reaction. The reaction was concentrated to 30 mL and chromatographed on silica gel (0%–100% EtOAc/hexanes followed by 10–30% MeOH/CHCl₃) to yield the desired product (198 mg, 25%). ¹HNMR (CDCl₃) δ: 7.41 (m, 3H), 7.30 (d, 1H, J=7.3), 6.90 (s, 1H), 4.02 (bs, 1H), 3.78 (s, 3H), 3.49 (s, 2H), 2.54 (s, 3H) ppm.

Part E: Preparation of Methyl 1-[3-(t-Butoxycarbonylaminomethyl)phenyl]-3-(methylthio) pyrazole-5-carboxylate.

Di-t-butyl dicarbonate (184 mg, 0.84 mmol) was added to a suspension of methyl 1-[3-(aminomethyl)phenyl]-3-(methylthio)pyrazole-5-carboxylate (195 mg, 0.70 mmol) in dry THF (8 mL.). After stirring 3 h., additional THF (5 mL) was added to aid solubility. The reaction was stirred an additional 16 h., and additional di-t-butyl dicarbonate (54 mg, 0.25 mmol) was added. After another 5 h., triethylamine (100 μL, 0.72 mmol) was added and stirred 2 h. The reaction was diluted with EtOAc and extracted twice with H₂O. The aqueous were combined and extracted with EtOAc. The organics were combined, dried over Na₂SO₄, filtered, evaporated, and chromatographed on silica gel (30% EtOAc) to yield the desired product (228 mg, 86%). ¹HNMR (CDCl₃) δ: 7.37 (m, 4H), 6.91 (s, 1H), 4.87 (bs, 1H), 4.38 (d, 2H, J=5.8), 3.79 (s, 3H), 2.56 (s, 3H), 1.46 (s, 9H) ppm.

Part F: Preparation of 1-[3-(t-Butoxycarbonylaminomethyl) phenyl]-3-(methylthio)pyrazole-5-carboxylic Acid.

To a solution of methyl 1-[3-(t-butoxycarbonylaminomethyl)phenyl]-3-(methylthio) pyrazole-5-carboxylate (50 mg, 0.13 mmol) in THF (2 mL) was added aq. LiOH (1.0 M, 160 µL, 0.16 mmol). The resulting solution was stirred for 19 h. Additional LiOH (30 µL, 0.03 mmol) was added and stirred for 3 h. The reaction was partitioned between H₂O and Et₂O/EtOAc. The aqueous extracts were neutralized with HCl (0.1 M, 1.0 mL) and ice. This aqueous solution was extracted once with Et₂O/ EtOAc. Additional HCl (0.1 M, 0.5 mL) was added and further extracted with Et₂O/EtOAc. A final pH of 3.5 was reached with additional HCl (0.1 M, 0.4 mL). This was extracted again with EtOAc. The organic extracts after acidification were combined, dried over MgSO₄, filtered, and evaporated to yield the desired product (54 mg, 100%). ¹HNMR (CDCl₃) δ: 7.33 (m, 4H), 6.97 (s, 1H), 4.35 (bd, 2H, J=4.4), 4.27 (bs, 1H), 2.55 (s, 3H), 1.45 (s, 9H) ppm.

Part G: Preparation of 1-[3-(t-Butoxycarbonylaminomethyl) phenyl]-5-[(2'-methylsulfonyl-[1,1']-biphen-4-yl) aminocarbonyl]-3-(methylthio)pyrazole.

DMF (3 or 4 drops) was added to a mixture of 1-[3-(t-butoxycarbonylaminomethyl)phenyl]-3-(methylthio) pyrazole-5-carboxylic acid (94 mg, 0.26 mmol) and oxalyl chloride (35 µL, 0.40 mmol) in dry CH₂Cl₂ (3 mL). The resulting solution was stirred for 55 min. and evaporated. After a few min. under high vacuum, the compound was redissolved in CH₂Cl₂ (3 mL), and 4-amino-2'-methylsulfonyl-[1,1']-biphenyl hydrochloride (85 mg, 0.30 mmol) and 4-dimethylaminopyridine (85 mg, 0.70 mmol) were added and stirred 20 h. The reaction was diluted with H₂O and extracted twice with EtOAc. The combined organics were extracted with aq. NaHCO₃ followed by aq. HCl (0.1 M, cooled with ice). Solid NaCl was added to aid separation. The organic layer was removed, and the aqueous solution was extracted an additional 2 times with EtOAc. The organic extracts were combined, dried over Na₂SO₄, filtered, and evaporated. The crude product was chromatographed on silica gel (50% EtOAc/hexanes) to yield the desired product (65 mg, 43%). ESI mass spectrum analysis m/z=615 (M+Na)⁺.

Part H: Preparation of 1-[3-(Aminomethyl)phenyl]-5-[(2'-methylsulfonyl-[1,1']-biphen-4-yl)aminocarbonyl]-3-(methylthio)pyrazole, Trifluoroacetic Acid Salt.

1-[3-(t-Butoxycarbonylaminomethyl)phenyl]-5-[(2'-methylsulfonyl-[1,1']-biphen-4-yl)aminocarbonyl]-3-(methylthio)pyrazole (65 mg, 0.11 mmol) was dissolved in CH₂Cl₂ (3 mL) and TFA (1 mL) and stirred 17 h. The reaction was evaporated and purified by prep. HPLC (10–90% MeCN/H₂O/0.5% TFA) to yield the desired product (37 mg, 55%). ¹HNMR (DMSO) δ: 10.78 (s, 1H), 8.21 (bs, 2H), 8.08 (d, 1H, J=7.7), 7.70 (m, 5H), 7.45 (m, 6H), 7.16 (s, 1H), 4.13 (bd, 2H, J=4.8), 2.84 (s, 3H), 2.57 (s, 3H) ppm. ESI mass spectrum analysis m/z=493 (M+H, 100).

Example 243

1-(3-Aminomethyl-4-fluorophenyl)-3-trifluoromethyl-5-[(3-fluoro-2'-methylsulfonyl-1,1']-biphen-4-yl)aminocarbonyl]-pyrazole, Trifluoroacetic Acid Salt Part A: Preparation of 1-(3-Cyano-4-fluorophenyl)-3-trifluoromethyl-5-methyl Pyrazole.

To a mixture of 3-cyano-4-fluorophenylhydrazine tin chloride (10 g, 26.6 mmol) in acetic acid (150 mL) was added 1,1,1-trifluoro-2,4-penpanedione (4.09 g, 26.6 mmol). The reaction mixture was brought to reflux overnight. Acetic acid was removed on rotary evaporator under reduced pressure. Residue was partitioned between ethyl acetate (200 mL) and water (150 mL). Organic phase was separated and washed with water (3×100 mL), dried over sodium sulfate; filtered, concentrated and subjected to silica-gel flash chromatography(ethyl acetate:hexane, 1:10) to afford 1-(3-cyano-4-fluorophenyl)-3-trifluoromethyl-5-methyl pyrazole(4.0 g). CI mass spectrum m/z (rel. intensity) 270 (M+H, 100).

Part B: Preparation of 1-(3-Cyano-4-fluorophenyl)-3-trifluoromethyl-5-bromomethyl Pyrazole.

To a solution of 1-(3-cyano-4-fluorophenyl)-3-trifluoromethyl-5-methyl pyrazole(4.0 g, 14.87 mmol) in carbon tetrachloride(50 mL) was added NBS (2.65 g, 14.87 mmol) and benzoyl peroxide (0.36 g, 1.48 mmol). The reaction mixture was brought to reflux overnight. Solvent was removed on rotary evaporator under reduced pressure. Residue was partitioned between ethyl acetate (80 mL) and sodium bicarbonate (sat. 80 mL). Organic phase was separated and washed with water (60 mL); dried over sodium sulfate; filtered, concentrated and subjected to silica-gel flash chromatography (ethyl acetate:hexane, 1:10) to afford 1-(3-cyano-4-fluorophenyl)-3-trifluoromethyl-5-bromomethyl pyrazole (2.5 g). CI mass spectrum m/z (rel. intensity) 348 (M+H, 100).

Part C: Preparation of 1-(3-Cyano-4-fluorophenyl)-3-trifluoromethyl-5-hydroxymethyl Pyrazole.

To a solution of 1-(3-cyano-4-fluorophenyl)-3-trifluoromethyl-5-bromomethyl pyrazole (2.5 g, 7.18 mmol) in DMSO (40 mL) was added copper (I) oxide (2.16 g, 15.08 mmol) and water (12 mL). The reaction mixture was stirred at 60° C. for 2 hours then cooled to RT and stirred at RT overnight. The next day, the mixture was filtered through celite, filter pad was washed with ethyl acetate (20 mL); the filtrate was partitioned between ethyl acetate (50 mL) and water (50 mL); organic phase was separated and washed with water (3×30 mL); dried over sodium sulfate; filtered, concentrated, flash chromatography (ethyl acetate:hexane, 1:6) to afford 1-(3-cyano-4-fluorophenyl)-3-trifluoromethyl-5-hydroxymethyl pyrazole (1.7 g). CI mass spectrum m/z (rel. intensity) 286 (M+H, 100).

Part D: Preparation of 1-(3-Cyano-4-fluorophenyl)-3-trifluoromethyl-5-hydroxycarbonylmethyl Pyrazole.

To a solution of 1-(3-cyano-4-fluorophenyl)-3-trifluoromethyl-5-hydroxymethyl pyrazole (1.5 g, 5.26 mmol) in acetonitrile (30 mL) was added NaIO₄ (2.65 g, 11.05 mmol), catalytic amount of RuCl₃ and water (30 mL) at 0° C. The reaction mixture was stirred at 0° C. to RT overnight. Acetonitrile was removed on rotary evaporator under reduced pressure. The residue was partitioned between athylacetate (60 mL) and HCl (10%, 25 mL). Organic phase was separated and dried over sodium sulfate, filtered and concentrated to give 1-(3-cyano-4-fluorophenyl)-3-trifluoromethyl-5-hydroxycarbonylmethyl pyrazole (1-.4 g). ESI mass spectrum m/z (rel. intensity) 298 (M–H, 100).

Part E 1-(3-Cyano-4-fluorophenyl)-3-trifluoromethyl-5-[(2'-methylsulfonyl-[1,1']-biphen-4-yl)aminocarbonyl]-pyrazole.

To a solution of 1-(3-cyano-4-fluorophenyl)-3-trifluoromethyl-5-hydroxycarbonylmethyl pyrazole (0.20 g, 0.67mmol) in methylene chloride (20 mL) was added ClCO-COCl (0.84 g, 6.7 mmol) and a drop of DMF. The reaction mixture was stirred at RT overnight. Methylene chloride and excess ClCOCOCl was removed on rotary evaporator. The residue was redissolved in methylene chloride (20 mL) and to the solution was added 2'-methylsulfonyl-[1,1']-3-fluoro-4-amino-biphenyl (0.20 g, 0.67 mmol) and DMAP (0.25 g, 2.01 mmol). The mixture was stirred at RT overnight. The next day, mehtylene chloride was removed on rotary evaporator under reduced pressure. The residue was partitioned between ethyl acetate (30 mL) and Hcl (10%, 20 mL). Organic phase was separated and washed with water (2×20 mL), dried over sodium sulfate, filtered and concentrated to leave 1-(3-cyano-4-fluorophenyl)-3-trifluoromethyl-5-[(2'-methylsulfonyl-[1,1']-biphen-4-yl)aminocarbonyl]-pyrazole (0.32 g). ESI mass spectrum m/z (rel. intensity) 569 (M+Na, 100).

Part F 1-(3-Aminomethyl-4-fluorophenyl)-3-trifluoromethyl-5-[(3-fluoro-2'-methylsulfonyl-(1,1']-biphen-4-yl)aminocarbonyl]-pyrazole Trifluoroacetic Acid Salt.

To a solution of 1-(3-cyano-4-fluorophenyl)-3-trifluoromethyl-5-[(3-fluoro-2'-methylsulfonyl-[1,1']-biphen-4-yl)aminocarbonyl]-pyrazole (50 mg) in ethanol (20 mL) was added palladium (10% on activated carbon, 40 mg). The mixture was hydrogenated at 45 psi overnight. The next day, the reaction mixture was filtered through celite, filtrate was concentrated and the residue was purified on HPLC (RP gradient) to give 1-(3-aminomethyl-4-fluorophenyl)-3-trifluoromethyl-5-[(2'-methylsulfonyl-[1,1']-biphen-4-yl)aminocarbonyl]-pyrazole (40mg) as Trifluoroacetic acid salt. ESI mass spectrum z (rel. intensity) 551 (M+H, 100).

Example 244

Ethyl 1-[3-(Aminomethyl)-phenyl]-5-[3-fluoro-2'-methylsulfonyl-[1,1']-biphen-4-yl)aminocarbonyl]pyrazole-3-carboxylate, Trifluoroacetic Acid Salt.

Part A. Preparation of Ethyl 4-(2-Furyl)-2,4-dioxobutanoate.

To a solution of sodium ethoxide (75 mL of a 21% solution in ethanol, 0.20 mol) in 300 mL of ethanol was added a mixture of 2-acetylfuran (20.0 g, 0.18 mol) and diethyloxalate (26.5 g, 0.18 mol) in 200 mL of tetrahydrofuran over 30 min. The resulting mixture was allowed to stir at room temperature for 18 h. The reaction mixture was filtered and the solids were washed with ether. The solids were dissolved in water and acidified with 10% HCl. The aqueous was extracted with ethyl acetate and the ethyl acetate layer was washed with brine, dried (MgSO$_4$) and concentrated in vacuo to afford 21.9 g (57%) of the title compound. $^1$HNMR (CDCl$_3$) δ: 7.68 (d, 1H), 7.35 (d, 1H), 6.93 (s, 1H), 6.62 (dd, 1H), 4.39 (q, 2H), 1.40 (t, 3H) ppm.

Part B. Preparation of Ethyl 1-[(3-Cyano)phenyl]-5-[fur-2-yl]pyrazole-3-carboxylate.

To a solution of ethyl 4-(2-furyl)-2,4-dioxobutanoate (3.00 g, 14.3 mmol) in 50 mL of absolute ethanol was added 3-hydrazinobenzonitrile (2.09 g, 15.7 mmol) and p-toluenesulfonic acid (2.45 g, 14.3 mmol). This mixture was stirred at 80° C. for 2 h. The reaction was concentrated in vacuo and the residue was taken up in ethyl acetate, filtered through a pad of silica gel and concentrated in vacuo. The residue was recrystallized from hexanes to afford 3.1 g (70%) of the title compound. $^1$HNMR (CDCl$_3$) δ: 7.80–7.70 (m, 4H), 7.58 (t, 1H), 7.42 (d, 1H), 7.16 (s, 1H), 6.42 (dd, 1H), 6.24 (d, 1H), 4.45 (q, 2H), 1.42 (t, 3H) ppm. ESI mass spectrum analysis m/z 308.1 (M+H)+.

Part C. Preparation of Ethyl 1-[(3-Cyano)phenyl]-5-[carboxy]pyrazole-3-carboxylate.

To a solution of ethyl 1-[(3-cyano)phenyl]-5-[fur-2-yl] pyrazole-3-carboxylate (1.00 g, 3.25 mmol) in 50 mL of a 2:3:2 mixture of acetonitrile/water/carbon tetrachloride was added sodium periodate (3.13 g, 14.64 mmol) and ruthenium trichloride hydrate (0.015 g, 0.071 mmol). The mixture was stirred at room temperature for 1 h and then was concentrated in vacuo. The residue was dissolved in ethyl acetate, washed with brine, dried (MgSO$_4$) and concentrated in vacuo. The residue was triturated with ether to afford 0.9 g (96%) of the title compound. $^1$HNMR (DMSO-d$_6$) δ: 8.15 (m, 1H), 7.99 (m, 1H), 7.91 (m, 1H), 7.87 (t, 1H), 7.38 (s, 1H), 4.30 (q, 2H), 1.27 (t, 3H) ppm. ESI mass spectrum analysis: (AP+) m/z 286.1 (M+H) +.

Part D. Preparation of Ethyl 1-(3-Cyanophenyl)-5-[(3-fluoro-2'-methylsulfonyl-[1,1']-biphen-4-yl)aminocarbonyl] pyrazole-3-carboxylate.

To a solution ethyl 1-[(3-cyano)phenyl]-5-[carboxy] pyrazole-3-carboxylate (0.49 g, 1.72 mmol) in 10 mL of benzene was added oxalyl chloride (0.22 mL, 2.58 mmol) and about 3 drops of dimethylformamide. This solution was allowed to stir at room temperature for 6 h and then was concentrated in vacuo. The residue was dissolved in methylene chloride and then there was added (3-fluoro-2'-methylsulfonyl-[1,1']-biphen-4-yl)amine (0.52 g, 1.72 mmol) and 4-dimethylaminopyridine (0.63 g, 5.17 mmol). The resulting mixture was stirred at room temperature for 18 h. The reaction was diluted with ethyl acetate, washed with 10% aq HCl, saturated aq sodium bicarbonate and brine, dried (MgSO$_4$) and concentrated in vacuo. The residue was purified by flash chromatography (elution with 2:1 hexanes/ethyl acetate) to afford the 0.70 g (76%) of the title compound. $^1$HNMR (CDCl$_3$) δ: 8.32 (t, 1H), 8.22 (dd, 1H), 8.07 (broad d, 1H), 7.87 (m, 1H), 7.79 (m, 2H), 7.70–7.58 (m, 3H), 7.45 (s, 1H), 7.36 (m, 2H), 7.20 (d, 1H), 4.49 (q, 2H), 2.73 (s, 3H), 1.45 (t, 3H) ppm. ESI mass spectrum analysis m/z 533.2 (M+H)+.

Part E. Preparation of Ethyl 1-[3-(Aminomethyl)phenyl]-5-[(3-fluoro-2'-methylsulfonyl-[1,1']-biphen-4-yl)aminocarbonyl]pyrazole-3-carboxylate, Trifluoroacetic Acid Salt.

To a solution of ethyl 1-[(3-cyano)phenyl]-5-[(3-fluoro)-(2'-methylsulfonyl-[1,1']-biphen-4-yl)aminocarbonyl] pyrazole-3-carboxylate (0.20 g, 0.38 mmol) in 100 mL of absolute ethanol was added 2 mL of trifluoroacetic acid and 50 mg of 10% palladium on carbon catalyst. This mixture was stirred under 50 psi of hydrogen on a Parr apparatus for 24 h. The mixture was filtered through a pad of celite and concentrated in vacuo. The residue was purified by prep HPLC (C18 reverse phase column, elution with a H$_2$O/CH$_3$CN gradient with 0.5% TFA) and lyophilized to afford 130 mg (53%) of the title compound as a white powder. $^1$HNMR (DMSO-d$_6$) δ: 9.76 (s, 1H), 8.64 (broad s, 3H), 7.94 (d, 1H), 7.67 (m, 1H), 7.50–7.37 (m, 5H), 7.28 (m, 2H), 7.12 (d, 1H), 7.05 (dd, 1H), 6.94 (d, 1H), 4.21 (q, 2H), 3.88 (broad s, 2H), 2.51 (s, 3H), 1.19 (t, 3H) ppm. ESI mass spectrum analysis m/z 537.2 (M+H)+.

Example 245

1-[3-(Aminomethyl)phenyl]-5-[(3-fluoro-2'-methylsulfonyl-[1,1']-biphen-4-yl)aminocarbonyl] pyrazole-3-carboxylic Acid, Trifluoroacetic Acid Salt.

To a solution of ethyl 1-[3-(aminomethyl)-phenyl]-5-[(3-fluoro-2'-methylsulfonyl-[1,1']-biphen-4-yl)aminocarbonyl]

pyrazole-3-carboxylate, trifluoroacetic acid salt (0.03 g, 0.05 mmol) in 5 mL of 1:1 ethanol/water was added potassium hydroxide (0.013 g, 0.23 mmol). This mixture was stirred at room temperature for 3 h and then was acidified by the addition of several drops of trifluoroacetic acid. The reaction was concentrated in vacuo and the residue was purified by prep HPLC (C18 reverse phase column, elution with a $H_2O/CH_3CN$ gradient with-0.5% TFA) and lyophilized to afford 15 mg (52%) of the title compound as a white powder. $^1$HNMR (DMSO-$d_6$) δ: 10.60 (s, 1H), 8.19 (broad s, 3H), 8.06 (d, 1H), 7.75 (m, 1H), 7.69–7.51 (m, 5H), 7.50 (m, 2H), 7.39 (d, 1H), 7.34 (dd, 1H), 7.21 (d, 1H), 4.11 (broad s, 2H), 2.90 (s, 3H) ppm. ESI mass spectrum analysis m/z 509.2 (M+H)+.

Example 246

1-[3-(Aminomethyl)phenyl]-3-[aminocarbonyl]-5-[3-fluoro-(2'-methylsulfonyl-[1,1']-biphen-4-yl) aminocarbonyl]pyrazole, Trifluoroacetic Acid Salt.

Part A. Preparation of Ethyl 1-[3-(N-(tert-Butyloxycarbonyl)aminomethyl)-phenyl]-5-[3-fluoro-(2'-methylsulfonyl-[1,1']-biphen-4-yl)aminocarbonyl]pyrazole-3-carboxylate.

To a solution of ethyl 1-[3-(aminomethyl)-phenyl]-5-[3-fluoro-(2'-methylsulfonyl-[1,1']-biphen-4-yl) aminocarbonyl]pyrazole-3-carboxylate from Example 244 (0.26 g, 0.40 mmol) in 10 mL of methylene chloride was added di-tert-butyl dicarbonate (0.09 g, 0.40 mmol) and 4-dimethylaminopyridine (0.15 g, 1.20 mmol). The resulting mixture was allowed to stir at room temperature for 18 h. The reaction was diluted with ethyl acetate and then was washed with 10% aq HCl, sat'd aq sodium bicarbonate and brine, dried (MgSO$_4$) and concentrated in vacuo. The residue was purified by flash chromatography (elution with 2:1 hexanes/ethyl acetate) to afford the 0.24 g (80%) of the title compound. $^1$HNMR (CDCl$_3$) δ: 8.28 (t, 1H), 8.14 (d, 1H), 7.89 (broad s, 1H), 7.56 (m, 2H), 7.45–7.35 (m, 4H), 7.30–7.20 (m, 3H), 7.11 (d, 1H), 4.86 (broad s, 1H), 4.40 (q, 2H), 4.33 (m, 2H), 2.65 (s, 3H), 1.40 (t, 3H), 1.37 (s, 9H) ppm. ESI (–ve) mass spectrum analysis m/z (relative intensity) m/z 635.2 (M–H, 100).

Part B. Preparation of 1-[3-(Aminomethyl)-phenyl]-3-[aminocarbonyl]-5-[3-fluoro-(2'-methylsulfonyl-[1,1']-biphen-4-yl)aminocarbonyl]pyrazole, Trifluoroacetic Acid Salt.

To a solution of ethyl 1-[3-(N-(tert-butyloxycarbonyl) aminomethyl)-phenyl]-5-[3-fluoro-(2'-methylsulfonyl-[1,1']-biphenyl-4-yl)aminocarbonyl]pyrazole-3-carboxylate (0.24 g, 0.38 mmol) in 20 mL of 1:1 tetrahydrofuran/water was added potassium hydroxide (0.08 g, 1.5 mmol). The resulting mixture was stirred at 60° C. for 1 h and then was cooled and concentrated in vacuo. The residue was diluted with water and extracted with 1:1 hexane/ethyl acetate. The organics were discarded. The aqueous layer was acidified with aq HCl and extracted with ethyl acetate. The extracts were washed with brine, dried (MgSO$_4$) and concentrated in vacuo. The residue was dissolved in 10 mL of acetonitrile, cooled to 0° C. and then there was added triethylamine (0.10 mL, 0.71 mmol) and iso-butyl chloroformate (0.067 mL, 0.52 mmol). This mixture was allowed to stir for 30 min and then there was added ammonia (0.95 mL of a 2M solution in methanol, 1.88 mmol) and the reaction was allowed to stir with warming to room temperature for 18 h. The reaction mixture was diluted with ethyl acetate and then was washed with 10% aq HCl, sat'd aq sodium bicarbonate and brine, dried (MgSO$_4$) and concentrated in vacuo. The residue was dissolved in 5 mL of trifluoroacetic acid and stirred at room temperature for 2 h and then was concentrated in vacuo. The residue was purified by prep HPLC (C18 reverse phase column, elution with a $H_2O/CH_3CN$ gradient with 0.5% TFA) and lyophilized to afford 115 mg (40%) of the title compound-as a white powder. $^1$HNMR (DMSO-$d_6$) δ: 9.53 (s, 1H), 8.78 (broad s, 3H), 8.04 (d, 1H), 7.86 (m, 1H), 7.64 (s, 1H), 7.52 (m, 1H), 7.42 (m, 2H), 7.37 (m, 3H), 7.20 (d, 1H), 7.17 (m, 2H), 7.04 (d, 1H), 6.15 (broad s, 1H), 3.99 (broad s, 2H), 2.60 (s, 3H) ppm. ESI (+ve) mass spectrum analysis m/z (relative intensity) (ESI) m/z 508.2 (M+H, 100).

Example 247

Ethyl 1-[3-(Aminomethyl)-phenyl]-3-trifluoromethyl-5-[(3-fluoro-2'-methylsulfonyl-[1,1']-biphen-4-yl)aminocarbonyl]pyrazole-4-carboxylate, Trifluoroacetic Acid Salt.

Part A. Preparation of N-(3-Cyanophenyl)-trifluoroacetohydrazonoyl Bromide.

To a solution of 3-hydrazinobenzonitrile HCl salt (1.3 g, 7.66 mmol) in 20 mL of absolute ethanol was added trifluoroacetaldehyde ethyl hemiacetal (1.33 g, 9.19 mmol). The resulting mixture was allowed to stir at 80° C. for 18 h and then the reaction was cooled and concentrated in vacuo. The residue was dissolved in 10 mL of dimethylformamide and then there was added N-bromosuccinimide (1.36 g, 7.66 mmol). The solution was allowed to stir at room temperature for 18 h. The reaction was diluted with ethyl acetate, washed with water, sat'd aq sodium bicarbonate and brine, dried (MgSO$_4$) and concentrated in vacuo to yield 2.1 g (95%) of the title compound which was sufficiently pure to be used without purification. $^1$HNMR (CDCl$_3$) δ: 8.16 (broad s, 1H), 7.47–7.30 (m, 4H) ppm.

Part B. Preparation of Ethyl 3-(2-Furyl)-3-oxopropanoate.

To a suspension of hexane-washed sodium hydride (3.5 g of 60% dispersion in mineral oil, 90.8 mmol) in 200 mL of tetrahydrofuran was added diethyl carbonate (10.7 g, 90.8 mmol) and 2-acetylfuran (5.0 g, 45.4 mmol). The resulting mixture was stirred at 70° C. for 1 h and then was cooled to room temperature and quenched by the slow addition of 10% aq HCl. The tetrahydrofuran was removed in vacuo and the aqueous was extracted with ethyl acetate. The organics were washed with water and brine, dried (MgSO$_4$) and concentrated in vacuo to yield 6.9 g (83%) of the title compound which was sufficiently pure to be used without purification. $^1$HNMR (CDCl$_3$) δ: 7.61 (t, 1H), 7.27 (dd, 1H), 6.57 (dd, 1H), 4.20 (q, 2H), 3.84 (s, 2H), 1.25 (t, 3H) ppm.

Part C. Preparation of Ethyl 1-[(3-Cyano)phenyl]-3-trifluoromethyl-5-[furyl-2-yl]pyrazole-4-carboxylate.

To a solution of ethyl 3-(2-furyl)-3-oxopropanoate (1.87 g, 10.26 mmol) in 20 mL of absolute ethanol was added sodium ethoxide (2.6 mL of a 21% solution in ethanol, 6.84 mmol). Then there was added N-(3-cyanophenyl)-trifluoroacetohydrazonoyl bromide (1.0 g, 3.42 mmol) in absolute ethanol. The resulting mixture was stirred at room temperature for 3 h and then was diluted with ether. The layers were separated and the organics were washed with water, sat'd sodium carbonate and brine, dried (MgSO$_4$) and concentrated in vacuo. The residue was purified by flash chromatography (elution with 4:1 hexanes/ethyl acetate) to afford 0.80 g (63%) of the title compound. 1HNMR (CDCl$_3$) δ: 7.71 (m, 1H), 7.60 (m, 1H), 7.53 (m, 2H), 7.44 (d, 1H), 6.95 (d, 1H), 6.55 (dd, 1H), 4.33 (q, 2H), 1.32 (t, 3H) ppm.

Part D. Preparation of Ethyl 1-[(3-Cyano)phenyl]-3-trifluoromethyl-5-[carboxy]pyrazole-4-carboxylate.

To a solution of ethyl 1-[(3-cyano)phenyl]-3-trifluoromethyl-5-[furyl-2-yl]pyrazole-4-carboxylate (0.75 g, 2.0 mmol) in 30 mL of a 2:3:2 mixture of acetonitrile/water/carbon tetrachloride was added sodium periodate (1.92 g, 9.0 mmol) and ruthenium trichloride hydrate (0.008 g, 0.04 mmol). The mixture was stirred at room temperature for 18 h and then was concentrated in vacuo. The residue was dissolved in ethyl acetate, washed with brine, dried (MgSO$_4$) and concentrated in vacuo. This residue was dissolved in 1:1 hexanes/ethyl acetate and extracted with sat'd aq sodium carbonate. The aqueous layer was acidified with HCl and then was extracted with ethyl acetate. These ethyl acetate extracts were washed with brine, dried (MgSO$_4$) and concentrated in vacuo to afford 0.40 g (56%) of the title compound which was sufficiently pure to be used without purification. $^1$HNMR (CDCl$_3$) δ: 7.82 (m, 1H), 7.71 (d, 1H), 7.64 (m, 2H), 4.55 (q, 2H), 1.47 (t, 3H) ppm. ESI (−ve) mass spectrum analysis m/z (relative intensity) 352.1 (M−H, 100).

Part E. Preparation of Ethyl 1-[(3-Cyano)phenyl]-3-trifluoromethyl-5-[(3-fluoro-2'-methylsulfonyl-[1,1']-biphen-4-yl)aminocarbonylpyrazole-4-carboxylate.

To a solution of ethyl 1-[(3-cyano)phenyl]-3-trifluoromethyl-5-[carboxy]pyrazole-4-carboxylate (0.33 g, 0.93 mmol) in 10 mL of methylene chloride was added oxalyl chloride (0.12 mL, 1.4 mmol) and about 3 drops of dimethylformamide. This solution was allowed to stir at room a temperature for 6 h and then was concentrated in vacuo. The residue was dissolved in methylene chloride and then there was added 4-dimethylaminopyridine (0.34 g, 2.79 mmol) and (2-fluoro-2'-methylsulfonyl-[1,1']-biphen-4-yl) amine hydrochloride (0.28 g, 0.93 mmol). The resulting mixture was stirred at room temperature for 18 h. The reaction was diluted with ethyl acetate, washed with 10% aq HCl, sat'd aq sodium bicarbonate and brine, dried (MgSO$_4$) and concentrated in vacuo. The residue was purified by flash chromatography (elution with 2:1 hexanes/ethyl acetate) to afford the 0.25 g (45%) of the title compound. $^1$HNMR (CDCl$_3$) δ: 11.27 (s, 1H), 8.29 (t, 1H), 8.21 (d, 1H), 7.79 (m, 2H), 7.67–7.52 (m, 4H), 7.40–7.30 (m, 2H), 7.18 (d, 1H), 4.51 (q, 2H), 2.73 (s, 3H), 1.45 (t, 3H) ppm. ESI (+ve) mass spectrum analysis m/z (relative intensity) 623.1 (M+Na, 100).

Part F. Preparation of Ethyl 1-[3-(Aminomethyl)-phenyl]-3-trifluoromethyl-5-[(3-fluoro-2'-methylsulfonyl-[1,1']-biphen-4-yl)aminocarbonyl]pyrazole-4-carboxylate, Trifluoroacetic Acid Salt.

To a solution of ethyl 1-[(3-cyano)phenyl]-3-trifluoromethyl-5-[(3-fluoro-2'-methylsulfonyl-[1,1']-biphen-4-yl)aminocarbonyl]pyrazole-4-carboxylate (0.13 g, 0.22 mmol) in 20 mL of absolute ethanol was added conc. HCl (0.018 mL, 0.22 mmol) and 20 mg of 10% palladium on carbon catalyst. This mixture was stirred under 1 atm of hydrogen for 18 h. The mixture was filtered through a pad of celite and concentrated in vacuo. The residue was purified by prep HPLC (C18 reverse phase column, elution with a H$_2$O/CH$_3$CN gradient with 0.5% TFA) and lyophilized to afford 35 mg (21%) of the title compound as a white powder. $^1$HNMR (DMSO-d$_6$) δ: 11.22 (s, 1H), 8.21 (broad s, 3H), 8.06 (dd, 1H), 7.87 (t, 1H), 7.80–7.40 (m, 6H), 7.38 (m, 2H), 7.22 (dd, 1H), 4.26 (q, 2H), 4.13 (broad q, 2H), 2.91 (s, 3H), 1.14 (t, 3H) ppm. ESI (+ve) mass spectrum analysis m/z (relative intensity) (AP+) 605.2 (M+H, 100).

Example 248

1-[3-(Aminamethyl)phenyl]-5-[(3-fluoro-2'-methylsulfonyl-[1,1']-biphen-4-yl)aminocarbonyl]-3-(methylthio)pyrazole, Trifluoroacetic Acid Salt Part A: Preparation of 1-[3-(t-Butoxycarbonylaminomethyl) phenyl]-5-[(3-fluoro-2'-methylsulfonyl-(1,1']-biphen-4-yl)aminocarbonyl]-3-(methylthio)pyrazole.

DMF (3 drops) was added to 1-[3-(t-butoxycarbonylaminomethyl)phenyl]-3-(methylthio) pyrazole-5-carboxylic acid (553 mg, 1.5 mmol) and oxalyl chloride (260 μL, 3.0 mmol) in dry CH$_2$Cl$_2$ (30 mL)). The resulting solution was stirred at room temperature for 1 h. and evaporated. The resulting solid was redissolved in dry CH$_2$Cl$_2$ (30 mL), and 4-dimethylaminopyridine (585 mg, 4.8 mmol) was added. After stirring 4 min., 4-amino-3-fluoro-2'-methylsulfonyl-[1,1']-biphenyl, hydrochloride (530 mg, 1.8 mmol) was added portionwise over 5 min., and stirred 22 h. The reaction was extracted once with sat. NaHCO$_3$. then once with a cooled solution of 0.1 M HCl. The organic layer was dried over MgSO$_4$, filtered, and evaporated. The crude product was chromatographed on silica gel (40–50% EtOAc/hexanes) to yield the desrired product (376 mg, 41%). $^1$HNMR (CDCl$_3$) δ: 8.38 (bt, 1H), 8.21 (dd, 1H, J=7.7, J'=1.1), 7.81 (bs, 1H), 7.65 (td, 1H, J=7.4, J'=1.4), 7.58 (td, 1H, J=7.7, J'=1.5), 7.43 (m, 4H), 7.32 (m, 2H), 7.17 (d, 1H, J=8.8), 6.84 (s, 1H), 4.90 (bs, 1H), 4.39 (d, 2H, J=6.3), 2.72 (s, 3H), 2.60 (s, 3H), 1.45 (s, 9H) ppm.

Part B: Preparation of 1-[3-(Aminomethyl)phenyl]-5-[(3-fluoro-2'-methylsulfonyl-[1,1']-biphen-4-yl) aminocarbonyl]-3-(methylthio)pyrazole.

1-[3-(t-Butoxycarbonylaminomethyl)phenyl]-5-[(3-fluoro-2'-methylsulfonyl-[1,1']-biphen-4-yl) aminocarbonyl]-3-(methylthio)pyrazole (287 mg, 0.47 mmol) was dissolved in CH$_2$Cl$_2$ (5 mL) and TFA (5 mL) and stirred at room temperature for 16 h. The reaction was evaporated and purified by prep. HPLC (10–70% MeCN/H$_2$O/0.05% TFA) to yield the desired product (271 mg, 92%). $^1$HNMR (DMSO-d$_6$) δ: 10.60 (s, 1H), 8.25 (bs, 2H), 8.13 (d, 1H, J=8.1), 7.82 (td, 1H, J=7.3, J'=1.5), 7.74 (m, 3H), 7.48 (m, 5H), 7.28 (d, 1H, J=8.4), 7.23 (s, 1H), 4.16 (d, 2H, J=5.8), 2.97 (s, 3H), 2.61 (s, 3H) ppm. APcI mass spectrum analysis m/z=511 (M+H, 100).

Example 249

1-[3-(Aminomethyl)phenyl]-5-[(3-fluoro-2'-methylsulfonyl-[1,1']-biphen-4-yl)aminocarbonyl]-3-(methylsulfonyl)pyrazole, Trifluoroacetic Acid Salt MCPBA (110 mg, 57–86%) was added t 1-[3-(t-butoxycarbonylaminomethyl)phenyl]-5-[(3-fluoro-2'-methylsulfonyl-[1,1']-biphen-4-yl)aminocarbonyl]-3-(methylthio)pyrazole (89 mg, 0.15 mmol) in CH$_2$Cl$_2$ (5 mL) and stirred at room temperature for 6 h. The reaction was extracted once with sat. Na$_2$SO$_3$, then once with sat. NaHCO3. The organic layer was dried over Na$_2$SO$_4$, filtered, and evaporated. The crude product was redissolved in CH$_2$Cl$_2$ (1.5 mL) and TFA (1.5 mL) and stirred at room temperature for 5 h. The resulting solution was evaporated and purified by prep. HPLC (10–70% MeCN/H$_2$O/0.05% TFA) to yield the desired product. $^1$HNMR (DMSO-d$_6$) δ: 10.75 (s, 1H), 8.20 (bs, 3H), 8.06 (dd, 1H, J=8.0, J'=1.5), 7.70 (m, 5H), 7.56 (m, 3H), 7.38 (m, 2H), 7.20(dd, J=8.1 and 1.7 Hz, 1H), 4.11 (d, 2H, J=5.5), 3.36 (s, 3H), 2.91 (s, 3H) ppm. ESI mass spectrum analysis m/z (relative intensity) 543 (M+H, 100).

Example 250

1-[3-(Aminomethyl)phenyl]-5-[(4-(5-(methoxyaminocarbonyl)imidazol-1-yl)phen-1-yl) aminocarbonyl]-3-trifluoromethylpyrazole, Trifluoroacetic Acid Salt.

Part A: A solution of 4-amino-nitrobenzene (5.3 g, 38.4 mmol) in ethyl alcohol (50 mL) was treated with n-butyl glyoxylate (10.0 g, 76.9 mmol). After stirring at reflux for 18 h, the reaction mixture was concentrated at reduced pressure. The residue was carried to the next step without purification. To the solution of the imine (10.0 g, 40.0 mmol) in methyl alcohol (50mL) was added potassium carbonate (11.0 g, 80.0 mmol) and tosylmethyl isocyanate (11.7 g, 60.0 mmol). The solution was stirred for 1 h at rt, then the solvent was removed under reduced pressure. The residue was treated with saturated sodium chloride solution and the mixture was extracted with methylene chloride. The organic extract was concentrated and triturated with methyl alcohol. The precipitate was collected and dried to afford an imidazole (5.9 g, 59%, 2 steps). Reduction to the aniline was accomplished in MeOH and 10% of Pd/C at 50 psi over 18 h. MS (ESI) m/z (rel. intensity), 216 ($M^+$+H, 100).

Part B: The product from part A was then coupled to 1-(3-cyanophenyl)-3-trifluoromethylpyrazole carboxylic acid via the acid chloride methodology previously described. The product was purified via silica gel column chromatography (hexane:ethyl acetate, 4:3) to afford pure coupled product. ESI mass spectrum analysis m/z (relative intensity) 481 (M++H, 100).

Part C: The product from part B (200 mg, 0.4 mmol) in THF (3 mL) was treated with 1N NaOH (0.8 mL, 0.8 mmol). The resultant reaction mixture was stirred for 18 h at rt, then acidified to pH 7 with 1N HCl, extracted with ethyl acetate, dried over magnesium sulfate and concentrated. The resultant acid (100 mg, 0.2 mmol) was dissolved in THF (5 mL), treated with DIEA (0.001 mL, 0.6 mmol), methoxylamine hydrochloride (0.030 g, 0.36 mmol) and TBTU (83 mg, 0.2 mmol) and stirred for 18 h at rt. The residue was treated with water and the mixture was extracted with ethyl acetate, dried over sodium sulphate and concentrated. Purification. by silca gel flash chromatography (methanol/methylene chloride, 1:9) afforded the methoxy hydroxamate intermediate (60 mg, 56%). ESI mass spectrum analysis m/z (rel. intensity), 496 ($M^+$+H, 100). Reduction of the nitrile to the benzylamine was then accomplished via standard conditions. $^1$HNMR (CD3OD) δ: 3.74 (s, 3H), 4.21 (s, 2H), 7.43 (s, 1H), 7.46 (m, 2H), 7.60 (m, 3H), 7.78 (m, 2H), 7.80 (m, 3H) ppm. ESI mass spectrum analysis m/z (relative intensity) 442 ($M^+$+H, 100).

Example 251

1-(3-Aminomethylphenyl)-5-[(4-(5-methyl-1,2,3-triazol-1-yl)phen-1-yl)aminocarbonyl]-3-trifluoromethylpyrazole, Trifluoroacetic Acid Salt.

Part A: A solution of 4-tert-butyl-[1-(4-nitrophenyl)]5-methyl-1,2,3-tiazol-1-yl-carboxylate (Maybridge Chemical Company, 0.5 g, 1.6 mmol) in TFA (10 mL) was refluxed over 18 h. The reaction mixture was concentrated at reduced pressure. The residue was then reduced to the aniline via standard conditions without purification. $^1$HNMR (CDCl$_3$) δ: 2.36 (s, 3H), 6.83 (d, J=8.8 Hz, 2H), 7.23 (d, J=8.8 Hz, 2H), 7.80 (s, 1H) ppm. mass spectrum m/z (relative intensity) 175 ($M^+$+H, 100).

Part B: The intermediate was then coupled to 1-(3-cyanophenyl)-3-trifluoromethylpyrazole carboxylic acid via the acid chloride methodology previously described followed by reduction of the nitrile to the benzylamine and purification via HPLC under reverse phase techniques and lyophilization to afford the title compound as a colorless solid. $^1$HNMR (CD3OD) δ: 2.35 (s, 3H), 4.22 (s, 2H), 7.51 (d, J=9.5 Hz, 2H), 7.55 (s, 1H), 7.60 (m, 3H), 7.65 (s, 1H), 7.71 (s, 1H), 7.89 (d, J=9.2 Hz, 2H) ppm. ESI mass spectrum analysis m/z (relative intensity) 500 ($M^+$+H, 100).

TABLE 1a

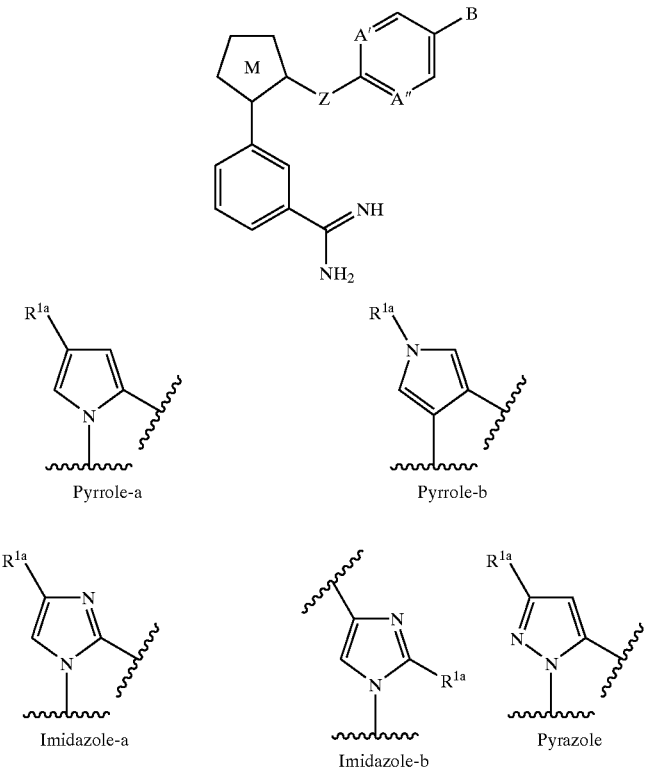

TABLE 1a-continued

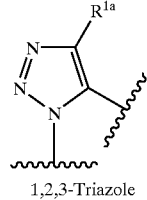 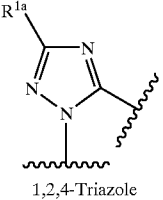 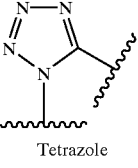

1,2,3-Triazole     1,2,4-Triazole     Tetrazole

| Ex | Ring M | Z | $R^{1a}$ | A' | A" | B | MS |
|---|---|---|---|---|---|---|---|
| 1 | pyrrole-a | CONH | H | CH | CH | 2-$H_2NSO_2$—$C_6H_4$ | 460.3 |
| 2 | pyrrole-a | CONH | H | CH | CH | 2-t-Bu—HNSO_2—$C_6H_4$ | 516.4 |
| 3 | pyrrole-a | CONH | Br | CH | CH | 2-$H_2NSO_2$—$C_6H_4$ | 538.2 |
| 4 | pyrrole-a | CONH | H | N | CH | 2-$H_2NSO_2$—$C_6H_4$ | 461.3 |
| 5 | pyrrole-b | CONH | benzyl | CH | CH | 2-$H_2NSO_2$—$C_6H_4$ | 550.3 |
| 6 | pyrrole-b | CONH | benzyl | CH | CH | 2-t-Bu—HNSO_2—$C_6H_4$ | 606.5 |
| 7 | imidazole-b | CONH | H | CH | CH | 2-$H_2HNSO_2$—$C_6H_4$ | 461.1 |
| 8 | imidazole-b | CONH | H | CH | CH | 2-t-Bu—HNSO_2—$C_6H_4$ | 517.2 |
| 9 | imidazole-a | CONH | H | CH | CH | 2-$H_2NSO_2$—$C_6H_4$ | 461.3 |
| 10 | pyrazole | CONH | $CH_3$ | CH | CH | 2-$H_2NSO_2$—$C_6H_4$ | 475.2 |
| 11 | pyrazole | NHCO | $CH_3$ | CH | CH | 2-$H_2NSO_2$—$C_6H_4$ | 475.2 |
| 12 | pyrazole | CONH | $CH_3$ | CH | CH | 2-(5'-$CF_3$-tetrazo-1'-yl)$C_6H_4$ | 532.4 |
| 13 | 4-Cl-pyrazole | CONH | $CH_3$ | CH | CH | 2-t-Bu—NHSO_2—$C_6H_4$ | 509.1 |
| 14 | pyrazole | CONH | $CF_3$ | CH | CH | 2-$H_2NSO_2$—$C_6H_4$ | 529.0 |
| 15 | 4-$CH_3O$-pyrazole | CONH | $CF_3$ | CH | CH | 2-$H_2NSO_2$—$C_6H_4$ | 559.4 |
| 16 | pyrazole | CONH | $CH_3$ | CH | CH | 1-imidazolyl | 386.2 |
| 17 | pyrazole | CONH | $CH_3$ | CH | CH | —O-2'-$CH_3SO_2$—$C_6H_4$ | 490.3 |
| 18 | pyrazole | $COCH_2$ | $CH_3$ | CH | CH | 2-$H_2NSO_2$—$C_6H_4$ | 474.2 |
| 19 | 1,2,3-triazole | CONH | H | CH | CH | 2-$H_2NSO_2$—$C_6H_4$ | 463.1 |
| 20 | tetrazole | CONH | — | CH | CH | 2-$CF_3$—$C_6H_4$ | 452.2 |
| 21 | tetrazole | $SCH_2$ | — | C—Cl | CH | 2-$H_2NSO_2$—$C_6H_4$ | 500.2 |
| 22 | tetrazole | $SOCH_2$ | — | C—Cl | CH | 2-$H_2NSO_2$—$C_6H_4$ | 516.2 |
| 23 | tetrazole | $SO_2CH_2$ | — | C—Cl | CH | 2-$H_2NSO_2$—$C_6H_4$ | 532.2 |
| 24 | tetrazole | CONH | — | CH | CH | 2-$H_2NSO_2$—$C_6H_4$ | 463.3 |
| 25 | pyrazole | CONH | $CH_3$ | N | CH | 2-$H_2NSO_2$—$C_6H_4$ | 476.3 |
| 26 | pyrazole | CONH | $CH_3$ | N | N | 2-$H_2NSO_2$—$C_6H_4$ | 477.2 |
| 27 | pyrazole | CONH | $CH_3$ | C—Cl | CH | 2-$H_2NSO_2$—$C_6H_4$ | 509.3 |
| 28 | pyrazole | CONH | $CH_3$ | C—F | CH | 2-$H_2NSO_2$—$C_6H_4$ | 493.2 |
| 29 | pyrazole | CONH | $CH_3$ | CH | CH | 2-$H_2NSO_2$-4-F—$C_6H_3$ | 493.3 |
| 30 | pyrazole | CONH | $CH_3$ | CH | CH | 2-$CF_3$—$C_6H_4$ | 464.3 |
| 31 | pyrazole | CONH | $CH_3$ | C—Cl | CH | 2-$CF_3$—$C_6H_4$ | 498.3 |
| 32 | pyrazole | CONH | $CH_3$ | C—F | CH | 2-$CF_3$—$C_6H_4$ | 482.2 |
| 33 | pyrazole | CONH | $CH_3$ | N | CH | 2-$CF_3$—$C_6H_4$ | 465.3 |
| 34 | pyrazole | CONH | $CH_3$ | CH | CH | 2-F—$C_6H_4$ | 414.3 |
| 35 | pyrazole | CONH | $CH_3$ | C—Cl | CH | 2-F—$C_6H_4$ | 448.0 |
| 36 | pyrazole | CONH | $CH_3$ | CH | CH | 2-$CH_3SO_2$—$C_6H_4$ | 474.3 |
| 37 | pyrazole | $CONCH_3$ | $CH_3$ | CH | CH | 2-$H_2NSO_2$—$C_6H_4$ | 489.3 |
| 38 | pyrazole | CONH | $C_4H_9$ | CH | CH | 2-$H_2NSO_2$—$C_6H_4$ | 517.4 |
| 39 | pyrazole | CONH | $C_4H_9$ | N | CH | 2-$H_2NSO_2$—$C_6H_4$ | 518.2 |
| 40 | pyrazole | CONH | $C_4H_9$ | N | CH | 2-$CF_3$—$C_6H_4$ | 506.3 |
| 41 | pyrazole | CONH | $CF_3$ | CH | CH | 2-$CH_3SO_2$—$C_6H_4$ | 528.2 |
| 42 | pyrazole | CONH | $CF_3$ | CH | CH | 2-$CF_3$—$C_6H_4$ | 518.2 |
| 43 | 4-$CH_3O$—pyrazole | CONH | $CF_3$ | CH | CH | 2-$CF_3$—$C_6H_4$ | 548.3 |
| 44 | pyrazole | CONH | $CH_3$ | CH | CH | $CF_3$ | 388.2 |
| 45 | imidazole-a | CONH | 4-$CH_3$ | CH | CH | 2-$H_2NSO_2$—$C_6H_4$ | 475.3 |
| 46 | 1,2,3-triazole | CONH | H | N | CH | 2-$H_2NSO_2$—$C_6H_4$ | 463.3 |
| 47 | 1,2,3-triazole | CONH | H | CH | CH | 2-$CF_3$—$C_6H_4$ | 451.3 |
| 48 | 1,2,4-triazole | CONH | $CF_3$ | CH | CH | 2-$H_2NSO_2$—$C_6H_4$ | 530.3 |

TABLE 1b

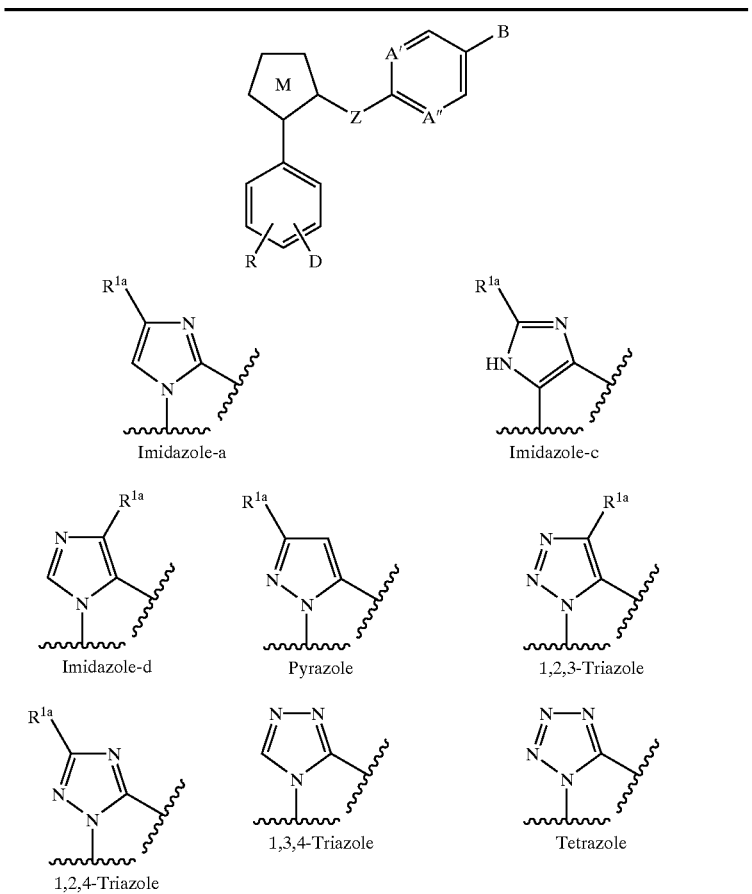

Unless otherwise indicated, D is at the meta position and is amidino (AM) and R is absent.

| Ex | M | Z | R¹ᵃ | A—B | MS |
|---|---|---|---|---|---|
| 49 | pyrazole | CONH | methyl | 4-(4'-chlorophenyl)-thiazol-2-yl | 437.1 |
| 50 | pyrazole | CONH | methyl | 2'-CF$_3$S-biphenyl | 496.1 |
| 51 | pyrazole | CONH | methyl | 2'-CF$_3$S(O)-biphenyl | 512 |
| 52 | pyrazole | CONH | methyl | 2'-CF$_3$S(O)$_2$-biphenyl | 528.1 |
| 53 | pyrazole | CONH | methyl | 4-carboxymethyl-C$_6$H$_4$ | 378.2 |
| 54 | pyrazole | CONH | methyl | 4-N,N—(CH$_3$)$_2$NC(O)—C$_6$H$_4$ | 391 |
| 55 | pyrazole | CONH | methyl | 4-N,N—(CH$_3$)$_2$NS(O)$_2$—C$_6$H$_4$ | 426 |
| 56 | pyrazole | CONH | methyl | 4-t-Bu—HNSO$_2$—C$_6$H$_4$ | 455 |
| 57 | pyrazole | CONH | methyl | 4-H$_2$NSO$_2$—C$_6$H$_4$ | 381.3 |
| 58 | pyrazole | CONH | methyl | 4-CF$_3$—C$_6$H$_4$ | 388.1 |
| 59 | pyrazole | CONH | methyl | 4-benzylsulfonyl-piperidyl | 481.2 |
| 60 | pyrazole | CONCH$_3$ | methyl | 2'-H$_2$NSO$_2$-biphenyl | 489.2 |
| 61 | pyrazole | CONH | methyl | 4'-F-biphenyl | 493.1 |
| 62 | pyrazole | CONH | methyl | 5-(2'-H$_2$NSO$_2$—C$_6$H$_4$-pyridin-2-yl | 476.1 |
| 63 | pyrazole (D = —CN) | CONH | methyl | 5-(2'-H$_2$NSO$_2$—C$_6$H$_4$-pyridin-2-yl | 459.1 |
| 64 | pyrazole | CONH | methyl | 2'-CF$_3$—biphenyl | 464.2 |
| 65 | pyrazole (D = CONH$_2$) | CONH | methyl | 2'-H$_2$NSO$_2$-biphenyl | 476.1 |
| 66 | pyrazole | CONH | methyl | 2'-H$_2$NSO$_2$-3-chlorobiphenyl | 509.1 |
| 67 | pyrazole | CONH | methyl | 2'-CF$_3$-3-chlorobiphenyl | 498.1 |
| 68 | pyrazole | CONH | C$_4$H$_9$ | 2'-H$_2$NSO$_2$-biphenyl | 517.2 |
| 69 | pyrazole | CONH | C$_4$H$_9$ | 2'-CF$_3$-biphenyl | 507.2 |
| 70 | pyrazole | CONH | C$_4$H$_9$ | 5-(2'-H$_2$NSO$_2$—C$_6$H$_4$)pyridin-2-yl | 518.2 |
| 71 | 4-CH$_3$O-pyrazole | CONH | CF$_3$ | 2'-CF$_3$-biphenyl | 548.2 |

TABLE 1b-continued

| | | | | | |
|---|---|---|---|---|---|
| 72 | pyrazole | CONH | $CF_3$ | 2'-$CF_3$-biphenyl | 518.1 |
| 73 | pyrazole | CONH | $CF_3$ | 2'-$SO_2CH_3$-biphenyl | 528.1 |
| 74 | pyrazole | CONH | methyl | 2'-$H_2NSO_2$-3-Br-biphenyl | 553.1 |
| 75 | pyrazole (D = $CONH_2$) | CONH | methyl | 2'-$H_2NSO_2$-3-Br-biphenyl | 554.1 |
| 76 | pyrazole | $COCH_2$ | methyl | 2'-$H_2NSO_2$-biphenyl | 474.2 |
| 77 | pyrazole (D = $CONH_2$) | CONH | methyl | 5-(2'-$H_2NSO_2$—$C_6H_4$)pyridin-2-yl | 477.1 |
| 78 | pyrazole | CONH | $CF_3$ | 5-(2'-t-Bu—$HNSO_2$—$C_6H_4$)pyrimidin-2-yl | 587.2 |
| 79 | pyrazole | CONH | $CF_3$ | 5-(2'-$H_2NSO_2$—$C_6H_4$)pyrimidin-2-yl | 531.1 |
| 80 | pyrazole (D = $CONH_2$) | CONH | $CF_3$ | 5-(2'-$H_2NSO_2$—$C_6H_4$)pyrimidin-2-yl | 532.1 |
| 81 | pyrazole (D = —CN) | CONH | $CF_3$ | 4'-imidazol-1-yl-$C_6H_4$ | 440.1 |
| 82 | pyrazole | CONH | $CF_3$ | 4'-morpholin-1-yl-$C_6H_4$ | 459.2 |
| 83 | pyrazole (D = $CONH_2$) | CONH | $CF_3$ | 4'-morpholin-1-yl-$C_6H_4$ | 460.1 |
| 84 | pyrazole | CONH | $CF_3$ | 5-(2'-$H_2NSO_2$—$C_6H_4$)pyridrin-2-yl | 530.1 |
| 85 | pyrazole (D = $CONH_2$) | CONH | $CF_3$ | 5-(2'-$H_2NSO_2$—$C_6H_4$)pyridin-2-yl | 531.1 |
| 86 | pyrazole | CONH | $CF_3$ | 4'-(3-methyltetrazol-1-yl)$C_6H_4$ | 456.2 |
| 87 | pyrazole | $NHSO_2$ | methyl | 2'-naphthyl | 406.1 |
| 88 | pyrazole | $NHSO_2$ | methyl | 2'-(4-bromo-$C_6H_4$ | 434.0 |
| 89 | pyrazole (D = $CH_2NH_2$) | CONH | methyl | 2'-$H_2NSO_2$-biphenyl | 462.2 |
| 90 | pyrazole (D = $CH_2NH_2$) | CONH | $CF_3$ | 2'-$H_2NSO_2$-biphenyl | 516.1 |
| 91 | pyrazole | CONH | methyl | 5-(2'-$CF_3$—$C_6H_4$)pyrid-2-yl | 465.2 |
| 92 | pyrazole | CONH | methyl | 5-(2'-$H_2NSO_2$—$C_6H_4$)pyrimidin-2 -yl | 477.2 |
| 93 | pyrazole | CONH | methyl | 2'-F-biphenyl | 414.2 |
| 94 | pyrazole | CONH | methyl | 3-Cl-2'-F-biphenyl | 448.1 |
| 95 | pyrazole | CONH | methyl | 3-F-2'-F-biphenyl | 482.2 |
| 96 | pyrazole | CONH | methyl | 3-F-2'-$H_2NSO_2$-biphenyl | 493.1 |
| 97 | pyrazole | CONH | methyl | 5-(2'-F—$C_6H_4$)pyrid-2-yl | 415.2 |
| 98 | pyrazole | CONH | methyl | 5-(2'-t-BU-$NHSO_2$-phenyl)pyrimidin-2-yl | 533.2 |
| 99 | pyrazole | CONH | methyl | 5-(2'-$H_2NSO_2$—$C_6H_4$)-([1,6]-dihydropyrimid-2-yl) | 579.2 |
| 100 | pyrazole | CONH | methyl | 4-pyrid-3'-yl-$C_6H_4$ | 379.2 |
| 101 | pyrazole | CONH | methyl | 2-(2'-pyridyl)ethyl | 349.2 |
| 102 | pyrazole | CONH | methyl | 3-($C_6H_4$)propyl | 362.2 |
| 103 | pyrazole | CONH | methyl | 4-(pyrid-2'-yl)$C_6H_4$ | 397.2 |
| 104 | pyrazole | CONH | methyl | 4-(i-propoxy)$C_6H_4$ | 378.2 |
| 105 | pyrazole | CONH | methyl | 5-(2'-$CF_3$-phenyl)pyrimidin-2-yl | 466.2 |
| 106 | pyrazole | CONH | methyl | 4-(piperidino-$SO_2$)$C_6H_4$ | 467.2 |
| 107 | pyrazole | CONH | methyl | 4-(piperidino-CO)$C_6H_4$ | 431.1 |
| 108 | pyrazole (R = F) | CONH | methyl | 2'-$H_2NSO_2$-biphenyl | 493 |
| 109 | pyrazole (D = $CONH_2$) (R = F) | CONH | methyl | 2'-$H_2NSO_2$-biphenyl | 494.1 |
| 110 | 3-pyrazole | CONH | 1-methyl | 2'-$H_2NSO_2$-biphenyl | 475.3 |
| 111 | pyrazole | CONH | methyl | 4-(pyrazol-4'-yl)$C_6H_4$ | 386.3 |
| 112 | pyrazole | CONH | methyl | 5-(2'-$SO_2CH_3$—$C_6H_4$)pyrid-2-yl | 475.2 |
| 113 | pyrazole | CONH | methyl | 5-(2'-$SO_2CH_3$—$C_6H_4$)pyrimid-2-yl | 476.2 |
| 114 | pyrazole (D = —CN) | CONH | methyl | 5-(2'-$SO_2CH_3$—$C_6H_4$)pyrimid-2-yl | 459.0 |
| 115 | pyrazole (D = $CONH_2$) | CONH | methyl | 5-(2'-$SO_2CH_3$—$C_6H_4$)pyrimid-2-yl | 477.1 |
| 116 | pyrazole (D = N—$NH_2$—AM) | CONH | methyl | 2'-t-Bu—$NHSO_2$-biphenyl | 490.2 |
| 117 | pyrazole (D = N—$NH_2$—AM) | CONH | methyl | 2'-$H_2NSO_2$-biphenyl | 546.2 |

TABLE 1b-continued

| # | Ring | Linker | Sub | Aryl | Mass |
|---|---|---|---|---|---|
| 118 | pyrazole (D = N—Me—N—HO—AM) | CONH | methyl | 2'-t-Bu—NHSO$_2$-biphenyl | 561.2 |
| 119 | pyrazole (D = N—Me—AM) | CONH | methyl | 2'-t-Bu—NHSO$_2$-biphenyl | 545.2 |
| 120 | pyrazole (D = N—Me—AM) | CONH | methyl | 2'-H$_2$NSO$_2$-biphenyl | 489.2 |
| 121 | tetrazole | CONH | — | 5-(2'-H$_2$NSO$_2$—C$_6$H$_4$)pyridin-2-yl | 464.2 |
| 122 | tetrazole (D = CONH$_2$) | CONH | — | 5-(2'-H$_2$NSO$_2$—C$_6$H$_4$)pyridin-2-yl | 465.1 |
| 123 | tetrazole | CONH | — | 5-(2'-CF$_3$—C$_6$H$_4$)pyridin-2-yl | 453.2 |
| 124 | tetrazole | CONH | — | 4-Br—C$_6$H$_4$ | 386.0 |
| 125 | tetrazole (D = CONH$_2$) | CONH | — | 5-(2'-CF$_3$—C$_6$H$_4$)pyridin-2-yl | 454.1 |
| 126 | tetrazole | CH$_2$ | — | 2'-CF$_3$-biphenyl | 423.2 |
| 127 | 1-(3-AM-phenyl)-methyl-pyrazole | CONH | methyl | 2'-H$_2$NSO$_2$-biphenyl | 489 |
| 128 | 1-(4-AM-phenyl)-methyl-pyrazole | CONH | methyl | 2'-H$_2$NSO$_2$-biphenyl | 489 |
| 129 | imidazole-a | CONH | — | 2'-H$_2$NSO$_2$-biphenyl | 461 |
| 130 | imidazole-a | CONH | 4-methyl | 2'-H$_2$NSO$_2$-biphenyl | 475.2 |
| 131 | imidazole-a | COHN | 5-Cl, 4-Me | 2'-H$_2$NSO$_2$-biphenyl | 509.1 |
| 132 | imidazole-c | CONH | 2-methyl | 2'-H$_2$NSO$_2$-biphenyl | 475.1 |
| 133 | pyrazole | CONH | methyl | 4'-(N-benzimidazol-1-yl)C$_6$H$_4$ | 436.2 |
| 134 | pyrazole (D = CONH$_2$) | CONH | methyl | 4'-(N-benzimidazol-1-yl)C$_6$H$_4$ | 437.2 |
| 135 | pyrazole | CONH | methyl | 4-(2'-methylimidazol-1-yl)C$_6$H$_4$ | 400.2 |
| 136 | pyrazole (D = CONH$_2$) | CONH | methyl | 4-(2'-methylimidazol-1-yl)C$_6$H$_4$ | 401.2 |
| 137 | pyrazole | CONH | methyl | 4'-(1,2,4-triazol-2-yl)C$_6$H$_4$ | 387.2 |
| 138 | pyrazole | CONH | methyl | 4'-cyclohexyl-C$_6$H$_4$ | 402.2 |
| 139 | pyrazole | CONH | methyl | biphenyl | 396.2 |
| 140 | pyrazole | CONH | methyl | 4'-morpholino-C$_6$H$_4$ | 405.2 |
| 141 | pyrazole | CONH | methyl | 4'-(2-CF$_3$-tetrazol-1-yl)C$_6$H$_4$ | 456.2 |
| 142 | pyrazole (D = CH$_2$NH$_2$) | CONH | methyl | 4'-(2-CF$_3$-tetrazol-1-yl)C$_6$H$_4$ | 443.2 |
| 143 | pyrazole | CONH | methyl | 4-(CH$_3$)$_2$NC(O)NH—C$_6$H$_4$ | 406.2 |
| 144 | pyrazole | CONH | methyl | 4-(CH$_3$)$_2$N—C$_6$H$_4$ | 391.2 |
| 145 | pyrazole (D = CONH$_2$) | CONH | methyl | 4-(CH$_3$)$_2$N—C$_6$H$_4$ | 392.2 |
| 146 | pyrazole | CONH | methyl | 4-tetrazol-1-yl-C$_6$H$_4$ | 388.2 |
| 147 | pyrazole (D = CONH$_2$) | CONH | methyl | 4-tetrazol-1-yl-C$_6$H$_4$ | 389.2 |
| 148 | pyrazole | CONH | methyl | 4-(N-acetylpiperazin-1-yl)C$_6$H$_4$ | 446.2 |
| 149 | pyrazole | CONH | methyl | 4-(N-t-butoxycarbonylpiperazin-1-yl)C$_6$H$_4$ | 504.3 |
| 150 | pyrazole | CONH | methyl | 4-(piperazin-1-yl)C$_6$H$_4$ | 404.2 |
| 151 | pyrazole | CONH | CF$_3$ | 4-cyclohexylphenyl | 456.2 |
| 152 | pyrazole | CONH | methyl | 4-(N-morpholino)-3-chloro-C$_6$H$_4$ | 439.2 |
| 153 | pyrazole | CONH | CH$_3$S | 2'-H$_2$NSO$_2$-biphenyl | 507.1 |
| 154 | pyrazole | CONH | CH$_3$SO | 2'-H$_2$NSO$_2$-biphenyl | 523.1 |
| 155 | pyrazole | CONH | CH$_3$SO$_2$ | 2'-H$_2$NSO$_2$-biphenyl | 539.1 |
| 156 | tetrazole (D = CONH$_2$) | CH$_2$ | — | 2'-CF$_3$-biphenyl | 424.1 |
| 157 | tetrazole (D = CONH$_2$) | CH$_2$ | — | 2'-H$_2$NSO$_2$-biphenyl | 435.1 |
| 158 | pyrazole | CONH | methyl | 4-cyclopentyloxyphenyl | 404.2 |
| 159 | pyrazole | CONH | methyl | 3-(pyrid-2-yl-NHCH$_2$)C$_6$H$_4$ | 426.2 |
| 160 | pyrazole | CONH | methyl | 4-(N-imidazolyl)phenyl | 386.2 |

TABLE 1b-continued

| | | | | | |
|---|---|---|---|---|---|
| 161 | pyrazole | CONH | $CF_3$ | 4-(N-morpholino)-3-Cl—$C_6H_4$ | 493.1 |
| 162 | pyrazole | CONH | methyl | 4-(N-pyrrolidino-carbonyl)-3-Cl-$C_6H_4$ | 451.2 |
| 163 | pyrazole | CONH | methyl | 4-(N-morpholino-carbonyl)-3-Cl—$C_6H_4$ | 433.2 |
| 164 | pyrazole<br>D = —CN | CONH | $CF_3$ | 4-(N-imidazolyl)phenyl | 423.2 |
| 165 | pyrazole | CONH | $CF_3$ | 4-(N-imidazolyl)phenyl | 440.2 |
| 166 | pyrazole | CONH | $CF_3$ | 4-(N-methyltetrazolon-1-yl)phenyl | 472.1 |
| 167 | pyrazole<br>(D = $CONH_2$) | $COCH_2$ | methyl | 2'-$H_2NSO_2$-biphenyl | 433.2 |
| 168 | pyrazole | CONH | methyl | 4-N-pyrrolidino-methylphenyl | 403.2 |
| 169 | pyrazole<br>(D = $NH_2$) | CONH | methyl | 2'-$H_2NSO_2$-biphenyl | 448.1 |
| 170 | pyrazole<br>(D = 2-$NH_2$) | CONH | methyl | 2'-$H_2NSO_2$-biphenyl | 448.1 |
| 171 | pyrazole<br>(D = $NH_2$)<br>(R = 4-Cl) | CONH | methyl | 2'-$H_2NSO_2$-biphenyl | 482.0 |
| 172 | pyrazole<br>(D = $NH_2$)<br>(R = 4-F) | CONH | methyl | 2'-$H_2NSO_2$-biphenyl | 466.0 |
| 173 | pyrazole<br>(D = $NH_2$)<br>(R = 4-OMe) | CONH | methyl | 2'-$H_2NSO_2$-biphenyl | 478.1 |
| 174 | tetrazole<br>(D = $NH_2$)<br>(R = 4-Cl) | CONH | — | 2'-$H_2NSO_2$-biphenyl | 470.0 |
| 175 | tetrazole<br>(D = $NH_2$)<br>(R = 4-Cl) | CONH | — | 5-(2'-$H_2NSO_2$—$C_6H_4$)pyridin-2-yl | 471.2 |
| 176 | tetrazole<br>(D = $NH_2$)<br>(R = 4-OMe) | CONH | — | 2'-$H_2NSO_2$-biphenyl | 466.0 |
| 177 | pyrazole<br>(D = $CH_2NH_2$) | CONH | methyl | 5-(2'-$H_2NSO_2$—$C_6H_4$)pyridin-2-yl | 463.3 |
| 178 | pyrazole<br>(D = $CH_2NH_2$)<br>(R = 4-$CH_3$) | CONH | methyl | 2'-$H_2NSO_2$-biphenyl | 476 |
| 179 | pyrazole<br>(D = $CH_2NH_2$)<br>(R = 4-F) | CONH | methyl | 2'-$H_2NSO_2$-biphenyl | 480 |
| 180 | pyrazole<br>(D = $CH_2NH_2$) | CONH | $CF_3$ | 4-(N-pyrrolidino-carbonyl)$C_6H_4$ | 458.2 |
| 181 | pyrazole<br>(D = *) | CONH | methyl | 2'-$H_2NSO_2$-biphenyl | 547.2 |
| 182 | pyrazole<br>(D = **) | CONH | methyl | 2'-t-Bu—$NHSO_2$-biphenyl | 603.2 |
| 183 | pyrazole<br>(D = **) | CONH | methyl | 2'-$H_2NSO_2$-biphenyl | 547.2 |
| 184 | pyrazole<br>(D = ***) | CONH | methyl | 2'-$H_2NSO_2$-biphenyl | 631.2 |
| 185 | 1-(pyrid-2-yl)-pyrazole | CONH | methyl | 3-F-2'-$H_2NSO_2$-biphenyl | 452 |
| 186 | 1-(6-Br-pyrid-2-yl)-pyrazole | CONH | methyl | 3-F-2'-$H_2NSO_2$-biphenyl | 530 |
| 187 | tetrazole<br>(D = 3-$NH_2$)<br>(R = 4-Cl) | CONH | — | 3-Cl-2'-$H_2NSO_2$-biphenyl | 504.0 |
| 188 | tetrazole<br>(D = 3-$NH_2$)<br>(R = 4-Cl) | CONH | — | 4-(N-pyrrolidino-carbonyl)$C_6H_4$ | 430 |
| 189 | tetrazole<br>(D = $CH_2NH_2$) | CONH | — | 2'-$H_2NSO_2$-biphenyl | 450.2 |
| 190 | 1,3,4-triazole<br>(D = $CH_2NH_2$) | CONH | H | 3-F-2'-$H_2NSO_2$-biphenyl | 467.9 |
| 191 | imidazole-d<br>(D = $CH_2NH_2$) | CONH | — | 2'-$H_2NSO_2$-biphenyl | 448.2 |
| 192 | imidazole-d<br>(D = $CH_2NH_2$) | CONH | — | 2'-$H_3CSO_2$-biphenyl | 447 |

TABLE 1b-continued

| | | | | | |
|---|---|---|---|---|---|
| 193 | imidazole-d | CONH | — | 2'-H$_2$NSO$_2$-biphenyl | 461.2 |
| 194 | pyrazole (D = CH$_2$NHCH$_3$) | CONH | methyl | 3-F-2'-H$_2$NSO$_2$-biphenyl | 494.1 |
| 195 | pyrazole (D = CH$_2$NHCH$_3$) | CONH | methyl | 3-F-2'-H$_3$CSO$_2$-biphenyl | 492.2 |
| 196 | pyrazole (D = CH$_2$NH$_2$) | CONH | 3-CF$_3$ 4-OCH$_3$ | 2'-H$_3$CSO$_2$-biphenyl | 545.1 |
| 197 | pyrazole (D = CH$_2$NH$_2$) | CONH | CF$_3$ | 2-F-4-(N-pyrrolidino-carbonyl)C$_6$H$_4$ | 476.2 |
| 198 | pyrazole (D = CH$_2$NH$_2$) | CONH | CF$_3$ | 3-F-4-(N-pyrrolidino-carbonyl)C$_6$H$_4$ | 476.2 |
| 199 | pyrazole (D = CH$_2$NH$_2$) | CONH | CF$_3$ | 2'-H$_3$CSO$_2$-biphenyl | 515.1 |
| 200 | pyrazole (D = CH$_2$NH$_2$) | CONH | CF$_3$ | 3-F-2'-H$_2$NSO$_2$-biphenyl | 534.1 |
| 201 | pyrazole (D = CH$_2$NH$_2$) | CONH | CF$_3$ | 5-(2'-H$_2$NSO$_2$—C$_6$H$_4$)[1,6-dihydro] pyrimidin-2-yl | 520.1 |
| 202 | pyrazole (D = CH$_2$NH$_2$) | CONH | CF$_3$ | 5-(2'-H$_2$NSO$_2$—C$_6$H$_4$)pyrimidin-2-yl | 518.1 |
| 203 | pyrazole (D = CH(CH$_3$)—NH$_2$) | CONH | CF$_3$ | 2'-H$_2$NSO$_2$-biphenyl | 530.1 |
| 204 | pyrazole (D = C(=NH)—N-morpholino) | CONH | CF$_3$ | 3-F-2'-H$_2$NSO$_2$-biphenyl | 616.9 |
| 205 | pyrazole (D = CH$_2$NH$_2$) | CH(OH)CH$_2$ | CF$_3$ | 2'-H$_2$NSO$_2$-biphenyl | 517.2 |
| 206 | pyrazole (D = CH$_2$NH$_2$) | CONH | CF$_3$ | 3-F-2'-H$_3$CSO$_2$-biphenyl | 532.9 |
| 207 | pyrazole (D = CH$_2$NH$_2$) | CONH | CF$_3$ | 5-(2'-H$_3$CSO$_2$—C$_6$H$_4$)pyrimidin-2-yl | 517.1 |
| 208 | pyrazole | CONH | CF$_3$ | 3-F-2'-H$_2$NSO$_2$-biphenyl | 546 |
| 209 | pyrazole | CONH | CF$_3$ | 3-F-2'-H$_3$CSO$_2$-biphenyl | 547.1 |
| 210 | pyrazole (D = CH$_2$NH$_2$) | COCH$_2$ | CF$_3$ | 2'-H$_2$NSO$_2$-biphenyl | 514.8 |
| 211 | pyrazole (D = CH$_2$NH$_2$) | CONH | CH$_2$SO$_2$—CH$_3$ | 2'-H$_2$NSO$_2$-biphenyl | 540.1 |
| 212 | pyrazole | CONH | CH$_2$NH—SO$_2$H$_3$ | 2'-H$_2$NSO$_2$-biphenyl | 568.1 |
| 213 | pyrazole (D = CH$_2$NH$_2$) | CONH | CH$_2$NH—SO$_2$CH$_3$ | 3-F-2'-H$_3$CSO$_2$-biphenyl | 572.1 |
| 214 | pyrazole (D = CH(=NH)NHCO$_2$CH$_3$) | CONH | methyl | 5-(2'-H$_2$NSO$_2$—C$_6$H$_4$)pyrimidin-2-yl | 535.1 |
| 215 | pyrazole (D = CH$_2$NH$_2$) | CONH | methyl | 2'-H$_3$CSO$_2$-biphenyl | 461.2 |
| 216 | pyrazole (D = CH$_2$NH$_2$) | CONH | CF$_3$ | 3-CH$_3$-2'-H$_3$CSO$_2$-biphenyl | 530.2 |
| 217 | 1,2,3-triazole (D = CH$_2$NH$_2$) | CONH | — | 3-F-2'-H$_3$CSO$_2$-biphenyl | 466.1 |
| 218 | pyrazole (D = CH$_2$NH$_2$) (R = 4-CH$_3$) | CONH | methyl | 2'-H$_2$NSO$_2$-biphenyl | 476.2 |
| 219 | pyrazole (D = CH$_2$NH$_2$) (R = 4-F) | CONH | methyl | 2'-H$_2$NSO$_2$-biphenyl | 480.2 |
| 220 | pyrazole (D = CH$_2$NH$_2$) (R = 4-Cl) | CONH | methyl | 2'-H$_2$NSO$_2$-biphenyl | 497.1 |
| 221 | pyrazole (D = CH$_2$NH$_2$) (R = 4-F) | CONH | CF$_3$ | 3-F-2'-H$_2$NSO$_2$-biphenyl | 551.9 |
| 222 | pyrazole (D = CH$_2$NH$_2$) | CONH | methyl | 3-F-2'-H$_2$NSO$_2$-biphenyl | 480 |
| 223 | pyrazole (D = CH$_2$NH$_2$) | CONH | methyl | 3-F-2'-H$_3$CSO$_2$-biphenyl | 479 |
| 224 | pyrazole | CONH | methyl | 3-F-4-(N-morpholino)phenyl | 423.2 |
| 225 | pyrazole (D = CH$_2$NH$_2$) | CONH | methyl | 3-F-4-(N-morpholino)phenyl | 410.2 |
| 226 | pyrazole (D = CH$_2$NH$_2$) | CONH | CF$_3$ | 3-F-4-(2'-CH$_3$-imidazol-1-yl)phenyl | 459.2 |

TABLE 1b-continued

| | | | | | |
|---|---|---|---|---|---|
| 227 | pyrazole (D = CN) | CH$_2$O | methyl | biphenyl | 420 |
| 228 | pyrazole | CH$_2$O | methyl | biphenyl | 437.2 |
| 229 | pyrazole (D = CONH$_2$) | CH$_2$O | methyl | biphenyl | 438.2 |
| 230 | pyrazole | CONH | CF$_3$ | 2-F-4-(N-morpholino)phenyl | 477.2 |
| 231 | pyrazole (D = CONH$_2$) | CONH | CF$_3$ | 2-F-4-(N-morpholino)phenyl | 478.1 |
| 232 | pyrazole (D = CH$_2$NH$_2$) | CONH | CF$_3$ | 3-CF$_3$-4-(N-morpholino)phenyl | 514 |
| 233 | pyrazole (D = CH$_2$NH$_2$) | CONH | ethyl | 3-F-2'-H$_2$NSO$_2$-biphenyl | 493.9 |
| 234 | pyrazole (D = CH$_2$NH$_2$) | CONH | ethyl | 3-F-2'-H$_3$CSO$_2$-biphenyl | 493 |
| 235 | pyrazole (D = CH$_2$NH$_2$) | CONH | ethyl | 2-F-4-(2'-H$_3$CSO$_2$-imidazolyl)phenyl | 465.2 |
| 236 | 1-(6-NH$_2$CH$_2$-pyrid-2-yl)-pyrazole | CONH | methyl | 2'-H$_2$NSO$_2$-biphenyl | 462.9 |
| 237 | 1-(6-C(=NH$_2$)NOH-pyrid-2-yl)-pyrazole | CONH | methyl | 2'-t-BuHNSO$_2$-biphenyl | 548.1 |
| 238 | 1-(6-AM-pyrid-2-yl)-pyrazole | CONH | methyl | 2'-H$_2$NSO$_2$-biphenyl | 476.2 |
| 239 | 1-(6-AM-pyrid-2-yl)-pyrazole | CONH | methyl | 3-F-2'-H$_3$CSO$_2$-biphenyl | 493.9 |
| 240 | pyrazole (D = CH$_2$NH$_2$) | CONH | methyl | 2-CH$_3$O-4-(N-morpholino)phenyl | 422.2 |
| 241 | pyrazole (D = CH$_2$NH$_2$) | CONH | methyl | 4-(3'-CH$_3$-5'-oxo-3'-pyrazolin-2'-yl)phenyl | 403.1 |
| 242 | pyrazole (D = CH$_2$NH$_2$) | CONH | SCH$_3$ | 2'-H$_3$CSO$_2$-biphenyl | 493 |
| 243 | pyrazole (D = CH$_2$NH$_2$) (R = 4-F) | CONH | CF$_3$ | 2'-H$_3$CSO$_2$-biphenyl | 551 |
| 244 | pyrazole (D = CH$_2$NH$_2$) | CONH | CO$_2$Et | 3-F-2'-H$_3$CSO$_2$-biphenyl | 537.2 |
| 245 | pyrazole (D = CH$_2$NH$_2$) | CONH | COOH | 3-F-2'-H$_3$CSO$_2$-biphenyl | 509.2 |
| 246 | pyrazole (D = CH$_2$NH$_2$) | CONH | CONH$_2$ | 2-F-2'-H$_3$CSO$_2$-biphenyl | 537.2 |
| 247 | pyrazole (D = CH$_2$NH$_2$) | CONH | 3-CF$_3$ 4-CO$_2$Et | 3-F-2'-H$_3$CSO$_2$-biphenyl | 605.2 |
| 248 | pyrazole (D = CH$_2$NH$_2$) | CONH | SCH$_3$ | 3-F-2'-H$_3$CSO$_2$-biphenyl | 511 |
| 249 | pyrazole (D = CH$_2$NH$_2$) | CONH | SO$_2$CH$_3$ | 3-F-2'-H$_3$CSO$_2$-biphenyl | 543 |
| 250 | pyrazole (D = CH$_2$NH$_2$) | CONH | CF$_3$ | 4-((5-CH$_3$ONHC(O))imidazol-1-yl)phenyl | 442 |
| 251 | pyrazole (D = CH$_2$NH$_2$) | CONH | CF$_3$ | 4-(5-CH$_3$-1,2,3-triazol-1-yl)phenyl | 500 |

*D = Ethylcarboxyamidino.
**D = 1"-imino-1"-N-morpholino)methyl.
***D = N-((5-methyl-2-oxo-1,3-dioxol-4-yl)methoxycarbonyl)amidino.

The following tables contain representative examples of the present invention. Each entry in each table is intended to be paired with each formulae at the start of the table. For example, in Table 2, example 1 is intended to be paired with each of formulae a–nn and in Table 3, example 1 is intended to be paired with each of formulae a–nn.

The following groups are intended for group A in the following tables.

 

2-pyridyl    3-pyridyl

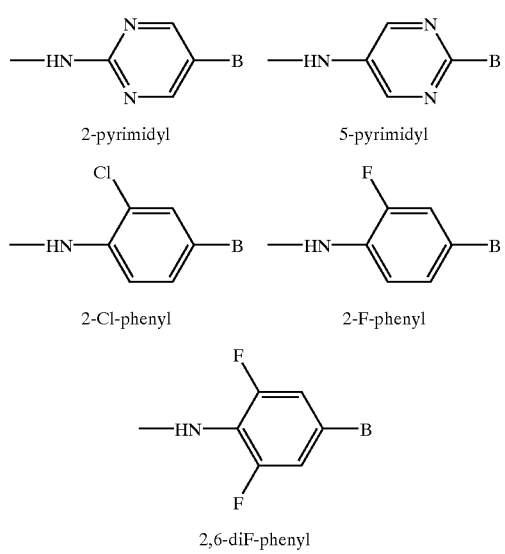
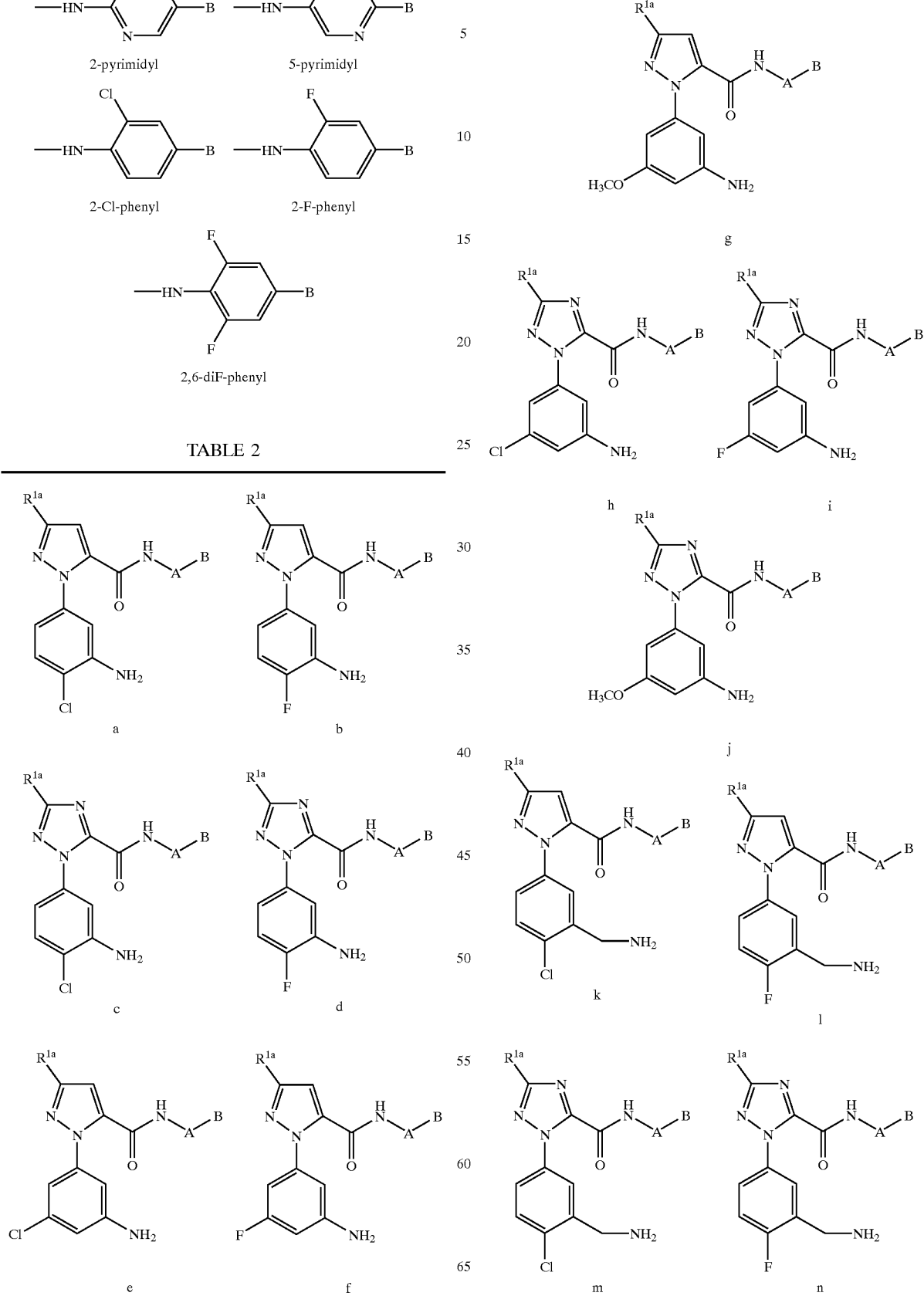

TABLE 2-continued
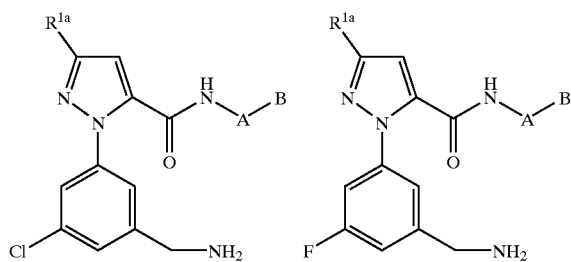
o    p
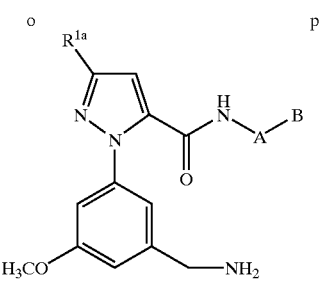
q
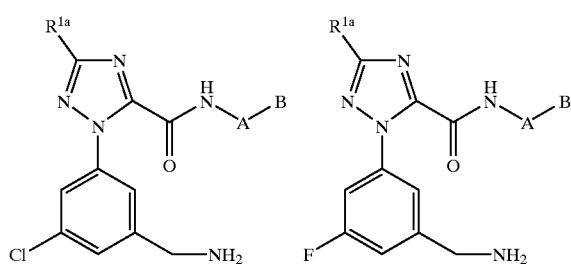
r    s
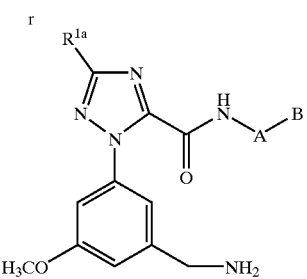
t
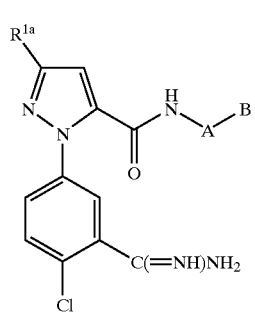
u    v
TABLE 2-continued
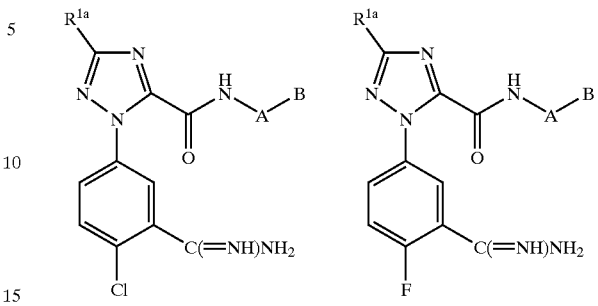
w    x
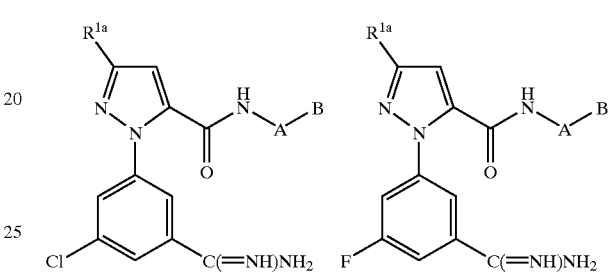
y    z
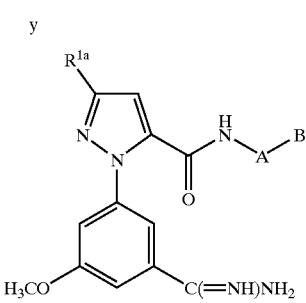
aa
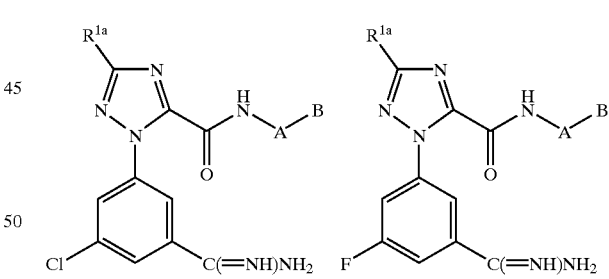
bb    cc
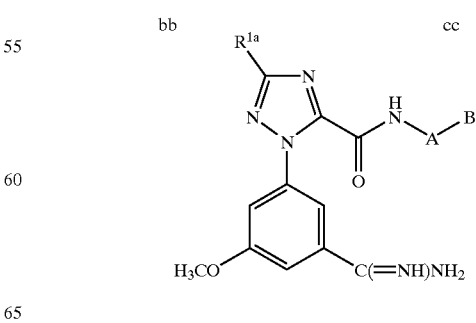
dd TABLE 2-continued
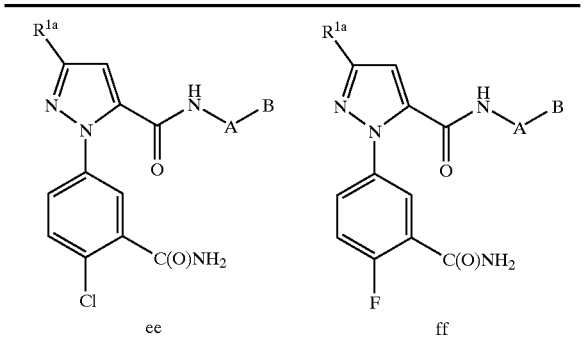
ee  ff
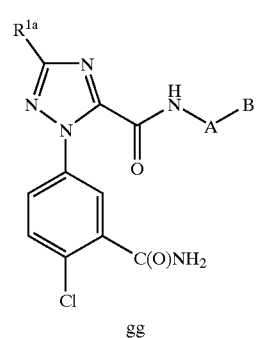
gg  hh
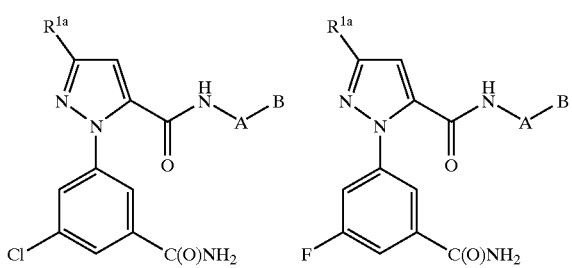
ii  jj
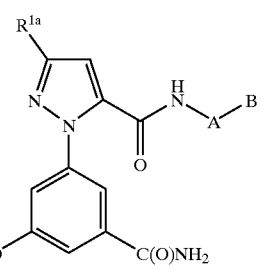
kk
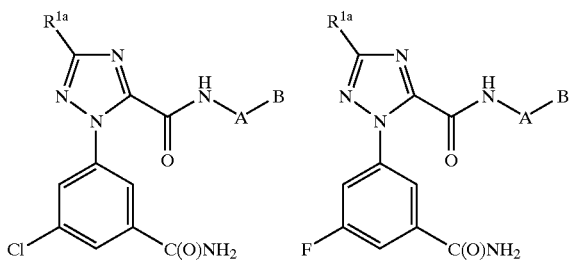
ll  mm
TABLE 2-continued
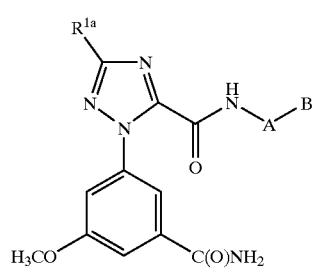
nn
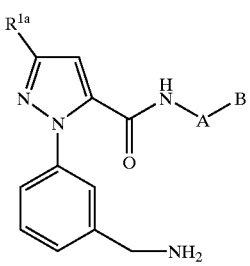
oo  pp
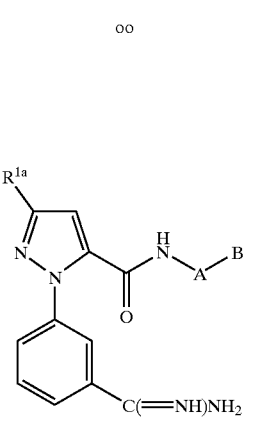
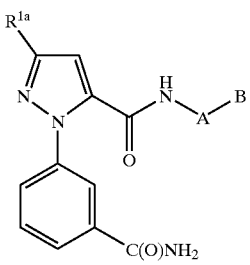
qq  rr
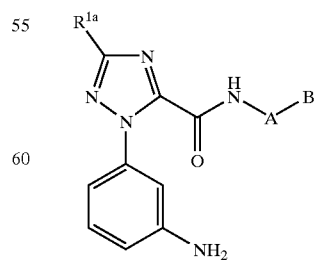
ss  tt TABLE 2-continued Structures uu and vv: 1,2,4-triazole-carboxamides with R1a substituent, N-A-B amide; uu has C(=NH)NH2 on the meta phenyl ring, vv has C(O)NH2 on the meta phenyl ring.

| Ex # | R$^{1a}$ | A | B |
|---|---|---|---|
| 1 | CH$_3$ | phenyl | 2-(aminosulfonyl)phenyl |
| 2 | CH$_3$ | phenyl | 2-(methylaminosulfonyl)phenyl |
| 3 | CH$_3$ | phenyl | 1-pyrrolidinocarbonyl |
| 4 | CH$_3$ | phenyl | 2-(methylsulfonyl)phenyl |
| 5 | CH$_3$ | phenyl | 4-morpholino |
| 6 | CH$_3$ | phenyl | 2-(1'-CF$_3$-tetrazol-2-yl)phenyl |
| 7 | CH$_3$ | phenyl | 4-morpholinocarbonyl |
| 8 | CH$_3$ | phenyl | 2-methyl-1-imidazolyl |
| 9 | CH$_3$ | phenyl | 5-methyl-1-imidazolyl |
| 10 | CH$_3$ | phenyl | 2-methylsulfonyl-1-imidazolyl |
| 11 | CH$_3$ | 2-pyridyl | 2-(aminosulfonyl)phenyl |
| 12 | CH$_3$ | 2-pyridyl | 2-(methylaminosulfonyl)phenyl |
| 13 | CH$_3$ | 2-pyridyl | 1-pyrrolidinocarbonyl |
| 14 | CH$_3$ | 2-pyridyl | 2-(methylsulfonyl)phenyl |
| 15 | CH$_3$ | 2-pyridyl | 4-morpholino |
| 16 | CH$_3$ | 2-pyridyl | 2-(1'-CF$_3$-tetrazol-2-yl)phenyl |
| 17 | CH$_3$ | 2-pyridyl | 4-morpholinocarbonyl |
| 18 | CH$_3$ | 2-pyridyl | 2-methyl-1-imidazolyl |
| 19 | CH$_3$ | 2-pyridyl | 5-methyl-1-imidazolyl |
| 20 | CH$_3$ | 2-pyridyl | 2-methylsulfonyl-1-imidazolyl |
| 21 | CH$_3$ | 3-pyridyl | 2-(aminosulfonyl)phenyl |
| 22 | CH$_3$ | 3-pyridyl | 2-(methylaminosulfonyl)phenyl |
| 23 | CH$_3$ | 3-pyridyl | 1-pyrrolidinocarbonyl |
| 24 | CH$_3$ | 3-pyridyl | 2-(methylsulfonyl)phenyl |
| 25 | CH$_3$ | 3-pyridyl | 4-morpholino |
| 26 | CH$_3$ | 3-pyridyl | 2-(1'-CF$_3$-tetrazol-2-yl)phenyl |
| 27 | CH$_3$ | 3-pyridyl | 4-morpholinocarbonyl |
| 28 | CH$_3$ | 3-pyridyl | 2-methyl-1-imidazolyl |
| 29 | CH$_3$ | 3-pyridyl | 5-methyl-1-imidazolyl |
| 30 | CH$_3$ | 3-pyridyl | 2-methylsulfonyl-1-imidazolyl |
| 31 | CH$_3$ | 2-pyrimidyl | 2-(aminosulfonyl)phenyl |
| 32 | CH$_3$ | 2-pyrimidyl | 2-(methylaminosulfonyl)phenyl |
| 33 | CH$_3$ | 2-pyrimidyl | 1-pyrrolidinocarbonyl |
| 34 | CH$_3$ | 2-pyrimidyl | 2-(methylsulfonyl)phenyl |
| 35 | CH$_3$ | 2-pyrimidyl | 4-morpholino |
| 36 | CH$_3$ | 2-pyrimidyl | 2-(1'-CF$_3$-tetrazol-2-yl)phenyl |
| 37 | CH$_3$ | 2-pyrimidyl | 4-morpholinocarbonyl |
| 38 | CH$_3$ | 2-pyrimidyl | 2-methyl-1-imidazolyl |
| 39 | CH$_3$ | 2-pyrimidyl | 5-methyl-1-imidazolyl |
| 40 | CH$_3$ | 2-pyrimidyl | 2-methylsulfonyl-1-imidazolyl |
| 41 | CH$_3$ | 5-pyrimidyl | 2-(aminosulfonyl)phenyl |
| 42 | CH$_3$ | 5-pyrimidyl | 2-(methylaminosulfonyl)phenyl |
| 43 | CH$_3$ | 5-pyrimidyl | 1-pyrrolidinocarbonyl |
| 44 | CH$_3$ | 5-pyrimidyl | 2-(methylsulfonyl)phenyl |
| 45 | CH$_3$ | 5-pyrimidyl | 4-morpholino |
| 46 | CH$_3$ | 5-pyrimidyl | 2-(1'-CF$_3$-tetrazol-2-yl)phenyl |
| 47 | CH$_3$ | 5-pyrimidyl | 4-morpholinocarbonyl |
| 48 | CH$_3$ | 5-pyrimidyl | 2-methyl-1-imidazolyl |
| 49 | CH$_3$ | 5-pyrimidyl | 5-methyl-1-imidazolyl |
| 50 | CH$_3$ | 5-pyrimidyl | 2-methylsulfonyl-1-imidazolyl |
| 51 | CH$_3$ | 2-Cl-phenyl | 2-(aminosulfonyl)phenyl |
| 52 | CH$_3$ | 2-Cl-phenyl | 2-(methylaminosulfonyl)phenyl |
| 53 | CH$_3$ | 2-Cl-phenyl | 1-pyrrolidinocarbonyl |
| 54 | CH$_3$ | 2-Cl-phenyl | 2-(methylsulfonyl)phenyl |
| 55 | CH$_3$ | 2-Cl-phenyl | 4-morpholino |
| 56 | CH$_3$ | 2-Cl-phenyl | 2-(1'-CF$_3$-tetrazol-2-yl)phenyl |
| 57 | CH$_3$ | 2-Cl-phenyl | 4-morpholinocarbonyl |
| 58 | CH$_3$ | 2-Cl-phenyl | 2-methyl-1-imidazolyl |
| 59 | CH$_3$ | 2-Cl-phenyl | 5-methyl-1-imidazolyl |
| 60 | CH$_3$ | 2-Cl-phenyl | 2-methylsulfonyl-1-imidazolyl |
| 61 | CH$_3$ | 2-F-phenyl | 2-(aminosulfonyl)phenyl |
| 62 | CH$_3$ | 2-F-phenyl | 2-(methylaminosulfonyl)phenyl |
| 63 | CH$_3$ | 2-F-phenyl | 1-pyrrolidinocarbonyl |
| 64 | CH$_3$ | 2-F-phenyl | 2-(methylsulfonyl)phenyl |
| 65 | CH$_3$ | 2-F-phenyl | 4-morpholino |
| 66 | CH$_3$ | 2-F-phenyl | 2-(1'-CF$_3$-tetrazol-2-yl)phenyl |
| 67 | CH$_3$ | 2-F-phenyl | 4-morpholinocarbonyl |
| 68 | CH$_3$ | 2-F-phenyl | 2-methyl-1-imidazolyl |
| 69 | CH$_3$ | 2-F-phenyl | 5-methyl-1-imidazolyl |
| 70 | CH$_3$ | 2-F-phenyl | 2-methylsulfonyl-1-imidazolyl |
| 71 | CH$_3$ | 2,6-diF-phenyl | 2-(aminosulfonyl)phenyl |
| 72 | CH$_3$ | 2,6-diF-phenyl | 2-(methylaminosulfonyl)phenyl |
| 73 | CH$_3$ | 2,6-diF-phenyl | 1-pyrrolidinocarbonyl |
| 74 | CH$_3$ | 2,6-diF-phenyl | 2-(methylsulfonyl)phenyl |
| 75 | CH$_3$ | 2,6-diF-phenyl | 4-morpholino |
| 76 | CH$_3$ | 2,6-diF-phenyl | 2-(1'-CF$_3$-tetrazol-2-yl)phenyl |
| 77 | CH$_3$ | 2,6-diF-phenyl | 4-morpholinocarbonyl |
| 78 | CH$_3$ | 2,6-diF-phenyl | 2-methyl-1-imidazolyl |
| 79 | CH$_3$ | 2,6-diF-phenyl | 5-methyl-1-imidazolyl |
| 80 | CH$_3$ | 2,6-diF-phenyl | 2-methylsulfonyl-1-imidazolyl |
| 81 | CH$_2$CH$_3$ | phenyl | 2-(aminosulfonyl)phenyl |
| 82 | CH$_2$CH$_3$ | phenyl | 2-(methylaminosulfonyl)phenyl |
| 83 | CH$_2$CH$_3$ | phenyl | 1-pyrrolidinocarbonyl |
| 84 | CH$_2$CH$_3$ | phenyl | 2-(methylsulfonyl)phenyl |
| 85 | CH$_2$CH$_3$ | phenyl | 4-morpholino |
| 86 | CH$_2$CH$_3$ | phenyl | 2-(1'-CF$_3$-tetrazol-2-yl)phenyl |
| 87 | CH$_2$CH$_3$ | phenyl | 4-morpholinocarbonyl |
| 88 | CH$_2$CH$_3$ | phenyl | 2-methyl-1-imidazolyl |
| 89 | CH$_2$CH$_3$ | phenyl | 5-methyl-1-imidazolyl |
| 90 | CH$_2$CH$_3$ | phenyl | 2-methylsulfonyl-1-imidazolyl |
| 91 | CH$_2$CH$_3$ | 2-pyridyl | 2-(aminosulfonyl)phenyl |
| 92 | CH$_2$CH$_3$ | 2-pyridyl | 2-(methylaminosulfonyl)phenyl |
| 93 | CH$_2$CH$_3$ | 2-pyridyl | 1-pyrrolidinocarbonyl |
| 94 | CH$_2$CH$_3$ | 2-pyridyl | 2-(methylsulfonyl)phenyl |
| 95 | CH$_2$CH$_3$ | 2-pyridyl | 4-morpholino |
| 96 | CH$_2$CH$_3$ | 2-pyridyl | 2-(1'-CF$_3$-tetrazol-2-yl)phenyl |
| 97 | CH$_2$CH$_3$ | 2-pyridyl | 4-morpholinocarbonyl |
| 98 | CH$_2$CH$_3$ | 2-pyridyl | 2-methyl-1-imidazolyl |
| 99 | CH$_2$CH$_3$ | 2-pyridyl | 5-methyl-1-imidazolyl |
| 100 | CH$_2$CH$_3$ | 2-pyridyl | 2-methylsulfonyl-1-imidazolyl |
| 101 | CH$_2$CH$_3$ | 3-pyridyl | 2-(aminosulfonyl)phenyl |
| 102 | CH$_2$CH$_3$ | 3-pyridyl | 2-(methylaminosulfonyl)phenyl |
| 103 | CH$_2$CH$_3$ | 3-pyridyl | 1-pyrrolidinocarbonyl |
| 104 | CH$_2$CH$_3$ | 3-pyridyl | 2-(methylsulfonyl)phenyl |
| 105 | CH$_2$CH$_3$ | 3-pyridyl | 4-morpholino |
| 106 | CH$_2$CH$_3$ | 3-pyridyl | 2-(1'-CF$_3$-tetrazol-2-yl)phenyl |
| 107 | CH$_2$CH$_3$ | 3-pyridyl | 4-morpholinocarbonyl |
| 108 | CH$_2$CH$_3$ | 3-pyridyl | 2-methyl-1-imidazolyl |
| 109 | CH$_2$CH$_3$ | 3-pyridyl | 5-methyl-1-imidazolyl |
| 110 | CH$_2$CH$_3$ | 3-pyridyl | 2-methylsulfonyl-1-imidazolyl |
| 111 | CH$_2$CH$_3$ | 2-pyrimidyl | 2-(aminosulfonyl)phenyl |
| 112 | CH$_2$CH$_3$ | 2-pyrimidyl | 2-(methylaminosulfonyl)phenyl |
| 113 | CH$_2$CH$_3$ | 2-pyrimidyl | 1-pyrrolidinocarbonyl |
| 114 | CH$_2$CH$_3$ | 2-pyrimidyl | 2-(methylsulfonyl)phenyl |
| 115 | CH$_2$CH$_3$ | 2-pyrimidyl | 4-morpholino |
| 116 | CH$_2$CH$_3$ | 2-pyrimidyl | 2-(1'-CF$_3$-tetrazol-2-yl)phenyl |
| 117 | CH$_2$CH$_3$ | 2-pyrimidyl | 4-morpholinocarbonyl |
| 118 | CH$_2$CH$_3$ | 2-pyrimidyl | 2-methyl-1-imidazolyl |
| 119 | CH$_2$CH$_3$ | 2-pyrimidyl | 5-methyl-1-imidazolyl |
| 120 | CH$_2$CH$_3$ | 2-pyrimidyl | 2-methylsulfonyl-1-imidazolyl |
| 121 | CH$_2$CH$_3$ | 5-pyrimidyl | 2-(aminosulfonyl)phenyl |
| 122 | CH$_2$CH$_3$ | 5-pyrimidyl | 2-(methylaminosulfonyl)phenyl |
| 123 | CH$_2$CH$_3$ | 5-pyrimidyl | 1-pyrrolidinocarbonyl |
| 124 | CH$_2$CH$_3$ | 5-pyrimidyl | 2-(methylsulfonyl)phenyl |
| 125 | CH$_2$CH$_3$ | 5-pyrimidyl | 4-morpholino |
| 126 | CH$_2$CH$_3$ | 5-pyrimidyl | 2-(1'-CF$_3$-tetrazol-2-yl)phenyl |
| 127 | CH$_2$CH$_3$ | 5-pyrimidyl | 4-morpholinocarbonyl |
| 128 | CH$_2$CH$_3$ | 5-pyrimidyl | 2-methyl-1-imidazolyl |
| 129 | CH$_2$CH$_3$ | 5-pyrimidyl | 5-methyl-1-imidazolyl |
| 130 | CH$_2$CH$_3$ | 5-pyrimidyl | 2-methylsulfonyl-1-imidazolyl |
| 131 | CH$_2$CH$_3$ | 2-Cl-phenyl | 2-(aminosulfonyl)phenyl |
| 132 | CH$_2$CH$_3$ | 2-Cl-phenyl | 2-(methylaminosulfonyl)phenyl |
| 133 | CH$_2$CH$_3$ | 2-Cl-phenyl | 1-pyrrolidinocarbonyl |
| 134 | CH$_2$CH$_3$ | 2-Cl-phenyl | 2-(methylsulfonyl)phenyl |
| 135 | CH$_2$CH$_3$ | 2-Cl-phenyl | 4-morpholino |
| 136 | CH$_2$CH$_3$ | 2-Cl-phenyl | 2-(1'-CF$_3$-tetrazol-2-yl)phenyl |
| 137 | CH$_2$CH$_3$ | 2-Cl-phenyl | 4-morpholinocarbonyl |
| 138 | CH$_2$CH$_3$ | 2-Cl-phenyl | 2-methyl-1-imidazolyl |
| 139 | CH$_2$CH$_3$ | 2-Cl-phenyl | 5-methyl-1-imidazolyl |

TABLE 2-continued

| | | | |
|---|---|---|---|
| 140 | CH$_2$CH$_3$ | 2-Cl-phenyl | 2-methylsulfonyl-1-imidazolyl |
| 141 | CH$_2$CH$_3$ | 2-F-phenyl | 2-(aminosulfonyl)phenyl |
| 142 | CH$_2$CH$_3$ | 2-F-phenyl | 2-(methylaminosulfonyl)phenyl |
| 143 | CH$_2$CH$_3$ | 2-F-phenyl | 1-pyrrolidinocarbonyl |
| 144 | CH$_2$CH$_3$ | 2-F-phenyl | 2-(methylsulfonyl)phenyl |
| 145 | CH$_2$CH$_3$ | 2-F-phenyl | 4-morpholino |
| 146 | CH$_2$CH$_3$ | 2-F-phenyl | 2-(1'-CF$_3$-tetrazol-2-yl)phenyl |
| 147 | CH$_2$CH$_3$ | 2-F-phenyl | 4-morpholinocarbonyl |
| 148 | CH$_2$CH$_3$ | 2-F-phenyl | 2-methyl-1-imidazolyl |
| 149 | CH$_2$CH$_3$ | 2-F-phenyl | 5-methyl-1-imidazolyl |
| 150 | CH$_2$CH$_3$ | 2-F-phenyl | 2-methylsulfonyl-1-imidazolyl |
| 151 | CH$_2$CH$_3$ | 2,6-diF-phenyl | 2-(aminosulfonyl)phenyl |
| 152 | CH$_2$CH$_3$ | 2,6-diF-phenyl | 2-(methylaminosulfonyl)phenyl |
| 153 | CH$_2$CH$_3$ | 2,6-diF-phenyl | 1-pyrrolidinocarbonyl |
| 154 | CH$_2$CH$_3$ | 2,6-diF-phenyl | 2-(methylsulfonyl)phenyl |
| 155 | CH$_2$CH$_3$ | 2,6-diF-phenyl | 4-morpholino |
| 156 | CH$_2$CH$_3$ | 2,6-diF-phenyl | 2-(1'-CF$_3$-tetrazol-2-yl)phenyl |
| 157 | CH$_2$CH$_3$ | 2,6-diF-phenyl | 4-morpholinocarbonyl |
| 158 | CH$_2$CH$_3$ | 2,6-diF-phenyl | 2-methyl-1-imidazolyl |
| 159 | CH$_2$CH$_3$ | 2,6-diF-phenyl | 5-methyl-1-imidazolyl |
| 160 | CH$_2$CH$_3$ | 2,6-diF-phenyl | 2-methylsulfonyl-1-imidazolyl |
| 161 | CF$_3$ | phenyl | 2-(aminosulfonyl)phenyl |
| 162 | CF$_3$ | phenyl | 2-(methylaminosulfonyl)phenyl |
| 163 | CF$_3$ | phenyl | 1-pyrrolidinocarbonyl |
| 164 | CF$_3$ | phenyl | 2-(methylsulfonyl)phenyl |
| 165 | CF$_3$ | phenyl | 4-morpholino |
| 166 | CF$_3$ | phenyl | 2-(1'-CF$_3$-tetrazol-2-yl)phenyl |
| 167 | CF$_3$ | phenyl | 4-morpholinocarbonyl |
| 168 | CF$_3$ | phenyl | 2-methyl-1-imidazolyl |
| 169 | CF$_3$ | phenyl | 5-methyl-1-imidazolyl |
| 170 | CF$_3$ | phenyl | 2-methylsulfonyl-1-imidazolyl |
| 171 | CF$_3$ | 2-pyridyl | 2-(aminosulfonyl)phenyl |
| 172 | CF$_3$ | 2-pyridyl | 2-(methylaminosulfonyl)phenyl |
| 173 | CF$_3$ | 2-pyridyl | 1-pyrrolidinocarbonyl |
| 174 | CF$_3$ | 2-pyridyl | 2-(methylsulfonyl)phenyl |
| 175 | CF$_3$ | 2-pyridyl | 4-morpholino |
| 176 | CF$_3$ | 2-pyridyl | 2-(1'-CF$_3$-tetrazol-2-yl)phenyl |
| 177 | CF$_3$ | 2-pyridyl | 4-morpholinocarbonyl |
| 178 | CF$_3$ | 2-pyridyl | 2-methyl-1-imidazolyl |
| 179 | CF$_3$ | 2-pyridyl | 5-methyl-1-imidazolyl |
| 180 | CF$_3$ | 2-pyridyl | 2-methylsulfonyl-1-imidazolyl |
| 181 | CF$_3$ | 3-pyridyl | 2-(aminosulfonyl)phenyl |
| 182 | CF$_3$ | 3-pyridyl | 2-(methylaminosulfonyl)phenyl |
| 183 | CF$_3$ | 3-pyridyl | 1-pyrrolidinocarbonyl |
| 184 | CF$_3$ | 3-pyridyl | 2-(methylsulfonyl)phenyl |
| 185 | CF$_3$ | 3-pyridyl | 4-morpholino |
| 186 | CF$_3$ | 3-pyridyl | 2-(1'-CF$_3$-tetrazol-2-yl)phenyl |
| 187 | CF$_3$ | 3-pyridyl | 4-morpholinocarbonyl |
| 188 | CF$_3$ | 3-pyridyl | 2-methyl-1-imidazolyl |
| 189 | CF$_3$ | 3-pyridyl | 5-methyl-1-imidazolyl |
| 190 | CF$_3$ | 3-pyridyl | 2-methylsulfonyl-1-imidazolyl |
| 191 | CF$_3$ | 2-pyrimidyl | 2-(aminosulfonyl)phenyl |
| 192 | CF$_3$ | 2-pyrimidyl | 2-(methylaminosulfonyl)phenyl |
| 193 | CF$_3$ | 2-pyrimidyl | 1-pyrrolidinocarbonyl |
| 194 | CF$_3$ | 2-pyrimidyl | 2-(methylsulfonyl)phenyl |
| 195 | CF$_3$ | 2-pyrimidyl | 4-morpholino |
| 196 | CF$_3$ | 2-pyrimidyl | 2-(1'-CF$_3$-tetrazol-2-yl)phenyl |
| 197 | CF$_3$ | 2-pyrimidyl | 4-morpholinocarbonyl |
| 198 | CF$_3$ | 2-pyrimidyl | 2-methyl-1-imidazolyl |
| 199 | CF$_3$ | 2-pyrimidyl | 5-methyl-1-imidazolyl |
| 200 | CF$_3$ | 2-pyrimidyl | 2-methylsulfonyl-1-imidazolyl |
| 201 | CF$_3$ | 5-pyrimidyl | 2-(aminosulfonyl)phenyl |
| 202 | CF$_3$ | 5-pyrimidyl | 2-(methylaminosulfonyl)phenyl |
| 203 | CF$_3$ | 5-pyrimidyl | 1-pyrrolidinocarbonyl |
| 204 | CF$_3$ | 5-pyrimidyl | 2-(methylsulfonyl)phenyl |
| 205 | CF$_3$ | 5-pyrimidyl | 4-morpholino |
| 206 | CF$_3$ | 5-pyrimidyl | 2-(1'-CF$_3$-tetrazol-2-yl)phenyl |
| 207 | CF$_3$ | 5-pyrimidyl | 4-morpholinocarbonyl |
| 208 | CF$_3$ | 5-pyrimidyl | 2-methyl-1-imidazolyl |
| 209 | CF$_3$ | 5-pyrimidyl | 5-methyl-1-imidazolyl |
| 210 | CF$_3$ | 5-pyrimidyl | 2-methylsulfonyl-1-imidazolyl |
| 211 | CF$_3$ | 2-Cl-phenyl | 2-(aminosulfonyl)phenyl |
| 212 | CF$_3$ | 2-Cl-phenyl | 2-(methylaminosulfonyl)phenyl |
| 213 | CF$_3$ | 2-Cl-phenyl | 1-pyrrolidinocarbonyl |
| 214 | CF$_3$ | 2-Cl-phenyl | 2-(methylsulfonyl)phenyl |
| 215 | CF$_3$ | 2-Cl-phenyl | 4-morpholino |
| 216 | CF$_3$ | 2-Cl-phenyl | 2-(1'-CF$_3$-tetrazol-2-yl)phenyl |
| 217 | CF$_3$ | 2-Cl-phenyl | 4-morpholinocarbonyl |
| 218 | CF$_3$ | 2-Cl-phenyl | 2-methyl-1-imidazolyl |
| 219 | CF$_3$ | 2-Cl-phenyl | 5-methyl-1-imidazolyl |
| 220 | CF$_3$ | 2-Cl-phenyl | 2-methylsulfonyl-1-imidazolyl |
| 221 | CF$_3$ | 2-F-phenyl | 2-(aminosulfonyl)phenyl |
| 222 | CF$_3$ | 2-F-phenyl | 2-(methylaminosulfonyl)phenyl |
| 223 | CF$_3$ | 2-F-phenyl | 1-pyrrolidinocarbonyl |
| 224 | CF$_3$ | 2-F-phenyl | 2-(methylsulfonyl)phenyl |
| 225 | CF$_3$ | 2-F-phenyl | 4-morpholino |
| 226 | CF$_3$ | 2-F-phenyl | 2-(1'-CF$_3$-tetrazol-2-yl)phenyl |
| 227 | CF$_3$ | 2-F-phenyl | 4-morpholinocarbonyl |
| 228 | CF$_3$ | 2-F-phenyl | 2-methyl-1-imidazolyl |
| 229 | CF$_3$ | 2-F-phenyl | 5-methyl-1-imidazolyl |
| 230 | CF$_3$ | 2-F-phenyl | 2-methylsulfonyl-1-imidazolyl |
| 231 | CF$_3$ | 2,6-diF-phenyl | 2-(aminosulfonyl)phenyl |
| 232 | CF$_3$ | 2,6-diF-phenyl | 2-(methylaminosulfonyl)phenyl |
| 233 | CF$_3$ | 2,6-diF-phenyl | 1-pyrrolidinocarbonyl |
| 234 | CF$_3$ | 2,6-diF-phenyl | 2-(methylsulfonyl)phenyl |
| 235 | CF$_3$ | 2,6-diF-phenyl | 4-morpholino |
| 236 | CF$_3$ | 2,6-diF-phenyl | 2-(1'-CF$_3$-tetrazol-2-yl)phenyl |
| 237 | CF$_3$ | 2,6-diF-phenyl | 4-morpholinocarbonyl |
| 238 | CF$_3$ | 2,6-diF-phenyl | 2-methyl-1-imidazolyl |
| 239 | CF$_3$ | 2,6-diF-phenyl | 5-methyl-1-imidazolyl |
| 240 | CF$_3$ | 2,6-diF-phenyl | 2-methylsulfonyl-1-imidazolyl |
| 241 | SCH$_3$ | phenyl | 2-(aminosulfonyl)phenyl |
| 242 | SCH$_3$ | phenyl | 2-(methylaminosulfonyl)phenyl |
| 243 | SCH$_3$ | phenyl | 1-pyrrolidinocarbonyl |
| 244 | SCH$_3$ | phenyl | 2-(methylsulfonyl)phenyl |
| 245 | SCH$_3$ | phenyl | 4-morpholino |
| 246 | SCH$_3$ | phenyl | 2-(1'-CF$_3$-tetrazol-2-yl)phenyl |
| 247 | SCH$_3$ | phenyl | 4-morpholinocarbonyl |
| 248 | SCH$_3$ | phenyl | 2-methyl-1-imidazolyl |
| 249 | SCH$_3$ | phenyl | 5-methyl-1-imidazolyl |
| 250 | SCH$_3$ | phenyl | 2-methylsulfonyl-1-imidazolyl |
| 251 | SCH$_3$ | 2-pyridyl | 2-(aminosulfonyl)phenyl |
| 252 | SCH$_3$ | 2-pyridyl | 2-(methylaminosulfonyl)phenyl |
| 253 | SCH$_3$ | 2-pyridyl | 1-pyrrolidinocarbonyl |
| 254 | SCH$_3$ | 2-pyridyl | 2-(methylsulfonyl)phenyl |
| 255 | SCH$_3$ | 2-pyridyl | 4-morpholino |
| 256 | SCH$_3$ | 2-pyridyl | 2-(1'-CF$_3$-tetrazol-2-yl)phenyl |
| 257 | SCH$_3$ | 2-pyridyl | 4-morpholinocarbonyl |
| 258 | SCH$_3$ | 2-pyridyl | 2-methyl-1-imidazolyl |
| 259 | SCH$_3$ | 2-pyridyl | 5-methyl-1-imidazolyl |
| 260 | SCH$_3$ | 2-pyridyl | 2-methylsulfonyl-1-imidazolyl |
| 261 | SCH$_3$ | 3-pyridyl | 2-(aminosulfonyl)phenyl |
| 262 | SCH$_3$ | 3-pyridyl | 2-(methylaminosulfonyl)phenyl |
| 263 | SCH$_3$ | 3-pyridyl | 1-pyrrolidinocarbonyl |
| 264 | SCH$_3$ | 3-pyridyl | 2-(methylsulfonyl)phenyl |
| 265 | SCH$_3$ | 3-pyridyl | 4-morpholino |
| 266 | SCH$_3$ | 3-pyridyl | 2-(1'-CF$_3$-tetrazol-2-yl)phenyl |
| 267 | SCH$_3$ | 3-pyridyl | 4-morpholinocarbonyl |
| 268 | SCH$_3$ | 3-pyridyl | 2-methyl-1-imidazolyl |
| 269 | SCH$_3$ | 3-pyridyl | 5-methyl-1-imidazolyl |
| 270 | SCH$_3$ | 3-pyridyl | 2-methylsulfonyl-1-imidazolyl |
| 271 | SCH$_3$ | 2-pyrimidyl | 2-(aminosulfonyl)phenyl |
| 272 | SCH$_3$ | 2-pyrimidyl | 2-(methylaminosulfonyl)phenyl |
| 273 | SCH$_3$ | 2-pyrimidyl | 1-pyrrolidinocarbonyl |
| 274 | SCH$_3$ | 2-pyrimidyl | 2-(methylsulfonyl)phenyl |
| 275 | SCH$_3$ | 2-pyrimidyl | 4-morpholino |
| 276 | SCH$_3$ | 2-pyrimidyl | 2-(1'-CF$_3$-tetrazol-2-yl)phenyl |
| 277 | SCH$_3$ | 2-pyrimidyl | 4-morpholinocarbonyl |
| 278 | SCH$_3$ | 2-pyrimidyl | 2-methyl-1-imidazolyl |
| 279 | SCH$_3$ | 2-pyrimidyl | 5-methyl-1-imidazolyl |
| 280 | SCH$_3$ | 2-pyrimidyl | 2-methylsulfonyl-1-imidazolyl |
| 281 | SCH$_3$ | 5-pyrimidyl | 2-(aminosulfonyl)phenyl |
| 282 | SCH$_3$ | 5-pyrimidyl | 2-(methylaminosulfonyl)phenyl |
| 283 | SCH$_3$ | 5-pyrimidyl | 1-pyrrolidinocarbonyl |
| 284 | SCH$_3$ | 5-pyrimidyl | 2-(methylsulfonyl)phenyl |
| 285 | SCH$_3$ | 5-pyrimidyl | 4-morpholino |
| 286 | SCH$_3$ | 5-pyrimidyl | 2-(1'-CF$_3$-tetrazol-2-yl)phenyl |
| 287 | SCH$_3$ | 5-pyrimidyl | 4-morpholinocarbonyl |
| 288 | SCH$_3$ | 5-pyrimidyl | 2-methyl-1-imidazolyl |
| 289 | SCH$_3$ | 5-pyrimidyl | 5-methyl-1-imidazolyl |
| 290 | SCH$_3$ | 5-pyrimidyl | 2-methylsulfonyl-1-imidazolyl |
| 291 | SCH$_3$ | 2-Cl-phenyl | 2-(aminosulfonyl)phenyl |
| 292 | SCH$_3$ | 2-Cl-phenyl | 2-(methylaminosulfonyl)phenyl |
| 293 | SCH$_3$ | 2-Cl-phenyl | 1-pyrrolidinocarbonyl |
| 294 | SCH$_3$ | 2-Cl-phenyl | 2-(methylsulfonyl)phenyl |
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |

TABLE 2-continued

| | | | |
|---|---|---|---|
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |
| 364 | SOCH$_3$ | 5-pyrimidyl | 2-(methylsulfonyl)phenyl |
| 365 | SOCH$_3$ | 5-pyrimidyl | 4-morpholino |
| 366 | SOCH$_3$ | 5-pyrimidyl | 2-(1'-CF$_3$-tetrazol-2-yl)phenyl |
| 367 | SOCH$_3$ | 5-pyrimidyl | 4-morpholinocarbonyl |
| 368 | SOCH$_3$ | 5-pyrimidyl | 2-methyl-1-imidazolyl |
| 369 | SOCH$_3$ | 5-pyrimidyl | 5-methyl-1-imidazolyl |
| 370 | SOCH$_3$ | 5-pyrimidyl | 2-methylsulfonyl-1-imidazolyl |
| 371 | SOCH$_3$ | 2-Cl-phenyl | 2-(aminosulfonyl)phenyl |
| 372 | SOCH$_3$ | 2-Cl-phenyl | 2-(methylaminosulfonyl)phenyl |
| 373 | SOCH$_3$ | 2-Cl-phenyl | 1-pyrrolidinocarbonyl |
| 374 | SOCH$_3$ | 2-Cl-phenyl | 2-(methylsulfonyl)phenyl |
| 375 | SOCH$_3$ | 2-Cl-phenyl | 4-morpholino |
| 376 | SOCH$_3$ | 2-Cl-phenyl | 2-(1'-CF$_3$-tetrazol-2-yl)phenyl |
| 377 | SOCH$_3$ | 2-Cl-phenyl | 4-morpholinocarbonyl |
| 378 | SOCH$_3$ | 2-Cl-phenyl | 2-methyl-1-imidazolyl |
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |

TABLE 2-continued

| # | | | |
|---|---|---|---|
| 456 | $SO_2CH_3$ | 2-Cl-phenyl | 2-(1'-$CF_3$-tetrazol-2-yl)phenyl |
| 457 | $SO_2CH_3$ | 2-Cl-phenyl | 4-morpholinocarbonyl |
| 458 | $SO_2CH_3$ | 2-Cl-phenyl | 2-methyl-1-imidazolyl |
| 459 | $SO_2CH_3$ | 2-Cl-phenyl | 5-methyl-1-imidazolyl |
| 460 | $SO_2CH_3$ | 2-Cl-phenyl | 2-methylsulfonyl-1-imidazolyl |
| 461 | $SO_2CH_3$ | 2-F-phenyl | 2-(aminosulfonyl)phenyl |
| 462 | $SO_2CH_3$ | 2-F-phenyl | 2-(methylaminosulfonyl)phenyl |
| 463 | $SO_2CH_3$ | 2-F-phenyl | 1-pyrrolidinocarbonyl |
| 464 | $SO_2CH_3$ | 2-F-phenyl | 2-(methylsulfonyl)phenyl |
| 465 | $SO_2CH_3$ | 2-F-phenyl | 4-morpholino |
| 466 | $SO_2CH_3$ | 2-F-phenyl | 2-(1'-$CF_3$-tetrazol-2-yl)phenyl |
| 467 | $SO_2CH_3$ | 2-F-phenyl | 4-morpholinocarbonyl |
| 468 | $SO_2CH_3$ | 2-F-phenyl | 2-methyl-1-imidazolyl |
| 469 | $SO_2CH_3$ | 2-F-phenyl | 5-methyl-1-imidazolyl |
| 470 | $SO_2CH_3$ | 2-F-phenyl | 2-methylsulfonyl-1-imidazolyl |
| 471 | $SO_2CH_3$ | 2,6-diF-phenyl | 2-(aminosulfonyl)phenyl |
| 472 | $SO_2CH_3$ | 2,6-diF-phenyl | 2-(methylaminosulfonyl)phenyl |
| 473 | $SO_2CH_3$ | 2,6-diF-phenyl | 1-pyrrolidinocarbonyl |
| 474 | $SO_2CH_3$ | 2,6-diF-phenyl | 2-(methylsulfonyl)phenyl |
| 475 | $SO_2CH_3$ | 2,6-diF-phenyl | 4-morpholino |
| 476 | $SO_2CH_3$ | 2,6-diF-phenyl | 2-(1'-$CF_3$-tetrazol-2-yl)phenyl |
| 477 | $SO_2CH_3$ | 2,6-diF-phenyl | 4-morpholinocarbonyl |
| 478 | $SO_2CH_3$ | 2,6-diF-phenyl | 2-methyl-1-imidazolyl |
| 479 | $SO_2CH_3$ | 2,6-diF-phenyl | 5-methyl-1-imidazolyl |
| 480 | $SO_2CH_3$ | 2,6-diF-phenyl | 2-methylsulfonyl-1-imidazolyl |
| 481 | $CH_2NH-SO_2CH_3$ | phenyl | 2-(aminosulfonyl)phenyl |
| 482 | $CH_2NH-SO_2CH_3$ | phenyl | 2-(methylaminosulfonyl)phenyl |
| 483 | $CH_2NH-SO_2CH_3$ | phenyl | 1-pyrrolidinocarbonyl |
| 484 | $CH_2NH-SO_2CH_3$ | phenyl | 2-(methylsulfonyl)phenyl |
| 485 | $CH_2NH-SO_2CH_3$ | phenyl | 4-morpholino |
| 486 | $CH_2NH-SO_2CH_3$ | phenyl | 2-(1'-$CF_3$-tetrazol-2-yl)phenyl |
| 487 | $CH_2NH-SO_2CH_3$ | phenyl | 4-morpholinocarbonyl |
| 488 | $CH_2NH-SO_2CH_3$ | phenyl | 2-methyl-1-imidazolyl |
| 489 | $CH_2NH-SO_2CH_3$ | phenyl | 5-methyl-1-imidazolyl |
| 490 | $CH_2NH-SO_2CH_3$ | phenyl | 2-methylsulfonyl-1-imidazolyl |
| 491 | $CH_2NH-SO_2CH_3$ | 2-pyridyl | 2-(aminosulfonyl)phenyl |
| 492 | $CH_2NH-SO_2CH_3$ | 2-pyridyl | 2-(methylaminosulfonyl)phenyl |
| 493 | $CH_2NH-SO_2CH_3$ | 2-pyridyl | 1-pyrrolidinocarbonyl |
| 494 | $CH_2NH-SO_2CH_3$ | 2-pyridyl | 2-(methylsulfonyl)phenyl |
| 495 | $CH_2NH-SO_2CH_3$ | 2-pyridyl | 4-morpholino |
| 496 | $CH_2NH-SO_2CH_3$ | 2-pyridyl | 2-(1'-$CF_3$-tetrazol-2-yl)phenyl |
| 497 | $CH_2NH-SO_2CH_3$ | 2-pyridyl | 4-morpholinocarbonyl |
| 498 | $CH_2NH-SO_2CH_3$ | 2-pyridyl | 2-methyl-1-imidazolyl |
| 499 | $CH_2NH-SO_2CH_3$ | 2-pyridyl | 5-methyl-1-imidazolyl |
| 500 | $CH_2NH-SO_2CH_3$ | 2-pyridyl | 2-methylsulfonyl-1-imidazolyl |
| 501 | $CH_2NH-SO_2CH_3$ | 3-pyridyl | 2-(aminosulfonyl)phenyl |
| 502 | $CH_2NH-SO_2CH_3$ | 3-pyridyl | 2-(methylaminosulfonyl)phenyl |
| 503 | $CH_2NH-SO_2CH_3$ | 3-pyridyl | 1-pyrrolidinocarbonyl |
| 504 | $CH_2NH-SO_2CH_3$ | 3-pyridyl | 2-(methylsulfonyl)phenyl |
| 505 | $CH_2NH-SO_2CH_3$ | 3-pyridyl | 4-morpholino |
| 506 | $CH_2NH-SO_2CH_3$ | 3-pyridyl | 2-(1'-$CF_3$-tetrazol-2-yl)phenyl |
| 507 | $CH_2NH-SO_2CH_3$ | 3-pyridyl | 4-morpholinocarbonyl |
| 508 | $CH_2NH-SO_2CH_3$ | 3-pyridyl | 2-methyl-1-imidazolyl |
| 509 | $CH_2NH-SO_2CH_3$ | 3-pyridyl | 5-methyl-1-imidazolyl |
| 510 | $CH_2NH-SO_2CH_3$ | 3-pyridyl | 2-methylsulfonyl-1-imidazolyl |
| 511 | $CH_2NH-SO_2CH_3$ | 2-pyrimidyl | 2-(aminosulfonyl)phenyl |
| 512 | $CH_2NH-SO_2CH_3$ | 2-pyrimidyl | 2-(methylaminosulfonyl)phenyl |
| 513 | $CH_2NH-SO_2CH_3$ | 2-pyrimidyl | 1-pyrrolidinocarbonyl |
| 514 | $CH_2NH-SO_2CH_3$ | 2-pyrimidyl | 2-(methylsulfonyl)phenyl |
| 515 | $CH_2NH-SO_2CH_3$ | 2-pyrimidyl | 4-morpholino |
| 516 | $CH_2NH-SO_2CH_3$ | 2-pyrimidyl | 2-(1'-$CF_3$-tetrazol-2-yl)phenyl |
| 517 | $CH_2NH-SO_2CH_3$ | 2-pyrimidyl | 4-morpholinocarbonyl |
| 518 | $CH_2NH-SO_2CH_3$ | 2-pyrimidyl | 2-methyl-1-imidazolyl |
| 519 | $CH_2NH-SO_2CH_3$ | 2-pyrimidyl | 5-methyl-1-imidazolyl |
| 520 | $CH_2NH-SO_2CH_3$ | 2-pyrimidyl | 2-methylsulfonyl-1-imidazolyl |
| 521 | $CH_2NH-SO_2CH_3$ | 5-pyrimidyl | 2-(aminosulfonyl)phenyl |
| 522 | $CH_2NH-SO_2CH_3$ | 5-pyrimidyl | 2-(methylaminosulfonyl)phenyl |
| 523 | $CH_2NH-SO_2CH_3$ | 5-pyrimidyl | 1-pyrrolidinocarbonyl |
| 524 | $CH_2NH-SO_2CH_3$ | 5-pyrimidyl | 2-(methylsulfonyl)phenyl |
| 525 | $CH_2NH-SO_2CH_3$ | 5-pyrimidyl | 4-morpholino |
| 526 | $CH_2NH-SO_2CH_3$ | 5-pyrimidyl | 2-(1'-$CF_3$-tetrazol-2-yl)phenyl |
| 527 | $CH_2NH-SO_2CH_3$ | 5-pyrimidyl | 4-morpholinocarbonyl |
| 528 | $CH_2NH-SO_2CH_3$ | 5-pyrimidyl | 2-methyl-1-imidazolyl |
| 529 | $CH_2NH-SO_2CH_3$ | 5-pyrimidyl | 5-methyl-1-imidazolyl |
| 530 | $CH_2NH-SO_2CH_3$ | 5-pyrimidyl | 2-methylsulfonyl-1-imidazolyl |
| 531 | $CH_2NH-SO_2CH_3$ | 2-Cl-phenyl | 2-(aminosulfonyl)phenyl |
| 532 | $CH_2NH-SO_2CH_3$ | 2-Cl-phenyl | 2-(methylaminosulfonyl)phenyl |
| 533 | $CH_2NH-SO_2CH_3$ | 2-Cl-phenyl | 1-pyrrolidinocarbonyl |
| 534 | $CH_2NH-SO_2CH_3$ | 2-Cl-phenyl | 2-(methylsulfonyl)phenyl |
| 535 | $CH_2NH-SO_2CH_3$ | 2-Cl-phenyl | 4-morpholino |
| 536 | $CH_2NH-SO_2CH_3$ | 2-Cl-phenyl | 2-(1'-$CF_3$-tetrazol-2-yl)phenyl |
| 537 | $CH_2NH-SO_2CH_3$ | 2-Cl-phenyl | 4-morpholinocarbonyl |
| 538 | $CH_2NH-SO_2CH_3$ | 2-Cl-phenyl | 2-methyl-1-imidazolyl |
| 539 | $CH_2NH-SO_2CH_3$ | 2-Cl-phenyl | 5-methyl-1-imidazolyl |
| 540 | $CH_2NH-SO_2CH_3$ | 2-Cl-phenyl | 2-methylsulfonyl-1-imidazolyl |
| 541 | $CH_2NH-SO_2CH_3$ | 2-F-phenyl | 2-(aminosulfonyl)phenyl |
| 542 | $CH_2NH-SO_2CH_3$ | 2-F-phenyl | 2-(methylaminosulfonyl)phenyl |
| 543 | $CH_2NH-SO_2CH_3$ | 2-F-phenyl | 1-pyrrolidinocarbonyl |
| 544 | $CH_2NH-SO_2CH_3$ | 2-F-phenyl | 2-(methylsulfonyl)phenyl |
| 545 | $CH_2NH-SO_2CH_3$ | 2-F-phenyl | 4-morpholino |
| 546 | $CH_2NH-SO_2CH_3$ | 2-F-phenyl | 2-(1'-$CF_3$-tetrazol-2-yl)phenyl |

TABLE 2-continued

| | | | |
|---|---|---|---|
| 547 | CH$_2$NH—SO$_2$CH$_3$ | 2-F-phenyl | 4-morpholinocarbonyl |
| 548 | CH$_2$NH—SO$_2$CH$_3$ | 2-F-phenyl | 2-methyl-1-imidazolyl |
| 549 | CH$_2$NH—SO$_2$CH$_3$ | 2-F-phenyl | 5-methyl-1-imidazolyl |
| 550 | CH$_2$NH—SO$_2$CH$_3$ | 2-F-phenyl | 2-methylsulfonyl-1-imidazolyl |
| 551 | CH$_2$NH—SO$_2$CH$_3$ | 2,6-diF-phenyl | 2-(aminosulfonyl)phenyl |
| 552 | CH$_2$NH—SO$_2$CH$_3$ | 2,6-diF-phenyl | 2-(methylaminosulfonyl)phenyl |
| 553 | CH$_2$NH—SO$_2$CH$_3$ | 2,6-diF-phenyl | 1-pyrrolidinocarbonyl |
| 554 | CH$_2$NH—SO$_2$CH$_3$ | 2,6-diF-phenyl | 2-(methylsulfonyl)phenyl |
| 555 | CH$_2$NH—SO$_2$CH$_3$ | 2,6-diF-phenyl | 4-morpholino |
| 556 | CH$_2$NH—SO$_2$CH$_3$ | 2,6-diF-phenyl | 2-(1'-CF$_3$-tetrazol-2-yl)phenyl |
| 557 | CH$_2$NH—SO$_2$CH$_3$ | 2,6-diF-phenyl | 4-morpholinocarbonyl |
| 558 | CH$_2$NH—SO$_2$CH$_3$ | 2,6-diF-phenyl | 2-methyl-1-imidazolyl |
| 559 | CH$_2$NH—SO$_2$CH$_3$ | 2,6-diF-phenyl | 5-methyl-1-imidazolyl |
| 560 | CH$_2$NH—SO$_2$CH$_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF$_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF$_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF$_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF$_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF$_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF$_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF$_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-CF$_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-CF$_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-CF$_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-CF$_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-CF$_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-CF$_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |

TABLE 2-continued

| | | |
|---|---|---|
| 691 F | 2-Cl-phenyl | 2-(aminosulfonyl)phenyl |
| 692 F | 2-Cl-phenyl | 2-(methylaminosulfonyl)phenyl |
| 693 F | 2-Cl-phenyl | 1-pyrrolidinocarbonyl |
| 694 F | 2-Cl-phenyl | 2-(methylsulfonyl)phenyl |
| 695 F | 2-Cl-phenyl | 4-morpholino |
| 696 F | 2-Cl-phenyl | 2-(1'-$CF_3$-tetrazol-2-yl)phenyl |
| 697 F | 2-Cl-phenyl | 4-morpholinocarbonyl |
| 698 F | 2-Cl-phenyl | 2-methyl-1-imidazolyl |
| 699 F | 2-Cl-phenyl | 5-methyl-1-imidazolyl |
| 700 F | 2-Cl-phenyl | 2-methylsulfonyl-1-imidazolyl |
| 701 F | 2-F-phenyl | 2-(aminosulfonyl)phenyl |
| 702 F | 2-F-phenyl | 2-(methylaminosulfonyl)phenyl |
| 703 F | 2-F-phenyl | 1-pyrrolidinocarbonyl |
| 704 F | 2-F-phenyl | 2-(methylsulfonyl)phenyl |
| 705 F | 2-F-phenyl | 4-morpholino |
| 706 F | 2-F-phenyl | 2-(1'-$CF_3$-tetrazol-2-yl)phenyl |
| 707 F | 2-F-phenyl | 4-morpholinocarbonyl |
| 708 F | 2-F-phenyl | 2-methyl-1-imidazolyl |
| 709 F | 2-F-phenyl | 5-methyl-1-imidazolyl |
| 710 F | 2-F-phenyl | 2-methylsulfonyl-1-imidazolyl |
| 711 F | 2,6-diF-phenyl | 2-(aminosulfonyl)phenyl |
| 712 F | 2,6-diF-phenyl | 2-(methylaminosulfonyl)phenyl |
| 713 F | 2,6-diF-phenyl | 1-pyrrolidinocarbonyl |
| 714 F | 2,6-diF-phenyl | 2-(methylsulfonyl)phenyl |
| 715 F | 2,6-diF-phenyl | 4-morpholino |
| 716 F | 2,6-diF-phenyl | 2-(1'-$CF_3$-tetrazol-2-yl)phenyl |
| 717 F | 2,6-diF-phenyl | 4-morpholinocarbonyl |
| 718 F | 2,6-diF-phenyl | 2-methyl-1-imidazolyl |
| 719 F | 2,6-diF-phenyl | 5-methyl-1-imidazolyl |
| 720 F | 2,6-diF-phenyl | 2-methylsulfonyl-1-imidazolyl |
| 721 $CO_2CH_3$ | phenyl | 2-(aminosulfonyl)phenyl |
| 722 $CO_2CH_3$ | phenyl | 2-(methylaminosulfonyl)phenyl |
| 723 $CO_2CH_3$ | phenyl | 1-pyrrolidinocarbonyl |
| 724 $CO_2CH_3$ | phenyl | 2-(methylsulfonyl)phenyl |
| 725 $CO_2CH_3$ | phenyl | 4-morpholino |
| 726 $CO_2CH_3$ | phenyl | 2-(1'-$CF_3$-tetrazol-2-yl)phenyl |
| 727 $CO_2CH_3$ | phenyl | 4-morpholinocarbonyl |
| 728 $CO_2CH_3$ | phenyl | 2-methyl-1-imidazolyl |
| 729 $CO_2CH_3$ | phenyl | 5-methyl-1-imidazolyl |
| 730 $CO_2CH_3$ | phenyl | 2-methylsulfonyl-1-imidazolyl |
| 731 $CO_2CH_3$ | 2-pyridyl | 2-(aminosulfonyl)phenyl |
| 732 $CO_2CH_3$ | 2-pyridyl | 2-(methylaminosulfonyl)phenyl |
| 733 $CO_2CH_3$ | 2-pyridyl | 1-pyrrolidinocarbonyl |
| 734 $CO_2CH_3$ | 2-pyridyl | 2-(methylsulfonyl)phenyl |
| 735 $CO_2CH_3$ | 2-pyridyl | 4-morpholino |
| 736 $CO_2CH_3$ | 2-pyridyl | 2-(1'-$CF_3$-tetrazol-2-yl)phenyl |
| 737 $CO_2CH_3$ | 2-pyridyl | 4-morpholinocarbonyl |
| 738 $CO_2CH_3$ | 2-pyridyl | 2-methyl-1-imidazolyl |
| 739 $CO_2CH_3$ | 2-pyridyl | 5-methyl-1-imidazolyl |
| 740 $CO_2CH_3$ | 2-pyridyl | 2-methylsulfonyl-1-imidazolyl |
| 741 $CO_2CH_3$ | 3-pyridyl | 2-(aminosulfonyl)phenyl |
| 742 $CO_2CH_3$ | 3-pyridyl | 2-(methylaminosulfonyl)phenyl |
| 743 $CO_2CH_3$ | 3-pyridyl | 1-pyrrolidinocarbonyl |
| 744 $CO_2CH_3$ | 3-pyridyl | 2-(methylsulfonyl)phenyl |
| 745 $CO_2CH_3$ | 3-pyridyl | 4-morpholino |
| 746 $CO_2CH_3$ | 3-pyridyl | 2-(1'-$CF_3$-tetrazol-2-yl)phenyl |
| 747 $CO_2CH_3$ | 3-pyridyl | 4-morpholinocarbonyl |
| 748 $CO_2CH_3$ | 3-pyridyl | 2-methyl-1-imidazolyl |
| 749 $CO_2CH_3$ | 3-pyridyl | 5-methyl-1-imidazolyl |
| 750 $CO_2CH_3$ | 3-pyridyl | 2-methylsulfonyl-1-imidazolyl |
| 751 $CO_2CH_3$ | 2-pyrimidyl | 2-(aminosulfonyl)phenyl |
| 752 $CO_2CH_3$ | 2-pyrimidyl | 2-(methylaminosulfonyl)phenyl |
| 753 $CO_2CH_3$ | 2-pyrimidyl | 1-pyrrolidinocarbonyl |
| 754 $CO_2CH_3$ | 2-pyrimidyl | 2-(methylsulfonyl)phenyl |
| 755 $CO_2CH_3$ | 2-pyrimidyl | 4-morpholino |
| 756 $CO_2CH_3$ | 2-pyrimidyl | 2-(1'-$CF_3$-tetrazol-2-yl)phenyl |
| 757 $CO_2CH_3$ | 2-pyrimidyl | 4-morpholinocarbonyl |
| 758 $CO_2CH_3$ | 2-pyrimidyl | 2-methyl-1-imidazolyl |
| 759 $CO_2CH_3$ | 2-pyrimidyl | 5-methyl-1-imidazolyl |
| 760 $CO_2CH_3$ | 2-pyrimidyl | 2-methylsulfonyl-1-imidazolyl |
| 761 $CO_2CH_3$ | 5-pyrimidyl | 2-(aminosulfonyl)phenyl |
| 762 $CO_2CH_3$ | 5-pyrimidyl | 2-(methylaminosulfonyl)phenyl |
| 763 $CO_2CH_3$ | 5-pyrimidyl | 1-pyrrolidinocarbonyl |
| 764 $CO_2CH_3$ | 5-pyrimidyl | 2-(methylsulfonyl)phenyl |
| 765 $CO_2CH_3$ | 5-pyrimidyl | 4-morpholino |
| 766 $CO_2CH_3$ | 5-pyrimidyl | 2-(1'-$CF_3$-tetrazol-2-yl)phenyl |
| 767 $CO_2CH_3$ | 5-pyrimidyl | 4-morpholinocarbonyl |
| 768 $CO_2CH_3$ | 5-pyrimidyl | 2-methyl-1-imidazolyl |
| 769 $CO_2CH_3$ | 5-pyrimidyl | 5-methyl-1-imidazolyl |
| 770 $CO_2CH_3$ | 5-pyrimidyl | 2-methylsulfonyl-1-imidazolyl |
| 771 $CO_2CH_3$ | 2-Cl-phenyl | 2-(aminosulfonyl)phenyl |
| 772 $CO_2CH_3$ | 2-Cl-phenyl | 2-(methylaminosulfonyl)phenyl |
| 773 $CO_2CH_3$ | 2-Cl-phenyl | 1-pyrrolidinocarbonyl |
| 774 $CO_2CH_3$ | 2-Cl-phenyl | 2-(methylsulfonyl)phenyl |
| 775 $CO_2CH_3$ | 2-Cl-phenyl | 4-morpholino |
| 776 $CO_2CH_3$ | 2-Cl-phenyl | 2-(1'-$CF_3$-tetrazol-2-yl)phenyl |
| 777 $CO_2CH_3$ | 2-Cl-phenyl | 4-morpholinocarbonyl |
| 778 $CO_2CH_3$ | 2-Cl-phenyl | 2-methyl-1-imidazolyl |
| 779 $CO_2CH_3$ | 2-Cl-phenyl | 5-methyl-1-imidazolyl |
| 780 $CO_2CH_3$ | 2-Cl-phenyl | 2-methylsulfonyl-1-imidazolyl |
| 781 $CO_2CH_3$ | 2-F-phenyl | 2-(aminosulfonyl)phenyl |
| 782 $CO_2CH_3$ | 2-F-phenyl | 2-(methylaminosulfonyl)phenyl |
| 783 $CO_2CH_3$ | 2-F-phenyl | 1-pyrrolidinocarbonyl |
| 784 $CO_2CH_3$ | 2-F-phenyl | 2-(methylsulfonyl)phenyl |
| 785 $CO_2CH_3$ | 2-F-phenyl | 4-morpholino |
| 786 $CO_2CH_3$ | 2-F-phenyl | 2-(1'-$CF_3$-tetrazol-2-yl)phenyl |
| 787 $CO_2CH_3$ | 2-F-phenyl | 4-morpholinocarbonyl |
| 788 $CO_2CH_3$ | 2-F-phenyl | 2-methyl-1-imidazolyl |
| 789 $CO_2CH_3$ | 2-F-phenyl | 5-methyl-1-imidazolyl |
| 790 $CO_2CH_3$ | 2-F-phenyl | 2-methylsulfonyl-1-imidazolyl |
| 791 $CO_2CH_3$ | 2,6-diF-phenyl | 2-(aminosulfonyl)phenyl |
| 792 $CO_2CH_3$ | 2,6-diF-phenyl | 2-(methylaminosulfonyl)phenyl |
| 793 $CO_2CH_3$ | 2,6-diF-phenyl | 1-pyrrolidinocarbonyl |
| 794 $CO_2CH_3$ | 2,6-diF-phenyl | 2-(methylsulfonyl)phenyl |
| 795 $CO_2CH_3$ | 2,6-diF-phenyl | 4-morpholino |
| 796 $CO_2CH_3$ | 2,6-diF-phenyl | 2-(1'-$CF_3$-tetrazol-2-yl)phenyl |
| 797 $CO_2CH_3$ | 2,6-diF-phenyl | 4-morpholinocarbonyl |
| 798 $CO_2CH_3$ | 2,6-diF-phenyl | 2-methyl-1-imidazolyl |
| 799 $CO_2CH_3$ | 2,6-diF-phenyl | 5-methyl-1-imidazolyl |
| 800 $CO_2CH_3$ | 2,6-diF-phenyl | 2-methylsulfonyl-1-imidazolyl |
| 801 $CH_2OCH_3$ | phenyl | 2-(aminosulfonyl)phenyl |
| 802 $CH_2OCH_3$ | phenyl | 2-(methylaminosulfonyl)phenyl |
| 803 $CH_2OCH_3$ | phenyl | 1-pyrrolidinocarbonyl |
| 804 $CH_2OCH_3$ | phenyl | 2-(methylsulfonyl)phenyl |
| 805 $CH_2OCH_3$ | phenyl | 4-morpholino |
| 806 $CH_2OCH_3$ | phenyl | 2-(1'-$CF_3$-tetrazol-2-yl)phenyl |
| 807 $CH_2OCH_3$ | phenyl | 4-morpholinocarbonyl |
| 808 $CH_2OCH_3$ | phenyl | 2-methyl-1-imidazolyl |
| 809 $CH_2OCH_3$ | phenyl | 5-methyl-1-imidazolyl |
| 810 $CH_2OCH_3$ | phenyl | 2-methylsulfonyl-1-imidazolyl |
| 811 $CH_2OCH_3$ | 2-pyridyl | 2-(aminosulfonyl)phenyl |
| 812 $CH_2OCH_3$ | 2-pyridyl | 2-(methylaminosulfonyl)phenyl |
| 813 $CH_2OCH_3$ | 2-pyridyl | 1-pyrrolidinocarbonyl |
| 814 $CH_2OCH_3$ | 2-pyridyl | 2-(methylsulfonyl)phenyl |
| 815 $CH_2OCH_3$ | 2-pyridyl | 4-morpholino |
| 816 $CH_2OCH_3$ | 2-pyridyl | 2-(1'-$CF_3$-tetrazol-2-yl)phenyl |
| 817 $CH_2OCH_3$ | 2-pyridyl | 4-morpholinocarbonyl |
| 818 $CH_2OCH_3$ | 2-pyridyl | 2-methyl-1-imidazolyl |
| 819 $CH_2OCH_3$ | 2-pyridyl | 5-methyl-1-imidazolyl |
| 820 $CH_2OCH_3$ | 2-pyridyl | 2-methylsulfonyl-1-imidazolyl |
| 821 $CH_2OCH_3$ | 3-pyridyl | 2-(aminosulfonyl)phenyl |
| 822 $CH_2OCH_3$ | 3-pyridyl | 2-(methylaminosulfonyl)phenyl |
| 823 $CH_2OCH_3$ | 3-pyridyl | 1-pyrrolidinocarbonyl |
| 824 $CH_2OCH_3$ | 3-pyridyl | 2-(methylsulfonyl)phenyl |
| 825 $CH_2OCH_3$ | 3-pyridyl | 4-morpholino |
| 826 $CH_2OCH_3$ | 3-pyridyl | 2-(1'-$CF_3$-tetrazol-2-yl)phenyl |
| 827 $CH_2OCH_3$ | 3-pyridyl | 4-morpholinocarbonyl |
| 828 $CH_2OCH_3$ | 3-pyridyl | 2-methyl-1-imidazolyl |
| 829 $CH_2OCH_3$ | 3-pyridyl | 5-methyl-1-imidazolyl |
| 830 $CH_2OCH_3$ | 3-pyridyl | 2-methylsulfonyl-1-imidazolyl |
| 831 $CH_2OCH_3$ | 2-pyrimidyl | 2-(aminosulfonyl)phenyl |
| 832 $CH_2OCH_3$ | 2-pyrimidyl | 2-(methylaminosulfonyl)phenyl |
| 833 $CH_2OCH_3$ | 2-pyrimidyl | 1-pyrrolidinocarbonyl |
| 834 $CH_2OCH_3$ | 2-pyrimidyl | 2-(methylsulfonyl)phenyl |
| 835 $CH_2OCH_3$ | 2-pyrimidyl | 4-morpholino |
| 836 $CH_2OCH_3$ | 2-pyrimidyl | 2-(1'-$CF_3$-tetrazol-2-yl)phenyl |
| 837 $CH_2OCH_3$ | 2-pyrimidyl | 4-morpholinocarbonyl |
| 838 $CH_2OCH_3$ | 2-pyrimidyl | 2-methyl-1-imidazolyl |
| 839 $CH_2OCH_3$ | 2-pyrimidyl | 5-methyl-1-imidazolyl |
| 840 $CH_2OCH_3$ | 2-pyrimidyl | 2-methylsulfonyl-1-imidazolyl |
| 841 $CH_2OCH_3$ | 5-pyrimidyl | 2-(aminosulfonyl)phenyl |
| 842 $CH_2OCH_3$ | 5-pyrimidyl | 2-(methylaminosulfonyl)phenyl |
| 843 $CH_2OCH_3$ | 5-pyrimidyl | 1-pyrrolidinocarbonyl |
| 844 $CH_2OCH_3$ | 5-pyrimidyl | 2-(methylsulfonyl)phenyl |
| 845 $CH_2OCH_3$ | 5-pyrimidyl | 4-morpholino |
| 846 $CH_2OCH_3$ | 5-pyrimidyl | 2-(1'-$CF_3$-tetrazol-2-yl)phenyl |
| 847 $CH_2OCH_3$ | 5-pyrimidyl | 4-morpholinocarbonyl |
| 848 $CH_2OCH_3$ | 5-pyrimidyl | 2-methyl-1-imidazolyl |

TABLE 2-continued

| | | | |
|---|---|---|---|
| 849 | CH₂OCH₃ | 5-pyrimidyl | 5-methyl-1-imidazolyl |
| 850 | CH₂OCH₃ | 5-pyrimidyl | 2-methylsulfonyl-1-imidazolyl |
| 851 | CH₂OCH₃ | 2-Cl-phenyl | 2-(aminosulfonyl)phenyl |
| 852 | CH₂OCH₃ | 2-Cl-phenyl | 2-(methylaminosulfonyl)phenyl |
| 853 | CH₂OCH₃ | 2-Cl-phenyl | 1-pyrrolidinocarbonyl |
| 854 | CH₂OCH₃ | 2-Cl-phenyl | 2-(methylsulfonyl)phenyl |
| 855 | CH₂OCH₃ | 2-Cl-phenyl | 4-morpholino |
| 856 | CH₂OCH₃ | 2-Cl-phenyl | 2-(1'-CF₃-tetrazol-2-yl)phenyl |
| 857 | CH₂OCH₃ | 2-Cl-phenyl | 4-morpholinocarbonyl |
| 858 | CH₂OCH₃ | 2-Cl-phenyl | 2-methyl-1-imidazolyl |
| 859 | CH₂OCH₃ | 2-Cl-phenyl | 5-methyl-1-imidazolyl |
| 860 | CH₂OCH₃ | 2-Cl-phenyl | 2-methylsulfonyl-1-imidazolyl |
| 861 | CH₂OCH₃ | 2-F-phenyl | 2-(aminosulfonyl)phenyl |
| 862 | CH₂OCH₃ | 2-F-phenyl | 2-(methylaminosulfonyl)phenyl |
| 863 | CH₂OCH₃ | 2-F-phenyl | 1-pyrrolidinocarbonyl |
| 864 | CH₂OCH₃ | 2-F-phenyl | 2-(methylsulfonyl)phenyl |
| 865 | CH₂OCH₃ | 2-F-phenyl | 4-morpholino |
| 866 | CH₂OCH₃ | 2-F-phenyl | 2-(1'-CF₃-tetrazol-2-yl)phenyl |
| 867 | CH₂OCH₃ | 2-F-phenyl | 4-morpholinocarbonyl |
| 868 | CH₂OCH₃ | 2-F-phenyl | 2-methyl-1-imidazolyl |
| 869 | CH₂OCH₃ | 2-F-phenyl | 5-methyl-1-imidazolyl |
| 870 | CH₂OCH₃ | 2-F-phenyl | 2-methylsulfonyl-1-imidazolyl |
| 871 | CH₂OCH₃ | 2,6-diF-phenyl | 2-(aminosulfonyl)phenyl |
| 872 | CH₂OCH₃ | 2,6-diF-phenyl | 2-(methylaminosulfonyl)phenyl |
| 873 | CH₂OCH₃ | 2,6-diF-phenyl | 1-pyrrolidinocarbonyl |
| 874 | CH₂OCH₃ | 2,6-diF-phenyl | 2-(methylsulfonyl)phenyl |
| 875 | CH₂OCH₃ | 2,6-diF-phenyl | 4-morpholino |
| 876 | CH₂OCH₃ | 2,6-diF-phenyl | 2-(1'-CF₃-tetrazol-2-yl)phenyl |
| 877 | CH₂OCH₃ | 2,6-diF-phenyl | 4-morpholinocarbonyl |
| 878 | CH₂OCH₃ | 2,6-diF-phenyl | 2-methyl-1-imidazolyl |
| 879 | CH₂OCH₃ | 2,6-diF-phenyl | 5-methyl-1-imidazolyl |
| 880 | CH₂OCH₃ | 2,6-diF-phenyl | 2-methylsulfonyl-1-imidazolyl |
| 881 | CONH₂ | phenyl | 2-(aminosulfonyl)phenyl |
| 882 | CONH₂ | phenyl | 2-(methylaminosulfonyl)phenyl |
| 883 | CONH₂ | phenyl | 1-pyrrolidinocarbonyl |
| 884 | CONH₂ | phenyl | 2-(methylsulfonyl)phenyl |
| 885 | CONH₂ | phenyl | 4-morpholino |
| 886 | CONH₂ | phenyl | 2-(1'-CF₃-tetrazol-2-yl)phenyl |
| 887 | CONH₂ | phenyl | 4-morpholinocarbonyl |
| 888 | CONH₂ | phenyl | 2-methyl-1-imidazolyl |
| 889 | CONH₂ | phenyl | 5-methyl-1-imidazolyl |
| 890 | CONH₂ | phenyl | 2-methylsulfonyl-1-imidazolyl |
| 891 | CONH₂ | 2-pyridyl | 2-(aminosulfonyl)phenyl |
| 892 | CONH₂ | 2-pyridyl | 2-(methylaminosulfonyl)phenyl |
| 893 | CONH₂ | 2-pyridyl | 1-pyrrolidinocarbonyl |
| 894 | CONH₂ | 2-pyridyl | 2-(methylsulfonyl)phenyl |
| 895 | CONH₂ | 2-pyridyl | 4-morpholino |
| 896 | CONH₂ | 2-pyridyl | 2-(1'-CF₃-tetrazol-2-yl)phenyl |
| 897 | CONH₂ | 2-pyridyl | 4-morpholinocarbonyl |
| 898 | CONH₂ | 2-pyridyl | 2-methyl-1-imidazolyl |
| 899 | CONH₂ | 2-pyridyl | 5-methyl-1-imidazolyl |
| 900 | CONH₂ | 2-pyridyl | 2-methylsulfonyl-1-imidazolyl |
| 901 | CONH₂ | 3-pyridyl | 2-(aminosulfonyl)phenyl |
| 902 | CONH₂ | 3-pyridyl | 2-(methylaminosulfonyl)phenyl |
| 903 | CONH₂ | 3-pyridyl | 1-pyrrolidinocarbonyl |
| 904 | CONH₂ | 3-pyridyl | 2-(methylsulfonyl)phenyl |
| 905 | CONH₂ | 3-pyridyl | 4-morpholino |
| 906 | CONH₂ | 3-pyridyl | 2-(1'-CF₃-tetrazol-2-yl)phenyl |
| 907 | CONH₂ | 3-pyridyl | 4-morpholinocarbonyl |
| 908 | CONH₂ | 3-pyridyl | 2-methyl-1-imidazolyl |
| 909 | CONH₂ | 3-pyridyl | 5-methyl-1-imidazolyl |
| 910 | CONH₂ | 3-pyridyl | 2-methylsulfonyl-1-imidazolyl |
| 911 | CONH₂ | 2-pyrimidyl | 2-(aminosulfonyl)phenyl |
| 912 | CONH₂ | 2-pyrimidyl | 2-(methylaminosulfonyl)phenyl |
| 913 | CONH₂ | 2-pyrimidyl | 1-pyrrolidinocarbonyl |
| 914 | CONH₂ | 2-pyrimidyl | 2-(methylsulfonyl)phenyl |
| 915 | CONH₂ | 2-pyrimidyl | 4-morpholino |
| 916 | CONH₂ | 2-pyrimidyl | 2-(1'-CF₃-tetrazol-2-yl)phenyl |
| 917 | CONH₂ | 2-pyrimidyl | 4-morpholinocarbonyl |
| 918 | CONH₂ | 2-pyrimidyl | 2-methyl-1-imidazolyl |
| 919 | CONH₂ | 2-pyrimidyl | 5-methyl-1-imidazolyl |
| 920 | CONH₂ | 2-pyrimidyl | 2-methylsulfonyl-1-imidazolyl |
| 921 | CONH₂ | 5-pyrimidyl | 2-(aminosulfonyl)phenyl |
| 922 | CONH₂ | 5-pyrimidyl | 2-(methylaminosulfonyl)phenyl |
| 923 | CONH₂ | 5-pyrimidyl | 1-pyrrolidinocarbonyl |
| 924 | CONH₂ | 5-pyrimidyl | 2-(methylsulfonyl)phenyl |
| 925 | CONH₂ | 5-pyrimidyl | 4-morpholino |
| 926 | CONH₂ | 5-pyrimidyl | 2-(1'-CF₃-tetrazol-2-yl)phenyl |
| 927 | CONH₂ | 5-pyrimidyl | 4-morpholinocarbonyl |
| 928 | CONH₂ | 5-pyrimidyl | 2-methyl-1-imidazolyl |
| 929 | CONH₂ | 5-pyrimidyl | 5-methyl-1-imidazolyl |
| 930 | CONH₂ | 5-pyrimidyl | 2-methylsulfonyl-1-imidazolyl |
| 931 | CONH₂ | 2-Cl-phenyl | 2-(aminosulfonyl)phenyl |
| 932 | CONH₂ | 2-Cl-phenyl | 2-(methylaminosulfonyl)phenyl |
| 933 | CONH₂ | 2-Cl-phenyl | 1-pyrrolidinocarbonyl |
| 934 | CONH₂ | 2-Cl-phenyl | 2-(methylsulfonyl)phenyl |
| 935 | CONH₂ | 2-Cl-phenyl | 4-morpholino |
| 936 | CONH₂ | 2-Cl-phenyl | 2-(1'-CF₃-tetrazol-2-yl)phenyl |
| 937 | CONH₂ | 2-Cl-phenyl | 4-morpholinocarbonyl |
| 938 | CONH₂ | 2-Cl-phenyl | 2-methyl-1-imidazolyl |
| 939 | CONH₂ | 2-Cl-phenyl | 5-methyl-1-imidazolyl |
| 940 | CONH₂ | 2-Cl-phenyl | 2-methylsulfonyl-1-imidazolyl |
| 941 | CONH₂ | 2-F-phenyl | 2-(aminosulfonyl)phenyl |
| 942 | CONH₂ | 2-F-phenyl | 2-(methylaminosulfonyl)phenyl |
| 943 | CONH₂ | 2-F-phenyl | 1-pyrrolidinocarbonyl |
| 944 | CONH₂ | 2-F-phenyl | 2-(methylsulfonyl)phenyl |
| 945 | CONH₂ | 2-F-phenyl | 4-morpholino |
| 946 | CONH₂ | 2-F-phenyl | 2-(1'-CF₃-tetrazol-2-yl)phenyl |
| 947 | CONH₂ | 2-F-phenyl | 4-morpholinocarbonyl |
| 948 | CONH₂ | 2-F-phenyl | 2-methyl-1-imidazolyl |
| 949 | CONH₂ | 2-F-phenyl | 5-methyl-1-imidazolyl |
| 950 | CONH₂ | 2-F-phenyl | 2-methylsulfonyl-1-imidazolyl |
| 951 | CONH₂ | 2,6-diF-phenyl | 2-(aminosulfonyl)phenyl |
| 952 | CONH₂ | 2,6-diF-phenyl | 2-(methylaminosulfonyl)phenyl |
| 953 | CONH₂ | 2,6-diF-phenyl | 1-pyrrolidinocarbonyl |
| 954 | CONH₂ | 2,6-diF-phenyl | 2-(methylsulfonyl)phenyl |
| 955 | CONH₂ | 2,6-diF-phenyl | 4-morpholino |
| 956 | CONH₂ | 2,6-diF-phenyl | 2-(1'-CF₃-tetrazol-2-yl)phenyl |
| 957 | CONH₂ | 2,6-diF-phenyl | 4-morpholinocarbonyl |
| 958 | CONH₂ | 2,6-diF-phenyl | 2-methyl-1-imidazolyl |
| 959 | CONH₂ | 2,6-diF-phenyl | 5-methyl-1-imidazolyl |
| 960 | CONH₂ | 2,6-diF-phenyl | 2-methylsulfonyl-1-imidazolyl |

TABLE 3

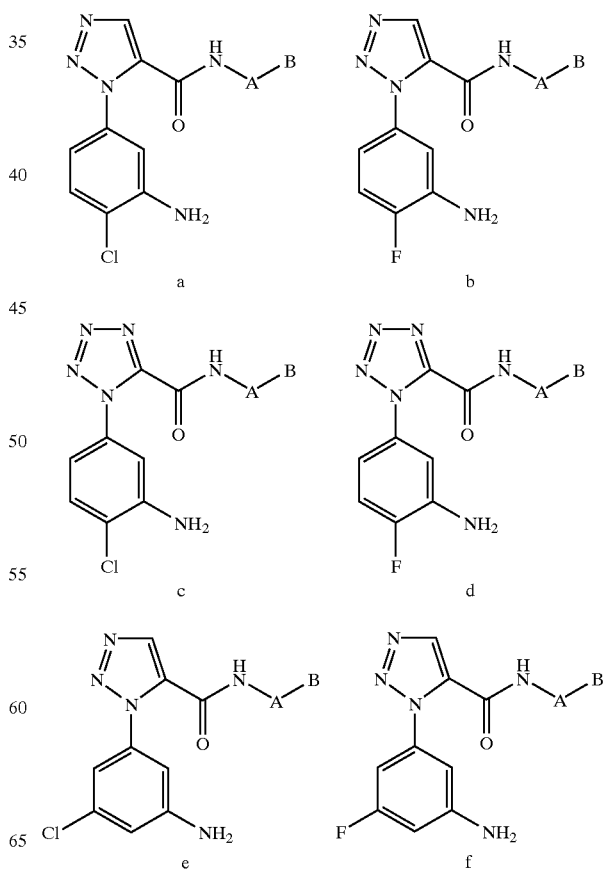

TABLE 3-continued
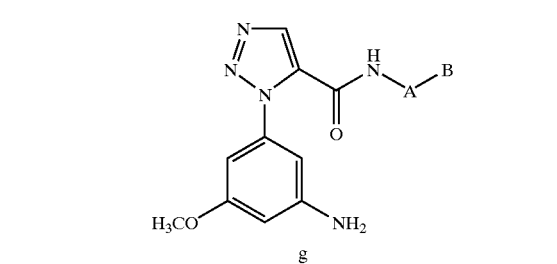
g
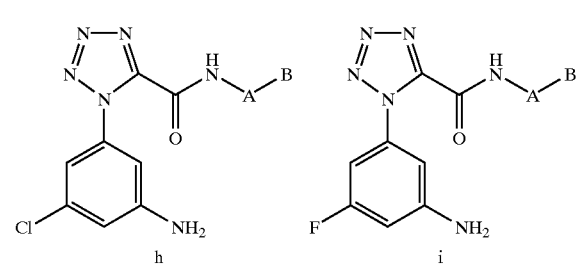
h    i
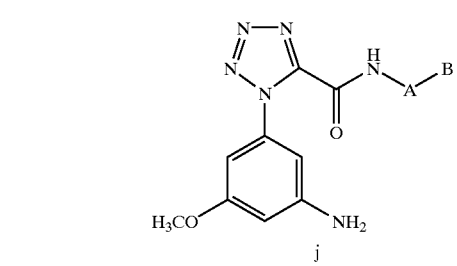
j
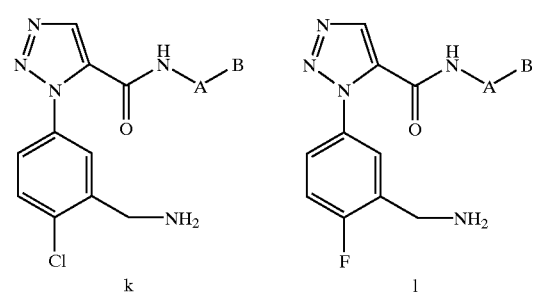
k    l
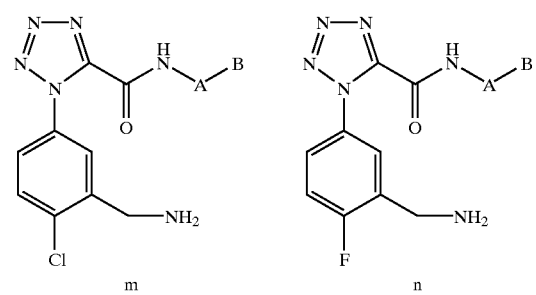
m    n
TABLE 3-continued
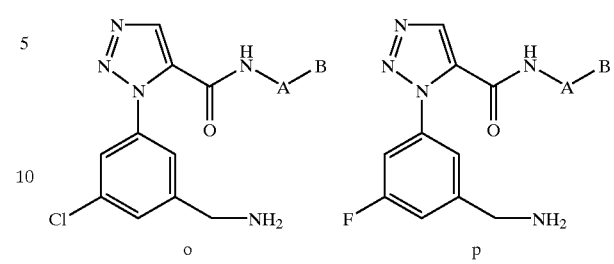
o    p
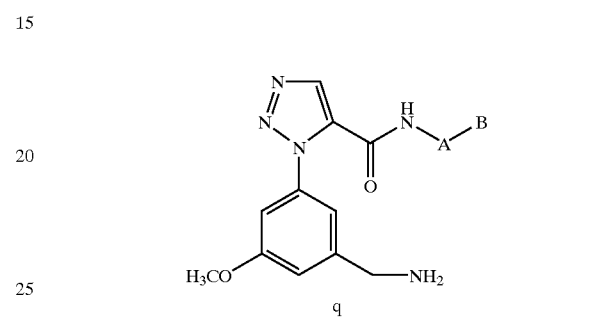
q
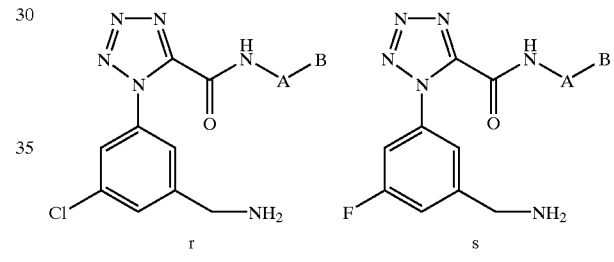
r    s
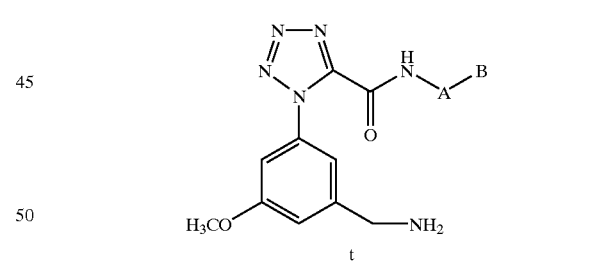
t
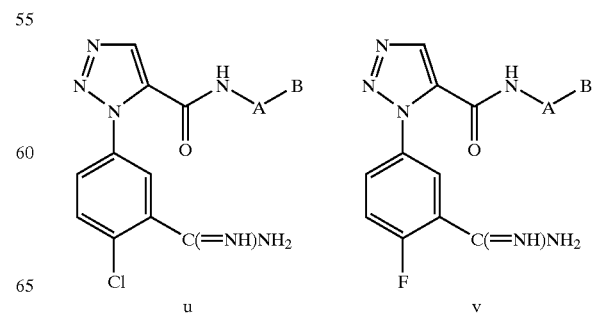
u    v TABLE 3-continued
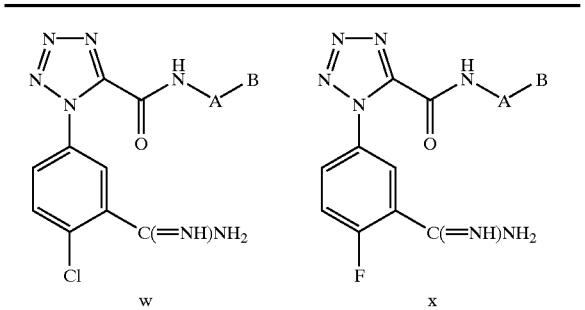
w    x
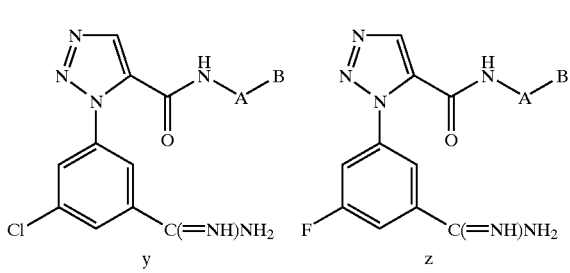
y    z
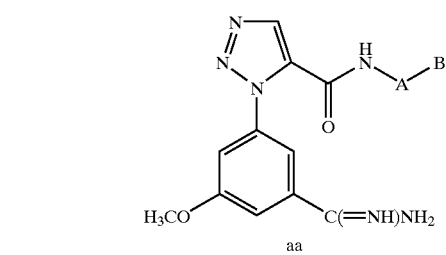
aa
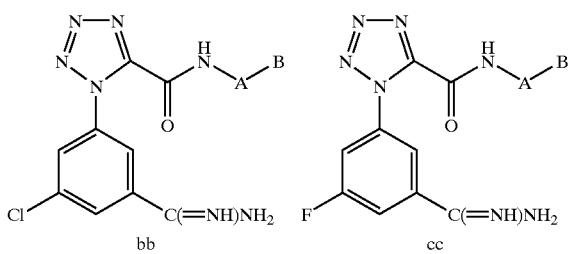
bb    cc
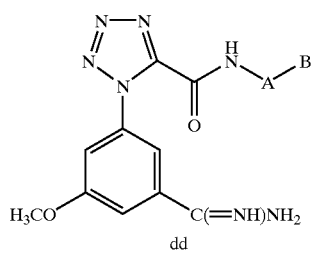
dd
TABLE 3-continued
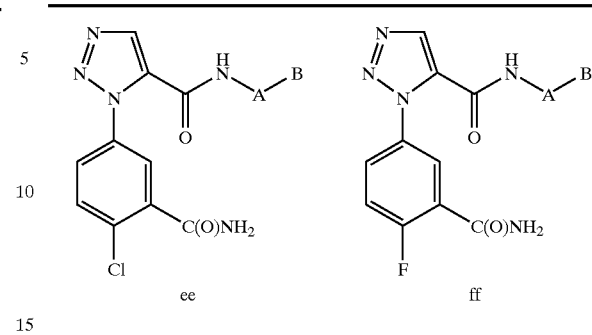
ee    ff
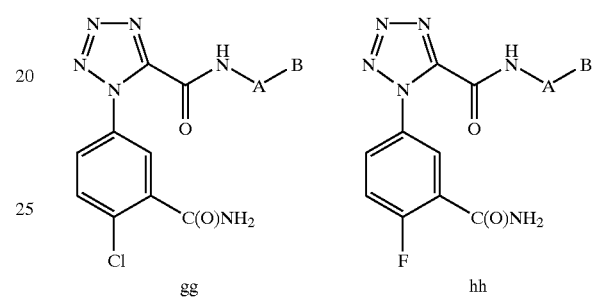
gg    hh
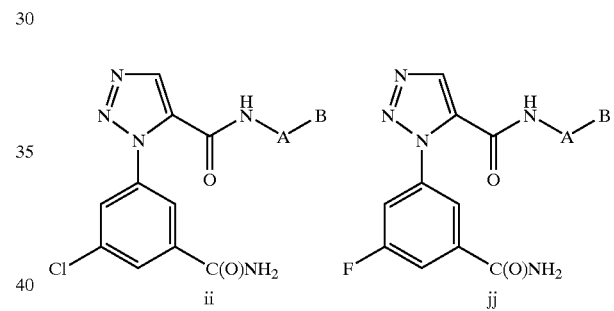
ii    jj
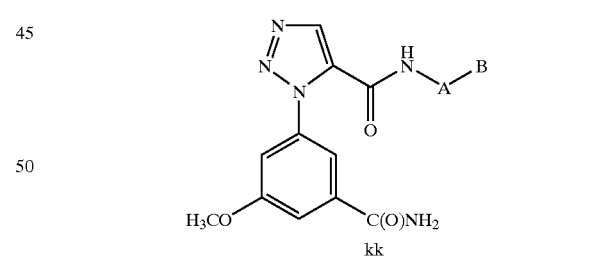
kk
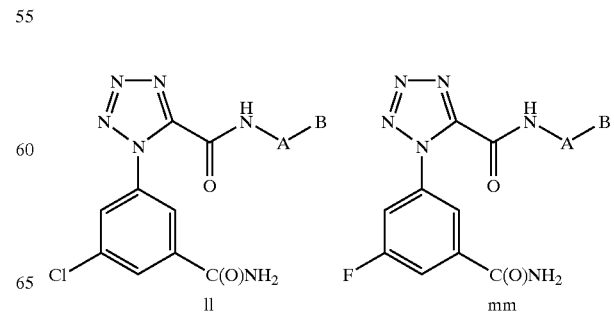
ll    mm TABLE 3-continued Structure nn: 1-(3-methoxy-5-carbamoylphenyl)-tetrazole-5-carboxamide N-A-B Structure oo: 1-(3-aminophenyl)-triazole-5-carboxamide N-A-B Structure pp: 1-(3-aminomethylphenyl)-triazole-5-carboxamide N-A-B Structure qq: 1-(3-amidinophenyl)-triazole-5-carboxamide N-A-B Structure rr: 1-(3-carbamoylphenyl)-triazole-5-carboxamide N-A-B Structure ss: 1-(3-aminophenyl)-tetrazole-5-carboxamide N-A-B Structure tt: 1-(3-aminomethylphenyl)-tetrazole-5-carboxamide N-A-B Structure uu: 1-(3-amidinophenyl)-tetrazole-5-carboxamide N-A-B Structure vv: 1-(3-carbamoylphenyl)-tetrazole-5-carboxamide N-A-B

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-CF$_3$-tetrazol-2-yl)phenyl |
| 17 | 2-pyridyl | 4-morpholinocarbonyl |
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-CF$_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-CF$_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl) phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-CF$_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-CF$_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |
| 66 | 2-F-phenyl | 2-(1'-CF$_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |

TABLE 4
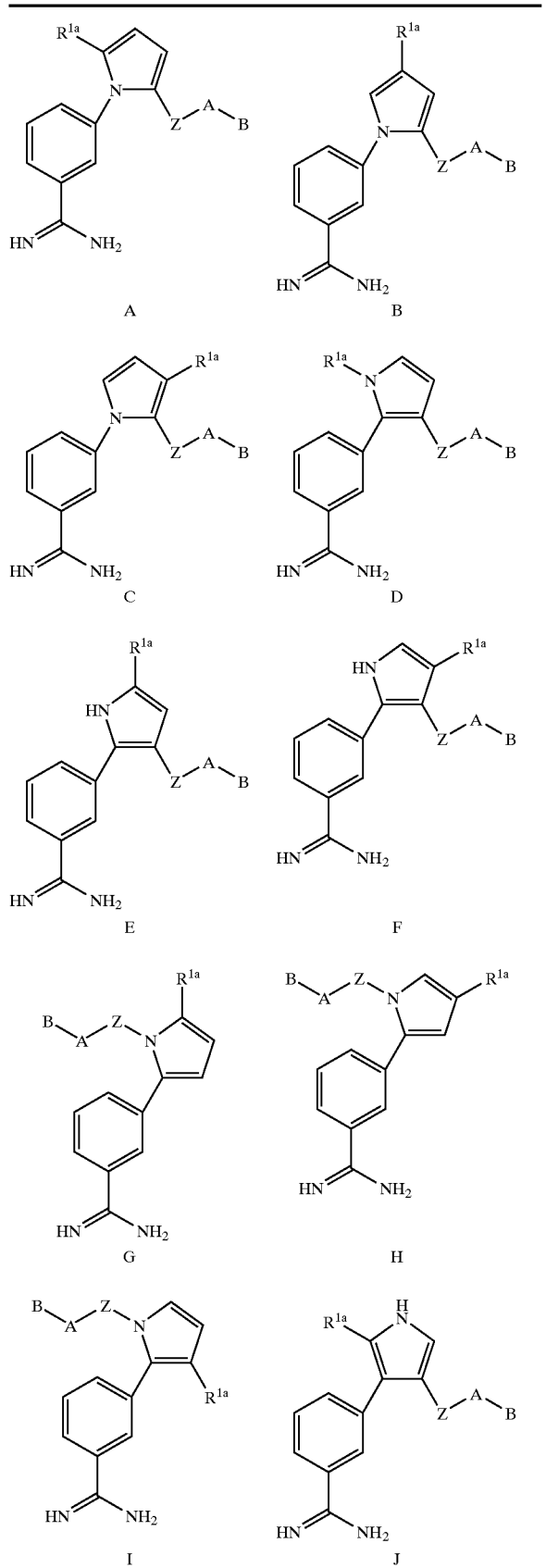
TABLE 4-continued
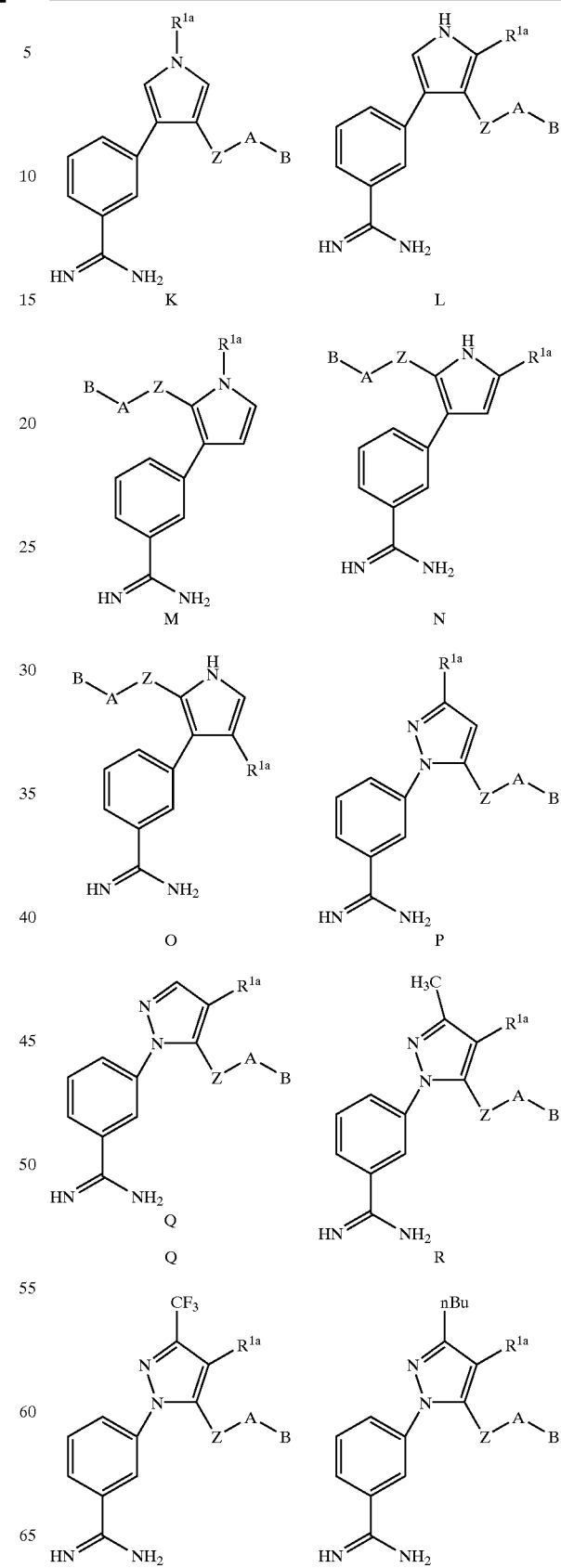

TABLE 4-continued
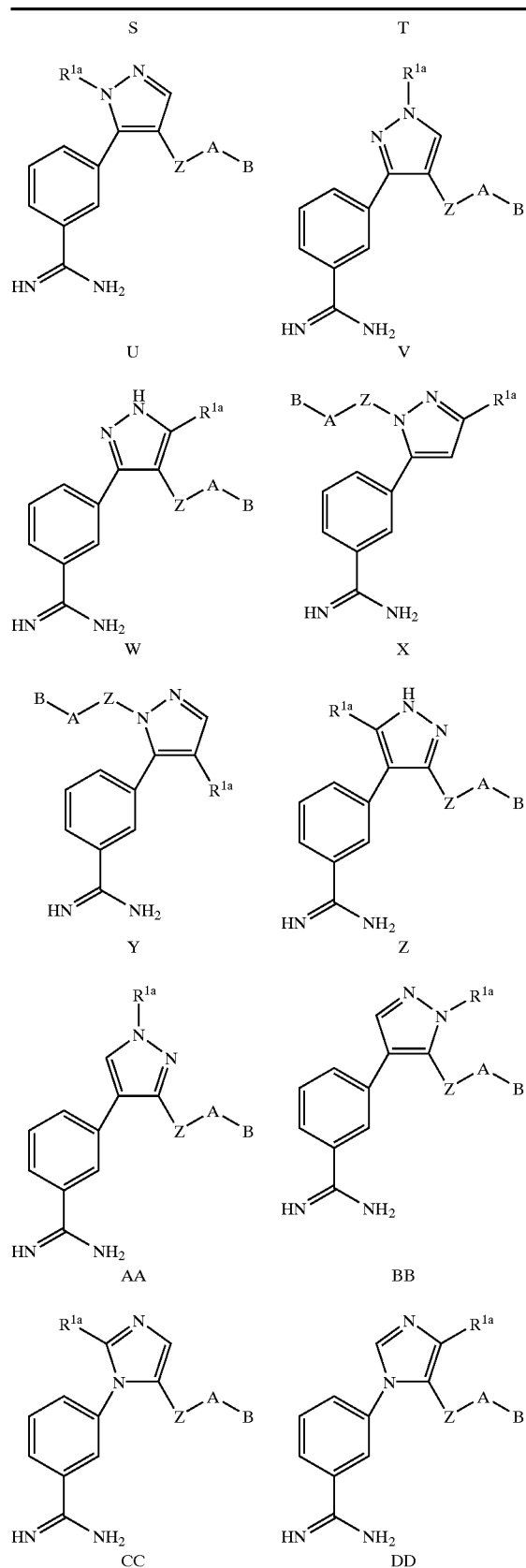
TABLE 4-continued
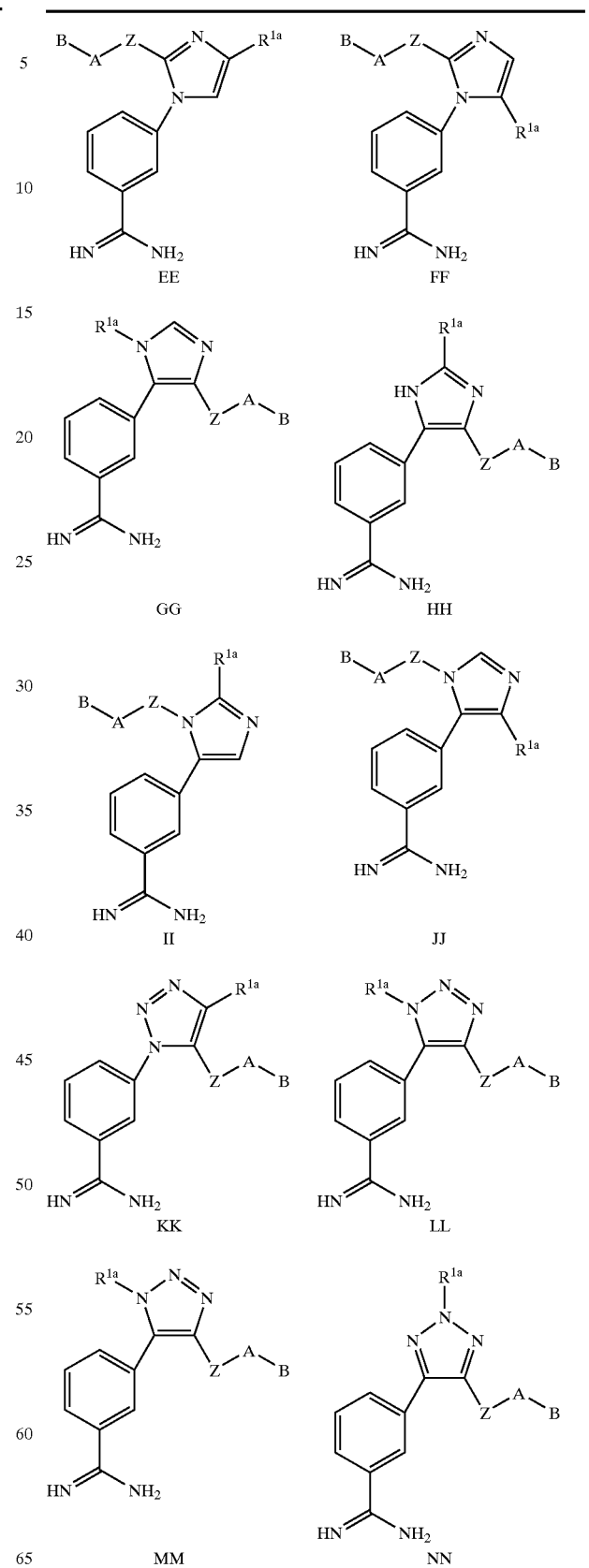

TABLE 4-continued

Structures:
- OO: triazole with R¹ᵃ on N1, phenyl-amidine substituent, Z-A-B chain
- PP: triazole with B-A-Z-N substitution and R¹ᵃ, phenyl-amidine
- QQ: 1,2,4-triazole with R¹ᵃ, Z-A-B, phenyl-amidine
- RR: 1,2,4-triazole with R¹ᵃ, phenyl, Z-A-B, amidine
- SS: 1,2,4-triazole with B-A-Z and R¹ᵃ, phenyl-amidine
- TT: 1,2,4-triazole with R¹ᵃ, Z-A-B, phenyl-amidine
- UU: tetrazole with phenyl-amidine and Z-A-B
- VV: tetrazole isomer with phenyl-amidine and Z-A-B

| Ex # | R¹ᵃ | A | B |
| --- | --- | --- | --- |
| 1 | CH₃ | phenyl | 2-(aminosulfonyl)phenyl |
| 2 | CH₃ | phenyl | 2-(methylaminosulfonyl)phenyl |
| 3 | CH₃ | phenyl | 1-pyrrolidinocarbonyl |
| 4 | CH₃ | phenyl | 2-(methylsulfonyl)phenyl |
| 5 | CH₃ | phenyl | 4-morpholino |
| 6 | CH₃ | phenyl | 2-(1'-CF₃-tetrazol-2-yl)phenyl |
| 7 | CH₃ | phenyl | 4-morpholinocarbonyl |
| 8 | CH₃ | phenyl | 2-methyl-1-imidazolyl |
| 9 | CH₃ | phenyl | 5-methyl-1-imidazolyl |
| 10 | CH₃ | phenyl | 2-methylsulfonyl-1-imidazolyl |
| 11 | CH₃ | 2-pyridyl | 2-(aminosulfonyl)phenyl |
| 12 | CH₃ | 2-pyridyl | 2-(methylaminosulfonyl)phenyl |
| 13 | CH₃ | 2-pyridyl | 1-pyrrolidinocarbonyl |
| 14 | CH₃ | 2-pyridyl | 2-(methylsulfonyl)phenyl |
| 15 | CH₃ | 2-pyridyl | 4-morpholino |
| 16 | CH₃ | 2-pyridyl | 2-(1'-CF₃-tetrazol-2-yl)phenyl |
| 17 | CH₃ | 2-pyridyl | 4-morpholinocarbonyl |
| 18 | CH₃ | 2-pyridyl | 2-methyl-1-imidazolyl |
| 19 | CH₃ | 2-pyridyl | 5-methyl-1-imidazolyl |
| 20 | CH₃ | 2-pyridyl | 2-methylsulfonyl-1-imidazolyl |
| 21 | CH₃ | 3-pyridyl | 2-(aminosulfonyl)phenyl |
| 22 | CH₃ | 3-pyridyl | 2-(methylaminosulfonyl)phenyl |
| 23 | CH₃ | 3-pyridyl | 1-pyrrolidinocarbonyl |
| 24 | CH₃ | 3-pyridyl | 2-(methylsulfonyl)phenyl |
| 25 | CH₃ | 3-pyridyl | 4-morpholino |
| 26 | CH₃ | 3-pyridyl | 2-(1'-CF₃-tetrazol-2-yl)phenyl |
| 27 | CH₃ | 3-pyridyl | 4-morpholinocarbonyl |
| 28 | CH₃ | 3-pyridyl | 2-methyl-1-imidazolyl |
| 29 | CH₃ | 3-pyridyl | 5-methyl-1-imidazolyl |
| 30 | CH₃ | 3-pyridyl | 2-methylsulfonyl-1-imidazolyl |
| 31 | CH₃ | 2-pyrimidyl | 2-(aminosulfonyl)phenyl |
| 32 | CH₃ | 2-pyrimidyl | 2-(methylaminosulfonyl)phenyl |
| 33 | CH₃ | 2-pyrimidyl | 1-pyrrolidinocarbonyl |
| 34 | CH₃ | 2-pyrimidyl | 2-(methylsulfonyl)phenyl |
| 35 | CH₃ | 2-pyrimidyl | 4-morpholino |
| 36 | CH₃ | 2-pyrimidyl | 2-(1'-CF₃-tetrazol-2-yl)phenyl |
| 37 | CH₃ | 2-pyrimidyl | 4-morpholinocarbonyl |
| 38 | CH₃ | 2-pyrimidyl | 2-methyl-1-imidazolyl |
| 39 | CH₃ | 2-pyrimidyl | 5-methyl-1-imidazolyl |
| 40 | CH₃ | 2-pyrimidyl | 2-methylsulfonyl-1-imidazolyl |
| 41 | CH₃ | 5-pyrimidyl | 2-(aminosulfonyl)phenyl |
| 42 | CH₃ | 5-pyrimidyl | 2-(methylaminosulfonyl)phenyl |
| 43 | CH₃ | 5-pyrimidyl | 1-pyrrolidinocarbonyl |
| 44 | CH₃ | 5-pyrimidyl | 2-(methylsulfonyl)phenyl |
| 45 | CH₃ | 5-pyrimidyl | 4-morpholino |
| 46 | CH₃ | 5-pyrimidyl | 2-(1'-CF₃-tetrazol-2-yl)phenyl |
| 47 | CH₃ | 5-pyrimidyl | 4-morpholinocarbonyl |
| 48 | CH₃ | 5-pyrimidyl | 2-methyl-1-imidazolyl |
| 49 | CH₃ | 5-pyrimidyl | 5-methyl-1-imidazolyl |
| 50 | CH₃ | 5-pyrimidyl | 2-methylsulfonyl-1-imidazolyl |
| 51 | CH₃ | 2-Cl-phenyl | 2-(aminosulfonyl)phenyl |
| 52 | CH₃ | 2-Cl-phenyl | 2-(methylaminosulfonyl)phenyl |
| 53 | CH₃ | 2-Cl-phenyl | 1-pyrrolidinocarbonyl |
| 54 | CH₃ | 2-Cl-phenyl | 2-(methylsulfonyl)phenyl |
| 55 | CH₃ | 2-Cl-phenyl | 4-morpholino |
| 56 | CH₃ | 2-Cl-phenyl | 2-(1'-CF₃-tetrazol-2-yl)phenyl |
| 57 | CH₃ | 2-Cl-phenyl | 4-morpholinocarbonyl |
| 58 | CH₃ | 2-Cl-phenyl | 2-methyl-1-imidazolyl |
| 59 | CH₃ | 2-Cl-phenyl | 5-methyl-1-imidazolyl |
| 60 | CH₃ | 2-Cl-phenyl | 2-methylsulfonyl-1-imidazolyl |
| 61 | CH₃ | 2-F-phenyl | 2-(aminosulfonyl)phenyl |
| 62 | CH₃ | 2-F-phenyl | 2-(methylaminosulfonyl)phenyl |
| 63 | CH₃ | 2-F-phenyl | 1-pyrrolidinocarbonyl |
| 64 | CH₃ | 2-F-phenyl | 2-(methylsulfonyl)phenyl |
| 65 | CH₃ | 2-F-phenyl | 4-morpholino |
| 66 | CH₃ | 2-F-phenyl | 2-(1'-CF₃-tetrazol-2-yl)phenyl |
| 67 | CH₃ | 2-F-phenyl | 4-morpholinocarbonyl |
| 68 | CH₃ | 2-F-phenyl | 2-methyl-1-imidazolyl |
| 69 | CH₃ | 2-F-phenyl | 5-methyl-1-imidazolyl |
| 70 | CH₃ | 2-F-phenyl | 2-methylsulfonyl-1-imidazolyl |
| 71 | CH₃ | 2,6-diF-phenyl | 2-(aminosulfonyl)phenyl |
| 72 | CH₃ | 2,6-diF-phenyl | 2-(methylaminosulfonyl)phenyl |
| 73 | CH₃ | 2,6-diF-phenyl | 1-pyrrolidinocarbonyl |
| 74 | CH₃ | 2,6-diF-phenyl | 2-(methylsulfonyl)phenyl |
| 75 | CH₃ | 2,6-diF-phenyl | 4-morpholino |
| 76 | CH₃ | 2,6-diF-phenyl | 2-(1'-CF₃-tetrazol-2-yl)phenyl |
| 77 | CH₃ | 2,6-diF-phenyl | 4-morpholinocarbonyl |
| 78 | CH₃ | 2,6-diF-phenyl | 2-methyl-1-imidazolyl |
| 79 | CH₃ | 2,6-diF-phenyl | 5-methyl-1-imidazolyl |
| 80 | CH₃ | 2,6-diF-phenyl | 2-methylsulfonyl-1-imidazolyl |
| 81 | CH₂CH₃ | phenyl | 2-(aminosulfonyl)phenyl |
| 82 | CH₂CH₃ | phenyl | 2-(methylaminosulfonyl)phenyl |
| 83 | CH₂CH₃ | phenyl | 1-pyrrolidinocarbonyl |
| 84 | CH₂CH₃ | phenyl | 2-(methylsulfonyl)phenyl |
| 85 | CH₂CH₃ | phenyl | 4-morpholino |
| 86 | CH₂CH₃ | phenyl | 2-(1'-CF₃-tetrazol-2-yl)phenyl |
| 87 | CH₂CH₃ | phenyl | 4-morpholinocarbonyl |
| 88 | CH₂CH₃ | phenyl | 2-methyl-1-imidazolyl |
| 89 | CH₂CH₃ | phenyl | 5-methyl-1-imidazolyl |
| 90 | CH₂CH₃ | phenyl | 2-methylsulfonyl-1-imidazolyl |
| 91 | CH₂CH₃ | 2-pyridyl | 2-(aminosulfonyl)phenyl |
| 92 | CH₂CH₃ | 2-pyridyl | 2-(methylaminosulfonyl)phenyl |
| 93 | CH₂CH₃ | 2-pyridyl | 1-pyrrolidinocarbonyl |
| 94 | CH₂CH₃ | 2-pyridyl | 2-(methylsulfonyl)phenyl |
| 95 | CH₂CH₃ | 2-pyridyl | 4-morpholino |
| 96 | CH₂CH₃ | 2-pyridyl | 2-(1'-CF₃-tetrazol-2-yl)phenyl |
| 97 | CH₂CH₃ | 2-pyridyl | 4-morpholinocarbonyl |

TABLE 4-continued

| | | | |
|---|---|---|---|
| 98 | CH$_2$CH$_3$ | 2-pyridyl | 2-methyl-1-imidazolyl |
| 99 | CH$_2$CH$_3$ | 2-pyridyl | 5-methyl-1-imidazolyl |
| 100 | CH$_2$CH$_3$ | 2-pyridyl | 2-methylsulfonyl-1-imidazolyl |
| 101 | CH$_2$CH$_3$ | 3-pyridyl | 2-(aminosulfonyl)phenyl |
| 102 | CH$_2$CH$_3$ | 3-pyridyl | 2-(methylaminosulfonyl)phenyl |
| 103 | CH$_2$CH$_3$ | 3-pyridyl | 1-pyrrolidinocarbonyl |
| 104 | CH$_2$CH$_3$ | 3-pyridyl | 2-(methylsulfonyl)phenyl |
| 105 | CH$_2$CH$_3$ | 3-pyridyl | 4-morpholino |
| 106 | CH$_2$CH$_3$ | 3-pyridyl | 2-(1'-CF$_3$-tetrazol-2-yl)phenyl |
| 107 | CH$_2$CH$_3$ | 3-pyridyl | 4-morpholinocarbonyl |
| 108 | CH$_2$CH$_3$ | 3-pyridyl | 2-methyl-1-imidazolyl |
| 109 | CH$_2$CH$_3$ | 3-pyridyl | 5-methyl-1-imidazolyl |
| 110 | CH$_2$CH$_3$ | 3-pyridyl | 2-methylsulfonyl-1-imidazolyl |
| 111 | CH$_2$CH$_3$ | 2-pyrimidyl | 2-(aminosulfonyl)phenyl |
| 112 | CH$_2$CH$_3$ | 2-pyrimidyl | 2-(methylaminosulfonyl)phenyl |
| 113 | CH$_2$CH$_3$ | 2-pyrimidyl | 1-pyrrolidinocarbonyl |
| 114 | CH$_2$CH$_3$ | 2-pyrimidyl | 2-(methylsulfonyl)phenyl |
| 115 | CH$_2$CH$_3$ | 2-pyrimidyl | 4-morpholino |
| 116 | CH$_2$CH$_3$ | 2-pyrimidyl | 2-(1'-CF$_3$-tetrazol-2-yl)phenyl |
| 117 | CH$_2$CH$_3$ | 2-pyrimidyl | 4-morpholinocarbonyl |
| 118 | CH$_2$CH$_3$ | 2-pyrimidyl | 2-methyl-1-imidazolyl |
| 119 | CH$_2$CH$_3$ | 2-pyrimidyl | 5-methyl-1-imidazolyl |
| 120 | CH$_2$CH$_3$ | 2-pyrimidyl | 2-methylsulfonyl-1-imidazolyl |
| 121 | CH$_2$CH$_3$ | 5-pyrimidyl | 2-(aminosulfonyl)phenyl |
| 122 | CH$_2$CH$_3$ | 5-pyrimidyl | 2-(methylaminosulfonyl)phenyl |
| 123 | CH$_2$CH$_3$ | 5-pyrimidyl | 1-pyrrolidinocarbonyl |
| 124 | CH$_2$CH$_3$ | 5-pyrimidyl | 2-(methylsulfonyl)phenyl |
| 125 | CH$_2$CH$_3$ | 5-pyrimidyl | 4-morpholino |
| 126 | CH$_2$CH$_3$ | 5-pyrimidyl | 2-(1'-CF$_3$-tetrazol-2-yl)phenyl |
| 127 | CH$_2$CH$_3$ | 5-pyrimidyl | 4-morpholinocarbonyl |
| 128 | CH$_2$CH$_3$ | 5-pyrimidyl | 2-methyl-1-imidazolyl |
| 129 | CH$_2$CH$_3$ | 5-pyrimidyl | 5-methyl-1-imidazolyl |
| 130 | CH$_2$CH$_3$ | 5-pyrimidyl | 2-methylsulfonyl-1-imidazolyl |
| 131 | CH$_2$CH$_3$ | 2-Cl-phenyl | 2-(aminosulfonyl)phenyl |
| 132 | CH$_2$CH$_3$ | 2-Cl-phenyl | 2-(methylaminosulfonyl)phenyl |
| 133 | CH$_2$CH$_3$ | 2-Cl-phenyl | 1-pyrrolidinocarbonyl |
| 134 | CH$_2$CH$_3$ | 2-Cl-phenyl | 2-(methylsulfonyl)phenyl |
| 135 | CH$_2$CH$_3$ | 2-Cl-phenyl | 4-morpholino |
| 136 | CH$_2$CH$_3$ | 2-Cl-phenyl | 2-(1'-CF$_3$-tetrazol-2-yl)phenyl |
| 137 | CH$_2$CH$_3$ | 2-Cl-phenyl | 4-morpholinocarbonyl |
| 138 | CH$_2$CH$_3$ | 2-Cl-phenyl | 2-methyl-1-imidazolyl |
| 139 | CH$_2$CH$_3$ | 2-Cl-phenyl | 5-methyl-1-imidazolyl |
| 140 | CH$_2$CH$_3$ | 2-Cl-phenyl | 2-methylsulfonyl-1-imidazolyl |
| 141 | CH$_2$CH$_3$ | 2-F-phenyl | 2-(aminosulfonyl)phenyl |
| 142 | CH$_2$CH$_3$ | 2-F-phenyl | 2-(methylaminosulfonyl)phenyl |
| 143 | CH$_2$CH$_3$ | 2-F-phenyl | 1-pyrrolidinocarbonyl |
| 144 | CH$_2$CH$_3$ | 2-F-phenyl | 2-(methylsulfonyl)phenyl |
| 145 | CH$_2$CH$_3$ | 2-F-phenyl | 4-morpholino |
| 146 | CH$_2$CH$_3$ | 2-F-phenyl | 2-(1'-CF$_3$-tetrazol-2-yl)phenyl |
| 147 | CH$_2$CH$_3$ | 2-F-phenyl | 4-morpholinocarbonyl |
| 148 | CH$_2$CH$_3$ | 2-F-phenyl | 2-methyl-1-imidazolyl |
| 149 | CH$_2$CH$_3$ | 2-F-phenyl | 5-methyl-1-imidazolyl |
| 150 | CH$_2$CH$_3$ | 2-F-phenyl | 2-methylsulfonyl-1-imidazolyl |
| 151 | CH$_2$CH$_3$ | 2,6-diF-phenyl | 2-(aminosulfonyl)phenyl |
| 152 | CH$_2$CH$_3$ | 2,6-diF-phenyl | 2-(methylaminosulfonyl)phenyl |
| 153 | CH$_2$CH$_3$ | 2,6-diF-phenyl | 1-pyrrolidinocarbonyl |
| 154 | CH$_2$CH$_3$ | 2,6-diF-phenyl | 2-(methylsulfonyl)phenyl |
| 155 | CH$_2$CH$_3$ | 2,6-diF-phenyl | 4-morpholino |
| 156 | CH$_2$CH$_3$ | 2,6-diF-phenyl | 2-(1'-CF$_3$-tetrazol-2-yl)phenyl |
| 157 | CH$_2$CH$_3$ | 2,6-diF-phenyl | 4-morpholinocarbonyl |
| 158 | CH$_2$CH$_3$ | 2,6-diF-phenyl | 2-methyl-1-imidazolyl |
| 159 | CH$_2$CH$_3$ | 2,6-diF-phenyl | 5-methyl-1-imidazolyl |
| 160 | CH$_2$CH$_3$ | 2,6-diF-phenyl | 2-methylsulfonyl-1-imidazolyl |
| 161 | CF$_3$ | phenyl | 2-(aminosulfonyl)phenyl |
| 162 | CF$_3$ | phenyl | 2-(methylaminosulfonyl)phenyl |
| 163 | CF$_3$ | phenyl | 1-pyrrolidinocarbonyl |
| 164 | CF$_3$ | phenyl | 2-(methylsulfonyl)phenyl |
| 165 | CF$_3$ | phenyl | 4-morpholino |
| 166 | CF$_3$ | phenyl | 2-(1'-CF$_3$-tetrazol-2-yl)phenyl |
| 167 | CF$_3$ | phenyl | 4-morpholinocarbonyl |
| 168 | CF$_3$ | phenyl | 2-methyl-1-imidazolyl |
| 169 | CF$_3$ | phenyl | 5-methyl-1-imidazolyl |
| 170 | CF$_3$ | phenyl | 2-methylsulfonyl-1-imidazolyl |
| 171 | CF$_3$ | 2-pyridyl | 2-(aminosulfonyl)phenyl |
| 172 | CF$_3$ | 2-pyridyl | 2-(methylaminosulfonyl)phenyl |
| 173 | CF$_3$ | 2-pyridyl | 1-pyrrolidinocarbonyl |
| 174 | CF$_3$ | 2-pyridyl | 2-(methylsulfonyl)phenyl |
| 175 | CF$_3$ | 2-pyridyl | 4-morpholino |
| 176 | CF$_3$ | 2-pyridyl | 2-(1'-CF$_3$-tetrazol-2-yl)phenyl |
| 177 | CF$_3$ | 2-pyridyl | 4-morpholinocarbonyl |
| 178 | CF$_3$ | 2-pyridyl | 2-methyl-1-imidazolyl |
| 179 | CF$_3$ | 2-pyridyl | 5-methyl-1-imidazolyl |
| 180 | CF$_3$ | 2-pyridyl | 2-methylsulfonyl-1-imidazolyl |
| 181 | CF$_3$ | 3-pyridyl | 2-(aminosulfonyl)phenyl |
| 182 | CF$_3$ | 3-pyridyl | 2-(methylaminosulfonyl)phenyl |
| 183 | CF$_3$ | 3-pyridyl | 1-pyrrolidinocarbonyl |
| 184 | CF$_3$ | 3-pyridyl | 2-(methylsulfonyl)phenyl |
| 185 | CF$_3$ | 3-pyridyl | 4-morpholino |
| 186 | CF$_3$ | 3-pyridyl | 2-(1'-CF$_3$-tetrazol-2-yl)phenyl |
| 187 | CF$_3$ | 3-pyridyl | 4-morpholinocarbonyl |
| 188 | CF$_3$ | 3-pyridyl | 2-methyl-1-imidazolyl |
| 189 | CF$_3$ | 3-pyridyl | 5-methyl-1-imidazolyl |
| 190 | CF$_3$ | 3-pyridyl | 2-methylsulfonyl-1-imidazolyl |
| 191 | CF$_3$ | 2-pyrimidyl | 2-(aminosulfonyl)phenyl |
| 192 | CF$_3$ | 2-pyrimidyl | 2-(methylaminosulfonyl)phenyl |
| 193 | CF$_3$ | 2-pyrimidyl | 1-pyrrolidinocarbonyl |
| 194 | CF$_3$ | 2-pyrimidyl | 2-(methylsulfonyl)phenyl |
| 195 | CF$_3$ | 2-pyrimidyl | 4-morpholino |
| 196 | CF$_3$ | 2-pyrimidyl | 2-(1'-CF$_3$-tetrazol-2-yl)phenyl |
| 197 | CF$_3$ | 2-pyrimidyl | 4-morpholinocarbonyl |
| 198 | CF$_3$ | 2-pyrimidyl | 2-methyl-1-imidazolyl |
| 199 | CF$_3$ | 2-pyrimidyl | 5-methyl-1-imidazolyl |
| 200 | CF$_3$ | 2-pyrimidyl | 2-methylsulfonyl-1-imidazolyl |
| 201 | CF$_3$ | 5-pyrimidyl | 2-(aminosulfonyl)phenyl |
| 202 | CF$_3$ | 5-pyrimidyl | 2-(methylaminosulfonyl)phenyl |
| 203 | CF$_3$ | 5-pyrimidyl | 1-pyrrolidinocarbonyl |
| 204 | CF$_3$ | 5-pyrimidyl | 2-(methylsulfonyl)phenyl |
| 205 | CF$_3$ | 5-pyrimidyl | 4-morpholino |
| 206 | CF$_3$ | 5-pyrimidyl | 2-(1'-CF$_3$-tetrazol-2-yl)phenyl |
| 207 | CF$_3$ | 5-pyrimidyl | 4-morpholinocarbonyl |
| 208 | CF$_3$ | 5-pyrimidyl | 2-methyl-1-imidazolyl |
| 209 | CF$_3$ | 5-pyrimidyl | 5-methyl-1-imidazolyl |
| 210 | CF$_3$ | 5-pyrimidyl | 2-methylsulfonyl-1-imidazolyl |
| 211 | CF$_3$ | 2-Cl-phenyl | 2-(aminosulfonyl)phenyl |
| 212 | CF$_3$ | 2-Cl-phenyl | 2-(methylaminosulfonyl)phenyl |
| 213 | CF$_3$ | 2-Cl-phenyl | 1-pyrrolidinocarbonyl |
| 214 | CF$_3$ | 2-Cl-phenyl | 2-(methylsulfonyl)phenyl |
| 215 | CF$_3$ | 2-Cl-phenyl | 4-morpholino |
| 216 | CF$_3$ | 2-Cl-phenyl | 2-(1'-CF$_3$-tetrazol-2-yl)phenyl |
| 217 | CF$_3$ | 2-Cl-phenyl | 4-morpholinocarbonyl |
| 218 | CF$_3$ | 2-Cl-phenyl | 2-methyl-1-imidazolyl |
| 219 | CF$_3$ | 2-Cl-phenyl | 5-methyl-1-imidazolyl |
| 220 | CF$_3$ | 2-Cl-phenyl | 2-methylsulfonyl-1-imidazolyl |
| 221 | CF$_3$ | 2-F-phenyl | 2-(aminosulfonyl)phenyl |
| 222 | CF$_3$ | 2-F-phenyl | 2-(methylaminosulfonyl)phenyl |
| 223 | CF$_3$ | 2-F-phenyl | 1-pyrrolidinocarbonyl |
| 224 | CF$_3$ | 2-F-phenyl | 2-(methylsulfonyl)phenyl |
| 225 | CF$_3$ | 2-F-phenyl | 4-morpholino |
| 226 | CF$_3$ | 2-F-phenyl | 2-(1'-CF$_3$-tetrazol-2-yl)phenyl |
| 227 | CF$_3$ | 2-F-phenyl | 4-morpholinocarbonyl |
| 228 | CF$_3$ | 2-F-phenyl | 2-methyl-1-imidazolyl |
| 229 | CF$_3$ | 2-F-phenyl | 5-methyl-1-imidazolyl |
| 230 | CF$_3$ | 2-F-phenyl | 2-methylsulfonyl-1-imidazolyl |
| 231 | CF$_3$ | 2,6-diF-phenyl | 2-(aminosulfonyl)phenyl |
| 232 | CF$_3$ | 2,6-diF-phenyl | 2-(methylaminosulfonyl)phenyl |
| 233 | CF$_3$ | 2,6-diF-phenyl | 1-pyrrolidinocarbonyl |
| 234 | CF$_3$ | 2,6-diF-phenyl | 2-(methylsulfonyl)phenyl |
| 235 | CF$_3$ | 2,6-diF-phenyl | 4-morpholino |
| 236 | CF$_3$ | 2,6-diF-phenyl | 2-(1'-CF$_3$-tetrazol-2-yl)phenyl |
| 237 | CF$_3$ | 2,6-diF-phenyl | 4-morpholinocarbonyl |
| 238 | CF$_3$ | 2,6-diF-phenyl | 2-methyl-1-imidazolyl |
| 239 | CF$_3$ | 2,6-diF-phenyl | 5-methyl-1-imidazolyl |
| 240 | CF$_3$ | 2,6-diF-phenyl | 2-methylsulfonyl-1-imidazolyl |
| 241 | SCH$_3$ | phenyl | 2-(aminosulfonyl)phenyl |
| 242 | SCH$_3$ | phenyl | 2-(methylaminosulfonyl)phenyl |
| 243 | SCH$_3$ | phenyl | 1-pyrrolidinocarbonyl |
| 244 | SCH$_3$ | phenyl | 2-(methylsulfonyl)phenyl |
| 245 | SCH$_3$ | phenyl | 4-morpholino |
| 246 | SCH$_3$ | phenyl | 2-(1'-CF$_3$-tetrazol-2-yl)phenyl |
| 247 | SCH$_3$ | phenyl | 4-morpholinocarbonyl |
| 248 | SCH$_3$ | phenyl | 2-methyl-1-imidazolyl |
| 249 | SCH$_3$ | phenyl | 5-methyl-1-imidazolyl |
| 250 | SCH$_3$ | phenyl | 2-methylsulfonyl-1-imidazolyl |
| 251 | SCH$_3$ | 2-pyridyl | 2-(aminosulfonyl)phenyl |
| 252 | SCH$_3$ | 2-pyridyl | 2-(methylaminosulfonyl)phenyl |
| 253 | SCH$_3$ | 2-pyridyl | 1-pyrrolidinocarbonyl |
| 254 | SCH$_3$ | 2-pyridyl | 2-(methylsulfonyl)phenyl |
| 255 | SCH$_3$ | 2-pyridyl | 4-morpholino |

TABLE 4-continued

| | | | |
|---|---|---|---|
| 256 | SCH₃ | 2-pyridyl | 2-(1'-CF₃-tetrazol-2-yl)phenyl |
| 257 | SCH₃ | 2-pyridyl | 4-morpholinocarbonyl |
| 258 | SCH₃ | 2-pyridyl | 2-methyl-1-imidazolyl |
| 259 | SCH₃ | 2-pyridyl | 5-methyl-1-imidazolyl |
| 260 | SCH₃ | 2-pyridyl | 2-methylsulfonyl-1-imidazolyl |
| 261 | SCH₃ | 3-pyridyl | 2-(aminosulfonyl)phenyl |
| 262 | SCH₃ | 3-pyridyl | 2-(methylaminosulfonyl)phenyl |
| 263 | SCH₃ | 3-pyridyl | 1-pyrrolidinocarbonyl |
| 264 | SCH₃ | 3-pyridyl | 2-(methylsulfonyl)phenyl |
| 265 | SCH₃ | 3-pyridyl | 4-morpholino |
| 266 | SCH₃ | 3-pyridyl | 2-(1'-CF₃-tetrazol-2-yl)phenyl |
| 267 | SCH₃ | 3-pyridyl | 4-morpholinocarbonyl |
| 268 | SCH₃ | 3-pyridyl | 2-methyl-1-imidazolyl |
| 269 | SCH₃ | 3-pyridyl | 5-methyl-1-imidazolyl |
| 270 | SCH₃ | 3-pyridyl | 2-methylsulfonyl-1-imidazolyl |
| 271 | SCH₃ | 2-pyrimidyl | 2-(aminosulfonyl)phenyl |
| 272 | SCH₃ | 2-pyrimidyl | 2-(methylaminosulfonyl)phenyl |
| 273 | SCH₃ | 2-pyrimidyl | 1-pyrrolidinocarbonyl |
| 274 | SCH₃ | 2-pyrimidyl | 2-(methylsulfonyl)phenyl |
| 275 | SCH₃ | 2-pyrimidyl | 4-morpholino |
| 276 | SCH₃ | 2-pyrimidyl | 2-(1'-CF₃-tetrazol-2-yl)phenyl |
| 277 | SCH₃ | 2-pyrimidyl | 4-morpholinocarbonyl |
| 278 | SCH₃ | 2-pyrimidyl | 2-methyl-1-imidazolyl |
| 279 | SCH₃ | 2-pyrimidyl | 5-methyl-1-imidazolyl |
| 280 | SCH₃ | 2-pyrimidyl | 2-methylsulfonyl-1-imidazolyl |
| 281 | SCH₃ | 5-pyrimidyl | 2-(aminosulfonyl)phenyl |
| 282 | SCH₃ | 5-pyrimidyl | 2-(methylaminosulfonyl)phenyl |
| 283 | SCH₃ | 5-pyrimidyl | 1-pyrrolidinocarbonyl |
| 284 | SCH₃ | 5-pyrimidyl | 2-(methylsulfonyl)phenyl |
| 285 | SCH₃ | 5-pyrimidyl | 4-morpholino |
| 286 | SCH₃ | 5-pyrimidyl | 2-(1'-CF₃-tetrazol-2-yl)phenyl |
| 287 | SCH₃ | 5-pyrimidyl | 4-morpholinocarbonyl |
| 288 | SCH₃ | 5-pyrimidyl | 2-methyl-1-imidazolyl |
| 289 | SCH₃ | 5-pyrimidyl | 5-methyl-1-imidazolyl |
| 290 | SCH₃ | 5-pyrimidyl | 2-methylsulfonyl-1-imidazolyl |
| 291 | SCH₃ | 2-Cl-phenyl | 2-(aminosulfonyl)phenyl |
| 292 | SCH₃ | 2-Cl-phenyl | 2-(methylaminosulfonyl)phenyl |
| 293 | SCH₃ | 2-Cl-phenyl | 1-pyrrolidinocarbonyl |
| 294 | SCH₃ | 2-Cl-phenyl | 2-(methylsulfonyl)phenyl |
| 295 | SCH₃ | 2-Cl-phenyl | 4-morpholino |
| 296 | SCH₃ | 2-Cl-phenyl | 2-(1'-CF₃-tetrazol-2-yl)phenyl |
| 297 | SCH₃ | 2-Cl-phenyl | 4-morpholinocarbonyl |
| 298 | SCH₃ | 2-Cl-phenyl | 2-methyl-1-imidazolyl |
| 299 | SCH₃ | 2-Cl-phenyl | 5-methyl-1-imidazolyl |
| 300 | SCH₃ | 2-Cl-phenyl | 2 methylsulfonyl-1-imidazolyl |
| 301 | SCH₃ | 2-F-phenyl | 2-(aminosulfonyl)phenyl |
| 302 | SCH₃ | 2-F-phenyl | 2-(methylaminosulfonyl)phenyl |
| 303 | SCH₃ | 2-F-phenyl | 1-pyrrolidinocarbonyl |
| 304 | SCH₃ | 2-F-phenyl | 2-(methylsulfonyl)phenyl |
| 305 | SCH₃ | 2-F-phenyl | 4-morpholino |
| 306 | SCH₃ | 2-F-phenyl | 2-(1'-CF₃-tetrazol-2-yl)phenyl |
| 307 | SCH₃ | 2-F-phenyl | 4-morpholinocarbonyl |
| 308 | SCH₃ | 2-F-phenyl | 2-methyl-1-imidazolyl |
| 309 | SCH₃ | 2-F-phenyl | 5-methyl-1-imidazolyl |
| 310 | SCH₃ | 2-F-phenyl | 2-methylsulfonyl-1-imidazolyl |
| 311 | SCH₃ | 2,6-diF-phenyl | 2-(aminosulfonyl)phenyl |
| 312 | SCH₃ | 2,6-diF-phenyl | 2-(methylaminosulfonyl)phenyl |
| 313 | SCH₃ | 2,6-diF-phenyl | 1-pyrrolidinocarbonyl |
| 314 | SCH₃ | 2,6-diF-phenyl | 2-(methylsulfonyl)phenyl |
| 315 | SCH₃ | 2,6-diF-phenyl | 4-morpholino |
| 316 | SCH₃ | 2,6-diF-phenyl | 2-(1'-CF₃-tetrazol-2-yl)phenyl |
| 317 | SCH₃ | 2,6-diF-phenyl | 4-morpholinocarbonyl |
| 318 | SCH₃ | 2,6-diF-phenyl | 2-methyl-1-imidazolyl |
| 319 | SCH₃ | 2,6-diF-phenyl | 5-methyl-1-imidazolyl |
| 320 | SCH₃ | 2,6-diF-phenyl | 2-methylsulfonyl-1-imidazolyl |
| 321 | SOCH₃ | phenyl | 2-(aminosulfonyl)phenyl |
| 322 | SOCH₃ | phenyl | 2-(methylaminosulfonyl)phenyl |
| 323 | SOCH₃ | phenyl | 1-pyrrolidinocarbonyl |
| 324 | SOCH₃ | phenyl | 2-(methylsulfonyl)phenyl |
| 325 | SOCH₃ | phenyl | 4-morpholino |
| 326 | SOCH₃ | phenyl | 2-(1'-CF₃-tetrazol-2-yl)phenyl |
| 327 | SOCH₃ | phenyl | 4-morpholinocarbonyl |
| 328 | SOCH₃ | phenyl | 2-methyl-1-imidazolyl |
| 329 | SOCH₃ | phenyl | 5-methyl-1-imidazolyl |
| 330 | SOCH₃ | phenyl | 2-methylsulfonyl-1-imidazolyl |
| 331 | SOCH₃ | 2-pyridyl | 2-(aminosulfonyl)phenyl |
| 332 | SOCH₃ | 2-pyridyl | 2-(methylaminosulfonyl)phenyl |
| 333 | SOCH₃ | 2-pyridyl | 1-pyrrolidinocarbonyl |
| 334 | SOCH₃ | 2-pyridyl | 2-(methylsulfonyl)phenyl |
| 335 | SOCH₃ | 2-pyridyl | 4-morpholino |
| 336 | SOCH₃ | 2-pyridyl | 2-(1'-CF₃-tetrazol-2-yl)phenyl |
| 337 | SOCH₃ | 2-pyridyl | 4-morpholinocarbonyl |
| 338 | SOCH₃ | 2-pyridyl | 2-methyl-1-imidazolyl |
| 339 | SOCH₃ | 2-pyridyl | 5-methyl-1-imidazolyl |
| 340 | SOCH₃ | 2-pyridyl | 2-methylsulfonyl-1-imidazolyl |
| 341 | SOCH₃ | 3-pyridyl | 2-(aminosulfonyl)phenyl |
| 342 | SOCH₃ | 3-pyridyl | 2-(methylaminosulfonyl)phenyl |
| 343 | SOCH₃ | 3-pyridyl | 1-pyrrolidinocarbonyl |
| 344 | SOCH₃ | 3-pyridyl | 2-(methylsulfonyl)phenyl |
| 345 | SOCH₃ | 3-pyridyl | 4-morpholino |
| 346 | SOCH₃ | 3-pyridyl | 2-(1'-CF₃-tetrazol-2-yl)phenyl |
| 347 | SOCH₃ | 3-pyridyl | 4-morpholinocarbonyl |
| 348 | SOCH₃ | 3-pyridyl | 2-methyl-1-imidazolyl |
| 349 | SOCH₃ | 3-pyridyl | 5-methyl-1-imidazolyl |
| 350 | SOCH₃ | 3-pyridyl | 2-methylsulfonyl-1-imidazolyl |
| 351 | SOCH₃ | 2-pyrimidyl | 2-(aminosulfonyl)phenyl |
| 352 | SOCH₃ | 2-pyrimidyl | 2-(methylaminosulfonyl)phenyl |
| 353 | SOCH₃ | 2-pyrimidyl | 1-pyrrolidinocarbonyl |
| 354 | SOCH₃ | 2-pyrimidyl | 2-(methylsulfonyl)phenyl |
| 355 | SOCH₃ | 2-pyrimidyl | 4-morpholino |
| 356 | SOCH₃ | 2-pyrimidyl | 2-(1'-CF₃-tetrazol-2-yl)phenyl |
| 357 | SOCH₃ | 2-pyrimidyl | 4-morpholinocarbonyl |
| 358 | SOCH₃ | 2-pyrimidyl | 2-methyl-1-imidazolyl |
| 359 | SOCH₃ | 2-pyrimidyl | 5-methyl-1-imidazolyl |
| 360 | SOCH₃ | 2-pyrimidyl | 2-methylsulfonyl-1-imidazolyl |
| 361 | SOCH₃ | 5-pyrimidyl | 2-(aminosulfonyl)phenyl |
| 362 | SOCH₃ | 5-pyrimidyl | 2-(methylaminosulfonyl)phenyl |
| 363 | SOCH₃ | 5-pyrimidyl | 1-pyrrolidinocarbonyl |
| 364 | SOCH₃ | 5-pyrimidyl | 2-(methylsulfonyl)phenyl |
| 365 | SOCH₃ | 5-pyrimidyl | 4-morpholino |
| 366 | SOCH₃ | 5-pyrimidyl | 2-(1'-CF₃-tetrazol-2-yl)phenyl |
| 367 | SOCH₃ | 5-pyrimidyl | 4-morpholinocarbonyl |
| 368 | SOCH₃ | 5-pyrimidyl | 2-methyl-1-imidazolyl |
| 369 | SOCH₃ | 5-pyrimidyl | 5-methyl-1-imidazolyl |
| 370 | SOCH₃ | 5-pyrimidyl | 2-methylsulfonyl-1-imidazolyl |
| 371 | SOCH₃ | 2-Cl-phenyl | 2-(aminosulfonyl)phenyl |
| 372 | SOCH₃ | 2-Cl-phenyl | 2-(methylaminosulfonyl)phenyl |
| 373 | SOCH₃ | 2-Cl-phenyl | 1-pyrrolidinocarbonyl |
| 374 | SOCH₃ | 2-Cl-phenyl | 2-(methylsulfonyl)phenyl |
| 375 | SOCH₃ | 2-Cl-phenyl | 4-morpholino |
| 376 | SOCH₃ | 2-Cl-phenyl | 2-(1'-CF₃-tetrazol-2-yl)phenyl |
| 377 | SOCH₃ | 2-Cl-phenyl | 4-morpholinocarbonyl |
| 378 | SOCH₃ | 2-Cl-phenyl | 2-methyl-1-imidazolyl |
| 379 | SOCH₃ | 2-Cl-phenyl | 5-methyl-1-imidazolyl |
| 380 | SOCH₃ | 2-Cl-phenyl | 2-methylsulfonyl-1-imidazolyl |
| 381 | SOCH₃ | 2-F-phenyl | 2-(aminosulfonyl)phenyl |
| 382 | SOCH₃ | 2-F-phenyl | 2-(methylaminosulfonyl)phenyl |
| 383 | SOCH₃ | 2-F-phenyl | 1-pyrrolidinocarbonyl |
| 384 | SOCH₃ | 2-F-phenyl | 2-(methylsulfonyl)phenyl |
| 385 | SOCH₃ | 2-F-phenyl | 4-morpholino |
| 386 | SOCH₃ | 2-F-phenyl | 2-(1'-CF₃-tetrazol-2-yl)phenyl |
| 387 | SOCH₃ | 2-F-phenyl | 4-morpholinocarbonyl |
| 388 | SOCH₃ | 2-F-phenyl | 2-methyl-1-imidazolyl |
| 389 | SOCH₃ | 2-F-phenyl | 5-methyl-1-imidazolyl |
| 390 | SOCH₃ | 2-F-phenyl | 2-methylsulfonyl-1-imidazolyl |
| 391 | SOCH₃ | 2,6-diF-phenyl | 2-(aminosulfonyl)phenyl |
| 392 | SOCH₃ | 2,6-diF-phenyl | 2-(methylaminosulfonyl)phenyl |
| 393 | SOCH₃ | 2,6-diF-phenyl | 1-pyrrolidinocarbonyl |
| 394 | SOCH₃ | 2,6-diF-phenyl | 2-(methylsulfonyl)phenyl |
| 395 | SOCH₃ | 2,6-diF-phenyl | 4-morpholino |
| 396 | SOCH₃ | 2,6-diF-phenyl | 2-(1'-CF₃-tetrazol-2-yl)phenyl |
| 397 | SOCH₃ | 2,6-diF-phenyl | 4-morpholinocarbonyl |
| 398 | SOCH₃ | 2,6-diF-phenyl | 2-methyl-1-imidazolyl |
| 399 | SOCH₃ | 2,6-diF-phenyl | 5-methyl-1-imidazolyl |
| 400 | SOCH₃ | 2,6-diF-phenyl | 2-methylsulfonyl-1-imidazolyl |
| 401 | SO₂CH₃ | phenyl | 2-(aminosulfonyl)phenyl |
| 402 | SO₂CH₃ | phenyl | 2-(methylaminosulfonyl)phenyl |
| 403 | SO₂CH₃ | phenyl | 1-pyrrolidinocarbonyl |
| 404 | SO₂CH₃ | phenyl | 2-(methylsulfonyl)phenyl |
| 405 | SO₂CH₃ | phenyl | 4-morpholino |
| 406 | SO₂CH₃ | phenyl | 2-(1'-CF₃-tetrazol-2-yl)phenyl |
| 407 | SO₂CH₃ | phenyl | 4-morpholinocarbonyl |
| 408 | SO₂CH₃ | phenyl | 2-methyl-1-imidazolyl |
| 409 | SO₂CH₃ | phenyl | 5-methyl-1-imidazolyl |
| 410 | SO₂CH₃ | phenyl | 2-methylsulfonyl-1-imidazolyl |
| 411 | SO₂CH₃ | 2-pyridyl | 2-(aminosulfonyl)phenyl |
| 412 | SO₂CH₃ | 2-pyridyl | 2-(methylaminosulfonyl)phenyl |
| 413 | SO₂CH₃ | 2-pyridyl | 1-pyrrolidinocarbonyl |

TABLE 4-continued

| | | | |
|---|---|---|---|
| 414 | SO₂CH₃ | 2-pyridyl | 2-(methylsulfonyl)phenyl |
| 415 | SO₂CH₃ | 2-pyridyl | 4-morpholino |
| 416 | SO₂CH₃ | 2-pyridyl | 2-(1'-CF₃-tetrazol-2-yl)phenyl |
| 417 | SO₂CH₃ | 2-pyridyl | 4-morpholinocarbonyl |
| 418 | SO₂CH₃ | 2-pyridyl | 2-methyl-1-imidazolyl |
| 419 | SO₂CH₃ | 2-pyridyl | 5-methyl-1-imidazolyl |
| 420 | SO₂CH₃ | 2-pyridyl | 2-methylsulfonyl-1-imidazolyl |
| 421 | SO₂CH₃ | 3-pyridyl | 2-(aminosulfonyl)phenyl |
| 422 | SO₂CH₃ | 3-pyridyl | 2-(methylaminosulfonyl)phenyl |
| 423 | SO₂CH₃ | 3-pyridyl | 1-pyrrolidinocarbonyl |
| 424 | SO₂CH₃ | 3-pyridyl | 2-(methylsulfonyl)phenyl |
| 425 | SO₂CH₃ | 3-pyridyl | 4-morpholino |
| 426 | SO₂CH₃ | 3-pyridyl | 2-(1'-CF₃-tetrazol-2-yl)phenyl |
| 427 | SO₂CH₃ | 3-pyridyl | 4-morpholinocarbonyl |
| 428 | SO₂CH₃ | 3-pyridyl | 2-methyl-1-imidazolyl |
| 429 | SO₂CH₃ | 3-pyridyl | 5-methyl-1-imidazolyl |
| 430 | SO₂CH₃ | 3-pyridyl | 2-methylsulfonyl-1-imidazolyl |
| 431 | SO₂CH₃ | 2-pyrimidyl | 2-(aminosulfonyl)phenyl |
| 432 | SO₂CH₃ | 2-pyrimidyl | 2-(methylaminosulfonyl)phenyl |
| 433 | SO₂CH₃ | 2-pyrimidyl | 1-pyrrolidinocarbonyl |
| 434 | SO₂CH₃ | 2-pyrimidyl | 2-(methylsulfonyl)phenyl |
| 435 | SO₂CH₃ | 2-pyrimidyl | 4-morpholino |
| 436 | SO₂CH₃ | 2-pyrimidyl | 2-(1'-CF₃-tetrazol-2-yl)phenyl |
| 437 | SO₂CH₃ | 2-pyrimidyl | 4-morpholinocarbonyl |
| 438 | SO₂CH₃ | 2-pyrimidyl | 2-methyl-1-imidazolyl |
| 439 | SO₂CH₃ | 2-pyrimidyl | 5-methyl-1-imidazolyl |
| 440 | SO₂CH₃ | 2-pyrimidyl | 2-methylsulfonyl-1-imidazolyl |
| 441 | SO₂CH₃ | 5-pyrimidyl | 2-(aminosulfonyl)phenyl |
| 442 | SO₂CH₃ | 5-pyrimidyl | 2-(methylaminosulfonyl)phenyl |
| 443 | SO₂CH₃ | 5-pyrimidyl | 1-pyrrolidinocarbonyl |
| 444 | SO₂CH₃ | 5-pyrimidyl | 2-(methylsulfonyl)phenyl |
| 445 | SO₂CH₃ | 5-pyrimidyl | 4-morpholino |
| 446 | SO₂CH₃ | 5-pyrimidyl | 2-(1'-CF₃-tetrazol-2-yl)phenyl |
| 447 | SO₂CH₃ | 5-pyrimidyl | 4-morpholinocarbonyl |
| 448 | SO₂CH₃ | 5-pyrimidyl | 2-methyl-1-imidazolyl |
| 449 | SO₂CH₃ | 5-pyrimidyl | 5-methyl-1-imidazolyl |
| 450 | SO₂CH₃ | 5-pyrimidyl | 2-methylsulfonyl-1-imidazolyl |
| 451 | SO₂CH₃ | 2-Cl-phenyl | 2-(aminosulfonyl)phenyl |
| 452 | SO₂CH₃ | 2-Cl-phenyl | 2-(methylaminosulfonyl)phenyl |
| 453 | SO₂CH₃ | 2-Cl-phenyl | 1-pyrrolidinocarbonyl |
| 454 | SO₂CH₃ | 2-Cl-phenyl | 2-(methylsulfonyl)phenyl |
| 455 | SO₂CH₃ | 2-Cl-phenyl | 4-morpholino |
| 456 | SO₂CH₃ | 2-Cl-phenyl | 2-(1'-CF₃-tetrazol-2-yl)phenyl |
| 457 | SO₂CH₃ | 2-Cl-phenyl | 4-morpholinocarbonyl |
| 458 | SO₂CH₃ | 2-Cl-phenyl | 2-methyl-1-imidazolyl |
| 459 | SO₂CH₃ | 2-Cl-phenyl | 5-methyl-1-imidazolyl |
| 460 | SO₂CH₃ | 2-Cl-phenyl | 2-methylsulfonyl-1-imidazolyl |
| 461 | SO₂CH₃ | 2-F-phenyl | 2-(aminosulfonyl)phenyl |
| 462 | SO₂CH₃ | 2-F-phenyl | 2-(methylaminosulfonyl)phenyl |
| 463 | SO₂CH₃ | 2-F-phenyl | 1-pyrrolidinocarbonyl |
| 464 | SO₂CH₃ | 2-F-phenyl | 2-(methylsulfonyl)phenyl |
| 465 | SO₂CH₃ | 2-F-phenyl | 4-morpholino |
| 466 | SO₂CH₃ | 2-F-phenyl | 2-(1'-CF₃-tetrazol-2-yl)phenyl |
| 467 | SO₂CH₃ | 2-F-phenyl | 4-morpholinocarbonyl |
| 468 | SO₂CH₃ | 2-F-phenyl | 2-methyl-1-imidazolyl |
| 469 | SO₂CH₃ | 2-F-phenyl | 5-methyl-1-imidazolyl |
| 470 | SO₂CH₃ | 2-F-phenyl | 2-methylsulfonyl-1-imidazolyl |
| 471 | SO₂CH₃ | 2,6-diF-phenyl | 2-(aminosulfonyl)phenyl |
| 472 | SO₂CH₃ | 2,6-diF-phenyl | 2-(methylaminosulfonyl)phenyl |
| 473 | SO₂CH₃ | 2,6-diF-phenyl | 1-pyrrolidinocarbonyl |
| 474 | SO₂CH₃ | 2,6-diF-phenyl | 2-(methylsulfonyl)phenyl |
| 475 | SO₂CH₃ | 2,6-diF-phenyl | 4-morpholino |
| 476 | SO₂CH₃ | 2,6-diF-phenyl | 2-(1'-CF₃-tetrazol-2-yl)phenyl |
| 477 | SO₂CH₃ | 2,6-diF-phenyl | 4-morpholinocarbonyl |
| 478 | SO₂CH₃ | 2,6-diF-phenyl | 2-methyl-1-imidazolyl |
| 479 | SO₂CH₃ | 2,6-diF-phenyl | 5-methyl-1-imidazolyl |
| 480 | SO₂CH₃ | 2,6-diF-phenyl | 2-methylsulfonyl-1-imidazolyl |
| 481 | CH₂NH—SO₂CH₃ | phenyl | 2-(aminosulfonyl)phenyl |
| 482 | CH₂NH—SO₂CH₃ | phenyl | 2-(methylaminosulfonyl)phenyl |
| 483 | CH₂NH—SO₂CH₃ | phenyl | 1-pyrrolidinocarbonyl |
| 484 | CH₂NH—SO₂CH₃ | phenyl | 2-(methylsulfonyl)phenyl |
| 485 | CH₂NH—SO₂CH₃ | phenyl | 4-morpholino |
| 486 | CH₂NH—SO₂CH₃ | phenyl | 2-(1'-CF₃-tetrazol-2-yl)phenyl |
| 487 | CH₂NH—SO₂CH₃ | phenyl | 4-morpholinocarbonyl |
| 488 | CH₂NH—SO₂CH₃ | phenyl | 2-methyl-1-imidazolyl |
| 489 | CH₂NH—SO₂CH₃ | phenyl | 5-methyl-1-imidazolyl |
| 490 | CH₂NH—SO₂CH₃ | phenyl | 2-methylsulfonyl-1-imidazolyl |
| 491 | CH₂NH—SO₂CH₃ | 2-pyridyl | 2-(aminosulfonyl)phenyl |
| 492 | CH₂NH—SO₂CH₃ | 2-pyridyl | 2-(methylaminosulfonyl)phenyl |
| 493 | CH₂NH—SO₂CH₃ | 2-pyridyl | 1-pyrrolidinocarbonyl |
| 494 | CH₂NH—SO₂CH₃ | 2-pyridyl | 2-(methylsulfonyl)phenyl |
| 495 | CH₂NH—SO₂CH₃ | 2-pyridyl | 4-morpholino |
| 496 | CH₂NH—SO₂CH₃ | 2-pyridyl | 2-(1'-CF₃-tetrazol-2-yl)phenyl |
| 497 | CH₂NH—SO₂CH₃ | 2-pyridyl | 4-morpholinocarbonyl |
| 498 | CH₂NH—SO₂CH₃ | 2-pyridyl | 2-methyl-1-imidazolyl |
| 499 | CH₂NH—SO₂CH₃ | 2-pyridyl | 5-methyl-1-imidazolyl |
| 500 | CH₂NH—SO₂CH₃ | 2-pyridyl | 2-methylsulfonyl-1-imidazolyl |
| 501 | CH₂NH—SO₂CH₃ | 3-pyridyl | 2-(aminosulfonyl)phenyl |
| 502 | CH₂NH—SO₂CH₃ | 3-pyridyl | 2-(methylaminosulfonyl)phenyl |
| 503 | CH₂NH—SO₂CH₃ | 3-pyridyl | 1-pyrrolidinocarbonyl |
| 504 | CH₂NH—SO₂CH₃ | 3-pyridyl | 2-(methylsulfonyl)phenyl |
| 505 | CH₂NH—SO₂CH₃ | 3-pyridyl | 4-morpholino |
| 506 | CH₂NH—SO₂CH₃ | 3-pyridyl | 2-(1'-CF₃-tetrazol-2-yl)phenyl |
| 507 | CH₂NH—SO₂CH₃ | 3-pyridyl | 4-morpholinocarbonyl |
| 508 | CH₂NH—SO₂CH₃ | 3-pyridyl | 2-methyl-1-imidazolyl |
| 509 | CH₂NH—SO₂CH₃ | 3-pyridyl | 5-methyl-1-imidazolyl |
| 510 | CH₂NH—SO₂CH₃ | 3-pyridyl | 2-methylsulfonyl-1-imidazolyl |
| 511 | CH₂NH—SO₂CH₃ | 2-pyrimidyl | 2-(aminosulfonyl)phenyl |
| 512 | CH₂NH—SO₂CH₃ | 2-pyrimidyl | 2-(methylaminosulfonyl)phenyl |
| 513 | CH₂NH—SO₂CH₃ | 2-pyrimidyl | 1-pyrrolidinocarbonyl |
| 514 | CH₂NH—SO₂CH₃ | 2-pyrimidyl | 2-(methylsulfonyl)phenyl |
| 515 | CH₂NH—SO₂CH₃ | 2-pyrimidyl | 4-morpholino |
| 516 | CH₂NH—SO₂CH₃ | 2-pyrimidyl | 2-(1'-CF₃-tetrazol-2-yl)phenyl |
| 517 | CH₂NH—SO₂CH₃ | 2-pyrimidyl | 4-morpholinocarbonyl |
| 518 | CH₂NH—SO₂CH₃ | 2-pyrimidyl | 2-methyl-1-imidazolyl |
| 519 | CH₂NH—SO₂CH₃ | 2-pyrimidyl | 5-methyl-1-imidazolyl |
| 520 | CH₂NH—SO₂CH₃ | 2-pyrimidyl | 2-methylsulfonyl-1-imidazolyl |
| 521 | CH₂NH—SO₂CH₃ | 5-pyrimidyl | 2-(aminosulfonyl)phenyl |
| 522 | CH₂NH—SO₂CH₃ | 5-pyrimidyl | 2-(methylaminosulfonyl)phenyl |
| 523 | CH₂NH—SO₂CH₃ | 5-pyrimidyl | 1-pyrrolidinocarbonyl |
| 524 | CH₂NH—SO₂CH₃ | 5-pyrimidyl | 2-(methylsulfonyl)phenyl |
| 525 | CH₂NH—SO₂CH₃ | 5-pyrimidyl | 4-morpholino |

TABLE 4-continued

| | | | |
|---|---|---|---|
| 526 | CH₂NH—SO₂CH₃ | 5-pyrimidyl | 2-(1'-CF₃-tetrazol-2-yl)phenyl |
| 527 | CH₂NH—SO₂CH₃ | 5-pyrimidyl | 4-morpholinocarbonyl |
| 528 | CH₂NH—SO₂CH₃ | 5-pyrimidyl | 2-methyl-1-imidazolyl |
| 529 | CH₂NH—SO₂CH₃ | 5-pyrimidyl | 5-methyl-1-imidazolyl |
| 530 | CH₂NH—SO₂CH₃ | 5-pyrimidyl | 2-methylsulfonyl-1-imidazolyl |
| 531 | CH₂NH—SO₂CH₃ | 2-Cl-phenyl | 2-(aminosulfonyl)phenyl |
| 532 | CH₂NH—SO₂CH₃ | 2-Cl-phenyl | 2-(methylaminosulfonyl)phenyl |
| 533 | CH₂NH—SO₂CH₃ | 2-Cl-phenyl | 1-pyrrolidinocarbonyl |
| 534 | CH₂NH—SO₂CH₃ | 2-Cl-phenyl | 2-(methylsulfonyl)phenyl |
| 535 | CH₂NH—SO₂CH₃ | 2-Cl-phenyl | 4-morpholino |
| 536 | CH₂NH—SO₂CH₃ | 2-Cl-phenyl | 2-(1'-CF₃-tetrazol-2-yl)phenyl |
| 537 | CH₂NH—SO₂CH₃ | 2-Cl-phenyl | 4-morpholinocarbonyl |
| 538 | CH₂NH—SO₂CH₃ | 2-Cl-phenyl | 2-methyl-1-imidazolyl |
| 539 | CH₂NH—SO₂CH₃ | 2-Cl-phenyl | 5-methyl-1-imidazolyl |
| 540 | CH₂NH—SO₂CH₃ | 2-Cl-phenyl | 2-methylsulfonyl-1-imidazolyl |
| 541 | CH₂NH—SO₂CH₃ | 2-F-phenyl | 2-(aminosulfonyl)phenyl |
| 542 | CH₂NH—SO₂CH₃ | 2-F-phenyl | 2-(methylaminosulfonyl)phenyl |
| 543 | CH₂NH—SO₂CH₃ | 2-F-phenyl | 1-pyrrolidinocarbonyl |
| 544 | CH₂NH—SO₂CH₃ | 2-F-phenyl | 2-(methylsulfonyl)phenyl |
| 545 | CH₂NH—SO₂CH₃ | 2-F-phenyl | 4-morpholino |
| 546 | CH₂NH—SO₂CH₃ | 2-F-phenyl | 2-(1'-CF₃-tetrazol-2-yl)phenyl |
| 547 | CH₂NH—SO₂CH₃ | 2-F-phenyl | 4-morpholinocarbonyl |
| 548 | CH₂NH—SO₂CH₃ | 2-F-phenyl | 2-methyl-1-imidazolyl |
| 549 | CH₂NH—SO₂CH₃ | 2-F-phenyl | 5-methyl-1-imidazolyl |
| 550 | CH₂NH—SO₂CH₃ | 2-F-phenyl | 2-methylsulfonyl-1-imidazolyl |
| 551 | CH₂NH—SO₂CH₃ | 2,6-diF-phenyl | 2-(aminosulfonyl)phenyl |
| 552 | CH₂NH—SO₂CH₃ | 2,6-diF-phenyl | 2-(methylaminosulfonyl)phenyl |
| 553 | CH₂NH—SO₂CH₃ | 2,6-diF-phenyl | 1-pyrrolidinocarbonyl |
| 554 | CH₂NH—SO₂CH₃ | 2,6-diF-phenyl | 2-(methylsulfonyl)phenyl |
| 555 | CH₂NH—SO₂CH₃ | 2,6-diF-phenyl | 4-morpholino |
| 556 | CH₂NH—SO₂CH₃ | 2,6-diF-phenyl | 2-(1'-CF₃-tetrazol-2-yl)phenyl |
| 557 | CH₂NH—SO₂CH₃ | 2,6-diF-phenyl | 4-morpholinocarbonyl |
| 558 | CH₂NH—SO₂CH₃ | 2,6-diF-phenyl | 2-methyl-1-imidazolyl |
| 559 | CH₂NH—SO₂CH₃ | 2,6-diF-phenyl | 5-methyl-1-imidazolyl |
| 560 | CH₂NH—SO₂CH₃ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF₃-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF₃-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF₃-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | i-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF₃-tetrazol-2 yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF₃-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF₃-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF₃-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-CF₃-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-CF₃-tetrazol-2-yl)phenyl |
| 647 | F | phenyl | 4-morpholinocarbonyl |
| 648 | F | phenyl | 2-methyl-1-imidazolyl |

TABLE 4-continued

| | | | |
|---|---|---|---|
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-$CF_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-$CF_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | S-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-$CF_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |

TABLE 4-continued

| | | | |
|---|---|---|---|
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |
| 871 | $CH_2OCH_3$ | 2,6-diF-phenyl | 2-(aminosulfonyl)phenyl |
| 872 | $CH_2OCH_3$ | 2,6-diF-phenyl | 2-(methylaminosulfonyl)phenyl |
| 873 | $CH_2OCH_3$ | 2,6-diF-phenyl | 1-pyrrolidinocarbonyl |
| 874 | $CH_2OCH_3$ | 2,6-diF-phenyl | 2-(methylsulfonyl)phenyl |
| 875 | $CH_2OCH_3$ | 2,6-diF-phenyl | 4-morpholino |
| 876 | $CH_2OCH_3$ | 2,6-diF-phenyl | 2-(1'-$CF_3$-tetrazol-2-yl)phenyl |
| 877 | $CH_2OCH_3$ | 2,6-diF-phenyl | 4-morpholinocarbonyl |
| 878 | $CH_2OCH_3$ | 2,6-diF-phenyl | 2-methyl-1-imidazolyl |
| 879 | $CH_2OCH_3$ | 2,6-diF-phenyl | 5-methyl-1-imidazolyl |
| 880 | $CH_2OCH_3$ | 2,6-diF-phenyl | 2-methylsulfonyl-1-imidazolyl |
| 881 | $CONH_2$ | phenyl | 2-(aminosulfonyl)phenyl |
| 882 | $CONH_2$ | phenyl | 2-(methylaminosulfonyl)phenyl |
| 883 | $CONH_2$ | phenyl | 1-pyrrolidinocarbonyl |
| 884 | $CONH_2$ | phenyl | 2-(methylsulfonyl)phenyl |
| 885 | $CONH_2$ | phenyl | 4-morpholino |
| 886 | $CONH_2$ | phenyl | 2-(1'-$CF_3$-tetrazol-2-yl)phenyl |
| 887 | $CONH_2$ | phenyl | 4-morpholinocarbonyl |
| 888 | $CONH_2$ | phenyl | 2-methyl-1-imidazolyl |
| 889 | $CONH_2$ | phenyl | 5-methyl-1-imidazolyl |
| 890 | $CONH_2$ | phenyl | 2-methylsulfonyl-1-imidazolyl |
| 891 | $CONH_2$ | 2-pyridyl | 2-(aminosulfonyl)phenyl |
| 892 | $CONH_2$ | 2-pyridyl | 2-(methylaminosulfonyl)phenyl |
| 893 | $CONH_2$ | 2-pyridyl | 1-pyrrolidinocarbonyl |
| 894 | $CONH_2$ | 2-pyridyl | 2-(methylsulfonyl)phenyl |
| 895 | $CONH_2$ | 2-pyridyl | 4-morpholino |
| 896 | $CONH_2$ | 2-pyridyl | 2-(1'-$CF_3$-tetrazol-2-yl)phenyl |
| 897 | $CONH_2$ | 2-pyridyl | 4-morpholinocarbonyl |
| 898 | $CONH_2$ | 2-pyridyl | 2-methyl-1-imidazolyl |
| 899 | $CONH_2$ | 2-pyridyl | 5-methyl-1-imidazolyl |
| 900 | $CONH_2$ | 2-pyridyl | 2-methylsulfonyl-1-imidazolyl |
| 901 | $CONH_2$ | 3-pyridyl | 2-(aminosulfonyl)phenyl |
| 902 | $CONH_2$ | 3-pyridyl | 2-(methylaminosulfonyl)phenyl |
| 903 | $CONH_2$ | 3-pyridyl | 1-pyrrolidinocarbonyl |
| 904 | $CONH_2$ | 3-pyridyl | 2-(methylsulfonyl)phenyl |
| 905 | $CONH_2$ | 3-pyridyl | 4-morpholino |
| 906 | $CONH_2$ | 3-pyridyl | 2-(1'-$CF_3$-tetrazol-2 yl)phenyl |
| 907 | $CONH_2$ | 3-pyridyl | 4-morpholinocarbonyl |
| 908 | $CONH_2$ | 3-pyridyl | 2-methyl-1-imidazolyl |
| 909 | $CONH_2$ | 3-pyridyl | 5-methyl-1-imidazolyl |
| 910 | $CONH_2$ | 3-pyridyl | 2-methylsulfonyl-1-imidazolyl |
| 911 | $CONH_2$ | 2-pyrimidyl | 2-(aminosulfonyl)phenyl |
| 912 | $CONH_2$ | 2-pyrimidyl | 2-(methylaminosulfonyl)phenyl |
| 913 | $CONH_2$ | 2-pyrimidyl | 1-pyrrolidinocarbonyl |
| 914 | $CONH_2$ | 2-pyrimidyl | 2-(methylsulfonyl)phenyl |
| 915 | $CONH_2$ | 2-pyrimidyl | 4-morpholino |
| 916 | $CONH_2$ | 2-pyrimidyl | 2-(1'-$CF_3$-tetrazol-2 yl)phenyl |
| 917 | $CONH_2$ | 2-pyrimidyl | 4-morpholinocarbonyl |
| 918 | $CONH_2$ | 2-pyrimidyl | 2-methyl-1-imidazolyl |
| 919 | $CONH_2$ | 2-pyrimidyl | 5-methyl-1-imidazolyl |
| 920 | $CONH_2$ | 2-pyrimidyl | 2-methylsulfonyl-1-imidazolyl |
| 921 | $CONH_2$ | 5-pyrimidyl | 2-(aminosulfonyl)phenyl |
| 922 | $CONH_2$ | 5-pyrimidyl | 2-(methylaminosulfonyl)phenyl |
| 923 | $CONH_2$ | 5-pyrimidyl | 1-pyrrolidinocarbonyl |
| 924 | $CONH_2$ | 5-pyrimidyl | 2-(methylsulfonyl)phenyl |
| 925 | $CONH_2$ | 5-pyrimidyl | 4-morpholino |
| 926 | $CONH_2$ | 5-pyrimidyl | 2-(1'-$CF_3$-tetrazol-2 yl)phenyl |
| 927 | $CONH_2$ | 5-pyrimidyl | 4-morpholinocarbonyl |
| 928 | $CONH_2$ | 5-pyrimidyl | 2-methyl-1-imidazolyl |
| 929 | $CONH_2$ | 5-pyrimidyl | 5-methyl-1-imidazolyl |
| 930 | $CONH_2$ | 5-pyrimidyl | 2-methylsulfonyl-1-imidazolyl |
| 931 | $CONH_2$ | 2-Cl-phenyl | 2-(aminosulfonyl)phenyl |
| 932 | $CONH_2$ | 2-Cl-phenyl | 2-(methylaminosulfonyl)phenyl |
| 933 | $CONH_2$ | 2-Cl-phenyl | 1-pyrrolidinocarbonyl |
| 934 | $CONH_2$ | 2-Cl-phenyl | 2-(methylsulfonyl)phenyl |
| 935 | $CONH_2$ | 2-Cl-phenyl | 4-morpholino |
| 936 | $CONH_2$ | 2-Cl-phenyl | 2-(1'-$CF_3$-tetrazol-2 yl)phenyl |
| 937 | $CONH_2$ | 2-Cl-phenyl | 4-morpholinocarbonyl |
| 938 | $CONH_2$ | 2-Cl-phenyl | 2-methyl-1-imidazolyl |
| 939 | $CONH_2$ | 2-Cl-phenyl | 5-methyl-1-imidazolyl |
| 940 | $CONH_2$ | 2-Cl-phenyl | 2-methylsulfonyl-1-imidazolyl |
| 941 | $CONH_2$ | 2-F-phenyl | 2-(aminosulfonyl)phenyl |
| 942 | $CONH_2$ | 2-F-phenyl | 2-(methylaminosulfonyl)phenyl |
| 943 | $CONH_2$ | 2-F-phenyl | 1-pyrrolidinocarbonyl |
| 944 | $CONH_2$ | 2-F-phenyl | 2-(methylsulfonyl)phenyl |
| 945 | $CONH_2$ | 2-F-phenyl | 4-morpholino |
| 946 | $CONH_2$ | 2-F-phenyl | 2-(1'-$CF_3$-tetrazol-2 yl)phenyl |
| 947 | $CONH_2$ | 2-F-phenyl | 4-morpholinocarbonyl |
| 948 | $CONH_2$ | 2-F-phenyl | 2-methyl-1-imidazolyl |
| 949 | $CONH_2$ | 2-F-phenyl | 5-methyl-1-imidazolyl |
| 950 | $CONH_2$ | 2-F-phenyl | 2-methylsulfonyl-1-imidazolyl |
| 951 | $CONH_2$ | 2,6-diF-phenyl | 2-(aminosulfonyl)phenyl |
| 952 | $CONH_2$ | 2,6-diF-phenyl | 2-(methylaminosulfonyl)phenyl |
| 953 | $CONH_2$ | 2,6-diF-phenyl | 1-pyrrolidinocarbonyl |
| 954 | $CONH_2$ | 2,6-diF-phenyl | 2-(methylsulfonyl)phenyl |
| 955 | $CONH_2$ | 2,6-diF-phenyl | 4-morpholino |
| 956 | $CONH_2$ | 2,6-diF-phenyl | 2-(1'-$CF_3$-tetrazol-2 yl)phenyl |
| 957 | $CONH_2$ | 2,6-diF-phenyl | 4-morpholinocarbonyl |
| 958 | $CONH_2$ | 2,6-diF-phenyl | 2-methyl-1-imidazolyl |
| 959 | $CONH_2$ | 2,6-diF-phenyl | 5-methyl-1-imidazolyl |
| 960 | $CONH_2$ | 2,6-diF-phenyl | 2-methylsulfonyl-1-imidazolyl |

TABLE 5

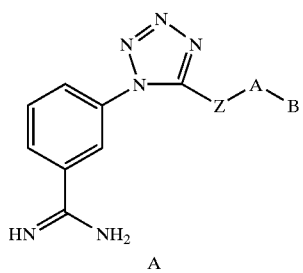

A

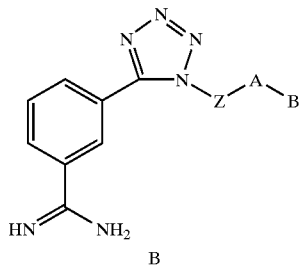

B

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-$CF_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-$CF_3$-tetrazol-2-yl)phenyl |
| 17 | 2-pyridyl | 4-morpholinocarbonyl |
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-$CF_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-$CF_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-$CF_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |

TABLE 5-continued

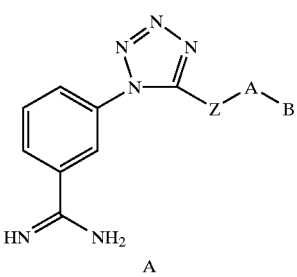

A

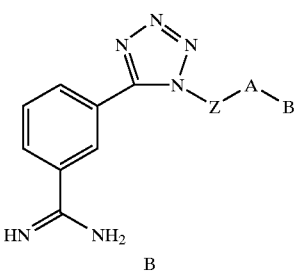

B

| Ex # | A | B |
|---|---|---|
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-$CF_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |
| 66 | 2-F-phenyl | 2-(1'-$CF_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-$CF_3$-tetrazol-2-yl)phenyl |
| 77 | 2,6-diF-phenyl | 4-morpholinocarbonyl |
| 78 | 2,6-diF-phenyl | 2-methyl-1-imidazolyl |
| 79 | 2,6-diF-phenyl | 5-methyl-1-imidazolyl |
| 80 | 2,6-diF-phenyl | 2-methylsulfonyl-1-imidazolyl |

TABLE 6

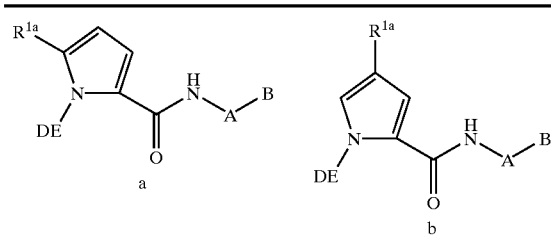

a b

TABLE 6-continued
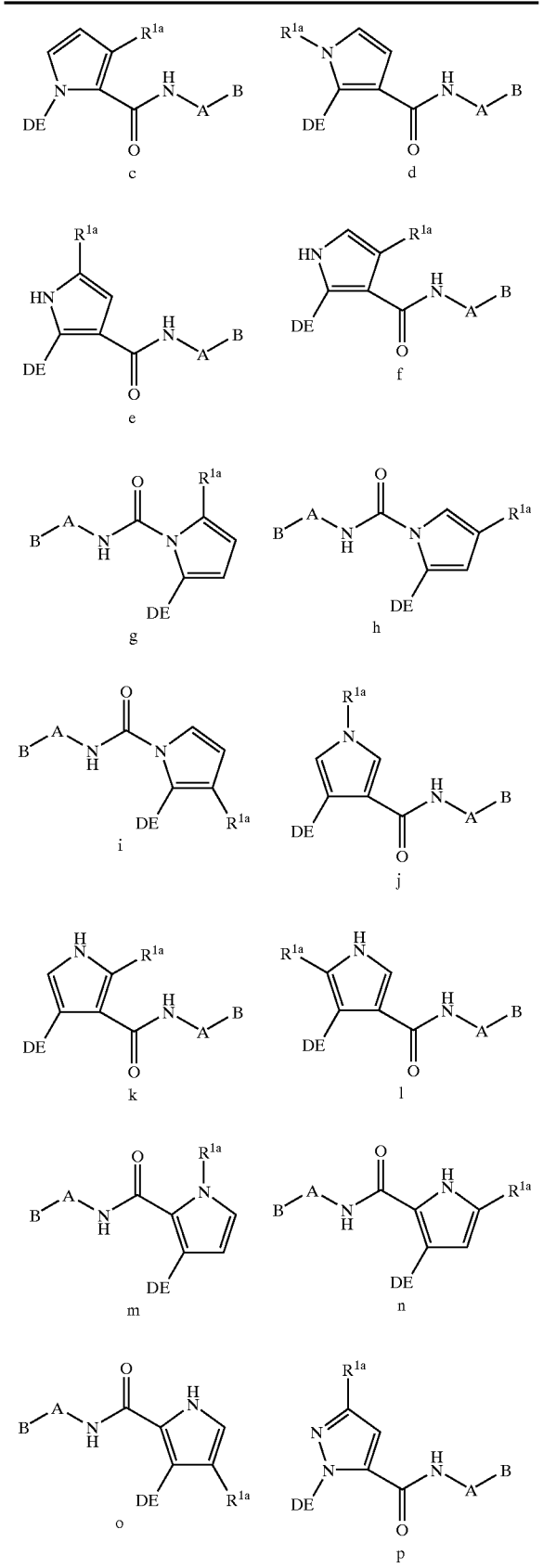
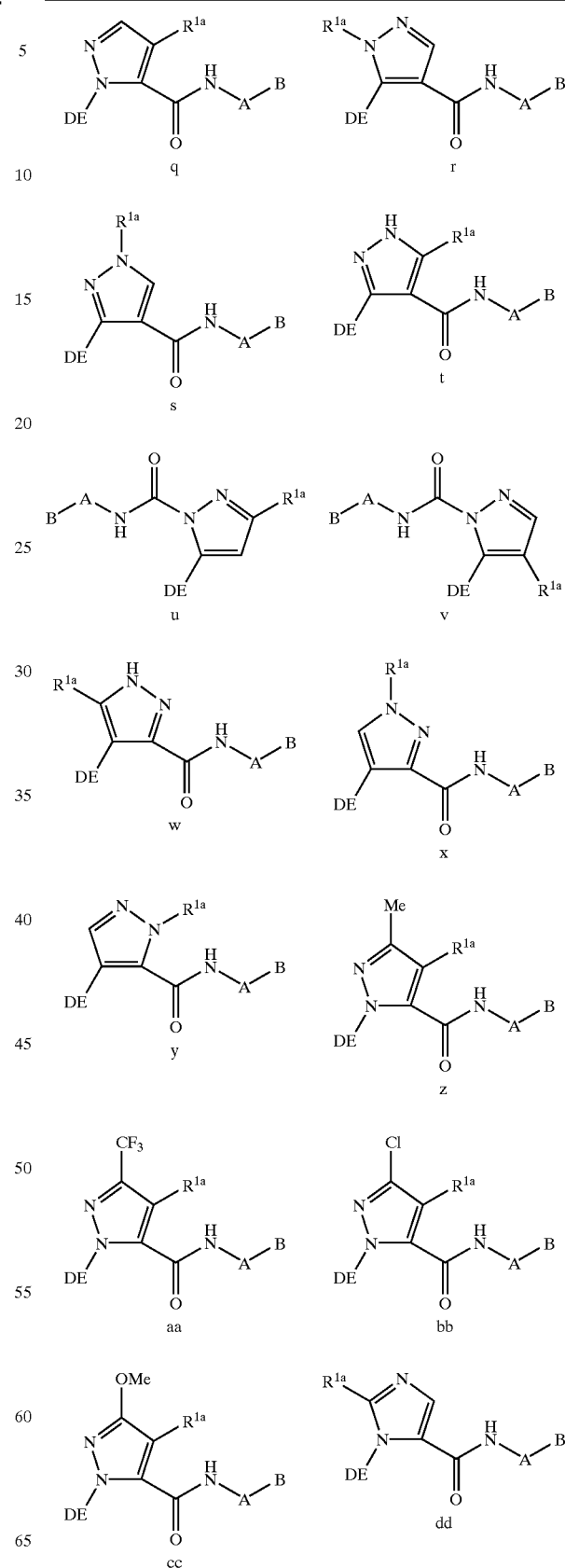

TABLE 6-continued

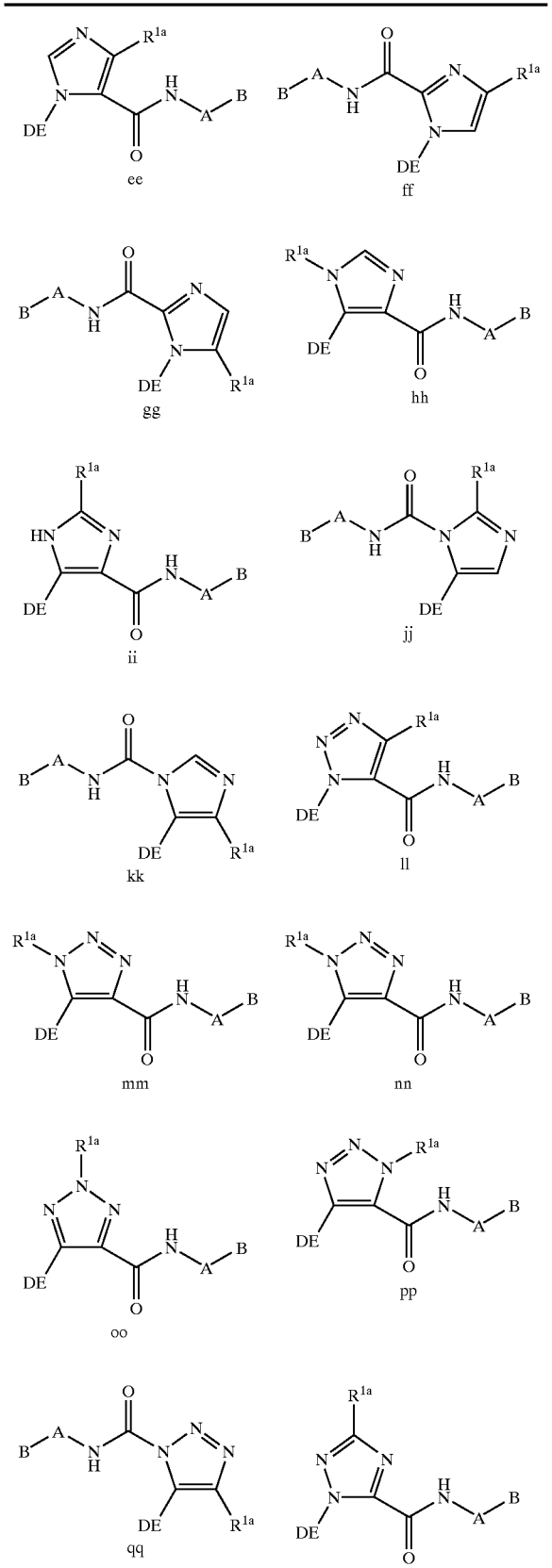

For each example, DE is:
(A) pyridin-4-yl-CH$_2$,
(B) 2-amino-pyrimidin-4-yl,
(C) 6-amino-pyridin-2-yl,
(D) 3-amidino-4-F-phenyl, or
(E) N-amidino-3-piperidinyl.

| Ex # | R$^{1a}$ | A | B |
|---|---|---|---|
| 1 | CH$_3$ | phenyl | 2-(aminosulfonyl)phenyl |
| 2 | CH$_3$ | phenyl | 2-(methylaminosulfonyl)phenyl |
| 3 | CH$_3$ | phenyl | 1-pyrrolidinocarbonyl |
| 4 | CH$_3$ | phenyl | 2-(methylsulfonyl)phenyl |
| 5 | CH$_3$ | phenyl | 4-morpholino |
| 6 | CH$_3$ | phenyl | 2-(1'-CF$_3$-tetrazol-2-yl)phenyl |
| 7 | CH$_3$ | phenyl | 4-morpholinocarbonyl |
| 8 | CH$_3$ | phenyl | 2-methyl-1-imidazolyl |
| 9 | CH$_3$ | phenyl | 5-methyl-1-imidazolyl |
| 10 | CH$_3$ | phenyl | 2-methylsulfonyl-1-imidazolyl |
| 11 | CH$_3$ | 2-pyridyl | 2-(aminosulfonyl)phenyl |
| 12 | CH$_3$ | 2-pyridyl | 2-(methylaminosulfonyl)phenyl |
| 13 | CH$_3$ | 2-pyridyl | 1-pyrrolidinocarbonyl |
| 14 | CH$_3$ | 2-pyridyl | 2-(methylsulfonyl)phenyl |
| 15 | CH$_3$ | 2-pyridyl | 4-morpholino |
| 16 | CH$_3$ | 2-pyridyl | 2-(1'-CF$_3$-tetrazol-2-yl)phenyl |
| 17 | CH$_3$ | 2-pyridyl | 4-morpholinocarbonyl |
| 18 | CH$_3$ | 2-pyridyl | 2-methyl-1-imidazolyl |
| 19 | CH$_3$ | 2-pyridyl | 5-methyl-1-imidazolyl |
| 20 | CH$_3$ | 2-pyridyl | 2-methylsulfonyl-1-imidazolyl |
| 21 | CH$_3$ | 3-pyridyl | 2-(aminosulfonyl)phenyl |
| 22 | CH$_3$ | 3-pyridyl | 2-(methylaminosulfonyl)phenyl |
| 23 | CH$_3$ | 3-pyridyl | 1-pyrrolidinocarbonyl |
| 24 | CH$_3$ | 3-pyridyl | 2-(methylsulfonyl)phenyl |
| 25 | CH$_3$ | 3-pyridyl | 4-morpholino |
| 26 | CH$_3$ | 3-pyridyl | 2-(1'-CF$_3$-tetrazol-2-yl)phenyl |
| 27 | CH$_3$ | 3-pyridyl | 4-morpholinocarbonyl |
| 28 | CH$_3$ | 3-pyridyl | 2-methyl-1-imidazolyl |
| 29 | CH$_3$ | 3-pyridyl | 5-methyl-1-imidazolyl |
| 30 | CH$_3$ | 3-pyridyl | 2-methylsulfonyl-1-imidazolyl |
| 31 | CH$_3$ | 2-pyrimidyl | 2-(aminosulfonyl)phenyl |

TABLE 6-continued

| | | | |
|---|---|---|---|
| 32 | CH$_3$ | 2-pyrimidyl | 2-(methylaminosulfonyl)phenyl |
| 33 | CH$_3$ | 2-pyrimidyl | 1-pyrrolidinocarbonyl |
| 34 | CH$_3$ | 2-pyrimidyl | 2-(methylsulfonyl)phenyl |
| 35 | CH$_3$ | 2-pyrimidyl | 4-morpholino |
| 36 | CH$_3$ | 2-pyrimidyl | 2-(1'-CF$_3$-tetrazol-2-yl)phenyl |
| 37 | CH$_3$ | 2-pyrimidyl | 4-morpholinocarbonyl |
| 38 | CH$_3$ | 2-pyrimidyl | 2-methyl-1-imidazolyl |
| 39 | CH$_3$ | 2-pyrimidyl | 5-methyl-1-imidazolyl |
| 40 | CH$_3$ | 2-pyrimidyl | 2-methylsulfonyl-1-imidazolyl |
| 41 | CH$_3$ | 5-pyrimidyl | 2-(aminosulfonyl)phenyl |
| 42 | CH$_3$ | 5-pyrimidyl | 2-(methylaminosulfonyl)phenyl |
| 43 | CH$_3$ | 5-pyrimidyl | 1-pyrrolidinocarbonyl |
| 44 | CH$_3$ | 5-pyrimidyl | 2-(methylsulfonyl)phenyl |
| 45 | CH$_3$ | 5-pyrimidyl | 4-morpholino |
| 46 | CH$_3$ | 5-pyrimidyl | 2-(1'-CF$_3$-tetrazol-2-yl)phenyl |
| 47 | CH$_3$ | 5-pyrimidyl | 4-morpholinocarbonyl |
| 48 | CH$_3$ | 5-pyrimidyl | 2-methyl-1-imidazolyl |
| 49 | CH$_3$ | 5-pyrimidyl | 5-methyl-1-imidazolyl |
| 50 | CH$_3$ | 5-pyrimidyl | 2-methylsulfonyl-1-imidazolyl |
| 51 | CH$_3$ | 2-Cl-phenyl | 2-(aminosulfonyl)phenyl |
| 52 | CH$_3$ | 2-Cl-phenyl | 2-(methylaminosulfonyl)phenyl |
| 53 | CH$_3$ | 2-Cl-phenyl | 1-pyrrolidinocarbonyl |
| 54 | CH$_3$ | 2-Cl-phenyl | 2-(methylsulfonyl)phenyl |
| 55 | CH$_3$ | 2-Cl-phenyl | 4-morpholino |
| 56 | CH$_3$ | 2-Cl-phenyl | 2-(1'-CF$_3$-tetrazol-2-yl)phenyl |
| 57 | CH$_3$ | 2-Cl-phenyl | 4-morpholinocarbonyl |
| 58 | CH$_3$ | 2-Cl-phenyl | 2-methyl-1-imidazolyl |
| 59 | CH$_3$ | 2-Cl-phenyl | 5-methyl-1-imidazolyl |
| 60 | CH$_3$ | 2-Cl-phenyl | 2-methylsulfonyl-1-imidazolyl |
| 61 | CH$_3$ | 2-F-phenyl | 2-(aminosulfonyl)phenyl |
| 62 | CH$_3$ | 2-F-phenyl | 2-(methylaminosulfonyl)phenyl |
| 63 | CH$_3$ | 2-F-phenyl | 1-pyrrolidinocarbonyl |
| 64 | CH$_3$ | 2-F-phenyl | 2-(methylsulfonyl)phenyl |
| 65 | CH$_3$ | 2-F-phenyl | 4-morpholino |
| 66 | CH$_3$ | 2-F-phenyl | 2-(1'-CF$_3$-tetrazol-2-yl)phenyl |
| 67 | CH$_3$ | 2-F-phenyl | 4-morpholinocarbonyl |
| 68 | CH$_3$ | 2-F-phenyl | 2-methyl-1-imidazolyl |
| 69 | CH$_3$ | 2-F-phenyl | 5-methyl-1-imidazolyl |
| 70 | CH$_3$ | 2-F-phenyl | 2-methylsulfonyl-1-imidazolyl |
| 71 | CH$_3$ | 2,6-diF-phenyl | 2-(aminosulfonyl)phenyl |
| 72 | CH$_3$ | 2,6-diF-phenyl | 2-(methylaminosulfonyl)phenyl |
| 73 | CH$_3$ | 2,6-diF-phenyl | 1-pyrrolidinocarbonyl |
| 74 | CH$_3$ | 2,6-diF-phenyl | 2-(methylsulfonyl)phenyl |
| 75 | CH$_3$ | 2,6-diF-phenyl | 4-morpholino |
| 76 | CH$_3$ | 2,6-diF-phenyl | 2-(1'-CF$_3$-tetrazol-2-yl)phenyl |
| 77 | CH$_3$ | 2,6-diF-phenyl | 4-morpholinocarbonyl |
| 78 | CH$_3$ | 2,6-diF-phenyl | 2-methyl-1-imidazolyl |
| 79 | CH$_3$ | 2,6-diF-phenyl | 5-methyl-1-imidazolyl |
| 80 | CH$_3$ | 2,6-diF-phenyl | 2-methylsulfonyl-1-imidazolyl |
| 81 | CH$_2$CH$_3$ | phenyl | 2-(aminosulfonyl)phenyl |
| 82 | CH$_2$CH$_3$ | phenyl | 2-(methylaminosulfonyl)phenyl |
| 83 | CH$_2$CH$_3$ | phenyl | 1-pyrrolidinocarbonyl |
| 84 | CH$_2$CH$_3$ | phenyl | 2-(methylsulfonyl)phenyl |
| 85 | CH$_2$CH$_3$ | phenyl | 4-morpholino |
| 86 | CH$_2$CH$_3$ | phenyl | 2-(1'-CF$_3$-tetrazol-2-yl)phenyl |
| 87 | CH$_2$CH$_3$ | phenyl | 4-morpholinocarbonyl |
| 88 | CH$_2$CH$_3$ | phenyl | 2-methyl-1-imidazolyl |
| 89 | CH$_2$CH$_3$ | phenyl | 5-methyl-1-imidazolyl |
| 90 | CH$_2$CH$_3$ | phenyl | 2-methylsulfonyl-1-imidazolyl |
| 91 | CH$_2$CH$_3$ | 2-pyridyl | 2-(aminosulfonyl)phenyl |
| 92 | CH$_2$CH$_3$ | 2-pyridyl | 2-(methylaminosulfonyl)phenyl |
| 93 | CH$_2$CH$_3$ | 2-pyridyl | 1-pyrrolidinocarbonyl |
| 94 | CH$_2$CH$_3$ | 2-pyridyl | 2-(methylsulfonyl)phenyl |
| 95 | CH$_2$CH$_3$ | 2-pyridyl | 4-morpholino |
| 96 | CH$_2$CH$_3$ | 2-pyridyl | 2-(1'-CF$_3$-tetrazol-2-yl)phenyl |
| 97 | CH$_2$CH$_3$ | 2-pyridyl | 4-morpholinocarbonyl |
| 98 | CH$_2$CH$_3$ | 2-pyridyl | 2-methyl-1-imidazolyl |
| 99 | CH$_2$CH$_3$ | 2-pyridyl | 5-methyl-1-imidazolyl |
| 100 | CH$_2$CH$_3$ | 2-pyridyl | 2-methylsulfonyl-1-imidazolyl |
| 101 | CH$_2$CH$_3$ | 3-pyridyl | 2-(aminosulfonyl)phenyl |
| 102 | CH$_2$CH$_3$ | 3-pyridyl | 2-(methylaminosulfonyl)phenyl |
| 103 | CH$_2$CH$_3$ | 3-pyridyl | 1-pyrrolidinocarbonyl |
| 104 | CH$_2$CH$_3$ | 3-pyridyl | 2-(methylsulfonyl)phenyl |
| 105 | CH$_2$CH$_3$ | 3-pyridyl | 4-morpholino |
| 106 | CH$_2$CH$_3$ | 3-pyridyl | 2-(1'-CF$_3$-tetrazol-2-yl)phenyl |
| 107 | CH$_2$CH$_3$ | 3-pyridyl | 4-morpholinocarbonyl |
| 108 | CH$_2$CH$_3$ | 3-pyridyl | 2-methyl-1-imidazolyl |
| 109 | CH$_2$CH$_3$ | 3-pyridyl | 5-methyl-1-imidazolyl |
| 110 | CH$_2$CH$_3$ | 3-pyridyl | 2-methylsulfonyl-1-imidazolyl |
| 111 | CH$_2$CH$_3$ | 2-pyrimidyl | 2-(aminosulfonyl)phenyl |
| 112 | CH$_2$CH$_3$ | 2-pyrimidyl | 2-(methylaminosulfonyl)phenyl |
| 113 | CH$_2$CH$_3$ | 2-pyrimidyl | 1-pyrrolidinocarbonyl |
| 114 | CH$_2$CH$_3$ | 2-pyrimidyl | 2-(methylsulfonyl)phenyl |
| 115 | CH$_2$CH$_3$ | 2-pyrimidyl | 4-morpholino |
| 116 | CH$_2$CH$_3$ | 2-pyrimidyl | 2-(1'-CF$_3$-tetrazol-2-yl)phenyl |
| 117 | CH$_2$CH$_3$ | 2-pyrimidyl | 4-morpholinocarbonyl |
| 118 | CH$_2$CH$_3$ | 2-pyrimidyl | 2-methyl-1-imidazolyl |
| 119 | CH$_2$CH$_3$ | 2-pyrimidyl | 5-methyl-1-imidazolyl |
| 120 | CH$_2$CH$_3$ | 2-pyrimidyl | 2-methylsulfonyl-1-imidazolyl |
| 121 | CH$_2$CH$_3$ | 5-pyrimidyl | 2-(aminosulfonyl)phenyl |
| 122 | CH$_2$CH$_3$ | 5-pyrimidyl | 2-(methylaminosulfonyl)phenyl |
| 123 | CH$_2$CH$_3$ | 5-pyrimidyl | 1-pyrrolidinocarbonyl |
| 124 | CH$_2$CH$_3$ | 5-pyrimidyl | 2-(methylsulfonyl)phenyl |
| 125 | CH$_2$CH$_3$ | 5-pyrimidyl | 4-morpholino |
| 126 | CH$_2$CH$_3$ | 5-pyrimidyl | 2-(1'-CF$_3$-tetrazol-2-yl)phenyl |
| 127 | CH$_2$CH$_3$ | 5-pyrimidyl | 4-morpholinocarbonyl |
| 128 | CH$_2$CH$_3$ | 5-pyrimidyl | 2-methyl-1-imidazolyl |
| 129 | CH$_2$CH$_3$ | 5-pyrimidyl | 5-methyl-1-imidazolyl |
| 130 | CH$_2$CH$_3$ | 5-pyrimidyl | 2-methylsulfonyl-1-imidazolyl |
| 131 | CH$_2$CH$_3$ | 2-Cl-phenyl | 2-(aminosulfonyl)phenyl |
| 132 | CH$_2$CH$_3$ | 2-Cl-phenyl | 2-(methylaminosulfonyl)phenyl |
| 133 | CH$_2$CH$_3$ | 2-Cl-phenyl | 1-pyrrolidinocarbonyl |
| 134 | CH$_2$CH$_3$ | 2-Cl-phenyl | 2-(methylsulfonyl)phenyl |
| 135 | CH$_2$CH$_3$ | 2-Cl-phenyl | 4-morpholino |
| 136 | CH$_2$CH$_3$ | 2-Cl-phenyl | 2-(1'-CF$_3$-tetrazol-2-yl)phenyl |
| 137 | CH$_2$CH$_3$ | 2-Cl-phenyl | 4-morpholinocarbonyl |
| 138 | CH$_2$CH$_3$ | 2-Cl-phenyl | 2-methyl-1-imidazolyl |
| 139 | CH$_2$CH$_3$ | 2-Cl-phenyl | 5-methyl-1-imidazolyl |
| 140 | CH$_2$CH$_3$ | 2-Cl-phenyl | 2-methylsulfonyl-1-imidazolyl |
| 141 | CH$_2$CH$_3$ | 2-F-phenyl | 2-(aminosulfonyl)phenyl |
| 142 | CH$_2$CH$_3$ | 2-F-phenyl | 2-(methylaminosulfonyl)phenyl |
| 143 | CH$_2$CH$_3$ | 2-F-phenyl | 1-pyrrolidinocarbonyl |
| 144 | CH$_2$CH$_3$ | 2-F-phenyl | 2-(methylsulfonyl)phenyl |
| 145 | CH$_2$CH$_3$ | 2-F-phenyl | 4-morpholino |
| 146 | CH$_2$CH$_3$ | 2-F-phenyl | 2-(1'-CF$_3$-tetrazol-2-yl)phenyl |
| 147 | CH$_2$CH$_3$ | 2-F-phenyl | 4-morpholinocarbonyl |
| 148 | CH$_2$CH$_3$ | 2-F-phenyl | 2-methyl-1-imidazolyl |
| 149 | CH$_2$CH$_3$ | 2-F-phenyl | 5-methyl-1-imidazolyl |
| 150 | CH$_2$CH$_3$ | 2-F-phenyl | 2-methylsulfonyl-1-imidazolyl |
| 151 | CH$_2$CH$_3$ | 2,6-diF-phenyl | 2-(aminosulfonyl)phenyl |

TABLE 6-continued

| | | | |
|---|---|---|---|
| 152 | CH$_2$CH$_3$ | 2,6-diF-phenyl | 2-(methylaminosulfonyl)phenyl |
| 153 | CH$_2$CH$_3$ | 2,6-diF-phenyl | 1-pyrrolidinocarbonyl |
| 154 | CH$_2$CH$_3$ | 2,6-diF-phenyl | 2-(methylsulfonyl)phenyl |
| 155 | CH$_2$CH$_3$ | 2,6-diF-phenyl | 4-morpholino |
| 156 | CH$_2$CH$_3$ | 2,6-diF-phenyl | 2-(1'-CF$_3$-tetrazol-2-yl)phenyl |
| 157 | CH$_2$CH$_3$ | 2,6-diF-phenyl | 4-morpholinocarbonyl |
| 158 | CH$_2$CH$_3$ | 2,6-diF-phenyl | 2-methyl-1-imidazolyl |
| 159 | CH$_2$CH$_3$ | 2,6-diF-phenyl | 5-methyl-1-imidazolyl |
| 160 | CH$_2$CH$_3$ | 2,6-diF-phenyl | 2-methylsulfonyl-1-imidazolyl |
| 161 | CF$_3$ | phenyl | 2-(aminosulfonyl)phenyl |
| 162 | CF$_3$ | phenyl | 2-(methylaminosulfonyl)phenyl |
| 163 | CF$_3$ | phenyl | 1-pyrrolidinocarbonyl |
| 164 | CF$_3$ | phenyl | 2-(methylsulfonyl)phenyl |
| 165 | CF$_3$ | phenyl | 4-morpholino |
| 166 | CF$_3$ | phenyl | 2-(1'-CF$_3$-tetrazol-2-yl)phenyl |
| 167 | CF$_3$ | phenyl | 4-morpholinocarbonyl |
| 168 | CF$_3$ | phenyl | 2-methyl-1-imidazolyl |
| 169 | CF$_3$ | phenyl | 5-methyl-1-imidazolyl |
| 170 | CF$_3$ | phenyl | 2-methylsulfonyl-1-imidazolyl |
| 171 | CF$_3$ | 2-pyridyl | 2-(aminosulfonyl)phenyl |
| 172 | CF$_3$ | 2-pyridyl | 2-(methylaminosulfonyl)phenyl |
| 173 | CF$_3$ | 2-pyridyl | 1-pyrrolidinocarbonyl |
| 174 | CF$_3$ | 2-pyridyl | 2-(methylsulfonyl)phenyl |
| 175 | CF$_3$ | 2-pyridyl | 4-morpholino |
| 176 | CF$_3$ | 2-pyridyl | 2-(1'-CF$_3$-tetrazol-2-yl)phenyl |
| 177 | CF$_3$ | 2-pyridyl | 4-morpholinocarbonyl |
| 178 | CF$_3$ | 2-pyridyl | 2-methyl-1-imidazolyl |
| 179 | CF$_3$ | 2-pyridyl | 5-methyl-1-imidazolyl |
| 180 | CF$_3$ | 2-pyridyl | 2-methylsulfonyl-1-imidazolyl |
| 181 | CF$_3$ | 3-pyridyl | 2-(aminosulfonyl)phenyl |
| 182 | CF$_3$ | 3-pyridyl | 2-(methylaminosulfonyl)phenyl |
| 183 | CF$_3$ | 3-pyridyl | 1-pyrrolidinocarbonyl |
| 184 | CF$_3$ | 3-pyridyl | 2-(methylsulfonyl)phenyl |
| 185 | CF$_3$ | 3-pyridyl | 4-morpholino |
| 186 | CF$_3$ | 3-pyridyl | 2-(1'-CF$_3$-tetrazol-2-yl)phenyl |
| 187 | CF$_3$ | 3-pyridyl | 4-morpholinocarbonyl |
| 188 | CF$_3$ | 3-pyridyl | 2-methyl-1-imidazolyl |
| 189 | CF$_3$ | 3-pyridyl | 5-methyl-1-imidazolyl |
| 190 | CF$_3$ | 3-pyridyl | 2-methylsulfonyl-1-imidazolyl |
| 191 | CF$_3$ | 2-pyrimidyl | 2-(aminosulfonyl)phenyl |
| 192 | CF$_3$ | 2-pyrimidyl | 2-(methylaminosulfonyl)phenyl |
| 193 | CF$_3$ | 2-pyrimidyl | 1-pyrrolidinocarbonyl |
| 194 | CF$_3$ | 2-pyrimidyl | 2-(methylsulfonyl)phenyl |
| 195 | CF$_3$ | 2-pyrimidyl | 4-morpholino |
| 196 | CF$_3$ | 2-pyrimidyl | 2-(1'-CF$_3$-tetrazol-2-yl)phenyl |
| 197 | CF$_3$ | 2-pyrimidyl | 4-morpholinocarbonyl |
| 198 | CF$_3$ | 2-pyrimidyl | 2-methyl-1-imidazolyl |
| 199 | CF$_3$ | 2-pyrimidyl | 5-methyl-1-imidazolyl |
| 200 | CF$_3$ | 2-pyrimidyl | 2-methylsulfonyl-1-imidazolyl |
| 201 | CF$_3$ | 5-pyrimidyl | 2-(aminosulfonyl)phenyl |
| 202 | CF$_3$ | 5-pyrimidyl | 2-(methylaminosulfonyl)phenyl |
| 203 | CF$_3$ | 5-pyrimidyl | 1-pyrrolidinocarbonyl |
| 204 | CF$_3$ | 5-pyrimidyl | 2-(methylsulfonyl)phenyl |
| 205 | CF$_3$ | 5-pyrimidyl | 4-morpholino |
| 206 | CF$_3$ | 5-pyrimidyl | 2-(1'-CF$_3$-tetrazol-2-yl)phenyl |
| 207 | CF$_3$ | 5-pyrimidyl | 4-morpholinocarbonyl |
| 208 | CF$_3$ | 5-pyrimidyl | 2-methyl-1-imidazolyl |
| 209 | CF$_3$ | 5-pyrimidyl | 5-methyl-1-imidazolyl |
| 210 | CF$_3$ | 5-pyrimidyl | 2-methylsulfonyl-1-imidazolyl |
| 211 | CF$_3$ | 2-Cl-phenyl | 2-(aminosulfonyl)phenyl |
| 212 | CF$_3$ | 2-Cl-phenyl | 2-(methylaminosulfonyl)phenyl |
| 213 | CF$_3$ | 2-Cl-phenyl | 1-pyrrolidinocarbonyl |
| 214 | CF$_3$ | 2-Cl-phenyl | 2-(methylsulfonyl)phenyl |
| 215 | CF$_3$ | 2-Cl-phenyl | 4-morpholino |
| 216 | CF$_3$ | 2-Cl-phenyl | 2-(1'-CF$_3$-tetrazol-2-yl)phenyl |
| 217 | CF$_3$ | 2-Cl-phenyl | 4-morpholinocarbonyl |
| 218 | CF$_3$ | 2-Cl-phenyl | 2-methyl-1-imidazolyl |
| 219 | CF$_3$ | 2-Cl-phenyl | 5-methyl-1-imidazolyl |
| 220 | CF$_3$ | 2-Cl-phenyl | 2-methylsulfonyl-1-imidazolyl |
| 221 | CF$_3$ | 2-F-phenyl | 2-(aminosulfonyl)phenyl |
| 222 | CF$_3$ | 2-F-phenyl | 2-(methylaminosulfonyl)phenyl |
| 223 | CF$_3$ | 2-F-phenyl | 1-pyrrolidinocarbonyl |
| 224 | CF$_3$ | 2-F-phenyl | 2-(methylsulfonyl)phenyl |
| 225 | CF$_3$ | 2-F-phenyl | 4-morpholino |
| 226 | CF$_3$ | 2-F-phenyl | 2-(1'-CF$_3$-tetrazol-2-yl)phenyl |
| 227 | CF$_3$ | 2-F-phenyl | 4-morpholinocarbonyl |
| 228 | CF$_3$ | 2-F-phenyl | 2-methyl-1-imidazolyl |
| 229 | CF$_3$ | 2-F-phenyl | 5-methyl-1-imidazolyl |
| 230 | CF$_3$ | 2-F-phenyl | 2-methylsulfonyl-1-imidazolyl |
| 231 | CF$_3$ | 2,6-diF-phenyl | 2-(aminosulfonyl)phenyl |
| 232 | CF$_3$ | 2,6-diF-phenyl | 2-(methylaminosulfonyl)phenyl |
| 233 | CF$_3$ | 2,6-diF-phenyl | 1-pyrrolidinocarbonyl |
| 234 | CF$_3$ | 2,6-diF-phenyl | 2-(methylsulfonyl)phenyl |
| 235 | CF$_3$ | 2,6-diF-phenyl | 4-morpholino |
| 236 | CF$_3$ | 2,6-diF-phenyl | 2-(1'-CF$_3$-tetrazol-2-yl)phenyl |
| 237 | CF$_3$ | 2,6-diF-phenyl | 4-morpholinocarbonyl |
| 238 | CF$_3$ | 2,6-diF-phenyl | 2-methyl-1-imidazolyl |
| 239 | CF$_3$ | 2,6-diF-phenyl | 5-methyl-1-imidazolyl |
| 240 | CF$_3$ | 2,6-diF-phenyl | 2-methylsulfonyl-1-imidazolyl |
| 241 | SCH$_3$ | phenyl | 2-(aminosulfonyl)phenyl |
| 242 | SCH$_3$ | phenyl | 2-(methylaminosulfonyl)phenyl |
| 243 | SCH$_3$ | phenyl | 1-pyrrolidinocarbonyl |
| 244 | SCH$_3$ | phenyl | 2-(methylsulfonyl)phenyl |
| 245 | SCH$_3$ | phenyl | 4-morpholino |
| 246 | SCH$_3$ | phenyl | 2-(1'-CF$_3$-tetrazol-2-yl)phenyl |
| 247 | SCH$_3$ | phenyl | 4-morpholinocarbonyl |
| 248 | SCH$_3$ | phenyl | 2-methyl-1-imidazolyl |
| 249 | SCH$_3$ | phenyl | 5-methyl-1-imidazolyl |
| 250 | SCH$_3$ | phenyl | 2-methylsulfonyl-1-imidazolyl |
| 251 | SCH$_3$ | 2-pyridyl | 2-(aminosulfonyl)phenyl |
| 252 | SCH$_3$ | 2-pyridyl | 2-(methylaminosulfonyl)phenyl |
| 253 | SCH$_3$ | 2-pyridyl | 1-pyrrolidinocarbonyl |
| 254 | SCH$_3$ | 2-pyridyl | 2-(methylsulfonyl)phenyl |
| 255 | SCH$_3$ | 2-pyridyl | 4-morpholino |
| 256 | SCH$_3$ | 2-pyridyl | 2-(1'-CF$_3$-tetrazol-2-yl)phenyl |
| 257 | SCH$_3$ | 2-pyridyl | 4-morpholinocarbonyl |
| 258 | SCH$_3$ | 2-pyridyl | 2-methyl-1-imidazolyl |
| 259 | SCH$_3$ | 2-pyridyl | 5-methyl-1-imidazolyl |
| 260 | SCH$_3$ | 2-pyridyl | 2-methylsulfonyl-1-imidazolyl |
| 261 | SCH$_3$ | 3-pyridyl | 2-(aminosulfonyl)phenyl |
| 262 | SCH$_3$ | 3-pyridyl | 2-(methylaminosulfonyl)phenyl |
| 263 | SCH$_3$ | 3-pyridyl | 1-pyrrolidinocarbonyl |
| 264 | SCH$_3$ | 3-pyridyl | 2-(methylsulfonyl)phenyl |
| 265 | SCH$_3$ | 3-pyridyl | 4-morpholino |
| 266 | SCH$_3$ | 3-pyridyl | 2-(1'-CF$_3$-tetrazol-2-yl)phenyl |
| 267 | SCH$_3$ | 3-pyridyl | 4-morpholinocarbonyl |
| 268 | SCH$_3$ | 3-pyridyl | 2-methyl-1-imidazolyl |
| 269 | SCH$_3$ | 3-pyridyl | 5-methyl-1-imidazolyl |
| 270 | SCH$_3$ | 3-pyridyl | 2-methylsulfonyl-1-imidazolyl |
| 271 | SCH$_3$ | 2-pyrimidyl | 2-(aminosulfonyl)phenyl |

TABLE 6-continued

| | | | |
|---|---|---|---|
| 272 | SCH$_3$ | 2-pyrimidyl | 2-(methylaminosulfonyl)phenyl |
| 273 | SCH$_3$ | 2-pyrimidyl | 1-pyrrolidinocarbonyl |
| 274 | SCH$_3$ | 2-pyrimidyl | 2-(methylsulfonyl)phenyl |
| 275 | SCH$_3$ | 2-pyrimidyl | 4-morpholino |
| 276 | SCH$_3$ | 2-pyrimidyl | 2-(1'-CF$_3$-tetrazol-2-yl)phenyl |
| 277 | SCH$_3$ | 2-pyrimidyl | 4-morpholinocarbonyl |
| 278 | SCH$_3$ | 2-pyrimidyl | 2-methyl-1-imidazolyl |
| 279 | SCH$_3$ | 2-pyrimidyl | 5-methyl-1-imidazolyl |
| 280 | SCH$_3$ | 2-pyrimidyl | 2-methylsulfonyl-1-imidazolyl |
| 281 | SCH$_3$ | 5-pyrimidyl | 2-(aminosulfonyl)phenyl |
| 282 | SCH$_3$ | 5-pyrimidyl | 2-(methylaminosulfonyl)phenyl |
| 283 | SCH$_3$ | 5-pyrimidyl | 1-pyrrolidinocarbonyl |
| 284 | SCH$_3$ | 5-pyrimidyl | 2-(methylsulfonyl)phenyl |
| 285 | SCH$_3$ | 5-pyrimidyl | 4-morpholino |
| 286 | SCH$_3$ | 5-pyrimidyl | 2-(1'-CF$_3$-tetrazol-2-yl)phenyl |
| 287 | SCH$_3$ | 5-pyrimidyl | 4-morpholinocarbonyl |
| 288 | SCH$_3$ | 5-pyrimidyl | 2-methyl-1-imidazolyl |
| 289 | SCH$_3$ | 5-pyrimidyl | 5-methyl-1-imidazolyl |
| 290 | SCH$_3$ | 5-pyrimidyl | 2-methylsulfonyl-1-imidazolyl |
| 291 | SCH$_3$ | 2-Cl-phenyl | 2-(aminosulfonyl)phenyl |
| 292 | SCH$_3$ | 2-Cl-phenyl | 2-(methylaminosulfonyl)phenyl |
| 293 | SCH$_3$ | 2-Cl-phenyl | 1-pyrrolidinocarbonyl |
| 294 | SCH$_3$ | 2-Cl-phenyl | 2-(methylsulfonyl)phenyl |
| 295 | SCH$_3$ | 2-Cl-phenyl | 4-morpholino |
| 296 | SCH$_3$ | 2-Cl-phenyl | 2-(1'-CF$_3$-tetrazol-2-yl)phenyl |
| 297 | SCH$_3$ | 2-Cl-phenyl | 4-morpholinocarbonyl |
| 298 | SCH$_3$ | 2-Cl-phenyl | 2-methyl-1-imidazolyl |
| 299 | SCH$_3$ | 2-Cl-phenyl | 5-methyl-1-imidazolyl |
| 300 | SCH$_3$ | 2-Cl-phenyl | 2-methylsulfonyl-1-imidazolyl |
| 301 | SCH$_3$ | 2-F-phenyl | 2-(aminosulfonyl)phenyl |
| 302 | SCH$_3$ | 2-F-phenyl | 2-(methylaminosulfonyl)phenyl |
| 303 | SCH$_3$ | 2-F-phenyl | 1-pyrrolidinocarbonyl |
| 304 | SCH$_3$ | 2-F-phenyl | 2-(methylsulfonyl)phenyl |
| 305 | SCH$_3$ | 2-F-phenyl | 4-morpholino |
| 306 | SCH$_3$ | 2-F-phenyl | 2-(1'-CF$_3$-tetrazol-2-yl)phenyl |
| 307 | SCH$_3$ | 2-F-phenyl | 4-morpholinocarbonyl |
| 308 | SCH$_3$ | 2-F-phenyl | 2-methyl-1-imidazolyl |
| 309 | SCH$_3$ | 2-F-phenyl | 5-methyl-1-imidazolyl |
| 310 | SCH$_3$ | 2-F-phenyl | 2-methylsulfonyl-1-imidazolyl |
| 311 | SCH$_3$ | 2,6-diF-phenyl | 2-(aminosulfonyl)phenyl |
| 312 | SCH$_3$ | 2,6-diF-phenyl | 2-(methylaminosulfonyl)phenyl |
| 313 | SCH$_3$ | 2,6-diF-phenyl | 1-pyrrolidinocarbonyl |
| 314 | SCH$_3$ | 2,6-diF-phenyl | 2-(methylsulfonyl)phenyl |
| 315 | SCH$_3$ | 2,6-diF-phenyl | 4-morpholino |
| 316 | SCH$_3$ | 2,6-diF-phenyl | 2-(1'-CF$_3$-tetrazol-2-yl)phenyl |
| 317 | SCH$_3$ | 2,6-diF-phenyl | 4-morpholinocarbonyl |
| 318 | SCH$_3$ | 2,6-diF-phenyl | 2-methyl-1-imidazolyl |
| 319 | SCH$_3$ | 2,6-diF-phenyl | 5-methyl-1-imidazolyl |
| 320 | SCH$_3$ | 2,6-diF-phenyl | 2-methylsulfonyl-1-imidazolyl |
| 321 | SOCH$_3$ | phenyl | 2-(aminosulfonyl)phenyl |
| 322 | SOCH$_3$ | phenyl | 2-(methylaminosulfonyl)phenyl |
| 323 | SOCH$_3$ | phenyl | 1-pyrrolidinocarbonyl |
| 324 | SOCH$_3$ | phenyl | 2-(methylsulfonyl)phenyl |
| 325 | SOCH$_3$ | phenyl | 4-morpholino |
| 326 | SOCH$_3$ | phenyl | 2-(1'-CF$_3$-tetrazol-2-yl)phenyl |
| 327 | SOCH$_3$ | phenyl | 4-morpholinocarbonyl |
| 328 | SOCH$_3$ | phenyl | 2-methyl-1-imidazolyl |
| 329 | SOCH$_3$ | phenyl | 5-methyl-1-imidazolyl |
| 330 | SOCH$_3$ | phenyl | 2-methylsulfonyl-1-imidazolyl |
| 331 | SOCH$_3$ | 2-pyridyl | 2-(aminosulfonyl)phenyl |
| 332 | SOCH$_3$ | 2-pyridyl | 2-(methylaminosulfonyl)phenyl |
| 333 | SOCH$_3$ | 2-pyridyl | 1-pyrrolidinocarbonyl |
| 334 | SOCH$_3$ | 2-pyridyl | 2-(methylsulfonyl)phenyl |
| 335 | SOCH$_3$ | 2-pyridyl | 4-morpholino |
| 336 | SOCH$_3$ | 2-pyridyl | 2-(1'-CF$_3$-tetrazol-2-yl)phenyl |
| 337 | SOCH$_3$ | 2-pyridyl | 4-morpholinocarbonyl |
| 338 | SOCH$_3$ | 2-pyridyl | 2-methyl-1-imidazolyl |
| 339 | SOCH$_3$ | 2-pyridyl | 5-methyl-1-imidazolyl |
| 340 | SOCH$_3$ | 2-pyridyl | 2-methylsulfonyl-1-imidazolyl |
| 341 | SOCH$_3$ | 3-pyridyl | 2-(aminosulfonyl)phenyl |
| 342 | SOCH$_3$ | 3-pyridyl | 2-(methylaminosulfonyl)phenyl |
| 343 | SOCH$_3$ | 3-pyridyl | 1-pyrrolidinocarbonyl |
| 344 | SOCH$_3$ | 3-pyridyl | 2-(methylsulfonyl)phenyl |
| 345 | SOCH$_3$ | 3-pyridyl | 4-morpholino |
| 346 | SOCH$_3$ | 3-pyridyl | 2-(1'-CF$_3$-tetrazol-2-yl)phenyl |
| 347 | SOCH$_3$ | 3-pyridyl | 4-morpholinocarbonyl |
| 348 | SOCH$_3$ | 3-pyridyl | 2-methyl-1-imidazolyl |
| 349 | SOCH$_3$ | 3-pyridyl | 5-methyl-1-imidazolyl |
| 350 | SOCH$_3$ | 3-pyridyl | 2-methylsulfonyl-1-imidazolyl |
| 351 | SOCH$_3$ | 2-pyrimidyl | 2-(aminosulfonyl)phenyl |
| 352 | SOCH$_3$ | 2-pyrimidyl | 2-(methylaminosulfonyl)phenyl |
| 353 | SOCH$_3$ | 2-pyrimidyl | 1-pyrrolidinocarbonyl |
| 354 | SOCH$_3$ | 2-pyrimidyl | 2-(methylsulfonyl)phenyl |
| 355 | SOCH$_3$ | 2-pyrimidyl | 4-morpholino |
| 356 | SOCH$_3$ | 2-pyrimidyl | 2-(1'-CF$_3$-tetrazol-2-yl)phenyl |
| 357 | SOCH$_3$ | 2-pyrimidyl | 4-morpholinocarbonyl |
| 358 | SOCH$_3$ | 2-pyrimidyl | 2-methyl-1-imidazolyl |
| 359 | SOCH$_3$ | 2-pyrimidyl | 5-methyl-1-imidazolyl |
| 360 | SOCH$_3$ | 2-pyrimidyl | 2-methylsulfonyl-1-imidazolyl |
| 361 | SOCH$_3$ | 5-pyrimidyl | 2-(aminosulfonyl)phenyl |
| 362 | SOCH$_3$ | 5-pyrimidyl | 2-(methylaminosulfonyl)phenyl |
| 363 | SOCH$_3$ | 5-pyrimidyl | 1-pyrrolidinocarbonyl |
| 364 | SOCH$_3$ | 5-pyrimidyl | 2-(methylsulfonyl)phenyl |
| 365 | SOCH$_3$ | 5-pyrimidyl | 4-morpholino |
| 366 | SOCH$_3$ | 5-pyrimidyl | 2-(1'-CF$_3$-tetrazol-2-yl)phenyl |
| 367 | SOCH$_3$ | 5-pyrimidyl | 4-morpholinocarbonyl |
| 368 | SOCH$_3$ | 5-pyrimidyl | 2-methyl-1-imidazolyl |
| 369 | SOCH$_3$ | 5-pyrimidyl | 5-methyl-1-imidazolyl |
| 370 | SOCH$_3$ | 5-pyrimidyl | 2-methylsulfonyl-1-imidazolyl |
| 371 | SOCH$_3$ | 2-Cl-phenyl | 2-(aminosulfonyl)phenyl |
| 372 | SOCH$_3$ | 2-Cl-phenyl | 2-(methylaminosulfonyl)phenyl |
| 373 | SOCH$_3$ | 2-Cl-phenyl | 1-pyrrolidinocarbonyl |
| 374 | SOCH$_3$ | 2-Cl-phenyl | 2-(methylsulfonyl)phenyl |
| 375 | SOCH$_3$ | 2-Cl-phenyl | 4-morpholino |
| 376 | SOCH$_3$ | 2-Cl-phenyl | 2-(1'-CF$_3$-tetrazol-2-yl)phenyl |
| 377 | SOCH$_3$ | 2-Cl-phenyl | 4-morpholinocarbonyl |
| 378 | SOCH$_3$ | 2-Cl-phenyl | 2-methyl-1-imidazolyl |
| 379 | SOCH$_3$ | 2-Cl-phenyl | 5-methyl-1-imidazolyl |
| 380 | SOCH$_3$ | 2-Cl-phenyl | 2-methylsulfonyl-1-imidazolyl |
| 381 | SOCH$_3$ | 2-F-phenyl | 2-(aminosulfonyl)phenyl |
| 382 | SOCH$_3$ | 2-F-phenyl | 2-(methylaminosulfonyl)phenyl |
| 383 | SOCH$_3$ | 2-F-phenyl | 1-pyrrolidinocarbonyl |
| 384 | SOCH$_3$ | 2-F-phenyl | 2-(methylsulfonyl)phenyl |
| 385 | SOCH$_3$ | 2-F-phenyl | 4-morpholino |
| 386 | SOCH$_3$ | 2-F-phenyl | 2-(1'-CF$_3$-tetrazol-2-yl)phenyl |
| 387 | SOCH$_3$ | 2-F-phenyl | 4-morpholinocarbonyl |
| 388 | SOCH$_3$ | 2-F-phenyl | 2-methyl-1-imidazolyl |
| 389 | SOCH$_3$ | 2-F-phenyl | 5-methyl-1-imidazolyl |
| 390 | SOCH$_3$ | 2-F-phenyl | 2-methylsulfonyl-1-imidazolyl |
| 391 | SOCH$_3$ | 2,6-diF-phenyl | 2-(aminosulfonyl)phenyl |

TABLE 6-continued

| | | | |
|---|---|---|---|
| 392 | SOCH$_3$ | 2,6-diF-phenyl | 2-(methylaminosulfonyl)phenyl |
| 393 | SOCH$_3$ | 2,6-diF-phenyl | 1-pyrrolidinocarbonyl |
| 394 | SOCH$_3$ | 2,6-diF-phenyl | 2-(methylsulfonyl)phenyl |
| 395 | SOCH$_3$ | 2,6-diF-phenyl | 4-morpholino |
| 396 | SOCH$_3$ | 2,6-diF-phenyl | 2-(1'-CF$_3$-tetrazol-2-yl)phenyl |
| 397 | SOCH$_3$ | 2,6-diF-phenyl | 4-morpholinocarbonyl |
| 398 | SOCH$_3$ | 2,6-diF-phenyl | 2-methyl-1-imidazolyl |
| 399 | SOCH$_3$ | 2,6-diF-phenyl | 5-methyl-1-imidazolyl |
| 400 | SOCH$_3$ | 2,6-diF-phenyl | 2-methylsulfonyl-1-imidazolyl |
| 401 | SO$_2$CH$_3$ | phenyl | 2-(aminosulfonyl)phenyl |
| 402 | SO$_2$CH$_3$ | phenyl | 2-(methylaminosulfonyl)phenyl |
| 403 | SO$_2$CH$_3$ | phenyl | 1-pyrrolidinocarbonyl |
| 404 | SO$_2$CH$_3$ | phenyl | 2-(methylsulfonyl)phenyl |
| 405 | SO$_2$CH$_3$ | phenyl | 4-morpholino |
| 406 | SO$_2$CH$_3$ | phenyl | 2-(1'-CF$_3$-tetrazol-2-yl)phenyl |
| 407 | SO$_2$CH$_3$ | phenyl | 4-morpholinocarbonyl |
| 408 | SO$_2$CH$_3$ | phenyl | 2-methyl-1-imidazolyl |
| 409 | SO$_2$CH$_3$ | phenyl | 5-methyl-1-imidazolyl |
| 410 | SO$_2$CH$_3$ | phenyl | 2-methylsulfonyl-1-imidazolyl |
| 411 | SO$_2$CH$_3$ | 2-pyridyl | 2-(aminosulfonyl)phenyl |
| 412 | SO$_2$CH$_3$ | 2-pyridyl | 2-(methylaminosulfonyl)phenyl |
| 413 | SO$_2$CH$_3$ | 2-pyridyl | 1-pyrrolidinocarbonyl |
| 414 | SO$_2$CH$_3$ | 2-pyridyl | 2-(methylsulfonyl)phenyl |
| 415 | SO$_2$CH$_3$ | 2-pyridyl | 4-morpholino |
| 416 | SO$_2$CH$_3$ | 2-pyridyl | 2-(1'-CF$_3$-tetrazol-2-yl)phenyl |
| 417 | SO$_2$CH$_3$ | 2-pyridyl | 4-morpholinocarbonyl |
| 418 | SO$_2$CH$_3$ | 2-pyridyl | 2-methyl-1-imidazolyl |
| 419 | SO$_2$CH$_3$ | 2-pyridyl | 5-methyl-1-imidazolyl |
| 420 | SO$_2$CH$_3$ | 2-pyridyl | 2-methylsulfonyl-1-imidazolyl |
| 421 | SO$_2$CH$_3$ | 3-pyridyl | 2-(aminosulfonyl)phenyl |
| 422 | SO$_2$CH$_3$ | 3-pyridyl | 2-(methylaminosulfonyl)phenyl |
| 423 | SO$_2$CH$_3$ | 3-pyridyl | 1-pyrrolidinocarbonyl |
| 424 | SO$_2$CH$_3$ | 3-pyridyl | 2-(methylsulfonyl)phenyl |
| 425 | SO$_2$CH$_3$ | 3-pyridyl | 4-morpholino |
| 426 | SO$_2$CH$_3$ | 3-pyridyl | 2-(1'-CF$_3$-tetrazol-2-yl)phenyl |
| 427 | SO$_2$CH$_3$ | 3-pyridyl | 4-morpholinocarbonyl |
| 428 | SO$_2$CH$_3$ | 3-pyridyl | 2-methyl-1-imidazolyl |
| 429 | SO$_2$CH$_3$ | 3-pyridyl | 5-methyl-1-imidazolyl |
| 430 | SO$_2$CH$_3$ | 3-pyridyl | 2-methylsulfonyl-1-imidazolyl |
| 431 | SO$_2$CH$_3$ | 2-pyrimidyl | 2-(aminosulfonyl)phenyl |
| 432 | SO$_2$CH$_3$ | 2-pyrimidyl | 2-(methylaminosulfonyl)phenyl |
| 433 | SO$_2$CH$_3$ | 2-pyrimidyl | 1-pyrrolidinocarbonyl |
| 434 | SO$_2$CH$_3$ | 2-pyrimidyl | 2-(methylsulfonyl)phenyl |
| 435 | SO$_2$CH$_3$ | 2-pyrimidyl | 4-morpholino |
| 436 | SO$_2$CH$_3$ | 2-pyrimidyl | 2-(1'-CF$_3$-tetrazol-2-yl)phenyl |
| 437 | SO$_2$CH$_3$ | 2-pyrimidyl | 4-morpholinocarbonyl |
| 438 | SO$_2$CH$_3$ | 2-pyrimidyl | 2-methyl-1-imidazolyl |
| 439 | SO$_2$CH$_3$ | 2-pyrimidyl | 5-methyl-1-imidazolyl |
| 440 | SO$_2$CH$_3$ | 2-pyrimidyl | 2-methylsulfonyl-1-imidazolyl |
| 441 | SO$_2$CH$_3$ | 5-pyrimidyl | 2-(aminosulfonyl)phenyl |
| 442 | SO$_2$CH$_3$ | 5-pyrimidyl | 2-(methylaminosulfonyl)phenyl |
| 443 | SO$_2$CH$_3$ | 5-pyrimidyl | 1-pyrrolidinocarbonyl |
| 444 | SO$_2$CH$_3$ | 5-pyrimidyl | 2-(methylsulfonyl)phenyl |
| 445 | SO$_2$CH$_3$ | 5-pyrimidyl | 4-morpholino |
| 446 | SO$_2$CH$_3$ | 5-pyrimidyl | 2-(1'-CF$_3$-tetrazol-2-yl)phenyl |
| 447 | SO$_2$CH$_3$ | 5-pyrimidyl | 4-morpholinocarbonyl |
| 448 | SO$_2$CH$_3$ | 5-pyrimidyl | 2-methyl-1-imidazolyl |
| 449 | SO$_2$CH$_3$ | 5-pyrimidyl | 5-methyl-1-imidazolyl |
| 450 | SO$_2$CH$_3$ | 5-pyrimidyl | 2-methylsulfonyl-1-imidazolyl |
| 451 | SO$_2$CH$_3$ | 2-Cl-phenyl | 2-(aminosulfonyl)phenyl |
| 452 | SO$_2$CH$_3$ | 2-Cl-phenyl | 2-(methylaminosulfonyl)phenyl |
| 453 | SO$_2$CH$_3$ | 2-Cl-phenyl | 1-pyrrolidinocarbonyl |
| 454 | SO$_2$CH$_3$ | 2-Cl-phenyl | 2-(methylsulfonyl)phenyl |
| 455 | SO$_2$CH$_3$ | 2-Cl-phenyl | 4-morpholino |
| 456 | SO$_2$CH$_3$ | 2-Cl-phenyl | 2-(1'-CF$_3$-tetrazol-2-yl)phenyl |
| 457 | SO$_2$CH$_3$ | 2-Cl-phenyl | 4-morpholinocarbonyl |
| 458 | SO$_2$CH$_3$ | 2-Cl-phenyl | 2-methyl-1-imidazolyl |
| 459 | SO$_2$CH$_3$ | 2-Cl-phenyl | 5-methyl-1-imidazolyl |
| 460 | SO$_2$CH$_3$ | 2-Cl-phenyl | 2-methylsulfonyl-1-imidazolyl |
| 461 | SO$_2$CH$_3$ | 2-F-phenyl | 2-(aminosulfonyl)phenyl |
| 462 | SO$_2$CH$_3$ | 2-F-phenyl | 2-(methylaminosulfonyl)phenyl |
| 463 | SO$_2$CH$_3$ | 2-F-phenyl | 1-pyrrolidinocarbonyl |
| 464 | SO$_2$CH$_3$ | 2-F-phenyl | 2-(methylsulfonyl)phenyl |
| 465 | SO$_2$CH$_3$ | 2-F-phenyl | 4-morpholino |
| 466 | SO$_2$CH$_3$ | 2-F-phenyl | 2-(1'-CF$_3$-tetrazol-2-yl)phenyl |
| 467 | SO$_2$CH$_3$ | 2-F-phenyl | 4-morpholinocarbonyl |
| 468 | SO$_2$CH$_3$ | 2-F-phenyl | 2-methyl-1-imidazolyl |
| 469 | SO$_2$CH$_3$ | 2-F-phenyl | 5-methyl-1-imidazolyl |
| 470 | SO$_2$CH$_3$ | 2-F-phenyl | 2-methylsulfonyl-1-imidazolyl |
| 471 | SO$_2$CH$_3$ | 2,6-diF-phenyl | 2-(aminosulfonyl)phenyl |
| 472 | SO$_2$CH$_3$ | 2,6-diF-phenyl | 2-(methylaminosulfonyl)phenyl |
| 473 | SO$_2$CH$_3$ | 2,6-diF-phenyl | 1-pyrrolidinocarbonyl |
| 474 | SO$_2$CH$_3$ | 2,6-diF-phenyl | 2-(methylsulfonyl)phenyl |
| 475 | SO$_2$CH$_3$ | 2,6-diF-phenyl | 4-morpholino |
| 476 | SO$_2$CH$_3$ | 2,6-diF-phenyl | 2-(1'-CF$_3$-tetrazol-2-yl)phenyl |
| 477 | SO$_2$CH$_3$ | 2,6-diF-phenyl | 4-morpholinocarbonyl |
| 478 | SO$_2$CH$_3$ | 2,6-diF-phenyl | 2-methyl-1-imidazolyl |
| 479 | SO$_2$CH$_3$ | 2,6-diF-phenyl | 5-methyl-1-imidazolyl |
| 480 | SO$_2$CH$_3$ | 2,6-diF-phenyl | 2-methylsulfonyl-1-imidazolyl |
| 481 | CH$_2$NH—SO$_2$CH$_3$ | phenyl | 2-(aminosulfonyl)phenyl |
| 482 | CH$_2$NH—SO$_2$CH$_3$ | phenyl | 2-(methylaminosulfonyl)phenyl |
| 483 | CH$_2$NH—SO$_2$CH$_3$ | phenyl | 1-pyrrolidinocarbonyl |
| 484 | CH$_2$NH—SO$_2$CH$_3$ | phenyl | 2-(methylsulfonyl)phenyl |
| 485 | CH$_2$NH—SO$_2$CH$_3$ | phenyl | 4-morpholino |
| 486 | CH$_2$NH—SO$_2$CH$_3$ | phenyl | 2-(1'-CF$_3$-tetrazol-2-yl)phenyl |
| 487 | CH$_2$NH—SO$_2$CH$_3$ | phenyl | 4-morpholinocarbonyl |
| 488 | CH$_2$NH—SO$_2$CH$_3$ | phenyl | 2-methyl-1-imidazolyl |
| 489 | CH$_2$NH—SO$_2$CH$_3$ | phenyl | 5-methyl-1-imidazolyl |
| 490 | CH$_2$NH—SO$_2$CH$_3$ | phenyl | 2-methylsulfonyl-1-imidazolyl |
| 491 | CH$_2$NH—SO$_2$CH$_3$ | 2-pyridyl | 2-(aminosulfonyl)phenyl |
| 492 | CH$_2$NH—SO$_2$CH$_3$ | 2-pyridyl | 2-(methylaminosulfonyl)phenyl |
| 493 | CH$_2$NH—SO$_2$CH$_3$ | 2-pyridyl | 1-pyrrolidinocarbonyl |
| 494 | CH$_2$NH—SO$_2$CH$_3$ | 2-pyridyl | 2-(methylsulfonyl)phenyl |
| 495 | CH$_2$NH—SO$_2$CH$_3$ | 2-pyridyl | 4-morpholino |
| 496 | CH$_2$NH—SO$_2$CH$_3$ | 2-pyridyl | 2-(1'-CF$_3$-tetrazol-2-yl)phenyl |
| 497 | CH$_2$NH—SO$_2$CH$_3$ | 2-pyridyl | 4-morpholinocarbonyl |
| 498 | CH$_2$NH—SO$_2$CH$_3$ | 2-pyridyl | 2-methyl-1-imidazolyl |
| 499 | CH$_2$NH—SO$_2$CH$_3$ | 2-pyridyl | 5-methyl-1-imidazolyl |
| 500 | CH$_2$NH—SO$_2$CH$_3$ | 2-pyridyl | 2-methylsulfonyl-1-imidazolyl |
| 501 | CH$_2$NH—SO$_2$CH$_3$ | 3-pyridyl | 2-(aminosulfonyl)phenyl |
| 502 | CH$_2$NH—SO$_2$CH$_3$ | 3-pyridyl | 2-(methylaminosulfonyl)phenyl |
| 503 | CH$_2$NH—SO$_2$CH$_3$ | 3-pyridyl | 1-pyrrolidinocarbonyl |
| 504 | CH$_2$NH—SO$_2$CH$_3$ | 3-pyridyl | 2-(methylsulfonyl)phenyl |
| 505 | CH$_2$NH—SO$_2$CH$_3$ | 3-pyridyl | 4-morpholino |
| 506 | CH$_2$NH—SO$_2$CH$_3$ | 3-pyridyl | 2-(1'-CF$_3$-tetrazol-2-yl)phenyl |
| 507 | CH$_2$NH—SO$_2$CH$_3$ | 3-pyridyl | 4-morpholinocarbonyl |
| 508 | CH$_2$NH—SO$_2$CH$_3$ | 3-pyridyl | 2-methyl-1-imidazolyl |
| 509 | CH$_2$NH—SO$_2$CH$_3$ | 3-pyridyl | 5-methyl-1-imidazolyl |
| 510 | CH$_2$NH—SO$_2$CH$_3$ | 3-pyridyl | 2-methylsulfonyl-1-imidazolyl |

TABLE 6-continued

| | | | |
|---|---|---|---|
| 511 | CH$_2$NH—SO$_2$CH$_3$ | 2-pyrimidyl | 2-(aminosulfonyl)phenyl |
| 512 | CH$_2$NH—SO$_2$CH$_3$ | 2-pyrimidyl | 2-(methylaminosulfonyl)phenyl |
| 513 | CH$_2$NH—SO$_2$CH$_3$ | 2-pyrimidyl | 1-pyrrolidinocarbonyl |
| 514 | CH$_2$NH—SO$_2$CH$_3$ | 2-pyrimidyl | 2-(methylsulfonyl)phenyl |
| 515 | CH$_2$NH—SO$_2$CH$_3$ | 2-pyrimidyl | 4-morpholino |
| 516 | CH$_2$NH—SO$_2$CH$_3$ | 2-pyrimidyl | 2-(1'-CF$_3$-tetrazol-2-yl)phenyl |
| 517 | CH$_2$NH—SO$_2$CH$_3$ | 2-pyrimidyl | 4-morpholinocarbonyl |
| 518 | CH$_2$NH—SO$_2$CH$_3$ | 2-pyrimidyl | 2-methyl-1-imidazolyl |
| 519 | CH$_2$NH—SO$_2$CH$_3$ | 2-pyrimidyl | 5-methyl-1-imidazolyl |
| 520 | CH$_2$NH—SO$_2$CH$_3$ | 2-pyrimidyl | 2-methylsulfonyl-1-imidazolyl |
| 521 | CH$_2$NH—SO$_2$CH$_3$ | 5-pyrimidyl | 2-(aminosulfonyl)phenyl |
| 522 | CH$_2$NH—SO$_2$CH$_3$ | 5-pyrimidyl | 2-(methylaminosulfonyl)phenyl |
| 523 | CH$_2$NH—SO$_2$CH$_3$ | 5-pyrimidyl | 1-pyrrolidinocarbonyl |
| 524 | CH$_2$NH—SO$_2$CH$_3$ | 5-pyrimidyl | 2-(methylsulfonyl)phenyl |
| 525 | CH$_2$NH—SO$_2$CH$_3$ | 5-pyrimidyl | 4-morpholino |
| 526 | CH$_2$NH—SO$_2$CH$_3$ | 5-pyrimidyl | 2-(1'-CF$_3$-tetrazol-2-yl)phenyl |
| 527 | CH$_2$NH—SO$_2$CH$_3$ | 5-pyrimidyl | 4-morpholinocarbonyl |
| 528 | CH$_2$NH—SO$_2$CH$_3$ | 5-pyrimidyl | 2-methyl-1-imidazolyl |
| 529 | CH$_2$NH—SO$_2$CH$_3$ | 5-pyrimidyl | 5-methyl-1-imidazolyl |
| 530 | CH$_2$NH—SO$_2$CH$_3$ | 5-pyrimidyl | 2-methylsulfonyl-1-imidazolyl |
| 531 | CH$_2$NH—SO$_2$CH$_3$ | 2-Cl-phenyl | 2-(aminosulfonyl)phenyl |
| 532 | CH$_2$NH—SO$_2$CH$_3$ | 2-Cl-phenyl | 2-(methylaminosulfonyl)phenyl |
| 533 | CH$_2$NH—SO$_2$CH$_3$ | 2-Cl-phenyl | 1-pyrrolidinocarbonyl |
| 534 | CH$_2$NH—SO$_2$CH$_3$ | 2-Cl-phenyl | 2-(methylsulfonyl)phenyl |
| 535 | CH$_2$NH—SO$_2$CH$_3$ | 2-Cl-phenyl | 4-morpholino |
| 536 | CH$_2$NH—SO$_2$CH$_3$ | 2-Cl-phenyl | 2-(1'-CF$_3$-tetrazol-2-yl)phenyl |
| 537 | CH$_2$NH—SO$_2$CH$_3$ | 2-Cl-phenyl | 4-morpholinocarbonyl |
| 538 | CH$_2$NH—SO$_2$CH$_3$ | 2-Cl-phenyl | 2-methyl-1-imidazolyl |
| 539 | CH$_2$NH—SO$_2$CH$_3$ | 2-Cl-phenyl | 5-methyl-1-imidazolyl |
| 540 | CH$_2$NH—SO$_2$CH$_3$ | 2-Cl-phenyl | 2-methylsulfonyl-1-imidazolyl |
| 541 | CH$_2$NH—SO$_2$CH$_3$ | 2-F-phenyl | 2-(aminosulfonyl)phenyl |
| 542 | CH$_2$NH—SO$_2$CH$_3$ | 2-F-phenyl | 2-(methylaminosulfonyl)phenyl |
| 543 | CH$_2$NH—SO$_2$CH$_3$ | 2-F-phenyl | 1-pyrrolidinocarbonyl |
| 544 | CH$_2$NH—SO$_2$CH$_3$ | 2-F-phenyl | 2-(methylsulfonyl)phenyl |
| 545 | CH$_2$NH—SO$_2$CH$_3$ | 2-F-phenyl | 4-morpholino |
| 546 | CH$_2$NH—SO$_2$CH$_3$ | 2-F-phenyl | 2-(1'-CF$_3$-tetrazol-2-yl)phenyl |
| 547 | CH$_2$NH—SO$_2$CH$_3$ | 2-F-phenyl | 4-morpholinocarbonyl |
| 548 | CH$_2$NH—SO$_2$CH$_3$ | 2-F-phenyl | 2-methyl-1-imidazolyl |
| 549 | CH$_2$NH—SO$_2$CH$_3$ | 2-F-phenyl | 5-methyl-1-imidazolyl |
| 550 | CH$_2$NH—SO$_2$CH$_3$ | 2-F-phenyl | 2-methylsulfonyl-1-imidazolyl |
| 551 | CH$_2$NH—SO$_2$CH$_3$ | 2,6-diF-phenyl | 2-(aminosulfonyl)phenyl |
| 552 | CH$_2$NH—SO$_2$CH$_3$ | 2,6-diF-phenyl | 2-(methylaminosulfonyl)phenyl |
| 553 | CH$_2$NH—SO$_2$CH$_3$ | 2,6-diF-phenyl | 1-pyrrolidinocarbonyl |
| 554 | CH$_2$NH—SO$_2$CH$_3$ | 2,6-diF-phenyl | 2-(methylsulfonyl)phenyl |
| 555 | CH$_2$NH—SO$_2$CH$_3$ | 2,6-diF-phenyl | 4-morpholino |
| 556 | CH$_2$NH—SO$_2$CH$_3$ | 2,6-diF-phenyl | 2-(1'-CF$_3$-tetrazol-2-yl)phenyl |
| 557 | CH$_2$NH—SO$_2$CH$_3$ | 2,6-diF-phenyl | 4-morpholinocarbonyl |
| 558 | CH$_2$NH—SO$_2$CH$_3$ | 2,6-diF-phenyl | 2-methyl-1-imidazolyl |
| 559 | CH$_2$NH—SO$_2$CH$_3$ | 2,6-diF-phenyl | 5-methyl-1-imidazolyl |
| 560 | CH$_2$NH—SO$_2$CH$_3$ | 2,6-diF-phenyl | 2-methylsulfonyl-1-imidazolyl |
| 561 | Cl | phenyl | 2-(aminosulfonyl)phenyl |
| 562 | Cl | phenyl | 2-(methylaminosulfonyl)phenyl |
| 563 | Cl | phenyl | 1-pyrrolidinocarbonyl |
| 564 | Cl | phenyl | 2-(methylsulfonyl)phenyl |
| 565 | Cl | phenyl | 4-morpholino |
| 566 | Cl | phenyl | 2-(1'-CF$_3$-tetrazol-2-yl)phenyl |
| 567 | Cl | phenyl | 4-morpholinocarbonyl |
| 568 | Cl | phenyl | 2-methyl-1-imidazolyl |
| 569 | Cl | phenyl | 5-methyl-1-imidazolyl |
| 570 | Cl | phenyl | 2-methylsulfonyl-1-imidazolyl |
| 571 | Cl | 2-pyridyl | 2-(aminosulfonyl)phenyl |
| 572 | Cl | 2-pyridyl | 2-(methylaminosulfonyl)phenyl |
| 573 | Cl | 2-pyridyl | 1-pyrrolidinocarbonyl |
| 574 | Cl | 2-pyridyl | 2-(methylsulfonyl)phenyl |
| 575 | Cl | 2-pyridyl | 4-morpholino |
| 576 | Cl | 2-pyridyl | 2-(1'-CF$_3$-tetrazol-2-yl)phenyl |
| 577 | Cl | 2-pyridyl | 4-morpholinocarbonyl |
| 578 | Cl | 2-pyridyl | 2-methyl-1-imidazolyl |
| 579 | Cl | 2-pyridyl | 5-methyl-1-imidazolyl |
| 580 | Cl | 2-pyridyl | 2-methylsulfonyl-1-imidazolyl |
| 581 | Cl | 3-pyridyl | 2-(aminosulfonyl)phenyl |
| 582 | Cl | 3-pyridyl | 2-(methylaminosulfonyl)phenyl |
| 583 | Cl | 3-pyridyl | 1-pyrrolidinocarbonyl |
| 584 | Cl | 3-pyridyl | 2-(methylsulfonyl)phenyl |
| 585 | Cl | 3-pyridyl | 4-morpholino |
| 586 | Cl | 3-pyridyl | 2-(1'-CF$_3$-tetrazol-2-yl)phenyl |
| 587 | Cl | 3-pyridyl | 4-morpholinocarbonyl |
| 588 | Cl | 3-pyridyl | 2-methyl-1-imidazolyl |
| 589 | Cl | 3-pyridyl | 5-methyl-1-imidazolyl |
| 590 | Cl | 3-pyridyl | 2-methylsulfonyl-1-imidazolyl |
| 591 | Cl | 2-pyrimidyl | 2-(aminosulfonyl)phenyl |
| 592 | Cl | 2-pyrimidyl | 2-(methylaminosulfonyl)phenyl |
| 593 | Cl | 2-pyrimidyl | 1-pyrrolidinocarbonyl |
| 594 | Cl | 2-pyrimidyl | 2-(methylsulfonyl)phenyl |
| 595 | Cl | 2-pyrimidyl | 4-morpholino |
| 596 | Cl | 2-pyrimidyl | 2-(1'-CF$_3$-tetrazol-2-yl)phenyl |
| 597 | Cl | 2-pyrimidyl | 4-morpholinocarbonyl |
| 598 | Cl | 2-pyrimidyl | 2-methyl-1-imidazolyl |
| 599 | Cl | 2-pyrimidyl | 5-methyl-1-imidazolyl |
| 600 | Cl | 2-pyrimidyl | 2-methylsulfonyl-1-imidazolyl |
| 601 | Cl | 5-pyrimidyl | 2-(aminosulfonyl)phenyl |
| 602 | Cl | 5-pyrimidyl | 2-(methylaminosulfonyl)phenyl |
| 603 | Cl | 5-pyrimidyl | 1-pyrrolidinocarbonyl |
| 604 | Cl | 5-pyrimidyl | 2-(methylsulfonyl)phenyl |
| 605 | Cl | 5-pyrimidyl | 4-morpholino |
| 606 | Cl | 5-pyrimidyl | 2-(1'-CF$_3$-tetrazol-2-yl)phenyl |
| 607 | Cl | 5-pyrimidyl | 4-morpholinocarbonyl |
| 608 | Cl | 5-pyrimidyl | 2-methyl-1-imidazolyl |
| 609 | Cl | 5-pyrimidyl | 5-methyl-1-imidazolyl |
| 610 | Cl | 5-pyrimidyl | 2-methylsulfonyl-1-imidazolyl |
| 611 | Cl | 2-Cl-phenyl | 2-(aminosulfonyl)phenyl |
| 612 | Cl | 2-Cl-phenyl | 2-(methylaminosulfonyl)phenyl |
| 613 | Cl | 2-Cl-phenyl | 1-pyrrolidinocarbonyl |
| 614 | Cl | 2-Cl-phenyl | 2-(methylsulfonyl)phenyl |
| 615 | Cl | 2-Cl-phenyl | 4-morpholino |
| 616 | Cl | 2-Cl-phenyl | 2-(1'-CF$_3$-tetrazol-2-yl)phenyl |
| 617 | Cl | 2-Cl-phenyl | 4-morpholinocarbonyl |
| 618 | Cl | 2-Cl-phenyl | 2-methyl-1-imidazolyl |
| 619 | Cl | 2-Cl-phenyl | 5-methyl-1-imidazolyl |
| 620 | Cl | 2-Cl-phenyl | 2-methylsulfonyl-1-imidazolyl |
| 621 | Cl | 2-F-phenyl | 2-(aminosulfonyl)phenyl |
| 622 | Cl | 2-F-phenyl | 2-(methylaminosulfonyl)phenyl |
| 623 | Cl | 2-F-phenyl | 1-pyrrolidinocarbonyl |
| 624 | Cl | 2-F-phenyl | 2-(methylsulfonyl)phenyl |
| 625 | Cl | 2-F-phenyl | 4-morpholino |
| 626 | Cl | 2-F-phenyl | 2-(1'-CF$_3$-tetrazol-2-yl)phenyl |
| 627 | Cl | 2-F-phenyl | 4-morpholinocarbonyl |
| 628 | Cl | 2-F-phenyl | 2-methyl-1-imidazolyl |
| 629 | Cl | 2-F-phenyl | 5-methyl-1-imidazolyl |
| 630 | Cl | 2-F-phenyl | 2-methylsulfonyl-1-imidazolyl |

TABLE 6-continued

| | | | |
|---|---|---|---|
| 631 | Cl | 2,6-diF-phenyl | 2-(aminosulfonyl)phenyl |
| 632 | Cl | 2,6-diF-phenyl | 2-(methylaminosulfonyl)phenyl |
| 633 | Cl | 2,6-diF-phenyl | 1-pyrrolidinocarbonyl |
| 634 | Cl | 2,6-diF-phenyl | 2-(methylsulfonyl)phenyl |
| 635 | Cl | 2,6-diF-phenyl | 4-morpholino |
| 636 | Cl | 2,6-diF-phenyl | 2-(1'-$CF_3$-tetrazol-2-yl)phenyl |
| 637 | Cl | 2,6-diF-phenyl | 4-morpholinocarbonyl |
| 638 | Cl | 2,6-diF-phenyl | 2-methyl-1-imidazolyl |
| 639 | Cl | 2,6-diF-phenyl | 5-methyl-1-imidazolyl |
| 640 | Cl | 2,6-diF-phenyl | 2-methylsulfonyl-1-imidazolyl |
| 641 | F | phenyl | 2-(aminosulfonyl)phenyl |
| 642 | F | phenyl | 2-(methylaminosulfonyl)phenyl |
| 643 | F | phenyl | 1-pyrrolidinocarbonyl |
| 644 | F | phenyl | 2-(methylsulfonyl)phenyl |
| 645 | F | phenyl | 4-morpholino |
| 646 | F | phenyl | 2-(1'-$CF_3$-tetrazol-2-yl)phenyl |
| 647 | F | phenyl | 4-morpholinocarbonyl |
| 648 | F | phenyl | 2-methyl-1-imidazolyl |
| 649 | F | phenyl | 5-methyl-1-imidazolyl |
| 650 | F | phenyl | 2-methylsulfonyl-1-imidazolyl |
| 651 | F | 2-pyridyl | 2-(aminosulfonyl)phenyl |
| 652 | F | 2-pyridyl | 2-(methylaminosulfonyl)phenyl |
| 653 | F | 2-pyridyl | 1-pyrrolidinocarbonyl |
| 654 | F | 2-pyridyl | 2-(methylsulfonyl)phenyl |
| 655 | F | 2-pyridyl | 4-morpholino |
| 656 | F | 2-pyridyl | 2-(1'-$CF_3$-tetrazol-2-yl)phenyl |
| 657 | F | 2-pyridyl | 4-morpholinocarbonyl |
| 658 | F | 2-pyridyl | 2-methyl-1-imidazolyl |
| 659 | F | 2-pyridyl | 5-methyl-1-imidazolyl |
| 660 | F | 2-pyridyl | 2-methylsulfonyl-1-imidazolyl |
| 661 | F | 3-pyridyl | 2-(aminosulfonyl)phenyl |
| 662 | F | 3-pyridyl | 2-(methylaminosulfonyl)phenyl |
| 663 | F | 3-pyridyl | 1-pyrrolidinocarbonyl |
| 664 | F | 3-pyridyl | 2-(methylsulfonyl)phenyl |
| 665 | F | 3-pyridyl | 4-morpholino |
| 666 | F | 3-pyridyl | 2-(1'-$CF_3$-tetrazol-2-yl)phenyl |
| 667 | F | 3-pyridyl | 4-morpholinocarbonyl |
| 668 | F | 3-pyridyl | 2-methyl-1-imidazolyl |
| 669 | F | 3-pyridyl | 5-methyl-1-imidazolyl |
| 670 | F | 3-pyridyl | 2-methylsulfonyl-1-imidazolyl |
| 671 | F | 2-pyrimidyl | 2-(aminosulfonyl)phenyl |
| 672 | F | 2-pyrimidyl | 2-(methylaminosulfonyl)phenyl |
| 673 | F | 2-pyrimidyl | 1-pyrrolidinocarbonyl |
| 674 | F | 2-pyrimidyl | 2-(methylsulfonyl)phenyl |
| 675 | F | 2-pyrimidyl | 4-morpholino |
| 676 | F | 2-pyrimidyl | 2-(1'-$CF_3$-tetrazol-2-yl)phenyl |
| 677 | F | 2-pyrimidyl | 4-morpholinocarbonyl |
| 678 | F | 2-pyrimidyl | 2-methyl-1-imidazolyl |
| 679 | F | 2-pyrimidyl | 5-methyl-1-imidazolyl |
| 680 | F | 2-pyrimidyl | 2-methylsulfonyl-1-imidazolyl |
| 681 | F | 5-pyrimidyl | 2-(aminosulfonyl)phenyl |
| 682 | F | 5-pyrimidyl | 2-(methylaminosulfonyl)phenyl |
| 683 | F | 5-pyrimidyl | 1-pyrrolidinocarbonyl |
| 684 | F | 5-pyrimidyl | 2-(methylsulfonyl)phenyl |
| 685 | F | 5-pyrimidyl | 4-morpholino |
| 686 | F | 5-pyrimidyl | 2-(1'-$CF_3$-tetrazol-2-yl)phenyl |
| 687 | F | 5-pyrimidyl | 4-morpholinocarbonyl |
| 688 | F | 5-pyrimidyl | 2-methyl-1-imidazolyl |
| 689 | F | 5-pyrimidyl | 5-methyl-1-imidazolyl |
| 690 | F | 5-pyrimidyl | 2-methylsulfonyl-1-imidazolyl |
| 691 | F | 2-Cl-phenyl | 2-(aminosulfonyl)phenyl |
| 692 | F | 2-Cl-phenyl | 2-(methylaminosulfonyl)phenyl |
| 693 | F | 2-Cl-phenyl | 1-pyrrolidinocarbonyl |
| 694 | F | 2-Cl-phenyl | 2-(methylsulfonyl)phenyl |
| 695 | F | 2-Cl-phenyl | 4-morpholino |
| 696 | F | 2-Cl-phenyl | 2-(1'-$CF_3$-tetrazol-2-yl)phenyl |
| 697 | F | 2-Cl-phenyl | 4-morpholinocarbonyl |
| 698 | F | 2-Cl-phenyl | 2-methyl-1-imidazolyl |
| 699 | F | 2-Cl-phenyl | 5-methyl-1-imidazolyl |
| 700 | F | 2-Cl-phenyl | 2-methylsulfonyl-1-imidazolyl |
| 701 | F | 2-F-phenyl | 2-(aminosulfonyl)phenyl |
| 702 | F | 2-F-phenyl | 2-(methylaminosulfonyl)phenyl |
| 703 | F | 2-F-phenyl | 1-pyrrolidinocarbonyl |
| 704 | F | 2-F-phenyl | 2-(methylsulfonyl)phenyl |
| 705 | F | 2-F-phenyl | 4-morpholino |
| 706 | F | 2-F-phenyl | 2-(1'-$CF_3$-tetrazol-2-yl)phenyl |
| 707 | F | 2-F-phenyl | 4-morpholinocarbonyl |
| 708 | F | 2-F-phenyl | 2-methyl-1-imidazolyl |
| 709 | F | 2-F-phenyl | 5-methyl-1-imidazolyl |
| 710 | F | 2-F-phenyl | 2-methylsulfonyl-1-imidazolyl |
| 711 | F | 2,6-diF-phenyl | 2-(aminosulfonyl)phenyl |
| 712 | F | 2,6-diF-phenyl | 2-(methylaminosulfonyl)phenyl |
| 713 | F | 2,6-diF-phenyl | 1-pyrrolidinocarbonyl |
| 714 | F | 2,6-diF-phenyl | 2-(methylsulfonyl)phenyl |
| 715 | F | 2,6-diF-phenyl | 4-morpholino |
| 716 | F | 2,6-diF-phenyl | 2-(1'-$CF_3$-tetrazol-2-yl)phenyl |
| 717 | F | 2,6-diF-phenyl | 4-morpholinocarbonyl |
| 718 | F | 2,6-diF-phenyl | 2-methyl-1-imidazolyl |
| 719 | F | 2,6-diF-phenyl | 5-methyl-1-imidazolyl |
| 720 | F | 2,6-diF-phenyl | 2-methylsulfonyl-1-imidazolyl |
| 721 | $CO_2CH_3$ | phenyl | 2-(aminosulfonyl)phenyl |
| 722 | $CO_2CH_3$ | phenyl | 2-(methylaminosulfonyl)phenyl |
| 723 | $CO_2CH_3$ | phenyl | 1-pyrrolidinocarbonyl |
| 724 | $CO_2CH_3$ | phenyl | 2-(methylsulfonyl)phenyl |
| 725 | $CO_2CH_3$ | phenyl | 4-morpholino |
| 726 | $CO_2CH_3$ | phenyl | 2-(1'-$CF_3$-tetrazol-2-yl)phenyl |
| 727 | $CO_2CH_3$ | phenyl | 4-morpholinocarbonyl |
| 728 | $CO_2CH_3$ | phenyl | 2-methyl-1-imidazolyl |
| 729 | $CO_2CH_3$ | phenyl | 5-methyl-1-imidazolyl |
| 730 | $CO_2CH_3$ | phenyl | 2-methylsulfonyl-1-imidazolyl |
| 731 | $CO_2CH_3$ | 2-pyridyl | 2-(aminosulfonyl)phenyl |
| 732 | $CO_2CH_3$ | 2-pyridyl | 2-(methylaminosulfonyl)phenyl |
| 733 | $CO_2CH_3$ | 2-pyridyl | 1-pyrrolidinocarbonyl |
| 734 | $CO_2CH_3$ | 2-pyridyl | 2-(methylsulfonyl)phenyl |
| 735 | $CO_2CH_3$ | 2-pyridyl | 4-morpholino |
| 736 | $CO_2CH_3$ | 2-pyridyl | 2-(1'-$CF_3$-tetrazol-2-yl)phenyl |
| 737 | $CO_2CH_3$ | 2-pyridyl | 4-morpholinocarbonyl |
| 738 | $CO_2CH_3$ | 2-pyridyl | 2-methyl-1-imidazolyl |
| 739 | $CO_2CH_3$ | 2-pyridyl | 5-methyl-1-imidazolyl |
| 740 | $CO_2CH_3$ | 2-pyridyl | 2-methylsulfonyl-1-imidazolyl |
| 741 | $CO_2CH_3$ | 3-pyridyl | 2-(aminosulfonyl)phenyl |
| 742 | $CO_2CH_3$ | 3-pyridyl | 2-(methylaminosulfonyl)phenyl |
| 743 | $CO_2CH_3$ | 3-pyridyl | 1-pyrrolidinocarbonyl |
| 744 | $CO_2CH_3$ | 3-pyridyl | 2-(methylsulfonyl)phenyl |
| 745 | $CO_2CH_3$ | 3-pyridyl | 4-morpholino |
| 746 | $CO_2CH_3$ | 3-pyridyl | 2-(1'-$CF_3$-tetrazol-2-yl)phenyl |
| 747 | $CO_2CH_3$ | 3-pyridyl | 4-morpholinocarbonyl |
| 748 | $CO_2CH_3$ | 3-pyridyl | 2-methyl-1-imidazolyl |
| 749 | $CO_2CH_3$ | 3-pyridyl | 5-methyl-1-imidazolyl |
| 750 | $CO_2CH_3$ | 3-pyridyl | 2-methylsulfonyl-1-imidazolyl |

TABLE 6-continued

| | | | |
|---|---|---|---|
| 751 | $CO_2CH_3$ | 2-pyrimidyl | 2-(aminosulfonyl)phenyl |
| 752 | $CO_2CH_3$ | 2-pyrimidyl | 2-(methylaminosulfonyl)phenyl |
| 753 | $CO_2CH_3$ | 2-pyrimidyl | 1-pyrrolidinocarbonyl |
| 754 | $CO_2CH_3$ | 2-pyrimidyl | 2-(methylsulfonyl)phenyl |
| 755 | $CO_2CH_3$ | 2-pyrimidyl | 4-morpholino |
| 756 | $CO_2CH_3$ | 2-pyrimidyl | 2-(1'-$CF_3$-tetrazol-2-yl)phenyl |
| 757 | $CO_2CH_3$ | 2-pyrimidyl | 4-morpholinocarbonyl |
| 758 | $CO_2CH_3$ | 2-pyrimidyl | 2-methyl-1-imidazolyl |
| 759 | $CO_2CH_3$ | 2-pyrimidyl | 5-methyl-1-imidazolyl |
| 760 | $CO_2CH_3$ | 2-pyrimidyl | 2-methylsulfonyl-1-imidazolyl |
| 761 | $CO_2CH_3$ | 5-pyrimidyl | 2-(aminosulfonyl)phenyl |
| 762 | $CO_2CH_3$ | 5-pyrimidyl | 2-(methylaminosulfonyl)phenyl |
| 763 | $CO_2CH_3$ | 5-pyrimidyl | 1-pyrrolidinocarbonyl |
| 764 | $CO_2CH_3$ | 5-pyrimidyl | 2-(methylsulfonyl)phenyl |
| 765 | $CO_2CH_3$ | 5-pyrimidyl | 4-morpholino |
| 766 | $CO_2CH_3$ | 5-pyrimidyl | 2-(1'-$CF_3$-tetrazol-2-yl)phenyl |
| 767 | $CO_2CH_3$ | 5-pyrimidyl | 4-morpholinocarbonyl |
| 768 | $CO_2CH_3$ | 5-pyrimidyl | 2-methyl-1-imidazolyl |
| 769 | $CO_2CH_3$ | 5-pyrimidyl | 5-methyl-1-imidazolyl |
| 770 | $CO_2CH_3$ | 5-pyrimidyl | 2-methylsulfonyl-1-imidazolyl |
| 771 | $CO_2CH_3$ | 2-Cl-phenyl | 2-(aminosulfonyl)phenyl |
| 772 | $CO_2CH_3$ | 2-Cl-phenyl | 2-(methylaminosulfonyl)phenyl |
| 773 | $CO_2CH_3$ | 2-Cl-phenyl | 1-pyrrolidinocarbonyl |
| 774 | $CO_2CH_3$ | 2-Cl-phenyl | 2-(methylsulfonyl)phenyl |
| 775 | $CO_2CH_3$ | 2-Cl-phenyl | 4-morpholino |
| 776 | $CO_2CH_3$ | 2-Cl-phenyl | 2-(1'-$CF_3$-tetrazol-2-yl)phenyl |
| 777 | $CO_2CH_3$ | 2-Cl-phenyl | 4-morpholinocarbonyl |
| 778 | $CO_2CH_3$ | 2-Cl-phenyl | 2-methyl-1-imidazolyl |
| 779 | $CO_2CH_3$ | 2-Cl-phenyl | 5-methyl-1-imidazolyl |
| 780 | $CO_2CH_3$ | 2-Cl-phenyl | 2-methylsulfonyl-1-imidazolyl |
| 781 | $CO_2CH_3$ | 2-F-phenyl | 2-(aminosulfonyl)phenyl |
| 782 | $CO_2CH_3$ | 2-F-phenyl | 2-(methylaminosulfonyl)phenyl |
| 783 | $CO_2CH_3$ | 2-F-phenyl | 1-pyrrolidinocarbonyl |
| 784 | $CO_2CH_3$ | 2-F-phenyl | 2-(methylsulfonyl)phenyl |
| 785 | $CO_2CH_3$ | 2-F-phenyl | 4-morpholino |
| 786 | $CO_2CH_3$ | 2-F-phenyl | 2-(1'-$CF_3$-tetrazol-2-yl)phenyl |
| 787 | $CO_2CH_3$ | 2-F-phenyl | 4-morpholinocarbonyl |
| 788 | $CO_2CH_3$ | 2-F-phenyl | 2-methyl-1-imidazolyl |
| 789 | $CO_2CH_3$ | 2-F-phenyl | 5-methyl-1-imidazolyl |
| 790 | $CO_2CH_3$ | 2-F-phenyl | 2-methylsulfonyl-1-imidazolyl |
| 791 | $CO_2CH_3$ | 2,6-diF-phenyl | 2-(aminosulfonyl)phenyl |
| 792 | $CO_2CH_3$ | 2,6-diF-phenyl | 2-(methylaminosulfonyl)phenyl |
| 793 | $CO_2CH_3$ | 2,6-diF-phenyl | 1-pyrrolidinocarbonyl |
| 794 | $CO_2CH_3$ | 2,6-diF-phenyl | 2-(methylsulfonyl)phenyl |
| 795 | $CO_2CH_3$ | 2,6-diF-phenyl | 4-morpholino |
| 796 | $CO_2CH_3$ | 2,6-diF-phenyl | 2-(1'-$CF_3$-tetrazol-2-yl)phenyl |
| 797 | $CO_2CH_3$ | 2,6-diF-phenyl | 4-morpholinocarbonyl |
| 798 | $CO_2CH_3$ | 2,6-diF-phenyl | 2-methyl-1-imidazolyl |
| 799 | $CO_2CH_3$ | 2,6-diF-phenyl | 5-methyl-1-imidazolyl |
| 800 | $CO_2CH_3$ | 2,6-diF-phenyl | 2-methylsulfonyl-1-imidazolyl |
| 801 | $CH_2OCH_3$ | phenyl | 2-(aminosulfonyl)phenyl |
| 802 | $CH_2OCH_3$ | phenyl | 2-(methylaminosulfonyl)phenyl |
| 803 | $CH_2OCH_3$ | phenyl | 1-pyrrolidinocarbonyl |
| 804 | $CH_2OCH_3$ | phenyl | 2-(methylsulfonyl)phenyl |
| 805 | $CH_2OCH_3$ | phenyl | 4-morpholino |
| 806 | $CH_2OCH_3$ | phenyl | 2-(1'-$CF_3$-tetrazol-2-yl)phenyl |
| 807 | $CH_2OCH_3$ | phenyl | 4-morpholinocarbonyl |
| 808 | $CH_2OCH_3$ | phenyl | 2-methyl-1-imidazolyl |
| 809 | $CH_2OCH_3$ | phenyl | 5-methyl-1-imidazolyl |
| 810 | $CH_2OCH_3$ | phenyl | 2-methylsulfonyl-1-imidazolyl |
| 811 | $CH_2OCH_3$ | 2-pyridyl | 2-(aminosulfonyl)phenyl |
| 812 | $CH_2OCH_3$ | 2-pyridyl | 2-(methylaminosulfonyl)phenyl |
| 813 | $CH_2OCH_3$ | 2-pyridyl | 1-pyrrolidinocarbonyl |
| 814 | $CH_2OCH_3$ | 2-pyridyl | 2-(methylsulfonyl)phenyl |
| 815 | $CH_2OCH_3$ | 2-pyridyl | 4-morpholino |
| 816 | $CH_2OCH_3$ | 2-pyridyl | 2-(1'-$CF_3$-tetrazol-2-yl)phenyl |
| 817 | $CH_2OCH_3$ | 2-pyridyl | 4-morpholinocarbonyl |
| 818 | $CH_2OCH_3$ | 2-pyridyl | 2-methyl-1-imidazolyl |
| 819 | $CH_2OCH_3$ | 2-pyridyl | 5-methyl-1-imidazolyl |
| 820 | $CH_2OCH_3$ | 2-pyridyl | 2-methylsulfonyl-1-imidazolyl |
| 821 | $CH_2OCH_3$ | 3-pyridyl | 2-(aminosulfonyl)phenyl |
| 822 | $CH_2OCH_3$ | 3-pyridyl | 2-(methylaminosulfonyl)phenyl |
| 823 | $CH_2OCH_3$ | 3-pyridyl | 1-pyrrolidinocarbonyl |
| 824 | $CH_2OCH_3$ | 3-pyridyl | 2-(methylsulfonyl)phenyl |
| 825 | $CH_2OCH_3$ | 3-pyridyl | 4-morpholino |
| 826 | $CH_2OCH_3$ | 3-pyridyl | 2-(1'-$CF_3$-tetrazol-2-yl)phenyl |
| 827 | $CH_2OCH_3$ | 3-pyridyl | 4-morpholinocarbonyl |
| 828 | $CH_2OCH_3$ | 3-pyridyl | 2-methyl-1-imidazolyl |
| 829 | $CH_2OCH_3$ | 3-pyridyl | 5-methyl-1-imidazolyl |
| 830 | $CH_2OCH_3$ | 3-pyridyl | 2-methylsulfonyl-1-imidazolyl |
| 831 | $CH_2OCH_3$ | 2-pyrimidyl | 2-(aminosulfonyl)phenyl |
| 832 | $CH_2OCH_3$ | 2-pyrimidyl | 2-(methylaminosulfonyl)phenyl |
| 833 | $CH_2OCH_3$ | 2-pyrimidyl | 1-pyrrolidinocarbonyl |
| 834 | $CH_2OCH_3$ | 2-pyrimidyl | 2-(methylsulfonyl)phenyl |
| 835 | $CH_2OCH_3$ | 2-pyrimidyl | 4-morpholino |
| 836 | $CH_2OCH_3$ | 2-pyrimidyl | 2-(1'-$CF_3$-tetrazol-2-yl)phenyl |
| 837 | $CH_2OCH_3$ | 2-pyrimidyl | 4-morpholinocarbonyl |
| 838 | $CH_2OCH_3$ | 2-pyrimidyl | 2-methyl-1-imidazolyl |
| 839 | $CH_2OCH_3$ | 2-pyrimidyl | 5-methyl-1-imidazolyl |
| 840 | $CH_2OCH_3$ | 2-pyrimidyl | 2-methylsulfonyl-1-imidazolyl |
| 841 | $CH_2OCH_3$ | 5-pyrimidyl | 2-(aminosulfonyl)phenyl |
| 842 | $CH_2OCH_3$ | 5-pyrimidyl | 2-(methylaminosulfonyl)phenyl |
| 843 | $CH_2OCH_3$ | 5-pyrimidyl | 1-pyrrolidinocarbonyl |
| 844 | $CH_2OCH_3$ | 5-pyrimidyl | 2-(methylsulfonyl)phenyl |
| 845 | $CH_2OCH_3$ | 5-pyrimidyl | 4-morpholino |
| 846 | $CH_2OCH_3$ | 5-pyrimidyl | 2-(1'-$CF_3$-tetrazol-2-yl)phenyl |
| 847 | $CH_2OCH_3$ | 5-pyrimidyl | 4-morpholinocarbonyl |
| 848 | $CH_2OCH_3$ | 5-pyrimidyl | 2-methyl-1-imidazolyl |
| 849 | $CH_2OCH_3$ | 5-pyrimidyl | 5-methyl-1-imidazolyl |
| 850 | $CH_2OCH_3$ | 5-pyrimidyl | 2-methylsulfonyl-1-imidazolyl |
| 851 | $CH_2OCH_3$ | 2-Cl-phenyl | 2-(aminosulfonyl)phenyl |
| 852 | $CH_2OCH_3$ | 2-Cl-phenyl | 2-(methylaminosulfonyl)phenyl |
| 853 | $CH_2OCH_3$ | 2-Cl-phenyl | 1-pyrrolidinocarbonyl |
| 854 | $CH_2OCH_3$ | 2-Cl-phenyl | 2-(methylsulfonyl)phenyl |
| 855 | $CH_2OCH_3$ | 2-Cl-phenyl | 4-morpholino |
| 856 | $CH_2OCH_3$ | 2-Cl-phenyl | 2-(1'-$CF_3$-tetrazol-2-yl)phenyl |
| 857 | $CH_2OCH_3$ | 2-Cl-phenyl | 4-morpholinocarbonyl |
| 858 | $CH_2OCH_3$ | 2-Cl-phenyl | 2-methyl-1-imidazolyl |
| 859 | $CH_2OCH_3$ | 2-Cl-phenyl | 5-methyl-1-imidazolyl |
| 860 | $CH_2OCH_3$ | 2-Cl-phenyl | 2-methylsulfonyl-1-imidazolyl |
| 861 | $CH_2OCH_3$ | 2-F-phenyl | 2-(aminosulfonyl)phenyl |
| 862 | $CH_2OCH_3$ | 2-F-phenyl | 2-(methylaminosulfonyl)phenyl |
| 863 | $CH_2OCH_3$ | 2-F-phenyl | 1-pyrrolidinocarbonyl |
| 864 | $CH_2OCH_3$ | 2-F-phenyl | 2-(methylsulfonyl)phenyl |
| 865 | $CH_2OCH_3$ | 2-F-phenyl | 4-morpholino |
| 866 | $CH_2OCH_3$ | 2-F-phenyl | 2-(1'-$CF_3$-tetrazol-2-yl)phenyl |
| 867 | $CH_2OCH_3$ | 2-F-phenyl | 4-morpholinocarbonyl |
| 868 | $CH_2OCH_3$ | 2-F-phenyl | 2-methyl-1-imidazolyl |
| 869 | $CH_2OCH_3$ | 2-F-phenyl | 5-methyl-1-imidazolyl |
| 870 | $CH_2OCH_3$ | 2-F-phenyl | 2-methylsulfonyl-1-imidazolyl |

TABLE 6-continued

| # | | | |
|---|---|---|---|
| 871 | CH$_2$OCH$_3$ | 2,6-diF-phenyl | 2-(aminosulfonyl)phenyl |
| 872 | CH$_2$OCH$_3$ | 2,6-diF-phenyl | 2-(methylaminosulfonyl)phenyl |
| 873 | CH$_2$OCH$_3$ | 2,6-diF-phenyl | 1-pyrrolidinocarbonyl |
| 874 | CH$_2$OCH$_3$ | 2,6-diF-phenyl | 2-(methylsulfonyl)phenyl |
| 875 | CH$_2$OCH$_3$ | 2,6-diF-phenyl | 4-morpholino |
| 876 | CH$_2$OCH$_3$ | 2,6-diF-phenyl | 2-(1'-CF$_3$-tetrazol-2-yl)phenyl |
| 877 | CH$_2$OCH$_3$ | 2,6-diF-phenyl | 4-morpholinocarbonyl |
| 878 | CH$_2$OCH$_3$ | 2,6-diF-phenyl | 2-methyl-1-imidazolyl |
| 879 | CH$_2$OCH$_3$ | 2,6-diF-phenyl | 5-methyl-1-imidazolyl |
| 880 | CH$_2$OCH$_3$ | 2,6-diF-phenyl | 2-methylsulfonyl-1-imidazolyl |
| 881 | CONH$_2$ | phenyl | 2-(aminosulfonyl)phenyl |
| 882 | CONH$_2$ | phenyl | 2-(methylaminosulfonyl)phenyl |
| 883 | CONH$_2$ | phenyl | 1-pyrrolidinocarbonyl |
| 884 | CONH$_2$ | phenyl | 2-(methylsulfonyl)phenyl |
| 885 | CONH$_2$ | phenyl | 4-morpholino |
| 886 | CONH$_2$ | phenyl | 2-(1'-CF$_3$-tetrazol-2-yl)phenyl |
| 887 | CONH$_2$ | phenyl | 4-morpholinocarbonyl |
| 888 | CONH$_2$ | phenyl | 2-methyl-1-imidazolyl |
| 889 | CONH$_2$ | phenyl | 5-methyl-1-imidazolyl |
| 890 | CONH$_2$ | phenyl | 2-methylsulfonyl-1-imidazolyl |
| 891 | CONH$_2$ | 2-pyridyl | 2-(aminosulfonyl)phenyl |
| 892 | CONH$_2$ | 2-pyridyl | 2-(methylaminosulfonyl)phenyl |
| 893 | CONH$_2$ | 2-pyridyl | 1-pyrrolidinocarbonyl |
| 894 | CONH$_2$ | 2-pyridyl | 2-(methylsulfonyl)phenyl |
| 895 | CONH$_2$ | 2-pyridyl | 4-morpholino |
| 896 | CONH$_2$ | 2-pyridyl | 2-(1'-CF$_3$-tetrazol-2-yl)phenyl |
| 897 | CONH$_2$ | 2-pyridyl | 4-morpholinocarbonyl |
| 898 | CONH$_2$ | 2-pyridyl | 2-methyl-1-imidazolyl |
| 899 | CONH$_2$ | 2-pyridyl | 5-methyl-1-imidazolyl |
| 900 | CONH$_2$ | 2-pyridyl | 2-methylsulfonyl-1-imidazolyl |
| 901 | CONH$_2$ | 3-pyridyl | 2-(aminosulfonyl)phenyl |
| 902 | CONH$_2$ | 3-pyridyl | 2-(methylaminosulfonyl)phenyl |
| 903 | CONH$_2$ | 3-pyridyl | 1-pyrrolidinocarbonyl |
| 904 | CONH$_2$ | 3-pyridyl | 2-(methylsulfonyl)phenyl |
| 905 | CONH$_2$ | 3-pyridyl | 4-morpholino |
| 906 | CONH$_2$ | 3-pyridyl | 2-(1'-CF$_3$-tetrazol-2-yl)phenyl |
| 907 | CONH$_2$ | 3-pyridyl | 4-morpholinocarbonyl |
| 908 | CONH$_2$ | 3-pyridyl | 2-methyl-1-imidazolyl |
| 909 | CONH$_2$ | 3-pyridyl | 5-methyl-1-imidazolyl |
| 910 | CONH$_2$ | 3-pyridyl | 2-methylsulfonyl-1-imidazolyl |
| 911 | CONH$_2$ | 2-pyrimidyl | 2-(aminosulfonyl)phenyl |
| 912 | CONH$_2$ | 2-pyrimidyl | 2-(methylaminosulfonyl)phenyl |
| 913 | CONH$_2$ | 2-pyrimidyl | 1-pyrrolidinocarbonyl |
| 914 | CONH$_2$ | 2-pyrimidyl | 2-(methylsulfonyl)phenyl |
| 915 | CONH$_2$ | 2-pyrimidyl | 4-morpholino |
| 916 | CONH$_2$ | 2-pyrimidyl | 2-(1'-CF$_3$-tetrazol-2-yl)phenyl |
| 917 | CONH$_2$ | 2-pyrimidyl | 4-morpholinocarbonyl |
| 918 | CONH$_2$ | 2-pyrimidyl | 2-methyl-1-imidazolyl |
| 919 | CONH$_2$ | 2-pyrimidyl | 5-methyl-1-imidazolyl |
| 920 | CONH$_2$ | 2-pyrimidyl | 2-methylsulfonyl-1-imidazolyl |
| 921 | CONH$_2$ | 5-pyrimidyl | 2-(aminosulfonyl)phenyl |
| 922 | CONH$_2$ | 5-pyrimidyl | 2-(methylaminosulfonyl)phenyl |
| 923 | CONH$_2$ | 5-pyrimidyl | 1-pyrrolidinocarbonyl |
| 924 | CONH$_2$ | 5-pyrimidyl | 2-(methylsulfonyl)phenyl |
| 925 | CONH$_2$ | 5-pyrimidyl | 4-morpholino |
| 926 | CONH$_2$ | 5-pyrimidyl | 2-(1'-CF$_3$-tetrazol-2-yl)phenyl |
| 927 | CONH$_2$ | 5-pyrimidyl | 4-morpholinocarbonyl |
| 928 | CONH$_2$ | 5-pyrimidyl | 2-methyl-1-imidazolyl |
| 929 | CONH$_2$ | 5-pyrimidyl | 5-methyl-1-imidazolyl |
| 930 | CONH$_2$ | 5-pyrimidyl | 2-methylsulfonyl-1-imidazolyl |
| 931 | CONH$_2$ | 2-Cl-phenyl | 2-(aminosulfonyl)phenyl |
| 932 | CONH$_2$ | 2-Cl-phenyl | 2-(methylaminosulfonyl)phenyl |
| 933 | CONH$_2$ | 2-Cl-phenyl | 1-pyrrolidinocarbonyl |
| 934 | CONH$_2$ | 2-Cl-phenyl | 2-(methylsulfonyl)phenyl |
| 935 | CONH$_2$ | 2-Cl-phenyl | 4-morpholino |
| 936 | CONH$_2$ | 2-Cl-phenyl | 2-(1'-CF$_3$-tetrazol-2-yl)phenyl |
| 937 | CONH$_2$ | 2-Cl-phenyl | 4-morpholinocarbonyl |
| 938 | CONH$_2$ | 2-Cl-phenyl | 2-methyl-1-imidazolyl |
| 939 | CONH$_2$ | 2-Cl-phenyl | 5-methyl-1-imidazolyl |
| 940 | CONH$_2$ | 2-Cl-phenyl | 2-methylsulfonyl-1-imidazolyl |
| 941 | CONH$_2$ | 2-F-phenyl | 2-(aminosulfonyl)phenyl |
| 942 | CONH$_2$ | 2-F-phenyl | 2-(methylaminosulfonyl)phenyl |
| 943 | CONH$_2$ | 2-F-phenyl | 1-pyrrolidinocarbonyl |
| 944 | CONH$_2$ | 2-F-phenyl | 2-(methylsulfonyl)phenyl |
| 945 | CONH$_2$ | 2-F-phenyl | 4-morpholino |
| 946 | CONH$_2$ | 2-F-phenyl | 2-(1'-CF$_3$-tetrazol-2-yl)phenyl |
| 947 | CONH$_2$ | 2-F-phenyl | 4-morpholinocarbonyl |
| 948 | CONH$_2$ | 2-F-phenyl | 2-methyl-1-imidazolyl |
| 949 | CONH$_2$ | 2-F-phenyl | 5-methyl-1-imidazolyl |
| 950 | CONH$_2$ | 2-F-phenyl | 2-methylsulfonyl-1-imidazolyl |
| 951 | CONH$_2$ | 2,6-diF-phenyl | 2-(aminosulfonyl)phenyl |
| 952 | CONH$_2$ | 2,6-diF-phenyl | 2-(methylaminosulfonyl)phenyl |
| 953 | CONH$_2$ | 2,6-diF-phenyl | 1-pyrrolidinocarbonyl |
| 954 | CONH$_2$ | 2,6-diF-phenyl | 2-(methylsulfonyl)phenyl |
| 955 | CONH$_2$ | 2,6-diF-phenyl | 4-morpholino |
| 956 | CONH$_2$ | 2,6-diF-phenyl | 2-(1'-CF$_3$-tetrazol-2-yl)phenyl |
| 957 | CONH$_2$ | 2,6-diF-phenyl | 4-morpholinocarbonyl |
| 958 | CONH$_2$ | 2,6-diF-phenyl | 2-methyl-1-imidazolyl |
| 959 | CONH$_2$ | 2,6-diF-phenyl | 5-methyl-1-imidazolyl |
| 960 | CONH$_2$ | 2,6-diF-phenyl | 2-methylsulfonyl-1-imidazolyl |

TABLE 7

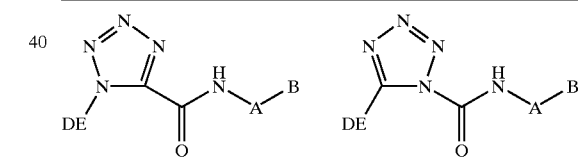

For each example, DE is:
(A) pyridin-4-yl-CH$_2$,
(B) 2-amino-pyrimidin-4-yl,
(C) 6-amino-pyridin-2-yl,
(D) 3-amidino-4-F-phenyl, or
(E) N-amidino-3-piperidinyl.

| Ex # | A | B |
|---|---|---|
| 1 | phenyl | 2-(aminosulfonyl)phenyl |
| 2 | phenyl | 2-(methylaminosulfonyl)phenyl |
| 3 | phenyl | 1-pyrrolidinocarbonyl |
| 4 | phenyl | 2-(methylsulfonyl)phenyl |
| 5 | phenyl | 4-morpholino |
| 6 | phenyl | 2-(1'-CF$_3$-tetrazol-2-yl)phenyl |
| 7 | phenyl | 4-morpholinocarbonyl |
| 8 | phenyl | 2-methyl-1-imidazolyl |
| 9 | phenyl | 5-methyl-1-imidazolyl |
| 10 | phenyl | 2-methylsulfonyl-1-imidazolyl |
| 11 | 2-pyridyl | 2-(aminosulfonyl)phenyl |
| 12 | 2-pyridyl | 2-(methylaminosulfonyl)phenyl |
| 13 | 2-pyridyl | 1-pyrrolidinocarbonyl |
| 14 | 2-pyridyl | 2-(methylsulfonyl)phenyl |
| 15 | 2-pyridyl | 4-morpholino |
| 16 | 2-pyridyl | 2-(1'-CF$_3$-tetrazol-2-yl)phenyl |
| 17 | 2-pyridyl | 4-morpholinocarbonyl |

TABLE 7-continued

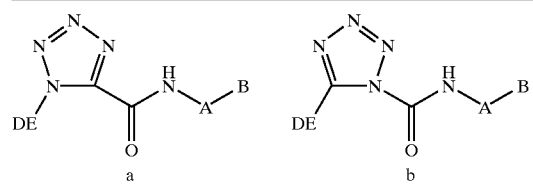

a b

For each example, DE is:
(A) pyridin-4-yl-CH$_2$,
(B) 2-amino-pyrimidin-4-yl,
(C) 6-amino-pyridin-2-yl,
(D) 3-amidino-4-F-phenyl, or
(E) N-amidino-3-piperidinyl.

| Ex # | A | B |
|---|---|---|
| 18 | 2-pyridyl | 2-methyl-1-imidazolyl |
| 19 | 2-pyridyl | 5-methyl-1-imidazolyl |
| 20 | 2-pyridyl | 2-methylsulfonyl-1-imidazolyl |
| 21 | 3-pyridyl | 2-(aminosulfonyl)phenyl |
| 22 | 3-pyridyl | 2-(methylaminosulfonyl)phenyl |
| 23 | 3-pyridyl | 1-pyrrolidinocarbonyl |
| 24 | 3-pyridyl | 2-(methylsulfonyl)phenyl |
| 25 | 3-pyridyl | 4-morpholino |
| 26 | 3-pyridyl | 2-(1'-CF$_3$-tetrazol-2-yl)phenyl |
| 27 | 3-pyridyl | 4-morpholinocarbonyl |
| 28 | 3-pyridyl | 2-methyl-1-imidazolyl |
| 29 | 3-pyridyl | 5-methyl-1-imidazolyl |
| 30 | 3-pyridyl | 2-methylsulfonyl-1-imidazolyl |
| 31 | 2-pyrimidyl | 2-(aminosulfonyl)phenyl |
| 32 | 2-pyrimidyl | 2-(methylaminosulfonyl)phenyl |
| 33 | 2-pyrimidyl | 1-pyrrolidinocarbonyl |
| 34 | 2-pyrimidyl | 2-(methylsulfonyl)phenyl |
| 35 | 2-pyrimidyl | 4-morpholino |
| 36 | 2-pyrimidyl | 2-(1'-CF$_3$-tetrazol-2-yl)phenyl |
| 37 | 2-pyrimidyl | 4-morpholinocarbonyl |
| 38 | 2-pyrimidyl | 2-methyl-1-imidazolyl |
| 39 | 2-pyrimidyl | 5-methyl-1-imidazolyl |
| 40 | 2-pyrimidyl | 2-methylsulfonyl-1-imidazolyl |
| 41 | 5-pyrimidyl | 2-(aminosulfonyl)phenyl |
| 42 | 5-pyrimidyl | 2-(methylaminosulfonyl)phenyl |
| 43 | 5-pyrimidyl | 1-pyrrolidinocarbonyl |
| 44 | 5-pyrimidyl | 2-(methylsulfonyl)phenyl |
| 45 | 5-pyrimidyl | 4-morpholino |
| 46 | 5-pyrimidyl | 2-(1'-CF$_3$-tetrazol-2-yl)phenyl |
| 47 | 5-pyrimidyl | 4-morpholinocarbonyl |
| 48 | 5-pyrimidyl | 2-methyl-1-imidazolyl |
| 49 | 5-pyrimidyl | 5-methyl-1-imidazolyl |
| 50 | 5-pyrimidyl | 2-methylsulfonyl-1-imidazolyl |
| 51 | 2-Cl-phenyl | 2-(aminosulfonyl)phenyl |
| 52 | 2-Cl-phenyl | 2-(methylaminosulfonyl)phenyl |
| 53 | 2-Cl-phenyl | 1-pyrrolidinocarbonyl |
| 54 | 2-Cl-phenyl | 2-(methylsulfonyl)phenyl |
| 55 | 2-Cl-phenyl | 4-morpholino |
| 56 | 2-Cl-phenyl | 2-(1'-CF$_3$-tetrazol-2-yl)phenyl |
| 57 | 2-Cl-phenyl | 4-morpholinocarbonyl |
| 58 | 2-Cl-phenyl | 2-methyl-1-imidazolyl |
| 59 | 2-Cl-phenyl | 5-methyl-1-imidazolyl |
| 60 | 2-Cl-phenyl | 2-methylsulfonyl-1-imidazolyl |
| 61 | 2-F-phenyl | 2-(aminosulfonyl)phenyl |
| 62 | 2-F-phenyl | 2-(methylaminosulfonyl)phenyl |
| 63 | 2-F-phenyl | 1-pyrrolidinocarbonyl |
| 64 | 2-F-phenyl | 2-(methylsulfonyl)phenyl |
| 65 | 2-F-phenyl | 4-morpholino |
| 66 | 2-F-phenyl | 2-(1'-CF$_3$-tetrazol-2-yl)phenyl |
| 67 | 2-F-phenyl | 4-morpholinocarbonyl |
| 68 | 2-F-phenyl | 2-methyl-1-imidazolyl |
| 69 | 2-F-phenyl | 5-methyl-1-imidazolyl |
| 70 | 2-F-phenyl | 2-methylsulfonyl-1-imidazolyl |
| 71 | 2,6-diF-phenyl | 2-(aminosulfonyl)phenyl |
| 72 | 2,6-diF-phenyl | 2-(methylaminosulfonyl)phenyl |
| 73 | 2,6-diF-phenyl | 1-pyrrolidinocarbonyl |
| 74 | 2,6-diF-phenyl | 2-(methylsulfonyl)phenyl |
| 75 | 2,6-diF-phenyl | 4-morpholino |
| 76 | 2,6-diF-phenyl | 2-(1'-CF$_3$-tetrazol-2-yl)phenyl |
| 77 | 2,6-diF-phenyl | 4-morpholinocarbonyl |
| 78 | 2,6-diF-phenyl | 2-methyl-1-imidazolyl |

TABLE 7-continued

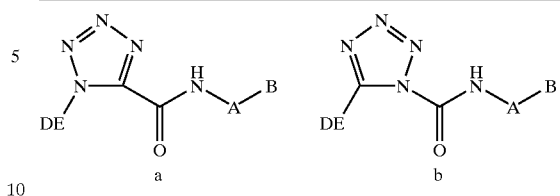

a b

For each example, DE is:
(A) pyridin-4-yl-CH$_2$,
(B) 2-amino-pyrimidin-4-yl,
(C) 6-amino-pyridin-2-yl,
(D) 3-amidino-4-F-phenyl, or
(E) N-amidino-3-piperidinyl.

| Ex # | A | B |
|---|---|---|
| 79 | 2,6-diF-phenyl | 5-methyl-1-imidazolyl |
| 80 | 2,6-diF-phenyl | 2-methylsulfonyl-1-imidazolyl |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:
$v_o$ is the velocity of the control in the absence of inhibitor;
$v_s$ is the velocity in the presence of inhibitor;
I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 10 \mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than $10 \mu m$, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier-selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be. administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

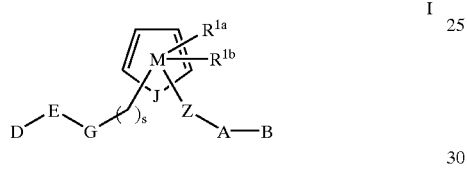

or a stereoisomer or pharmaceutically acceptable salt thereof, wherein;

ring M is pyrazole and $R^{1b}$ is not present;

J is N or NH;

D is selected from CN, $C(=NR^8)NR^7R^9$, $NHC(=NR^8)NR^7R^9$, $NR^8CH(=NR^7)$, $C(O)NR^7R^8$, and $(CR^8R^9)_t NR^7R^8$, provided that D is substituted meta or para to G on E;

E is selected from phenyl, pyridyl, pyrimidyl, pyrazinyl, pyridazinyl, and piperidinyl substituted with 1 R;

alternatively, D—E—G together represent pyridyl substituted with 1 R;

R is selected from H, halogen, $(CH_2)_tOR^3$, $C_{1-4}$ alkyl, $OCF_3$, and $CF_3$;

G is absent or is selected from $NHCH_2$, $OCH_2$, and $SCH_2$, provided that when s is 0, then G is attached to a carbon atom on ring M;

Z is selected from a $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)O(CH_2)_r$, $(CH_2)_rOC(O)(CH_2)_r$, $(CH_2)_rC(O)NR^3(CH_2)_r$, $(CH_2)_rNR^3C(O)(CH_2)_r$, $(CH_2)_rOC(O)O(CH_2)_r$, $(CH_2)_rOC(O)NR^3(CH_2)_r$, $(CH_2)_rNR^3C(O)O(CH_2)_r$, $(CH_2)_r NR^3C(O)NR^3(CH_2)_r$, $(CH_2)_rS(O)_p(CH_2)_r$, $(CH_2)_r SO_2NR^3(CH_2)_r$, $(CH_2)_rNR^3SO_2(CH_2)_r$, and $(CH_2)_r NR^3SO_2NR^3(CH_2)_r$, provided that Z does not form a N—N, N—O, N—S, $NCH_2N$, $NCH_2O$, or $NCH_2S$ bond with ring M or group A;

$R^{1a}$ is independently absent or selected from —$(CH_2)_r$— $R^{1'}$, $NHCH_2R^{1'}$, $OCH_2R^{1'}$, $SCH_2R^{1'}$, $NH(CH_2)_2(CH_2)_rR^{1'}$, $O(CH_2)_2(CH_2)_rR^{1'}$, and $S(CH_2)_2 (CH_2)_rR^{1'}$, or combined to form a 5–8 membered saturated, partially saturated or unsaturated ring substituted with 0–2 $R^4$ and which contains from 0–2 heteroatoms selected from the group consisting of N, O, and S;

$R^{1'}$ is selected from H, $C_{1-3}$ alkyl, halo, $(CF_2)_rCF_3$, $OR^2$, $NR^2R^{2a}$, $C(O)R^{2c}$, $OC(O)R^2$, $(CF_2)_rCO_2R^{2c}$, $S(O)_p R^{2b}$, $NR^2(CH_2)_rOR^2$, $NR^2C(O)R^{2b}$, $NR^2C(O)NHR^{2b}$, $NR^2C(O)_2R^{2a}$, $OC(O)NR^{2b}$, $C(O)NR^2R^{2a}$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1''}$ is selected from H, $C(O)R^{2b}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$ combine to form a 5 or 6 membered saturated, partially saturated or unsaturated ring substituted with 0–2 $R^{4b}$ which contains from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

A is pyrimidyl substituted with 0–2 $R^4$;

B is selected from:
X-Y, $NR^2R^{2a}$, $C(=NR^2)NR^2R^{2a}$, $NR^2C(=NR^2)NR^2R^{2a}$,
$C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

X is selected from $C_{1-4}$ alkylene, —$CR^2(CR^2R^{2b})$ $(CH_2)_t$—, —$C(O)$—, —$C(=NR)$—, —$CR^2 (NR^{1''}R^2)$—, —$CR^2(OR^2)$—, —$CR^2(SR^2)$—, —$C(O) CR^2R^{2a}$—, —$CR^2R^{2a}C(O)$, —$S(O)_p$—, —$S(O)_p CR^2R^{2a}$—, —$CR^2R^{2a}S(O)_p$—, —$S(O)_2NR^2$—, —$NR^2S(O)_2$—, —$NR^2S(O)_2CR^2R^{2a}$—, —$CR^2R^{2a}S (O)_2NR^2$—, —$NR^2S(O)_2NR^2$—, —$C(O)NR^2$—, $(O)_2NR^2$—, —$NR^2C(O)$—, —$C(O)NR^2CR^2R^{2a}$—, —$NR^2C(O)$—, —$C(O)NR^2CR^2R^{2a}$—, —$NR^2C(O) CR^2R^{2a}$—, —$CR^2R^{2a}C(O)NR^2$—, —$CR^2R^{2a}NR^2C (O)$—, —$NR^2C(O)O$—, —$OC(O)NR^2$—, —$NR^2C(O) NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
$(CH_2)_rNR^2R^{2a}$, provided that X-Y do not form a N—N, O—N, or S—N bond, $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

$R^4$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_tR^{1''}$, $O(CH_2)_2(CH_2)_tR^{1''}$, and $S(CH_2)_2(CH_2)_tR^{1''}$, alternatively, one $R^4$ is a 5–6 membered aromatic heterocycle containing from 1–4 heteroatoms selected from the group consisting of N, O, and S;

$R^{4a}$, at each occurrence, is selected from =O, $(CH_2)_rOR^2$, halo, $C_{1-4}$ alkyl, —CN, $NO_2$, $(CH_2)_rNR^2R^{2a}$, $(CH_2)_rC(O)R^{2b}$, $NR^2C(O)R^{2b}$, $C(O)NR^2R^{2a}$, $NR^2C(O)NR^2R^{2a}$, $C(=NR^2)NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from =O, $(CH_2)_rOR^3$, halo, $C_{1-4}$ alkyl, —CN, $NO_2$, $(CH_2)_rNR^3R^{3a}$, $(CH_2)_rC(O)R^3$, $NR^3C(O)R^{3a}$, $C(O)NR^3R^{3a}$, $NR^3C(O)NR^3R^{3a}$, $C(=NR^3)NR^3R^{3a}$, $NH^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;

p, at each occurrence, is selected from 0, 1, and 2;

r, at each occurrence, is selected from 0, 1, 2, and 3;

s, at each occurrence, is selected from 0, 1, and 2; and, t, at each occurrence, is selected from 0 and 1;

provided that D—E—G—$(CH_2)_s$— and —Z—A—B are not both benzamidines.

2. A compound according to claim 1, wherein the compound is of formula Ib:

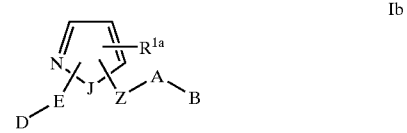

Ib wherein, groups D—E— and —Z—A—B are attached to adjacent atoms on the ring;

Z is selected from a $CH_2O$, $OCH_2$, $CH_2NH$, $NHCH_2$, $C(O)$, $CH_2C(O)$, $C(O)CH_2$, $NHC(O)$, $C(O)NH$, $CH_2S(O)_2$, $S(O)_2(CH_2)$, $SO_2NH$, and $NHSO_2$, provided that Z does not form a N—N, N—O, $NCH_2N$, or $NCH_2O$ bond with ring M or group A;

B is selected from: X-Y, $NR^2R^{2a}$, $C(=NR^2)NR^2R^{2a}$, $NR^2C(=NR^2)NR^2R^{2a}$ and one of the following carbocyclic and heterocyclic systems which are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

X is selected from $C_{1-4}$ alkylene, —C(O)—, —C(=NR)—, —C(O)CR$^2$R$^{2a}$—, —CR$^2$R$^{2a}$C(O), —C(O)NR$^2$—, —NR$^2$C(O)—, —C(O)NR$^2$CR$^2$R$^{2a}$—, —NR$^2$C(O)CR$^2$R$^{2a}$—, —CR$^2$R$^{2a}$C(O)NR$^2$—, —CR$^2$R$^{2a}$NR$^2$C(O)—, —NR$^2$C(O)NR$^2$—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

Y is $NR^2R^{2a}$, provided that X-Y do not form a N—N or O—N bond;

alternatively, Y is selected from one of the following carbocyclic and heterocyclic systems which are substituted with 0–2 $R^{4a}$;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

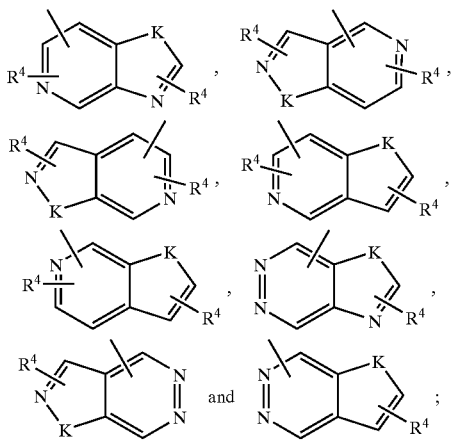

K is selected from O, S, NH, and N.

3. A compound according to claim 2, the compound is of formula IIa:

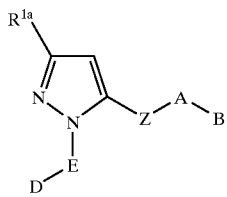

IIa wherein;

Z is selected from a C(O), CH$_2$C(O), C(O)CH$_2$, NHC(O), C(O)NH, CH$_2$S(O)$_2$, S(O)$_2$(CH$_2$), SO$_2$NH, and NHSO$_2$, provided that Z does not form a N—N or NCH$_2$N bond with ring M or group A.

4. A compound according to claim 3, wherein;

E is phenyl substituted with R or 2-pyridyl substituted with R;

D is selected from NH$_2$, C(O)NH$_2$, C(=NH)NH$_2$, CH$_2$NH$_2$, CH$_2$NHCH$_3$, CH(CH$_3$)NH$_2$, and C(CH$_3$)$_2$NH$_2$, provided that D is substituted meta or para to ring M on E; and, R is selected from H, OCH$_3$, Cl, and F.

5. A compound according to claim 4, wherein;

D—E is selected from 3-aminophenyl, 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl)phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, and 6-(2-amino-2-propyl)pyrid-2-yl.

6. A compound according to claim 3, wherein;

Z is C(O)CH$_2$ and CONH, provided that Z does not form a N—N bond with group A;

B is selected from X-Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

7. A compound according to claim 6, wherein;

A is 2-pyrimidyl; and,

B is selected from the group: 2-CF$_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1'-CF$_3$-tetrazol-2-yl)phenyl, 4-morpholinocarbonyl, 2-methyl-1-imidazolyl, 5-methyl-1-imidazolyl, 2-methylsulfonyl-1-imidazolyl, and 5-methyl-1,2,3-triazolyl.

8. A compound according to claim 3, wherein;

E is phenyl substituted with R or 2-pyridyl substituted with R;

D is selected from NH$_2$, C(O)NH$_2$, C(=NH)NH$_2$, CH$_2$NH$_2$, CH$_2$NHCH$_3$, CH(CH$_3$)NH$_2$, and C(CH$_3$)$_2$NH$_2$, provided that D is substituted meta or para to ring M on E; and, R is selected from H, OCH$_3$, Cl, and F;

Z is C(O)CH$_2$ and CONH, provided that Z does not form a N—N bond with group A;

B is selected from X-Y, phenyl, pyrrolidino, morpholino, 1,2,3-triazolyl, and imidazolyl, and is substituted with 0–1 R$^{4a}$;

R$^4$, at each occurrence, is selected from OH, (CH$_2$)$_r$OR$^2$, halo, C$_{1-4}$ alkyl, (CH$_2$)$_r$NR$^2$R$^{2a}$, and (CF$_2$)$_r$CF$_3$;

R$^{4a}$ is selected from C$_{1-4}$ alkyl, CF$_3$, S(O)$_p$R$^5$, SO$_2$NR$^2$R$^{2a}$, and 1-CF$_3$-tetrazol-2-yl;

R$^5$, at each occurrence, is selected from CF$_3$, C$_{1-6}$ alkyl, phenyl, and benzyl;

X is CH$_2$ or C(O); and,

Y is selected from pyrrolidino and morpholino.

9. A compound according to claim 8, wherein;

D—E is selected from 3-aminophenyl, 3-amidinophenyl, 3-aminomethylphenyl, 3-aminocarbonylphenyl, 3-(methylaminomethyl)phenyl, 3-(1-aminoethyl)phenyl, 3-(2-amino-2-propyl)phenyl, 4-chloro-3-aminophenyl, 4-chloro-3-amidinophenyl, 4-chloro-3-aminomethylphenyl, 4-chloro-3-(methylaminomethyl)phenyl, 4-fluoro-3-aminophenyl, 4-fluoro-3-amidinophenyl, 4-fluoro-3-aminomethylphenyl, 4-fluoro-3-(methylaminomethyl)phenyl, 6-aminopyrid-2-yl, 6-amidinopyrid-2-yl, 6-aminomethylpyrid-2-yl, 6-aminocarbonylpyrid-2-yl, 6-(methylaminomethyl)pyrid-2-yl, 6-(1-aminoethyl)pyrid-2-yl, 6-(2-amino-2-propyl)pyrid-2-yl;

A is 2-pyrimidyl; and,

B is selected from the group: 2-CF$_3$-phenyl, 2-(aminosulfonyl)phenyl, 2-(methylaminosulfonyl)phenyl, 2-(dimethylaminosulfonyl)phenyl, 1-pyrrolidinocarbonyl, 2-(methylsulfonyl)phenyl, 4-morpholino, 2-(1-CF$_3$-tetrazol-2-yl)phenyl, 4-morpholinocarbonyl, 2-methyl-1-imidazolyl, 5-methyl-1-imidazolyl, 2-methylsulfonyl-1-imidazolyl and, 5-methyl-1,2,3-triazolyl.

10. A compound according to claim 3, wherein;

D is selected from C(=NR$^8$)NR$^7$R$^9$, C(O)NR$^7$R$^8$, NR$^7$R$^8$, and CH$_2$NR$^7$R$^8$, provided that D is substituted meta or para to ring M on E;

E is phenyl substituted with R or pyridyl substituted with R;

R is selected from H, Cl, F, $OR^3$, $CH_3$, $CH_2CH_3$, $OCF_3$, and $CF_3$;

Z is selected from C(O), $CH_2C(O)$, $C(O)CH_2$, NHC(O), and C(O)NH, provided that Z does not form a N—N bond with ring M or group A;

$R^{1a}$ is independently absent or selected from —$(CH_2)_r$—$R^{1'}$, $NHCH_2R^{1''}$, $OCH_2R^{1''}$, $SCH_2R^{1''}$, $NH(CH_2)_2(CH_2)_rR^{1'}$, $O(CH_2)_2(CH_2)_rR^{1'}$, and $S(CH_2)_2(CH_2)_rR^{1'}$, or combined to form a 5–8 membered saturated, partially saturated or unsaturated ring substituted with 0–2 $R^4$ and which contains from 0–2 heteroatoms selected from the group consisting of N, O, and S;

$R^{1'}$, at each occurrence, is selected from H, $C_{1-3}$ alkyl, halo, $(CF_2)_rCF_3$, $OR^2$, $NR^2R^{2a}$, $C(O)R^{2c}$, $(CF_2)_r$ $CO_2R^{2c}$, $S(O)_pR^{2b}$, $NR^2(CH_2)_rOR^2$, $NR^2C(O)R^{2b}$, $NR^2C(O)_2R^{2d}$, $C(O)NR^2R^{2a}$, $SO_2NR^2R^{2a}$, and $NR^2SO_2R^{2b}$;

B is selected from: X-Y, $NR^2R^{2a}$, $C(=NR^2)NR^2R^{2a}$, $NR^2C(=NR^2)NR^2R^{2a}$ and one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

X is selected from $CH_2$, —C(O)—, —C(=NR)—, —C(O)$NR^2$—, —$NR^2C(O)$—, —$NR^2C(O)NR^2$—, —$NR^2$—, and O;

Y is $NR^2R^{2a}$, provided that X-Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^4$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $C(=NH)NH_2$, $NHC(=NH)NH_2$, $SO_2NR^2R^{2a}$, $NR^2SO_2$—$C_{1-4}$ alkyl, $NR^2SO_2R^5$, $S(O)_pR^5$, and $(CF_2)_rCF_3$;

$R^{4a}$, at each occurrence, is selected from =O, OH, Cl, F, $C_{1-4}$ alkyl, $(CH_2)_rNR^2R^{2a}$, $(CH_2)_rC(O)R^{2b}$, $NR^2C(O)R^{2b}$, $C(O)NR^2R^{2a}$, $C(=NH)NH_2$, $NHC(=NH)NH_2$, $SO_2NR^2R^{2a}$, $NR^2SO_2$—$C_{1-4}$ alkyl, $NR^2SO_2R^5$, $S(O)_pR^5$, $(CF_2)_rCF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $OR^2$, Cl, F, $CH_3$, CN, $NO_2$, $(CH_2)_rNR^2R^{2a}$, $(CH_2)_rC(O)R^{2b}$, $NR^2C(O)R^{2b}$, $C(=NH)NH_2$, $NHC(=NH)NH_2$, and $SO_2NR^2R^{2a}$;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, benzyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and benzyl; and alternatively, $R^7$ and $R^8$ combine to form a morpholino group; and, $R^9$, at each occurrence, is selected from H, $C_{1-6}$ alkyl and benzyl.

11. A compound according to claim 10, wherein;

E is phenyl substituted with R or 2-pyridyl substituted with R;

R is selected from H, Cl, F, $OCH_3$, $CH_3$, $OCF_3$, and $CF_3$;

Z is selected from a $C(O)CH_2$ and C(O)NH, provided that Z does not form a N—N bond with group A;

$R^{1a}$ is selected from H, $CH_3$, $CH_2CH_3$, Cl, F, $CF_3$, $OCH_3$, $NR^2R^{2a}$, $S(O)_pR^{2b}$, $CH_2S(O)_pR^{2b}$, $CH_2NR^2S(O)_2R^{2b}$, $C(O)R^{2c}$, $CH_2C(O)R^{2c}$, $C(O)NR^2R^{2a}$, and $SO_2NR^2R^{2a}$;

B is selected from: X-Y and one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

X is selected from $CH_2$, —C(O)—, —C(=NR)—, —C(O)$NR^2$—, —$NR^2C(O)$—, —$NR^2C(O)NR^2$—, —$NR^2$—, and O;

Y is $NR^2R^{2a}$, provided that X-Y do not form a N—N or O—N bond;

alternatively, Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, and 1,3,4-triazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a 5 or 6 membered saturated, partially unsaturated, or unsaturated ring which contains from 0–1 additional heteroatoms selected from the group consisting of N, O, and S;

$R^3$, at each occurrence, is selected from H, $CH_3$, $CH_2CH_3$, and phenyl;

$R^{3a}$, at each occurrence, is selected from H, $CH_3$, $CH_2CH_3$, and phenyl;

$R^4$, at each occurrence, is selected from OH, Cl, F, $CH_3$, $CH_2CH_3$, $NR^2R^{2a}$, $CH_2NR^2R^{2a}$, $C(O)R^{2b}$, $NR^2C(O)R^{2b}$, $C(O)NR^2R^{2a}$, and $CF_3$;

$R^{4a}$, at each occurrence, is selected from OH, Cl, F, $CH_3$, $CH_2CH_3$, $NR^2R^{2a}$, $CH_2NR^2R^{2a}$, $C(O)R^{2b}$, $C(O)NR^2R^{2a}$, $SO_2NR^2R^{2a}$, $S(O)_pR^5$, $CF_3$, and 1-$CF_3$-tetrazol-2-yl;

$R^5$, at each occurrence, is selected from $CF_3$, $C_{1-6}$ alkyl, phenyl substituted with 0–2 $R^6$, and benzyl substituted with 1 $R^6$;

$R^6$, at each occurrence, is selected from H, OH, $OCH_3$, Cl, F, $CH_3$, CN, $NO_2$, $NR^2R^{2a}$, $CH_2NR^2R^{2a}$, and $SO_2NR^2R^{2a}$;

$R^7$, at each occurrence, is selected from H, OH, $C_{13}$ alkyl, $C_{1-3}$ alkylcarbonyl, $C_{1-3}$ alkoxy, $C_{1-4}$ alkoxycarbonyl, benzyl, phenoxy, phenoxycarbonyl, benzylcarbonyl, $C_{1-4}$ alkylcarbonyloxy $C_{1-4}$ alkoxycarbonyl, phenylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $CH_3$, and benzyl; and, alternatively, $R^7$ and $R^8$ combine to form a morpholino group;

$R^9$, at each occurrence, is selected from H, $CH_3$, and benzyl.

12. A compound according to claim 11, wherein;

$R^{1a}$ is selected from H, $CH_3$, $CH_2CH_3$, Cl, F, $CF_3$, $OCH_3$, $NR^2R^{2a}$, $S(O)_pR^{2b}$, $C(O)NR^2R^{2a}$, $CH_2S(O)_pR^{2b}$, $C(O)R^{2c}$, $CH_2C(O)R^{2c}$, and $SO_2NR^2R^{2a}$;

B is selected from: X-Y and one of the following carbocyclic and heterocyclic systems which are substituted with 0–2 $R^{4a}$;
phenyl, piperazinyl, pyridyl, pyrimidyl, morpholinyl, pyrrolidinyl, imidazolyl, and 1,2,3-triazolyl;

X is selected from —C(O)— and O;

Y is $NR^2R^{2a}$, provided that X-Y do not form a O—N bond;

alternatively, Y is selected from one of the following carbocyclic and heterocyclic systems which are substituted with 0–2 $R^{4a}$;
phenyl, piperazinyl, pyridyl, pyrimidyl, morpholinyl, pyrrolidinyl, imidazolyl, and 1,2,3-trriazolyl;

$R^2$, at each occurrence, is selected from H, $CF_3$, $CH_3$, benzyl, and phenyl;

$R^{2a}$, at each occurrence, is selected from H, $CF_3$, $CH_3$, benzyl, and phenyl;

$R^{2b}$, at each occurrence, is selected from $CF_3$, $OCH_3$, $CH_3$, benzyl, and phenyl;

$R^{2c}$, at each occurrence, is selected from $CF_3$, OH, $OCH_3$, $CH_3$, benzyl, and phenyl;

alternatively, $R^2$ and $R^{2a}$ combine to form a ring system selected from pyrrolidinyl, piperazinyl and morpholino;

$R^4$, at each occurrence, is selected from Cl, F, $CH_3$, $NR^2R^{2a}$, and $CF_3$;

$R^{4a}$, at each occurrence, is selected from Cl, F, $CH_3$, $SO_2NR^2R^{2a}$, $S(O)_pR^5$, and $CF_3$; and, $R^5$, at each occurrence, is selected from $CF_3$ and $CH_3$.

13. A compound according to claim 1, wherein the compound is selected from the group:

1-(3-amidinophenyl)-3-methyl-2-[[5-(2'-aminosulfonylphenyl-1-yl)pyrimidin-2-yl]-aminocarbonyl]pyrazole;

1-(3-amidinophenyl)-5-[[5-(2'-t-butylaminosulfonylphenyl)pyrimidin-2-yl]aminocarbonyl]-3-trifluoromethyl-pyrazole;

1-(3-amidinophenyl)-5-[[5-(2'-aminosulfonylphenyl)pyrimidin-2-yl]aminocarbonyl]-3-trifluoromethyl-pyrazole;

1-(3-aminocarbonylphenyl)-5-[[5-(2'-aminosulfonylphenyl)pyrimidin-2-yl]aminocarbonyl]-3-trifluoromethyl-pyrazole;

1-(3-amidinophenyl)-3-methyl-5-[(5-(2'-aminosulfonyl-1-yl)pyrimid-5-yl)aminocarbonyl]pyrazole;

1-(3-amidinophenyl)-3-methyl-5-[[5-(2'-tertbutylaminosulfonylphenyl)pyrimid-2-yl]aminocarbonyl]pyrazole;

1-(3-amidinophenyl)-3-methyl-5-[(5-(2'-trifluoromethylphenyl)-pyrimidin-2-yl]aminocarbonyl]pyrazole;

1-(3-amidinophenyl)-3-methyl-5-([5-(2'-methylsulfonylphenyl)pyrimid-2-yl]aminocarbonyl)pyrazole;

1-(3-cyanophenyl)-3-methyl-5-([5-(2'-methylsulfonylphenyl)pyrimid-2-yl]aminocarbonyl)pyrazole;

1-(3-aminocarbonylphenyl)-3-methyl-5-([5-(2'-methylsulfonylphenyl)pyrimid-2-yl]aminocarbonyl)pyrazole;

1-(3-aminomethylphenyl)-5-[(5-(2'-aminosulfonylphenyl)pyrimid-2-yl)aminocarbonyl]-3-trifluoromethyl-pyrazole;

1-(3-aminomethylphenyl)-5-[(5-(2'-methylsulfonylphenyl)pyrimid-2-yl)aminocarbonyl]-3-trifluoromethyl-pyrazole;

1-(3-(N-carboxymethyl)amidinophenyl)-5-[(5-(2'-aminosulfonylphenyl)pyrimid-2-yl)aminocarbonyl]-3-methyl-pyrazole;

and pharmaceutically acceptable salts thereof.

14. A pharmaceutical composition, comprising: a pharmaceutically acceptable carrier and a therapeutically effective amount of a compound according to claim 1 or a pharmaceutically acceptable salt thereof.

15. A pharmaceutical composition, comprising: a pharmaceutically acceptable carrier and a therapeutically effective amount of a compound according to claim 2 or a pharmaceutically acceptable salt thereof.

16. A pharmaceutical composition, comprising: a pharmaceutically acceptable carrier and a therapeutically effective amount of a compound according to claim 3 or a pharmaceutically acceptable salt thereof.

17. A pharmaceutical composition, comprising: a pharmaceutically acceptable carrier and a therapeutically effective amount of a compound according to claim 4 or a pharmaceutically acceptable salt thereof.

18. A pharmaceutical composition, comprising: a pharmaceutically acceptable carrier and a therapeutically effective amount of a compound according to claim 5 or a pharmaceutically acceptable salt thereof.

19. A pharmaceutical composition, comprising: a pharmaceutically acceptable carrier and a therapeutically effective amount of a compound according to claim 6 or a pharmaceutically acceptable salt thereof.

20. A pharmaceutical composition, comprising: a pharmaceutically acceptable carrier and a therapeutically effective amount of a compound according to claim 7 or a pharmaceutically acceptable salt thereof.

21. A pharmaceutical composition, comprising: a pharmaceutically acceptable carrier and a therapeutically effective amount of a compound according to claim 8 or a pharmaceutically acceptable salt thereof.

22. A pharmaceutical composition, comprising: a pharmaceutically acceptable carrier and a therapeutically effective amount of a compound according to claim 9 or a pharmaceutically acceptable salt thereof.

23. A pharmaceutical composition, comprising: a pharmaceutically acceptable carrier and a therapeutically effective amount of a compound according to claim 10 or a pharmaceutically acceptable salt thereof.

24. A pharmaceutical composition, comprising: a pharmaceutically acceptable carrier and a therapeutically effective amount of a compound according to claim 11 or a pharmaceutically acceptable salt thereof.

25. A pharmaceutical composition, comprising: a pharmaceutically acceptable carrier and a therapeutically effective amount of a compound according to claim 12 or a pharmaceutically acceptable salt thereof.

26. A pharmaceutical composition, comprising: a pharmaceutically acceptable carrier and a therapeutically effective amount of a compound according to claim 13 or a pharmaceutically acceptable salt thereof.

27. A method for treating a thromboembolic disorder, comprising: administering to a patient in need thereof a therapeutically effective amount of a compound according to claim 1 or a pharmaceutically acceptable salt thereof.

28. A method for treating a thromboembolic disorder, comprising: administering to a patient in need thereof a therapeutically effective amount of a compound according to claim 2 or a pharmaceutically acceptable salt thereof.

29. A method for treating a thromboembolic disorder, comprising: administering to a patient in need thereof a therapeutically effective amount of a compound according to claim 3 or a pharmaceutically acceptable salt thereof.

30. A method for treating a thromboembolic disorder, comprising: administering to a patient in need thereof a therapeutically effective amount of a compound according to claim 4 or a pharmaceutically acceptable salt thereof.

31. A method for treating a thromboembolic disorder, comprising: administering to a patient in need thereof a therapeutically effective amount of a compound according to claim 5 or a pharmaceutically acceptable salt thereof.

32. A method for treating a thromboembolic disorder, comprising: administering to a patient in need thereof a therapeutically effective amount of a compound according to claim 6 or a pharmaceutically acceptable salt thereof.

33. A method for treating a thromboembolic disorder, comprising: administering to a patient in need thereof a therapeutically effective amount of a compound according to claim 7 or a pharmaceutically acceptable salt thereof.

34. A method for treating a thromboembolic disorder, comprising: administering to a patient in need thereof a therapeutically effective amount of a compound according to claim 8 or a pharmaceutically acceptable salt thereof.

35. A method for treating a thromboembolic disorder, comprising: administering to a patient in need thereof a therapeutically effective amount of a compound according to claim 9 or a pharmaceutically acceptable salt thereof.

36. A method for treating a thromboembolic disorder, comprising: administering to a patient in need thereof a therapeutically effective amount of a compound according to claim 10 or a pharmaceutically acceptable salt thereof.

37. A method for treating a thromboembolic disorder, comprising: administering to a patient in need thereof a therapeutically effective amount of a compound according to claim 11 or a pharmaceutically acceptable salt thereof.

38. A method for treating a thromboembolic. disorder, comprising: administering to a patient in need thereof a therapeutically effective amount of a compound according to claim 11 or a pharmaceutically acceptable salt thereof.

39. A method for treating a thromboembolic disorder, comprising: administering to a patient in need thereof a therapeutically effective amount of a compound according to claim 12 or a pharmaceutically acceptable salt thereof.

40. A method according to claim 27, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

41. A method according to claim 28, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

42. A method according to claim 29, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

43. A method according to claim 30, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

44. A method according to claim 31, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

45. A method according to claim 32, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

46. A method according to claim 33, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

47. A method according to claim 34, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

48. A method according to claim 37, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

49. A method according to claim 36, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

50. A method according to claim 37, wherein the thromboembolic disorder is.selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

51. A method according to claim 38, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

52. A method according to claim 39, wherein the thromboembolic disorder is selected from the group consisting of arterial cardiovascular thromboembolic disorders, venous cardiovascular thromboembolic disorders, arterial cerebrovascular thromboembolic disorders, venous cerebrovascular thromboembolic disorders, unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, and pulmonary embolism.

\* \* \* \* \*